United States Patent
Hagiwara et al.

(10) Patent No.: US 7,625,948 B2
(45) Date of Patent: Dec. 1, 2009

(54) ESTER COMPOUND AND MEDICINAL USE THEREOF

(75) Inventors: Atsushi Hagiwara, Takatsuki (JP); Yasuhiro Ohe, Takatsuki (JP); Naoya Odani, Takatsuki (JP); Shizue Watanabe, Takatsuki (JP); Taku Ikenogami, Takatsuki (JP); Takashi Kawai, Takatsuki (JP); Kenya Madono, Takatsuki (JP); Toshio Taniguchi, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 348 days.

(21) Appl. No.: 10/492,831

(22) PCT Filed: Feb. 28, 2003

(86) PCT No.: PCT/JP03/02398

§ 371 (c)(1), (2), (4) Date: Oct. 8, 2004

(87) PCT Pub. No.: WO03/072532

PCT Pub. Date: Sep. 4, 2003

(65) Prior Publication Data
US 2005/0075367 A1    Apr. 7, 2005

(30) Foreign Application Priority Data
Feb. 28, 2002    (JP) ............... 2002-053876

(51) Int. Cl.
| | | |
|---|---|---|
| A61K 31/265 | (2006.01) | |
| A61K 31/21 | (2006.01) | |
| A61K 31/235 | (2006.01) | |
| C07C 205/00 | (2006.01) | |
| C07C 229/00 | (2006.01) | |
| C07C 69/76 | (2006.01) | |

(52) U.S. Cl. .............. 514/512; 514/513; 514/532; 514/533; 560/21; 560/22; 560/45; 560/47; 560/55

(58) Field of Classification Search .............. 560/21, 560/22, 45, 47, 55; 514/512, 513, 532, 533
See application file for complete search history.

(56) References Cited

U.S. PATENT DOCUMENTS

| | | | |
|---|---|---|---|
| 5,521,170 A | 5/1996 | Setoi et al. | |
| 5,683,682 A * | 11/1997 | Betts ............... | 425/65 |
| 5,684,014 A | 11/1997 | Muller et al. | |
| 5,827,875 A | 10/1998 | Dickson, Jr. et al. | |
| 5,962,440 A | 10/1999 | Sulsky | |
| 6,057,339 A | 5/2000 | Gregg | |
| 6,121,283 A | 9/2000 | Chang et al. | |
| 6,171,599 B1 | 1/2001 | Miyamoto et al. | |
| 6,211,242 B1 | 4/2001 | Setoi et al. | |
| 6,235,730 B1 | 5/2001 | Sato et al. | |
| 6,288,234 B1 | 9/2001 | Griffin | |
| 6,369,075 B1 | 4/2002 | Ruggeri et al. | |
| 6,509,038 B2 | 1/2003 | Baert et al. | |
| 6,617,325 B1 | 9/2003 | Lehmann-Lintz et al. | |
| 6,713,489 B2 | 3/2004 | Ruggeri et al. | |
| 6,818,644 B1 | 11/2004 | Lehmann-Lintz et al. | |
| 6,943,185 B2 | 9/2005 | Susilo et al. | |
| 7,081,255 B2 | 7/2006 | Baert et al. | |

(Continued)

FOREIGN PATENT DOCUMENTS

CA    2079938    4/1993

(Continued)

OTHER PUBLICATIONS

Fischer et al, Journal of the Chemical Society (B), Rates of Base-catalyzed Hydrolysis of Substituted Aryl Benzoates, 1971, pp. 1818-1819.*

(Continued)

*Primary Examiner*—Paul A Zucker
(74) *Attorney, Agent, or Firm*—Finnegan, Henderson, Farabow, Garrett & Dunner, LLP

(57) ABSTRACT

A novel therapeutic agent for hyperlipidemia, which is an ester compound represented by the formula (1″)

(1″)

(wherein
$R^1$ and $R^2$ are each hydrogen atom or optionally substituted aryl, etc.;
X is —COO— or —CON($R^{10}$)—;
$R^3$ and $R^4$ are each hydrogen atom, $C_1$-$C_6$alkyl or $C_1$-$C_6$alkoxy, etc.;
$R^5$, $R^6$ and $R^7$ are each hydrogen atom, $C_1$-$C_6$ alkyl or $C_1$-$C_6$ alkoxy, etc.;
$R^8$ and $R^9$ are each independently hydrogen atom, $C_1$-$C_6$alkyl, —CON($R^{18}$)($R^{19}$) or —COO($R^{20}$), etc.;
ring A, ring B and ring C are each independently aryl or heterocycle residue, etc.;
$Alk^1$ and $Alk^2$ are each independently alkanediyl, etc.;
l and m are each an integer of 0 or 1 to 3) or a prodrug thereof, or a pharmaceutically acceptable salt of either.

The therapeutic agent selectively inhibits MTP in the small intestine, thus causes no such side effect as a fatty liver.

37 Claims, No Drawings

U.S. PATENT DOCUMENTS

| | | | |
|---|---|---|---|
| 2001/0007678 | A1 | 7/2001 | Baert |
| 2002/0012706 | A1 | 1/2002 | Vladyka, Jr. |
| 2002/0028943 | A1 | 3/2002 | Griffin |
| 2002/0032238 | A1 | 3/2002 | Priepke et al. |
| 2003/0044528 | A1 | 3/2003 | Tanno et al. |
| 2003/0114442 | A1 | 6/2003 | Heckel et al. |
| 2004/0058903 | A1 | 3/2004 | Takasugi et al. |
| 2005/0075367 | A1 | 4/2005 | Hagiwara et al. |
| 2006/0030623 | A1 | 2/2006 | Furukawa et al. |
| 2006/0089392 | A1 | 4/2006 | Hagiwara et al. |
| 2006/0153913 | A1 | 7/2006 | Yamane et al. |
| 2006/0205726 | A1 | 9/2006 | Hagiwara et al. |

FOREIGN PATENT DOCUMENTS

| | | |
|---|---|---|
| CA | 2 291 471 | 12/1999 |
| CA | 2 324 800 | 10/2000 |
| CA | 2 376 881 | 1/2001 |
| EP | 1 099 701 A1 | 5/2001 |
| EP | 1 350 792 A1 | 10/2003 |
| EP | 1 769 793 A1 | 4/2007 |
| JP | 47-25189 | 10/1972 |
| JP | 57-206612 | 2/1982 |
| JP | 3-1288 B | 1/1991 |
| JP | 3-28404 B | 1/1991 |
| JP | 05-097672 | 4/1993 |
| JP | 07-002800 | 1/1995 |
| JP | 08-179504 | 7/1996 |
| JP | 08-208476 | 8/1996 |
| JP | 9-59159 | 3/1997 |
| JP | 9-309834 | 12/1997 |
| JP | 11-035555 | 2/1999 |
| JP | 11-228569 | 8/1999 |
| JP | 11-509238 | 8/1999 |
| JP | 11-246404 | 9/1999 |
| JP | 2000-169395 | 6/2000 |
| JP | 2000-281561 | 10/2000 |
| JP | 2001-172180 | 6/2001 |
| JP | 2002-220345 | 8/2002 |
| JP | 2003-505373 | 2/2003 |
| JP | 2003-73261 | 3/2003 |
| JP | 2003-509505 | 3/2003 |
| JP | 2003-531099 | 10/2003 |
| JP | 2003-321424 | 11/2003 |
| JP | 2004-10575 | 1/2004 |
| JP | 2004-510763 | 4/2004 |
| KR | 1999-0075252 A | 10/1999 |
| WO | WO 9640640 | 12/1996 |
| WO | WO 97/262240 | 7/1997 |
| WO | WO 97/43257 | 11/1997 |
| WO | WP 98/23593 | 6/1998 |
| WO | WO 1998/47875 | 10/1998 |
| WO | WO 99/63929 | 12/1999 |
| WO | WO 00/05201 | 2/2000 |
| WO | WO 2000/32582 | 6/2000 |
| WO | WO 2000/37422 | 6/2000 |
| WO | WO 2000/56726 | 9/2000 |
| WO | WO 01/00183 | 1/2001 |
| WO | WO 01/00184 | 1/2001 |
| WO | WO 01/00189 | 1/2001 |
| WO | WO 2001/05762 | 1/2001 |
| WO | WO 01/12601 | 2/2001 |
| WO | WO 2001/21604 | 3/2001 |
| WO | WO 2001/47898 | 7/2001 |
| WO | WO 2001/47899 | 7/2001 |
| WO | WO 2001/53260 | 7/2001 |
| WO | WO 01/77077 A1 | 10/2001 |
| WO | WO 2001/97810 | 12/2001 |
| WO | WO 02/04403 A1 | 1/2002 |
| WO | WO 2002/20501 | 3/2002 |
| WO | WO 02/28835 A1 | 4/2002 |
| WO | WO 2002/42271 | 5/2002 |
| WO | WO 2002/42291 | 5/2002 |
| WO | WO 02/48141 | 6/2002 |
| WO | WO 2002/051385 | 7/2002 |
| WO | WO 2002/081460 | 10/2002 |
| WO | WO 2002/098839 | 12/2002 |
| WO | WO 2003/072532 | 9/2003 |
| WO | WO 2005/021486 | 3/2005 |
| WO | WO 2006/008962 | 1/2006 |
| WO | WO 2006/043510 | 4/2006 |
| WO | WO 2006/046623 | 5/2006 |

OTHER PUBLICATIONS

Ksander, G. M. et al., "Diaminoindanes as Microsomal Triglyceride Transfer Protein Inhibitors", Journal of Medicinal Chemistry, 2001, vol. 44, No. 26, pp. 4677-4687 (2001).

Wetterau, J. R. et al., "Purification and Characterization of Microsomal Triglyceride and Cholesteryl Ester Transfer Protein from Bovine Liver Microsomes", Chemistry and Physics of Lipids, vol. 38, pp. 205-222 (1985).

Robl, Jeffrey A. et al., "A Novel Series of Highly Potent Benzimidazole-Based Microsomal Triglyceride Transfer Protein Inhibitors," Journal of Medicinal Chemistry, vol. 44, No. 6, (2001) pp. 851-856.

International Search Report of PCT/JP03/02398 dated Jun. 3, 2003.

Aggarwal et al., BMC Cardiovascular Disorders, 2005, 5:30, pp. 1-8.

Anastasiou, Theordore J., et al., "Syntheses of aminosalicylate-based poluanhydride prodrugs: esters, amides, and azos,"Polymer Preprints (American Chemical Society, Division of Polymer Chemistry) 42(2), 121-122 (2001).

Chiou, W.L. et al., Pharmaceutical Application of Solid Dispersion Systems, J. Pharm. Sci. 60 (1971) 1281-1302.

Hagiwara et al., CAPLUS AN 2003:696857 (Feb. 28, 2003), 2 pages only.

Shiomi et al., MTP inhibitor decreases plasma cholesterol levels in LDL receptor-deficient WHHL rabbits by lowering the VLDL secretion, European Journal of Pharmacology, vol. 431, pp. 127-131 (2001).

European Search Report of Application No. 04772363.0 dated Jan. 23, 2008.

PCT International Search Report (PCT/JP2004/012407) dated Feb. 15, 2005.

PCT International Search Report (PCT/JP2005/012448) dated Aug. 9, 2005.

PCT International Search Report (PCT/JP2005/019744) dated Dec. 13, 2005.

PCT International Search Report (PCT/JP2005/019041) dated Jan. 24, 2006.

http://www.mayoclinic.com/health/arteriosclerosis-atherosclerosis/DS00525/DSECTION=8.

http://www.mayoclinic.com/health/obesity/DS00314/DSECTION=7.

Rx for Success, Lipid Levels - The Rick of Arteriosclerosis, Prudential Financial, 2002, 2 pages.

http://www.nhlbi.nih.gov/health/dci/Diseases/Cad/CAD_WhatIs.html.

Japan Tobacco Inc. Clinical Development (Apr. 27, 2007).

http://cholesterol.about.com/od/treatments/a/mttpinhibitor.htm.

SciFinder Scholar, version 2007.1; Chemical Abstracts Service, Columbus, OH; RN 339202-67-4 (accessed Feb. 6, 2008).

SciFinder Scholar, version 2007.1; Chemical Abstracts Service, Columbus, OH; RN 339202-91-4 (accessed Feb. 6, 2008).

SciFinder Scholar, version 2007.1; Chemical Abstracts Service, Columbus, OH; RN 516466-52-7 (accessed Feb. 6, 2008).

SciFinder Scholar, version 2007.1; Chemical Abstracts Service, Columbus, OH; RN 901355-00-8 (accessed Feb. 6, 2008).

SciFinder Scholar, version 2007.1; Chemical Abstracts Service, Columbus, OH; RN 888922-25-6 (accessed Feb. 6, 2008).

SciFinder Scholar, version 2007.1; Chemical Abstracts Service, Columbus, OH; RN 900909-90-2 (accessed Feb. 6, 2008.

Williams, Spencer J. et al., "Novel Microsomal Triglyceride Transfer Protein Inhibitors," Expert Opinion on Therapeutic Patents, 2003, 13, 479-88.

Office Action in Copending U.S. Appl. No. 11/250,636 dated Jan. 7, 2009.

Li, Bing et al., "N-(Arylacetyl)-biphenylalanines as Potent Vla-4 Antagonists," Bioorganic & Medicinal Chemistry Letters 2002, 12, 2141-2144.

Nakamura, Toshio et al., "Imidazole Derivatives as New Potent and Selective 20-Hete Synthase Inhibitors," Bioorganic & Medicinal Chemistry Letters 2004, 14, 333-336.

Patani, George a. et al., "Bioisosterism: a Rational Approach in Drug Design," Chemical Reviews 1996, 96, 3147-3176.

Wermuth, Camille G., "Molecular Variation Based on Isosteric Replacements," in Chapter 13, the Practice of Medicinal Chemistry, Academic: 1996.

Office Action in Copending Application No. 11/250,636 dated Jun. 2, 2009.

* cited by examiner

ESTER COMPOUND AND MEDICINAL USE THEREOF

This application is a US national stage application of PCT application PCT/JP03/02398 filed on Feb. 28, 2003, and claims benefit of priority of Japan Application No.: JP2002-53876, filed Feb. 28, 2002, the contents of which are hereby incorporated by reference.

TECHNICAL FIELD

The present invention relates to a novel ester compound, and also relates to a pharmaceutical composition comprising a novel ester compound which selectively inhibits microsomal triglyceride transfer protein (MTP) in the small intestine or a prodrug thereof, or a pharmaceutically acceptable salt of either. Further, the present invention relates to an agent for the treatment or prophylaxis of hyperlipidemia, arteriosclerosis, coronary artery diseases, obesity, diabetes or hypertension comprising a novel ester compound which selectively inhibits MTP in the small intestine or a prodrug thereof, or a pharmaceutically acceptable salt of either as an active ingredient. In addition, the present invention relates to an agent for the treatment or prophylaxis of hyperlipidemia, arteriosclerosis, coronary artery diseases, obesity, diabetes or hypertension, which has a novel function that has never been known before.

BACKGROUND ART

It has been said that hyperlipidemia, diabetes, hypertension or the like is one of the risk factors for arteriosclerosis. Hyperlipidemia is a condition where the concentration of lipid such as cholesterol is abnormally elevated in the blood. Types of hyperlipidemia, depending on the cause, include primary hyperlipidemia caused by genetic abnormality in enzyme, protein, lipoprotein and the like which participate in the metabolism of low-density lipoprotein (LDL), secondary hyperlipidemia due to various disease or drug administration, and acquired hyperlipidemia basically resulting from overnutrition.

Meanwhile, lipid taken in from food is absorbed in the small intestine by the action of bile acid, and secreted as chylomicron in the blood via lymphatic vessels. The triglyceride moiety of the secreted chylomicrons is hydrolyzed to free fatty acids by the action of lipoprotein lipase (LPL) existing in capillary vessels to become chylomicron remnants having a high content of cholesteryl ester (CE), which is then absorbed in the liver by the mediation of chylomicron remnant receptor in the liver. Further, in the liver, the absorbed chylomicron remnant and free fatty acid are converted to CE and TG, respectively, which are then associated with apolipoprotein B synthesized on rough surfaced endoplasmic reticulum to form very low density lipoprotein (VLDL). The VLDL is transferred to the Golgi apparatus, modified and secreted outside cells, and it becomes intermediate density lipoprotein (IDL) by the action of LPL. The IDL is converted to LDL by the action of hepatic triglyceride lipase (HTGL), and lipids are distributed to peripheral tissues.

It has long been indicated that, during the above-mentioned formation of chylomicron in the small intestine or VLDL in the liver, a protein having TG- or CE-transfer activity is existing in microsomal fractions of the small intestine or liver. Meanwhile, the protein, i.e. MTP (microsomal triglyceride transfer protein) was purified and separated from microsomal fractions of bovine liver by Wetterau et al. in 1985 (Wetterau J. R. et al: Chem. Phys. Lipids 38, 205-222(1985)). MTP, however, began attracting a lot of attention in the field of clinical medicine only after it was reported in 1993 that the cause of abetalipoproteinemia lay in the deficit of MTP. In other word, the disease is characterized in that, while the genes related to apolipoprotein B are normal, apolipoprotein B is hardly detected in the serum, the level of serum cholesterol is 50 mg/dL or lower, the level of serum triglyceride is extremely low and, moreover, lipoproteins including apolipoprotein B such as chylomicron, VLDL, LDL, etc. do not at all exist in the blood. By this finding, it has been shown that MTP is an integral protein involved in the association between apolipoprotein B and TG or CE, i.e. the formation of VLDL or chylomicron, and plays an essential role in secretion thereof.

Since lipid is by nature insoluble in water, lipid in the blood is combined with a hydrophilic protein known as apolipoprotein and exists as so-called lipoprotein. All the VLDL, IDL, LDL or chylomicron, etc. related to hyperlipidemia are a lipoprotein.

MTP exists in the microsome fractions of hepatocytes and intestinal epithelial cells, and catalyses the transfer of TG or CE in cells. In the liver and small intestine, along with the synthesis of apolipoprotein (apolipoprotein B100 in the liver and apolipoprotein B48 in the small intestine), TG and CE are combined with respective apolipoprotein B by the transfer activity of MTP, and thus VLDL or chylomicron is formed. As a result, those lipoproteins are secreted outside the cells as VLDL in the liver or as chylomicron in the small intestine. It should be said that MTP is indispensable for the construction of those lipoproteins. Namely, if the activity of MTP is blocked, the transfer of lipid such as TG and CE, etc. to apolipoprotein is inhibited, whereby formation of a lipoprotein can be inhibited.

On the other hand, it has been elucidated that LDL in general is closely related to the progression of arteriosclerosis. That is, LDL permeating endothelium of blood vessels is deposited in intercellular matrix of vessel wall, where oxidative denaturation takes place and lipid peroxides or denaturated proteins induce a series of inflammation reactions. Consequently, macrophage invasion, leading to lipid deposit or foaming cells, migration or proliferation of smooth muscle cells and increase in intercellular matrix, etc. take place, which leads to the development of arteriosclerosis plaque. On the basis of the above, it is supposed to be possible to prevent or treat arteriosclerosis, coronary artery diseases or hypertension by reducing the level of LDL.

As already mentioned, it is possible to inhibit the formation of lipoprotein such as chylomicron, VLDL, LDL, etc. by inhibiting the action of MTP. Accordingly, it has been expected that it should become possible to control lipoprotein such as TG, cholesterol and LDL, etc. in blood and to control lipid in cells by adjusting the activity of MTP, and therefore, a novel agent for the treatment or prophylaxis of hyperlipidemia, arteriosclerosis, coronary artery diseases, diabetes, obesity, or hypertension, and further, an agent for the treatment or prophylaxis of pancreatitis, hypercholesterolemia, hyperglyceridemia, etc. has been expected to be provided.

However, with the development of MTP inhibitors, some cases of fatty liver were reported and concern over hepatotoxicity has been raised.

For these reasons, a novel MTP inhibitor causing no side effect such as a fatty liver, etc. has been strongly desired.

In the conventional manners, combined therapies of various combinations of different antihyperlipidemic drugs have been tried. However, when, for example, astatin-type drug and a resin-type drug are given together, undesirable side effects such as increased GTO and GPT, constipation, blocking of absorption of vitamin A, D, E and K and the like are observed. On the other hand, when a statin-type drug and a fibrate drug are given together, side effects such as rhabdomyolysis or increased CPK (creative phosphokinase) are observed. Thus, with regard to a combined therapy for hyperlipidemia, a medicament for a combined administration which can be administered in combination with a conventional antihyperlipidemic drug without causing any above-mentioned side effect has been desired.

Meanwhile, examples of the known compound having MTP inhibitory activity with a similar structure of the compounds of the present invention are described below.

The following compound is disclosed in WO97/26240.

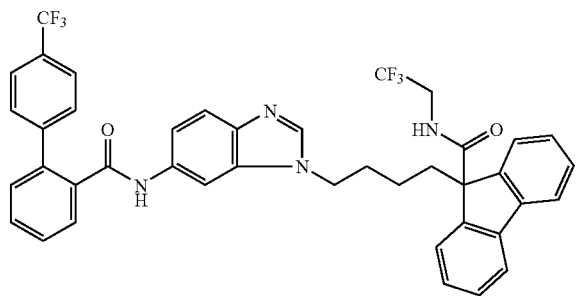

The following compound is disclosed in WO97/43257.

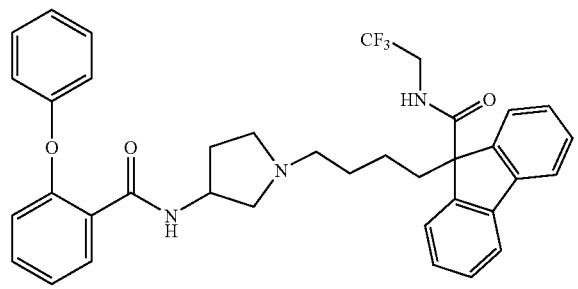

The following compound is disclosed in WO98/23593.

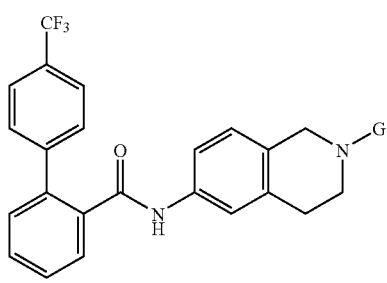

The following compound is disclosed in WO99/63929.

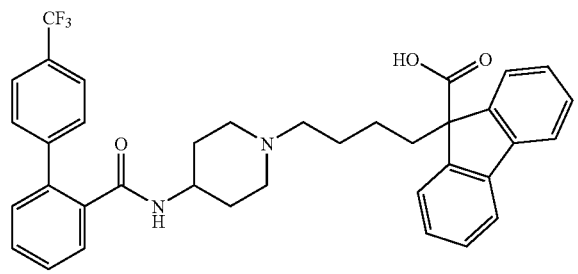

The following compound is disclosed in WO2000/5201.

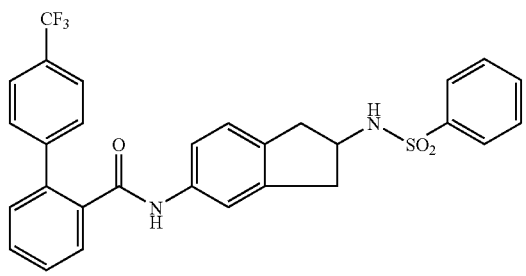

The following compound is disclosed in J. Med. Chem. (2001), 44(6) p. 851-856.

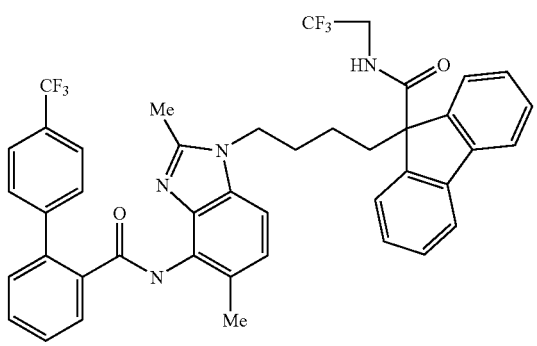

The following compound is disclosed in EP 1099701.

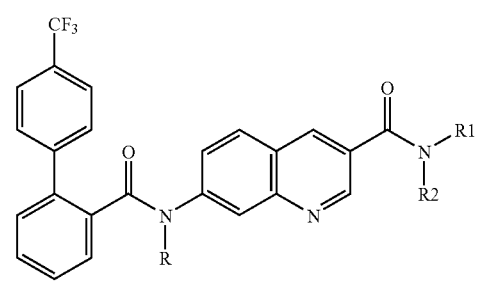

The following compound is disclosed in WO2001/77077.

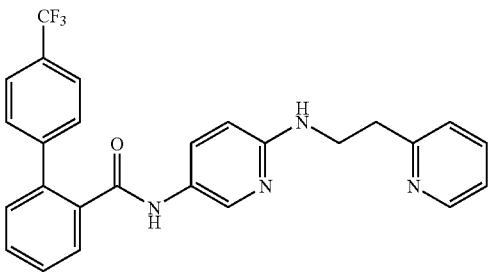

The following compound is disclosed in J. Med. Chem. (2001), 44(6) p. 4677-4687.

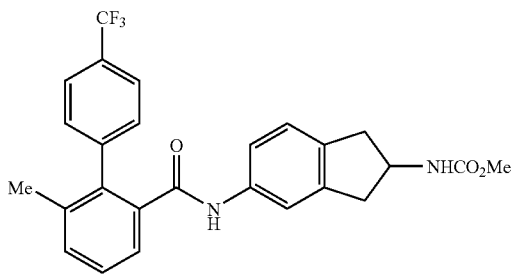

The following compound is disclosed in WO2002/4403.

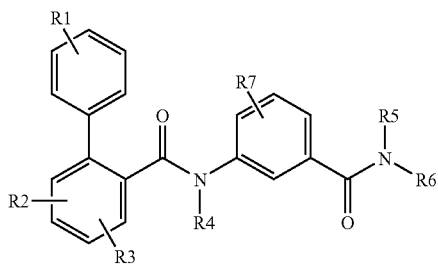

In the above literatures, however, there is no disclosure of a compound comprising ester as the essential structure as that disclosed in the present invention, much less the disclosure of the data indicating that when a compound has the structure disclosed in the present invention, the compound selectively inhibits MTP in the small intestine while rarely affects MTP in the liver.

DISCLOSURE OF THE INVENTION

Although the development of new antihyperlipidemic drugs working due to its MTP inhibitory activity has been advanced nowadays, those drugs are not satisfactory in terms of the level of action and the accompanying side effect such as a fatty liver, etc. Thus, the development of an antihyperlipidemic drug causing no side effect against the liver that is seen in the case of conventional MTP inhibitors and also having excellent MTP inhibitory activity has been strongly desired.

The inventors and those involved in the present invention have carried out intensive studies to provide a novel MTP inhibitor causing no above-mentioned side effect such as a fatty liver. As a result, they have found that an MTP inhibitor, which selectively inhibits MTP in the small intestine but substantially does not inhibit MTP in the liver, significantly lowers the level of unnecessary TG or cholesterol without causing a side effect such as a fatty liver, etc. Surprisingly, they have also found that the compound having ester structure represented by the below-mentioned formula (1) is immediately metabolized in the small intestine, blood or liver, which makes it possible for the compound to selectively affect MTP in the small intestine without substantially inhibiting MTP in the liver.

To be more specific, according to the conventional drug design concept for the preparation of a prodrug, the carboxylic acid which is the active principle is esterified to improve the absorption rate in the small intestine and is immediately metabolized in blood to reproduce carboxylic acid which is the active principle. On the other hand, a drug design concept that is different from the above concept for the preparation of a prodrug is used in the present invention. Namely, by introducing at least one ester in a molecular body of a compound having MTP inhibitory activity, the compound is, after it exerts MTP inhibitory activity on mucous membranes of the small intestine, immediately metabolized by an esterase or a metabolic enzyme, etc. in the small intestine, portal (blood) and liver to be transformed to corresponding carboxylic acid and alcohol which do not have MTP inhibitory activity. This is completely a new concept, by means of which MTP in the liver is not substantially affected and MTP in the small intestine is selectively inhibited. Further, the compounds of the present invention show strong MTP inhibitory activity in vitro, thus potently inhibit MTP in the small intestine and significantly lower triglyceride and cholesterol in blood. In addition, the compounds of the present invention significantly lower non-HDL cholesterol and, surprisingly, increase plasma HDL cholesterol.

Accordingly, the inventors of the present invention have found that when a compound comprises the ester structure represented by the below-mentioned formula (1), the compound is immediately metabolized in the small intestine, blood or liver after it strongly inhibits MTP in the small intestine and hence MTP in the liver is not substantially inhibited, whereby they have completed the present invention.

Thus, the present invention relates to (1) An ester compound represented by the formula (1)

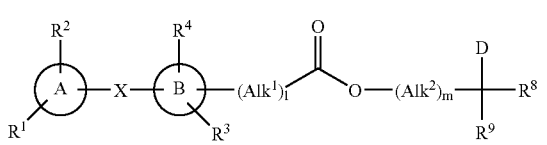

wherein $R^1$ and $R^2$ are each hydrogen, $C_1$-$C_6$ alkyl, $C_3$-$C_7$ cycloalkyl, $C_1$-$C_6$ alkoxy, halo $C_1$-$C_6$ alkyl, halo $C_1$-$C_6$ alkyloxy, optionally substituted $C_6$-$C_{14}$ aryl, optionally substituted $C_7$-$C_{16}$ aralkyl, optionally substituted $C_6$-$C_{14}$ aryloxy, optionally substituted $C_7$-$C_{16}$ aralkyloxy, optionally substituted $C_7$-$C_{15}$ arylcarbonyl, optionally substituted heterocycle, $C_2$-$C_7$ alkoxycarbonyl, halogen, $C_2$-$C_6$ alkenyl, —N($R^{40}$)($R^{41}$) wherein $R^{40}$ and $R^{41}$ are each independently hydrogen or optionally substituted $C_6$-$C_{14}$ aryl;

ring A is $C_6$-$C_{14}$ aryl, heterocycle, or

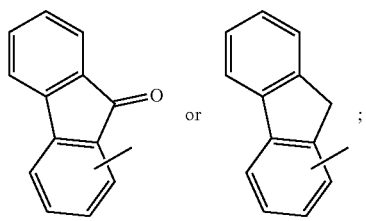

X is —COO—$(CH_2)_n$—, —CON($R^{10}$)-$(CH_2)_n$— or —N($R^{10}$)—CO—$(CH_2)_n$— wherein $R^{10}$ is hydrogen, $C_1$-$C_6$ alkyl or $C_3$-$C_7$ cycloalkyl and n is an integer of 0 to 3;

$R^3$ and $R^4$ are each independently hydrogen, hydroxy, halogen, optionally substituted $C_1$-$C_6$ alkyl, $C_1$-$C_6$ alkoxy, halo $C_1$-$C_6$ alkyl, $C_7$-$C_{16}$ aralkyloxy, $C_1$-$C_6$ acyl, optionally substituted heterocycle, —CON($R^{11}$)($R^{12}$) (wherein $R^{11}$ and $R^{12}$ are each independently hydrogen, $C_1$-$C_6$ alkyl, optionally substituted $C_6$-$C_{14}$ aryl, optionally substituted $C_7$-$C_{16}$ aralkyl, $C_1$-$C_6$ alkoxy, or $R^{11}$ and $R^{12}$ may be taken together with the nitrogen to which they are attached to form

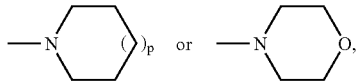

wherein p is an integer of 0 to 2), —(CH$_2$)$_q$-N($R^{13}$)($R^{14}$) (wherein $R^{13}$ and $R^{14}$ are each independently hydrogen, $C_1$-$C_6$ alkyl, $C_2$-$C_7$ alkoxycarbonyl, $C_1$-$C_6$ acyl, or $R^{13}$ and $R^{14}$ may be taken together with the nitrogen to which they are attached to form

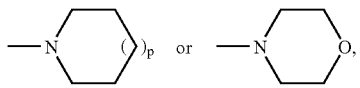

wherein p has the same meaning as defined above and q is an integer of 0 to 3), or —CO($R^{15}$) (wherein $R^{15}$ is hydroxy, $C_1$-$C_6$ alkoxy, optionally substituted $C_6$-$C_{14}$ aryloxy, optionally substituted $C_7$-$C_{16}$ aralkyloxy or $C_1$-$C_6$ alkyl);

ring B is

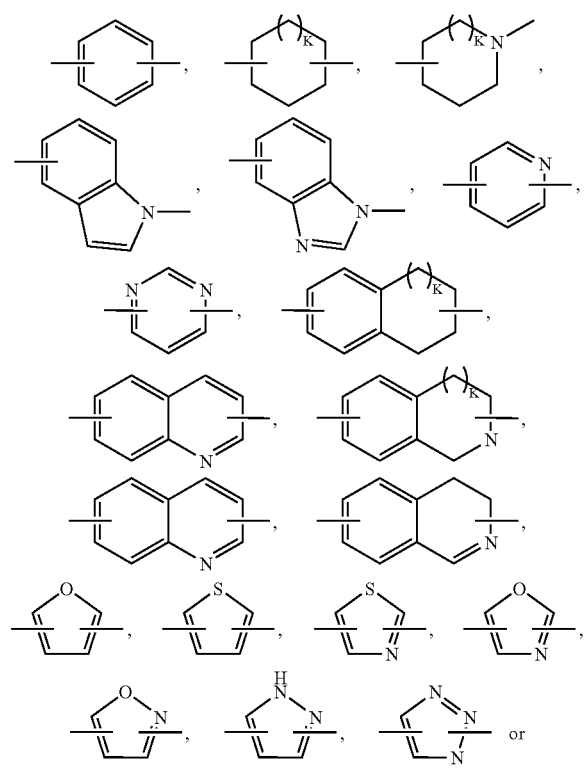

-continued

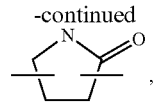

wherein K is an integer of 0 to 2, or ring B may be taken together with $R^3$, $R^{10}$ and the nitrogen bound to $R^{10}$ to form

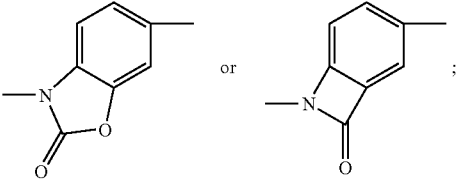

Alkl$^1$ is alkanediyl or alkenediyl;
Alkl$^2$ is alkanediyl or alkenediyl;
l is an integer of 0 to 3;
m is an integer of 0 to 3;
D is $C_1$-$C_6$ alkyl, $C_2$-$C_6$ alkenyl, $C_2$-$C_7$ alkoxycarbonyl, —N($R^{42}$)—CO($R^{43}$) (wherein $R^{42}$ is hydrogen or $C_1$-$C_6$ alkyl and $R^{43}$ is $C_6$-$C_{14}$ aryl or $C_7$-$C_{16}$ aralkyl), or the group represented by the following formula

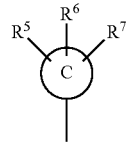

(wherein $R^5$, $R^6$ and $R^7$ are each independently hydrogen, $C_1$-$C_6$ alkyl, $C_1$-$C_6$ alkoxy, $C_2$-$C_7$ alkoxycarbonyl, carboxyl, halogen, cyano, nitro, halo $C_1$-$C_6$ alkyl, $C_1$-$C_6$ acyl, hydroxy, amino, optionally substituted $C_6$-$C_{14}$ aryl, or —(CH$_2$)$_r$—CON($R^{16}$)($R^{17}$) (wherein $R^{16}$ and $R^{17}$ are each independently hydrogen, $C_1$-$C_6$ alkyl or halo $C_1$-$C_6$ alkyl and r is an integer of 0 to 3);

ring C is $C_6$-$C_{14}$ aryl, $C_7$-$C_{15}$ arylcarbonylamino, $C_8$-$C_{17}$ aralkylcarbonylamino, heterocycle residue, $C_3$-$C_7$ cycloalkyl or $C_7$-$C_{16}$ aralkyl, or ring C may be taken together with $R^7$ and $R^8$ to form

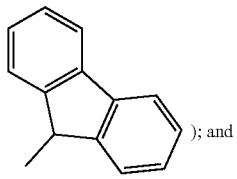

); and $R^8$ and $R^9$ are each independently hydrogen, $C_1$-$C_6$ alkyl, optionally substituted $C_6$-$C_{14}$ aryl, hydroxy $C_1$-$C_6$ alkyl, —CON($R^{18}$)($R^{19}$) (wherein $R^{18}$ and $R^{19}$ are each independently hydrogen, $C_1$-$C_6$ alkyl, $C_3$-$C_7$ cycloalkyl, halo $C_1$-$C_6$ alkyl, $C_2C_{1-2}$ alkoxyalkyl or optionally substituted $C_6$-$C_{14}$ aryl), —COO($R^{20}$) or —(CH$_2$)$_s$—OCO($R^{20}$) (wherein $R^{20}$ is hydrogen, $C_1$-$C_6$ alkyl or $C_3$-$C_7$ cycloalkyl; s is an integer of 0 to 3), —N($R^{21}$)($R^{22}$)(wherein $R^{21}$ and $R^{22}$ are each independently hydrogen, $C_1$-$C_6$ alkyl, $C_1$-$C_6$ acyl, $C_1$-$C_6$ alkylsulfonyl, or R²¹ and R²² may be taken together with the nitrogen to which they are attached to form

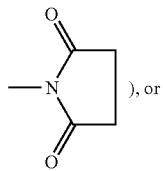

), or

R⁸ and R⁹ may be taken together to form C₃-C₇ cycloalkyl, or a prodrug thereof, or a pharmaceutically acceptable salt of either;

(2) The ester compound or a prodrug thereof, or a pharmaceutically acceptable salt of either according to the above (1), wherein D is $C_1$-$C_6$ alkyl, $C_2$-$C_6$ alkenyl, $C_2$-$C_7$ alkoxycarbonyl or —N(R⁴²)—CO(R⁴³) in which R⁴² and R⁴³ each has the same meaning as defined above;

(3) The ester compound or a prodrug thereof, or a pharmaceutically acceptable salt of either according to the above (1), wherein D is the group represented by the formula

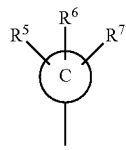

in which R⁵, R⁶ and R⁷ each has the same meaning as defined above;

(4) The ester compound or a prodrug thereof, or a pharmaceutically acceptable salt of either according to the above (3), wherein the ring C is

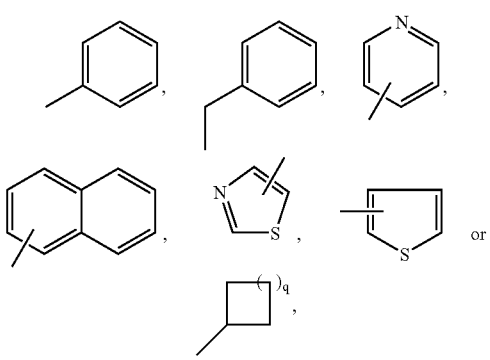

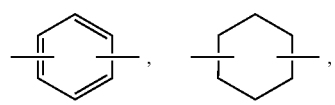

in which q is an integer of 0 to 3;

(5) The ester compound or a prodrug thereof, or a pharmaceutically acceptable salt of either according to the above (2) or (4), wherein ring B is

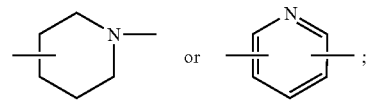

-continued

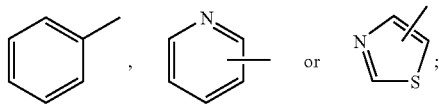

(6) The ester compound or a prodrug thereof, or a pharmaceutically acceptable salt of either according to the above (5), wherein ring A is

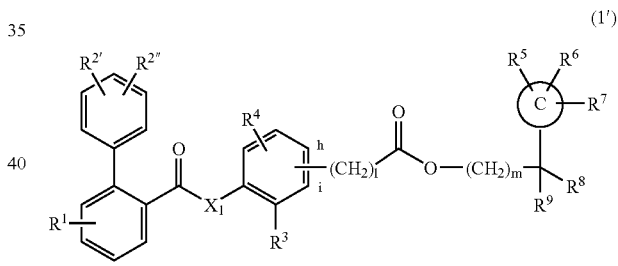

(7) The ester compound or a prodrug thereof, or a pharmaceutically acceptable salt of either according to the above (6), wherein X is —CON(R¹⁰)-(CH₂)$_n$— in which R¹⁰ and n each has the same meaning as defined above;

(8) The ester compound or a prodrug thereof, or a pharmaceutically acceptable salt of either according to the above (6), wherein X is —COO—(CH₂)$_n$— in which n has the same meaning as defined above;

(9) The ester compound or a prodrug thereof, or a pharmaceutically acceptable salt of either according to the above (7) or (8), wherein n is 0;

(10) The ester compound or a prodrug thereof, or a pharmaceutically acceptable salt of either according to the above (10), which is represented by the formula (1')

(1')

[Structure of formula (1')]

wherein

R²' and R²" are each independently hydrogen, $C_1$-$C_6$ alkyl, $C_3$-$C_7$ cycloalkyl, $C_1$-$C_6$ alkoxy, halogen, halo $C_1$-$C_6$ alkyl, $C_1$-$C_6$ acyl, $C_2$-$C_6$ alkenyl or cyano;

X₁ is —O— or —NR¹⁰— wherein R¹⁰ is hydrogen, $C_1$-$C_6$ alkyl or $C_3$-$C_7$ cycloalkyl; and R¹, R³, R⁴, R⁵, R⁶, R⁷, R⁸, R⁹, ring C, l and m each has the same meaning as defined above, or a prodrug thereof, or a pharmaceutically acceptable salt of either;

(11) The ester compound or a prodrug thereof, or a pharmaceutically acceptable salt of either according to the above (10), wherein the ring C is

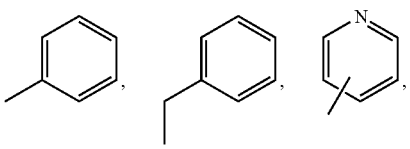

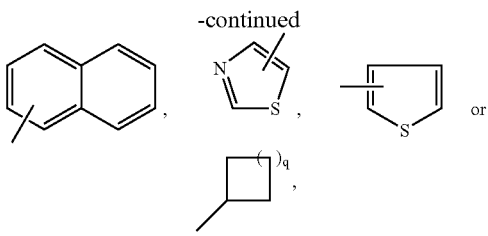

in which q is an integer of 0 to 3;

(12) The ester compound or a prodrug thereof, or a pharmaceutically acceptable salt of either according to the above (11), wherein $X_1$ is —$NR^{10}$— in which $R^{10}$ has the same meaning as defined above;

(13) The ester compound or a prodrug thereof, or a pharmaceutically acceptable salt of either according to the above (11), wherein $X_1$ is —O—;

(14) The ester compound or a prodrug thereof, or a pharmaceutically acceptable salt of either according to the above (10) to (13), wherein the group —$(CH_2)_1$— is located at the h-position of the benzene ring in the formula (1');

(15) The ester compound or a prodrug thereof, or a pharmaceutically acceptable salt of either according to the above (10) to (13), wherein the group —$(CH_2)_1$— is located at the i-position of the benzene ring in the formula (1');

(16) The ester compound or a prodrug thereof, or a pharmaceutically acceptable salt of either according to the above (10) to (15), wherein $R^8$ and $R^9$ are each independently —$CON(R^{18})(R^{19})$— in which $R^{18}$ and $R^{19}$ each has the same meaning as defined above;

(17) The ester compound or a prodrug thereof, or a pharmaceutically acceptable salt of either according to the above (10) to (15), wherein $R^8$ and $R^9$ are each independently —$COO(R^{20})$— in which $R^{20}$ has the same meaning as defined above;

(18) The ester compound or a prodrug thereof, or a pharmaceutically acceptable salt of either according to the above (12) to (17), wherein the ring C is $C_6$-$C_{14}$ aryl;

(19) The ester compound or a prodrug thereof, or a pharmaceutically acceptable salt of either according to the above (18), wherein $C_6$-$C_{14}$ aryl is phenyl;

(20) The ester compound or a prodrug thereof, or a pharmaceutically acceptable salt of either according to the above (12) to (17), wherein the ring C is $C_3$-$C_7$ cycloalkyl;

(21) The ester compound or a prodrug thereof, or a pharmaceutically acceptable salt of either according to the above (12) to (17), wherein the ring C is

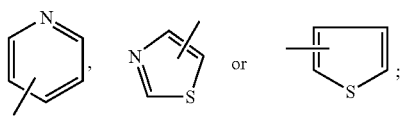

(22) The ester compound or a prodrug thereof, or a pharmaceutically acceptable salt of either according to the above (1), which is selected from the group consisting of {4-[(4'-trifluoromethyl-biphenyl-2-carbonyl)-amino]-phenyl}-acetic acid 2,2-bis-ethylcarbamoyl-2-phenyl-ethyl ester, 2-phenyl-2-{2-[4-(4'-trifluoromethyl-biphenyl-2-carbonyloxy)-phenyl]-acetoxymethyl}-malonic acid diethyl ester, 2-(2-{3-methyl-4-[(4'-trifluoromethyl-biphenyl-2-carbonyl)-amino]-phenyl}-acetoxymethyl)-2-phenyl-malonic acid diethyl ester, 2-(2-{4-[methyl-(4'-trifluoromethyl-biphenyl-2-carbonyl)-amino]-phenyl}-acetoxymethyl)-2-phenyl-malonic acid diethyl ester, {3-ethyl-4-[(4'-trifluoromethyl-biphenyl-2-carbonyl)-amino]-phenyl}-acetic acid 2,2-bis-ethylcarbamoyl-2-phenyl-ethyl ester, {4-[(4'-trifluoromethyl-biphenyl-2-carbonyl)-amino]-phenyl}-acetic acid 9-(2,2,2-trifluoro-ethylcarbamoyl)-9h-fluoren-9-ylmethyl ester, 2-{4-[(4'-trifluoromethyl-biphenyl-2-carbonyl)-amino]-phenyl}-propionic acid 9-(2,2,2-trifluoro-ethylcarbamoyl)-9h-fluoren-9-ylmethyl ester, {4-[(4'-trifluoromethyl-biphenyl-2-carbonyl)-amino]-phenyl}-acetic acid 2-phenyl-2-(2,2,2-trifluoro-ethylcarbamoyl)-ethyl ester, 2-phenyl-2-(2-{4-[(4'-trifluoromethyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 1-(2,2,2-trifluoro-ethylcarbamoyl)-cyclopentylmethyl ester, 2-phenyl-2-(2-{4-[(4'-trifluoromethyl-biphenyl-2-carbonyl)-amino]-phenyl}-acetoxymethyl)-malonic acid diisopropyl ester, {4-[(4'-trifluoromethyl-biphenyl-2-carbonyl)-amino]-phenyl}-acetic acid 2-phenyl-2,2-bis-(2,2,2-trifluoro-ethylcarbamoyl)-ethyl ester, 2-phenyl-2-(2-{4-[(4'-trifluoromethyl-biphenyl-2-carbonyl)-amino]-phenyl}-acetoxymethyl)-malonic acid dimethyl ester, 2-cyclopentyl-2-(2-{4-[(4'-trifluoromethyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 1-(2,2,2-trifluoro-ethylcarbamoyl)-cyclohexylmethyl ester, 2-phenyl-2-{2-[4-(2-trifluoromethyl-benzoylamino)-phenyl]-acetoxymethyl}-malonic acid diethyl ester, 2-{2-[4-(2-phenoxy-benzoylamino)-phenyl]-acetoxymethyl}-2-phenyl-malonic acid diethyl ester, 2-{2-[4-(2-butoxy-benzoylamino)-phenyl]-acetoxymethyl}-2-phenyl-malonic acid diethyl ester, 2-phenyl-2-{2-[4-(2-trifluoromethyl-benzoyloxy)-phenyl]-acetoxymethyl}-malonic acid diethyl ester, 2-{2-[4-(2-benzoyl-benzoyloxy)-phenyl]-acetoxymethyl}-2-phenyl-malonic acid diethyl ester, 2-{2-[4-(2-benzoyl-benzoylamino)-phenyl]-acetoxymethyl}-2-phenyl-malonic acid diethyl ester, 2-phenyl-2-(2-{4-[(4'-trifluoromethyl-biphenyl-2-carbonyl)-amino]-phenyl}-acetoxymethyl)-malonic acid dicyclohexyl ester, {4-[(4'-trifluoromethyl-biphenyl-2-carbonyl)-amino]-phenyl}-acetic acid 2,2-bis-cyclohexylcarbamoyl-2-phenyl-ethyl ester, {4-[(4'-trifluoromethyl-biphenyl-2-carbonyl)-amino]-phenyl}-acetic acid 2-phenyl-2,2-bis-phenylcarbamoyl-ethyl ester, {4-[(4'-trifluoromethyl-biphenyl-2-carbonyl)-amino]-phenyl}-acetic acid 2,2-bis-isopropylcarbamoyl-2-phenyl-ethyl ester, 2-benzyl-2-(2-{4-[(4'-trifluoromethyl-biphenyl-2-carbonyl)-amino]-phenyl}-acetoxymethyl)-malonic acid diethyl ester, 2-(2-{2-methyl-4-[(4'-trifluoromethyl-biphenyl-2-carbonyl)-amino]-phenyl}-acetoxymethyl)-2-phenyl-malonic acid diethyl ester, 4'-trifluoromethyl-biphenyl-2-carboxylic acid 4-[2-phenyl-2,2-bis-(2,2,2-trifluoro-ethylcarbamoyl)-ethoxycarbonylmethyl]-phenyl ester, biphenyl-2-carboxylic acid 4-[2-phenyl-2,2-bis-(2,2,2-trifluoro-ethylcarbamoyl)-ethoxycarbonylmethyl]-phenyl ester, 2-butoxy-benzoic acid 4-[2-phenyl-2,2-bis-(2,2,2-trifluoro-ethylcarbamoyl)-ethoxycarbonylmethyl]-phenyl ester, 2-cyclohexyl-2-(2-{4-[(4'-trifluoromethyl-biphenyl-2-carbonyl)-amino]-phenyl}-acetoxymethyl)-malonic acid diethyl ester, {4-[(biphenyl-2-carbonyl)-amino]-phenyl}-acetic acid 2-phenyl-2,2-bis-(2,2,2-trifluoro-ethylcarbamoyl)-ethyl ester,

[4-(2-phenoxy-benzoylamino)-phenyl]-acetic acid 2-phenyl-2,2-bis-(2,2,2-trifluoro-ethylcarbamoyl)-ethyl ester, 2-phenyl-2-{2-(2-trifluoromethyl-4-[(4'-trifluoromethyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 2-phenyl-2,2-bis-propylcarbamoyl-ethyl ester, {4-[(4'-trifluoromethyl-biphenyl-2-carbonyl)-amino]-phenyl}-acetic acid 2,2-bis-methylcarbamoyl-2-phenyl-ethyl ester, 2-pyridin-2-yl-2-(2-{4-[(4'-trifluoromethyl-biphenyl-2-carbonyl)-amino]-phenyl}-acetoxymethyl)-malonic acid diethyl ester, 2-pyridin-3-yl-2-(2-{4-[(4'-trifluoromethyl-biphenyl-2-carbonyl)-amino]-phenyl}-acetoxymethyl)-malonic acid diethyl ester, 4'-trifluoromethyl-biphenyl-2-carboxylic acid 4-(2,2-bis-ethylcarbamoyl-2-phenyl-ethoxycarbonylmethyl)-phenyl ester, 2-phenyl-2-(2-{3-trifluoromethyl-4-[(4'-trifluoromethyl-biphenyl-2-carbonyl)-amino]-phenyl}-acetoxymethyl)-malonic acid diethyl ester,

[4-(2-butoxy-benzoylamino)-phenyl]-acetic acid 2-phenyl-2,2-bis-(2,2,2-trifluoro-ethylcarbamoyl)-ethyl ester, {4-[(4'-trifluoromethyl-biphenyl-2-carbonyl)-amino]-phenyl}-acetic acid 2,2-bis-butylcarbamoyl-2-phenyl-ethyl ester, 2-(2-{4-[(9-oxo-9h-fluorene-1-carbonyl)-amino]-phenyl}-acetoxymethyl)-2-phenyl-malonic acid diethyl ester, 2-(2-{4-[(9h-fluorene-1-carbonyl)-amino]-phenyl}-acetoxymethyl)-2-phenyl-malonic acid diethyl ester, {3-methyl-4-[(4'-trifluoromethyl-biphenyl-2-carbonyl)-amino]-phenyl}-acetic acid 2,2-bis-ethylcarbamoyl-2-phenyl-ethyl ester, 2-(2-{4-[(4'-methyl-biphenyl-2-carbonyl)-amino]-phenyl}-acetoxymethyl)-2-phenyl-malonic acid diethyl ester, 2-(2-{4-[(4'-methoxy-biphenyl-2-carbonyl)-amino]-phenyl}-acetoxymethyl)-2-phenyl-malonic acid diethyl ester, {4-[(4'-trifluoromethyl-biphenyl-2-carbonyl)-amino]-phenyl}-acetic acid 3,3-bis-ethylcarbamoyl-3-phenyl-propyl ester, {4-[(4'-trifluoromethyl-biphenyl-2-carbonyl)-amino]-phenyl}-acetic acid 3-phenyl-3,3-bis-propylcarbamoyl-propyl ester, {4-[(biphenyl-2-carbonyl)-amino]-phenyl}-acetic acid 2,2-bis-ethylcarbamoyl-2-phenyl-ethyl ester,

[4-(2-phenoxy-benzoylamino)-phenyl]-acetic acid 2,2-bis-ethylcarbamoyl-2-phenyl-ethyl ester,

[4-(2-butoxy-benzoylamino)-phenyl]-acetic acid 2,2-bis-ethylcarbamoyl-2-phenyl-ethyl ester, 2-phenyl-2-(2-{4-[(3'-trifluoromethyl-biphenyl-2-carbonyl)-amino]-phenyl}-acetoxymethyl)-malonic acid diethyl ester, 2-(2-{4-[2-(4-fluoro-benzoyl)-benzoylamino]-phenyl}-acetoxymethyl)-2-phenyl-malonic acid diethyl ester, 4'-trifluoromethyl-biphenyl-2-carboxylic acid 4-(2,2-bis-ethylcarbamoyl-2-phenyl-ethoxycarbonylmethyl)-2-chloro-phenyl ester, 2-phenyl-2-{2-[4-(2-thiophen-3-yl-benzoylamino)-phenyl]-acetoxymethyl}-malonic acid diethyl ester, 2-(2-{4-[(biphenyl-3-carbonyl)-amino]-phenyl}-acetoxymethyl)-2-phenyl-malonic acid diethyl ester, 2-(2-{4-[isopropyl-(4'-trifluoromethyl-biphenyl-2-carbonyl)-amino]-phenyl}-acetoxymethyl)-2-phenyl-malonic acid diethyl ester, 2-(2-{4-[cyclohexyl-(4'-trifluoromethyl-biphenyl-2-carbonyl)-amino]-phenyl}-acetoxymethyl)-2-phenyl-malonic acid diethyl ester, 2-{2-[4-(2-isopropyl-benzoylamino)-phenyl]-acetoxymethyl}-2-phenyl-malonic acid diethyl ester, 2-{2-[4-(2-benzyl-benzoylamino)-phenyl]-acetoxymethyl}-2-phenyl-malonic acid diethyl ester, 2-phenyl-2-(2-{4-[(4'-trifluoromethyl-biphenyl-2-carbonyl)-amino]-phenyl}-acetoxymethyl)-malonic acid dipropyl ester, 2-phenyl-2-(2-{4-[(4'-trifluoromethyl-biphenyl-2-carbonyl)-amino]-phenyl}-acetoxymethyl)-malonic acid diisobutyl ester, 2-phenyl-2-{2-[4-(2-trifluoromethoxy-benzoylamino)-phenyl]-acetoxymethyl}-malonic acid diethyl ester, 2-{2-[4-(2-butoxycarbonyl-benzoylamino)-phenyl]-acetoxymethyl}-2-phenyl-malonic acid diethyl ester, {4-[(4'-trifluoromethyl-biphenyl-2-carbonyl)-amino]-phenyl}-acetic acid 2,2-bis-isobutylcarbamoyl-2-phenyl-ethyl ester, {4-[(4'-trifluoromethyl-biphenyl-2-carbonyl)-amino]-phenyl}-acetic acid 2,2-bis-(3-methyl-butylcarbamoyl)-2-phenyl-ethyl ester, 2-(2-{4-[ethyl-(4'-trifluoromethyl-biphenyl-2-carbonyl)-amino]-phenyl}-acetoxymethyl)-2-phenyl-malonic acid diethyl ester,

[4-(2-cyclohexyl-benzoylamino)-phenyl]-acetic acid 2,2-bis-ethylcarbamoyl-2-phenyl-ethyl ester, {4-(4'-chloro-biphenyl-2-carbonyl)-amino)-phenyl}-acetic acid 2,2-bis-ethylcarbamoyl-2-phenyl-ethyl ester, {4-[(3',4'-dichloro-biphenyl-2-carbonyl)-amino]-phenyl}-acetic acid 2,2-bis-ethylcarbamoyl-2-phenyl-ethyl ester, {3-methyl-4-[(4'-trifluoromethyl-biphenyl-2-carbonyl)-amino]-phenyl}-acetic acid 2-phenyl-2,2-bis-propylcarbamoyl-ethyl ester, {4-[(4'-trifluoromethyl-biphenyl-2-carbonyl)-amino]-phenyl}-acetic acid 2.2-bis-(2-methoxy-ethylcarbamoyl)-2-phenyl-ethyl ester, 2-[2-(4-{[2-methyl-4-(4-trifluoromethyl-phenyl)-thiazole-5-carbonyl]-amino}-phenyl)-acetoxymethyl]-2-phenyl-malonic acid diethyl ester, (4-{[2-methyl-4-(4-trifluoromethyl-phenyl)-thiazole-5-carbonyl]-amino}-phenyl)-acetic acid 2,2-bis-ethylcarbamoyl-2-phenyl-ethyl ester, (4-{[2-(4-trifluoromethyl-phenyl)-pyridine-3-carbonyl]-amino}-phenyl)-acetic acid 2,2-bis-ethylcarbamoyl-2-phenyl-ethyl ester, (3-methyl-4-{[2-(4-trifluoromethyl-phenyl)-pyridine-3-carbonyl]-amino}-phenyl)-acetic acid 2,2-bis-ethylcarbamoyl-2-phenyl-ethyl ester, 2-(2-{3-ethyl-4-[(4'-trifluoromethyl-biphenyl-2-carbonyl)-amino]-phenyl}-acetoxymethyl)-2-phenyl-malonic acid diethyl ester, {3-isopropyl-4-[(4'-trifluoromethyl-biphenyl-2-carbonyl)-amino]-phenyl}-acetic acid 2,2-bis-ethylcarbamoyl-2-phenyl-ethyl ester, 2-(2-{3-isopropyl-4-[(4'-trifluoromethyl-biphenyl-2-carbonyl)-amino]-phenyl}-acetoxymethyl)-2-phenyl-malonic acid diethyl ester, {3-ethyl-4-[(4'-trifluoromethyl-biphenyl-2-carbonyl)-amino]-phenyl}-acetic acid 3,3-bis-ethylcarbamoyl-3-phenyl-propyl ester, {3-isobutyl-4-[(4'-trifluoromethyl-biphenyl-2-carbonyl)-amino]-phenyl}-acetic acid 2,2-bis-ethylcarbamoyl-2-phenyl-ethyl ester, 2-(2-{3-isobutyl-4-[(4'-trifluoromethyl-biphenyl-2-carbonyl)-amino]-phenyl}-acetoxymethyl)-2-phenyl-malonic acid diethyl ester, 2-(2-{3-chloro-4-[(4'-trifluoromethyl-biphenyl-2-carbonyl)-amino]-phenyl}-acetoxymethyl)-2-phenyl-malonic acid diethyl ester, 2-(2-{3-bromo-4-[(4'-trifluoromethyl-biphenyl-2-carbonyl)-amino]-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 2-phenyl-2,2-bis-propylcarbamoyl-ethyl ester, {3-methylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 3,3-bis-ethylcarbamoyl-3-phenyl-propyl ester, 2-(2-{3-dimethylcarbamoyl-4-[(4'-trifluoromethyl-biphenyl-2-carbonyl)-amino]-phenyl}-acetoxymethyl)-2-phenyl-malonic acid diethyl ester, {3-benzylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 4,4-bis-ethylcarbamoyl-4-phenyl-butyl ester, {3-diethylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-diisopropylcarbamoyl-4-[(4'-trifluoromethyl-biphenyl-2-carbonyl)-amino]-phenyl}-acetic acid 2,2-bis-ethylcarbamoyl-2-phenyl-ethyl ester, 2-(2-{3-diethylcarbamoyl-4-[(4'-trifluoromethyl-biphenyl-2-carbonyl)-amino]-phenyl}-acetoxymethyl)-2-phenyl-malonic acid diethyl ester, 2-(2-{3-diisopropylcarbamoyl-4-[(4'-trifluoromethyl-biphenyl-2-carbonyl)-amino]-phenyl}-acetoxymethyl)-2-phenyl-malonic acid diethyl ester, {3-(isopropyl-methyl-carbamoyl)-4-[(4'-trifluoromethyl-biphenyl-2-carbonyl)-amino]-phenyl}-acetic acid 2,2-bis-ethylcarbamoyl-2-phenyl-ethyl ester, 2-(2-{3-(ethyl-methyl-carbamoyl)-4-[(4'-trifluoromethyl-biphenyl-2-carbonyl)-amino]-phenyl}-acetoxymethyl)-2-phenyl-malonic acid diethyl ester, {3-(ethyl-methyl-carbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(ethyl-methyl-carbamoyl)-4-[(4'-trifluoromethyl-biphenyl-2-carbonyl)-amino]-phenyl}-acetic acid 3,3-bis-ethylcarbamoyl-3-phenyl-propyl ester, {3-(piperidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(pyrrolidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(pyrrolidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propyl-carbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propyl-carbamoyl)-4-[(4'-trifluoromethyl-biphenyl-2-carbonyl)-amino]-phenyl}-acetic acid 3,3-bis-ethylcarbamoyl-3-phenyl-propyl ester, {3-dimethylcarbamoyl-4-[(4'-trifluoromethyl-biphenyl-2-carbonyl)-amino]-phenyl}-acetic acid 2-ethylcarbamoyl-2-phenyl-ethyl ester, 2-phenyl-2-(2-{3-(pyrrolidine-1-carbonyl)-4-[(4'-trifluoromethyl-biphenyl-2-carbonyl)-amino]-phenyl}-acetoxymethyl)-malonic acid diethyl ester, 2-phenyl-2-(2-{3-(piperidine-1-carbonyl)-4-[(4'-trifluoromethyl-biphenyl-2-carbonyl)-amino]-phenyl}-acetoxymethyl)-malonic acid diethyl ester, {3-dimethylcarbamoyl-4-[(4'-trifluoromethyl-biphenyl-2-carbonyl)-amino]-phenyl}-acetic acid 2-phenyl-2-propionylamino-ethyl ester, {3-dimethylcarbamoyl-4-[(4'-trifluoromethyl-biphenyl-2-carbonyl)-amino]-phenyl}-acetic acid 2-phenyl-2-propionylamino-ethyl ester, {3-dimethylcarbamoyl-4-[(4'-trifluoromethyl-biphenyl-2-carbonyl)-amino]-phenyl}-acetic acid 2-(2,5-dioxo-pyrrolidin-1-yl)-2-phenyl-ethyl ester, {3-dimethylcarbamoyl-4-[(4'-trifluoromethyl-biphenyl-2-carbonyl)-amino]-phenyl}-acetic acid 2-ethylcarbamoyl-benzyl ester, {3-dimethylcarbamoyl-4-[(4'-trifluoromethyl-biphenyl-2-carbonyl)-amino]-phenyl}-acetic acid 2-ethylcarbamoylmethyl-benzyl ester, {3-dimethylcarbamoyl-4-[(4'-trifluoromethyl-biphenyl-2-carbonyl)-amino]-phenyl}-acetic acid 2-isopropylamino-2-phenyl-ethyl ester hydrochloride,

[3-dimethylcarbamoyl-4-(2-trifluoromethyl-benzoylamino)-phenyl]-acetic acid 2,2-bis-ethylcarbamoyl-2-phenyl-ethyl ester, 2-{2-[3-dimethylcarbamoyl-4-(2-trifluoromethyl-benzoylamino)-phenyl]-acetoxymethyl}-2-phenyl-malonic acid diethyl ester, 2-[2-(2-{3-dimethylcarbamoyl-4-[(4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(4'-fluoro-biphenyl-2-carbonyl)-amino]-phenyl}-acetoxymethyl)-2-phenyl-malonic acid diethyl ester, 2-(2-{4-[(4'-bromo-biphenyl-2-carbonyl)-amino-3-dimethylcarbamoyl-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-acetylamino-2-phenyl-ethyl ester, {3-dimethylcarbamoyl-4-[(4'-trifluoromethyl-biphenyl-2-carbonyl)-amino]-phenyl}-acetic acid-2-butyrylamino-2-phenyl-ethyl ester,

[4-(2-benzoyl-benzoylamino)-3-dimethylcarbamoyl-phenyl]-acetic acid 2,2-bis-ethylcarbamoyl-2-phenyl-ethyl ester,
2-{2-[4-(2-benzoyl-benzoylamino)-3-dimethylcarbamoyl-phenyl]-acetoxymethyl}-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-malonic acid dimethyl ester,
2-cyclopentyl-2-(2-{3-dimethylcarbamoyl-4-[(4'-trifluoromethyl-biphenyl-2-carbonyl)-amino]-phenyl}-acetoxymethyl)-malonic acid diethyl ester,
2-cyclohexyl-2-(2-{3-dimethylcarbamoyl-4-[(4'-trifluoromethyl-biphenyl-2-carbonyl)-amino]-phenyl}-acetoxymethyl)-malonic acid diethyl ester,
2-(2-{4-[(4'-chloro-biphenyl-2-carbonyl)-amino]-3-dimethylcarbamoyl-phenyl}-acetoxymethyl)-2-phenyl-malonic acid diethyl ester,
2-(2-{4-[(4'-acetyl-biphenyl-2-carbonyl)-amino]-3-dimethylcarbamoyl-phenyl}-acetoxymethyl)-2-phenyl-malonic acid diethyl ester,
[3-dimethylcarbamoyl-4-(2-phenoxy-benzoylamino)-phenyl]-acetic acid 2,2-bis-ethylcarbamoyl-2-phenyl-ethyl ester,
2-{2-[3-dimethylcarbamoyl-4-(2-phenoxy-benzoylamino)-phenyl]-acetoxymethyl}-2-phenyl-malonic acid diethyl ester,
2-(2-{4-[(4'-cyano-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(4-methyl-4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(5-methyl-4'-trifluoromethyl-biphenyl-2-carbonyl)-amino]-phenyl}-acetoxymethyl)-2-phenyl-malonic acid diethyl ester,
{3-dimethylcarbamoyl-4-[(4'-trifluoromethyl-biphenyl-2-carbonyl)-amino]-phenyl}-acetic acid 2-methanesulfonylamino-2-phenyl-ethyl ester,
3-(2-{3-dimethylcarbamoyl-4-[(4'-trifluoromethyl-biphenyl-2-carbonyl)-amino]-phenyl}-acetoxy)-2-phenyl-propionic acid ethyl ester,
{3-dimethylcarbamoyl-4-[(4'-trifluoromethyl-biphenyl-2-carbonyl)-amino]-phenyl}-acetic acid 2-(methyl-propionyl-amino)-2-phenyl-ethyl ester,
2-[3-(2-{3-dimethylcarbamoyl-4-[(4'-trifluoromethyl-biphenyl-2-carbonyl)-amino]-phenyl}-acetoxy)-propyl]-2-phenyl-malonic acid diethyl ester,
2-(2-{3-dimethylcarbamoyl-4-[(5-methoxy-4'-trifluoromethyl-biphenyl-2-carbonyl)-amino]-phenyl}-acetoxymethyl)-2-phenyl-malonic acid diethyl ester,
2-(2-{4-[(5-chloro-4'-trifluoromethyl-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(6-methyl-4'-trifluoromethyl-biphenyl-2-carbonyl)-amino]-phenyl}-acetoxymethyl)-2-phenyl-malonic acid diethyl ester)
2-(2-{3-dimethylcarbamoyl-4-[(4'-trifluoromethyl-biphenyl-2-carbonyl)-amino]-phenyl}-acetoxymethyl)-2-phenyl-malonic acid di-2,2,2-trifluoroethyl ester,
2-(2-{3-dimethylcarbamoyl-4-[(2'-fluoro-4'-trifluoromethyl-biphenyl-2-carbonyl)-amino]-phenyl}-acetoxymethyl)-2-phenyl-malonic acid diethyl ester,
2-(2-{5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester,
2-(2-{3-bromo-5-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{3-chloro-5-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(3'-fluoro-4'-trifluoromethyl-biphenyl-2-carbonyl)-amino]-phenyl}-acetoxymethyl)-2-phenyl-malonic acid diethyl ester,
2-(2-{4-[(3'-chloro-4'-trifluoromethyl-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-(5-nitro-pyridin-2-yl)-malonic acid diethyl ester,
2-(5-amino-pyridin-2-yl)-2-(2-{3-dimethylcarbamoyl-4-[(4'-trifluoromethyl-biphenyl-2-carbonyl)-amino]-phenyl}-acetoxymethyl)-malonic acid diethyl ester,
2-(2-{3-dimethylcarbamoyl-4-[(4'-trifluoromethyl-biphenyl-2-carbonyl)-amino]-phenyl}-acetoxymethyl)-2-pyridin-2-yl-malonic acid diethyl ester,
2-(2-{3-chloro-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester,
2-(2-{3-bromo-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-o-tolyl-malonic acid diethyl ester,
2-(2-{3-dimethylcarbamoyl-4-[(4'-trifluoromethyl-biphenyl-2-carbonyl)-amino]-phenyl}-acetoxymethyl)-2-m-tolyl-malonic acid diethyl ester,
2-(2-{3-dimethylcarbamoyl-4-[(4'-trifluoromethyl-biphenyl-2-carbonyl)-amino]-phenyl}-acetoxymethyl)-2-p-tolyl-malonic acid diethyl ester,
2-(2-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester,
2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester,
2-(4-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-succinic acid diethyl ester,
2-(2-{3-dimethylcarbamoyl-4-[(4'-trifluoromethyl-biphenyl-2-carbonyl)-amino]-phenyl}-acetoxymethyl)-2-(2-methoxy-phenyl)-malonic acid diethyl ester,
2-(2-{3-dimethylcarbamoyl-4-[(4'-trifluoromethyl-biphenyl-2-carbonyl)-amino]-phenyl}-acetoxymethyl)-2-(3-methoxy-phenyl)-malonic acid diethyl ester,
2-(2-{3-dimethylcarbamoyl-4-[(4'-trifluoromethyl-biphenyl-2-carbonyl)-amino]-phenyl}-acetoxymethyl)-2-(4-methoxy-phenyl)-malonic acid diethyl ester,
2-(2-{4-[(5,4'-bis-trifluoromethyl-biphenyl-2-carbonyl)-amino]-3-dimethylcarbamoyl-phenyl}-acetoxymethyl)-2-phenyl-malonic acid diethyl ester,
2-(2-{4-[(6-chloro-4'-trifluoromethyl-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(6-fluoro-4'-trifluoromethyl-biphenyl-2-carbonyl)-amino]-phenyl}-acetoxymethyl)-2-phenyl-malonic acid diethyl ester, 2-[2-(2-{3-dimethylcarbamoyl-4-[(5-methyl-4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(5-ethoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-isopropoxy-4'-trifluoromethyl-biphenyl-2-carbonyl)-amino]-phenyl}-acetoxymethyl)-2-phenyl-malonic acid diethyl ester, 2-[2-(2-{4-[(5,4'-bis-trifluoromethyl-biphenyl-2-carbonyl)-amino]-3-dimethylcarbamoyl-phenyl}-acetoxy)-ethyl]-2-phenyl-malonic acid diethyl ester, 2-(2-{3-dimethylcarbamoyl-4-[(6-methoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3-methyl-4'-trifluoromethyl-biphenyl-2-carbonyl)-amino]-phenyl}-acetoxymethyl)-2-phenyl-malonic acid diethyl ester, 2-{2-[4-(2,4-bis-trifluoromethyl-benzoylamino)-3-dimethylcarbamoyl-phenyl]-acetoxymethyl}-2-phenyl-malonic acid diethyl ester, 2-(2-{3-dimethylcarbamoyl-4-[(4'-methyl-biphenyl-2-carbonyl)-amino]-phenyl}-acetoxymethyl)-2-phenyl-malonic acid diethyl ester, 2-ethyl-4-trifluoromethyl-benzoylamino)-phenyl-acetoxymethyl -2-phenyl-malonic acid diethyl ester, 2-(2-{3-dimethylcarbamoyl-4-[(4'-ethyl-biphenyl-2-carbonyl)-amino]-phenyl}-acetoxymethyl)-2-phenyl-malonic acid diethyl ester, 2-(2-{3-dimethylcarbamoyl-4-[(4'-isopropenyl-biphenyl-2-carbonyl)-amino]-phenyl}-acetoxymethyl)-2-phenyl-malonic acid diethyl ester, 2-(2-{3-dimethylcarbamoyl-4-[(4'-isopropyl-biphenyl-2-carbonyl)-amino]-phenyl}-acetoxymethyl)-2-phenyl-malonic acid diethyl ester, 2-{2-[3-dimethylcarbamoyl-4-(2-isopropenyl-4-trifluoromethyl-benzoylamino)-phenyl]-acetoxymethyl}-2-phenyl-malonic acid diethyl ester, 2-{2-[3-dimethylcarbamoyl-4-(2-isopropyl-4-trifluoromethyl-benzoylamino)-phenyl]-acetoxymethyl}-2-phenyl-malonic acid diethyl ester, 2-(2-{3-dimethylcarbamoyl-4-[2-(3-trifluoromethyl-phenylamino)-benzoylamino]-phenyl}-acetoxymethyl)-2-phenyl-malonic acid diethyl ester, 2-{2-[3-dimethylcarbamoyl-4-(4'-trifluoromethyl-biphenyl-2-carbonyloxy)-phenyl]-acetoxymethyl}-2-phenyl-malonic acid diethyl ester, 2-(2-{3-dimethylcarbamoyl-4-[2-(3-trifluoromethyl-phenoxy)-benzoylamino]-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-ethyl-2-phenyl-butyl ester, 2-(2-{3-dimethylcarbamoyl-4-[2-(4-trifluoromethyl-phenoxy)-benzoylamino]-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 1-phenyl-cyclopropylmethyl ester, {3-dimethylcarbamoyl-4-[(4'-trifluoromethyl-biphenyl-2-carbonyl)-amino]-phenyl}-acetic acid 2,2-diphenyl-ethyl ester, {3-dimethylcarbamoyl-4-[(4'-trifluoromethyl-biphenyl-2-carbonyl)-amino]-phenyl}-acetic acid 1-phenyl-cyclopentylmethyl ester, {3-dimethylcarbamoyl-4-[(4'-trifluoromethyl-biphenyl-2-carbonyl)-amino]-phenyl}-acetic acid 3-hydroxy-2-hydroxymethyl-2-phenyl-propyl ester, {3-dimethylcarbamoyl-4-[(4'-trifluoromethyl-biphenyl-2-carbonyl)-amino]-phenyl}-acetic acid 3-acetoxy-2-acetoxymethyl-2-phenyl-propyl ester, 2-(2-{3-dimethylcarbamoyl-4-[(4'-trifluoromethyl-biphenyl-2-carbonyl)-amino]-phenyl}-acetoxymethyl)-2-thiophen-2-yl-malonic acid diethyl ester, 2-(2-{3-dimethylcarbamoyl-4-[(4'-trifluoromethyl-biphenyl-2-carbonyl)-amino]-phenyl}-acetoxymethyl)-2-thiophen-3-yl-malonic acid diethyl ester, 2-(2-{4-dimethylcarbamoyl-5-[(4'-trifluoromethyl-biphenyl-2-carbonyl)-amino]-pyridin-2-yl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-thiazol-2-yl-malonic acid diethyl ester, 2-(2-{3-dimethylcarbamoyl-4-[(4'-trifluoromethyl-biphenyl-2-carbonyl)-amino]-phenyl}-acetoxymethyl)-2-isopropyl-malonic acid diethyl ester, 2-sec-butyl-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-isobutyl-malonic acid diethyl ester, 2-(2-{3-dimethylcarbamoyl-4-[(4'-trifluoromethyl-biphenyl-2-carbonyl)-amino]-phenyl}-acetoxymethyl)-2-propyl-malonic acid diethyl ester, 2-(2-{3-dimethylcarbamoyl-4-[(4'-trifluoromethyl-biphenyl-2-carbonyl)-amino]-phenyl}-acetoxymethyl)-2-ethyl-malonic acid diethyl ester, 2-butyl-2-(2-{3-dimethylcarbamoyl-4-[(4'-trifluoromethyl-biphenyl-2-carbonyl)-amino]-phenyl}-acetoxymethyl)-malonic acid diethyl ester, 2-allyl-2-(2-{3-dimethylcarbamoyl-4-[(4'-trifluoromethyl-biphenyl-2-carbonyl)-amino]-phenyl}-acetoxymethyl)-malonic acid diethyl ester, 3-(2-{3-dimethylcarbamoyl-4-[(4'-trifluoromethyl-biphenyl-2-carbonyl)-amino]-phenyl}-acetoxy)-2,2-bis-ethoxycarbonyl-propionic acid ethyl ester, 2-(2-{3-dimethylcarbamoyl-4-[(4'-trifluoromethyl-biphenyl-2-carbonyl)-amino]-phenyl}-acetoxymethyl)-2-(1-methyl-butyl)-malonic acid diethyl ester, 2-(2-{3-ethoxy-4-[(4'-trifluoromethyl-biphenyl-2-carbonyl)-amino]-phenyl}-acetoxymethyl)-2-phenyl-malonic acid diethyl ester, {3-hydroxy-4-[(4'-trifluoromethyl-biphenyl-2-carbonyl)-amino]-phenyl}-acetic acid 2,2-bis-ethylcarbamoyl-2-phenyl-ethyl ester, {3-methoxy-4-[(4'-trifluoromethyl-biphenyl-2-carbonyl)-amino)-phenyl}-acetic acid 2,2-bis-ethylcarbamoyl-2-phenyl-ethyl ester, 2-(2-{3-methoxy-4-[(4'-trifluoromethyl-biphenyl-2-carbonyl)-amino]-phenyl}-acetoxymethyl)-2-phenyl-malonic acid diethyl ester, {3-methoxy-4-[(4'-trifluoromethyl-biphenyl-2-carbonyl)-amino]-phenyl}-acetic acid 2-phenyl-2,2-bis-propylcarbamoyl-ethyl ester, {3-methoxy-4-[(4'-trifluoromethyl-biphenyl-2-carbonyl)-amino]-phenyl}-acetic acid 3,3-bis-ethylcarbamoyl-3-phenyl-propyl ester, {3-ethoxy-4-[(4'-trifluoromethyl-biphenyl-2-carbonyl)-amino]-phenyl}-acetic acid 2,2-bis-ethylcarbamoyl-2-phenyl-ethyl ester, {3-ethoxy-4-[(4'-trifluoromethyl-biphenyl-2-carbonyl)-amino]-phenyl}-acetic acid 3,3-bis-ethylcarbamoyl-3-phenyl-propyl ester, 2-(2-{3-isopropoxy-4-[(4'-trifluoromethyl-biphenyl-2-carbonyl)-amino]-phenyl}-acetoxymethyl)-2-phenyl-malonic acid diethyl ester, {3-isopropoxy-4-[(4'-trifluoromethyl-biphenyl-2-carbonyl)-amino]-phenyl}-acetic acid 2,2-bis-ethylcarbamoyl-2-phenyl-ethyl ester, {3-isopropoxy-4-[(4'-trifluoromethyl-biphenyl-2-carbonyl)-amino]-phenyl}-acetic acid 3,3-bis-ethylcarbamoyl-3-phenyl-propyl ester, {3-propoxy-4-[(4'-trifluoromethyl-biphenyl-2-carbonyl)-amino]-phenyl}-acetic acid 2,2-bis-ethylcarbamoyl-2-phenyl-ethyl ester, {3-benzyloxy-4-[(4'-trifluoromethyl-biphenyl-2-carbonyl)-amino]-phenyl}-acetic acid 2,2-bis-ethylcarbamoyl-2-phenyl-ethyl ester, 2-(2-{3-benzyloxy-4-[(4'-trifluoromethyl-biphenyl-2-carbonyl)-amino]-phenyl}-acetoxymethyl)-2-phenyl-malonic acid diethyl ester, 2-(2-{3-hydroxy-4-[(4'-trifluoromethyl-biphenyl-2-carbonyl)-amino]-phenyl}-acetoxymethyl)-2-phenyl-malonic acid diethyl ester, 2-{2-[3-methoxy-4-(4'-trifluoromethyl-biphenyl-2-carbonyloxy)-phenyl]-acetoxymethyl}-2-phenyl-malonic acid diethyl ester, {3-dimethylamino-4-[(4'-trifluoromethyl-biphenyl-2-carbonyl)-amino]-phenyl}-acetic acid 2,2-bis-ethylcarbamoyl-2-phenyl-ethyl ester, {3-piperidin-1-yl-4-[(4'-trifluoromethyl-biphenyl-2-carbonyl)-amino]-phenyl}-acetic acid 2,2-bis-ethylcarbamoyl-2-phenyl-ethyl ester, {3-pyrrolidin-1-yl-4-[(4'-trifluoromethyl-biphenyl-2-carbonyl)-amino]-phenyl}-acetic acid 2,2-bis-ethylcarbamoyl-2-phenyl-ethyl ester, 2-phenyl-2-(2-{3-piperidin-1-yl-4-[(4'-trifluoromethyl-biphenyl-2-carbonyl)-amino]-phenyl}-acetoxymethyl)-malonic acid diethyl ester, 2-phenyl-2-(2-{3-pyrrolidin-1-yl-4-[(4'-trifluoromethyl-biphenyl-2-carbonyl)-amino]-phenyl}-acetoxymethyl)-malonic acid diethyl ester, 2-(2-{3-dimethylamino-4-[(4'-trifluoromethyl-biphenyl-2-carbonyl)-amino]-phenyl}-acetoxymethyl)-2-phenyl-malonic acid diethyl ester, 2-(2-{3-morpholin-4-yl-4-[(4'-trifluoromethyl-biphenyl-2-carbonyl)-amino]-phenyl}-acetoxymethyl)-2-phenyl-malonic acid diethyl ester, 2-(2-{3-diethylamino-4-[(4'-trifluoromethyl-biphenyl-2-carbonyl)-amino]-phenyl}-acetoxymethyl)-2-phenyl-malonic acid diethyl ester, 2-[2-(2-{2-methyl-3-[(4'-trifluoromethyl-biphenyl-2-carbonyl)-amino]-phenyl}-acetoxy)-ethyl]-2-phenyl-malonic acid diethyl ester, 2-phenyl-2-(2-{3-[(4'-trifluoromethyl-biphenyl-2-carbonyl)-amino]-phenyl}-acetoxymethyl)-malonic acid diethyl ester, 2-phenyl-2-[2-(2-{3-[(4'-trifluoromethyl-biphenyl-2-carbonyl)-amino]-phenyl}-acetoxy)-ethyl]-malonic acid diethyl ester, {3-[(4'-trifluoromethyl-biphenyl-2-carbonyl)-amino]-phenyl}-acetic acid 3,3-bis-ethylcarbamoyl-3-phenyl-propyl ester, {3-[(4'-trifluoromethyl-biphenyl-2-carbonyl)-amino]-phenyl}-acetic acid 3-phenyl-3,3-bis-propylcarbamoyl-propyl ester, 2-[2-(2-{4-methyl-3-[(4'-trifluoromethyl-biphenyl-2-carbonyl)-amino]-phenyl}-acetoxy)-ethyl]-2-phenyl-malonic acid diethyl ester, 2-[2-(2-{2-methyl-5-[(4'-trifluoromethyl-biphenyl-2-carbonyl)-amino]-phenyl}-acetoxy)-ethyl]-2-phenyl-malonic acid diethyl ester, {3-[(4'-trifluoromethyl-biphenyl-2-carbonyl)-amino]-phenyl}-acetic acid 3,3-bis-isopropylcarbamoyl-3-phenyl-propyl ester, {2-methyl-3-[(4'-trifluoromethyl-biphenyl-2-carbonyl)-amino]-phenyl}-acetic acid 3,3-bis-ethylcarbamoyl-3-phenyl-propyl ester, {2-methyl-3-[(4'-trifluoromethyl-biphenyl-2-carbonyl)-amino]-phenyl}-acetic acid 4,4-bis-ethylcarbamoyl-4-phenyl-butyl ester, {2-methyl-3-[(4'-trifluoromethyl-biphenyl-2-carbonyl)-amino]-phenyl}-acetic acid 3-phenyl-3,3-bis-propylcarbamoyl-propyl ester, {2-methoxy-3-[(4'-trifluoromethyl-biphenyl-2-carbonyl)-amino]-phenyl}-acetic acid 3,3-bis-ethylcarbamoyl-3-phenyl-propyl ester, 2-[2-(2-{2-methoxy-3-[(4'-trifluoromethyl-biphenyl-2-carbonyl)-amino]-phenyl}-acetoxy)-ethyl]-2-phenyl-malonic acid diethyl ester, {2-ethoxy-3-[(4'-trifluoromethyl-biphenyl-2-carbonyl)-amino]-phenyl}-acetic acid 3,3-bis-ethylcarbamoyl-3-phenyl-propyl ester, 2-[2-(2-{2-ethoxy-3-[(4'-trifluoromethyl-biphenyl-2-carbonyl)-amino]-phenyl}-acetoxy)-ethyl]-2-phenyl-malonic acid diethyl ester, 2-[2-(2-{2-isopropoxy-3-[(4'-trifluoromethyl-biphenyl-2-carbonyl)-amino]-phenyl}-acetoxy)-ethyl]-2-phenyl-malonic acid diethyl ester, 2-[2-(2-{2-methoxycarbonyl-3-[(4'-trifluoromethyl-biphenyl-2-carbonyl)-amino]-phenyl}-acetoxy)-ethyl]-2-phenyl-malonic acid diethyl ester, 2-[2-(2-{2-ethoxy-5-methyl-3-[(4'-trifluoromethyl-biphenyl-2-carbonyl)-amino]-phenyl}-acetoxy)-ethyl]-2-phenyl-malonic acid diethyl ester, 4-[(4'-trifluoromethyl-biphenyl-2-carbonyl)-amino]-benzoic acid 2-[9-(2,2,2-trifluoro-ethylcarbamoyl)-9h-fluoren-9-yl]-ethyl ester, 4-[(4'-trifluoromethyl-biphenyl-2-carbonyl)-amino]-benzoic acid 2-(9h-fluoren-9-yl)-ethyl ester, n-biphenyl-2-yl-terephthalamic acid 2-[9-(2,2,2-trifluoro-ethylcarbamoyl)-9h-fluoren-9-yl]-ethyl ester, 4-[(4'-trifluoromethyl-biphenyl-2-carbonyl)-amino]-benzoic acid 2-[(biphenyl-2-carbonyl)-amino]-ethyl ester, 4-[(4'-trifluoromethyl-biphenyl-2-carbonyl)-amino]-benzoic acid 2-(2-biphenyl-2-yl-acetylamino)-ethyl ester, 4-[(4'-trifluoromethyl-biphenyl-2-carbonyl)-amino]-benzoic acid 3-naphthalen-1-yl-3-(2,2,2-trifluoro-ethylcarbamoyl)-propyl ester, 4-[(4'-trifluoromethyl-biphenyl-2-carbonyl)-amino]-benzoic acid 3-[2-(2,2,2-trifluoro-ethylcarbamoyl)-naphthalen-1-yl]-propyl ester, 4-[(4'-trifluoromethyl-biphenyl-2-carbonyl)-amino]-benzoic acid 3,3-diphenyl-3-(2,2,2-trifluoro-ethylcarbamoyl)-propyl ester, 4-[(4'-trifluoromethyl-biphenyl-2-carbonyl)-amino]-benzoic acid 3-biphenyl-2-yl-3-(2,2,2-trifluoro-ethylcarbamoyl)-propyl ester, 4-[(4'-trifluoromethyl-biphenyl-2-carbonyl)-amino]-benzoic acid 3-phenyl-3-(2,2,2-trifluoro-ethylcarbamoyl)-propyl ester, 4-[(4'-trifluoromethyl-biphenyl-2-carbonyl)-amino]-benzoic acid 2-[8-(2,2,2-trifluoro-ethylcarbamoyl)-naphthalen-1-yl]-ethyl ester, 4-[(4'-trifluoromethyl-biphenyl-2-carbonyl)-amino]-benzoic acid 3-(2,6-dichloro-phenyl)-3-(2,2,2-trifluoro-ethylcarbamoyl)-propyl ester, 4-[(4'-trifluoromethyl-biphenyl-2-carbonyl)-amino]-benzoic acid 3-(2-chloro-phenyl)-3-(2,2,2-trifluoro-ethylcarbamoyl)-propyl ester, 2-phenyl-2-(2-{4-[(4'-trifluoromethyl-biphenyl-2-carbonyl)-amino]-benzoyloxy}-ethyl)-malonic acid diethyl ester, 2-(2-{3-methyl-4-[(4'-trifluoromethyl-biphenyl-2-carbonyl)-amino]-benzoyloxy}-ethyl)-2-phenyl-malonic acid diethyl ester, 2-(2-{2-chloro-4-[(4'-trifluoromethyl-biphenyl-2-carbonyl)-amino]-benzoyloxy}-ethyl)-2-phenyl-malonic acid diethyl ester, 2-phenyl-2-{2-[4-(4'-trifluoromethyl-biphenyl-2-carbonyloxy)-benzoyloxy]-ethyl}-malonic acid diethyl ester, 2-{2-[4-(2-benzoyl-benzoyloxy)-benzoyloxy]-ethyl}-2-phenyl-malonic acid diethyl ester, 4-[(4'-trifluoromethyl-biphenyl-2-carbonyl)-amino]-benzoic acid 3,3-bis-ethylcarbamoyl-3-phenyl-propyl ester, 4'-trifluoromethyl-biphenyl-2-carboxylic acid 4-(3,3-bis-ethylcarbamoyl-3-phenyl-propoxycarbonyl)-2-chloro-phenyl ester, 4'-trifluoromethyl-biphenyl-2-carboxylic acid 4-(3,3-bis-ethylcarbamoyl-3-phenyl-propoxycarbonyl)-phenyl ester, 4'-trifluoromethyl-biphenyl-2-carboxylic acid 4-(3,3-bis-ethylcarbamoyl-3-phenyl-propoxycarbonyl)-2,6-dichloro-phenyl ester, 4-methyl-4-[(4'-trifluoromethyl-biphenyl-2-carbonyl)-amino]-cyclohexanecarboxylic acid 2-[9-(2,2,2-trifluoro-ethylcarbamoyl)-9h-fluoren-9-yl]-ethyl ester, 4-[(4'-trifluoromethyl-biphenyl-2-carbonyl)-amino]-cyclohexanecarboxylic acid 2-[9-(2,2,2-trifluoro-ethylcarbamoyl)-9h-fluoren-9-yl]-ethyl ester, 4-[(4'-trifluoromethyl-biphenyl-2-carbonyl)-amino]-cyclohexanecarboxylic acid 3-phenyl-3-(2,2,2-trifluoro-ethylcarbamoyl)-propyl ester, 2-phenyl-2-{4-[(4'-trifluoromethyl-biphenyl-2-carbonyl)-amino]-cyclohexanecarbonyloxymethyl}-malonic acid diethyl ester, 2-phenyl-2-(2-{4-[(4'-trifluoromethyl-biphenyl-2-carbonyl)-amino-cyclohexanecarbonyloxy}-ethyl)-malonic acid diethyl ester, 2-phenyl-2-(2-{4-[(4'-trifluoromethyl-biphenyl-2-carbonyl)-amino]-piperidin-1-yl}-acetoxymethyl)-malonic acid diethyl ester, 2-phenyl-2-{2-(4-[(4'-trifluoromethyl-biphenyl-2-carbonyl)-amino]-indol-1-yl}-acetoxymethyl)-malonic acid diethyl ester, 2-(2-{2-methyl-4-[(4'-trifluoromethyl-biphenyl-2-carbonyl)-amino]-benzoimidazol-1-yl}-acetoxymethyl)-2-phenyl-malonic acid diethyl ester,

[2-oxo-3-(4'-trifluoromethyl-biphenyl-2-carbonyl)-2,3-dihydro-benzooxazol-6-yl]-acetic acid 2,2-bis-ethylcarbamoyl-2-phenyl-ethyl ester, 2-{2-(3-ethoxycarbonyl-4-[(4'-trifluoromethyl-biphenyl-2-carbonyl)-amino]-phenyl}-acetoxymethyl)-2-phenyl-malonic acid diethyl ester, 2-(3-{3-dimethylcarbamoyl-4-[(4'-trifluoromethyl-biphenyl-2-carbonyl)-amino]-phenyl}-propionyloxymethyl)-2-phenyl-malonic acid diethyl ester, 4-{[(4'-trifluoromethyl-biphenyl-2-carbonyl)-amino]-methyl}-benzoic acid 2,2-bis-ethylcarbamoyl-2-phenyl-ethyl ester, 3-{4-[(4'-trifluoromethyl-biphenyl-2-carbonyl)-amino]-phenyl}-propionic acid ethylcarbamoyl-phenyl-methyl ester, 5-(2,2-bis-ethylcarbamoyl-2-phenyl-ethoxycarbonyl-methyl)-2-[(4'-trifluoromethyl-biphenyl-2-carbonyl)-amino]-benzoic acid benzyl ester, 5-(2,2-bis-ethylcarbamoyl-2-phenyl-ethoxycarbonyl-methyl)-2-[(4'-trifluoromethyl-biphenyl-2-carbonyl)-amino]-benzoic acid, 5-(2,2-bis-ethylcarbamoyl-2-phenyl-ethoxycarbonyl-methyl)-2-[(4'-trifluoromethyl-biphenyl-2-carbonyl)-amino]-benzoic acid ethyl ester, 2-phenyl-2-(2-{4-[(4'-trifluoromethyl-biphenyl-2-carbonyl)-amino]-benzoimidazol-1-yl}-acetoxymethyl)-malonic acid diethyl ester, 3-([(4'-trifluoromethyl-biphenyl-2-carbonyl)-amino]-methyl)-benzoic acid 3,3-bis-ethylcarbamoyl-3-phenyl-propyl ester, 5-(2,2-bis-ethylcarbamoyl-2-phenyl-ethoxycarbonyl-methyl)-2-[(4'-trifluoromethyl-biphenyl-2-carbonyl)-amino]-benzoic acid methyl ester, 2-(2-{3-benzyloxycarbonyl-4-[(4'-trifluoromethyl-biphenyl-2-carbonyl)-amino]-phenyl}-acetoxymethyl)-2-phenyl-malonic acid diethyl ester, 2-(2-{3-carboxy-4-[(4'-trifluoromethyl-biphenyl-2-carbonyl)-amino]-phenyl}-acetoxymethyl)-2-phenyl-malonic acid diethyl ester, 2-{2-[2-oxo-3-(4'-trifluoromethyl-biphenyl-2-carbonyl)-2,3-dihydro-benzooxazol-6-yl]-acetoxymethyl}-2-phenyl-malonic acid diethyl ester, 2-{2-[8-oxo-7-(4'-trifluoromethyl-biphenyl-2-carbonyl)-7-aza-bicyclo[4.2.0]octa-[(6),2,4-trien-3-yl]-acetoxymethyl}-2-phenyl-malonic acid diethyl ester, 2-(2-{3-isopropoxycarbonyl-4-[(4'-trifluoromethyl-biphenyl-2-carbonyl)-amino]-phenyl}-acetoxymethyl)-2-phenyl-malonic acid diethyl ester, 2-(2-{3-methoxycarbonyl-4-[(4'-trifluoromethyl-biphenyl-2-carbonyl)-amino]-phenyl}-acetoxymethyl)-2-phenyl-malonic acid diethyl ester, 2-[2-(3-dimethylcarbamoyl-4-{[1-(2-nitrol-4-trifluoro-methyl-phenyl)-pyrrolidine-2-carbonyl]-amino}-phenyl)-acetoxymethyl]-2-phenyl-malonic acid diethyl ester, 2-(2-{3-acetylamino-4-[(4'-trifluoromethyl-biphenyl-2-carbonyl)-amino]-phenyl}-acetoxymethyl)-2-phenyl-malonic acid diethyl ester, 2-(2-{3-methoxycarbonylamino-4-[(4'-trifluoromethyl-biphenyl-2-carbonyl)-amino]-phenyl}-acetoxymethyl)-2-phenyl-malonic acid diethyl ester, 2-(2-{3-(4-methyl-thiazol-2-yl)-4-[(4'-trifluoromethyl-biphenyl-2-carbonyl)-amino]-phenyl}-acetoxymethyl)-2-phenyl-malonic acid diethyl ester, 2-phenyl-2-(2-{6-[(4'-trifluoromethyl-biphenyl-2-carbonyl)-amino]-biphenyl-3-yl}-acetoxymethyl)-malonic acid diethyl ester, 2-(2-{3-formyl-4-[(4'-trifluoromethyl-biphenyl-2-carbonyl)-amino]-phenyl}-acetoxymethyl)-2-phenyl-malonic acid diethyl ester, 2-(2-{3-dimethylaminomethyl-4-[(4'-trifluoromethyl-biphenyl-2-carbonyl)-amino]-phenyl}-acetoxymethyl)-2-phenyl-malonic acid diethyl ester, 2-(2-{3-(methoxy-methyl-carbamoyl)-4-[(4'-trifluoromethyl-biphenyl-2-carbonyl)-amino]-phenyl}-acetoxymethyl)-2-phenyl-malonic acid diethyl ester, 2-(2-{3-isobutyryl-4-[(4'-trifluoromethyl-biphenyl-2-carbonyl)-amino]-phenyl}-acetoxymethyl)-2-phenyl-malonic acid diethyl ester, and 2-(2-{3-(1-hydroxy-2-methyl-propyl)-4-[(4'-trifluoromethyl-biphenyl-2-carbonyl)-amino]-phenyl}-acetoxymethyl)-2-phenyl-malonic acid diethyl ester;

(23) The ester compound or a prodrug thereof, or a pharmaceutically acceptable salt of either according to the above (1), which is selected from the group consisting of 4-[(4'-trifluoromethyl-biphenyl-2-carbonyl)-amino]-phenyl}-acetic acid 2,2-bis-ethylcarbamoyl-2-phenyl-ethyl ester, 2-phenyl-2-{2-[4-[(4'-trifluoromethyl-biphenyl-2-carbonyloxy)-phenyl]-acetoxymethyl}-malonic acid diethyl ester, 2-(2-{3-methyl-4-[(4'-trifluoromethyl-biphenyl-2-carbonyl)-amino]-phenyl}-acetoxymethyl)-2-phenyl-malonic acid diethyl ester, 2-(2-{4-[methyl-(4'-trifluoromethyl-biphenyl-2-carbonyl)-amino]-phenyl}-acetoxymethyl)-2-phenyl-malonic acid diethyl ester, {3-ethyl-4-[(4'-trifluoromethyl-biphenyl-2-carbonyl)-amino]-phenyl}-acetic acid 2,2-bis-ethylcarbamoyl-2-phenyl-ethyl ester, {4-[(4'-trifluoromethyl-biphenyl-2-carbonyl)-amino]-phenyl}-acetic acid 9-(2,2,2-trifluoro-ethylcarbamoyl)-9h-fluoren-9-ylmethyl ester, {4-[(4'-trifluoromethyl-biphenyl-2-carbonyl)-amino]-phenyl}-propionic acid 9-(2,2,2-trifluoro-ethylcarbamoyl)-9h-fluoren-9-ylmethyl ester, {4-[(4'-trifluoromethyl-biphenyl-2-carbonyl)-amino]-phenyl}-acetic acid 2-phenyl-2-(2,2,2-trifluoro-ethylcarbamoyl)-ethyl ester, 2-phenyl-2-(2-{4-[4'-trifluoromethyl-biphenyl-2-carbonyl)-amino]-phenyl}-acetoxymethyl)-malonic acid diethyl ester, 2-phenyl-2-(2-{4-[(4'-trifluoromethyl-biphenyl-2-carbonyl)-amino]-phenyl}-acetoxymethyl)-malonic acid diisopropyl ester, {4-[(4'-trifluoromethyl-biphenyl-2-carbonyl)-amino]-phenyl}-acetic acid 2-phenyl-2,2-bis-(2,2,2-trifluoro-ethylcarbamoyl)-ethyl ester, 2-phenyl-2-(2-{4-[(4'-trifluoromethyl-biphenyl-2-carbonyl)-amino]-phenyl}-acetoxymethyl)-malonic acid dimethyl ester, 2-cyclopentyl-2-(2-{4-[(4'-trifluoromethyl-biphenyl-2-carbonyl)-amino]-phenyl}-acetoxymethyl)-malonic acid diethyl ester, 2-phenyl-2-(2-{4-[(4'-trifluoromethyl-biphenyl-2-carbonyl)-amino]-phenyl}-acetoxymethyl)-malonic acid dicyclohexyl ester, {4-[(4'-trifluoromethyl-biphenyl-2-carbonyl)-amino]-phenyl}-acetic acid 2,2-bis-cyclohexylcarbamoyl-2-phenyl-ethyl ester, {4-[(4'-trifluoromethyl-biphenyl-2-carbonyl)-amino]-phenyl}-acetic acid 2-phenyl-2,2-bis-phenylcarbamoyl-ethyl ester, {4-[(4'-trifluoromethyl-biphenyl-2-carbonyl)-amino]-phenyl}-acetic acid 2,2-bis-isopropylcarbamoyl-2-phenyl-ethyl ester, 2-benzyl-2-(2-{4-[(4'-trifluoromethyl-biphenyl-2-carbonyl)-amino]-phenyl}-acetoxymethyl-malonic acid diethyl ester, 2-(2-{2-methyl-4-[(4'-trifluoromethyl-biphenyl-2-carbonyl)-amino]-phenyl}-acetoxymethyl)-2-phenyl-malonic acid diethyl ester, 4'-trifluoromethyl-biphenyl-2-carboxylic acid 4-[2-phenyl-2,2-bis-(2,2,2-trifluoro-ethylcarbamoyl)-ethoxycarbonyl-methyl]-phenyl ester, biphenyl-2-carboxylic acid 4-[2-phenyl-2,2-bis-(2,2,2-trifluoro-ethylcarbamoyl)-ethoxycarbonylmethyl]-phenyl ester, 2-cyclohexyl-2-(2-{4-[(4'-trifluoromethyl-biphenyl-2-carbonyl)-amino]-phenyl}-acetoxymethyl)-malonic acid diethyl ester, {4-[(biphenyl-2-carbonyl)-amino]-phenyl}-acetic acid 2-phenyl-2,2-bis-(2,2,2-trifluoro-ethylcarbamoyl)-ethyl ester, 2-phenyl-2-(2-{2-trifluoromethyl-4-[(4'-trifluoromethyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 2,2-bis-methylcarbamoyl-2-phenyl-ethyl ester, 2-pyridin-2-yl-2-(2-{4-[(4'-trifluoromethyl-biphenyl-2-carbonyl)-amino]-phenyl}-acetoxymethyl-malonic acid diethyl ester, 2-pyridin-3-yl-2-(2-{4-[(4'-trifluoromethyl-biphenyl-2-carbonyl)-amino]-phenyl}-acetoxymethyl)-malonic acid diethyl ester, 4'-trifluoromethyl-biphenyl-2-carboxylic acid 4-(2,2-bis-ethylcarbamoyl-2-phenyl-ethoxycarbonylmethyl)-phenyl ester, 2-phenyl-2-(2-{3-trifluoromethyl-4-[(4'-trifluoro-methyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 2,2-bis-butylcarbamoyl-2-phenyl-ethyl ester, {3-methyl-4-[(4'-trifluoromethyl-biphenyl-2-carbonyl)-amino]-phenyl}-acetic acid 2,2-bis-ethylcarbamoyl-2-phenyl-ethyl ester, 2-(2-{4-[(4'-methyl-biphenyl-2-carbonyl}-amino]-phenyl}-acetoxymethyl)-2-phenyl-malonic acid diethyl ester, 2-(2-{4-[(4'-methoxy-biphenyl-2-carbonyl}-amino]-phenyl}-acetoxymethyl)-2-phenyl-malonic acid diethyl ester, {4-[(4'-trifluoromethyl-biphenyl-2-carbonyl}-amino]-phenyl}-acetic acid 3,3-bis-ethylcarbamoyl-3-phenyl-propyl ester, {4-[(4'-trifluoromethyl-biphenyl-2-carbonyl}-amino]-phenyl}-acetic acid 3-phenyl-3,3-bis-propylcarbamoyl-propyl ester, {4-[(biphenyl-2-carbonyl)-amino]-phenyl}-acetic acid 2,2-bis-ethylcarbamoyl-2-phenyl-ethyl ester, 2-phenyl-2-(2-{4-[(3'-trifluoromethyl-biphenyl-2-carbonyl)-amino]-phenyl}-acetoxymethyl)-malonic acid diethyl ester, 4'-trifluoromethyl-biphenyl-2-carboxylic acid 4-(2,2-bis-ethylcarbamoyl-2-phenyl-ethoxycarbonylmethyl)-2-chloro-phenyl ester, 2-(2-{4-[isopropyl-(4'-trifluoromethyl-biphenyl-2-carbonyl}-amino]-phenyl}-acetoxymethyl)-2-phenyl-malonic acid diethyl ester, 2-(2-{4-[cyclohexyl-(4'-trifluoromethyl-biphenyl-2-carbonyl}-amino]-phenyl}-acetoxymethyl)-2-phenyl-malonic acid diethyl ester, 2-phenyl-2-(2-{4-[(4'-trifluoromethyl-biphenyl-2-carbonyl)-amino]-phenyl}-acetoxymethyl)-malonic acid dipropyl ester, 2-phenyl-2-(2-{4-[(4'-trifluoromethyl-biphenyl-2-carbonyl)-amino]-phenyl}-acetoxymethyl)-malonic acid diisobutyl ester, {4-[(4'-trifluoromethyl-biphenyl-2-carbonyl}-amino]-phenyl}-acetic acid 2,2-bis-isobutylcarbamoyl-2-phenyl-ethyl ester, {4-[(4'-trifluoromethyl-biphenyl-2-carbonyl}-amino]-phenyl}-acetic acid 2,2-bis-(3-methyl-butylcarbamoyl-2-phenyl-ethyl ester, 2-(2-{4-[ethyl-(4'-trifluoromethyl-biphenyl-2-carbonyl)-amino]-phenyl}-acetoxymethyl)-2-phenyl-malonic acid diethyl ester, {4-[(4'-chloro-biphenyl-2-carbonyl)-amino]-phenyl}-acetic acid 2,2-bis-(ethylcarbamoyl-2-phenyl-ethyl ester, {4-[(3',4'-dichloro-biphenyl-2-carbonyl)-amino]-phenyl}-acetic acid 2,2-bis-(ethylcarbamoyl-2-phenyl-ethyl ester, {3-methyl-4-[(4'-trifluoromethyl-biphenyl-2-carbonyl}-amino]-phenyl}-acetic acid 2-phenyl-2,2-bis-propylcarbamoyl-ethyl ester, 4-[(4'-trifluoromethyl-biphenyl-2-carbonyl}-amino]-phenyl}-acetic acid 2,2-bis-(2-methoxy-ethylcarbamoyl)-2-phenyl-ethyl ester, 2-(2-{3-ethyl-4-[(4'-trifluoromethyl-biphenyl-2-carbonyl}-amino]-phenyl}-acetoxymethyl)-2-phenyl-malonic acid diethyl ester, {3-isopropyl-4-[(4'-trifluoromethyl-biphenyl-2-carbonyl}-amino]-phenyl}-acetic acid 2,2-bis-ethylcarbamoyl-2-phenyl-ethyl ester, 2-(2-{3-isopropyl-4-[(4'-trifluoromethyl-biphenyl-2-carbonyl)-amino]-phenyl}-acetoxymethyl)-2-phenyl-malonic acid diethyl ester, {3-ethyl-4-[(4'-trifluoromethyl-biphenyl-2-carbonyl)-amino]-phenyl}-acetic acid 3,3-bis-ethylcarbamoyl-3-phenyl-propyl ester, {3-isobutyl-4-[(4'-trifluoromethyl-biphenyl-2-carbonyl)-amino]-phenyl}-acetic acid 2,2-bis-ethylcarbamoyl-2-phenyl-ethyl ester, 2-(2-{3-isobutyl-4-[(4'-trifluoromethyl-biphenyl-2-carbonyl)-amino]-phenyl}-acetoxymethyl)-2-phenyl-malonic acid diethyl ester, 2-(2-{3-chloro-4-[(4'-trifluoromethyl-biphenyl-2-carbonyl)-amino]-phenyl}-acetoxymethyl)-2-phenyl-malonic acid diethyl ester, 2-(2-{3-bromo-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-phenyl-2,2-bis-propylcarbamoyl-ethyl ester, {3-methylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 3,3-bis-ethylcarbamoyl-3-phenyl-ethyl ester, 2-(2-{3-diethylcarbamoyl-4-[(4'-trifluoromethyl-biphenyl-2-carbonyl)-amino]-phenyl}-acetoxymethyl)-2-phenyl-malonic acid diethyl ester, {3-benzylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 4,4'-bis-ethylcarbamoyl-4-phenyl-butyl ester, {3-diethylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-diisopropylcarbamoyl-4-[(4'-trifluoromethyl-biphenyl-2-carbonyl)-amino]-phenyl}-acetic acid 2,2-bis-ethylcarbamoyl-2-phenyl-ethyl ester, 2-(2-{3-diethylcarbamoyl-4-[(4'-trifluoromethyl-biphenyl-2-carbonyl)-amino]-phenyl}-acetoxymethyl)-2-phenyl-malonic acid diethyl ester, 2-(2-{3-diisopropylcarbamoyl-4-[(4'-trifluoromethyl-biphenyl-2-carbonyl)-amino]-phenyl}-acetoxymethyl)-2-phenyl-malonic acid diethyl ester, {3-(isopropyl-methylcarbamoyl)-4-[(4'-trifluoro-methyl-biphenyl-2-carbonyl)-amino]-phenyl}-acetic acid 2,2-bis-ethylcarbamoyl-2-phenyl-ethyl ester, 2-(2-{3-(ethyl-methylcarbamoyl)-4-[(4'-trifluoro-methyl-biphenyl-2-carbonyl)-amino]-phenyl}-acetoxymethyl)-2-phenyl-malonic acid diethyl ester, {3-(ethyl-methylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(ethyl-methylcarbamoyl)-4-[(4'-trifluoromethyl-biphenyl-2-carbonyl)-amino]-phenyl}-acetic acid 3,3-bis-ethylcarbamoyl-3-phenyl-propyl ester, {3-(piperidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(pyrrolidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 3,3-bis-ethylcarbamoyl-3-phenyl-ethyl ester, {3-(dimethylcarbamoyl)-4-[(4'-trifluoromethyl-biphenyl-2-carbonyl)-amino]-phenyl}-acetic acid 2-ethyl-carbamoyl-2-phenyl-ethyl ester, 2-phenyl-2-(2-{3-(pyrrolidine-1-carbonyl)-4-[(4'-trifluoromethyl-biphenyl-2-carbonyl)-amino]-phenyl}-acetoxymethyl)-malonic acid diethyl ester, 2-phenyl-2-(2-{3-(piperidine-1-carbonyl)-4-[(4'-trifluoromethyl-biphenyl-2-carbonyl)-amino]-phenyl}-acetoxymethyl)-malonic acid diethyl ester, {3-dimethylcarbamoyl-4-[(4'-trifluoromethyl-biphenyl-2-carbonyl)-amino]-phenyl}-acetic acid 2-phenyl-2-propionylamino-ethyl ester, {3-dimethylcarbamoyl-4-[(4'-trifluoromethyl-biphenyl-2-carbonyl)-amino]-phenyl∇-acetic acid 2-phenyl-2-propionylamino-ethyl ester, {3-dimethylcarbamoyl-4-[(4'-trifluoromethyl-biphenyl-2-carbonyl)-amino]-phenyl}-acetic acid 2-(2,5-dioxo-pyrrolidin-1-yl)-2-phenyl-ethyl ester, {3-dimethylcarbamoyl-4-[(4'-trifluoromethyl-biphenyl-2-carbonyl)-amino]-phenyl}-acetic acid 2-ethylcarbamoyl-benzyl ester, {3-dimethylcarbamoyl-4-[(4'-trifluoromethyl-biphenyl-2-carbonyl)-amino]-phenyl}-acetic acid 2-ethylcarbamoyl-methyl-benzyl ester, {3-dimethylcarbamoyl-4-[(4'-trifluoromethyl-biphenyl-2-carbonyl)-amino]-phenyl}-acetic acid 2-isopropylamino-2-phenyl-ethyl ester hydrochloride, 2-[2-(2-{3-dimethylcarbamoyl-4-[(4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(4'-fluoro-biphenyl-2-carbonyl)-amino]-phenyl}-acetoxymethyl)-2-phenyl-malonic acid diethyl ester, 2-(2-{4-[(4'-bromo-biphenyl-2-carbonyl)-amino]-3-dimethylcarbamoyl-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-acetylamino-2-phenyl-ethyl ester, {3-dimethylcarbamoyl-4-[(4'-trifluoromethyl-biphenyl-2-carbonyl)-amino]-phenyl}-acetic acid 2-butyrylamino-2-phenyl-ethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid dimethyl ester, 2-cyclopentyl-2-(2-{3-dimethylcarbamoyl-4-[(4'-trifluoromethyl-biphenyl-2-carbonyl)-amino]-phenyl}-acetoxymethyl)-malonic acid diethyl ester, 2-cyclohexyl-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{4-[(4'-chloro-biphenyl-2-carbonyl)-amino]-3-dimethylcarbamoyl-phenyl}-acetoxymethyl)-2-phenyl-malonic acid diethyl ester, 2-(2-{4-[(4'-acetyl-biphenyl-2-carbonyl)-amino]-3-dimethylcarbamoyl-phenyl}-acetoxymethyl)-2-phenyl-malonic acid diethyl ester, 2-(2-{4-[(4'-cyano-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-methyl-4'-trifluoromethyl-biphenyl-2-carbonyl)-amino]-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-methanesulfonylamino-2-phenyl-ethyl ester, 3-(2-{3-dimethylcarbamoyl-4-[(4'-trifluoromethyl-biphenyl-2-carbonyl)-amino]-phenyl}-acetoxy)-2-phenyl-propionic acid ethyl ester, {3-dimethylcarbamoyl-4-[(4'-trifluoromethyl-biphenyl-2-carbonyl)-amino]-phenyl}-acetic acid 2-(methyl-propionyl-amino)-2-phenyl-ethyl ester, 2-[3-(2-{3-dimethylcarbamoyl-4-[(4'-trifluoromethyl-biphenyl-2-carbonyl)-amino]-phenyl}-acetoxy)-propyl]-2-phenyl-malonic acid diethyl ester, 2-(2-{3-dimethylcarbamoyl-4-[(5-methoxy-4'-trifluoromethyl-biphenyl-2-carbonyl)-amino]-phenyl]-acetoxymethyl]-2-phenyl-malonic acid diethyl ester, 2-(2-{4-[5-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid di-2,2,2-trifluoroethyl ester, 2-(2-{3-dimethylcarbamoyl-4-[(2'-fluoro-4'-trifluoromethyl-biphenyl-2-carbonyl)-amino]-phenyl}-acetoxymethyl)-2-phenyl-malonic acid diethyl ester, 2-(2-{5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-4-[(4'-trifluoromethyl-biphenyl-2-carbonyl)-amino]-phenyl}-acetoxymethyl)-2-phenyl-malonic acid diethyl ester, 2-(2-{3-chloro-5-dimethylcarbamoyl-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3'-fluoro-4'-trifluoromethyl-biphenyl-2-carbonyl)-amino]-phenyl}-acetoxymethyl)-2-phenyl-malonic acid diethyl ester, 2-(2-{4-(3'-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-nitro-pyridin-2-yl)-malonic acid diethyl ester, 2-(5-amino-pyridin-2-yl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-pyridin-2-yl-malonic acid diethyl ester, 2-(2-{3-chloro-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-o-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-m-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-p-tolyl-malonic acid diethyl ester, 2-(2-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(4-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-succinic acid diethyl ester, 2-(2-{3-dimethylcarbamoyl-4-[(4'-trifluoromethyl-biphenyl-2-carbonyl)-amino]-phenyl}-acetoxymethyl)-2-(2-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(4-methoxy-phenyl)-malonic acid diethyl ester, 2-(2-{4-(5,4'-bis-trifluoromethyl-biphenyl-2-carbonyl)-amino]-3-dimethylcarbamoyl-phenyl}-acetoxymethyl)-2-phenyl}-malonic acid diethyl ester, 2-(2-{4-(6-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-fluoro-4'-trifluoromethyl-biphenyl-2-carbonyl)-amino]-phenyl}-acetoxymethyl)-2-phenyl-malonic acid diethyl ester, 2-[2-(2-{3-dimethylcarbamoyl-4-[(5-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-ethoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-isopropoxy-4'-trifluoromethyl-biphenyl-2-carbonyl)-amino]-phenyl}-acetoxymethyl)-2-phenyl-malonic acid diethyl ester, 2-[2-(2-{4-[(5,4'-bis-4'-trifluoromethyl-biphenyl-2-carbonyl)-amino]-3-dimethylcarbamoyl-phenyl}-acetoxy)-ethyl]-2-phenyl-malonic acid diethyl ester, 2-(2-{3-dimethylcarbamoyl-4-[(6-methoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3-methyl-4'-trifluoromethyl-biphenyl-2-carbonyl)-amino]-phenyl}-acetoxymethyl)-2-phenyl-malonic acid diethyl ester, 2-(2-{4-(2,4-bis-trifluoromethyl-benzoylamino)-3-dimethylcarbamoyl-phenyl]-acetoxymethyl}-2-phenyl-malonic acid diethyl ester, 2-(2-{3-dimethylcarbamoyl-4-[(4'-methyl-biphenyl-2-carbonyl)-amino]-phenyl}-acetoxymethyl)-2-phenyl-malonic acid diethyl ester, 2-{2-[3-dimethylcarbamoyl-4-(2-ethyl-4-trifluoromethyl-benzoylamino)-phenyl]-acetoxymethyl}-2-phenyl-malonic acid diethyl ester, 2-(2-{3-dimethylcarbamoyl-4-[(4'-ethyl-biphenyl-2-carbonyl)-amino]-phenyl}-acetoxymethyl)-2-phenyl-malonic acid diethyl ester, 2-(2-{3-dimethylcarbamoyl-4-[(4'-isopropenyl-biphenyl-2-carbonyl)-amino]-phenyl}-acetoxymethyl)-2-phenyl-malonic acid diethyl ester, 2-(2-{3-dimethylcarbamoyl-4-[(4'-isopropyl-biphenyl-2-carbonyl)-amino]-phenyl}-acetoxymethyl)-2-phenyl-malonic acid diethyl ester, 2-{2-[3-dimethylcarbamoyl-4-[(4'-trifluoromethyl-biphenyl-2-carbonyloxy)-phenyl]-acetoxymethyl}-2-phenyl-malonic acid diethyl ester, {3-dimethylcarbamoyl-4-[(4'-trifluoromethyl-biphenyl-2-carbonyl)-amino]-phenyl}-acetic acid 2-ethyl-2-phenyl-butyl ester, {3-dimethylcarbamoyl-4-[(4'-trifluoromethyl-biphenyl-2-carbonyl)-amino]-phenyl}-acetic acid 1-phenyl-cyclopropylmethyl ester, {3-dimethylcarbamoyl-4-[(4'-trifluoromethyl-biphenyl-2-carbonyl)-amino]-phenyl}-acetic acid 2,2-diphenyl-ethyl ester, {3-dimethylcarbamoyl-4-[(4'-trifluoromethyl-biphenyl-2-carbonyl)-amino]-phenyl}-acetic acid 1-phenyl-cyclopentylmethyl ester, {3-dimethylcarbamoyl-4-[(4'-trifluoromethyl-biphenyl-2-carbonyl)-amino]-phenyl}-acetic acid 3-hydroxy-2-hydroxymethyl-2-phenyl-propyl ester, {3-dimethylcarbamoyl-4-[(4'-trifluoromethyl-biphenyl-2-carbonyl)-amino]-phenyl}-acetic acid 3-acetoxy-2-acetoxymethyl-2-phenyl-propyl ester, 2-(2-{3-dimethylcarbamoyl-4-[(4'-trifluoromethyl-biphenyl-2-carbonyl)-amino]-phenyl}-acetoxymethyl)-2-thiophen-2-yl-malonic acid diethyl ester, 2-(2-{3-dimethylcarbamoyl-4-[(4'-trifluoromethyl-biphenyl-2-carbonyl)-amino]-phenyl}-acetoxymethyl)-2-thiophen-3-yl-malonic acid diethyl ester, 2-(2-{4-dimethylcarbamoyl-5-[(4'-trifluoromethyl-biphenyl-2-carbonyl)-amino]-pyridin-2-yl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-thiazol-2-yl-malonic acid diethyl ester, 2-(2-{3-ethoxy-4-[(4'-trifluoromethyl-biphenyl-2-carbonyl)-amino]-phenyl}-acetoxymethyl)-2-phenyl-malonic acid diethyl ester, {3-hydroxy-4-[(4'-trifluoromethyl-biphenyl-2-carbonyl)-amino]-phenyl}-acetic acid 2,2-bis-ethylcarbamoyl-2-phenyl-ethyl ester, {3-methoxy-4-[(4'-trifluoromethyl-biphenyl-2-carbonyl)-amino]-phenyl}-acetic acid 2,2-bis-ethylcarbamoyl-2-phenyl-ethyl ester, 2-(2-{3-methoxy-4-[(4'-trifluoromethyl-biphenyl-2-carbonyl)-amino]-phenyl}-acetoxymethyl)-2-phenyl-malonic acid diethyl ester, {3-methoxy-4-[(4'-trifluoromethyl-biphenyl-2-carbonyl)-amino]-phenyl}-acetic acid 2-phenyl-2,2-bis-propylcarbamoyl-ethyl ester, {3-methoxy-4-[(4'-trifluoromethyl-biphenyl-2-carbonyl)-amino]-phenyl}-acetic acid 3,3-bis-ethylcarbamoyl-3-phenyl-propyl ester, {3-ethoxy-4-[(4'-trifluoromethyl-biphenyl-2-carbonyl)-amino]-phenyl}-acetic acid 2,2-bis-ethylcarbamoyl-2-phenyl-ethyl ester, {3-ethoxy-4-[(4'-trifluoromethyl-biphenyl-2-carbonyl)-amino]-phenyl}-acetic acid 3,3-bis-ethylcarbamoyl-3-phenyl-propyl ester, 2-(2-{3-isopropoxy-4-[(4'-trifluoromethyl-biphenyl-2-carbonyl)-amino]-phenyl}-acetoxymethyl)-2-phenyl-malonic acid diethyl ester, {3-isopropoxy-4-[(4'-trifluoromethyl-biphenyl-2-carbonyl)-amino]-phenyl}-acetic acid 2,2-bis-ethylcarbamoyl-2-phenyl-ethyl ester, {3-isopropoxy-4-[(4'-trifluoromethyl-biphenyl-2-carbonyl)-amino]-phenyl}-acetic acid 3,3-bis-ethylcarbamoyl-3-phenyl-propyl ester, {3-propoxy-4-[(4'-trifluoromethyl-biphenyl-2-carbonyl)-amino]-phenyl}-acetic acid 2,2-bis-ethylcarbamoyl-2-phenyl-ethyl ester, {3-benzyloxy-4-[(4'-trifluoromethyl-biphenyl-2-carbonyl)-amino]-phenyl}-acetic acid 2,2-bis-ethylcarbamoyl-2-phenyl-ethyl ester, 2-(2-{3-benzyloxy-4-[(4'-trifluoromethyl-biphenyl-2-carbonyl)-amino]-phenyl}-acetoxymethyl)-2-phenyl-malonic acid diethyl ester, 2-(2-{3-hydroxy-4-[(4'-trifluoromethyl-biphenyl-2-carbonyl)-amino]-phenyl}-acetoxymethyl)-2-phenyl-malonic acid diethyl ester, 2-(2-{3-methoxy-4-[(4'-trifluoromethyl-biphenyl-2-carbonyloxy)-phenyl]-acetoxymethyl}-2-phenyl-malonic acid diethyl ester, {3-dimethylamino-4-[(4'-trifluoromethyl-biphenyl-2-carbonyl)-amino]-phenyl}-acetic acid 2,2-bis-ethylcarbamoyl-2-phenyl-ethyl ester, {3-piperidin-1-yl-4-[(4'-trifluoromethyl-biphenyl-2-carbonyl)-amino]-phenyl}-acetic acid 2,2-bis-ethylcarbamoyl-2-phenyl-ethyl ester, {3-pyrrolidin-1-yl-4-[(4'-trifluoromethyl-biphenyl-2-carbonyl)-amino]-phenyl}-acetic acid 2,2-bis-ethylcarbamoyl-2-phenyl-ethyl ester,
2-phenyl-2-(2-{3-piperidin-1-yl-4-[(4'-trifluoromethyl-biphenyl-2-carbonyl)-amino]-phenyl}-acetoxymethyl)-malonic acid diethyl ester,
2-phenyl-2-(2-{3-pyrrolidin-1-yl-4-[(4'-trifluoromethyl-biphenyl-2-carbonyl)-amino]-phenyl}-acetoxymethyl)-malonic acid diethyl ester,
2-(2-{3-dimethylamino-4-[(4'-trifluoromethyl-biphenyl-2-carbonyl)-amino]-phenyl}-acetoxymethyl)-2-phenyl-malonic acid diethyl ester,
{2-{3-morpholin-4-yl-4-[(4'-trifluoromethyl-biphenyl-2-carbonyl)-amino]-phenyl}-acetoxymethyl)-2-phenyl-malonic acid diethyl ester,
2-(2-{3-diethylamino-4-[(4'-trifluoromethyl-biphenyl-2-carbonyl)-amino]-phenyl}-acetoxymethyl)-2-phenyl-malonic acid diethyl ester,
2-[2-(2-{2-methyl-3-[(4'-trifluoromethyl-biphenyl-2-carbonyl)-amino]-phenyl}-acetoxy)-ethyl]-2-phenyl-malonic acid diethyl ester,
2-phenyl-2-(2-{3-[(4'-trifluoromethyl-biphenyl-2-carbonyl)-amino]-phenyl}-acetoxymethyl)-malonic acid diethyl ester,
2-phenyl-2-[2-(2-{3-[(4'-trifluoromethyl-biphenyl-2-carbonyl)-amino]-phenyl}-acetoxy)-ethyl]-malonic acid diethyl ester,
{3-[(4'-trifluoromethyl-biphenyl-2-carbonyl)-amino]-phenyl}-acetic acid 3,3-bis-ethylcarbamoyl-3-phenyl-propyl ester,
{3-[(4'-trifluoromethyl-biphenyl-2-carbonyl)-amino]-phenyl}-acetic acid 2,2-bis-ethylcarbamoyl-2-phenyl-ethyl ester,
{3-[(4'-trifluoromethyl-biphenyl-2-carbonyl)-amino]-phenyl}-acetic acid 3-phenyl-3,3-bis-propylcarbamoyl-propyl ester,
2-[2-(2-{4-methyl-3-[(4'-trifluoromethyl-biphenyl-2-carbonyl)-amino]-phenyl}-acetoxy-ethyl)-2-phenyl-malonic acid diethyl ester,
2-[2-(2-{2-methyl-5-[(4'-trifluoromethyl-biphenyl-2-carbonyl)-amino]-phenyl}-acetoxy)-ethyl]-2-phenyl-malonic acid diethyl ester,
{3-[(4'-trifluoromethyl-biphenyl-2-carbonyl)-amino]-phenyl}-acetic acid 3,3-bis-isopropylcarbamoyl-3-phenyl-propyl ester,
{2-methyl-3-[(4'-trifluoromethyl-biphenyl-2-carbonyl)-amino)-phenyl}-acetic acid 3,3-bis-ethylcarbamoyl-3-phenyl-propyl ester,
{2-methyl-3-[(4'-trifluoromethyl-biphenyl-2-carbonyl)-amino]-phenyl}-acetic acid 4,4-bis-ethylcarbamoyl-4-phenyl-butyl ester,
{2-methyl-3-[(4'-trifluoromethyl-biphenyl-2-carbonyl)-amino]-phenyl}-acetic acid 3-phenyl-3,3-bis-propylcarbamoyl-propyl ester,
{2-methoxy-3-[(4'-trifluoromethyl-biphenyl-2-carbonyl)-amino]-phenyl}-acetic acid 3,3-bis-ethylcarbamoyl-3-phenyl-propyl ester,
2-[2-(2-{2-methoxy-3-[(4'-trifluoromethyl-biphenyl-2-carbonyl)-amino]-phenyl}-acetoxy)-ethyl]-2-phenyl-malonic acid diethyl ester,
{2-ethoxy-3-[(4'-trifluoromethyl-biphenyl-2-carbonyl)-amino]-phenyl}-acetic acid 3,3-bis-ethylcarbamoyl-3-phenyl-propyl ester,
2-[2-(2-{2-ethoxy-3-[(4'-trifluoromethyl-biphenyl-2-carbonyl)-amino]-phenyl}-acetoxy)-ethyl]-2-phenyl-malonic acid diethyl ester,
2-[2-(2-{2-isopropoxy-3-[(4'-trifluoromethyl-biphenyl-2-carbonyl)-amino]-phenyl}-acetoxy)-ethyl]-2-phenyl-malonic acid diethyl ester,
2-[2-(2-{2-methoxycarbonyl-3-[(4'-trifluoromethyl-biphenyl-2-carbonyl)-amino]-phenyl}-acetoxy)-ethyl]-2-phenyl-malonic acid diethyl ester,
2-[2-(2-{2-ethoxy-5-methyl-3-[(4'-trifluoromethyl-biphenyl-2-carbonyl)-amino]-phenyl}-acetoxy)-ethyl]-2-phenyl-malonic acid diethyl ester,
4-[(4'-trifluoromethyl-biphenyl-2-carbonyl)-amino]-benzoic acid 2-[9-(2,2,2-trifluoro-ethylcarbamoyl)-9h-fluoren-9-yl]-ethyl ester,
4-[(4'-trifluoromethyl-biphenyl-2-carbonyl)-amino]-benzoic acid 2-[9h-fluoren-9-yl]-ethyl ester,
n-biphenyl-2-yl-terephthalamic acid 2-[9-(2,2,2-trifluoro-ethylcarbamoyl)-9h-fluoren-9-yl]-ethyl ester,
4-[(4'-trifluoromethyl-biphenyl-2-carbonyl)-amino]-benzoic acid 2-[(biphenyl-2-carbonyl)-amino]-ethyl ester,
4-[(4'-trifluoromethyl-biphenyl-2-carbonyl)-amino]-benzoic acid 2-(2-biphenyl-2-yl-acetylamino)-ethyl ester,
4-[(4'-trifluoromethyl-biphenyl-2-carbonyl)-amino]-benzoic acid 3-naphthalen-1-yl-3-(2,2,2-trifluoro-ethylcarbamoyl)-propyl ester,
4-[(4'-trifluoromethyl-biphenyl-2-carbonyl)-amino]-benzoic acid 3-[2-(2,2,2-trifluoro-ethylcarbamoyl)-naphthalen-1-yl]-propyl ester,
4-[(4'-trifluoromethyl-biphenyl-2-carbonyl)-amino]-benzoic acid 3,3-diphenyl-3-(2,2,2-trifluoro-ethylcarbamoyl)-propyl ester,
4-[(4'-trifluoromethyl-biphenyl-2-carbonyl)-amino]-benzoic acid 3-biphenyl-2-yl-3-(2,2,2-trifluoro-ethylcarbamoyl)-propyl ester,
4-[(4'-trifluoromethyl-biphenyl-2-carbonyl)-amino]-benzoic acid 3-phenyl-3-(2,2,2-trifluoro-ethylcarbamoyl)-propyl ester,
4-[(4'-trifluoromethyl-biphenyl-2-carbonyl)-amino]-benzoic acid 2-[8-(2,2,2-trifluoro-ethylcarbamoyl)-naphthalen-1-yl]-ethyl ester,
4-[(4'-trifluoromethyl-biphenyl-2-carbonyl)-amino]-benzoic acid 3-[(2,6-dichloro-phenyl)-3-(2,2,2-trifluoro-ethylcarbamoyl)-propyl ester,
4-[(4'-trifluoromethyl-biphenyl-2-carbonyl)-amino]-benzoic acid 3-(2-chloro-phenyl)-3-(2,2,2-trifluoro-ethylcarbamoyl)-propyl ester,
2-phenyl-2-(2-(4-[(4'-trifluoromethyl-biphenyl-2-carbonyl)-amino]-benzoyloxy}-ethyl)-malonic acid diethyl ester,
2-(2-{3-methyl-4-[(4'-trifluoromethyl-biphenyl-2-carbonyl)-amino]-benzoyloxy}-ethyl)-2-phenyl-malonic acid diethyl ester,
2-(2-{2-chloro-4-[(4'-trifluoromethyl-biphenyl-2-carbonyl)-amino]-benzoyloxy}-ethyl)-2-phenyl-malonic acid diethyl ester,
2-phenyl-2-{2-[4-[(4'-trifluoromethyl-biphenyl-2-carbonyloxy)-benzoyloxy]-ethyl}-malonic acid diethyl ester,
4-[(4'-trifluoromethyl-biphenyl-2-carbonyl)-amino]-benzoic acid 3,3-bis-ethylcarbamoyl-3-phenyl-propyl ester,
4'-trifluoromethyl-biphenyl-2-carboxylic acid 4-(3,3-bis-ethylcarbamoyl-3-phenyl-propoxycarbony)-2-chloro-phenyl ester,
4'-trifluoromethyl-biphenyl-2-carboxylic acid 4-(3,3-bis-ethylcarbamoyl-3-phenyl-propoxycarbonyl)-phenyl ester,
4'-trifluoromethyl-biphenyl-2-carboxylic acid 4-(3,3-bis-ethylcarbamoyl-3-phenyl-propoxycarbonyl)-2,6-dichloro-phenyl ester,
2-(2-{3-ethoxycarbonyl-4-[(4'-trifluoromethyl-biphenyl-2-carbonyl)-amino]-phenyl-acetoxymethyl}-2-phenyl-malonic acid diethyl ester, 2-(3-{3-dimethylcarbamoyl-4-[(4'-trifluoromethyl-biphenyl-2-carbonyl)-amino]-phenyl}-propionyloxymethyl)-2-phenyl-malonic acid diethyl ester,
2-{4-[(4'-trifluoromethyl-biphenyl-2-carbonyl)-amino]-phenyl}-propionic acid ethylcarbamoyl-phenyl-methyl ester,
5-(2,2-bis-ethylcarbamoyl-2-phenyl-ethoxycarbonyl-methyl)-2-4-[(4'-trifluoromethyl-biphenyl-2-carbonyl)-amino]-benzoic acid benzyl ester,
5-(2,2-bis-ethylcarbamoyl-2-phenyl-ethoxycarbonyl-methyl)-2-[(4'-trifluoromethyl-biphenyl-2-carbonyl)-amino]-benzoic acid,
5-(2,2-bis-ethylcarbamoyl-2-phenyl-ethoxycarbonyl-methyl)-2-[(4'-trifluoromethyl-biphenyl-2-carbonyl)-amino]-benzoic acid ethyl ester,
5-(2,2-bis-ethylcarbamoyl-2-phenyl-ethoxycarbonyl-methyl)-2-[(4'-trifluoromethyl-biphenyl-2-carbonyl)-amino]-benzoic acid methyl ester,
2-(2-{3-benzyloxycarbonyl-4-[(4'-trifluoromethyl-biphenyl-2-carbonyl)-amino]-phenyl}-acetoxymethyl)-2-phenyl-malonic acid diethyl ester,
2-(2-{3-carboxy-4-[(4'-trifluoromethyl-biphenyl-2-carbonyl)-amino]-phenyl}-acetoxymethyl)-2-phenyl-malonic acid diethyl ester,
2-(2-{3-isopropoxycarbonyl-4-[(4'-trifluoromethyl-biphenyl-2-carbonyl)-amino]-phenyl}-acetoxymethyl)-2-phenyl-malonic acid diethyl ester,
2-(2-{3-methoxycarbonyl-4-[(4'-trifluoromethyl-biphenyl-2-carbonyl)-amino]-phenyl}-acetoxymethyl)-2-phenyl-malonic acid diethyl ester,
2-(2-{3-acetylamino-4-[(4'-trifluoromethyl-biphenyl-2-carbonyl)-amino]-phenyl}-acetoxymethyl)-2-phenyl-malonic acid diethyl ester,
2-(2-{3-methoxycarbonylamino-4-[(4'-trifluoromethyl-biphenyl-2-carbonyl)-amino]-phenyl}-acetoxymethyl)-2-phenyl-malonic acid diethyl ester,
2-(2-{3-(4-methyl-thiazol-2-yl)-4-[(4'-trifluoromethyl-biphenyl-2-carbonyl)-amino]-phenyl}-acetoxymethyl)-2-phenyl-malonic acid diethyl ester,
2-phenyl-2-(2-{6-[(4'-trifluoromethyl-biphenyl-2-carbonyl)-amino]-biphenyl-3-yl}-acetoxymethyl)-malonic acid diethyl ester,
2-(2-{3-formyl-4-[(4'-trifluoromethyl-biphenyl-2-carbonyl)-amino]-phenyl}-acetoxymethyl)-2-phenyl-malonic acid diethyl ester,
2-(2-{3-dimethylaminomethyl-4-[(4'-trifluoromethyl-biphenyl-2-carbonyl)-amino]-phenyl}-3-acetoxymethyl)-2-phenyl-malonic acid diethyl ester,
2-(2-{3-methoxy-methylcarbamoyl)-4-[(4'-trifluoromethyl-biphenyl-2-carbonyl)-amino]-phenyl}-3-acetoxymethyl)-2-phenyl-malonic acid diethyl ester,
2-(2-{3-isobutyryl-4-[(4'-trifluoromethyl-biphenyl-2-carbonyl)-amino]-phenyl}-3-acetoxymethyl)-2-phenyl-malonic acid diethyl ester, and
2-(2-{3-(1-hydroxy-2-methyl-propyl)-4-[(4'-trifluoromethyl-biphenyl-2-carbonyl)-amino]-phenyl}-acetoxymethyl)-2-phenyl-malonic acid diethyl ester;
(24) The ester compound or a prodrug thereof, or a pharmaceutically acceptable salt of either according to the above (1), which is selected from the group consisting of
{4-[(4'-trifluoromethyl-biphenyl-2-carbonyl)-amino]-phenyl}-acetic acid 2,2-bis-ethylcarbamoyl-2-phenyl-ethyl ester,
2-phenyl-2-{2-[4-[(4'-trifluoromethyl-biphenyl-2-carbonyloxy)-phenyl]]-malonic acid diethyl ester,
2-(2-{3-methyl-4-[(4'-trifluoromethyl-biphenyl-2-carbonyl)-amino]-phenyl}-acetoxymethyl)-2-phenyl-malonic acid diethyl ester,
2-(2-{4-[methyl-[(4'-trifluoromethyl-biphenyl-2-carbonyl)-amino]-phenyl}-acetoxymethyl)-2-phenyl-malonic acid diethyl ester,
{3-ethyl-4-[(4'-trifluoromethyl-biphenyl-2-carbonyl)-amino]-2-phenyl}-acetic acid 2,2-bis-ethylcarbamoyl-phenyl-ethyl ester,
2-phenyl-2-(2-{4-[(4'-trifluoromethyl-biphenyl-2-carbonyl)-amino]-phenyl}-acetoxymethyl)-malonic acid diethyl ester,
2-phenyl-2-(2-{4-[(4'-trifluoromethyl-biphenyl-2-carbonyl)-amino]-phenyl}-acetoxymethyl)-malonic acid diisopropyl ester,
{4-[(4'-trifluoromethyl-biphenyl-2-carbonyl)-amino]-phenyl}-acetic acid 2-phenyl-2,2-bis-(2,2,2-trifluoro-ethylcarbamoyl)-ethyl ester,
2-phenyl-2-(2-{4-[(4'-trifluoromethyl-biphenyl-2-carbonyl)-amino]-phenyl}-acetoxymethyl)-malonic acid dimethyl ester,
2-cyclopentyl-2-(2-{4-[(4'-trifluoromethyl-biphenyl-2-carbonyl)-amino]-phenyl}-acetoxymethyl)-malonic acid diethyl ester,
2-phenyl-2-(2-{4-[(4'-trifluoromethyl-biphenyl-2-carbonyl)-amino]-phenyl}-acetoxymethyl)-malonic acid dicyclohexyl ester,
{4-[(4'-trifluoromethyl-biphenyl-2-carbonyl)-amino]-phenyl}-acetic acid 2,2-bis-cyclohexylcarbamoyl-2-phenyl ethyl ester,
{4-[(4'-trifluoromethyl-biphenyl-2-carbonyl)-amino]-phenyl}-acetic acid 2-phenyl-2,2-bis-phenylcarbamoyl-ethyl ester,
{4-[(4'-trifluoromethyl-biphenyl-2-carbonyl)-amino]-phenyl}-acetic acid 2,2-bis-isopropylcarbamoyl-2-phenyl-ethyl ester,
2-benzyl-2-(2-{4-[(4'-trifluoromethyl-biphenyl-2-carbonyl)-amino]-phenyl}-acetoxymethyl)-malonic acid diethyl ester,
2-(2-{2-methyl-4-[(4'-trifluoromethyl-biphenyl-2-carbonyl)-amino]-phenyl}-acetoxymethyl)-2-phenyl-malonic acid diethyl ester,
4'-trifluoromethyl-biphenyl-2-carboxylic acid 4-[2-phenyl-2,2-bis-(2,2,2-trifluoro-ethylcarbamoyl)-ethoxycarbonyl-methyl]-phenyl ester,
biphenyl-2-carboxylic acid 4-[2-phenyl-2,2-bis-(2,2,2-trifluoro-ethylcarbamoyl)-ethoxycarbonylmethyl]-phenyl ester,
2-cyclohexyl-2-(2-{4-[(4'-trifluoromethyl-biphenyl-2-carbonyl)-amino]-phenyl}-acetoxymethyl)-malonic acid diethyl ester,
{4-[(biphenyl-2-carbonyl)-amino]-phenyl}-acetic acid 2-phenyl-2,2-bis-(2,2,2-trifluoro-ethylcarbamoyl)-ethyl ester,
2-phenyl-2-(2-{2-trifluoromethyl-4-[(4'-trifluoromethyl-biphenyl-2-carbonyl)-amino]-phenyl}-acetoxymethyl)-malonic acid diethyl ester,
{4-[(4'-trifluoromethyl-biphenyl-2-carbonyl)-amino]-phenyl}-acetic acid 2,2-bis-methylcarbamoyl-2-phenyl-ethyl ester,
2-pyridin-2-yl-2-(2-{4-[(4'-trifluoromethyl-biphenyl-2-carbonyl)-amino]-phenyl}-acetoxymethyl)-malonic acid diethyl ester,
2-pyridin-3-yl-2-(2-{4-[(4'-trifluoromethyl-biphenyl-2-carbonyl)-amino]-phenyl}-acetoxymethyl)-malonic acid diethyl ester,
4'-trifluoromethyl-biphenyl-2-carbxylic acid 4-(2,2-bis-ethylcarbamoyl)-2-phenyl-ethoxycarbonylmethyl)-phenyl ester, 2-phenyl-2-(2-{3-trifluoromethyl-4-[(4'-trifluoromethyl-biphenyl-2-carbonyl)-amino]-phenyl}-acetoxymethyl)-malonic acid diethyl ester,
{4-[(4'-trifluoromethyl-biphenyl-2-carbonyl)-amino]-phenyl}-acetic acid 2,2-bis-butylcarbamoyl-2-phenyl-ethyl ester,
{3-methyl-4-[(4'-trifluoromethyl-biphenyl-2-carbonyl)-amino]-phenyl}-acetic acid 2,2-bis-ethylcarbamoyl-2-phenyl-ethyl ester,
2-(2-{4-[(4'-methyl-biphenyl-2-carbonyl)-amino]-phenyl}-acetoxymethyl)-2-phenyl-malonic acid diethyl ester,
2-(2-{4-[(4'-methoxy-biphenyl-2-carbonyl)-amino]-phenyl}-acetoxymethyl)-2-phenyl-malonic acid diethyl ester,
{4-[(4'-trifluoromethyl-biphenyl-2-carbonyl)-amino]-phenyl}-acetic acid 3,3-bis-ethylcarbamoyl-3-phenyl-propyl ester,
{4-[(4'-trifluoromethyl-biphenyl-2-carbonyl)-amino]-phenyl}-acetic acid 3-phenyl-3,3-bis-propylcarbamoyl-propyl ester,
{4-[(biphenyl-2-carbonyl)-amino]-phenyl}-acetic acid 2,2-bis-ethylcarbamoyl-2-phenyl-ethyl ester,
2-phenyl-2-(2-{4-[(3'-trifluoromethyl-biphenyl-2-carbonyl)-amino]-phenyl}-acetoxymethyl)-malonic acid diethyl ester,
4'-trifluoromethyl-biphenyl-2-carboxylic acid 4-(2,2-bis-ethylcarbamoyl)-2-phenyl-ethoxycarbonylmethyl)-2-chloro-phenyl ester,
2-(2-{4-[isopropyl-(4'-trifluoromethyl-biphenyl-2-carbonyl)-amino]-phenyl}-acetoxymethyl)-2-phenyl-malonic acid diethyl ester,
2-(2-{4-[cyclohexyl-(4'-trifluoromethyl-biphenyl-2-carbonyl)-amino]-phenyl}-acetoxymethyl)-2-phenyl-malonic acid diethyl ester,
2-phenyl-2-(2-{4-[(4'-trifluoromethyl-biphenyl-2-carbonyl)-amino]-phenyl}-acetoxymethyl)-malonic acid dipropyl ester,
2-phenyl-2-(2-{4-[(4'-trifluoromethyl-biphenyl-2-carbonyl)-amino]-phenyl}-acetoxymethyl)-malonic acid diisobutyl ester,
{4-[(4'-trifluoromethyl-biphenyl-2-carbonyl)-amino]-phenyl}-acetic acid 2,2-bis-isobutylcarbamoyl-2-phenyl-ethyl ester,
{4-[(4'-trifluoromethyl-biphenyl-2-carbonyl)-amino]-phenyl}-acetic acid 2,2-bis-(3-methyl-butylcarbamoyl)-2-phenyl-ethyl ester,
2-(2-{4-[ethyl-(4'-trifluoromethyl-biphenyl-2-carbonyl)-amino]-phenyl}-acetoxymethyl)-2-phenyl-malonic acid diethyl ester,
{4-[(4'-chloro-biphenyl-2-carbonyl)-amino]-phenyl}-acetic acid 2,2-bis-ethylcarbamoyl-2-phenyl-ethyl ester,
{4-[(3'4'-dichloro-biphenyl-2-carbonyl)-amino]-phenyl}-acetic acid 2,2-bis-ethylcarbamoyl-2-phenyl-ethyl ester,
{3-methyl-4-[(4'-trifluoromethyl-biphenyl-2-carbonyl)-amino]-phenyl}-acetic acid 2-phenyl-2,2-bis-propylcarbamoyl-ethyl ester,
{4-[(4'-trifluoromethyl-biphenyl-2-carbonyl)-amino]-phenyl}-acetic acid 2,2-bis-(2-methoxy-ethylcarbamoyl)-2-phenyl-ethyl ester,
2-(2-{3-ethyl-4-[(4'-trifluoromethyl-biphenyl-2-carbonyl)-amino]-phenyl}-acetoxymethyl)-2-phenyl-malonic acid diethyl ester,
{3-isopropyl-4-[(4'-trifluoromethyl-biphenyl-2-carbonyl)-amino]-phenyl}-acetic acid 2,2-bis-ethylcarbamoyl-2-phenyl-ethyl ester,
2-(2-{3-isopropyl-4-[(4'-trifluoromethyl-biphenyl-2-carbonyl)-amino]-phenyl}-acetoxymethyl)-2-phenyl-malonic acid diethyl ester,
{3-ethyl-4-[(4'-trifluoromethyl-biphenyl-2-carbonyl)-amino]-phenyl}-acetic acid 3,3-bis-ethylcarbamoyl-3-phenyl-propyl ester,
{3-isobutyl-4-[(4'-trifluoromethyl-biphenyl-2-carbonyl)-amino]-phenyl}-acetic acid 2,2-bis-ethylcarbamoyl-2-phenyl-ethyl ester,
2-(2-{3-isobutyl-4-[(4'-trifluoromethyl-biphenyl-2-carbonyl)-amino]-phenyl}-acetoxymethyl)-2-phenyl-malonic acid diethyl ester,
2-(2-{3-chloro-4-[(4'-trifluoromethyl-biphenyl-2-carbonyl)-amino]-phenyl}-acetoxymethyl)-2-phenyl-malonic acid diethyl ester,
2-(2-{3-bromo-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-malonic acid diethyl ester,
{3-dimethylcarbamoyl-4-[(4'-trifluoromethyl-biphenyl-2-carbonyl)-amino]-phenyl}-acetic acid 2-phenyl-2,2-bis-propylcarbamoyl-ethyl ester,
{3-methylcarbamoyl-4-[(4'-trifluoromethyl-biphenyl-2-carbonyl)-amino]-phenyl}-acetic acid 2,2-bis-ethylcarbamoyl-2-phenyl-ethyl ester,
{3-dimethylcarbamoyl-4-[(4'-trifluoromethyl-biphenyl-2-carbonyl)-amino]-phenyl}-acetic acid 3,3-bis-ethylcarbamoyl-3-phenyl-propyl ester,
2-(2-{3-diethylcarbamoyl-4-[(4'-trifluoromethyl-biphenyl-2-carbonyl)-amino]-phenyl}-acetoxymethyl)-2-phenyl-malonic acid diethyl ester,
{3-benzylcarbamoyl-4-[(4'-trifluoromethyl-biphenyl-2-carbonyl)-amino]-phenyl}-acetic acid 2,2-bis-ethylcarbamoyl-2-phenyl-ethyl ester,
{3-dimethylcarbamoyl-4-[(4'-trifluoromethyl-biphenyl-2-carbonyl)-amino]-phenyl}-acetic acid 4,4-bis-ethylcarbamoyl-4-phenyl-butyl ester,
{3-diethylcarbamoyl-4-[(4'-trifluoromethyl-biphenyl-2-carbonyl)-amino]-phenyl}-acetic acid 2,2-bis-ethylcarbamoyl-2-phenyl-ethyl ester,
{3-diisopropylcarbamoyl-4-[(4'-trifluoromethyl-biphenyl-2-carbonyl)-amino]-phenyl}-acetic acid 2,2-bis-ethylcarbamoyl-2-phenyl-ethyl ester,
2-(2-{3-diethylcarbamoyl-4-[(4'-trifluoromethyl-biphenyl-2-carbonyl)-amino]-phenyl}-acetoxymethyl)-2-phenyl-malonic acid diethyl ester,
2-(2-{3-diisopropylcarbamoyl-4-[(4'-trifluoromethyl-biphenyl-2-carbonyl)-amino)-phenyl}-acetoxymethyl)-2-phenyl-malonic acid diethyl ester,
{3-(isopropyl-methylcarbamoyl)-4-[(4'-trifluoromethyl-biphenyl-2-carbonyl)-amino]-phenyl}-acetic acid 2,2-bis-ethylcarbamoyl-2-phenyl-ethyl ester,
2-(2-{3-(ethyl-methylcarbamoyl)-4-[(4'-trifluoromethyl-biphenyl-2-carbonyl)-amino]-phenyl}-acetoxymethyl)-2-phenyl-malonic acid diethyl ester,
{3-(ethyl-methylcarbamoyl)-4-[(4'-trifluoromethyl-biphenyl-2-carbonyl)-amino]-phenyl}-acetic acid 2,2-bis-ethylcarbamoyl-2-phenyl-ethyl ester,
{3-(ethyl-methylcarbamoyl)-4-[(4'-trifluoromethyl-biphenyl-2-carbonyl)-amino]-phenyl}-acetic acid 3,3-bis-ethylcarbamoyl-3-phenyl-propyl ester,
{3-(piperidin-1-carbonyl)-4-[(4'-trifluoromethyl-biphenyl-2-carbonyl)-amino]-phenyl}-acetic acid 2,2-bis-ethylcarbamoyl-2-phenyl-ethyl ester,
{3-(pyrrolidin-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 3,3-bis-ethylcarbamoyl-3-phenyl-propyl ester, {3-dimethylcarbamoyl-4-[(4'-trifluoromethyl-biphenyl-2-carbonyl)-amino]-phenyl}-acetic acid 2-ethylcarbamoyl-2-phenyl-ethyl ester, 2-phenyl-2-(2-{3-pyrrolidin-1-carbonyl)-4-[(4'-trifluoromethyl-biphenyl-2-carbonyl)-amino]-phenyl}-acetoxymethyl)-malonic acid diethyl ester, 2-phenyl-2-(2-{3-piperidin-1-carbonyl)-4-[(4'-trifluoromethyl-biphenyl-2-carbonyl)-amino]-phenyl}-acetoxymethyl)-malonic acid diethyl ester, {3-dimethylcarbamoyl-4-[(4'-trifluoromethyl-biphenyl-2-carbonyl)-amino]-phenyl}-acetic acid 2-phenyl-2-propionylamino-ethyl ester, {3-dimethylcarbamoyl-4-[(4'-trifluoromethyl-biphenyl-2-carbonyl)-amino]-phenyl}-acetic acid 2-(2,5-dioxo-pyrrolidin-1-yl)-2-phenyl-ethyl ester, {3-dimethylcarbamoyl-4-[(4'-trifluoromethyl-biphenyl-2-carbonyl)-amino]-phenyl}-acetic acid 2-ethylcarbamoyl-benzyl ester, {3-dimethylcarbamoyl-4-[(4'-trifluoromethyl-biphenyl-2-carbonyl)-amino]-phenyl}-acetic acid 2-ethylcarbamoyl-methyl-benzyl ester, {3-dimethylcarbamoyl-4-[(4'-trifluoromethyl-biphenyl-2-carbonyl)-amino]-phenyl}-acetic acid 2-isopropylamino-2-phenyl-ethyl ester hydrochloride, 2-[2-(2-{3-dimethylcarbamoyl-4-[(4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(4'-fluoro-biphenyl-2-carbonyl)-amino]-phenyl}-acetoxymethyl)-2-phenyl-malonic acid diethyl ester, 2-(2-{4-[(4'-bromo-biphenyl-2-carbonyl)-amino]-3-dimethylcarbamoyl-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-acethylamino-2-phenyl-ethyl ester, {3-dimethylcarbamoyl-4-[(4'-trifluoromethyl-biphenyl-2-carbonyl)-amino]-phenyl}-acetic acid 2-butyrylamino-2-phenyl-ethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid dimethyl ester, 2-cyclopentyl-2-(2-{3-dimethylcarbamoyl-4-[(4'-trifluoromethyl-biphenyl-2-carbonyl)-amino]-phenyl}-acetoxymethyl)-malonic acid diethyl ester, 2-cyclohexyl-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{4-[(4'-chloro-biphenyl-2-carbonyl)-amino]-3-dimethylcarbamoyl-phenyl}-acetoxymethyl)-2-phenyl-malonic acid diethyl ester, 2-(2-{4-[(4'-acetyl-biphenyl-2-carbonyl)-amino]-3-dimethylcarbamoyl-phenyl}-acetoxymethyl)-2-phenyl-malonic acid diethyl ester, 2-(2-{4-[(4'-cyano-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4-methyl-4'-trifluromethyl-biphenyl-2-carbonyl)-amino]-phenyl}-acetoxymethyl)-2-phenyl-malonic acid diethyl ester, 2-(2-{3-dimethylcarbamoyl-4-[(5-methyl-4'-trifluromethyl-biphenyl-2-carbonyl)-amino]-phenyl}-acetoxymethyl)-2-phenyl-malonic acid diethyl ester, {3-dimethylcarbamoyl-4-[(4'-trifluoromethyl-biphenyl-2-carbonyl)-amino]-phenyl}-acetic acid 2-methanesulfonylamino-2-phenyl-ethyl ester, 3-(2-{3-dimethylcarbamoyl-4-[(4'-trifluoromethyl-biphenyl-2-carbonyl)-amino]-phenyl}-acetoxy)-2-phenyl-propionic acid ethyl ester, {3-dimethylcarbamoyl-4-[(4'-trifluoromethyl-biphenyl-2-carbonyl)-amino]-phenyl}-acetic acid 2-(methyl-propionyl-amino)-2-phenyl-ethyl ester, 2-[3-(2-{3-dimethylcarbamoyl-4-[(4'-trifluromethyl-biphenyl-2-carbonyl)-amino]-phenyl}-acetoxy)-propyl]-2-phenyl-malonic acid diethyl ester, 2-(2-{3-dimethylcarbamoyl-4-[(5-methoxy-4'-trifluromethyl-biphenyl-2-carbonyl)-amino]-phenyl}-acetoxymethyl)-2-phenyl-malonic acid diethyl ester, 2-(2-{4-[(5-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-methyl-4'-trifluromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid di-2,2,2-trifluoroethyl ester, 2-(2-{3-dimethylcarbamoyl-4-((2'-fluoro-4'-trifluromethyl-biphenyl-2-carbonyl)-amino]-phenyl}-acetoxymethyl)-2-phenyl-malonic acid diethyl ester, 2-(2-{5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-4-[(4'-trifluromethyl-biphenyl-2-carbonyl)-amino]-phenyl}-acetoxymethyl)-2-phenyl-malonic acid diethyl ester, 2-(2-{3-chloro-5-dimethylcarbamoyl-4-[(4'-trifluromethyl-biphenyl-2-carbonyl)-amino]-phenyl}-acetoxymethyl)-2-phenyl-malonic acid diethyl ester, 2-(2-{3-dimethylcarbamoyl-4-[(3'-fluoro-4'-trifluromethyl-biphenyl-2-carbonyl)-amino]-phenyl}-acetoxymethyl)-2-phenyl-malonic acid diethyl ester, 2-(2-{4-[(3'-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-nitro-pyridin-2-yl)-malonic acid diethyl ester, 2-(5-amino-pyridin-2-yl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-pyridin-2-yl-malonic acid diethyl ester, 2-(2-{3-chloro-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2o-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-m-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-p-tolyl-malonic acid diethyl ester, 2-(2-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(4-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-succinic acid diethyl ester, 2-(2-{3-dimethylcarbamoyl-4-[(4'-trifluoromethyl-biphenyl-2-carbonyl)-amino]-phenyl}-acetoxymethyl)-2-(2-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(4-methoxy-phenyl)-malonic acid diethyl ester, 2-(2-{4-[(5,4'-bis-trifluoromethyl-biphenyl-2-carbonyl)-amino]-3-dimethylcarbamoyl-phenyl}-acetoxymethyl)-2-phenyl-malonic acid diethyl ester, 2-(2-{4-[(6-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-fluoro-4'-trifluoromethyl-biphenyl-2-carbonyl)-amino]-phenyl}-acetoxymethyl)-2-phenyl-malonic acid diethyl ester, 2-[2-(2-{3-dimethylcarbamoyl-4-[(5-methyl-4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(5-ethoxy-4'-trifluromethyl-biphenyl-2-carbonyl)-amino]-phenyl}-acetoxymethyl)-2-phenyl-malonic acid diethyl ester, 2-(2-{3-dimethylcarbamoyl-4-[(5-isopropoxy-4'-trifluoromethyl-biphenyl-2-carbonyl)-amino]-phenyl}-acetoxymethyl)-2-phenyl-malonic acid diethyl ester, 2-[2-(2-{4-(5,4'-bis-trifluoromethyl-biphenyl-2-carbonyl)-amino]-3-dimethylcarbamoyl-phenyl}-acetoxy)-ethyl]-2-phenyl-malonic acid diethyl ester, 2-(2-{3-dimethylcarbamoyl-4-(6-methoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3-methyl-4'-trifluoromethyl-biphenyl-2-carbonyl)-amino]-phenyl}-acetoxymethyl)-2-phenyl-malonic acid diethyl ester, 2-(2-{4-(2,4-bis-trifluoromethyl-benzoylamino)-3-dimethylcarbamoyl-phenyl]-acetoxymethyl}-2-phenyl-malonic acid diethyl ester, 2-(2-{3-dimethylcarbamoyl-4-[(4'-methyl-biphenyl-2-carbonyl)-amino]-phenyl}-acetoxymethyl)-2-phenyl-malonic acid diethyl ester, 2-{2-[3-dimethylcarbamoyl-4-[(2-ethyl-4-trifluoromethyl-benzoylamino)-phenyl]-acetoxymethyl}-2-phenyl-malonic acid diethyl ester, 2-(2-{3-dimethylcarbamoyl-4-[(4'-ethyl-biphenyl-2-carbonyl)-amino]-phenyl}-acetoxymethyl)-2-phenyl-malonic acid diethyl ester, 2-(2-{3-dimethylcarbamoyl-4-[(4'-isopropenyl-biphenyl-2-carbonyl)-amino]-phenyl}-acetoxymethyl)-2-phenyl-malonic acid diethyl ester, 2-(2-{3-dimethylcarbamoyl-4-[(4'-isopropyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyloxy)-phenyl]]-acetoxymethyl}-2-phenyl-malonic acid diethyl ester, {3-dimethylcarbamoyl-4-[(4'-trifluoromethyl-biphenyl-2-carbonyl)-amino]-phenyl}-acetic acid 2-ethyl-2-phenyl-butyl ester, {3-dimethylcarbamoyl-4-[(4'-trifluoromethyl-biphenyl-2-carbonyl)-amino]-phenyl}-acetic acid 1-phenyl-cyclopropylmethyl ester, {3-dimethylcarbamoyl-4-[(4'-trifluoromethyl-biphenyl-2-carbonyl)-amino]-phenyl}-acetic acid 2,2-diphenyl-ethyl ester, {3-dimethylcarbamoyl-4-[(4'-trifluoromethyl-biphenyl-2-carbonyl)-amino]-phenyl}-acetic acid 1-phenyl-cyclopentylmethyl ester, {3-dimethylcarbamoyl-4-[(4'-trifluoromethyl-biphenyl-2-carbonyl)-amino]-phenyl}-acetic acid 3-hydroxy-2-hydroxymethyl-2-phenyl-propyl ester, {3-dimethylcarbamoyl-4-[(4'-trifluoromethyl-biphenyl-2-carbonyl)-amino]-phenyl}-acetic acid 3-acetoxymethyl-2-phenyl-propyl ester, 2-(2-{3-dimethylcarbamoyl-4-[(4'-trifluoromethyl-biphenyl-2-carbonyl)-amino]-phenyl}-acetoxymethyl]-2-thiophen-2-yl-malonic acid diethyl ester, 2-(2-{3-dimethylcarbamoyl-4-[(4'-trifluoromethyl-biphenyl-2-carbonyl)-amino]-phenyl}-acetoxymethyl]-2-thiophen-3-yl-malonic acid diethyl ester, 2-(2-{4-dimethylcarbamoyl-5-[(4'-trifluoromethyl-biphenyl-2-carbonyl)-amino]-pyridin-2-yl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl]-2-(3-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-thiazol-2-yl-malonic acid diethyl ester, 2-(2-{3-ethoxy-4-[(4'-trifluoromethyl-biphenyl-2-carbonyl)-amino]-phenyl}-acetoxymethyl)-2-phenyl-malonic acid diethyl ester, {3-hydroxy-4-[(4'-trifluoromethyl-biphenyl-2-carbonyl)-amino]-phenyl}-acetic acid 2,2-bis-ethylcarbamoyl-2-phenyl-ethyl ester {3-methoxy-4-[(4'-trifluoromethyl-biphenyl-2-carbonyl)-amino]-phenyl}-acetic acid 2,2-bis-ethylcarbamoyl-2-phenyl-ethyl ester 2-(2-{3-methoxy-4-[(4'-trifluoromethyl-biphenyl-2-carbonyl)-amino]-phenyl}-acetoxymethyl)-2-phenyl-malonic acid diethyl ester, {3-methoxy-4-[(4'-trifluoromethyl-biphenyl-2-carbonyl)-amino]-phenyl}-acetic acid 2-phenyl-2,2-bis-propylcarbamoyl-ethyl ester, {3-methoxy-4-[(4'-trifluoromethyl-biphenyl-2-carbonyl)-amino]-phenyl}-acetic acid 3,3-bis-ethylcarbamoyl-3-phenyl-propyl ester, {3-ethoxy-4-[(4'-trifluoromethyl-biphenyl-2-carbonyl)-amino]-phenyl}-acetic acid 2,2-bis-ethylcarbamoyl-2-phenyl-ethyl ester, {3-ethoxy-4-[(4'-trifluoromethyl-biphenyl-2-carbonyl)-amino]-phenyl}-acetic acid 3,3-bis-ethylcarbamoyl-3-phenyl-propyl ester, 2-(2-{3-isopropoxy-4-[(4'-trifluoromethyl-biphenyl-2-carbonyl)-amino]-phenyl}-acetoxymethyl)-2-phenyl-malonic acid diethyl ester, {3-isopropoxy-4-[(4'-trifluoromethyl-biphenyl-2-carbonyl)-amino]-phenyl}-acetic acid 2,2-bis-ethylcarbamoyl-2-phenyl-ethyl ester, {3-isopropoxy-4-[(4'-trifluoromethyl-biphenyl-2-carbonyl)-amino]-phenyl}-acetic acid 3,3-bis-ethylcarbamoyl-3-phenyl-propyl ester, {3-propoxy-4-[(4'-trifluoromethyl-biphenyl-2-carbonyl)-amino]-phenyl}-acetic acid 2,2-bis-ethylcarbamoyl-2-phenyl-ethyl ester, {3-benzyloxy-4-[(4'-trifluoromethyl-biphenyl-2-carbonyl)-amino]-phenyl}-acetic acid 2,2-bis-ethylcarbamoyl-2-phenyl-ethyl ester, 2-(2-{3-benzyloxy-4-[(4'-trifluoromethyl-biphenyl-2-carbonyl)-amino]-phenyl}-acetoxymethyl)-2-phenyl-malonic acid diethyl ester, 2-(2-{3-hydroxy-4-[(4'-trifluoromethyl-biphenyl-2-carbonyl)-amino]-phenyl}-acetoxymethyl)-2-phenyl-malonic acid diethyl ester, 2-(2-{3-methoxy-4-(4'-trifluoromethyl-biphenyl-2-carbonyloxy)-phenyl]-acetoxymethyl}-2-phenyl-malonic acid diethyl ester, {3-dimethylamino-4-[(4'-trifluoromethyl-biphenyl-2-carbonyl)-amino]-phenyl}-acetic acid 2,2-bis-ethylcarbamoyl-2-phenyl-ethyl ester, {3-piperidin-1-yl-4-[(4'-trifluoromethyl-biphenyl-2-carbonyl)-amino]-phenyl}-acetic acid 2,2-bis-ethylcarbamoyl-2-phenyl-ethyl ester, {3-pyrrolidin-1-yl-4-[(4'-trifluoromethyl-biphenyl-2-carbonyl)-amino]-phenyl}-acetic acid 2,2-bis-ethylcarbamoyl-2-phenyl-ethyl ester, 2-phenyl-2-(2-{3-piperidin-1-yl-4-[(4'-trifluoromethyl-biphenyl-2-carbonyl)-amino]-phenyl}-acetoxymethyl)-malonic acid diethyl ester, 2-phenyl-2-(2-{3-pyrrolidin-1-yl-4-[(4'-trifluoromethyl-biphenyl-2-carbonyl)-amino]-phenyl}-acetoxymethyl)-malonic acid diethyl ester, 2-(2-{3-dimethylamino-4-[(4'-trifluoromethyl-biphenyl-2-carbonyl)-amino]-phenyl}-acetoxymethyl)-2-phenyl-malonic acid diethyl ester, 2-(2-{3-morpholin-4-yl-4-[(4'-trifluoromethyl-biphenyl-2-carbonyl)-amino]-phenyl}-acetoxymethyl)-2-phenyl-malonic acid diethyl ester, 2-(2-{3-diethylamino-4-[(4'-trifluoromethyl-biphenyl-2-carbonyl)-amino]-phenyl}-acetoxymethyl)-2-phenyl-malonic acid diethyl ester, 2-[2-(2-{2-methyl-3-[(4'-trifluoromethyl-biphenyl-2-carbonyl)-amino]-phenyl}-acetoxy)-ethyl]-2-phenyl-malonic acid diethyl ester, 2-phenyl-2-(2-{3-[(4'-trifluoromethyl-biphenyl-2-carbonyl)-amino]-phenyl}-acetoxymethyl)-malonic acid diethyl ester, 2-phenyl-2-[2-(2-{3-[(4'-trifluoromethyl-biphenyl-2-carbonyl)-amino]-phenyl}-acetoxy)-ethyl]-malonic acid diethyl ester, {3-[(4'-trifluoromethyl-biphenyl-2-carbonyl)-amino]-phenyl}-acetic acid 3,3-bis-ethylcarbamoyl-3-phenyl-propyl ester, {3-[(4'-trifluoromethyl-biphenyl-2-carbonyl)-amino]-phenyl}-acetic acid 3-phenyl-3,3-bis-propylcarbamoyl-propyl ester, 2-[2-{2-[4-methyl-3-[(4'-trifluoromethyl-biphenyl-2-carbonyl)-amino]-phenyl}-acetoxy]-ethyl]-2-phenyl-malonic acid diethyl ester, 2-[2-(2-{2-methyl-5-[(4'-trifluoromethyl-biphenyl-2-carbonyl)-amino]-phenyl}-acetoxy)-ethyl]-2-phenyl-malonic acid diethyl ester, {3-[(4'-trifluoromethyl-biphenyl-2-carbonyl)-amino]-phenyl}-acetic acid 3,3-bis-isopropylcarbamoyl-3-phenyl-propyl ester, {2-methyl-3-[(4'-trifluoromethyl-biphenyl-2-carbonyl)-amino]-phenyl}-acetic acid 3,3-bis-ethylcarbamoyl-3-phenyl-propyl ester, {2-methyl-3-[(4'-trifluoromethyl-biphenyl-2-carbonyl)-amino]-phenyl}-acetic acid 4,4-bis-ethylcarbamoyl-4-phenyl-butyl ester, {2-methyl-3-[(4'-trifluoromethyl-biphenyl-2-carbonyl)-amino]-phenyl}-acetic acid 3-phenyl-3,3-bis-propylcarbamoyl-propyl ester, {2-methoxy-3-[(4'-trifluoromethyl-biphenyl-2-carbonyl)-amino]-phenyl}-acetic acid 3,3-bis-ethylcarbamoyl-3-phenyl-propyl ester, 2-[2-{2-(2-methoxy-3-[(4'-trifluoromethyl-biphenyl-2-carbonyl)-amino]-phenyl}-acetoxy)-ethyl]-2-phenyl-malonic acid diethyl ester, {2-ethoxy-3-[(4'-trifluoromethyl-biphenyl-2-carbonyl)-amino]-phenyl}-acetic acid 3,3-bis-ethylcarbamoyl-3-phenyl-propyl ester, 2-[2-(2-{2-ethoxy-3-[(4'-trifluoromethyl-biphenyl-2-carbonyl)-amino]-phenyl}-acetoxy)-ethyl]-2-phenyl-malonic acid diethyl ester, 2-[2-(2-{2-isopropoxy-3-[(4'-trifluoromethyl-biphenyl-2-carbonyl)-amino]-phenyl}-acetoxy)-ethyl]-2-phenyl-malonic acid diethyl ester, 2-[2-(2-{2-methoxycarbonyl-3-[(4'-trifluoromethyl-biphenyl-2-carbonyl)-amino]-phenyl}-acetoxy)-ethyl]-2-phenyl-malonic acid diethyl ester, 2-[2-(2-{2-ethoxy-5-methyl-3-[(4'-trifluoromethyl-biphenyl-2-carbonyl)-amino]-phenyl}-acetoxy)-ethyl]-2-phenyl-malonic acid diethyl ester, 4-[(4'-trifluoromethyl-biphenyl-2-carbonyl)-amino]-benzoic acid 2-[(biphenyl-2-carbonyl)-amino]-ethyl ester, 4-[(4'-trifluoromethyl-biphenyl-2-carbonyl)-amino]-benzoic acid 2-(2-biphenyl-2-yl-acetylamino)-ethyl ester, 4-[(4'-trifluoromethyl-biphenyl-2-carbonyl)-amino]-benzoic acid 3-naphthalen-1-yl-3-(2,2,2-trifluoroethylcarbamoyl)-propyl ester, 4-[(4'-trifluoromethyl-biphenyl-2-carbonyl)-amino]-benzoic acid 3-[2-(2,2,2-trifluoro-ethylcarbamoyl)-naphthalen-1-yl]-propyl ester, 4-[(4'-trifluoromethyl-biphenyl-2-carbonyl)-amino]-benzoic acid 3,3-diphenyl-3-(2,2,2-trifluoro-ethylcarbamoyl)-propyl ester, 4-[(4'-trifluoromethyl-biphenyl-2-carbonyl)-amino]-benzoic acid 3-biphenyl-2-yl-3-(2,2,2-trifluoro-ethylcarbamoyl)-propyl ester, 4-[(4'-trifluoromethyl-biphenyl-2-carbonyl)-amino]-benzoic acid 3-phenyl-3-(2,2,2-trifluoro-ethylcarbamoyl)-propyl ester, 4-[(4'-trifluoromethyl-biphenyl-2-carbonyl)-amino]-benzoic acid 2-[8-(2,2,2-trifluoro-ethylcarbamoyl)-naphthalen-1-yl]-ethyl ester, 4-[(4'-trifluoromethyl-biphenyl-2-carbonyl)-amino]-benzoic acid 3-(2,6-dichloro-phenyl)-3-(2,2,2-trifluoro-ethylcarbamoyl)-propyl ester, 4-[(4'-trifluoromethyl-biphenyl-2-carbonyl)-amino]-benzoic acid 3-(2-chloro-phenyl)-3-(2,2,2-trifluoro-ethylcarbamoyl)-propyl ester, 2-phenyl-2-(2-{4-[(4'-trifluoromethyl-biphenyl-2-carbonyl)-amino]-benzoyloxy}-ethyl)-malonic acid diethyl ester, 2-(2-{3-methyl-4-[(4'-trifluoromethyl-biphenyl-2-carbonyl)-amino]-benzoyloxy}-ethyl)-2-phenyl-malonic acid diethyl ester, 2-(2-{2-chloro-4-[(4'-trifluoromethyl-biphenyl-2-carbonyl)-amino]-benzoyloxy}-ethyl)-2-phenyl-malonic acid diethyl ester, 2-phenyl-2-{2-[4-(4'-trifluoromethyl-biphenyl-2-carbonyloxy)-benzoyloxy]-ethyl}-malonic acid diethyl ester, 4-[(4'-trifluoromethyl-biphenyl-2-carbonyl)-amino]-benzoic acid 3,3-bis-ethylcarbamoyl-3-phenyl-propyl ester, 4'-trifluoromethyl-biphenyl-2-carboxylic acid 4-(3,3-bis-ethylcarbamoyl-3-phenyl-propoxycarbonyl)-2-chlorophenyl ester, 4'-trifluoromethyl-biphenyl-2-carboxylic acid 4-(3,3-bis-ethylcarbamoyl-3-phenyl-propoxycarbonyl)-phenyl ester, 4'-trifluoromethyl-biphenyl-2-carboxylic acid 4-(3,3-bis-ethylcarbamoyl-3-phenyl-propoxycarbonyl)-2,6-dichloro-p henyl ester, 2-(2-{3-ethoxycarbonyl-4-[(4'-trifluoromethyl-biphenyl-2-carbonyl)-amino]-phenyl}-acetoxymethyl)-2-phenyl-malonic acid diethyl ester, 2-(3-{3-dimethylcarbamoyl-4-[(4'-trifluoromethyl-biphenyl-2-carbonyl)-amino]-phenyl}-propionyloxymethyl)-2-phenyl-malonic acid diethyl ester, 3-{4-[(4'-trifluoromethyl-biphenyl-2-carbonyl)-amino]-phenyl}-propionic acid ethylcarbamoyl-phenyl-methyl ester, 5-(2,2-bis-ethylcarbamoyl-2-phenyl-ethoxycarbonyl-methyl)-2-4-[(4'-trifluoromethyl-biphenyl-2-carbonyl)-amino]-benzoic acid benzyl ester, 5-(2,2-bis-ethylcarbamoyl-2-phenyl-ethoxycarbonyl-methyl)-2-4-[(4'-trifluoromethyl-biphenyl-2-carbonyl)-amino]-benzoic acid, 5-(2,2-bis-ethylcarbamoyl-2-phenyl-ethoxycarbonyl-methyl)-2-[(4'-trifluoromethyl-biphenyl-2-carbonyl)-amino]-benzoic acid ethyl ester, 5-(2,2-bis-ethylcarbamoyl-2-phenyl-ethoxycarbonyl-methyl)-2-[(4'-trifluoromethyl-biphenyl-2-carbonyl)-amino]-benzoic acid methyl ester, 2-(2-{3-benzyloxycarbonyl-4-[(4'-trifluoromethyl-biphenyl-2-carbonyl)-amino]-phenyl}-acetoxymethyl)-2-phenyl-malonic acid diethyl ester, 2-(2-{3-carboxy-4-[(4'-trifluoromethyl-biphenyl-2-carbonyl)-amino]-phenyl}-acetoxymethyl)-2-phenyl-malonic acid diethyl ester, 2-(2-{3-isopropoxycarbonyl-4-[(4'-trifluoromethyl-biphenyl-2-carbonyl)-amino]-phenyl}-acetoxymethyl)-2-phenyl-malonic acid diethyl ester, 2-(2-{3-methoxycarbonyl-4-[(4'-trifluoromethyl-biphenyl-2-carbonyl)-amino]-phenyl}-acetoxymethyl)-2-phenyl-malonic acid diethyl ester, 2-(2-{3-acetylamino-4-[(4'-trifluoromethyl-biphenyl-2-carbonyl)-amino]-phenyl}-acetoxymethyl)-2-phenyl-malonic acid diethyl ester, 2-(2-{3-methoxycarbonylamino-4-[(4'-trifluoromethyl-biphenyl-2-carbonyl)-amino]-phenyl}-acetoxymethyl)-2-phenyl-malonic acid diethyl ester, 2-(2-{3-(4-methyl-thiazol-2-yl)-4-[(4'-trifluoromethyl-biphenyl-2-carbonyl)-amino]-phenyl}-acetoxymethyl)-2-phenyl-malonic acid diethyl ester, 2-phenyl-(2-{6-[(4'-trifluoromethyl-biphenyl-2-carbonyl)-amino]-biphenyl-3-yl}-acetoxymethyl)-malonic acid diethyl ester, 2-(2-{3-formyl-4-[(4'-trifluoromethyl-biphenyl-2-carbonyl)-amino]-phenyl}-acetoxymethyl)-2-phenyl-malonic acid diethyl ester, 2-(2-{3-dimethylaminomethyl-4-[(4'-trifluoromethyl-biphenyl-2-carbonyl)-amino]-phenyl}-acetoxymethyl)-2-phenyl-malonic acid diethyl ester, 2-(2-{3-(methoxy-methylcarbamoyl)-4-[(4'-trifluoromethyl-biphenyl-2-carbonyl)-amino]-phenyl}-acetoxymethyl)-2-phenyl-malonic acid diethyl ester, 2-(2-{3-isobutyryl-4-[(4'-trifluoromethyl-biphenyl-2-carbonyl)-amino]-phenyl}-acetoxymethyl)-2-phenyl-malonic acid diethyl ester, and 2-(2-{3-(1-hydroxy-2-methyl-propyl)-4-[(4'-trifluoromethyl-biphenyl-2-carbonyl)-amino]-phenyl}-acetoxymethyl)-2-phenyl-malonic acid diethyl ester;

(25) The ester compound or a prodrug thereof, or a pharmaceutically acceptable salt of either according to the above (1), which is selected from the group consisting of {4-[(4'-trifluoromethyl-biphenyl-2-carbonyl)-amino]-phenyl}-acetic acid 2,2-bis-ethylcarbamoyl-2-phenyl-ethyl ester, {3-ethyl-4-[(4'-trifluoromethyl-biphenyl-2-carbonyl)-amino]-phenyl}-acetic acid 2,2-bis-ethylcarbamoyl-2-phenyl-ethyl ester, {4-[(4'-trifluoromethyl-biphenyl-2-carbonyl)-amino]-phenyl}-acetic acid 2-phenyl-2,2-bis-(2,2,2-trifluoro-ethylcarbamoyl)-ethyl ester, {4-[(4'-trifluoromethyl-biphenyl-2-carbonyl)-amino]-phenyl}-acetic acid 2,2-bis-cyclohexylcarbamoyl-2-phenyl-ethyl ester, {4-[(4'-trifluoromethyl-biphenyl-2-carbonyl)-amino]-phenyl}-acetic acid 2-phenyl-2,2-bis-phenylcarbamoyl-ethyl ester, {4-[(4'-trifluoromethyl-biphenyl-2-carbonyl)-amino]-phenyl}-acetic acid 2,2-bis-isopropylcaramoyl-2-phenyl-ethyl ester, 4'-trifluoromethyl-biphenyl-2-carboxylic acid 4-[2-phenyl-2,2-bis-(2,2,2-trifluoro-ethylcarbamoyl)-ethoxycarbonylmethyl]-phenyl ester, biphenyl-2-carboxylic acid 4-[2-phenyl-2,2-bis-(2,2,2-trifluoro-ethylcarbamoyl)-ethoxycarbonylmethyl]-phenyl ester, {4-[(biphenyl-2-carbonyl)-amino]-phenyl}-acetic acid 2-phenyl-2,2-bis-(2,2,2-trifluoro-ethylcarbamoyl)-ethyl ester, 2-phenyl-2-(2-{2-trifluoromethyl-4-[(4'-trifluoromethyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 2,2-bis-methylcarbamoyl-2-phenyl-ethyl ester, 4'-trifluoromethyl-biphenyl-2-carboxylic acid 4-(2,2-bis-ethylcarbamoyl-2-phenyl-ethoxycarbonylmethyl)-phenyl ester, {4-[(4'-trifluoromethyl-biphenyl-2-carbonyl)-amino]-phenyl}-acetic acid 2,2-bis-butylcarbamoyl-2-phenyl-ethyl ester, {3-methyl-4-[(4'-trifluoromethyl-biphenyl-2-carbonyl)-amino]-phenyl}-acetic acid 2,2-bis-ethylcarbamoyl-2-phenyl-ethyl ester, {4-[(4'-trifluoromethyl-biphenyl-2-carbonyl)-amino]-phenyl}-acetic acid 3,3-bis-ethylcarbamoyl-3-phenyl-propyl ester, {4-[(4'-trifluoromethyl-biphenyl-2-carbonyl)-amino]-phenyl}-acetic acid 3-phenyl-3,3-bis-propylcarbamoyl-propyl ester, {4-[(biphenyl-2-carbonyl)-amino]-phenyl}-acetic acid 2,2-bis-ethylcarbamoyl-2-phenyl ethyl ester, 4'-trifluoromethyl-biphenyl-2-carboxylic acid 4-(2,2-bis-ethylcarbamoyl-2-phenyl-ethoxycarbonylmethyl)-2-chloro-phenyl ester, {4-[(4'-trifluoromethyl-biphenyl-2-carbonyl)-amino]-phenyl}-acetic acid 2,2-bis-isobutylcarbamoyl-2-phenyl ethyl ester, {4-[(4'-trifluoromethyl-biphenyl-2-carbonyl)-amino]-phenyl}-acetic acid 2,2-bis-(3-methyl-butylcarbamoyl)-2-phenyl ethyl ester, {4-[(4'-chloro-biphenyl-2-carbonyl)-amino]-phenyl}-acetic acid 2,2-bis-ethylcarbamoyl-2-phenyl ethyl ester, {4-[(3',4'-dichloro-biphenyl-2-carbonyl)-amino]-phenyl}-acetic acid 2,2-bis-ethylcarbamoyl)-2-phenyl-ethyl ester, {3-methyl-4-[(4'-trifluoromethyl-biphenyl-2-carbonyl)-amino]-phenyl}-acetic acid 2-phenyl-2,2-bis-propylcarbamoyl)-ethyl ester, {4-[(4'-trifluoromethyl-biphenyl-2-carbonyl)-amino]-phenyl}-acetic acid 2,2-bis-(2-methoxy-ethylcarbamoyl)-2-phenyl-ethyl ester, {3-isopropyl-4-[(4'-trifluoromethyl-biphenyl-2-carbonyl)-amino]-phenyl}-acetic acid 2,2-bis-ethylcarbamoyl-phenyl-ethyl ester, {3-ethyl-4-[(4'-trifluoromethyl-biphenyl-2-carbonyl)-amino]-phenyl}-acetic acid 3,3-bis-ethylcarbamoyl-3-phenyl-propyl ester, {3-isobutyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 2-phenyl-2,2-bis-propylcarbamoyl-ethyl ester, {3-methylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 3,3-bis-ethylcarbamoyl-3-phenyl-propyl ester, {3-benzylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 4,4-bis-ethylcarbamoyl-4-phenyl-butyl ester, {3-diethylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-diisopropylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-(isopropyl-methylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(ethyl-methylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(ethyl-methylcarbamoyl)-4-[(4'-trifluoromethyl-biphenyl-2-carbonyl)-amino]-phenyl}-acetic acid 3,3-bis-ethylcarbamoyl-3-phenyl-propyl ester, {3-(piperidin-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(pyrrolidin-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 3,3-bis-ethylcarbamoyl-3-phenyl-propyl ester, {3-hydroxy-4-[(4'-trifluoromethyl-biphenyl-2-carbonyl)-amino]-phenyl}-acetic acid 2,2-bis-ethylcarbamoyl-2-phenyl-ethyl ester, {3-methoxy-4-[(4'-trifluoromethyl-biphenyl-2-carbonyl)-amino]-phenyl}-acetic acid 2,2-bis-ethylcarbamoyl-2-phenyl-ethyl ester, {3-methoxy-4-[(4'-trifluoromethyl-biphenyl-2-carbonyl)-amino]-phenyl}-acetic acid 2-phenyl-2,2-bis-propylcarbamoyl-ethyl ester, {3-methoxy-4-[(4'-trifluoromethyl-biphenyl-2-carbonyl)-amino]-phenyl}-acetic acid 3,3-bis-ethylcarbamoyl-3-phenyl-propyl ester, {3-ethoxy-4-[(4'-trifluoromethyl-biphenyl-2-carbonyl)-amino]-phenyl}-acetic acid 2,2-bis-ethylcarbamoyl-2-phenyl-ethyl ester, {3-ethoxy-4-[(4'-trifluoromethyl-biphenyl-2-carbonyl)-amino]-phenyl}-acetic acid 3,3-bis-ethylcarbamoyl-3-phenyl-propyl ester, {3-isopropoxy-4-[(4'-trifluoromethyl-biphenyl-2-carbonyl)-amino]-phenyl}-acetic acid 2,2-bis-ethylcarbamoyl-2-phenyl-ethyl ester, {3-isopropoxy-4-[(4'-trifluoromethyl-biphenyl-2-carbonyl)-amino]-phenyl}-acetic acid 3,3-bis-ethylcarbamoyl-3-phenyl-propyl ester, {3-propoxy-4-[(4'-trifluoromethyl-biphenyl-2-carbonyl)-amino]-phenyl}-acetic acid 2,2-bis-ethylcarbamoyl-2-phenyl-ethyl ester, {3-benzyloxy-4-[(4'-trifluoromethyl-biphenyl-2-carbonyl)-amino]-phenyl}-acetic acid 2,2-bis-ethylcarbamoyl-2-phenyl-ethyl ester, {3-dimethylamino-4-[(4'-trifluoromethyl-biphenyl-2-carbonyl)-amino]-phenyl}-acetic acid 2,2-bis-ethylcarbamoyl-2-phenyl-ethyl ester, {3-piperidin-1-yl-4-[(4'-trifluoromethyl-biphenyl-2-carbonyl)-amino]-phenyl}-acetic acid 2,2-bis-ethylcarbamoyl-2-phenyl-ethyl ester, {3-pyrrolidin-1-yl-4-[(4'-trifluoromethyl-biphenyl-2-carbonyl)-amino]-phenyl}-acetic acid 2,2-bis-ethylcarbamoyl-2-phenyl-ethyl ester, {3-[(4'-trifluoromethyl-biphenyl-2-carbonyl)-amino]-phenyl}-acetic acid 3,3-bis-ethylcarbamoyl-3-phenyl-propyl ester, {3-[(4'-trifluoromethyl-biphenyl-2-carbonyl)-amino]-phenyl}-acetic acid 3-phenyl-3,3-bis-propylcarbamoyl-propyl ester, {3-[(4'-trifluoromethyl-biphenyl-2-carbonyl)-amino]-phenyl}-acetic acid 3,3-bis-isopropylcarbamoyl-3-phenyl-propyl ester, {2-methyl-3-[(4'-trifluoromethyl-biphenyl-2-carbonyl)-amino]-phenyl}-acetic acid 3,3-bis-ethylcarbamoyl-3-phenyl-propyl ester, {2-methyl-3-[(4'-trifluoromethyl-biphenyl-2-carbonyl)-amino]-phenyl}-acetic acid 4,4-bis-ethylcarbamoyl-4-phenyl-butyl ester, {2-methyl-3-[(4'-trifluoromethyl-biphenyl-2-carbonyl)-amino]-phenyl}-acetic acid 3-phenyl-3,3-bis-propylcarbamoyl-propyl ester, {2-methoxy-3-[(4'-trifluoromethyl-biphenyl-2-carbonyl)-amino]-phenyl}-acetic acid 3,3-bis-ethylcarbamoyl-3-phenyl-propyl ester, {2-ethoxy-3-[(4'-trifluoromethyl-biphenyl-2-carbonyl)-amino]-phenyl}-acetic acid 3,3-bis-ethylcarbamoyl-3-phenyl-propyl ester, 4-[(4'-trifluoromethyl-biphenyl-2-carbonyl)-amino]-benzoic acid 3,3-bis-ethylcarbamoyl-3-phenyl-propyl ester,
4'-trifluoromethyl-biphenyl-2-carboxylic acid 4-(3,3-bis-ethylcarbamoyl-3-phenyl-propoxycarbonyl)-2-chloro-phenyl ester,
4'-trifluoromethyl-biphenyl-2-carboxylic acid 4-(3,3-bis-ethylcarbamoyl-3-phenyl-propoxycarbonyl)-phenyl ester,
4'-trifluoromethyl-biphenyl-2-carboxylic acid 4-(3,3-bis-ethylcarbamoyl-3-phenyl-propoxycarbonyl)-2,6-dichloro-phenyl ester,
5-(2,2-bis-ethylcarbamoyl-2-phenyl-ethoxycarbonyl-methyl)-2-[(4'-trifluoromethyl-biphenyl-2-carbonyl)-amino]-benzoic acid benzyl ester,
5-(2,2-bis-ethylcarbamoyl-2-phenyl-ethoxycarbonyl-methyl)-2-[(4'-trifluoromethyl-biphenyl-2-carbonyl)-amino]-benzoic acid,
5-(2,2-bis-ethylcarbamoyl-2-phenyl-ethoxycarbonyl-methyl)-2-[(4'-trifluoromethyl-biphenyl-2-carbonyl)-amino]-benzoic acid ethyl ester, and
5-(2,2-bis-ethylcarbamoyl-2-phenyl-ethoxycarbonyl-methyl)-2-[(4'-trifluoromethyl-biphenyl-2-carbonyl)-amino]-benzoic acid methyl ester;

(26) The ester compound or a prodrug thereof, or a pharmaceutically acceptable salt of either according to the above (1), which is selected from the group consisting of
2-phenyl-2-{2-[4-(4'-trifluoromethyl-biphenyl-2-carbonyloxy)-phenyl]-acetoxymethyl}-malonic acid diethyl ester,
2-(2-{3-methyl-4-[(4'-trifluoromethyl-biphenyl-2-carbonyl)-amino]-phenyl}-acetoxymethyl)-2-phenyl-malonic acid diethyl ester,
2-(2-{4-[methyl-(4'-trifluoromethyl-biphenyl-2-carbonyl)-amino]-phenyl}-acetoxymethyl)-2-phenyl-malonic acid diethyl ester,
2-phenyl-2-(2-{4-[(4'-trifluoromethyl-biphenyl-2-carbonyl)-amino]-phenyl}-acetoxymethyl)-malonic acid diethyl ester,
2-phenyl-2-(2-{4-[(4'-trifluoromethyl-biphenyl-2-carbonyl)-amino]-phenyl}-acetoxymethyl)-malonic acid diisopropyl ester,
2-phenyl-2-(2-{4-[(4'-trifluoromethyl-biphenyl-2-carbonyl)-amino]-phenyl}-acetoxymethyl)-malonic acid dimethyl ester,
2-cyclopentyl-2-(2-{4-[(4'-trifluoromethyl-biphenyl-2-carbonyl)-amino]-phenyl}-acetoxymethyl)-malonic acid diethyl ester,
2-phenyl-2-(2-{4-[(4'-trifluoromethyl-biphenyl-2-carbonyl)-amino]-phenyl}-acetoxymethyl)-malonic acid dicyclohexyl ester,
2-benzyl-2-(2-{4-[(4'-trifluoromethyl-biphenyl-2-carbonyl)-amino]-phenyl}-acetoxymethyl)-malonic acid diethyl ester,
2-(2-{2-methyl-4-[(4'-trifluoromethyl-biphenyl-2-carbonyl)-amino]-phenyl}-acetoxymethyl)-2-phenyl-malonic acid diethyl ester,
2-cyclohexyl-2-(2-{4-[(4'-trifluoromethyl-biphenyl-2-carbonyl)-amino]-phenyl}-acetoxymethyl)-malonic acid diethyl ester,
2-phenyl-2-(2-{2-trifluoromethyl-4-[(4'-trifluoromethyl-biphenyl-2-carbonyl)-amino]-phenyl}-acetoxymethyl)-malonic acid diethyl ester,
2-pyridin-2-yl-2-(2-{4-[(4'-trifluoromethyl-biphenyl-2-carbonyl)-amino]-phenyl}-acetoxymethyl)-malonic acid diethyl ester,
2-pyridin-3-yl-2-(2-{4-[(4'-trifluoromethyl-biphenyl-2-carbonyl)-amino]-phenyl}-acetoxymethyl)-malonic acid diethyl ester,
2-phenyl-2-(2-{3-trifluoromethyl-4-[(4'-trifluoromethyl-biphenyl-2-carbonyl)-amino]-phenyl}-acetoxymethyl)-malonic acid diethyl ester,
2-(2-{4-[(4'-methyl-biphenyl-2-carbonyl)-amino]-phenyl}-acetoxymethyl)-2-phenyl-malonic acid diethyl ester,
2-(2-{4-[(4'-methoxy-biphenyl-2-carbonyl)-amino]-phenyl}-acetoxymethyl)-2-phenyl-malonic acid diethyl ester,
2-phenyl-2-(2-{4-[(3'-trifluoromethyl-biphenyl-2-carbonyl)-amino]-phenyl}-acetoxymethyl)-malonic acid diethyl ester,
2-(2-{4-[isopropyl-(4'-trifluoromethyl-biphenyl-2-carbonyl)-amino]-phenyl}-acetoxymethyl)-2-phenyl-malonic acid diethyl ester,
2-(2-{4-[cyclohexyl-(4'-trifluoromethyl-biphenyl-2-carbonyl)-amino]-phenyl}-acetoxymethyl)-2-phenyl-malonic acid diethyl ester,
2-phenyl-2-(2-{4-[(4'-trifluoromethyl-biphenyl-2-carbonyl)-amino]-phenyl}-acetoxymethyl)-malonic acid dipropyl ester,
2-phenyl-2-(2-{4-[(4'-trifluoromethyl-biphenyl-2-carbonyl)-amino]-phenyl}-acetoxymethyl)-malonic acid diisobutyl ester,
2-(2-{4-[ethyl-(4'-trifluoromethyl-biphenyl-2-carbonyl)-amino]-phenyl}-acetoxymethyl)-2-phenyl-malonic acid diethyl ester,
2-(2-{3-ethyl-4-[(4'-trifluoromethyl-biphenyl-2-carbonyl)-amino]-phenyl}-acetoxymethyl)-2-phenyl-malonic acid diethyl ester,
2-(2-{3-isopropyl-4-[(4'-trifluoromethyl-biphenyl-2-carbonyl)-amino]-phenyl}-acetoxymethyl)-2-phenyl-malonic acid diethyl ester,
2-(2-{3-isobutyl-4-[(4'-trifluoromethyl-biphenyl-2-carbonyl)-amino]-phenyl}-acetoxymethyl)-2-phenyl-malonic acid diethyl ester,
2-(2-{3-chloro-4-[(4'-trifluoromethyl-biphenyl-2-carbonyl)-amino]-phenyl}-acetoxymethyl)-2-phenyl-malonic acid diethyl ester,
2-(2-{3-bromo-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{3-diethylcarbamoyl-4-[(4'-trifluoromethyl-biphenyl-2-carbonyl)-amino]-phenyl}-acetoxymethyl)-2-phenyl-malonic acid diethyl ester,
2-(2-{3-diisopropylcarbamoyl-4-[(4'-trifluoromethyl-biphenyl-2-carbonyl)-amino]-phenyl}-acetoxymethyl)-2-phenyl-malonic acid diethyl ester,
2-(2-{3-(ethyl-methylcarbamoyl)-4-[(4'-trifluoromethyl-biphenyl-2-carbonyl)-amino]-phenyl}-acetoxymethyl)-2-phenyl-malonic acid diethyl ester,
2-[2-(2-{3-dimethylcarbamoyl-4-[(4'-trifluoromethyl-biphenyl-2-carbonyl)-amino]-phenyl}-acetoxy)-ethyl]-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{4-[(4'-bromo-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-malonic acid diethyl ester,
2-cyclopentyl-2-(2-{3-dimethylcarbamoyl-4-[(4'-trifluoromethyl-biphenyl-2-carbonyl)-amino]-phenyl}-acetoxymethyl)-malonic acid diethyl ester, 2-cyclohexyl-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{4-[(4'-chloro-biphenyl-2-carbonyl)-amino]-3-dimethylcarbamoyl-phenyl}-acetoxymethyl)-2-phenyl-malonic acid diethyl ester, 2-(2-{4-[(4'-acetyl-biphenyl-2-carbonyl)-amino]-3-dimethylcarbamoyl-phenyl}-acetoxymethyl)-2-phenyl-malonic acid diethyl ester, 2-(2-{4-[(4'-cyano-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-methyl-4'-trifluoromethyl-biphenyl-2-carbonyl)-amino]-phenyl}-acetoxymethyl)-2-phenyl-malonic acid diethyl ester, 2-[3-(2-{3-dimethylcarbamoyl-4-[(4'-trifluoromethyl-biphenyl-2-carbonyl)-amino]-phenyl}-acetoxy)-propyl]-2-phenyl-malonic acid diethyl ester, 2-(2-{3-dimethylcarbamoyl-4-[(5-methoxy-4'-trifluoromethyl-biphenyl-2-carbonyl)-amino]-phenyl}-acetoxymethyl)-2-phenyl-malonic acid diethyl ester, 2-(2-{4-[(5-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(2'-fluoro-4'-trifluoromethyl-biphenyl-2-carbonyl)-amino]-phenyl}-acetoxymethyl)-2-phenyl-malonic acid diethyl ester, 2-(2-{5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-4-[(4'-trifluoromethyl-biphenyl-2-carbonyl)-amino]-phenyl}-acetoxymethyl)-2-phenyl-malonic acid diethyl ester, 2-(2-{3-chloro-5-dimethylcarbamoyl-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3'-fluoro-4'-trifluoromethyl-biphenyl-2-carbonyl)-amino]-phenyl}-acetoxymethyl)-2-phenyl-malonic acid diethyl ester, 2-(2-{4-[(3'-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-nitro-pyridin-2-yl)-malonic acid diethyl ester, 2-(5-amino-pyridin-2-yl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-pyridin-2-yl-malonic acid diethyl ester, 2-(2-{3-chloro-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-o-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-m-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-p-tolyl-malonic acid diethyl ester, 2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(4-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-succinic acid diethyl ester, 2-(2-{3-dimethylcarbamoyl-4-[(4'-trifluoromethyl-biphenyl-2-carbonyl)-amino]-phenyl}-acetoxymethyl)-2-(2-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(4-methoxy-phenyl)-malonic acid diethyl ester, 2-(2-{4-[(5,4'-bis-trifluoromethyl-biphenyl-2-carbonyl)-amino]-3-dimethylcarbamoyl-phenyl}-acetoxymethyl)-2-phenyl-malonic acid diethyl ester, 2-(2-{4-[(6-chloro-4'-trifluoromethyl-biphenyl-2-carbonyl)-amino]-3-dimethylcarbamoyl-phenyl}-acetoxymethyl)-2-phenyl)-malonic acid diethyl ester, 2-(2-{3-dimethylcarbamoyl-4-[(6-fluoro-4'-trifluoromethyl-biphenyl-2-carbonyl)-amino]-phenyl}-acetoxymethyl)-2-phenyl)-malonic acid diethyl ester, 2-[2-(2-{3-dimethylcarbamoyl-4-[(5-methyl-4'-trifluoromethyl-biphenyl-2-carbonyl)-amino]-phenyl}-acetoxy)-ethyl]-2-phenyl)-malonic acid diethyl ester, 2-(2-{3-dimethylcarbamoyl-4-[(5-ethoxy-4'-trifluoromethyl-biphenyl-2-carbonyl)-amino]-phenyl}-acetoxymethyl)-2-phenyl)-malonic acid diethyl ester, 2-(2-{3-dimethylcarbamoyl-4-[(5-isopropoxy-4'-trifluoromethyl-biphenyl-2-carbonyl)-amino]-phenyl}-acetoxymethyl)-2-phenyl)-malonic acid diethyl ester, 2-[2-(2-{4-[(5,4'-bis-trifluoromethyl-biphenyl-2-carbonyl)-amino]-3-dimethylcarbamoyl-phenyl}-acetoxy)-ethyl]-2-phenyl-malonic acid diethyl ester, 2-(2-{3-dimethylcarbamoyl-4-[(6-methoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-methyl-biphenyl-2-carbonyl)-amino]-phenyl}-acetoxymethyl)-2-phenyl-malonic acid diethyl ester, 2-(2-{3-dimethylcarbamoyl-4-[(4'-ethyl-biphenyl-2-carbonyl)-amino]-phenyl}-acetoxymethyl)-2-phenyl-malonic acid diethyl ester, 2-(2-{3-dimethylcarbamoyl-4-[(4'-isopropenyl-biphenyl-2-carbonyl)-amino]-phenyl}-acetoxymethyl)-2-phenyl-malonic acid diethyl ester, 2-(2-{3-dimethylcarbamoyl-4-[(4'-isopropyl-biphenyl-2-carbonyl)-amino]-phenyl}-acetoxymethyl)-2-phenyl-malonic acid diethyl ester, 2-{2-[3-dimethylcarbamoyl-4-[(4'-trifluoromethyl-biphenyl-2-carbonyloxy)-phenyl]-acetoxymethyl}-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-thiophen-2-yl-malonic acid diethyl ester, 2-(2-{3-dimethylcarbamoyl-4-[(4'-trifluoromethyl-biphenyl-2-carbonyl)-amino]-phenyl}-acetoxymethyl)-2-thiophen-3-yl-malonic acid diethyl ester, 2-(2-{4-dimethylcarbamoyl-5-[(4'-trifluoromethyl-biphenyl-2-carbonyl)-amino]-pyridin-2-yl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-thiazol-2-yl-malonic acid diethyl ester, 2-(2-{3-ethoxy-4-[(4'-trifluoromethyl-biphenyl-2-carbonyl)-amino]-phenyl}-acetoxymethyl)-2-phenyl-malonic acid diethyl ester, 2-(2-{3-methoxy-4-[(4'-trifluoromethyl-biphenyl-2-carbonyl)-amino]-phenyl}-acetoxymethyl)-2-phenyl-malonic acid diethyl ester, 2-(2-{3-isopropoxy-4-[(4'-trifluoromethyl-biphenyl-2-carbonyl)-amino]-phenyl}-acetoxymethyl)-2-phenyl-malonic acid diethyl ester, 2-(2-{3-benzyloxy-4-[(4'-trifluoromethyl-biphenyl-2-carbonyl)-amino]-phenyl}-acetoxymethyl)-2-phenyl-malonic acid diethyl ester, 2-(2-{3-hydroxy-4-[(4'-trifluoromethyl-biphenyl-2-carbonyl)-amino]-phenyl}-acetoxymethyl)-2-phenyl-malonic acid diethyl ester, 2-(2-{3-methoxy-4-[(4'-trifluoromethyl-biphenyl-2-carbonyloxy)-phenyl]-acetoxymethyl}-2-phenyl-malonic acid diethyl ester, 2-phenyl-2-{2-(3-piperidin-1-yl-4-[(4'-trifluoromethyl-biphenyl-2-carbonyl)-amino]-phenyl}-acetoxymethyl)-malonic acid diethyl ester, 2-phenyl-2-(2-{3-pyrrolidin-1-yl-4-[(4'-trifluoromethyl-biphenyl-2-carbonyl)-amino]-phenyl}-acetoxymethyl)-malonic acid diethyl ester, 2-(2-{3-dimethylamino-4-[(4'-trifluoromethyl-biphenyl-2-carbonyl)-amino]-phenyl}-acetoxymethyl)-2-phenyl-malonic acid diethyl ester, 2-(2-{3-morpholin-4-yl-4-[(4'-trifluoromethyl-biphenyl-2-carbonyl)-amino]-phenyl}-acetoxymethyl)-2-phenyl-malonic acid diethyl ester, 2-(2-{3-diethylamino-4-[(4'-trifluoromethyl-biphenyl-2-carbonyl)-amino]-phenyl}-acetoxymethyl)-2-phenyl-malonic acid diethyl ester, 2-[2-(2-{2-methyl-3-[(4'-trifluoromethyl-biphenyl-2-carbonyl)-amino]-phenyl}-acetoxy)-ethyl)-2-phenyl-malonic acid diethyl ester, 2-phenyl-2-(2-{3-[(4'-trifluoromethyl-biphenyl-2-carbonyl)-amino]-phenyl}-acetoxymethyl)-malonic acid diethyl ester, 2-phenyl-2-[2-(2-{3-[(4'-trifluoromethyl-biphenyl-2-carbonyl)-amino]-phenyl}-acetoxy)-ethyl]-malonic acid diethyl ester, 2-[2-(2-{4-methyl-3-[(4'-trifluoromethyl-biphenyl-2-carbonyl)-amino]-phenyl}-acetoxy)-ethyl]-2-phenyl-malonic acid diethyl ester, 2-[2-(2-{2-methyl-5-[(4'-trifluoromethyl-biphenyl-2-carbonyl)-amino]-phenyl}-acetoxy)-ethyl]-2-phenyl-malonic acid diethyl ester, 2-[2-(2-{2-methoxy-3-[(4'-trifluoromethyl-biphenyl-2-carbonyl)-amino]-phenyl}-acetoxy)-ethyl]-2-phenyl-malonic acid diethyl ester, 2-[2-(2-{2-ethoxy-3-[(4'-trifluoromethyl-biphenyl-2-carbonyl)-amino]-phenyl}-acetoxy)-ethyl]-2-phenyl-malonic acid diethyl ester, 2-[2-(2-{2-isopropoxy-3-[(4'-trifluoromethyl-biphenyl-2-carbonyl)-amino]-phenyl}-acetoxy)-ethyl]-2-phenyl-malonic acid diethyl ester, 2-[2-(2-{2-methoxycarbonyl-3-[(4'-trifluoromethyl-biphenyl-2-carbonyl)-amino]-phenyl}-acetoxy)-ethyl]-2-phenyl-malonic acid diethyl ester, 2-[2-(2-{2-ethoxy-5-methyl-3-[(4'-trifluoromethyl-biphenyl-2-carbonyl)-amino]-phenyl}-acetoxy)-ethyl]-2-phenyl-malonic acid diethyl ester, 2-phenyl-2-(2-{4-[(4'-trifluoromethyl-biphenyl-2-carbonyl)-amino]-benzoyloxy}-ethyl]-malonic acid diethyl ester, 2-(2-{3-methyl-4-[(4'-trifluoromethyl-biphenyl-2-carbonyl)-amino]-benzoyloxy}-ethyl)-2-phenyl-malonic acid diethyl ester, 2-(2-{2-chloro-4-[(4'-trifluoromethyl-biphenyl-2-carbonyl)-amino]-benzoyloxy}-ethyl)-2-phenyl-malonic acid diethyl ester, 2-phenyl-2-{2-[4-(4'-trifluoromethyl-biphenyl-2-carbonyloxy)-benzoyloxy]-ethyl}-malonic acid diethyl ester, 2-(2-{3-ethoxycarbonyl-4-[(4'-trifluoromethyl-biphenyl-2-carbonyl)-amino]-phenyl}-acetoxymethyl)-2-phenyl-malonic acid diethyl ester, 2-(3-{3-dimethylcarbamoyl-4-[(4'-trifluoromethyl-biphenyl-2-carbonyl)-amino]-phenyl}-propionyloxymethyl)-2-phenyl-malonic acid diethyl ester, 2-(2-{3-benzyloxycarbony-4-[(4'-trifluoromethyl-biphenyl-2-carbonyl)-amino]-phenyl}-acetoxymethyl)-2-phenyl-malonic acid diethyl ester, 2-(2-{3-carboxy-4-[(4'-trifluoromethyl-biphenyl-2-carbonyl)-amino]-phenyl}-acetoxymethyl)-2-phenyl-malonic acid diethyl ester, 2-(2-{3-isopropoxycarbonyl-4-[(4'-trifluoromethyl-biphenyl-2-carbonyl)-amino]-phenyl}-acetoxymethyl)-2-phenyl-malonic acid diethyl ester, 2-(2-{3-methoxycarbonyl-4-[(4'-trifluoromethyl-biphenyl-2-carbonyl)-amino]-phenyl}-acetoxymethyl)-2-phenyl-malonic acid diethyl ester, 2-(2-{3-acetylamino-4-[(4'-trifluoromethyl-biphenyl-2-carbonyl)-amino]-phenyl}-acetoxymethyl)-2-phenyl-malonic acid diethyl ester, 2-(2-{3-methoxycarbonylamino-4-[(4'-trifluoromethyl-biphenyl-2-carbonyl)-amino]-phenyl}-acetoxymethyl)-2-phenyl-malonic acid diethyl ester, 2-(2-{3-(4-methyl-thiazol-2-yl)-4-[(4'-trifluoromethyl-biphenyl-2-carbonyl)-amino]-phenyl}-acetoxymethyl)-2-phenyl-malonic acid diethyl ester, 2-phenyl-2-(2-{6-[(4'-trifluoromethyl-biphenyl-2-carbonyl)-amino]-biphenyl-3-yl}-acetoxymethyl)-malonic acid diethyl ester, 2-(2-{3-formyl-4-[(4'-trifluoromethyl-biphenyl-2-carbonyl)-amino]-phenyl}-acetoxymethyl)-2-phenyl-malonic acid diethyl ester, 2-(2-{3-dimethylaminomethyl-4-[(4'-trifluoromethyl-biphenyl-2-carbonyl)-amino]-phenyl}-acetoxymethyl)-2-phenyl-malonic acid diethyl ester, 2-(2-{3-(methoxy-methylcarbamoyl)-4-[(4'-trifluoromethyl-biphenyl-2-carbonyl)-amino]-phenyl}-acetoxymethyl)-2-phenyl-malonic acid diethyl ester, 2-(2-{3-isobutyryl-4-[(4'-trifluoromethyl-biphenyl-2-carbonyl)-amino]-phenyl}-acetoxymethyl)-2-phenyl-malonic acid diethyl ester, and 2-(2-{3-(1-hydroxy-2-methyl-propyl)-4-[(4'-trifluoromethyl-biphenyl-2-carbonyl)-amino]-phenyl}-acetoxymethyl)-2-phenyl-malonic acid diethyl ester;

(27) The ester compound or a prodrug thereof, or a pharmaceutically acceptable salt of either according to the above (1), which is selected from the group consisting of {4-[(4'-trifluoromethyl-biphenyl-2-carbonyl)-amino]-phenyl}-acetic acid 2,2-bis-ethylcarbamoyl-2-phenyl-ethyl ester, {3-ethyl-4-[(4'-trifluoromethyl-biphenyl-2-carbonyl)-amino]-phenyl}-acetic acid 2,2-bis-ethylcarbamoyl-2-phenyl-ethyl ester, {4-[(4'-trifluoromethyl-biphenyl-2-carbonyl)-amino]-phenyl}-acetic acid 2-phenyl-2,2-bis-(2,2,2-trifluoro-ethylcarbamoyl)-ethyl ester, {4-[(4'-trifluoromethyl-biphenyl-2-carbonyl)-amino]-phenyl}-acetic acid 2,2-bis-cyclohexylcarbamoyl-2-phenyl-ethyl ester, {4-[(4'-trifluoromethyl-biphenyl-2-carbonyl)-amino]-phenyl}-acetic acid 2-phenyl-2,2-bis-phenylcarbamoyl-ethyl ester, {4-[(4'-trifluoromethyl-biphenyl-2-carbonyl)-amino]-phenyl}-acetic acid 2,2-bis-isopropylcarbamoyl-2-phenyl-ethyl ester, {4-[(biphenyl-2-carbonyl)-amino]-phenyl}-acetic acid 2-phenyl-2,2-bis-(2,2,2-trifluoro-ethylcarbamoyl)-ethyl ester, 2-phenyl-2-(2-{2-trifluoromethyl-4-[(4'-trifluoromethyl-biphenyl-2-carbonyl)-amino]-phenyl}-acetoxymethyl)-malonic acid diethyl ester, {4-[(4'-trifluoromethyl-biphenyl-2-carbonyl)-amino]-phenyl}-acetic acid 2,2-bis-methylcarbamoyl-2-phenyl-ethyl ester, {4-[(4'-trifluoromethyl-biphenyl-2-carbonyl)-amino]-phenyl}-acetic acid 2,2-bis-butylcarbamoyl-2-phenyl-ethyl ester, {3-methyl-4-[(4'-trifluoromethyl-biphenyl-2-carbonyl)-amino]-phenyl}-acetic acid 2,2-bis-ethyl-carbamoyl-2-phenyl-ethyl ester, {4-[(4'-trifluoromethyl-biphenyl-2-carbonyl)-amino]-phenyl}-acetic acid 3,3-bis-ethylcarbamoyl-3-phenyl-propyl ester, {4-[(4'-trifluoromethyl-biphenyl-2-carbonyl)-amino]-phenyl}-acetic acid 3-phenyl-3,3-bis-propyl-carbamoyl-propyl ester, {4-[(biphenyl-2-carbonyl)-amino]-phenyl}-acetic acid 2,2-bis-ethylcarbamoyl-2-phenyl-ethyl ester, {4-[(4'-trifluoromethyl-biphenyl-2-carbonyl)-amino]-phenyl}-acetic acid 2,2-bis-isobutylcarbamoyl-2-phenyl-ethyl ester, {4-[(4'-trifluoromethyl-biphenyl-2-carbonyl)-amino]-phenyl}-acetic acid 2,2-bis-(3-methyl-butylcarbamoyl)-2-phenyl-ethyl ester, {4-[(4'-chloro-biphenyl-2-carbonyl)-amino]-phenyl}-acetic acid 2,2-bis-ethylcarbamoyl-2-phenyl-ethyl ester, {4-[(3',4'-dichloro-biphenyl-2-carbonyl)-amino]-phenyl}-acetic acid 2,2-bis-ethylcarbamoyl-2-phenyl-ethyl ester, {3-methyl-4-[(4'-trifluoromethyl-biphenyl-2-carbonyl)-amino]-phenyl}-acetic acid 2-phenyl-2,2-bis-propylcarbamoyl-ethyl ester, {4-[(4'-trifluoromethyl-biphenyl-2-carbonyl)-amino]-phenyl}-acetic acid 2,2-bis-(2-methoxy-ethylcarbamoyl)-2-phenyl-ethyl ester, {3-isopropyl-4-[(4'-trifluoromethyl-biphenyl-2-carbonyl)-amino]-phenyl}-acetic acid 2,2-bis-ethylcarbamoyl-2-phenyl-ethyl ester, {3-ethyl-4-[(4'-trifluoromethyl-biphenyl-2-carbonyl)-amino]-phenyl}-acetic acid 3,3-bis-ethyl-carbamoyl-3-phenyl-propyl ester, {3-isobutyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 2-phenyl-2,2-bis-propylcarbamoyl-ethyl ester, {3-methylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 3,3-bis-ethylcarbamoyl-3-phenyl-propyl ester, {3-benzylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-dimethylcarbamoyl-4-[(4'-trifluoromethyl-biphenyl-2-carbonyl)-amino]-phenyl}-acetic acid 4,4-bis-ethylcarbamoyl-4-phenyl-butyl ester, {3-diethylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-diisopropylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-(isopropyl-methylcarbamoyl-4-[(4'-trifluoromethyl-biphenyl-2-carbonyl)-amino]-phenyl}-acetic acid 2,2-bis-ethylcarbamoyl-2-phenyl-ethyl ester, {3-(ethyl-methylcarbamoyl-4-[(4'-trifluoromethyl-biphenyl-2-carbonyl)-amino]-phenyl}-acetic acid 3,3-bis-ethylcarbamoyl-3-phenyl-propyl ester, {3-(piperidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(pyrrolidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(methyl-propylcarbamoyl)-4-[(4'-trifluoromethyl-biphenyl-2-carbonyl)-amino]-phenyl}-acetic acid 3,3-bis-ethylcarbamoyl-3-phenyl-propyl ester, {3-hydroxy-4-[(4'-trifluoromethyl-biphenyl-2-carbonyl)-amino]-phenyl}-acetic acid 2,2-bis-ethylcarbamoyl-2-phenyl-ethyl ester, {3-methoxy-4-[(4'-trifluoromethyl-biphenyl-2-carbonyl)-amino]-phenyl}-acetic acid 2,2-bis-ethylcarbamoyl-2-phenyl-ethyl ester, {3-methoxy-4-[(4'-trifluoromethyl-biphenyl-2-carbonyl)-amino]-phenyl}-acetic acid 2-phenyl-2,2-bis-propylcarbamoyl-ethyl ester, {3-methoxy-4-[(4'-trifluoromethyl-biphenyl-2-carbonyl)-amino]-phenyl}-acetic acid 3,3-bis-ethylcarbamoyl-3-phenyl-propyl ester, {3-ethoxy-4-[(4'-trifluoromethyl-biphenyl-2-carbonyl)-amino]-phenyl}-acetic acid 2,2-bis-ethylcarbamoyl-2-phenyl-ethyl ester, {3-ethoxy-4-[(4'-trifluoromethyl-biphenyl-2-carbonyl)-amino]-phenyl}-acetic acid 3,3-bis-ethylcarbamoyl-3-phenyl-propyl ester, {3-isopropoxy-4-[(4'-trifluoromethyl-biphenyl-2-carbonyl)-amino]-phenyl}-acetic acid 2,2-bis-ethylcarbamoyl-2-phenyl-ethyl ester, {3-isopropoxy-4-[(4'-trifluoromethyl-biphenyl-2-carbonyl)-amino]-phenyl}-acetic acid 3,3-bis-ethylcarbamoyl-3-phenyl-propyl ester, {3-propoxy-4-[(4'-trifluoromethyl-biphenyl-2-carbonyl)-amino]-phenyl}-acetic acid 2,2-bis-ethylcarbamoyl-2-phenyl-ethyl ester, {3-benzyloxy-4-[(4'-trifluoromethyl-biphenyl-2-carbonyl)-amino]-phenyl}-acetic acid 2,2-bis-ethylcarbamoyl-2-phenyl-ethyl ester, {3-dimethylamino-4-[(4'-trifluoromethyl-biphenyl-2-carbonyl)-amino]-phenyl}-acetic acid 2,2-bis-ethylcarbamoyl-2-phenyl-ethyl ester, {3-piperidin-1-yl-4-[(4'-trifluoromethyl-biphenyl-2-carbonyl)-amino]-phenyl}-acetic acid 2,2-bis-ethylcarbamoyl-2-phenyl-ethyl ester, {3-pyrrolidin-1-yl-4-[(4'-trifluoromethyl-biphenyl-2-carbonyl)-amino]-phenyl}-acetic acid 2,2-bis-ethylcarbamoyl-2-phenyl-ethyl ester, 4-[(4'-trifluoromethyl-biphenyl-2-carbonyl)-amino]-benzoic acid 3,3-bis-ethylcarbamoyl-3-phenyl-propyl ester, 5-(2,2-bis-ethylcarbamoyl-2-phenyl-ethoxycarbonyl-methyl)-2-[(4'-trifluoromethyl-biphenyl-2-carbonyl)-amino]-benzoic acid benzyl ester, 5-(2,2-bis-ethylcarbamoyl-2-phenyl-ethoxycarbonyl-methyl)-2-[(4'-trifluoromethyl-biphenyl-2-carbonyl)-amino]-benzoic acid, 5-(2,2-bis-ethylcarbamoyl-2-phenyl-ethoxycarbonyl-methyl)-2-[(4'-trifluoromethyl-biphenyl-2-carbonyl)-amino]-benzoic acid ethyl ester, and 5-(2,2-bis-ethylcarbamoyl-2-phenyl-ethoxycarbonyl-methyl)-2-[(4'-trifluoromethyl-biphenyl-2-carbonyl)-amino]-benzoic acid methyl ester;

(28) The ester compound or a prodrug thereof, or a pharmaceutically acceptable salt of either according to the above (1), which is selected from the group consisting of 2-(2-{3-methyl-4-[(4'-trifluoromethyl-biphenyl-2-carbonyl)-amino]-phenyl}-acetoxymethyl)-2-phenyl-malonic acid diethyl ester, 2-(2-{4-[methyl-(4'-trifluoromethyl-biphenyl-2-carbonyl)-amino]-phenyl}-acetoxymethyl)-2-phenyl-malonic acid diethyl ester, 2-phenyl-2-(2-{4-[(4'-trifluoromethyl-biphenyl-2-carbonyl)-amino]-phenyl}-acetoxymethyl)-malonic acid diethyl ester, 2-phenyl-2-(2-{4-[(4'-trifluoromethyl-biphenyl-2-carbonyl)-amino]-phenyl}-acetoxymethyl)-malonic acid diisopropyl ester, 2-phenyl-2-(2-{4-[(4'-trifluoromethyl-biphenyl-2-carbonyl)-amino]-phenyl}-acetoxymethyl)-malonic acid dimethyl ester, 2-cyclopentyl-2-(2-{4-[(4'-trifluoromethyl-biphenyl-2-carbonyl)-amino]-phenyl}-acetoxymethyl)-malonic acid diethyl ester, 2-phenyl-2-(2-{4-[(4'-trifluoromethyl-biphenyl-2-carbonyl)-amino]-phenyl}-acetoxymethyl)-malonic acid dicyclohexyl ester, 2-benzyl-2-(2-[{4-[(4'-trifluoromethyl-biphenyl-2-carbonyl)-amino]-phenyl}-acetoxymethyl)-malonic acid diethyl ester, 2-(2-{2-methyl-4-[(4'-trifluoromethyl-biphenyl-2-carbonyl)-amino]-phenyl}-acetoxymethyl)-2-phenyl-malonic acid diethyl ester, 2-cyclohexyl-2-(2-{4-[(4'-trifluoromethyl-biphenyl-2-carbonyl)-amino]-phenyl}-acetoxymethyl)-malonic acid diethyl ester, 2-phenyl-2-(2-{2-trifluoromethyl-4-[(4'-trifluoromethyl-biphenyl-2-carbonyl)-amino]-phenyl}-acetoxymethyl)-malonic acid diethyl ester, 2-pyridin-2-yl-2-(2-{4-[(4'-trifluoromethyl-biphenyl-2-carbonyl)-amino]-phenyl}-acetoxymethyl)-malonic acid diethyl ester, 2-pyridin-3-yl-2-(2-{4-[(4'-trifluoromethyl-biphenyl-2-carbonyl)-amino]-phenyl}-acetoxymethyl)-malonic acid diethyl ester, 2-phenyl-2-(2-{3-trifluoromethyl-4-[(4'-trifluoromethyl-biphenyl-2-carbonyl)-amino]-phenyl}-acetoxymethyl)-malonic acid diethyl ester, 2-(2-{4-[(4'-methyl-biphenyl-2-carbonyl)-amino]-phenyl}-acetoxymethyl)-2-phenyl-malonic acid diethyl ester, 2-(2-{4-[(4'-methoxy-biphenyl-2-carbonyl)-amino]-phenyl}-acetoxymethyl)-2-phenyl-malonic acid diethyl ester, 2-phenyl-2-(2-{4-[(3'-trifluoromethyl-biphenyl-2-carbonyl)-amino]-phenyl}-acetoxymethyl)-malonic acid diethyl ester, 2-(2-{4-[isopropyl-(4'-trifluoromethyl-biphenyl-2-carbonyl)-amino]-phenyl}-acetoxymethyl)-2-phenyl-malonic acid diethyl ester, 2-(2-{4-[cyclohexyl-(4'-trifluoromethyl-biphenyl-2-carbonyl)-amino]-phenyl}-acetoxymethyl)-2-phenyl-malonic acid diethyl ester, 2-phenyl-2-(2-{4-[(4'-trifluoromethyl-biphenyl-2-carbonyl)-amino]-phenyl}-acetoxymethyl)-malonic acid dipropyl ester, 2-phenyl-2-(2-{4-[(4'-trifluoromethyl-biphenyl-2-carbonyl)-amino]-phenyl}-acetoxymethyl)-malonic acid diisobutyl ester, 2-(2-{4-[ethyl-(4'-trifluoromethyl-biphenyl-2-carbonyl)-amino]-phenyl}-acetoxymethyl)-2-phenyl-malonic acid diethyl ester, 2-(2-{3-ethyl-4-(4'-trifluoromethyl-biphenyl-2-carbonyl)-amino]-phenyl}-acetoxymethyl)-2-phenyl-malonic acid diethyl ester, 2-(2-{3-isopropyl-4-(4'-trifluoromethyl-biphenyl-2-carbonyl)-amino]-phenyl}-acetoxymethyl)-2-phenyl-malonic acid diethyl ester, 2-(2-{3-isobutyl-4-(4'-trifluoromethyl-biphenyl-2-carbonyl)-amino]-phenyl}-acetoxymethyl)-2-phenyl-malonic acid diethyl ester, 2-(2-{3-chloro-4-(4'-trifluoromethyl-biphenyl-2-carbonyl)-amino]-phenyl}-acetoxymethyl)-2-phenyl-malonic acid diethyl ester, 2-(2-{3-bromo-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid diethyl ester, 2-(2-{3-diethylcarbamoyl-4-[(4'-trifluoromethyl-biphenyl-2-carbonyl)-amino]-phenyl}-acetoxymethyl)-2-phenyl-malonic acid diethyl ester, 2-(2-{3-diisopropylcarbamoyl-4-[(4'-trifluoromethyl-biphenyl-2-carbonyl)-amino]-phenyl}-acetoxymethyl)-2-phenyl-malonic acid diethyl ester, 2-(2-{3-(ethyl-methylcarbamoyl)-4-[(4'-trifluoromethyl-biphenyl-2-carbonyl)-amino]-phenyl}-acetoxymethyl)-2-phenyl-malonic acid diethyl ester, {3-(ethyl-methylcarbamoyl)-4-[(4'-trifluoromethyl-biphenyl-2-carbonyl)-amino]-phenyl}-acetic acid 2,2-bis-ethylcarbamoyl-2-phenyl-ethyl ester, {3-(pyrrolidine-1-carbonyl)-4-[(4'-trifluoromethyl-biphenyl-2-carbonyl)-amino]-phenyl}-acetic acid 2,2-bis-ethylcarbamoyl-2-phenyl-ethyl ester, 2-phenyl-2-(2-{3-(pyrrolidine-1-carbonyl)-4-[(4'-trifluoromethyl-biphenyl-2-carbonyl)-amino]-phenyl}-acetoxymethyl)-malonic acid diethyl ester, 2-phenyl-2-(2-{3-(piperidine-1-carbonyl)-4-[(4'-trifluoromethyl-biphenyl-2-carbonyl)-amino]-phenyl}-acetoxymethyl)-malonic acid diethyl ester, 2-[2-(2-{3-dimethylcarbamoyl-4-[(4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(4'-fluoro-biphenyl-2-carbonyl)-amino]-phenyl}-acetoxymethyl)-2-phenyl-malonic acid diethyl ester, 2-(2-{4-[(4'-bromo-biphenyl-2-carbonyl)-amino]}-3-dimethylcarbamoyl-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid dimethyl ester, 2-cyclopentyl-2-(2-{3-dimethylcarbamoyl-4-[(4'-trifluoromethyl-biphenyl-2-carbonyl)-amino]-phenyl}-acetoxymethyl)-malonic acid diethyl ester, 2-cyclohexyl-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{4-[(4'-chloro-biphenyl-2-carbonyl)-amino]-3-dimethylcarbamoyl-phenyl}-acetoxymethyl)-2-phenyl-malonic acid diethyl ester, 2-(2-{4-[(4'-acetyl-biphenyl-2-carbonyl)-amino]-3-dimethylcarbamoyl-phenyl}-acetoxymethyl)-2-phenyl-malonic acid diethyl ester, 2-(2-{4-[(4'-cyano-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-methyl-4'-trifluoromethyl-biphenyl-2-carbonyl)-amino]-phenyl}-acetoxymethyl)-2-phenyl-malonic acid diethyl ester, 2-[3-(2-{3-dimethylcarbamoyl-4-[(4'-trifluoromethyl-biphenyl-2-carbonyl)-amino]-phenyl}-acetoxy)-propyl]-2-phenyl-malonic acid diethyl ester, 2-(2-{3-dimethylcarbamoyl-4-[(5-methoxy-4'-trifluoromethyl-biphenyl-2-carbonyl)-amino]-phenyl}-acetoxymethyl)-2-phenyl-malonic acid diethyl ester, 2-(2-{4-[(5-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-methyl-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-malonic acid 2,2,2-trifluoroethyl ester, 2-(2-{3-dimethylcarbamoyl-4-[(2'-fluoro-4'-trifluoromethyl-biphenyl-2-carbonyl)-amino]-phenyl}-acetoxymethyl)-2-phenyl-malonic acid diethyl ester, 2-(2-{5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-4-[(2'-fluoro-4'-trifluoromethyl-biphenyl-2-carbonyl)-amino]-phenyl}-acetoxymethyl)-2-phenyl-malonic acid diethyl ester, 2-(2-{3-chloro-5-dimethylcarbamoyl-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(3'-fluoro-4'-trifluoromethyl-biphenyl-2-carbonyl)-amino]-phenyl}-acetoxymethyl)-2-phenyl-malonic acid diethyl ester, 2-(2-{4-[(3'-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-nitro-pyridin-2-yl)-malonic acid diethyl ester, 2-(5-amino-pyridin-2-yl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-pyridin-2-yl-malonic acid diethyl ester, 2-(2-{3-chloro-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-bromo-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-o-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-m-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-p-tolyl-malonic acid diethyl ester, 2-(2-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(4-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-succinic acid diethyl ester, 2-(2-{3-dimethylcarbamoyl-4-[(4'-trifluoromethyl-biphenyl-2-carbonyl)-amino]-phenyl}-acetoxymethyl)-2-(2-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(4-methoxy-phenyl)-malonic acid diethyl ester, 2-(2-{4-[(5,4'-bis-trifluoromethyl-biphenyl-2-carbonyl)-amino]-3-dimethylcarbamoyl-phenyl}-acetoxymethyl)-2-phenyl-malonic acid diethyl ester, 2-(2-{4-[(6-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-fluoro-4'-trifluoromethyl-biphenyl-2-carbonyl)-amino]-phenyl}-acetoxymethyl)-2-phenyl-malonic acid diethyl ester, 2-[2-(2-{3-dimethylcarbamoyl-4-[(5-methyl-4'-trifluoromethyl-biphenyl-2-carbonyl)-amino]-phenyl}-acetoxy)-ethyl]-2-phenyl-malonic acid diethyl ester, 2-(3-dimethylcarbamoyl-4-[(5-ethoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-isopropoxy-4'-trifluoromethyl-biphenyl-2-carbonyl)-amino]-phenyl}-acetoxymethyl)-2-phenyl-malonic acid diethyl ester, 2-[2-(2-{4-(5,4'-bis-trifluoromethyl-biphenyl-2-carbonyl)-amino]-3-dimethylcarbamoyl-phenyl}-acetoxy)-ethyl]-2-phenyl-malonic acid diethyl ester, 2-(2-{3-dimethylcarbamoyl-4-(6-methoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-(3-methyl-4'-trifluoromethyl-biphenyl-2-carbonyl)-amino]-phenyl}-acetoxymethyl)-2-phenyl-malonic acid diethyl ester, 2-{2-{4-(2,4-bis-trifluoromethyl-benzoylamino)-3-dimethylcarbamoyl-phenyl]-acetoxymethyl}-2-phenyl-malonic acid diethyl ester, 2-(2-{3-dimethylcarbamoyl-4-[(4'-methyl-biphenyl-2-carbonyl)-amino]-phenyl}-acetoxymethyl)-2-phenyl-malonic acid diethyl ester, 2-{2-[3-dimethylcarbamoyl-4-(2-ethyl-4-trifluoromethyl-benzoylamino)-phenyl]-acetoxymethyl}-2-phenyl-malonic acid diethyl ester, 2-(2-{3-dimethylcarbamoyl-4-[(4'-ethyl-biphenyl-2-carbonyl)-amino]-phenyl}-acetoxymethyl)-2-phenyl-malonic acid diethyl ester, 2-(2-{3-dimethylcarbamoyl-4-[(4'-isopropenyl-biphenyl-2-carbonyl)-amino]-phenyl}-acetoxymethyl)-2-phenyl-malonic acid diethyl ester, 2-(2-{3-dimethylcarbamoyl-4-[(4'-isopropyl-biphenyl-2-carbonyl)-amino]-phenyl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-thiophen-2-yl-malonic acid diethyl ester, 2-(2-{3-dimethylcarbamoyl-4-[(4'-trifluoromethyl-biphenyl-2-carbonyl)-amino]-phenyl}-acetoxymethyl)-2-thiophen-3-yl-malonic acid diethyl ester, 2-(2-{4-dimethylcarbamoyl-5-[(4'-trifluoromethyl-biphenyl-2-carbonyl)-amino]-pyridin-2-yl}-acetoxymethyl)-2-phenyl-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(5-methyl-thiophen-2-yl)-malonic acid diethyl ester, 2-(2-{3-dimethylcarbamoyl-4-[(4'-trifluoromethyl-biphenyl-2-carbonyl)-amino]-phenyl}-acetoxymethyl)-2-thiazol-2-yl-malonic acid diethyl ester, 2-(2-{3-ethoxy-4-[(4'-trifluoromethyl-biphenyl-2-carbonyl)-amino]-phenyl}-acetoxymethyl)-2-phenyl-malonic acid diethyl ester, 2-(2-{3-methoxy-4-[(4'-trifluoromethyl-biphenyl-2-carbonyl)-amino]-phenyl}-acetoxymethyl)-2-phenyl-malonic acid diethyl ester, 2-(2-{3-isopropoxy-4-[(4'-trifluoromethyl-biphenyl-2-carbonyl)-amino]-phenyl}-acetoxymethyl)-2-phenyl-malonic acid diethyl ester, 2-(2-{3-benzyloxy-4-[(4'-trifluoromethyl-biphenyl-2-carbonyl)-amino]-phenyl}-acetoxymethyl)-2-phenyl-malonic acid diethyl ester, 2-(2-{3-hydroxy-4-[(4'-trifluoromethyl-biphenyl-2-carbonyl)-amino]-phenyl}-acetoxymethyl)-2-phenyl-malonic acid diethyl ester, 2-phenyl-2-(2-{3-piperidin-1-yl-4-[(4'-trifluoromethyl-biphenyl-2-carbonyl)-amino]-phenyl}-acetoxymethyl)-malonic acid diethyl ester, 2-phenyl-2-(2-{3-pyrrolidin-1-yl-4-[(4'-trifluoromethyl-biphenyl-2-carbonyl)-amino]-phenyl}-acetoxymethyl)-malonic acid diethyl ester, 2-(2-{3-dimethylamino-4-[(4'-trifluoromethyl-biphenyl-2-carbonyl)-amino]-phenyl}-acetoxymethyl)-2-phenyl-malonic acid diethyl ester, 2-(2-{3-morpholin-4-yl-4-[(4'-trifluoromethyl-biphenyl-2-carbonyl)-amino]-phenyl}-acetoxymethyl)-2-phenyl-malonic acid diethyl ester, 2-(2-{3-diethylamino-4-[(4'-trifluoromethyl-biphenyl-2-carbonyl)-amino]-phenyl}-acetoxymethyl)-2-phenyl-malonic acid diethyl ester, 2-(2-{2-chloro-4-[(4'-trifluoromethyl-biphenyl-2-carbonyl)-amino]-benzoyloxy}-ethyl)-2-phenyl-malonic acid diethyl ester, 2-(2-{3-ethoxycarbonyl-4-[(4'-trifluoromethyl-biphenyl-2-carbonyl)-amino]-phenyl}-acetoxymethyl)-2-phenyl-malonic acid diethyl ester, 2-(3-{3-dimethylcarbamoyl-4-[(4'-trifluoromethyl-biphenyl-2-carbonyl)-amino]-phenyl}-propionyloxymethyl)-2-phenyl-malonic acid diethyl ester, 2-(2-{3-benzyloxycarbonyl-4-[(4'-trifluoromethyl-biphenyl-2-carbonyl)-amino]-phenyl}-acetoxymethyl)-2-phenyl-malonic acid diethyl ester, 2-(2-{3-carboxy-4-[(4'-trifluoromethyl-biphenyl-2-carbonyl)-amino]-phenyl}-acetoxymethyl)-2-phenyl-malonic acid diethyl ester, 2-(2-{3-isopropoxycarbonyl-4-[(4'-trifluoromethyl-biphenyl-2-carbonyl)-amino]-phenyl}-acetoxymethyl)-2-phenyl-malonic acid diethyl ester, 2-(2-{3-methoxycarbonyl-4-[(4'-trifluoromethyl-biphenyl-2-carbonyl)-amino]-phenyl}-acetoxymethyl)-2-phenyl-malonic acid diethyl ester, 2-(2-{3-acetylamino-4-[(4'-trifluoromethyl-biphenyl-2-carbonyl)-amino]-phenyl}-acetoxymethyl)-2-phenyl-malonic acid diethyl ester, 2-(2-{3-methoxycarbonylamino-4-[(4'-trifluoromethyl-biphenyl-2-carbonyl)-amino]-phenyl}-acetoxymethyl)-2-phenyl-malonic acid diethyl ester, 2-(2-{3-(4-methyl-thiazol-2-yl)-4-[(4'-trifluoromethyl-biphenyl-2-carbonyl)-amino]-phenyl}-acetoxymethyl)-2-phenyl-malonic acid diethyl ester, 2-phenyl-2-(2-{6-[(4'-trifluoromethyl-biphenyl-2-carbonyl)-amino]-biphenyl-3-yl}-acetoxymethyl)-malonic acid diethyl ester, 2-(2-{3-formyl-[(4'-trifluoromethyl-biphenyl-2-carbonyl)-amino]-phenyl}-acetoxymethyl)-2-phenyl-malonic acid diethyl ester, 2-(2-{3-dimethylaminomethyl-4-[(4'-trifluoromethyl-biphenyl-2-carbonyl)-amino]-phenyl}-acetoxymethyl)-2-phenyl-malonic acid diethyl ester, 2-(2-{3-(methoxy-methylcarbamoyl)-4-[(4'-trifluoromethyl-biphenyl-2-carbonyl)-amino]-phenyl}-acetoxymethyl)-2-phenyl-malonic acid diethyl ester, 2-(2-{3-isobutyryl-4-[(4'-trifluoromethyl-biphenyl-2-carbonyl)-amino]-phenyl}-acetoxymethyl)-2-phenyl-malonic acid diethyl ester, and 2-(2-{3-(1-hydroxy-2-methyl-propyl)-4-[(4'-trifluoromethyl-biphenyl-2-carbonyl)-amino]-phenyl}-acetoxymethyl)-2-phenyl-malonic acid diethyl ester;

(29) The ester compound or a prodrug thereof, or a pharmaceutically acceptable salt of either according to the above (1), which is selected from the group consisting of
4'-trifluoromethyl-biphenyl-2-carboxylic acid 4-[2-phenyl-2,2-bis-(2,2,2-trifluoro-ethylcarbamoyl)-ethoxycarbonylmethyl]-phenyl ester,
biphenyl-2-carboxylic acid 4-[2-phenyl-2,2-bis-(2,2,2-trifluoro-ethylcarbamoyl)-ethoxycarbonylmethyl]-phenyl ester,
4'-trifluoromethyl-biphenyl-2-carboxylic acid 4-(2,2-bis-ethylcarbamoyl-2-phenyl-ethoxycarbonylmethyl)-phenyl ester,
4'-trifluoromethyl-biphenyl-2-carboxylic acid 4-(2,2-bis-ethylcarbamoyl-2-phenyl-ethoxycarbonylmethyl)-2-chloro-phenyl ester,
4'-trifluoromethyl-biphenyl-2-carboxylic acid 4-(3,3-bis-ethylcarbamoyl-3-phenyl-propoxycarbonylmethyl)-2-chloro-phenyl ester,
4'-trifluoromethyl-biphenyl-2-carboxylic acid 4-(3,3-bis-ethylcarbamoyl-3-phenyl-propoxycarbonyl)-phenyl ester, and
4'-trifluoromethyl-biphenyl-2-carboxylic acid 4-(3,3-bis-ethylcarbamoyl-3-phenyl-propoxycarbonyl)-2,6-dichloro-p henyl ester;

(30) The ester compound or a prodrug thereof, or a pharmaceutically acceptable salt of either according to the above (1), which is selected from the group consisting of
2-phenyl-2-{2-[4-(4'-trifluoromethyl-biphenyl-2-carbonyloxy)-phenyl]-acetoxymethyl}-malonic acid diethyl ester,
2-{2-[3-dimethylcarbamoyl-4-(4'-trifluoromethyl-biphenyl-2-carbonyloxy)-phenyl]-acetoxymethyl}-2-phenyl-malonic acid diethyl ester,
2-{2-[3-methoxy-4-(4'-trifluoromethyl-biphenyl-2-carbonyloxy)-phenyl]-acetoxymethyl}-2-phenyl malonic acid diethyl ester, and
4-[(4'-trifluoromethyl-biphenyl-2-carbonyl)-amino]-benzoic acid 3-[2-(2,2,2-trifluoro-ethylcarbamoyl)-naphthalen-1-yl]-propyl ester;

(31) The ester compound or a prodrug thereof, or a pharmaceutically acceptable salt of either according to the above (1), which is selected from the group consisting of
2-(2-{3-dimethylcarbamoyl-4-[(4'-trifluoromethyl-biphenyl-2-carbonyl)-amino]-phenyl}-acetoxymethyl)-2-isopropyl-malonic acid diethyl ester,
2-sec-butyl-2-(2-{3-dimethylcarbamoyl-4-[(4'-trifluoromethyl-biphenyl-2-carbonyl)-amino]-phenyl}-acetoxymethyl)-2-malonic acid diethyl ester,
2-(2-{3-dimethylcarbamoyl-4-[(4'-trifluoromethyl-biphenyl-2-carbonyl)-amino]-phenyl}-acetoxymethyl)-2-isobutyl-malonic acid diethyl ester,
2-(2-{3-dimethylcarbamoyl-4-[(4'-trifluoromethyl-biphenyl-2-carbonyl)-amino]-phenyl}-acetoxymethyl)-2-propyl-malonic acid diethyl ester,
2-(2-{3-dimethylcarbamoyl-4-[(4'-trifluoromethyl-biphenyl-2-carbonyl)-amino]-phenyl}-acetoxymethyl)-2-ethyl-malonic acid diethyl ester,
2-butyl-2-(2-{3-dimethylcarbamoyl-4-[(4'-trifluoromethyl-biphenyl-2-carbonyl)-amino]-phenyl}-acetoxymethyl)-malonic acid diethyl ester,
2-allyl-2-(2-{3-dimethylcarbamoyl-4-[(4'-trifluoromethyl-biphenyl-2-carbonyl)-amino]-phenyl}-acetoxymethyl)-malonic acid diethyl ester,
2-(2-{3-dimethylcarbamoyl-4-[(4'-trifluoromethyl-biphenyl-2-carbonyl)-amino]-phenyl}-acetoxy)-2,2-bis-ethoxycarbonyl-propionic acid ethyl ester, and
2-(2-{3-dimethylcarbamoyl-4-[(4'-trifluoromethyl-biphenyl-2-carbonyl)-amino]-phenyl}-acetoxymethyl)-2-(1-methyl-butyl)-malonic acid diethyl ester;

(32) A pharmaceutical composition, which comprises the ester compound or a prodrug thereof, or a pharmaceutically acceptable salt of either according to any of the above (1) to (31) and a pharmaceutically acceptable carrier;

(33) An MTP (microsomal triglyceride transfer protein) inhibitor, which comprises the ester compound or a prodrug thereof, or a pharmaceutically acceptable salt of either according to any of the above (1) to (31) as an active ingredient;

(34) An agent for the treatment or prophylaxis of hyperlipidemia, which comprises the ester compound or a prodrug thereof, or a pharmaceutically acceptable salt of either according to any of the above (1) to (31) as an active ingredient;

(35) An agent for the treatment or prophylaxis of arteriosclerosis, which comprises the ester compound or a prodrug thereof, or a pharmaceutically acceptable salt of either according to any of the above (1) to (31) as an active ingredient;

(36) An agent for the treatment or prophylaxis of coronary artery diseases, which comprises the ester compound or a prodrug thereof, or a pharmaceutically acceptable salt of either according to any of the above (1) to (31) as an active ingredient;

(37) An agent for the treatment or prophylaxis of obesity, which comprises the ester compound or a prodrug thereof, or a pharmaceutically acceptable salt of either according to any of the above (1) to (31) as an active ingredient;

(38) An agent for the treatment or prophylaxis of diabetes, which comprises the ester compound or a prodrug thereof, or a pharmaceutically acceptable salt of either according to any of the above (1) to (31) as an active ingredient;

(39) An agent for the treatment or prophylaxis of hypertension, which comprises the ester compound or a prodrug thereof, or a pharmaceutically acceptable salt of either according to any of the above (1) to (31) as an active ingredient;

(40) An agent for the treatment or prophylaxis of hyperlipidemia, arteriosclerosis, coronary artery diseases, obesity, diabetes or hypertension, which comprises MTP inhibitor selectively inhibiting MTP (microsomal triglyceride transfer protein) in the small intestine and a pharmaceutically acceptable carrier;

(41) The agent for the treatment or prophylaxis according to the above (40), wherein the MTP inhibitor does not substantially inhibit MTP in the liver but substantially inhibits only MTP in the small intestine;

(42) The agent for the treatment or prophylaxis according to the above (41), wherein after the administered MTP inhibitor inhibits MTP in the small intestine, it is metabolized in the small intestine, blood and liver to the amount at which the remaining MTP inhibitor in the liver does not substantially inhibit the MTP in the liver;

(43) The agent for the treatment or prophylaxis according to the above (42), wherein the remaining MTP inhibitor in the liver is metabolized to the state where TG-releasing activity of the liver is kept at the level of about 80% or more of the normal level;

(44) The agent for the treatment or prophylaxis according to the above (40) to (43), wherein the MTP inhibitor is a compound having at least one ester bond;

(45) The agent for the treatment or prophylaxis according to the above (44), wherein after the compound having at least one ester bond exerts MTP inhibitory activity, the ester moiety of the compound is metabolized in blood to become an inactive substance;

(46) The agent for the treatment or prophylaxis according to the above (40) to (45), wherein the MTP inhibitor is the ester compound or a prodrug thereof, or a pharmaceutically acceptable salt of either mentioned in any of the above (1) to (31);

(47) A method for the treatment or prophylaxis of hyperlipidemia, arteriosclerosis, coronary artery diseases, obesity, diabetes or hypertension, which comprises administering a compound selectively inhibiting MTP (microsomal triglyceride transfer protein) in the small intestine;

(48) The method according to the above (47), wherein after the compound inhibits MTP in the small intestine, it is metabolized in the small intestine, blood and liver to the amount at which remaining said compound in the liver does not substantially inhibit MTP in the liver;

(49) The method according to the above (47), wherein the remaining compound in the liver is metabolized to the state where TG-releasing activity of the liver is kept at the level of about 80% or more of the normal level;

(50) The method according to the above (47) to (49), wherein the compound has at least one ester bond;

(51) The method according to the above (50), wherein after the compound having at least ester bond exerts MTP inhibitory activity, the ester moiety of the compound is metabolized in blood to become an inactive substance;

(52) The method according to the above (47) to (52), wherein the compound is the ester compound or a prodrug thereof, or a pharmaceutically acceptable salt of either mentioned in any of the above (1) to (31);

(53) The agent for the treatment or prophylaxis according to the above (40) to (46), wherein the agent is an agent for the treatment or prophylaxis of hyperlipidemia which is used in combination with other antihyperlipidemic drug(s);

(54) The agent for the treatment or prophylaxis according to the above (53), wherein other antihyperlipidemic drug is a statin-type drug;

(55) The agent for the treatment or prophylaxis according to the above (54), wherein the statin-type drug is one or more drug(s) selected from the group consisting of lovastatin, simvastatin, pravastatin, fluvastatin, atorvastatin and cerivastatin;

(56) The agent for the treatment or prophylaxis according to the above (40) to (46), wherein the agent is an agent for the treatment or prophylaxis of obesity which is used in combination with other anti-obesity drug(s);

(57) The agent for the treatment or prophylaxis according to the above (56), wherein other anti-obesity drug is mazindol or/and orlistat;

(58) The agent for the treatment or prophylaxis according to the above (40) to (46), wherein the agent is an agent for the treatment or prophylaxis of diabetes which is used in combination with other anti-diabetic drug(s);

(59) The agent for the treatment or prophylaxis according to the above (58), wherein other anti-diabetic drug is one or more drug(s) selected from the group consisting of insulin preparations, sulfonylurea drugs, insulin secretagogues, sulfonamide drugs, biguanide drugs, α-glucosidase inhibitors and insulin resistance-improving drugs;

(60) The agent for the treatment or prophylaxis according to the above (59), wherein other anti-diabetic drug is one or more drug(s) selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, boglibose, acarbose and pioglitazone hydrochloride;

(61) The agent for the treatment or prophylaxis according to the above (40) to (46), wherein the agent is an agent for the treatment or prophylaxis of hypertension which is used in combination with other anti-hypertension drug(s);

(62) The agent for the treatment or prophylaxis according to the above (61), wherein other anti-hypertension drug is one or more drug(s) selected from the group consisting of loop diuretics, angiotensin converting enzyme inhibitors, angiotensin II receptor antagonists, calcium antagonists, β-blockers, α,β-blockers and α-blockers;

(63) The agent for the treatment or prophylaxis according to the above (62), wherein other anti-hypertension drug is one or more drug(s) selected from the group consisting of furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil and phentolamine mesylate;

(64) Use of the agent for the treatment or prophylaxis according to the above (34) to (46) and other antihyperlipidemic drug(s) for the treatment or prophylaxis of hyperlipidemia;

(65) The use according to the above (64), wherein other antihyperlipidemic drug is a statin-type drug;

(66) The use according to the above (64), wherein the statin-type drug is one or more drug(s) selected from the group consisting of lovastatin, simvastatin, pravastatin, fluvastatin, atorvastatin and cerivastatin;

(67) Use of the agent for the treatment or prophylaxis according to the above (34) to (46) and other anti-obesity drug(s) for the treatment or prophylaxis of obesity;

(68) The use according to the above (67), wherein other anti-obesity drug is mazindol or/and orlistat;

(69) Use of the agent for the treatment or prophylaxis according to the above (34) to (46) and other anti-diabetic drug(s) for the treatment or prophylaxis of diabetes;

(70) The use according to the above (69), wherein other anti-diabetic drugs are one or more drug(s) selected from the group consisting of insulin preparations, sulfonylurea drugs, insulin secretagogues, sulfonamide drugs, biguanide drugs, α-glucosidase inhibitors and insulin resistance improving drugs;

(71) The use according to the above (70), wherein other anti-diabetic drug is one or more drug(s) selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, boglibose, acarbose and pioglitazone hydrochloride;

(72) Use of the agent for the treatment or prophylaxis according to the above (34) to (46) and other anti-hypertension drug(s) for the treatment or prophylaxis of hypertension;

(73) The use according to the above (72), wherein other anti-hypertension drug is one or more drug(s) selected from the group consisting of loop diuretics, angiotension converting enzyme inhibitors, angiotension II receptor antagonists, calcium antagonists, beta-blockers, alpha/beta blockers and alpha blockers;

(74) The use according to the above (73), wherein other anti-hypertension drug is one or more drug(s) selected from the group consisting of furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil and phentolamine mesylate;

(75) A pharmaceutical composition comprising an effective amount of the ester compound or a prodrug thereof, or a pharmaceutically acceptable salt of either according to any of the above (1) to (31), a pharmaceutically acceptable, appropriate amount of ethanol and propylene glycol fatty acid ester;

(76) The pharmaceutical composition according to the above (75), which comprises 25 to 35% by weight of ethanol and 65 to 75% by weight of propylene glycol fatty acid ester;

(77) A capsule formulation comprising the pharmaceutical composition according to the above (75) or (76);

(78) The capsule formulation according to the above (77), wherein the capsule formulation is a hard capsule or soft capsule;

(79) A biphenyl compound represented by the formula (100)

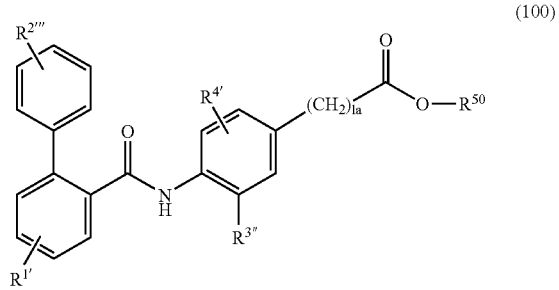

wherein
$R^{1'}$ is hydrogen, $C_1$-$C_6$ alkyl, halogen, halo $C_1$-$C_6$ alkyl or $C_1$-$C_6$ alkoxy;

$R^{2'''}$ is hydrogen, $C_1$-$C_6$ alkyl, halogen, halo $C_1$-$C_6$ alkyl or $C_2$-$C_6$ alkenyl;

$R^{3''}$ is $CON(R^{11a})(R^{12a})$ wherein $R^{11a}$ and $R^{12a}$ are each independently hydrogen, $C_1$-$C_6$ alkyl, optionally substituted $C_6$-$C_{14}$ aryl, optionally substituted $C_7$-$C_{16}$ aralkyl, $C_1$-$C_6$ alkoxy, or $R^{11a}$ and $R^{12a}$ may be taken together with the nitrogen to which they are attached to form

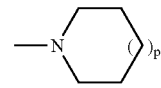

(in which p is an integer of 0 to 2);
$R^{4'}$ is hydrogen, halogen, $C_1$-$C_6$ alkyl or halo $C_1$-$C_6$ alkyl;
$R^{50}$ is hydrogen, $C_1$-$C_6$ alkyl, optionally substituted $C_6$-$C_{14}$ aryl or optionally substituted $C_7$-$C_{16}$ aralkyl; and
1a is an integer of 1 to 3, or a prodrug thereof, or a pharmaceutically acceptable salt of either; and

(80) The biphenyl compound according to the above (79), wherein
$R^{1'}$ is hydrogen,
$R^{2'''}$ is halo $C_1$-$C_6$ alkyl,
$R^{3''}$ is —$CON(R^{11b})(R^{12b})$ wherein $R^{11b}$ and $R^{12b}$ are each independently hydrogen or $C_1$-$C_6$ alkyl, or $R^{11b}$ and $R^{12b}$ may be taken together with the nitrogen to which they are attached to form.

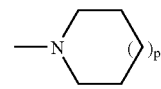

(in which p is an integer of 0 to 2),
$R^{4'}$ is hydrogen, and
$R^{50}$ is hydrogen or $C_1$-$C_6$ alkyl, or a prodrug thereof, or a pharmaceutically acceptable salt of either.

The definitions of each substituent used in the present invention are as follows.

"$C_1$-$C_6$ alkyl" refers to a straight- or branched-chain alkyl group having 1 to 6 carbon atom(s), and its example includes methyl, ethyl, propyl, isopropyl, butyl, isobutyl, sec-butyl, tert-butyl, pentyl, isopentyl, neopentyl, tert-pentyl or hexyl, etc., preferably a straight- or branched-chain alkyl group having 1 to 4 carbon atom(s), more preferably methyl, ethyl or isopropyl. Preferable examples for $R^1$, $R^2$, $R^{2'}$ and $R^{2''}$ include methyl, ethyl or isopropyl; preferable examples for $R^3$ and $R^4$ include methyl, ethyl, propyl, isopropyl, butyl or isobutyl; a preferable example for $R^5$, $R^6$ and $R^7$ includes methyl; preferable examples for $R^8$ and $R^9$ include methyl or ethyl; preferable examples for $R^{10}$ include methyl, ethyl or isopropyl; preferable examples for $R^{11}$ and $R^{12}$ include methyl, ethyl, propyl or isopropyl; preferable examples for $R^{13}$ and $R^{14}$ include methyl or ethyl; a preferable example for $R^{15}$ includes isopropyl; preferable examples for $R^{16}$ and $R^{17}$ include methyl or ethyl; preferable examples for $R^{18}$ and $R^{19}$ include methyl, ethyl, propyl, isopropyl, butyl, isobutyl, sec-butyl, tert-butyl, pentyl or isopentyl, more preferably ethyl; preferable examples for $R^{20}$ include methyl, ethyl, propyl, isopropyl or isobutyl, more preferably ethyl; a preferable example for $R^{21}$ and $R^{22}$ includes methyl; and preferable examples for D include ethyl, propyl, isopropyl, butyl, isobutyl, sec-butyl, sec-pentyl, etc.

Examples of the substituent for "optionally substituted $C_1$-$C_6$ alkyl" include halogen, carboxyl, hydroxy, amino, nitro, cyano, $C_1$-$C_6$ alkoxy, $C_7$-$C_{16}$ aralkyloxy, $C_2$-$C_7$ alkoxycarbonyl, $C_6$-$C_{14}$ aryl, $C_1$-$C_6$ alkylthio, $C_1$-$C_6$ alkylsulfinyl, $C_1$-$C_6$ alkylsulfonyl, $C_1$-$C_6$ alkylamino, acylamino and the like, among which hydroxy is preferable. The number of the substituents is 1 to 5, preferably 1 to 3.

"$C_3$-$C_7$ cycloalkyl" refers to a cycloalkyl having 3 to 7 carbon atoms, specifically cyclopropyl, cyclobutyl, cyclopentyl, cyclohexyl, 1-methylcyclohexyl or cycloheptyl. Preferable examples thereof include a cycloalkyl having 3 to 6 carbon atoms, specifically cyclopropyl, cyclobutyl, cyclopentyl or cyclohexyl. More preferable examples thereof include cyclopropyl or cyclohexyl. A preferable example for $R^1$ and $R^2$ includes cyclohexyl; a preferable example for $R^{10}$ includes cyclohexyl; a preferable example for $R^{18}$ and $R^{19}$ includes cyclohexyl; a preferable example for $R^{20}$ includes cyclohexyl; and preferable examples for ring C include cyclopentyl or cyclohexyl. It is also preferable that $R^8$ and $R^9$ are taken together to form cyclopentyl or cyclohexyl.

"$C_1$-$C_6$ alkoxy" refers to a straight- or branched-chain alkoxy group having 1 to 6 carbon atom(s), and its example includes methoxy, ethoxy, propoxy, isopropoxy, butoxy, tert-butoxy, pentyloxy, tert-pentyloxy or hexyloxy, etc., preferably an alkoxy having 1 to 4 carbon atom(s), such as methoxy, ethoxy, isopropoxy, butoxy or tert-butoxy, and more preferably methoxy or ethoxy. Preferable examples for $R^1$, $R^2$, $R^{2'}$ and $R^{2''}$ include methoxy, isopropoxy or butoxy; preferable examples for $R^3$ and $R^4$ include methoxy, ethoxy, propoxy or isopropoxy; preferable examples for $R^5$, $R^6$ and $R^7$ include methoxy or ethoxy; a preferable example for $R^{11}$ and $R^{12}$ includes methoxy; and preferable examples for $R^{15}$ include methoxy, ethoxy, propoxy or isopropoxy.

"Halogen" refers to chlorine, bromine, fluorine or the like. Preferable examples for $R^1$ include fluorine or chlorine; preferable examples for $R^{2'}$ and $R^{2''}$ include fluorine, chlorine or bromine; preferable examples for $R^3$ and $R^4$ include chlorine or bromine; and preferable examples for $R^5$, $R^6$ and $R^7$ include fluorine or chlorine.

"Halo $C_1$-$C_6$ alkyl" refers to said $C_1$-$C_6$ alkyl substituted with said halogen, and its example includes chloromethyl, bromomethyl, fluoromethyl, trifluoromethyl, trichloromethyl, tribromomethyl, trichloroethyl, pentafluoropropyl or chlorobutyl, etc., preferably chloromethyl, bromomethyl, fluoromethyl, trifluoromethyl, trifluoroethyl or trichloromethyl, and more preferably trifluoromethyl. A preferable example for $R^1$, $R^2$, $R^{2'}$ and $R^{2''}$ includes trifluoromethyl; a preferable example for $R^3$ and $R^4$ includes trifluoromethyl; a preferable example for $R^5$, $R^6$ and $R^7$ includes trifluoromethyl; preferable examples for $R^{16}$ and $R^{17}$ include trifluoromethyl or trifluoroethyl; and preferable examples for $R^{18}$ and $R^{19}$ include trifluoromethyl or trifluoroethyl.

"Halo $C_1$-$C_6$ alkyloxy" refers to, for example, chloromethyloxy, bromomethyloxy, fluoromethyloxy, trifluoromethyloxy, trichloromethyloxy, tribromomethyloxy, trichloroethyloxy, pentafluoropropyloxy or chlorobutyloxy, etc., preferably chloromethyloxy, bromomethyloxy, fluoromethyloxy, trifluoromethyloxy or trichloromethyloxy, and more preferably trifluoromethyloxy. A preferable example for $R^1$, $R^2$, $R^{2'}$ and $R^{2''}$ includes trifluoromethyloxy.

"$C_2$-$C_{12}$ alkoxyalkyl" refers to an alkoxyalkyl of which alkoxy moiety has the same meaning as said alkoxy and alkyl moiety has the same meaning as said alkyl, and its example includes methoxymethyl, ethoxymethyl, propoxymethyl, butoxymethyl, pentyloxymethyl, hexyloxymethyl, ethoxyethyl or methoxyethyl, etc. A preferable example for $R^{18}$ and $R^{19}$ includes methoxyethyl.

"$C_2$-$C_7$ alkylcarbonyl" refers to acetyl, propionyl, butyryl or pivaloyl, etc., and a preferable example for $R^{21}$ and $R^{22}$ includes acetyl.

"$C_1$-$C_7$ alkylsulfonyl" refers to methanesulfonyl, ethanesulfonyl, propylsulfonyl, butylsulfonyl, pentylsulfonyl or hexylsulfonyl, etc., and a preferable example for $R^{21}$ and $R^{22}$ includes methylsulfonyl.

"$C_2$-$C_7$ alkoxycarbonyl" refers to an alkoxycarbonyl of which alkyl moiety has 1 to 6 carbon atom(s) such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl or hexyloxycarbonyl, etc. Preferable examples thereof include methoxycarbonyl, ethoxycarbonyl, propoxycarbonyl or butoxycarbonyl. A preferable example for $R^2$ includes butoxycarbonyl; a preferable example for $R^5$, $R^6$ and $R^7$ includes methoxycarbonyl; a preferable example for $R^{13}$ and $R^{14}$ includes methoxycarbonyl; and a preferable example for D includes ethoxycarbonyl.

"$C_1$-$C_6$ acyl" refers to formyl having one carbon atom, or an alkanoyl having 2 to 6 carbon atoms such as acetyl, propionyl, butyryl or pivaloyl, etc., and its preferable examples include formyl, acetyl or pivaloyl. A preferable example for $R^2$ and $R^{2''}$ includes acetyl; a preferable example for $R^3$ includes formyl; a preferable example for $R^5$, $R^6$ and $R^7$ includes acetyl; a preferable example for $R^{13}$ and $R^{14}$ includes acetyl; and a preferable example for $R^{21}$ and $R^{22}$ includes acetyl.

"Alkanediyl" has preferably 1 to 6 carbon atom(s), and its example includes methylene, ethane-1,2-diyl, ethane-1,1-diyl, propane-1,3-diyl, butane-1,4-diyl, pentane-1,5-diyl, hexane-1,6-diyl, 1,1-dimethylethane-1,2-diyl, 1,1-diethyl-ethane-1,2-diyl, 2,2-dimethylethane-1,2-diyl, 2,2-diethyl-ethane-1,2-diyl, 1,1-dimethylpropane-1,3-diyl, 1,1-diethyl-propane-1,3-diyl, 2,2-dimethylpropane-1,3-diyl, 2,2-diethylpropane-1,3-diyl, 3,3-dimethylpropane-1,3-diyl or 3,3-diethylpropane-1,3-diyl, etc. Preferable examples for $Alk^1$ and $Alk^2$ include methylene, ethane-1,2-diyl, ethane-1,1-diyl, propane-1,3-diyl, etc.

"Alkenediyl" has preferably 2 to 6 carbon atom(s), and its example includes ethylene-1,2-diyl, 1-propene-1,3-diyl, 2-propene-1,3-diyl, 1-butene-1,4-diyl, 2-butene-1,4-diyl, 3-butene-1,4-diyl or 1,3-butadiene-1,4-diyl, etc. Preferable examples for $Alk^1$ and $Alk^2$ include ethylene-1,2-diyl, 1-propene-1,3-diyl, 2-propene-1,3-diyl, etc.

"$C_6$-$C_{14}$ aryl" refers to phenyl, naphthyl or biphenyl, etc., preferably phenyl.

In the "optionally substituted $C_6$-$C_{14}$ aryl", the substituent (s) is/are not particularly limited, and may be the same or different each other and is/are arbitrarily positioned. The number of substituents is not particularly limited so long as they are chemically acceptable, while the number is preferably around 1 to 3. Specifically, examples of the substituent include $C_1$-$C_6$ alkyl (e.g. methyl, ethyl, propyl, isopropyl, butyl, tert-butyl, etc.), hydroxy, $C_1$-$C_6$ alkoxy (e.g. methoxy, ethoxy, propoxy, butoxy, etc.), halogen (e.g. fluorine, chlorine, bromine, etc.), nitro, cyano, $C_1$-$C_6$ acyl (e.g. formyl, acetyl, propionyl, etc.), $C_1$-$C_6$ acyloxy (e.g. formyloxy, acetoxy, propionyloxy, etc.), mercapto, $C_1$-$C_6$ alkylthio (e.g. methylthio, ethylthio, propylthio, butylthio, isobutylthio, etc.), amino, $C_1$-$C_6$ alkylamino (e.g. methylamino, ethylamino, propylamino, butylamino, etc.), di($C_1$-$C_6$ alkyl) amino (e.g. dimethylamino, diethylamino, dipropylamino, dibutylamino, etc.), carboxyl, $C_2$-$C_7$ alkoxycarbonyl (e.g. methoxycarbonyl, ethoxycarbonyl, propoxycarbonyl, etc.), amido, trifluoromethyl, $C_1$-$C_6$ alkylsulfonyl (e.g. methylsulfonyl, ethylsulfonyl, etc.), aminosulfonyl, $C_3$-$C_7$ cycloalkyl (e.g. cyclopentyl, cyclohexyl, etc.), phenyl, acylamido (e.g. acetamido, propionylamido, etc.) and the like, among which hydroxy, $C_1$-$C_6$ alkyl, $C_1$-$C_6$ alkoxy, mercapto, $C_1$-$C_6$ alkylthio, halogen, trifluoromethyl, $C_1$-$C_6$ acyl, $C_2$-$C_7$ alkoxycarbonyl and acylamido are preferable.

A preferable example for $R^1$ and $R^2$ includes phenyl which may be substituted with halo $C_1$-$C_6$ alkyl (e.g. trifluoromethyl, etc.), $C_1$-$C_6$ alkyl (e.g. methyl, ethyl, etc.), halogen (e.g. fluorine, chlorine, bromine, etc.), $C_1$-$C_6$ alkoxy (e.g. methoxy, etc.), $C_1$-$C_6$ acyl (e.g. acetyl, etc.), $C_2$-$C_6$ alkenyl (e.g. isopropenyl, etc.) or cyano; a preferable example for $R^5$, $R^6$ and $R^7$ includes phenyl which may be substituted with halo $C_1$-$C_6$ alkyl (e.g. trifluoromethyl, etc.), $C_1$-$C_6$ alkyl (e.g. methyl, etc.), halogen (e.g. chlorine, etc.) or $C_1$-$C_6$ alkoxy (e.g. methoxy, etc.); a preferable example for $R^8$ and $R^9$ includes phenyl; a preferable example for $R^{11}$ and $R^{12}$ includes phenyl; a preferable example for $R^{18}$ and $R^{19}$ includes phenyl; a preferable example for $R^{43}$ includes biphenyl; a preferable example for ring A includes phenyl; and preferable examples for ring C include phenyl or naphthyl.

"$C_7$-$C_{16}$ aralkyl" refers to an arylalkyl, of which aryl moiety is phenyl (which may be substituted with 1 to 3 substituent(s) mentioned in the above description of aryl) and alkyl moiety is alkyl having 1 to 6 carbon atom(s). Examples thereof include benzyl, phenethyl, phenylpropyl, phenylbutyl or phenylhexyl, etc., among which benzyl or phenylethyl is preferable. A preferable example for $R^1$ and $R^2$ includes benzyl; a preferable example for $R^{11}$ and $R^{12}$ includes benzyl; and a preferable example for ring C includes benzyl.

"$C_6$-$C_{14}$ aryloxy" refers to phenoxy, naphthyloxy, etc. (where the phenyl group or naphthyl group may be substituted with 1 to 3 substituent(s) mentioned in the above description of aryl), preferably phenoxy. A preferable example for $R^1$ and $R^2$ includes phenoxy, and a preferable example for $R^{15}$ includes phenoxy.

"$C_7$-$C_{16}$ aralkyloxy" refers to an arylalkoxy of which alkoxy moiety has 1 to 4 carbon atom(s) (where the aryl group may be substituted with 1 to 3 substituent(s) mentioned in the above description of aryl), and example thereof includes benzyloxy, phenethyloxy, phenylpropyloxy, phenylbutyloxy, etc., preferably benzyloxy. A preferable example for $R^1$ and $R^2$ includes benzyloxy; a preferable example for $R^3$ includes benzyloxy; and a preferable example for $R^{15}$ includes benzyloxy.

"$C_7$-$C_{15}$ arylcarbonyl" refers to benzoyl, naphthoyl, etc. (where the phenyl group or naphthyl group may be substituted with 1 to 3 substituent(s) mentioned in the above description of aryl), preferably benzoyl. A preferable example for $R^1$ and $R^2$ includes benzoyl.

"$C_7$-$C_{15}$ arylcarbonylamino" refers to phenylcarbonylamino, naphthylcarbonylamino, etc. (where the phenyl group or naphthyl group may be substituted with 1 to 3 substituent(s) mentioned in the above description of aryl), preferably benzoyl. A preferable example for ring C includes phenylcarbonylamino.

"$C_8$-$C_{16}$ aralkylcarbonylamino" refers to benzylcarbonylamino, naphthylcarbonylamino, etc. (where the phenyl group or naphthyl group may be substituted with 1 to 3 substituent(s) mentioned in the above description of aryl), preferably benzylcarbonylamino. A preferable example for ring C includes benzylcarbonylamino.

"heterocycle" refers to a 5- to 6-membered heteroaromatic ring, a 5- to 6-membered saturated heterocycle or a 5- to 6-membered unsaturated heterocycle, any of which contains 1 to 3 heteroatom(s) selected from nitrogen, oxygen and sulfur as an atom constituting the ring other than carbon atom, or a fused heterocyclic ring in which said heterocycle and benzene ring are fused. Specifically, its example includes thiophen-2-yl, thiophen-3-yl, furan-2-yl, furan-3-yl, pyrrol-1-yl, pyrrol-2-yl, pyrrol-3-yl, imidazol-1-yl, imidazol-2-yl, imidazol-4-yl, imidazol-5-yl, pyrazol-1-yl, pyrazol-3-yl, pyrazol-4-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, pyrimidin-2-yl, pyrimidin-4-yl, pyrimidin-5-yl, pyridin-2-yl, pyridin-3-yl, pyridin-4-yl, pyrrolidin-2-yl, pyrrolidin-3-yl, benzothiophen-2-yl, benzothiophen-3-yl, benzofuran-2-yl, benzofuran-3-yl, indol-2-yl, indol-3-yl, benzimidazol-1-yl, benzimidazol-2-yl, benzothiazol-2-yl, benzoxazol-2-yl, quinolin-2-yl, quinolin-3-yl, quinolin-4-yl, isoquinolin-1-yl, isoquinolin-3-yl, isoquinolin-4-yl, 1,3,4-thiadiazol-2-yl, morpholin-4-yl, etc.

A preferable example for $R^1$ and $R^2$ includes thiophen-3-yl; preferable examples for ring A include imidazol-5-yl, thiazol-5-yl, pyridin-3-yl or pyrrolidin-2-yl; a preferable example for $R^3$ includes thiazol-2-yl; and preferable examples for ring C include pyridin-2-yl, pyridin-3-yl, thiophen-2-yl, thiophen-3-yl or thiazol-2-yl.

With regard to a substituent in "optionally substituted heterocycle", the same substituents as those mentioned in the above description of aryl may be exemplified. The number of substituents is not particularly limited so long as they are chemically acceptable, while the number is preferably around 1 to 3.

"$C_2$-$C_6$ alkenyl" refers to a straight- or branched-chain alkenyl group having 2 to 6 carbon atoms, and its example includes vinyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl, 2-ethylbutenyl, etc. A preferable example for $R^2$ and $R^{2''}$ includes n-propenyl, and a preferable example for D includes n-propenyl.

"Prodrug" of the compound refers to a derivative of the compound of the present invention, which has a group capable of being chemically or metabolically converted and shows pharmaceutical activity after it is hydrolyzed or solvolyzed or converted under physiological conditions.

For example, there may be listed a derivative in which a substituent such as —CO—$C_1$-$C_6$ alkyl, —$CO_2$—$C_1$-$C_6$ alkyl, —CONH—$C_1$-$C_6$ alkyl, —CO—$C_2$-$C_6$ alkenyl, —$CO_2$—$C_2$-$C_6$ alkenyl, —CONH—$C_2$-$C_6$ alkenyl, —CO—$C_6$-$C_{14}$ aryl, —$CO_2$—$C_6$-$C_{14}$ aryl, —CONH—$C_6$-$C_{14}$ aryl, —CO-heterocycle, —$CO_2$-heterocycle, —CONH-heterocycle, etc. (wherein any of said $C_1$-$C_6$ alkyl, $C_2$-$C_6$ alkenyl, $C_6$-$C_{14}$ aryl and heterocycle may be substituted with halogen, $C_1$-$C_6$ alkyl, hydroxy, $C_1$-$C_6$ alkoxy, carboxyl, amino, amino acid residue, —$PO_3H_2$, —$SO_3H$, —CO-polyethyleneglycol residue, —$CO_2$-polyethyleneglycol residue, —CO-polyethyleneglycol monoalkyl ether residue or —$CO_2$-polyethyleneglycol monoalkyl ether residue) is attached to the hydroxy group of the compound.

Also, there may be exemplified a derivative in which a substituent such as —CO—$C_1$-$C_6$ alkyl, —$CO_2$—$C_1$-$C_6$ alkyl, —CO—$C_2$-$C_6$ alkenyl, —$CO_2$—$C_2$-$C_6$ alkenyl, —$CO_2$—$C_6$-$C_{14}$ aryl, —CO—$C_6$-$C_{14}$ aryl, —CO-heterocycle, —$CO_2$-heterocycle, etc. (wherein any of said $C_1$-$C_6$ alkyl, $C_2$-$C_6$ alkenyl, $C_6$-$C_{14}$ aryl and heterocycle may be substituted with halogen, $C_1$-$C_6$ alkyl, hydroxy, $C_1$-$C_6$ alkoxy, carboxyl, amino, amino acid residue, —$PO_3H_2$, —$SO_3H$, —CO-polyethyleneglycol residue, —$CO_2$-polyethyleneglycol residue, —CO-polyethyleneglycol monoalkyl ether residue, —$CO_2$-polyethyleneglycol monoalkyl ether residue or —$PO_3H_2$, etc.) is attached to the amino group of the compound.

Furthermore, there may be exemplified a derivative in which a substituent such as $C_1$-$C_6$ alkoxy, $C_6$-$C_{14}$ aryloxy, etc. (wherein said $C_1$-$C_6$ alkoxy or $C_6$-$C_{14}$ aryloxy may be substituted with halogen, $C_1$-$C_6$ alkyl, hydroxy, $C_1$-$C_6$ alkoxy, carboxyl, amino, amino acid residue, —$PO_3H_2$, —$SO_3H$, polyethyleneglycol residue or polyethyleneglycol monoalkyl ether residue, etc.) is attached to the carboxyl group of the compound.

"Pharmaceutically acceptable salt" includes various inorganic acid addition salts such as hydrochloride, hydrobromide, sulphate, phosphate or nitrate, etc.; various organic acid addition salts such as acetate, propionate, succinate, glycolate, lactate, malate, oxalate, tartrate, citrate, maleate, fumarate, methanesulfonate, benzensulfonate, p-toluenesulfonate or ascorbate, etc.; or various salts with an amino acid such as aspartate or glutamate, etc., although it is not limited thereto. It may be hydrated compound, hydrate or solvate depending on the circumstances.

"MTP in the small intestine" refers to the MTP existing in small intestinal epithelial cells.

"MTP in the liver" refers to the MTP existing in hepatic cells.

The expression "selectively inhibit MTP in the small intestine" means the level of inhibition is at least about 5 times higher, preferably about 10 times higher, than MTP inhibition in other parts of body such as liver and heart, especially liver. To be more specific, on the basis of S9 metabolic stability test, it means that in the test using human or hamster S9 the remaining rate of unaltered form 10 minutes after the treatment with small intestine S9 is about 10 times or more higher than that in the case of the treatment with liver S9 (see Test Example 7).

The expression "it is metabolized to the amount at which the remaining MTP inhibitor in the liver does not substantially inhibit the MTP in the liver" means that almost all of the orally administered MTP inhibitors are metabolized to an inactive metabolite before arriving at the liver or at the moment of arriving at the liver and show substantially no MTP inhibitory activity in the liver, i.e. the MTP inhibitors are converted to those that do not substantially inhibit TG release from the liver. More specifically, it means the condition where TG-releasing activity of the liver is kept at the level of about 80% or more, preferably about 90% or more, more preferably 100% of the normal level. In terms of metabolism, it means that the ratio of inactive metabolite to unaltered form in portal vein blood is approximately 8 or more to 1 one hour after the oral administration to hamsters, i.e. about 80% or more of the agent (compound) is metabolized before arriving at the liver (see Test Example 6), or on the basis of liver S9 metabolic stability test, it means that 10 minutes after the test using human or hamster S9 the remaining rate of unaltered form is about 20% or less, preferably about 10% or less, more preferably about 8% or less (see Test Example 7).

The expression "MTP inhibitor does not substantially inhibit MTP in the liver" has essentially the same meaning with the above "it is metabolized to the amount at which the remaining MTP inhibitor in the liver does not substantially inhibit the MTP in the liver", and means the condition where TG-releasing activity of the liver is kept at the level of about 80% or more, preferably about 90% or more, more preferably 100% of the normal level.

As "pharmaceutically acceptable carrier", various organic or inorganic carrier materials which are conventionally used as formulation material are used, and it is formulated as excipient, lubricant, binder, disintegrating agent, solvent, solubilizer, suspending agent, isotonizing agent, buffer, soothing agent, etc. If desired, pharmaceutical additives such as preservative, antioxidant, coloring agent, sweetening agent, etc. may be also used. Preferable examples of said excipient include lactose, sucrose, D-mannitol, starch, crystalline cellulose, light anhydrous silicic acid, etc. Preferable examples of said lubricant include magnesium stearate, calcium stearate, talc, colloidal silica, etc. Preferable examples of said binder include crystalline cellulose, sucrose, D-mannitol, dextrin, hydroxypropyl cellulose, hydroxypropyl methylcellulose, polyvinylpyrrolidone, etc. Preferable examples of said disintegrating agent include starch, carboxymethylcellulose, carboxymethylcellulose calcium, crosscarmellose sodium, sodium carboxymethylstarch, etc. Preferable examples of said solvent include water for injection, alcohol, propylene glycol, macrogol, sesame-seed oil, corn oil, propylene glycol fatty acid ester, etc. Preferable examples of said solubilizer include polyethyleneglycol, propyleneglycol, D-mannitol, benzyl benzoate, ethanol, trisaminomethane, cholesterol, triethanolamine, sodium carbonate, sodium citrate, etc. Preferable examples of said suspending agent include surfactants (e.g. stearyl triethanolamine, sodium lauryl sulfate, lauryl aminopropionic acid, lecithin, benzalkonium chloride, benzethonium chloride, glycerin monostearate, etc), polyvinyl alcohol, polyvinylpyrrolidone, carboxymethylcellulose sodium, methylcellulose, hydroxymethyl cellulose, etc. Preferable examples of said isotonizing agent include sodium chloride, glycerin, D-mannitol, etc. Preferable examples of said buffer include phosphate, acetate, carbonate, citrate, etc. Preferable examples of said soothing agent include benzyl alcohol, etc. Preferable examples of said preservative include paraoxybenzoic acid esters, chlorobutanol, benzyl alcohol, phenethyl alcohol, dehydroacetic acid, sorbic acid, etc. Preferable examples of said antioxidant include sulfites, ascorbic acid, etc. Preferable examples of said sweetening agent include aspartame, saccharin sodium, stevia, etc. Preferable examples of said coloring agent include food colors such as food yellow No. 5, food red No. 2 and food blue No. 2, lake colors for food, iron oxide, etc.

BEST MODE FOR CARRYING OUT THE INVENTION

Detailed description is given below with respect to various substituents.

$R^1$ is preferably hydrogen; $C_1$-$C_6$ alkyl such as methyl, ethyl, etc.; $C_1$-$C_6$ alkoxy such as methoxy, isopropoxy, etc.; halogen such as fluorine, chlorine, etc.; halo $C_1$-$C_6$ alkyl such as trifluoromethyl, etc.; or $C_2$-$C_6$ alkenyl such as isopropenyl, etc.

$R^2$ is preferably phenyl (which may be substituted with halo $C_1$-$C_6$ alkyl such as trifluoromethymethyl, etc.; $C_1$-$C_6$ alkyl such as methyl, ethyl, etc.; halogen such as fluoro, chlorine, bromine, etc.; $C_1$-$C_6$ alkoxy such as methoxy, etc.; $C_1$-$C_6$ acyl such as acetyl, etc.; $C_2$-$C_6$ alkenyl such as isopropenyl, etc.; or cyano); $C_1$-$C_6$ alkyl such as ethyl, isopropyl, etc.; $C_3$-$C_7$ cycloalkyl such as cyclohexyl, etc.; $C_1$-$C_6$ alkoxy such as butoxy, etc.; halo $C_1$-$C_6$ alkyl such as trifluoromethyl, etc.; halo $C_1$-$C_6$ alkyloxy such as trifluoromethoxy, etc.; $C_7$-$C_{16}$ aralkyl such as benzyl, etc.; $C_6$-$C_{14}$ aryloxy such as phenoxy (of which aryl moiety may be substituted with halo $C_1$-$C_6$ alkyl such as trifluoromethyl, etc.), etc.; $C_7$-$C_{15}$ arylcarbonyl such as benzoyl (of which aryl moiety may be substituted with halogen such as chlorine, etc.), etc.; heterocycle such as thiophen-3-yl, etc.; $C_2$-$C_7$ alkoxycarbonyl such as butoxycarbonyl, etc.; —$N(R^{40})(R^{41})$ (wherein $R^{40}$ and $R^{41}$ are each independently hydrogen or optionally substituted phenyl).

$R^{2'}$ is preferably hydrogen or halogen such as chlorine, etc.

$R^{2''}$ is preferably hydrogen, halo $C_1$-$C_6$ alkyl such as trifluoromethyl, etc.; $C_1$-$C_6$ alkyl such as methyl, ethyl, etc.;

halogen such as fluorine, chlorine, bromine, etc.; $C_1$-$C_6$ alkoxy such as methoxy, etc.; $C_1$-$C_6$ acyl such as methylcarbonyl, etc.; $C_2$-$C_6$ alkenyl such as isopropenyl, etc.; or cyano.

Ring A is preferably

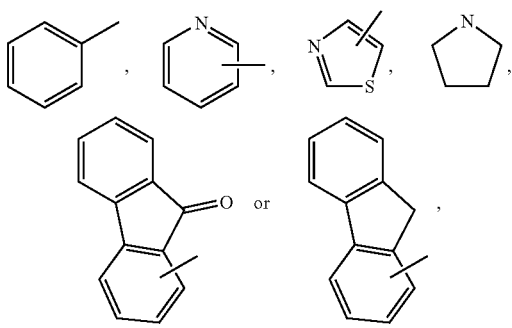

among which phenyl is especially preferred.

X is preferably —COO—, —N($R^{10}$)CO— or —CON($R^{10}$)— (wherein $R^{10}$ is hydrogen; $C_1$-$C_6$ alkyl such as methyl, isopropyl, etc.; or $C_3$-$C_7$ cycloalkyl such as cyclohexyl, etc.), among which —COO— or —CONH— is especially preferred.

Ring B is preferably

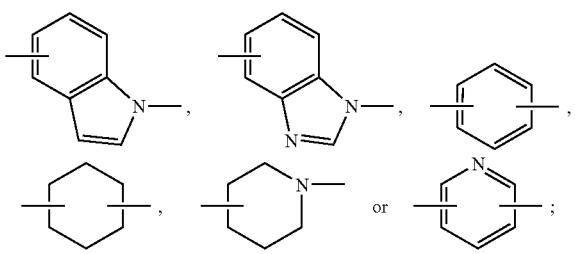

or more preferably

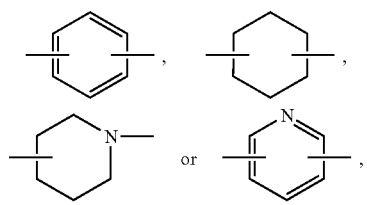

or most preferably

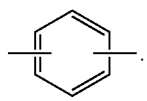

$R^3$ is preferably hydrogen; hydroxy; halogen such as chlorine, bromine, etc.; $C_1$-$C_6$ alkyl such as methyl, ethyl, isopropyl, etc.; substituted $C_1$-$C_6$ alkyl such as isobutyl substituted with hydroxy, etc.; $C_1$-$C_6$ alkoxy such as methoxy, ethoxy, propoxy, isopropoxy, etc.; halo $C_1$-$C_6$ alkyl such as trifluoromethyl, etc.; $C_7$-$C_{16}$ aralkyloxy such as benzyloxy, etc.; $C_1$-$C_6$ acyl such as formyl, etc.; optionally substituted heterocycle such as 4-methyl-thiazol-2-yl, etc.; —CON($R^{11}$)($R^{12}$) (wherein $R^{11}$ and $R^{12}$ are each independently hydrogen; $C_1$-$C_6$ alkyl such as methyl, ethyl, propyl, isopropyl, etc.; $C_6$-$C_{14}$ aryl such as phenyl, etc.; $C_7$-$C_{16}$ aralkyl such as benzyl, etc.; $C_1$-$C_6$ alkoxy such as methoxy, etc.; or $R^{11}$ and $R^{12}$ may be taken together with the nitrogen to form

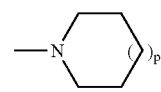

(wherein p is an integer of 0 or 1)); —N($R^{13}$)($R^{14}$) or —$CH_2$—N($R^{13}$)($R^{14}$) (wherein $R^{13}$ and $R^{14}$ are each independently hydrogen; $C_1$-$C_6$ alkyl such as methyl, ethyl, etc.; $C_2$-$C_7$ alkoxycarbonyl such as methoxycarbonyl, etc.; $C_1$-$C_6$ acyl such as acetyl, etc.; or $R^{13}$ and $R^{14}$ may be taken together with the nitrogen to which they are attached to form

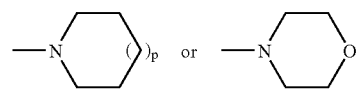

(wherein p has the same meaning as defined above)); or —CO($R^{15}$) (wherein $R^{15}$ is $C_1$-$C_6$ alkyl such as isopropyl, etc.; $C_1$-$C_6$ alkoxy such as methoxy, ethoxy, propoxy, isopropoxy, etc.; $C_7$-$C_{16}$ aralkyloxy such as benzyloxy, etc.; or hydroxy). Alternatively, $R^3$ and $R^{10}$ may be taken together with the nitrogen to which $R^{10}$ is attached and ring B to form

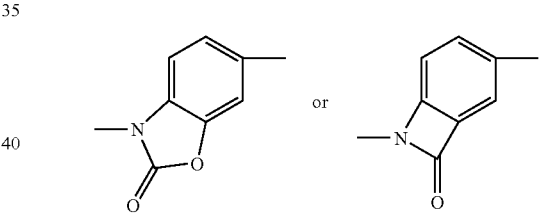

$R^4$ is preferably hydrogen or halogen such as fluorine, chlorine, bromine, etc.

Alk1$^1$ is preferably methylene or ethane-1,1-diyl.

l is preferably 0, 1 or 2.

Alk1$^2$ is preferably methylene.

m is preferably 0 or an integer of 1 to 3.

D is preferably $C_1$-$C_6$ alkyl such as ethyl, propyl, isopropyl, butyl, isobutyl, sec-butyl, sec-pentyl, etc.; $C_2$-$C_6$ alkenyl such as n-propenyl, etc.; $C_2$-$C_7$ alkoxycarbonyl such as ethoxycarbonyl, etc.; —N($R^{42}$)—CO($R^{43}$) (wherein $R^{42}$ is hydrogen or $C_1C_6$ alkyl; $R^{43}$ is $C_6$-$C_{14}$ aryl such as biphenyl, etc.; or $C_7$-$C_{16}$ aralkyl); or a group of the formula shown below:

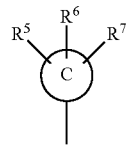

(wherein ring C, $R^5$, $R^6$ and $R^7$ each has the same meaning as defined above).

Ring C is preferably $C_6$-$C_{14}$ aryl such as phenyl, naphthyl, etc.; $C_3$-$C_7$ cycloalkyl such as cyclopentyl, cyclohexyl, etc.; $C_7$-$C_{16}$ aralkyl such as benzyl, etc.; or heterocycle such as pyridine-3-yl, thiophen-3-yl, thiazol-2-yl, etc. Alternatively, ring C may be take together with $R^7$ and $R^8$ to form

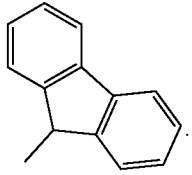

$R^5$ is preferably hydrogen; $C_1$-$C_6$ alkyl such as methyl, etc.; $C_1$-$C_6$ alkoxy such as methoxy, etc.; halogen such as chlorine, etc.; nitro; amino; $C_6$-$C_{14}$ aryl such as phenyl, etc.; or —CON$(R^{16})(R^{17})$ or —CH$_2$—CON$(R^{16})(R^{17})$ (wherein $R^{16}$ and $R^{17}$ are each independently hydrogen; $C_1$-$C_6$ alkyl such as ethyl, etc., or halo-$C_1$-$C_6$ alkyl such as 2,2,2-trifluoroethyl, etc.).

$R^6$ is preferably hydrogen or halogen such as chlorine, etc.

$R^7$ is preferably hydrogen.

$R^8$ and $R^9$ are each independently preferably hydrogen; $C_1$-$C_6$ alkyl such as ethyl, etc.; $C_6$-$C_{14}$ aryl such as phenyl, etc.; hydroxy-$C_1$-$C_6$ alkyl such as hydroxymethyl, etc.; —CON$(R^{18})(R^{19})$ (wherein $R^{18}$ and $R^{19}$ are each independently hydrogen; $C_1$-$C_6$ alkyl such as methyl, ethyl, propyl, isopropyl, butyl, isobutyl, etc.; $C_3$-$C_7$ cycloalkyl such as cyclohexyl, etc.; halo $C_1$-$C_6$ alkyl such as 2,2,2-trifluoroethyl, etc.; $C_2$-$C_{12}$ alkoxyalkyl such as methoxyethyl, etc.; or $C_6$-$C_{14}$ aryl such as phenyl, etc.); —COO$(R^{20})$ or —(CH$_2)_n$—OCO$(R^{20})$ (wherein $R^{20}$ is hydrogen; $C_1$-$C_6$ alkyl such as methyl, ethyl, propyl, isopropyl, isobutyl, etc.; or $C_3$-$C_7$ cycloalkyl such as cyclohexyl, etc., and n is an integer of 0 or 1); —N$(R^{21})(R^{22})$ (wherein $R^{21}$ and $R^{22}$ are each independently hydrogen; $C_1$-$C_6$ alkyl such as methyl, isopropyl, etc.; $C_1$-$C_6$ acyl such as acetyl, propionyl, butyryl, etc.; $C_1$-$C_6$ alkylsulfonyl such as methylsulfonyl, etc.; or $R^{21}$ and $R^{22}$ may be taken together with the nitrogen atom to which they are attached to form

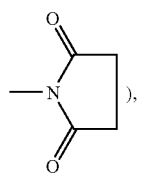

or $R^8$ and $R^9$ taken together may form $C_3$-$C_7$ cycloalkyl such as cyclopropyl, cyclohexyl, etc.

Preferred embodiments of various substituents and the substitution site will be illustrated below.

$R^1$ is preferably hydrogen, halo $C_1$-$C_6$ alkyl or $C_1$-$C_6$ alkyl, among which hydrogen is especially preferred.

$R^2$ is preferably phenyl (which may be substituted with halo $C_1$-$C_6$ alkyl such as trifluoromethyl, etc.; $C_1$-$C_6$ alkyl such as methyl, etc.; halogen such as chlorine, etc.; or $C_1$-$C_6$ alkoxy such as methoxy, etc.).

$R^{2'}$ is preferably hydrogen.

$R^{2''}$ is preferably hydrogen, halo-$C_1$-$C_6$ alkyl, halogen, $C_1$-$C_6$ alkyl or $C_1$-$C_6$ alkoxy, and trifluoromethyl is especially preferred.

X is preferably —COO— or —CON$(R^{10})$— ($R^{10}$ has the same meaning as defined above), among which —CONH— is especially preferred.

Ring B is preferably phenyl.

$R^3$ is preferably $C_1$-$C_6$ alkyl, $C_1$-$C_6$ alkoxy, —CON$(R^{11})(R^{12})$ (wherein $R^{11}$ and $R^{12}$ are each independently preferably hydrogen or $C_1$-$C_6$ alkyl) or —CO$(R^{15})$ (wherein $R^{15}$ is preferably $C_1$-$C_6$ alkoxy).

$R^4$ is preferably hydrogen or methyl, and especially preferably methyl.

Alk$^1$ is preferably methylene.

Alk$^2$ is preferably methylene.

l is preferably 0 or 1, especially 1.

m is preferably 1 or 2, especially 1 or 2.

D is preferably $C_1$-$C_6$ alkyl or a group of the formula shown below:

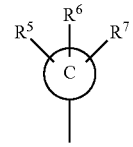

(wherein ring C, $R^5$, $R^6$ and $R^7$ each has the same meaning as defined above).

Ring C is preferably phenyl, pyridin-3-yl, thiophen-3-yl, thiophen-2-yl and thiazol-2-yl, among which phenyl is especially preferred.

$R^5$, $R^6$ and $R^7$ each is preferably hydrogen, halogen or $C_1$-$C_6$ alkyl, among which hydrogen is especially preferred.

$R^8$ and $R^9$ each is preferably hydrogen, $C_1$-$C_6$ alkyl, $C_6$-$C_{14}$ aryl, —CON$(R^{18})(R^{19})$ (wherein $R^{18}$ and $R^{19}$ each is preferably hydrogen or $C_1$-$C_6$ alkyl) or —COO$(R^{20})$ (wherein $R^{20}$ is preferably hydrogen or $C_1$-$C_6$ alkyl), among which —CON$(R^{18})(R^{19})$ (wherein $R^{18}$ and $R^{19}$ each is preferably hydrogen or $C_1$-$C_6$ alkyl) or —COO$(R^{20})$ (wherein $R^{20}$ is preferably hydrogen or $C_1$-$C_6$ alkyl) are more preferred, and —COO$(R^{20})$ (wherein $R^{20}$ is preferably $C_1$-$C_6$ alkyl) is especially preferred.

The substitution site of —(CH$_2$)$_l$— on the benzene ring in the formula (1') is preferably i-position.

The compounds of the present invention may include hydrates or solvates, depending on the case, and may further include their metabolites. Furthermore, the compounds of the present invention include racemates and optically active compounds. The optically active compounds are preferably those wherein one of enantiomers is in enantiomer excess of about 90% or higher, more preferably in enantiomer excess of about 99% or higher.

When the compounds of the present invention are used as an agent for the treatment or prophylaxis of hyperlipidemia or arteriosclerosis, they can be administered systemically or locally, and orally or parenterally. Though the dose may vary depending on the age, body weight, symptoms, therapeutic effect, etc., the daily dose per adult is in the range of 0.1 mg to 1 g per one dose and can be administered one to several times per day. Also, the compounds of the present invention can be administered to human beings as well as animals other than human beings, especially mammals, for the treatment or prevention of said diseases. The compounds of the present invention can be used in the same way for the treatment or prevention of coronary artery diseases, obesity, diabetes or hypertension.

In the formulation of the compounds of the present invention into solid compositions and liquid compositions for oral administration or injections, etc., for parenteral administration, there may be added appropriate additives such as diluents, dispersants, adsorbents, solubilizers, etc. In addition, the composition of the present invention may take the known form such as tablets, pills, powders, granules, suppositories, injections, eye drops, solutions, capsules, troches, aerosols, elixirs, suspensions, emulsions, syrups, etc.

When the compounds of the present invention are formulated into solid preparations such as tablets, pills, powders, granules, etc., examples of such an additive include lactose, mannitol, glucose, hydroxypropyl cellulose, microcrystalline cellulose, starch, polyvinylpyrrolidone, magnesium aluminometasilicate or powdery silicic anhydride. In the case where the compounds of the present invention are formulated into tablets or pills, they may be coated with a gastroenteric or enteric coating film containing a substance such as sucrose, gelatin, hydroxypropyl cellulose or hydroxymethyl cellulose phthalate. Furthermore, the tablets or pills may be multilayered tablets comprising two or more layers.

As the pharmaceutical compositions of the present invention, there are also exemplified capsules in which are filled liquid, semi-solid or solid contents prepared by dissolving the compounds of the present invention in a solvent and adding an additive thereto. Examples of said solvents are purified water, ethanol, vegetable oil, etc., among which ethanol or a mixture of purified water and ethanol is preferably used. Any additives commonly used in the preparation of capsules can be used without any particular limitation. Such additives include, for example, propylene glycol fatty acid esters; low molecular weight polyethylene glycols such as polyethylene glycol 200 to 600, etc., glycerine fatty acid esters thereof, and medium chain fatty acid triglycerides thereof; alcohols/polyols such as stearyl alcohol, cetanol, polyethylene glycol, etc., or esters thereof; lipids such as sesame oil, soy bean oil, peanut oil, corn oil, hydrogenated oil, paraffin oil, bleached wax; fatty acids such as triethyl citrate, triacetin, stearic acid, palmitic acid, myristic acid, etc., and derivatives thereof. These additives are suitable for preparing liquid or semi-solid contents. In the capsules of the present invention, propylene glycol fatty acid esters are preferable as such an additive. Examples of the propylene glycol fatty acid esters are propylene glycol monocaprylate (Capmul PG-8 (Brand name), Sefol 218 (Brand name), Capryo 190 (Brand name), propylene glycol monolaurate (Lauroglycol FCC (Brand name), propylene glycol monooleate (Myverol P-O6 (Brand name)), propylene glycol myristate, propylene glycol monostearate, propylene glycol lisinolate (Propymuls (Brand name)), propylene glycol dicaprylate/dicaprate (Captex (Trademark) 200 (Brand name)) propylene glycol dilaurate, propylene glycol distearate and propylene glycol dioctanoate (Captex (Trademark) 800 (Brand name)). Although there is no particular limitation to the materials constituting the capsules of the present invention, they include, for example, polysaccharides derived from natural products such as agar, alginic acid salt, starch, xanthan, dextran, etc; proteins such as gelatin, casein, etc.; chemically processed products such as hydroxystarch, pullulan, hydroxypropyl cellulose, hydroxypropyl methylcellulose, polyvinyl alcohol or derivatives thereof, polyacryl derivatives, polyvinylpyrrolidone or derivatives thereof, polyethylene glycol, etc.

In the case where the pharmaceutical compositions of the present invention are liquid formulations for oral administration such as pharmaceutically acceptable emulsions, solubilizers, suspensions, syrups or elixirs, etc., diluents to be used include, for example, purified water, ethanol, vegetable oils, emulsifiers, etc. In addition to such diluents, auxiliary agents such as wetting agents, suspending agents, sweeteners, condiments, flavors or antiseptics may be added to said liquid formulations.

In the case where the pharmaceutical compositions of the present invention are parenteral formulations such as injections, there are employed sterilized aqueous or non-aqueous solutions, solubilizers, suspending agents, emulsifiers, etc. Examples of the aqueous solutions, solubilizers and suspending agents include distilled water for injections, physiological saline, cyclodextrin, and derivatives thereof; organic amines such as triethanolamine, diethanolamine, monoethanolamine, triethylamine, etc.; and inorganic alkaline solutions. When aqueous solutions are employed, for example, propylene glycol, polyethylene glycol or vegetable oils such as olive oil, or alcohols such as ethanol may be further added. Further, surfactants (for mixed micelle formation) such as polyoxyethylene hydrogenated castor oils, sucrose fatty acid esters, or lecithin or hydrogenated lecithin (for liposome formation), etc. can be used as a solubilizer. Furthermore, with regard to the parenteral formulations of the present invention, they may be formulated into emulsions comprising non-aqueous solubilizers such as vegetable oils, together with lecithin, polyoxyethylene hydrogenated castor oil or polyoxyethylene-polyoxypropylene glycol, etc.

Further, the present invention provides a novel agent for the treatment or prophylaxis of hyperlipidemia, arteriosclerosis, coronary artery diseases, obesity, diabetes or hypertension with new functions that have never been known before. The agents of the present invention for the treatment or prevention of said diseases are characterized in that they selectively inhibit MTP (microsomal triglyceride transfer protein) in the small intestine. Among these agents, an agent which does not substantially inhibit MTP in the liver, while inhibits only MTP in the small intestine is desirable. Specifically, it is preferable that MTP inhibition of the agent in the liver is approximately ⅓ or less, preferably ¹⁄₁₀₀ or less when compared to that in the small intestine as estimated in terms of $ED_{50}$ or $ED_{20}$. As one preferred embodiment of the therapeutic or prophylactic agents of the present invention for said diseases, they inhibit MTP in the small intestine, and they are then metabolized in the small intestine, blood, and liver to the amount at which the residual agent arriving at the liver does not substantially inhibit MTP in the liver. It is particularly preferable that, when 300 mg/kg of the compound of the present invention is administered orally, the rate of liver TG release inhibition exerted by the residual compound reaching the liver is about 20% or less, preferably less than about 10%, more preferably about 0%. Specifically, it is desirable that the agent has about 40% or less, preferably about 20% or less inhibition rate of liver TG release when assayed by the method of Test Example 4 which will be hereinafter mentioned.

The pharmaceutical compositions or agents of the present invention can be used in combination with other pharmaceutical compositions or agents. As other agents, there may be exemplified drugs for the treatment or prophylaxis of hyperlipidemia, arteriosclerosis, coronary artery disease, obesity, diabetes, or hypertension, and they can be used solely or in combination with two or more kinds of said drugs. Examples of the antihyperlipidemic drugs include a statin-type drug, more specifically, lovastatin, simvastatin, pravastatin, fluvastatin, atorvastatin or cerivastatin. Examples of the anti-obesity drugs include mazindol or olristat. Examples of the anti-diabetic drugs include insulin preparations, sulfonylurea drugs, insulin secretion-promotor drugs, sulfonamide drugs, biguanide drugs, α-glucosidase inhibitors, insulin resistance-improving drugs, etc., more specifically insulin, glibenclamid, tolbutamide, glycopyramide, acetohexamide, glimepiride, tolazamide, gliclazide, nateglinide, glibuzol, metformin hydrochloride, buformin hydrochloride, voglibose, acarbose, pioglitazone hydrochloride, etc. Examples of the anti-hypertension drugs include loop diuretics, angiotensin converting enzyme inhibitors, angiotensin II receptor antagonists, Calcium antagonists, β-blockers, α,β-blockers and α-blockers, and more specifically, furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil, and phentolamine mesylate, etc.

There is no particular limitation to the timing for the administration of pharmaceutical compositions or agents and other drugs for combination use according to the present invention, and they may be administered simultaneously or intermittently.

The amount of such drugs for combination use can be determined based on their clinical doses, and can be chosen depending on the age, weight, condition, medication time, dosage form, method of administration, combination, etc. There is no particular limitation to the dosage form of the drugs for combination use, and it may be sufficient that the pharmaceutical compositions or agents and other drugs for combination use according to the present invention are combined at the time of administration.

Next, a process for preparing an ester compound represented by the formula (1) will be illustrated below as an example, but the process of the present invention is not limited thereto. In the process mentioned below, D is a group of the formula (2):

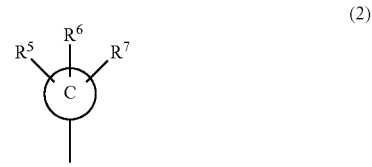

(2)

(wherein ring C, $R^5$, $R^6$ and $R^7$ each has the same meaning as defined above), and when D is $C_1$-$C_6$ alkyl, $C_2$-$C_6$ alkenyl, $C_2$-$C_7$ alkoxycarbonyl or —N($R^{42}$)—CO($R^{43}$) ($R^{42}$ and $R^{43}$ each has the same meaning as defined above), the compound can be prepared in the same.

In addition, the functional groups other than those to be reacted may be optionally protected in a previous stage and may be deprotected in an appropriate stage.

Further, the reaction in each step may be carried out in the usual manner, and separation and purification may be conducted by the appropriate selection or combination of conventional methods such as crystallization, recrystallization, column chromatography, preparative HPLC, etc.

Process 1

Among the compounds represented by the formula (1), a process for preparing compounds in which X is —CONH—$(CH_2)_n$— will be illustrated below.

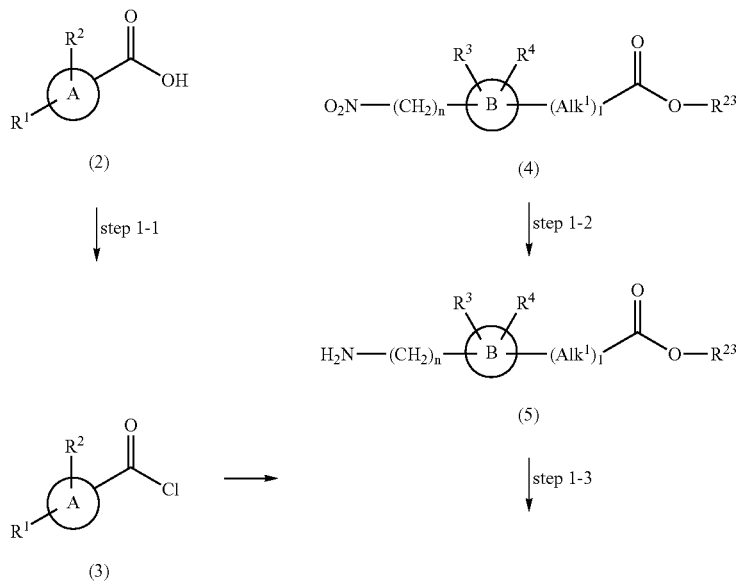

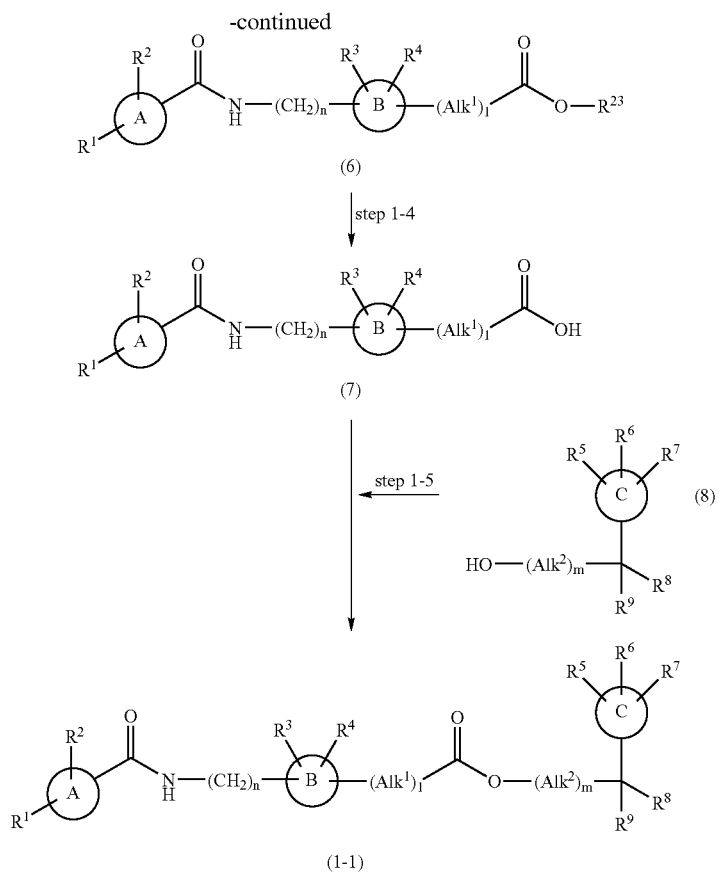

In the above reaction scheme, $R^1$, $R^2$, $R^3$, $R^4$, $R^5$, $R^6$, $R^7$, $R^8$, $R^9$, l, m, n, $Alk^1$, $Alk^2$, ring A, ring B, and ring C each has the same meaning as defined above and $R^{23}$ is $C_1$-$C_6$ alkyl.

Step 1-1

A carboxylic acid of the formula (2) is reacted with oxalyl chloride or thionyl chloride in a solvent to give an acid chloride of the formula (3).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc., and they may be used solely or in combination thereof. Preferred solvents in the present reaction include methylene chloride, chloroform or toluene, all of which contain a catalytic amount of N,N-dimethylformamide.

The reaction temperature is about −20° C. to 120° C., preferably about 0° C. to room temperature.

The reaction time is about 10 minutes to 8 hours, preferably about 30 minutes to 4 hours.

Step 1-2

This step is a general reduction process for the nitro group attached directly to the aromatic ring. A nitro compound of the formula (4) is hydrogenated in a solvent in the presence of a catalyst to give a compound of the formula (5).

The solvent used in the reaction includes, for example, ethers such as tetrahydrofuran, dioxane, 1,2-dimethoxyethane, etc.; alcohols such as methanol, ethanol, isopropyl alcohol, t-butanol, etc.; and esters such as ethyl acetate, methyl acetate, butyl acetate, etc.; and they are used solely or in combination thereof. Preferred solvents in the present reaction include alcohols such as methanol, ethanol, isopropyl alcohol, t-butanol, etc., and a mixture of said alcohol solvent and tetrahydrofuran and/or water.

The catalyst used in the reaction includes, for example, palladium-carbon, palladium hydroxide, Raney-Ni, platinum oxide, and among which palladium-carbon or reduced iron is preferred.

The reaction temperature is about 0° C. to 120° C., preferably about room temperature to 100° C.

The reaction time is about 30 minutes to 8 days, preferably about one hour to 96 hours.

Step 1-3

This step is a general condensation reaction between acid chlorides and amines. An acid chloride of the formula (3) is condensed with an amine of the formula (5) in a solvent in the presence of a base to give a compound of the formula (6).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc., and they can be used solely or in combination thereof. Preferred solvents in the present reaction include methylene chloride, chloroform, toluene, ethyl acetate or tetrahydrofuran.

Examples of the bases used in the present invention include organic bases such as triethylamine, pyridine, N-methylmorpholine, etc.; alkali metal hydroxides such as lithium hydroxide, sodium hydroxide, potassium hydroxide, etc.; and alkali metal carbonates such as sodium carbonate, potassium carbonate, sodium bicarbonate, potassium bicarbonate, etc., among which triethylamine, sodium hydroxide or sodium bicarbonate is preferable.

The reaction temperature is about 0° C. to 80° C., preferably about 0° C. to room temperature.

The reaction time is about 10 minutes to 48 hours, preferably about 30 minutes to 24 hours.

In the case of a compound of the formula (5) wherein $R^{23}$ is hydrogen, a compound of the formula (7) can be prepared by one step of condensation between an aminocarboxylic acid and an acid chloride (Schotten-Baumann reaction).

Alternatively, a compound of the formula (6) can be prepared by using a condensing agent (e.g. WSC-HOBT, DCC-HOBT) for a compound of the formula (2) and a compound of the formula (5). Further, a compound of the formula (6) may be provided by converting a compound of the formula (2) into its mixed anhydride, followed by the reaction in the presence of a base.

Step 1-4

This step is a general ester hydrolysis reaction using alkali. A compound of the formula (6) is hydrolysed in a solvent in the presence of a base to give a compound of the formula (7).

The solvent used in the reaction includes, for example, ethers such as diethyl ether, tetrahydrofuran, dioxane, 1,2-dimethoxyethane, diglyme, etc.; and alcohols such as methanol, ethanol, isopropyl alcohol, etc.; and they can be used solely or in combination thereof. Preferred solvents in the present reaction include a mixture of tetrahydrofuran and ethanol or methanol. Examples of the bases are aqueous solutions of alkali metal carbonates such as sodium carbonate, potassium carbonate, etc., or aqueous solutions of alkali metal hydroxides such as lithium hydroxide, sodium hydroxide, potassium hydroxide, etc., among which sodium hydroxide or lithium hydroxide is preferable.

The reaction temperature is about 0° C. to 120° C., preferably about room temperature to 80° C.

The reaction time is about 1 hour to 24 hours, preferably about 2.5 hours to 12 hours.

Step 1-5

This step is a general condensation reaction of a carboxylic acid with an alcohol.

A carboxylic acid of the formula (7) is condensed with an alcohol of the formula (8) in a solvent in the presence of a base and a condensing agent to give a compound of the formula (1-1) which is one of the objective compounds.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; polar solvents such as acetone, N,N-dimethylformamide, dimethyl sulfoxide, etc.; and they can be used solely or in combination thereof. Preferred solvents in the present reaction include tetrahydrofuran, acetone, methylene chloride or N,N-dimethylformamide.

Examples of the bases used in the reaction include organic bases such as triethylamine, pyridine, dimethylaminopyridine, N-methylmorpholine, etc., among which dimethylaminopyridine is preferred.

Examples of the condensing agents used in the reaction include 1-ethyl-3-(3'-dimethylaminopropyl)carbodiimide hydrochloride (WSC.HCl), dicyclohexylcarbodiimide (DCC), etc. among which 1-ethyl-3-(3'-dimethylaminopropyl)carbodiimide hydrochloride is preferred.

The reaction temperature is about 0° C. to 80° C., preferably about 0° C. to room temperature.

The reaction time is about 1 hour to 48 hours, preferably about 3 hours to 24 hours.

As an alternative process, a carboxylic acid of the formula (7) may be converted into its mixed anhydride and then reacted with an alcohol of the formula (8) in the presence of a base.

Process 1a

Process 1a as shown below is an alternative of Process 1.

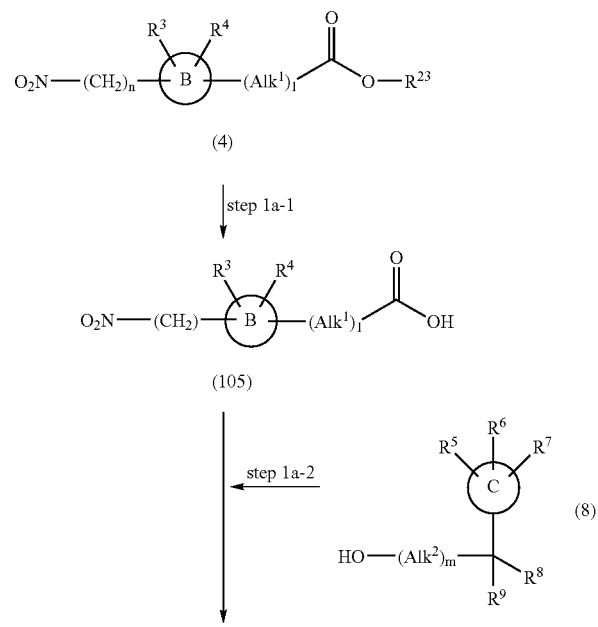

-continued

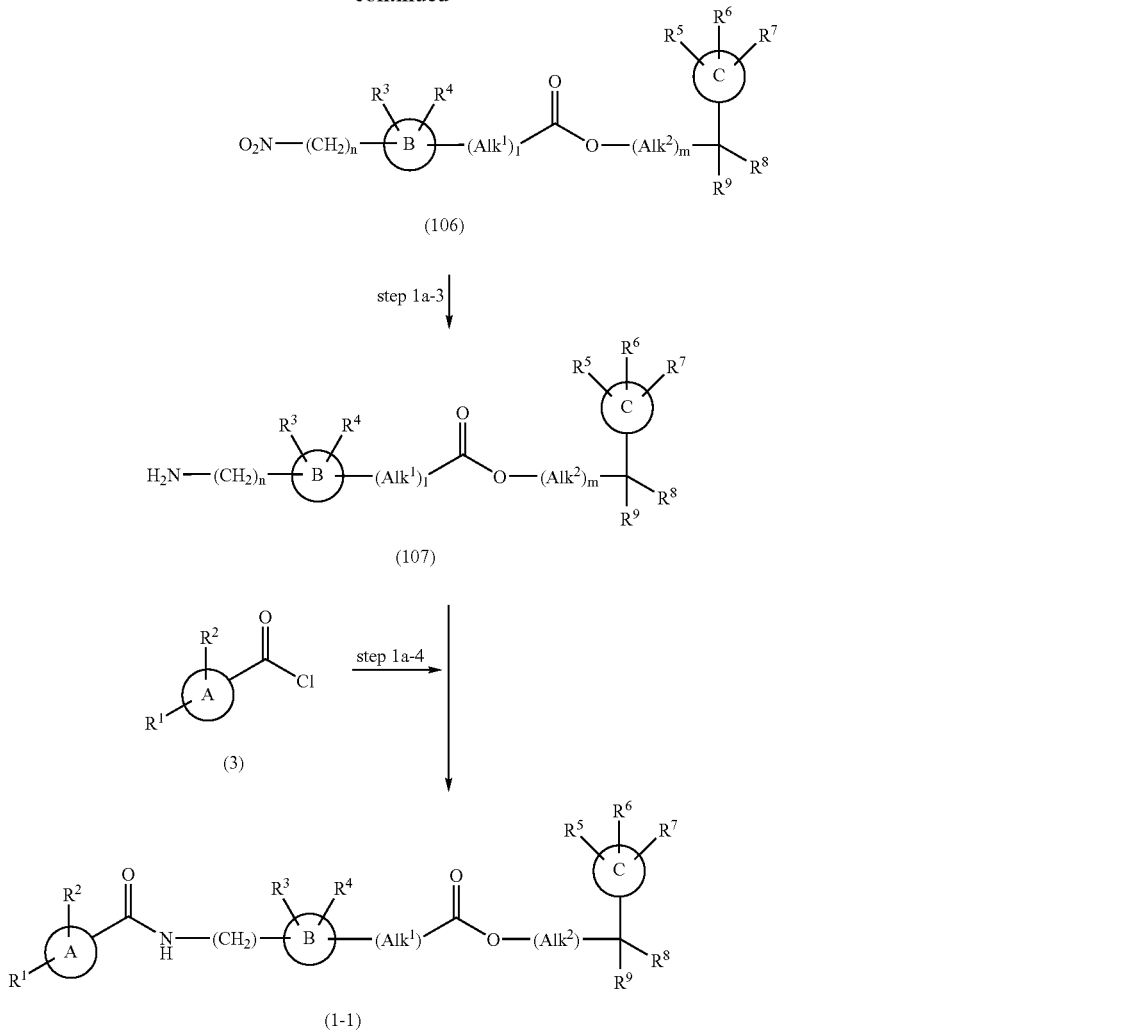

In the above reaction scheme, $R^1$, $R^2$, $R^3$, $R^4$, $R^5$, $R^6$, $R^7$, $R^8$, $R^9$, $R^{23}$, l, m, n, $Alk^1$, $Alk^2$, ring A, ring B and ring C each has the same meaning as defined above.

Step 1a-1

A compound of the formula (105) can be prepared from a compound of the formula (4) in a similar manner to Step 1-4 of Process 1.

Step 1a-2

A compound of the formula (106) can be prepared by condensing a carboxylic acid of the formula (105) with an alcohol of the formula (8) in a similar manner to Step 1-5 of Process 1.

Step 1a-3

A compound of the formula (107) can be prepared from a compound of the formula (106) in a similar manner to Step 1-2 of Process 1.

Step 1a-4

A compound of the formula (1-1) which is one of the objective compounds can be prepared by condensing an amine of the formula (107) with an acid chloride of the formula (3) in a similar manner to Step 1-3 of Process 1.

Process 2

Among the compounds represented by the formula (1), a process for preparing compounds in which X is —COO—$(CH_2)_n$— will be illustrated below.

Process 2

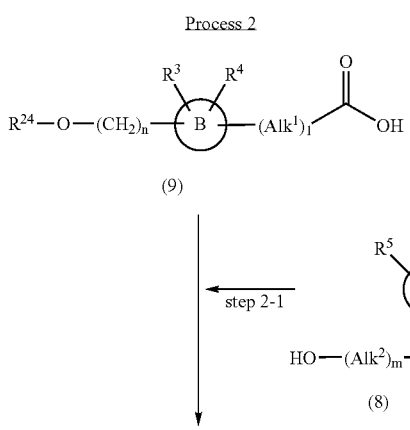

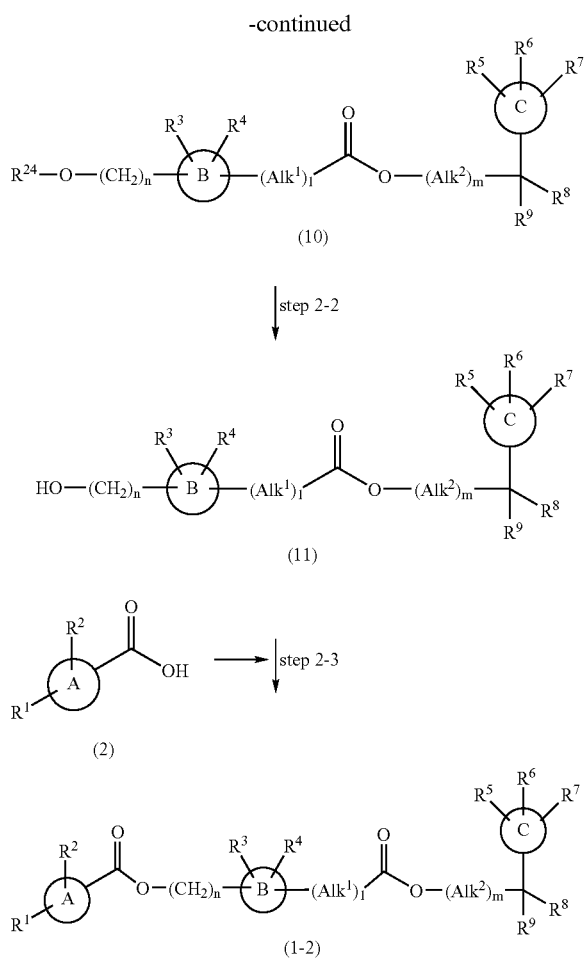

In the above reaction scheme, $R^1$, $R^2$, $R^3$, $R^4$, $R^5$, $R^6$, $R^7$, $R^8$, $R^9$, l, m, n, $Alk^1$, $Alk^2$, ring A, ring B and ring C each has the same meaning as defined above, and $R^{24}$ is a hydroxy-protecting group (for example, benzyl, p-methoxybenzyl, tert-butyl, trialkylsilyl, etc.).

Step 2-1

This step is a condensation reaction of a carboxylic acid with an alcohol similar to Step 1-5 of Process 1. A compound of the formula (10) can be prepared by condensing a carboxylic acid of the formula (9) with an alcohol of the formula (8) in a solvent in the presence of a base and a condensing agent.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; polar solvents such as acetone, N,N-dimethylformamide, dimethyl sulfoxide, water, etc.; and they can be used solely or in combination thereof. Preferred solvents in the present reaction include tetrahydrofuran, methylene chloride or N,N-dimethylformamide.

Examples of the bases used in the reaction include organic bases such as triethylamine, pyridine, dimethylaminopyridine, N-methylmorpholine, etc., among which dimethylaminopyridine is preferred.

Examples of the condensing agents used in the reaction include 1-ethyl-3-(3'-dimethylaminopropyl)carbodiimide hydrochloride (WSC.HCl), dicyclohexylcarbodiimide (DCC), etc., among which 1-ethyl-3-(3'-dimethylaminopropyl)carbodiimide hydrochloride is preferred.

The reaction temperature is about 0° C. to 80° C., preferably about 0° C. to room temperature.

The reaction time is about 2 hours to 48 hours, preferably about 6 hours to 24 hours.

Step 2-2

This step is a general deprotection method for hydroxy groups. For example, when $R^{24}$ is benzyl in a compound of the formula (10), the compound of the formula (10) is hydrogenated in a solvent in the presence of a catalyst to give a compound of the formula (11).

The solvent used in the reaction includes, for example, ethers such as tetrahydrofuran, dioxane, 1,2-dimethoxyethane, diglyme, etc.; alcohols such as methanol, ethanol, isopropyl alcohol, t-butanol, etc.; and esters such as ethyl acetate, methyl acetate, butyl acetate, etc.; and they can be used solely or in combination thereof. Preferred solvents in the present reaction are alcohols such as methanol, ethanol, isopropyl alcohol, t-butanol, etc.

Examples of the catalyst used in the reaction include palladium carbon, palladium hydroxide, Raney-Ni, platinum oxide, etc., among which palladium carbon is preferred.

The reaction temperature is about 0° C. to 80° C., preferably about 0° C. to room temperature.

The reaction time is about 1 hour to 16 hours, preferably about 2 hours to 8 hours.

Step 2-3

This step is a condensation reaction between a carboxylic acid and an alcohol similar to Step 1-5 of Process 1. A compound of the formula (11) is condensed with an alcohol of the formula (2) in a solvent in the presence of a base and a condensing agent to give a compound of the formula (1-2) which is one of the objective compounds.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; and polar solvents such as acetone, N,N-dimethylformamide, dimethyl sulfoxide, etc., and they can be used solely or in combination thereof. Preferred solvents in the present reaction are tetrahydrofuran, methylene chloride, dimethylformamide, etc.

Examples of the bases used in the reaction include organic bases such as triethylamine, pyridine, dimethylaminopyridine, N-methylmorpholine, etc., among which dimethylaminopyridine is preferred.

Examples of the condensing agents used in the reaction include 1-ethyl-3-(3'-dimethylaminopropyl)carbodiimide hydrochloride (WSC.HCl), dicyclohexylcarbodiimide (DCC), etc., among which 1-ethyl-3-(3'-dimethylaminopropyl)carbodiimide hydrochloride is preferred.

The reaction temperature is about 0° C. to 80° C., preferably about 0° C. to room temperature.

The reaction time is about 2 hours to 48 hours, preferably about 6 hours to 24 hours.

As an alternative process of Process 2, a phenol or an alcohol derivative derived from a compound of the formula (9) (wherein $R^{24}$ is p-methoxybenzyl and the carboxyl group is protected by benzyl ester) is subjected to removal of the p-methoxybenzyl group with 2,3-dichloro-5,6-dicyanobenzoquinone (DDQ), etc., followed by condensation with a compound of the formula (2). After removal of the benzyl group from the resulting compound, the deprotected compound is condensed with a compound of the formula (8) to give a compound of the formula (1-2) which is one of the objective compounds.

Process A

The following is an example of the process for preparing a compound of the formula (1) wherein ring B is

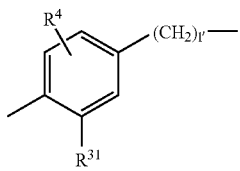

(wherein $R^4$ has the same meaning as defined above, $R^{31}$ is $C_1$-$C_6$ alkyl, and l' is 1).

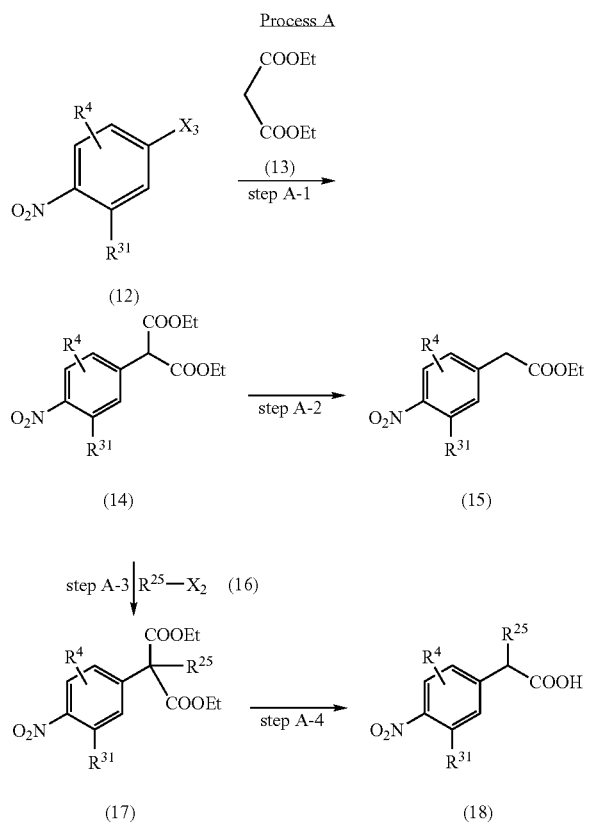

In the above reaction scheme, $R^{31}$ and $R^4$ each has the same meaning as defined above, $R^{25}$ is $C_{1-6}$ alkyl, $X_2$ and $X_3$ each is halogen, and Et is ethyl.

Step A-1

A compound of the formula (14) can be prepared by reacting a compound of the formula (12) with a malonic acid ester of the formula (13) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; and polar solvents such as N,N-dimethylformamide, dimethyl sulfoxide, etc., and they can be used solely or in combination thereof. A preferred solvent in the present reaction is N,N-dimethylformamide.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal amides such as sodium amide, lithium bistrimethylsilylamide, etc.; and alkali metal carbonates such as sodium carbonate, potassium carbonate, etc., among which sodium hydride is preferable.

The reaction temperature is about 0° C. to 120° C., preferably about room temperature to 100° C.

The reaction time is about 30 minutes to 24 hours, preferably about 1 hour to 12 hours.

Step A-2

This step is a hydrolysis reaction of esters, followed by decarboxylation. A compound of the formula (15) can be prepared by stirring a compound of the formula (14) under heating in a solvent in the presence of a base.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; and water; and they can be used solely or in combination thereof. Preferred solvents in the present reaction are mixtures of an alcohol and water.

Examples of the bases used in the reaction include alkali metal carbonates such as sodium carbonate, potassium carbonate, etc., and alkali metal hydroxides such as lithium hydroxide, sodium hydroxide, potassium hydroxide, etc., among which sodium hydroxide or potassium hydroxide is preferred.

The reaction temperature is about 0° C. to 150° C., preferably about 60° C. to 120° C.

The reaction time is about 10 minutes to 12 hours, preferably about 30 minutes to 6 hours.

In accordance with the Steps 1a-2, 1a-3 and 1a-4 of the Process 1a, compounds of the present invention can be prepared from a compound of the formula (15) obtained in the above Step A-2.

An example in the case where $Alk^1$ is a branched alkanediyl or alkenediyl will be illustrated below.

Step A-3

A compound of the formula (17) can be prepared by reacting a compound of the formula (14) with a compound of the formula (16) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; and polar solvents such as N,N-dimethylformamide, dimethyl sulfoxide, etc., and they can be used solely or in combination thereof. Preferred solvents in the present reaction are N,N-dimethylformamide, etc.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, sodium bicarbonate, potassium bicarbonate, etc.; alkali metal hydroxides such as lithium hydroxide, sodium hydroxide, potassium hydroxide, etc.; alkali metal carboxylates such as sodium acetate, potassium acetate, etc.; and alkali metal phosphates such as sodium phosphate, potassium phosphate, etc., among which sodium hydride is preferred.

The reaction temperature is about 0° C. to 120° C., preferably about room temperature to 100° C.

The reaction time is about 10 minutes to 24 hours, preferably about 30 minutes to 12 hours.

Step A-4

In a similar manner to Step A-2, a compound of the formula (18) can be prepared from a compound of the formula (17).

In accordance with the Steps 1a-2, 1a-3 and 1a-4 of the Process 1a, the compounds of the present invention can be prepared from a compound of the formula (18) obtained in the above Step A-4.

Process B

The following is an example of the process for preparing a compound of the formula (1) wherein ring B is

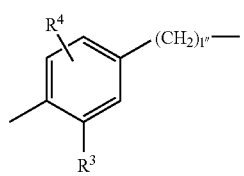

(wherein $R^3$ and $R^4$ each has the same meaning as defined above, and 1″ is 2 or 3).

Process B in case 1″ = 2

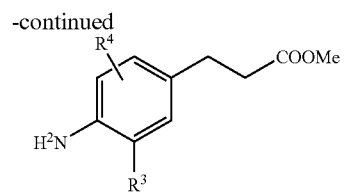

-continued

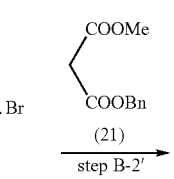

in case 1″ = 3

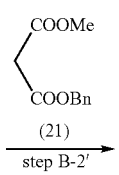

In the above reaction scheme, $R^3$ and $R^4$ each has the same meaning as defined above, Me is methyl, and Bn is benzyl.

Step B-1

A compound of the formula (20) can be prepared by reacting a compound of the formula (19) with a brominating agent in a solvent in the presence of a radical initiator (for example, 2,2'-azobisisobutyronitrile or benzoyl peroxide).

The solvent used in the reaction includes, for example, hydrocarbons such as benzene, etc., and halogenated hydrocarbons such as methylene chloride, chloroform, carbon tetrachloride, 1,2-dichloroethane, etc., and they can be used solely or in combination thereof. Preferred solvents in the present reaction are methylene chloride or carbon tetrachloride.

The brominating agent used in the reaction includes, for example, bromine, N-bromosuccinimide, etc., among which N-bromosuccinimide is preferred.

The reaction temperature is about room temperature to 120° C., preferably about 60° C. to 100° C. The reaction time is about 10 minutes to 8 hours, preferably about 30 minutes to 4 hours.

Step B-2

In a similar manner to Step A-1 of Process A, a compound of the formula (22) can be prepared by reacting a compound of the formula (20) with a compound of the formula (21).

Step B-2'

In a similar manner to Step A-1 of Process A, a compound of the formula (22') can be prepared by reacting a compound of the formula (20') (prepared from a compound of the formula (15) and a compound of the formula (22) via several steps) with a compound of the formula (21).

Step B-3

A compound of the formula (23) can be prepared by hydrogenating a compound of the formula (22) for debenzylation in a solvent, followed by decarboxylation.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; and water; and they can be used solely or in combination thereof. Preferred solvents in the present reaction are alcohols.

Examples of the catalyst used for the debenzylation include palladium carbon, palladium hydroxide, Raney-Ni, platinum oxide, etc., among which palladium carbon is preferred.

The reaction temperature in the debenzylation is preferably about room temperature to 80° C., and the reaction temperature in the decarboxylation is preferably 10° C. to 150° C.

The reaction time in the debenzylation is about 1 hour to 16 hours, preferably about 2 hours to 8 hours, and the reaction time in the decarboxylation is about 5 minutes to 4 hours, preferably about 10 minutes to 2 hours.

Step B-3'

In a similar manner to Step B-3 of Process B, a compound of the formula (23') can be prepared from a compound of the formula (22').

In accordance with the Steps 1-3, 1-4 and 1-5 of the process 1, the compounds of the present invention can be prepared from a compound of the formula (23) or (23') obtained in Step B-3 or B-3'.

Process C

The following is an example of the process for preparing a compound of the formula (1) wherein ring B is

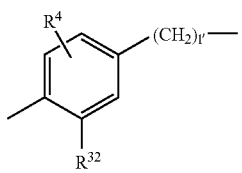

(wherein $R^4$ has the same meaning as defined above, $R^{32}$ is —CON($R^1$)($R^{12}$) in which $R^{11}$ and $R^{12}$ each has the same meaning as defined above, and 1' is 1).

Process C

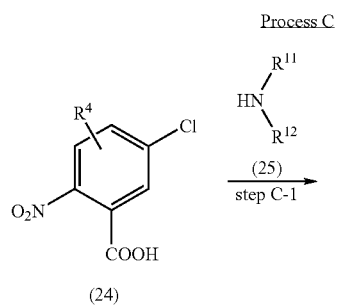

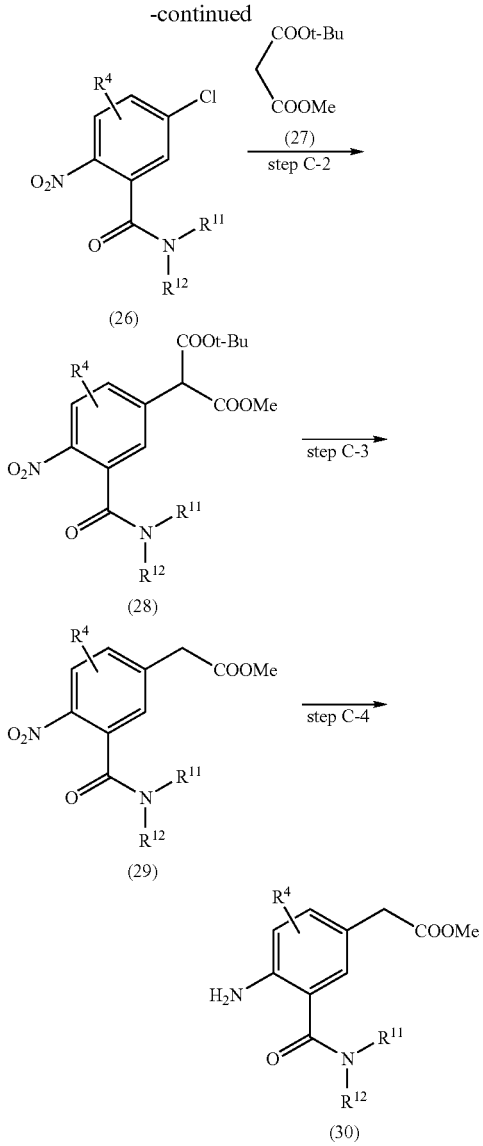

In the above reaction scheme, $R^4$, $R^{11}$ and $R^{12}$ each has the same meaning as defined above, Me is methyl and t-Bu is tert-butyl.

Step C-1

An acid chloride can be prepared from a compound of the formula (24) in a similar manner to Step 1-1 of Process 1. The resulting acid chloride is reacted with a compound of the formula (25) in a similar manner to Step 1-3 of Process 1 to give a compound of the formula (25).

Also, a compound of the formula (26) can be prepared by condensing a compound of the formula (24) with a compound of the formula (25) using a condensing agent (for example, WSC, HOBT). Alternatively, a compound of the formula (24) is converted into its mixed anhydride, followed by reaction with a compound of the formula (25) in the presence of a base, to give a compound of the formula (26).

Step C-2

In a similar manner to Step A-1 of Process A, a compound of the formula (28) can be prepared by reacting a compound of the formula (26) with a compound of the formula (27).

Step C-3

A compound of the formula (29) can be prepared by treating a compound of the formula (28) with an acid (trifluoroacetic acid, toluenesulfonic acid, methanesulfonic acid, etc.) in the presence or absence of a solvent under heating or at room temperature to convert the tert-butyl ester moiety into the carboxylic acid moiety, followed by decarboxylation.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; halogenated hydrocarbons such as methylene chloride, chloroform, carbon tetrachloride, 1,2-dichloroethane, etc.; and water; and they can be used solely or in combination thereof. Preferred solvents in the present reaction are methylene chloride, chloroform or toluene.

The reaction temperature is about 0° C. to 120° C., preferably about room temperature to 100° C. The reaction time is about 1 hour to 24 hours, preferably about 2 hours to 12 hours.

Step C-4

In a similar manner to Step 1-2 of Process 1, a compound of the formula (30) can be prepared from a compound of the formula (29).

In accordance with the Steps 1-3, 1-4 and 1-5 of Process 1, the compounds of the present invention can be prepared from a compound of the formula (30) obtained in the above Step C-4.

Process D

The following is an example of the process for preparing a compound of the formula (1) wherein ring B is

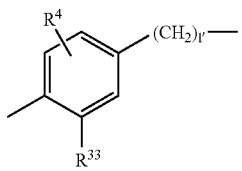

(wherein $R^4$ has the same meaning as defined above, $R^{33}$ is $C_{1-6}$ alkoxy or $C_{7-16}$ aralkyloxy, and $l'$ is 1).

Process D

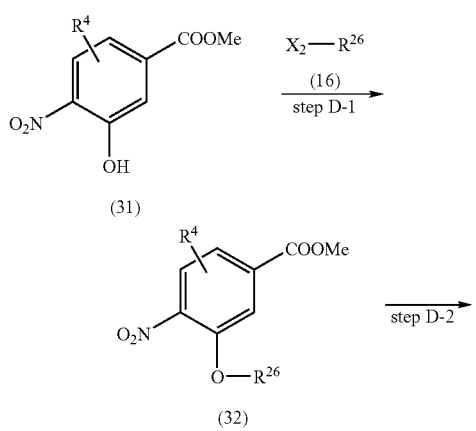

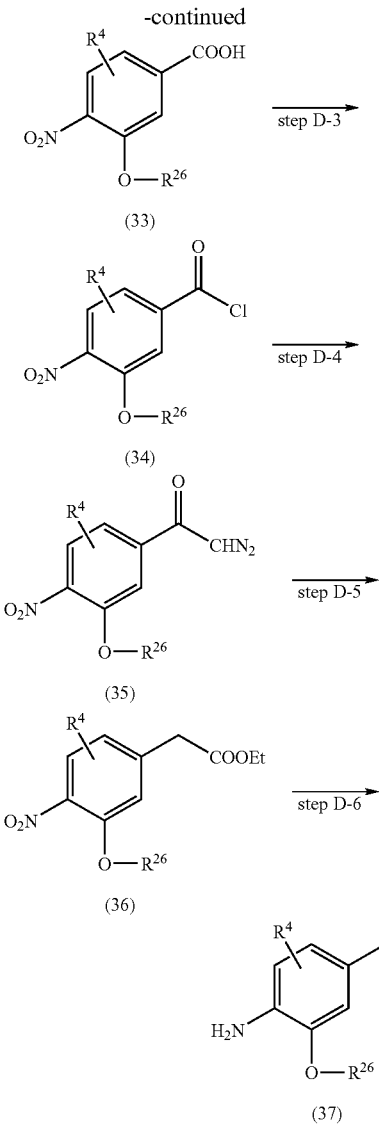

In the above reaction scheme, $R^4$, $X_2$, Me and Et each has the same meaning as defined above and $R^{26}$ is $C_{1-6}$ alkyl or $C_{7-16}$ aralkyl.

Step D-1

A compound of the formula (32) can be prepared by reacting a compound of the formula (31) with a compound of the formula (16) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; esters such as ethyl acetate, methyl acetate, butyl acetate, etc.; and polar solvents such as acetone, N,N-dimethylformamide, dimethyl sulfoxide, etc.; and they can be used solely or in combination thereof. A preferred solvents in the present reaction is N,N-dimethylformamide.

Examples of the bases used in the reaction include alkali metal hydrides such as sodium hydride, potassium hydride, etc., and alkali metal carbonates such as sodium carbonate, potassium carbonate, sodium bicarbonate, potassium bicarbonate, etc., among which sodium hydride is preferred.

The reaction temperature is about 0° C. to 100° C., preferably about room temperature to 80° C. The reaction time is about 2 hour to 48 hours, preferably about 6 hours to 24 hours.

Step D-2

A compound of the formula (33) can be prepared by hydrolyzing the ester moiety of a compound of the formula (32) in a solvent in the presence of a base.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, etc.; and water, and they can be used solely or in combination thereof. Preferred solvents in the present reaction are tetrahydrofuran or a mixture of tetrahydrofuran and ethanol or methanol.

Examples of the bases used in the reaction include alkali metal carbonates such as sodium carbonate, potassium carbonate, etc.; aqueous solutions of alkali metal hydroxides such as lithium hydroxide, sodium hydroxide, potassium hydroxide, etc., among which sodium hydroxide is preferred.

The reaction temperature is about 0° C. to 120° C., preferably about room temperature to 80° C.

The reaction time is about 1 hour to 24 hours, preferably about 2.5 hours to 12 hours.

Step D-3

In a similar manner to Step 1-1 of Process 1, a compound of the formula (34) can be prepared from a compound of the formula (33).

Step D-4

This process is a conversion reaction from acid chlorides to diazoketones. A compound of the formula (35) can be prepared by reacting a compound of the formula (34) with diazomethane in a solvent in the presence of a base.

The solvent used in the reaction includes, for example, ethers such as diethyl ether, tetrahydrofuran, dioxane, 1,2-dimethoxyethane, diglyme, etc., and they can be used solely or in combination thereof. Preferred solvents in the present reaction are diethyl ether or tetrahydrofuran.

Examples of the bases used in the reaction include organic bases such as triethylamine, pyridine, dimethylaminopyridine, N-methylmorpholine, etc., among which triethylamine is preferred.

The reaction temperature is about −20° C. to 50° C., preferably about 0° C. to room temperature.

The reaction time is about 2 hours to 48 hours, preferably about 6 hours to 24 hours.

Step D-5

This process is one carbon homologation (Arndt-Eistert synthesis) by α-diazoketone rearrangement (Wolff rearrangement). A compound of the formula (35) is reacted by use of a silver catalyst (for example, silver benzoate, silver oxide) in an alcohol in the presence of a base to give a compound of the formula (36).

The solvent (also served as the reaction reagents) used in the reaction includes, for example, alcohols such as methanol, ethanol, isopropyl alcohol, t-butanol, etc., and they can be used solely or in combination thereof. Preferred solvents (also served as the reaction reagents) in the present reaction are methanol or ethanol.

Examples of the bases used in the reaction include organic bases such as triethylamine, pyridine, dimethylaminopyridine, N-methylmorpholine, etc., among which triethylamine is preferred.

The reaction temperature is about room temperature to 120° C., preferably about 60° C. to 120° C.

The reaction time is about 2 hours to 36 hours, preferably about 4 hours to 18 hours.

Step D-6

In a similar manner to Step 1-2 of Process 1, a compound of the formula (37) can be prepared from a compound of the formula (36).

In accordance with the Steps 1-3, 1-4 and 1-5 of the above Process 1, the compounds of the present invention can be prepared from a compound of the formula (37) obtained in the above Step D-6. The resulting compound of the present invention is further subjected to the reactions of Step 2-2 of Process 2, whereby the substituent $-OR^{26}$ can be converted into $-OH$.

Process E

The following is an example of the process for preparing a compound of the formula (1) wherein ring B is

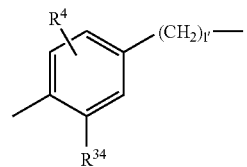

(wherein $R^4$ has the same meaning as defined above, $R^{34}$ is $-N(R^{13})(R^{14})$ in which $R^{13}$ and $R^{14}$ each has the same meaning as defined above), and 1' is 1).

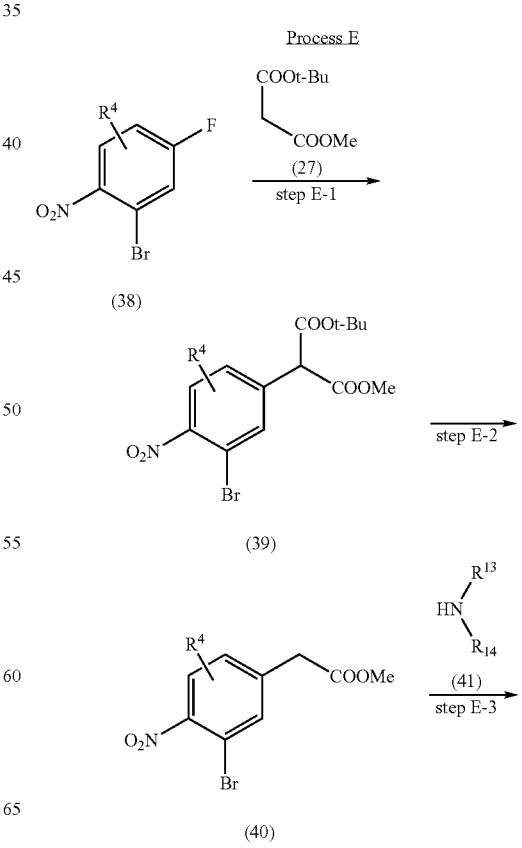

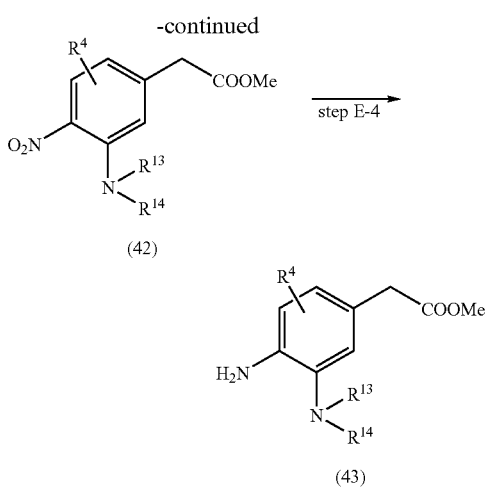

In the above reaction scheme, $R^4$, $R^{13}$, $R^{14}$, Me and t-Bu each has the same meaning as defined above.

Step E-1

In a similar manner to Step A-1 of Process A, a compound of the formula (39) can be prepared by reacting a compound of the formula (38) with a compound of the formula (27).

Step E-2

In a similar manner to Step C-3 of Process C, a compound of the formula (40) can be prepared from a compound of the formula (39).

Step E-3

A compound of the formula (42) can be prepared by reacting a compound of the formula (40) with a compound of the formula (41) without or in a solvent and in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; alcohols such as methanol, ethanol, isopropyl alcohol, t-butanol, etc.; esters such as ethyl acetate, methyl acetate, butyl acetate, etc.; and polar solvents such as N,N-dimethylformamide, dimethyl sulfoxide, etc.; and they can be used solely or in combination thereof. A preferred solvent in the present reaction is tetrahydrofuran.

Examples of the bases used in the reaction include organic bases such as triethylamine, pyridine, dimethylaminopyridine, N-methylmorpholine, etc., among which triethylamine or a mixture of triethylamine and dimethylaminopyridine is preferred.

The reaction temperature is about 0° C. to 120° C., preferably about room temperature to 100° C.

The reaction time is about 2 hours to 48 hours, preferably about 6 hours to 24 hours.

Step E-4

In a similar manner to Step 1-2 of Process 1, a compound of the formula (43) can be prepared from a compound of the formula (42).

In accordance with the Steps 1-3, 1-4 and 1-5 of the above Process 1, the compounds of the present invention can be prepared from a compound of the formula (43) obtained in the above Step E-4.

Process F

The following is an example of the process for preparing a compound of the formula (1) wherein ring B is

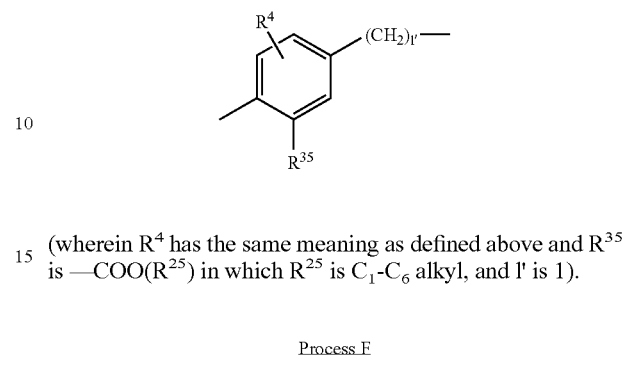

(wherein $R^4$ has the same meaning as defined above and $R^{35}$ is $—COO(R^{25})$ in which $R^{25}$ is $C_1$-$C_6$ alkyl, and l' is 1).

Process F

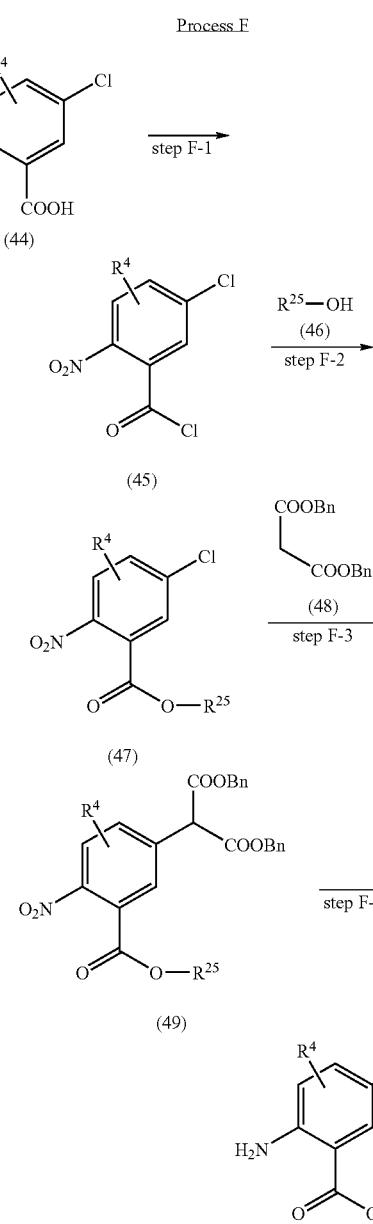

In the above reaction scheme, $R^4$, $R^{25}$ and Bn each has the same meaning as defined above.

Step F-1

In a similar manner to Step 1-1 of Process 1, a compound of the formula (45) can be prepared from a compound of the formula (44).

Step F-2

A compound of the formula (47) can be prepared by reacting a compound of the formula (45) with a compound of the formula (46) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. A preferred solvent in the present reaction is tetrahydrofuran.

Examples of the bases used in the reaction include organic bases such as triethylamine, pyridine, dimethylaminopyridine, N-methylmorpholine, etc., among which triethylamine is preferred.

The reaction temperature is about $-30°$ C. to $80°$ C., preferably about $-20°$ C. to room temperature.

The reaction time is about 2 hours to 48 hours, preferably about 6 hours to 24 hours.

Step F-3

In a similar manner to Step A-1 of Process A, a compound of the formula (49) can be prepared by reacting a compound of the formula (47) with a compound of the formula (48).

Step F-4

A compound of the formula (49) was reacted in a similar manner to Step 1-2 of Process 1, followed by debenzylation and decarboxylation to give a compound of the formula (50).

In accordance with the alternative process described in Step 1-3 and Step 1-5 of Process 1, the compounds of the present invention can be prepared from a compound of the formula (50) obtained in the above Step F-4.

Process G

The following is an example of the process for preparing a compound of the formula (1) wherein ring B is

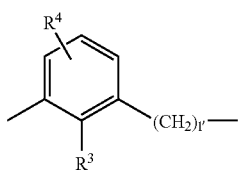

(wherein $R^3$ and $R^4$ each has the same meaning as defined above and l' is 1).

Process G

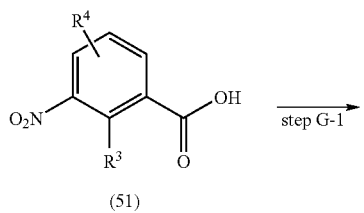

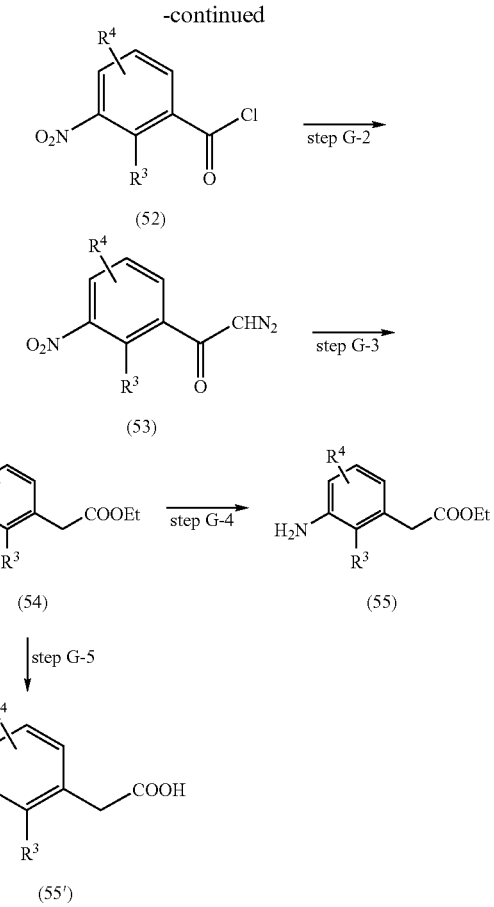

In the above reaction scheme, $R^3$, $R^4$ and Et each has the same meaning as defined above.

Step G-1

In a similar manner to Step 1-1 of Process 1, a compound of the formula (52) can be prepared from a compound of the formula (51).

Step G-2

In a similar manner to Step D-4 of Process D, a compound of the formula (53) can be prepared from a compound of the formula (52).

Step G-3

In a similar manner to Step D-5 of Process D, a compound of the formula (54) can be prepared from a compound of the formula (53).

Step G-4

In a similar manner to Step D-6 of Process D, a compound of the formula (55) can be prepared from a compound of the formula (54).

In accordance with Steps 1-3, 1-4 and 1-5 of the above Process 1, the compounds of the present invention can be prepared from a compound of the formula (55) obtained above in Step G-4.

Step G-5

In a similar manner to Step 1-4 of the above Process 1, a compound of the formula (55') can be prepared from a compound of the formula (54).

In accordance with Steps 1a-2, 1a-3 and 1a-4 of the above Process 1a, the compounds of the present invention can be prepared from a compound of the formula (55') obtained in the above Step G-5.

Process H

The following is an example of the process for preparing a compound of the formula (1) wherein ring B is

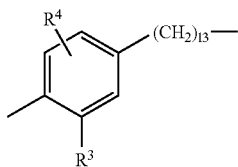

(wherein $R^3$ and $R^4$ each has the same meaning as defined above and 13 is 0).

Process H

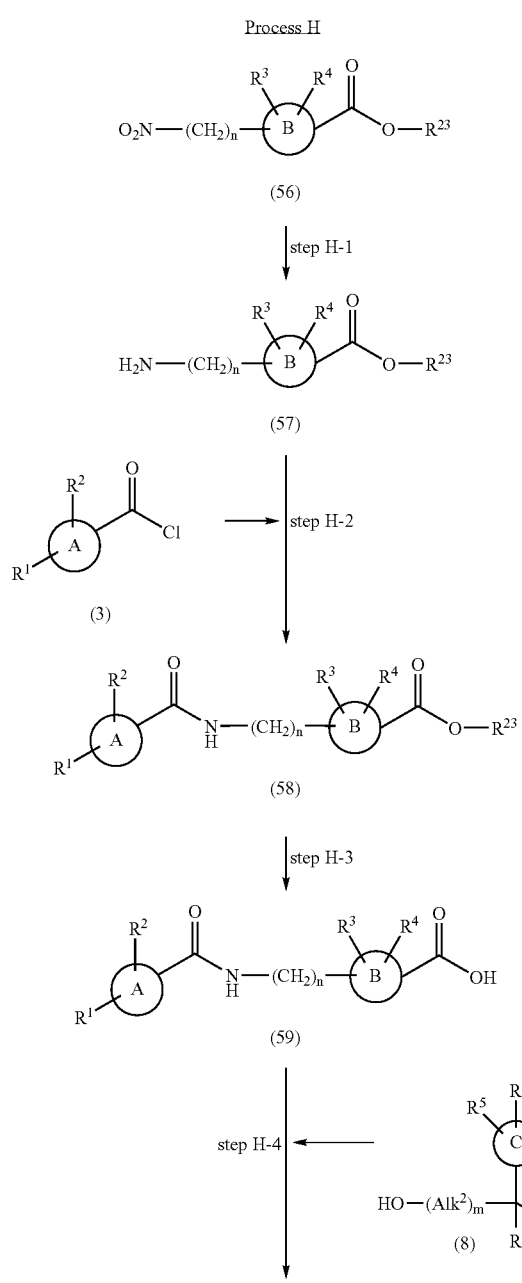

-continued

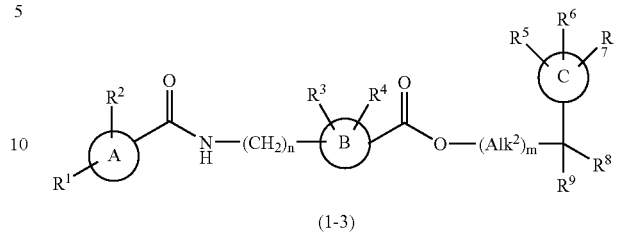

In the above reaction scheme, $R^1$, $R^2$, $R^3$, $R^4$, $R^5$, $R^6$, $R^7$, $R^8$, $R^9$, $R^{23}$, $Alk^2$, ring A, ring B, ring C, m and n each has the same meaning as defined above.

Step H-1

In a similar manner to Step 1-2 of Process 1, a compound of the formula (57) can be prepared from a compound of the formula (56).

Step H-2

In a similar manner to Step 1-3 of Process 1, a compound of the formula (58) can be prepared by reacting a compound of the formula (57) obtained in Step of H-1 (or commercially available product) with a compound of the formula (3).

Step H-3

In a similar manner to Step 1-4 of Process 1, a compound of the formula (59) can be prepared from a compound of the formula (58).

Step H-4

In a similar manner to Step 1-5 of Process 1, a compound of the formula (1-3) which is one of the objective compounds can be prepared by reacting a compound of the formula (59) with a compound of the formula (8).

Process I

The following is an example of the process for preparing a compound of the formula (1) wherein ring B is

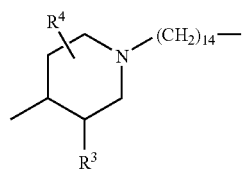

(wherein $R^3$ and $R^4$ each has the same meaning as defined above and 14 is 1 to 3).

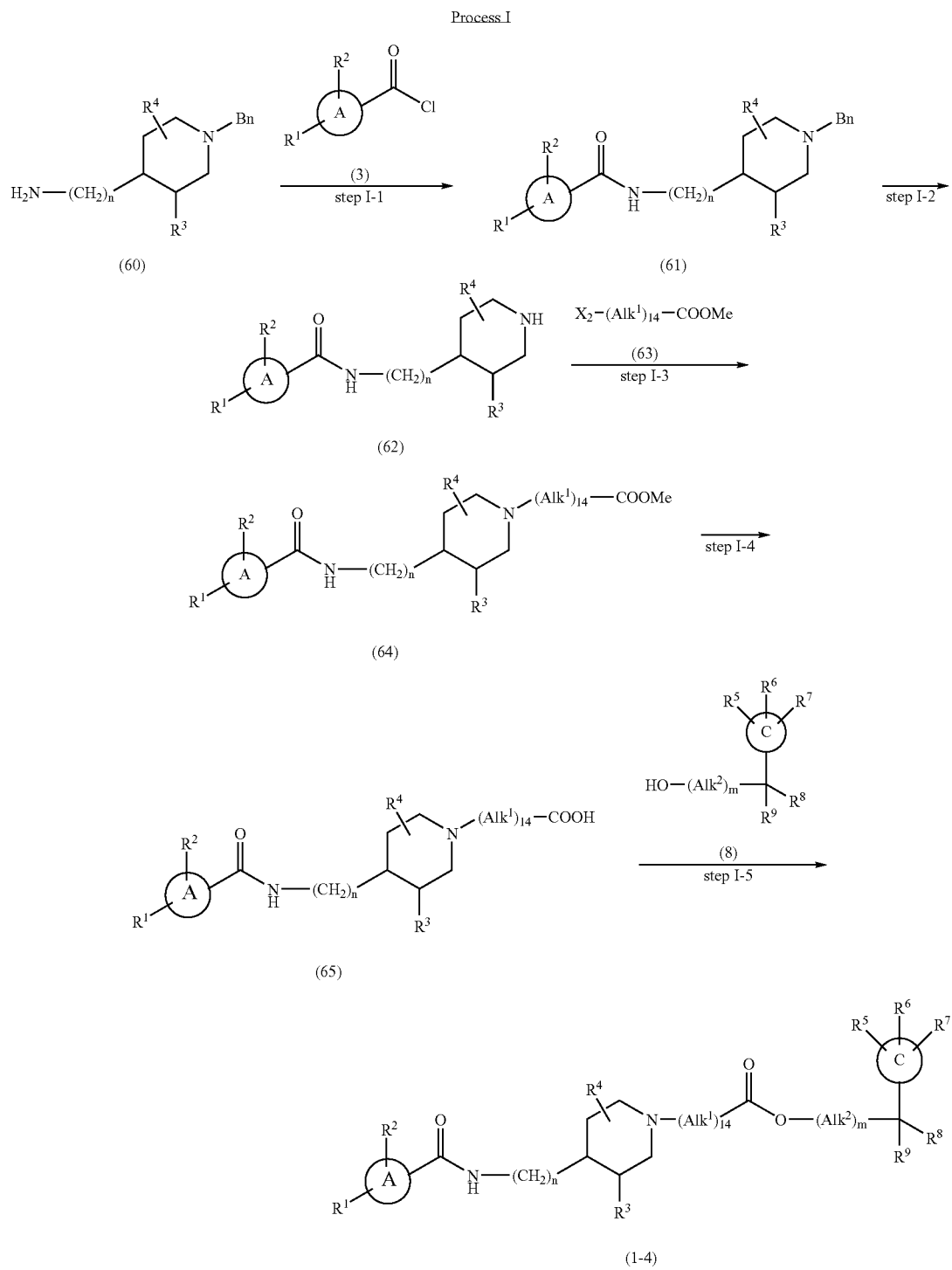

In the above reaction scheme, $R^1$, $R^2$, $R^3$, $R^4$, $R^5$, $R^6$, $R^7$, $R^8$, $R^9$, 14, m, n, ring A, ring C, Bn, Me, $Alk^1$, $Alk^2$ and $X_2$ each has the same meaning as defined above.

Step I-1

In a similar manner to Step 1-3 of Process 1, a compound of the formula (61) can be prepared by reacting a compound of the formula (60) with a compound of the formula (3).

Step I-2

Under conditions similar to Step 1-2 of Process 1, with the proviso that palladium hydroxide is used as a catalyst, a compound of the formula (62) can be prepared from a compound of the formula (61).

Step I-3

A compound of the formula (64) can be prepared by reacting a compound of the formula (62) with a compound of the formula (63) in a solvent in the presence of a base. Alternatively, $X_2$-$(Alk^1)_{14}$-COOEt (in the formula, $X_2$, $Alk^1$, 14 and Et each has the same meaning as defined above) may be used in place of a compound of the formula (63).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; esters such as ethyl acetate, methyl acetate, butyl acetate, etc.; polar solvents such as acetone, N,N-dimethylformamide, dimethyl sulfoxide, etc.; and they can be used solely or in combination thereof. A preferred solvent in the present reaction is N,N-dimethylformamide.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, etc.; alkali metal hydroxides such as lithium hydroxide, sodium hydroxide, potassium hydroxide, etc.; alkali metal carboxylates such as sodium acetate, potassium acetate, etc.; and alkali metal phosphates such as sodium phosphate, potassium phosphate, etc., among which potassium carbonate or sodium hydride is preferred.

The reaction temperature is about 0° C. to 150° C., preferably about room temperature to 100° C.

The reaction time is about 1 hour to 48 hours, preferably about 2 hours to 24 hours.

Step I-4

In a similar manner to Step 1-4 of Process 1, a compound of the formula (65) can be prepared from a compound of the formula (64).

Step I-5

In a similar manner to Step 1-5 of Process 1, a compound of the formula (1-4) which is one of the objective compounds can be prepared by reacting a compound of the formula (65) with a compound of the formula (8).

Process J

The following is an example of the process for preparing a compound of the formula (1) wherein ring B is

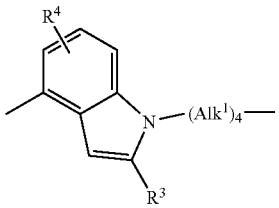

(wherein $R^3$, $R^4$ and $Alk^1$ each has the same meaning as defied above and 14 is 1 to 3).

Process J

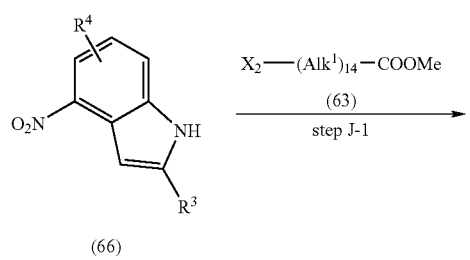

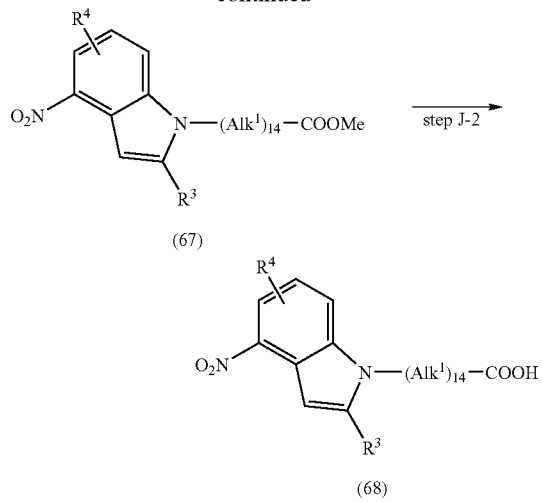

In the above reaction scheme, $R^3$, $R^4$, Me, $Alk^1$, 14 and $X_2$ each has the same meaning as defined above.

Step J-1

In a similar manner to Step I-3 of Process I, a compound of the formula (67) can be prepared by reacting a compound of the formula (66) with a compound of the formula (63). Alternatively, $X_2$-$(Alk^1)_{14}$-COOEt (in the formula $X_2$, $Alk^1$, 14 and Et each has the same meaning as defined above) may be used in place of a compound of the formula (63).

Step J-2

In accordance with the Step I-4 of Process I, a compound of the formula (68) can be prepared from a compound of the formula (67).

In a similar manner to Steps 1a-2, 1a-3 and 1a-4 of Process 1a, the compounds of the present invention can be prepared from a compound of the formula (68) obtained in the above Step J-2.

Process K

The following is an example of the process for preparing a compound of the formula (1) wherein ring B is

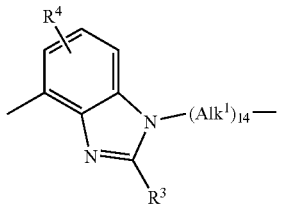

(wherein $R^3$, $R^4$, 14 and $Alk^1$ each has the same meaning as defined above).

Process K

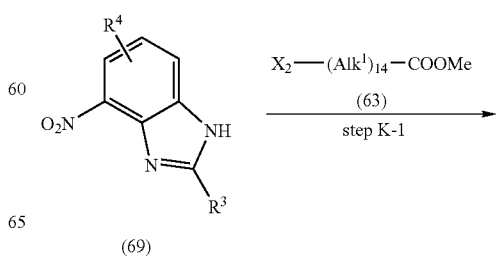

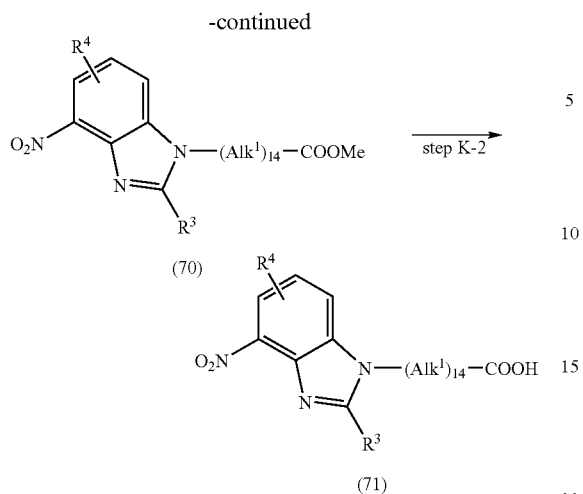

In the above reaction scheme, $R^3$, $R^4$, Me, 14, $Alk^1$ and $X_2$ each has the same meaning as defined above.

Step K-1

In a similar manner to Step I-3 of Process I, a compound of the formula (70) can be prepared by reacting a compound of the formula (69) with a compound of the formula (63). Alternatively, $X_2$-$(Alk^1)_{14}$-COOEt (in the formula $X_2$, $Alk^1$, 14 and Et each has the same meaning as defined above) may be used in place of a compound of the formula (63).

Step K-2

In a similar manner to Step I-4 of Process I, a compound of the formula (71) can be prepared from a compound of the formula (70).

In accordance with the Steps 1a-2, 1a-3 and 1a-4 of the above Process 1a, the compounds of the present invention can be prepared from a compound of the formula (71) obtained in the above Step K-2.

Process L

The following is an example of the process for preparing a compound of the formula (1) wherein $R^3$ of the ring B, and $R^{10}$ of the X are taken together to form

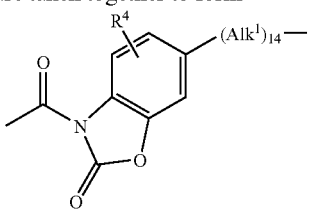

(wherein $R^4$, 14 and $Alk^1$ each has the same meaning as defined above).

Process L

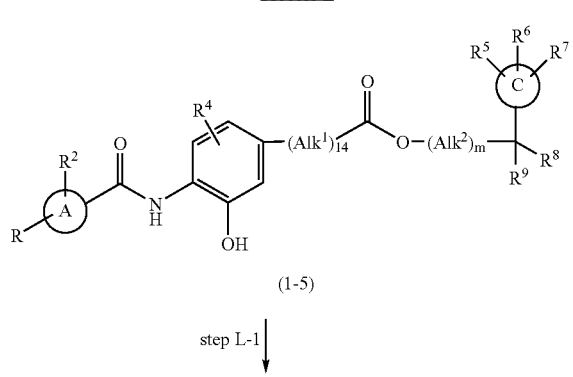

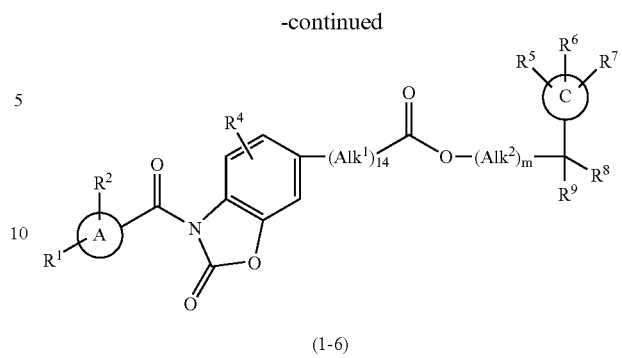

In the above reaction scheme, $R^1$, $R^2$, $R^4$, $R^5$, $R^6$, $R^7$, $R^8$, $R^9$, 14, m, ring A, ring C, $Alk^1$ and $Alk^2$ each has the same meaning as defined above.

Step L-1

A compound of the formula (1-5) obtained by debenzylation of a compound (wherein $R^{26}$ is benzyl) obtained in the Process 1 and the Process D is reacted with a phosgene equivalent reagent (for example, triphosgene or diphosgene, etc.) in a solvent in the presence of a base to give a compound of the formula (1-6).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and they can be used solely or in combination thereof. A preferred solvent in the present reaction is chloroform.

Examples of the bases used in the reaction include organic bases such as triethylamine, pyridine, dimethylaminopyridine, N-methylmorpholine, etc., among which triethylamine is preferred.

The reaction temperature is about −20° C. to 100° C., preferably about 0° C. to room temperature.

The reaction time is about 10 minutes to 4 hours, preferably about 30 minutes to 2 hours.

Process M

The following is an example of the process for preparing a compound of the formula (1) wherein $R^{10}$ is other than hydrogen.

Process M

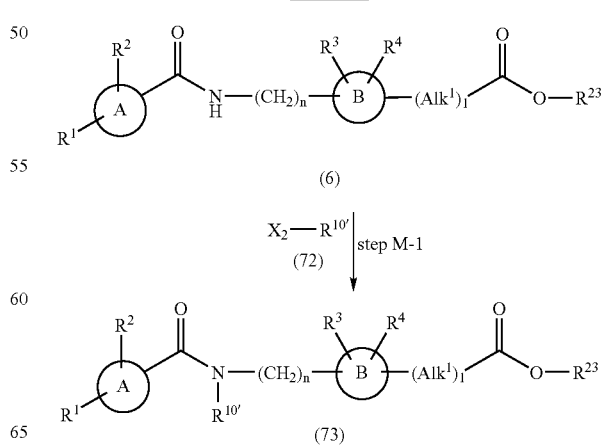

In the above reaction scheme, $R^1$, $R^2$, $R^3$, $R^4$, $R^{23}$, l, n, $X_2$, ring A, ring B, and $Alk^1$ each has the same meaning as defined above, and $R^{10'}$ is $C_1$-$C_6$ alkyl or $C_3$-$C_7$ cycloalkyl).

Step M-1

A compound of the formula (73) can be prepared by reacting a compound of the formula (6) obtained in the Step 1-3 of Process 1 with a compound of the formula (72) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; esters such as ethyl acetate, methyl acetate, butyl acetate, etc.; and polar solvents such as acetone, N,N-dimethylformamide, dimethyl sulfoxide, etc.; and they can be used solely or in combination thereof. A preferred solvent in the present reaction is N,N-dimethylformamide.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, etc.; alkali metal carboxylates such as sodium acetate, potassium acetate, etc.; and alkali metal phosphates such as sodium phosphate, potassium phosphate, etc., among which sodium hydride is preferred.

The reaction temperature is about 0° C. to 100° C., preferably about room temperature to 80° C.

The reaction time is about 1 hour to 24 hours, preferably about 2 hours to 8 hours.

In accordance with the above Steps 1-4 and 1-5, the compounds of the present invention can be prepared from a compound of the formula (73) obtained in the above Step M-1.

Process N

The following is an example of the process for preparing a compound of the formula (1) wherein $R^8$ and $R^9$ are each —CONH($R^{19'}$) (wherein $R^{19'}$ is $C_1$-$C_6$ alkyl).

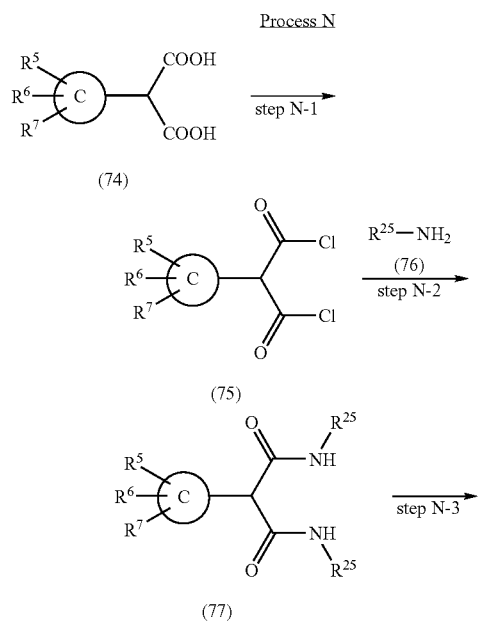

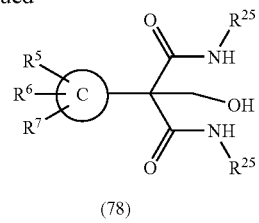

In the above reaction scheme, $R^5$, $R^6$, $R^7$, $R^{25}$ and ring C each has the same meaning as defined above.

Step N-1

A compound of the formula (75) can be prepared by reacting a compound of the formula (74) with thionyl chloride or oxalyl chloride in a solvent.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. A preferred solvent used in the present reaction is toluene containing a catalytic amount of N,N-dimethylformamide.

The reaction temperature is about room temperature to 120° C., preferably about 50° C. to 100° C.

The reaction time is about 10 minutes to 6 hours, preferably about 30 minutes to 3 hours.

Step N-2

A compound of the formula (77) can be prepared by reacting a compound of the formula (75) with a compound of the formula (76) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. Preferred solvents in the present reaction are methylene chloride or tetrahydrofuran.

Examples of the bases used in the reaction include organic bases such as triethylamine, pyridine, dimethylaminopyridine, N-methylmorpholine, etc., among which triethylamine is preferred.

The reaction temperature is about −40° C. to 60° C., preferably about −30° C. to room temperature.

The reaction time is about 2 hours to 48 hours, preferably about 6 hours to 24 hours.

Step N-3

A compound of the formula (78) can be prepared by reacting a compound of the formula (77) with paraformaldehyde or formalin without or in a solvent in the presence of a catalytic amount of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; alcohols such as methanol, ethanol, isopropyl alcohol, t-butanol, etc.; esters such as ethyl acetate, methyl acetate, butyl acetate, etc.; and polar solvents such as N,N-dimethylformamide, dimethyl sulfoxide, etc.; and they can be used solely or in combination thereof. A preferred solvent in the present reaction is tetrahydrofuran.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal hydroxides such as sodium hydroxide, potassium hydroxide, lithium hydroxide, etc.; alkali metal carbonates such as sodium carbonate, potassium carbonate, etc.; and organic bases such as triethylamine, diethylamine, pyridine, etc., among which potassium t-butoxide, sodium ethoxide or potassium hydroxide is preferred.

The reaction temperature is about 0° C. to 100° C., preferably about room temperature to 80° C.

The reaction time is about 10 minutes to 24 hours, preferably about 30 minutes to 12 hours.

In accordance with the above Processes 1, 1a and 2, the compounds of the present invention can be prepared using a compound of the formula (78) obtained in the above Step N-3 in place of a compound of the formula (8).

Process O

The following is an example of the process for preparing a compound of the formula (1) wherein $R^8$ and $R^9$ are each —COOR$^{25}$ (wherein $R^{25}$ is $C_1$-$C_6$ alkyl).

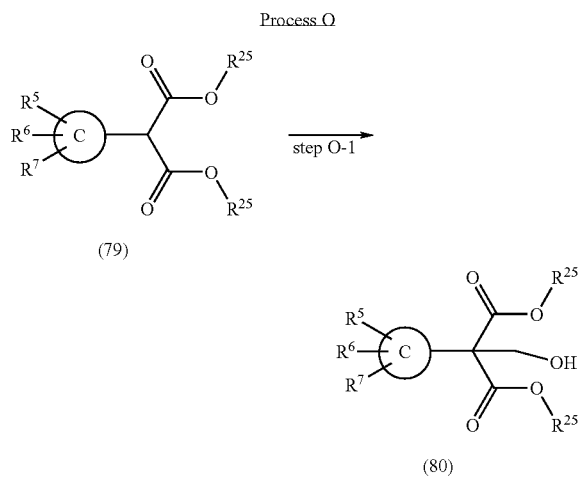

In the above reaction scheme, $R^5$, $R^6$, $R^7$, $R^{25}$ and ring C each has the same meaning as defined above.

Step O-1

In a similar manner to Step N-3 of Process N, a compound of the formula (80) can be prepared from a compound of the formula (79).

In accordance with the above Processes 1, 1a and 2, the compounds of the present invention can be prepared using a compound of the formula (80) obtained in the above Step O-1 in place of a compound of the formula (8).

Process P

The following is an example of the process for preparing a compound of the formula (1) wherein m is 2 or 3. In this process, tert-butyldimethylsilyl (TBS) may be used in place of benzyl (Bn).

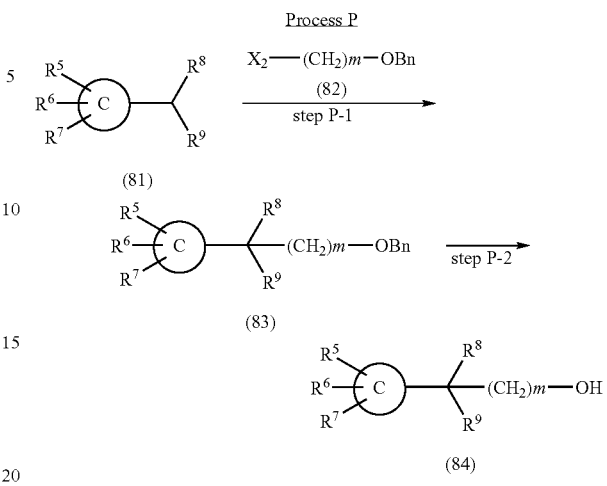

In the above reaction scheme, $R^5$, $R^6$, $R^7$, $R^8$, $R^9$, $X_2$, m, Bn and ring C each has the same meaning as defined above.

Step P-1

A compound of the formula (83) can be prepared by reacting a compound of the formula (81) with a compound of the formula (82) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; alcohols such as methanol, ethanol, isopropyl alcohol, t-butanol, etc.; esters such as ethyl acetate, methyl acetate, butyl acetate, etc.; and polar solvents such as N,N-dimethylformamide, dimethyl sulfoxide, etc.; and they can be used solely or in combination thereof. Preferred solvents in the present reaction are N,N-dimethylformamide or tetrahydrofuran.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, etc.; and organoalkali metals such as lithium diisopropylamide, etc., among which sodium hydride or lithium diisopropylamide is preferred.

The reaction temperature is about 0° C. to 100° C., preferably about room temperature to 80° C.

The reaction time is about 30 minutes to 48 hours, preferably about 2 hours to 24 hours.

Step P-2

In a similar manner to Step 2-2 of Process 2, a compound of the formula (84) can be prepared from a compound of the formula (83).

In accordance with the above Processes 1, 1a and 2, the compounds of the present invention can be prepared using a compound of the formula (84) obtained in the above Step P-2 in place of a compound of the formula (8).

EXAMPLES

The present invention is illustrated in more detail by Examples given below, but it goes without saying that the present invention is not limited thereto. In the Examples, Me is methyl, Et is ethyl, tBu is t-butyl and TBS is tert-butylmethylsilyl.

Example 1

4-[(4'-Trifluoromethylbiphenyl-2-carbonyl)amino]phenyl-acetic acid 2,2-bisethylcarbamoyl-2-phenyl-ethyl ester a) Phenylmalonic Acid Dichloride

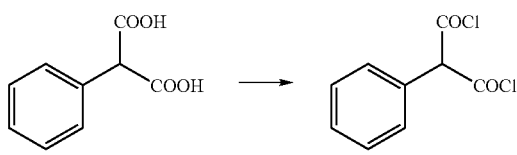

Thionyl chloride (13.7 mL) was added dropwise to a mixture of phenylmalonic acid (11.31 g), dimethylformamide (230 μL) and toluene (27 mL) under ice-cooling. The mixture was stirred at 80° C. for 70 minutes, and the solvent was removed off by evaporation. After azeotropic distillation with toluene, the residue was dried in vacuo to give the title compound (11.61 g).

b) Phenylmalonic Acid Diethylamide

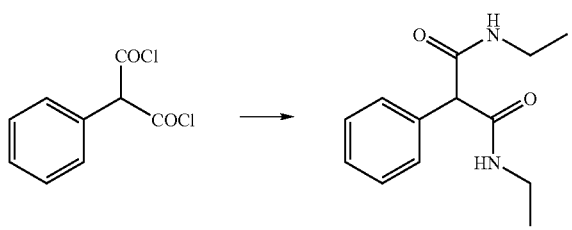

To a mixed solution of ethylamine in tetrahydrofuran (2M, 45.5 mL), triethylamine (13.9 mL) and methylene chloride (80 mL) was dropwise added the phenylmalonic acid dichloride (8.99 g) obtained in Example 1-a) at −20° C. The mixture was stirred overnight while the temperature was raised to room temperature, and then diluted with ethyl acetate after addition of 3N hydrochloric acid. The organic layer was washed with saturated brine, saturated aqueous sodium bicarbonate and saturated brine, dried over sodium sulfate and concentrated. The resulting solid was washed with ethyl acetate and hexane to give the title compound (4.85 g) as a white powder.

c) 2-Hydroxymethyl-2-phenylmalonic acid diethylamide

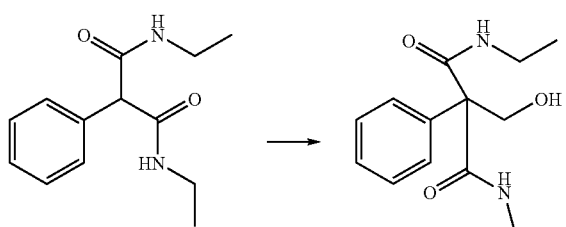

The phenylmalonic acid diethylamide (2.34 g) obtained in Example 1-b) and paraformamide (390 mg) were suspended in tetrahydrofuran (20 ml), and to this suspension was added potassium hydroxide (catalytic amount) at 60° C. The mixture was stirred for 5 hours and concentrated to remove the solvent. The residue was chromatographed on a column of silica gel with ethyl acetate:hexane=1:1 to give the title compound (2.31 g).

d) 4'-Trifluoromethylbiphenyl-2-carboxylic acid chloride

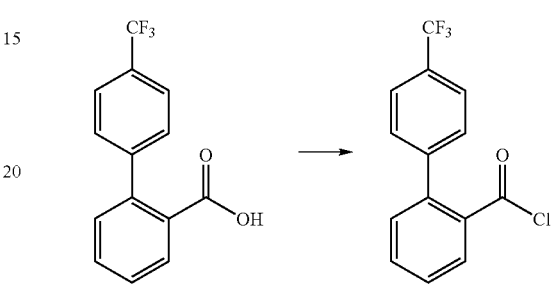

To a mixture of 4'-trifluoromethylbiphenyl-2-carboxylic acid (5.06 g), dimethylformamide (catalytic amount) and methylene chloride (30 mL) was added dropwise oxalyl chloride (2.43 mL) under ice-cooling. The mixture was stirred at room temperature for 100 minutes and the solvent was removed by evaporation. After azeotropic distillation with toluene, the residue was dried in vacuo to give the title compound (5.40 g).

e) 4-[(4'-Trifluoromethylbiphenyl-2-carbonyl)amino]phenyl-acetic acid ethyl ester

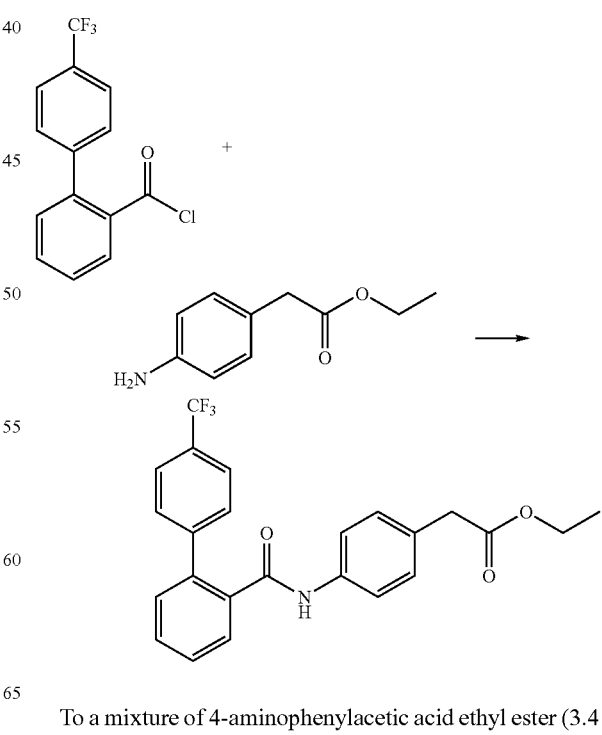

To a mixture of 4-aminophenylacetic acid ethyl ester (3.41 g), triethylamine (3.2 mL) and methylene chloride (30 mL)

was added dropwise a solution of the 4'-trifluoromethylbiphenyl-2-carboxylic acid chloride (5.40 g) obtained in Example 1-d) in methylene chloride (10 mL) under ice-cooling, and the mixture was stirred at room temperature overnight. After addition of 1N hydrochloric acid, the reaction mixture was diluted with ethyl acetate, and the organic layer was washed with saturated brine, saturated aqueous sodium bicarbonate and saturated brine, dried over sodium sulfate, and then concentrated to give the title compound (8.12 g).

f) 4-[(4'-Trifluoromethylbiphenyl-2-carbonyl)amino]phenyl-acetic acid

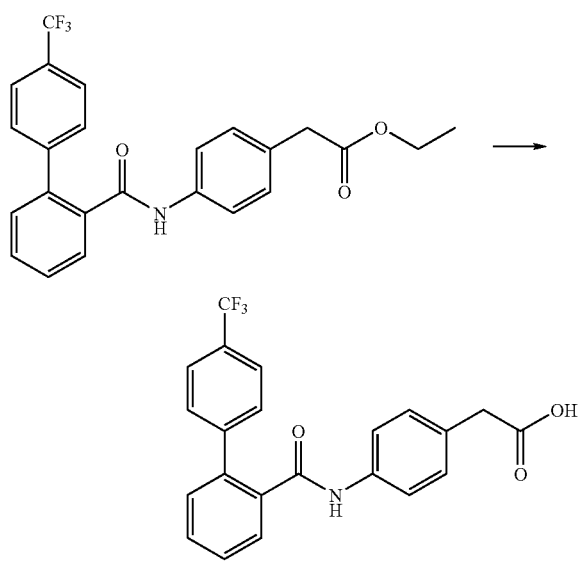

The 4-[(4'-Trifluoromethylbiphenyl-2-carbonyl)amino]phenylacetic acid ethyl ester (8.12 g) obtained in Example 1-e) was dissolved in 40 mL of tetrahydrofuran and 20 mL of ethanol. After addition of 4N sodium hydroxide (5 mL), the solution was stirred at room temperature for 5 hours and concentrated. The powder formed upon addition of 1N hydrochloric acid was collected by filtration and dried in vacuo to give the title compound (7.48 g).

g) 4-[(4'-Trifluoromethylbiphenyl-2-carbonyl)amino]phenyl-acetic acid 2,2-bisethylcarbamoyl-2-phenyl-ethyl ester

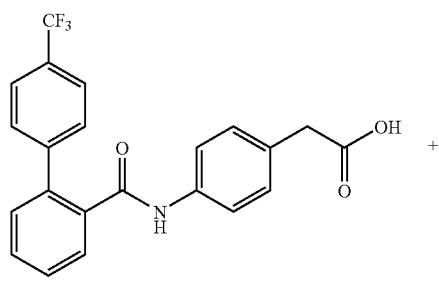
+

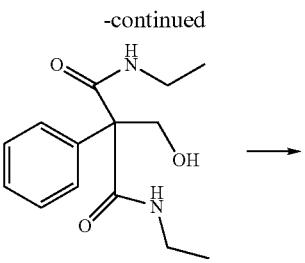

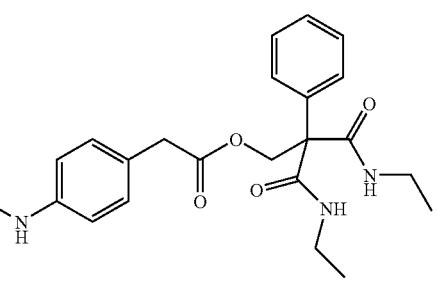

The 4-[(4'-Trifluoromethylbiphenyl-2-carbonyl)amino]phenylacetic acid (519 mg) obtained in Example 1-f), the 2-hydroxymethyl-2-phenylmalonic aid diethylamide (317 mg) obtained in Example 1-c), dimethylaminopyridine (171 mg) and 1-ethyl-3-(3'-dimethylaminopropyl)carbodiimide hydrochloride (WSC.HCl)(268 mg) were dissolved in methylene chloride (5 ml). The solution was stirred at room temperature for 6 hours and the solvent was removed off by evaporation. The residue was purified by column chromatography on silica gel with ethyl acetate:hexane=1:1 to 3:2 to give the title compound (725 mg) (see Table 1).

Example 1-2

2-Phenyl-2-{2-[4-(4'-trifluoromethylbiphenyl-2-carbonyloxy)phenyl]acetoxymethyl}malonic acid diethyl ester a) 2-Hydroxymethyl-2-phenylmalonic acid diethyl ester

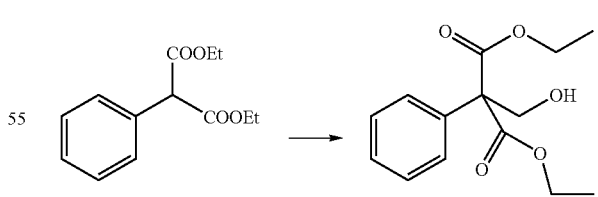

Paraformaldehyde (720 mg) was suspended in phenylmalonic acid diethyl ester (4.73 g), and a catalytic amount of potassium hydroxide was added thereto at 60° C. After stirring for 1.5 hours, the reaction mixture was purified by column chromatography on silica gel with ethyl acetate:hexane=1:5 to 1:2 to give the title compound (4.96 g).

b) 2-[2-(4-(Benzyloxyphenyl)acetoxymethyl]-2-phenylmalonic acid diethyl ester

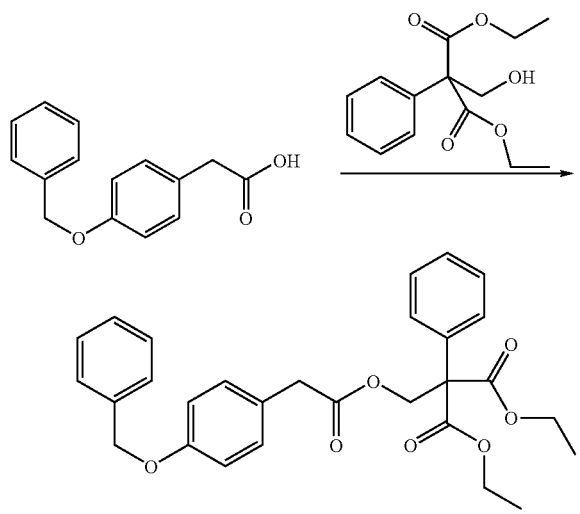

4-Benzyloxyphenylacetic acid (1.09 g) was suspended in methylene chloride (50 mL) and the suspension was dissolved by addition of dimethylaminopyridine (0.511 g). To the solution was added the 2-hydroxymethyl-2-phenylmalonic acid diethyl ester (1.20 g) obtained in Example 1-2a), and 1-ethyl-3-(3'-dimethylaminopropyl)carbodiimide hydrochloride (0.864 g) was portionwise added thereto. The mixture was stirred at room temperature overnight and then concentrated. The residue was purified by column chromatography on silica gel with ethyl acetate:hexane=1:4 to give the title compound (1.95 g) as a colorless oil.

c) 2-[2-(4-(Hydroxyphenyl)acetoxymethyl]-2-phenylmalonic acid diethyl ester

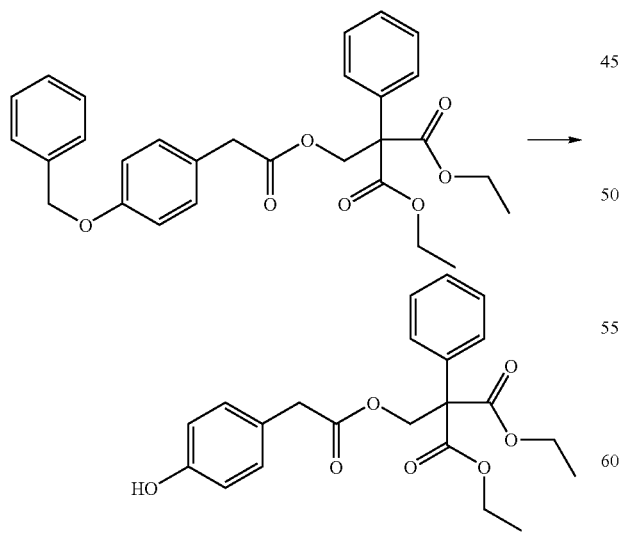

The 2-[2-(4-(Benzyloxyphenyl)acetoxymethyl]-2-phenylmalonic acid diethyl ester (1.95 g) obtained in Example 1-2b) was dissolved in methanol (2.5 mL). The solution was subjected to hydrogenation in the presence of 7.5% palladium-carbon (0.200 g) under normal pressure for 4 hours. The reaction solution was filtered through a Celite pad and concentrated to give the title compound (1.71 g) as a colorless oil.

d) 2-Phenyl-2-{2-[4-(4'-trifluoromethylbiphenyl-2-carbonyloxy)phenyl]acetoxymethyl}malonic acid diethyl ester

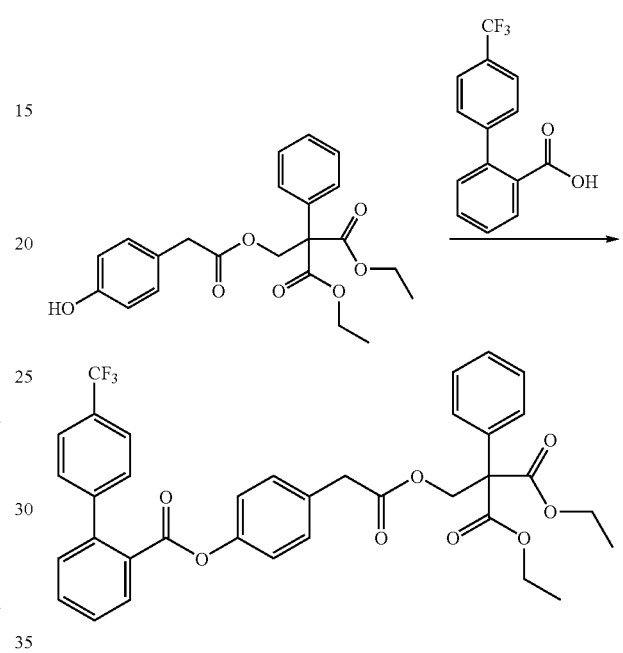

4'-Trifluoromethylbiphenyl-2-carboxylic acid (0.266 g) was suspended in methylene chloride (10 mL), and the suspension was dissolved by addition of 4-dimethylaminopyridine (0.122 g). To the solution was added the 2-[2-(4-(hydroxyphenyl)acetoxymethyl]-2-phenylmalonic acid diethyl ester (0.400 g) obtained in Example 1-2c), and 1-ethyl-3-(3'-dimethylaminopropyl)carbodiimide hydrochloride (0.192 g) was portionwise added thereto. The mixture was stirred at room temperature overnight and then concentrated. The residue was purified by column chromatography on silica gel with ethyl acetate:hexane=1:3 to give the title compound (0.55 g) as an amorphous powder (see Table 1).

Example 1-3

2-(2-{3-Methyl-4-[(4'-trifluoromethylbiphenyl-2-carbonyl)amino]phenyl}acetoxymethyl)-2-phenyl-malonic acid diethyl ester a) 2-(3-Methyl-4-nitrophenyl)malonic acid diethyl ester

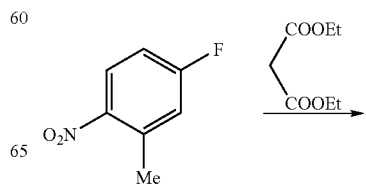

-continued

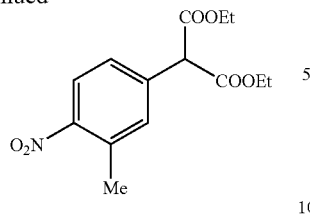

Sodium hydride (60% mineral oil; 0.599 g) was suspended in dimethylformamide (10 mL), and a solution of malonic acid diethyl ester (2.00 g) in dimethylformamide (10 mL) was added dropwise thereto under ice-cooling. After foam generation is stopped, a solution of 4-fluoro-2-methylnitrobenzene (1.94 g) in dimethylformamide (5 mL) was added thereto, and the reaction temperature was raised to 100° C., followed by stirring for 6 hours. The reaction mixture was concentrated, acidified with 1N hydrochloric acid and extracted with ethyl acetate. The extract was washed successively with water and saturated brine, dried over sodium sulfate and concentrated. The residue was purified by column chromatography on silica gel with ethyl acetate:hexane=1:5 to give the title compound (1.65 g) as a yellow oil.

b) (3-Methyl-4-nitrophenyl)acetic acid

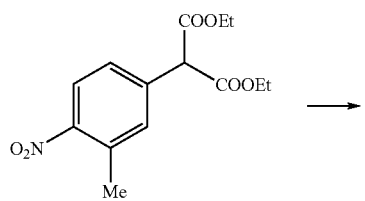

Potassium hydroxide (0.168 g) was dissolved in 7 mL of methanol and 1 mL of water, and the 2-(3-methyl-4-nitrophenyl)malonic acid diethyl ester (0.250 g) obtained in Example 1-3a) was dissolved in the solution. The solution was stirred at 100° C. for 2 hours and concentrated. The residue was acidified with 2N hydrochloric acid and extracted with ethyl acetate. The extract was washed with saturated brine, dried over sodium sulfate and concentrated to give the title compound (0.143 g) as a yellow solid.

c) 2-[2-(3-Methyl-4-nitrophenyl)acetoxymethyl]-2-phenyl-malonic acid diethyl ester

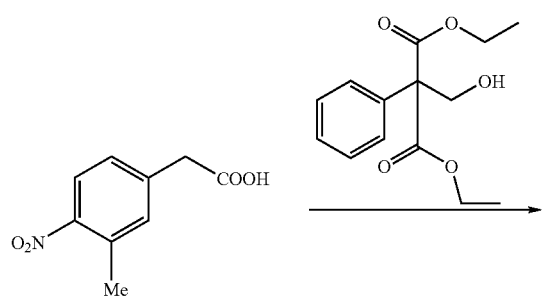

-continued

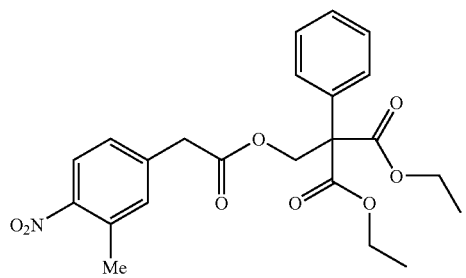

The (3-Methyl-4-nitrophenyl)acetic acid (0.143 g) obtained in Example 1-3b) was dissolved in methylene chloride (5 mL). To the solution were added 2-hydroxymethyl-2-phenylmalonic acid diethyl ester (0.195 g) obtained in Example 1-2a), 4-dimethylaminopyridine (0.090 g) and 1-ethyl-3-(3'-dimethylaminopropyl)carbodiimide hydrochloride (0.141 g), and the mixture was stirred at room temperature overnight. The reaction mixture was concentrated and the residue was purified by column chromatography on silica gel with ethyl acetate:hexane=1:4 to give the title compound (0.219 g) as a yellow oil.

d) 2-[2-(4-Amino-3-methylphenyl)acetoxymethyl]-2-phenyl-malonic acid diethyl ester

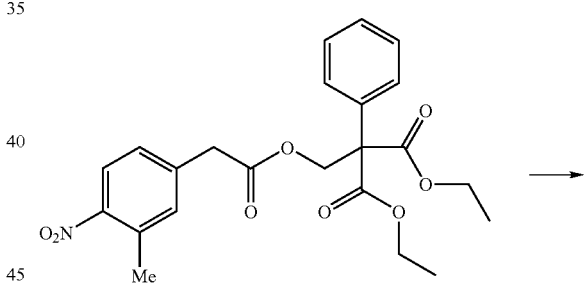

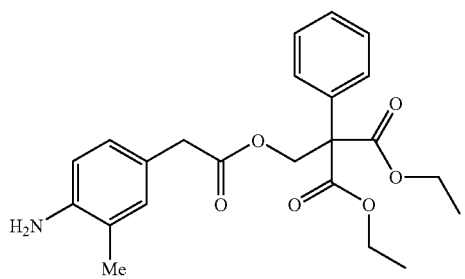

The 2-[2-(3-Methyl-4-nitrophenyl)acetoxymethyl]-2-phenyl-malonic acid diethyl ester (0.219 g) obtained in Example 1-3c) was dissolved in methanol (3 mL). The solution was subjected to hydrogenation in the presence of 7.5% palladium-carbon (0.030 g) under normal pressure to give the title compound (0.197 g) as a yellow oil.

e) 2-(2-{3-Methyl-4-[(4'-trifluoromethylbiphenyl-2-carbonyl)amino]phenyl}acetoxymethyl)-2-phenyl-malonic acid diethyl ester

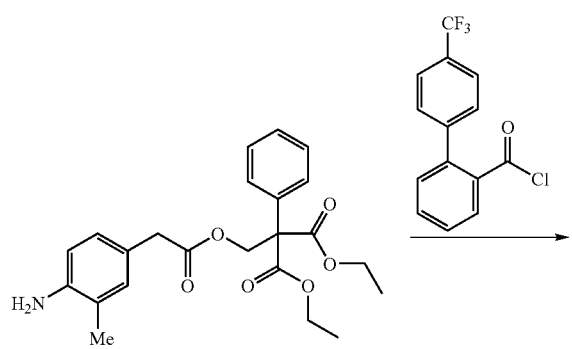

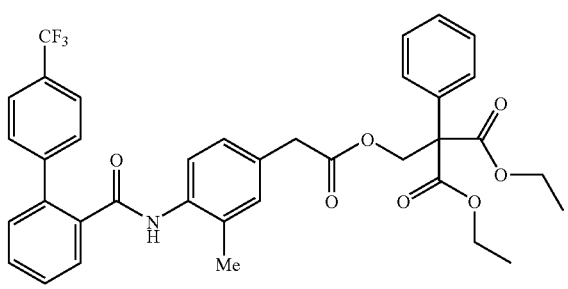

In a similar manner to Example 1d), 4'-trifluoro-methyl-2-biphenylcarboxylic acid (0.124 g) was converted into its corresponding acid chloride. On the other hand, the title compound (0.215 g) was obtained as a colorless amorphous from the 2-[2-(4-amino-3-methylphenyl)acetoxymethyl]-2-phenylmalonic acid diethyl ester (0.197 g) obtained in Example 1-3d) in a similar manner to Example 1e)(see Table 1).

Example 1-4

2-(2-{4-[Methyl-(4'-trifluoromethylbiphenyl-2-carbonyl)amino]phenyl}acetoxymethyl)-2-phenylmalonic acid diethyl ester a) {4-[Methyl-(4'-trifluoromethylbiphenyl-2-carbonyl)amino]phenyl}acetic acid ethyl ester

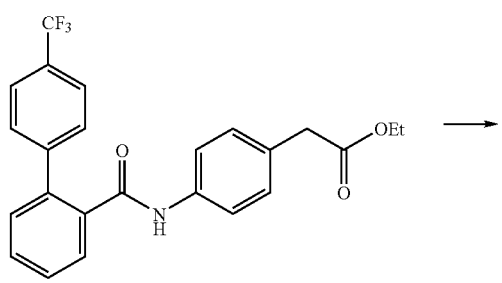

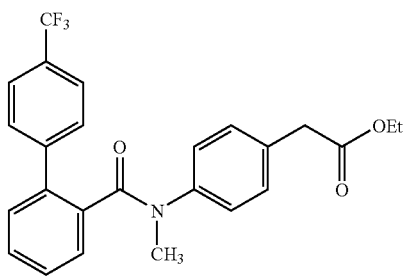

Sodium hydride (51 mg) was dissolved in dimethylformamide (5 mL), and the solution was cooled to 0° C. To the solution was added the 4-[(4'-trifluoromethylbiphenyl-2-carbonyl)amino]phenylacetic acid ethyl ester (500 mg) obtained in Example 1e), and the mixture was stirred for one hour. After addition of iodomethane (183 mg), the mixture was stirred at room temperature for 3 hours and water was then added. The reaction solution was concentrated, diluted with ethyl acetate, and washed with water. The resulting solution was dried over sodium sulfate and purified by column chromatography on silica gel with hexane:ethyl acetate=4:1 to give the title compound (141 mg).

b) 2-(2-{4-[Methyl-(4'-trifluoromethylbiphenyl-2-carbonyl)amino]phenyl}acetoxymethyl)-2-phenyl-malonic acid diethyl ester

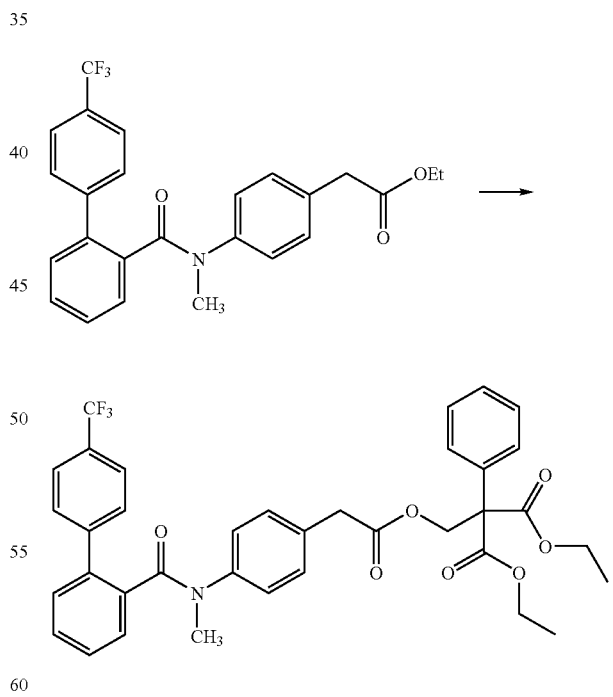

The {4-[Methyl-(4'-trifluoromethylbiphenyl-2-carbonyl)amino]phenyl}acetic acid ethyl ester (141 mg) obtained in Example 1-4a) was subjected to reactions similar to those in Examples 1f) and 1g) to give the title compound (56 mg)(see Table 1).

Example 1-5

{3-Ethyl-4-[(4'-trifluoromethylbiphenyl-2-carbonyl)amino]phenyl}acetic acid 2,2-bisethylcarbamoyl-2-phenylethyl ester a) 3-Ethyl-4-nitrophenylacetic acid ethyl ester

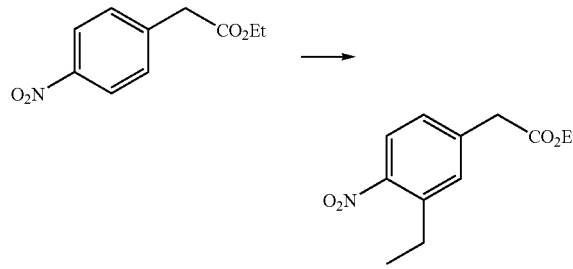

To a solution of 4-nitrophenylacetic acid ethyl ester (1.63 g) in tetrahydrofuran (100 mL) was dropwise added 2M ethyl magnesium chloride in tetrahydrofuran (3 mL) at −15° C. under argon atmosphere, and the mixture was stirred at the same temperature for 30 minutes. After further dropwise addition of 2M ethyl magnesium chloride in tetrahydrofuran (3 mL), the mixture was stirred at −15° C. for one hour, and 2,3-dichloro-5,6-dicyano-1,4-benzoquinone (3.0 g) was added thereto at the same temperature. The mixture was stirred overnight, and water (300 mL) was added thereto, followed by extraction with chloroform (150 mL×3). The organic layers were combined, washed with saturated brine, dried over sodium sulfate and purified by column chromatography on silica gel with hexane:ethyl acetate=10:1 to give the title compound (1.09 g).

b) {3-Ethyl-4-[(4'-trifluoromethylbiphenyl-2-carbonyl)amino]phenyl}acetic acid 2,2-bisethylcarbamoyl-2-phenylethyl ester

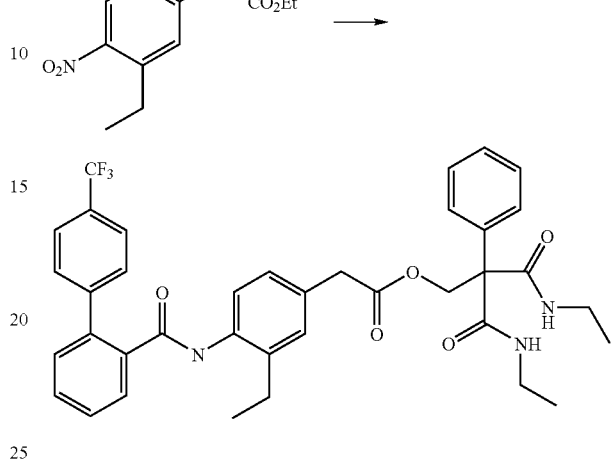

The 3-ethyl-4-nitrophenylacetic acid ethyl ester (1.05 g) obtained in Example 1-5a) was subjected to reactions similar to those in Example 1-3d), Example 1e), Example 1f) and Example 1g) to give the title compound (1.60 g)(see Table 1).

Examples 1-6 to 1-83

Compounds of Examples 1-6 to 1-85 were obtained in a similar manner to Examples 1 to 1-5. The compounds obtained were shown in Tables 2 to 17.

TABLE 1

| Example | Structure | NMR (δ, 300 MHz, CDCl₃) |
|---|---|---|
| 1 | [structure image] m.p. 88.4-91.2 | 1.05(6H, t, J=7.3Hz), 3.18-3.29(4H, m), 3.53(2H, s), 4.83(2H, s), 6.95(1H, br-s), 7.02-7.23(8H, m), 7.27-7.36(3H, m), 7.41-7.47(1H, m), 7.49-7.63(4H, m), 7.65-7.72(2H, m), 7.77-7.84(1H, m) |
| 1-2 | [structure image] | 1.19(6H, t, J=9.2Hz), 3.53(2H, s), 4.18(4H, q, J=9.2Hz), 4.82(2H, s), 6.79(2H, d, J=12Hz), 7.14(2H, d, J=12Hz), 7.29(5H, brs), 7.38-7.73(7H, m), 8.09(1H, dd, J=1.2Hz, J=7.5Hz). |

TABLE 1-continued

| Example | Structure | NMR (δ, 300 MHz, CDCl₃) |
|---|---|---|
| 1-3 | 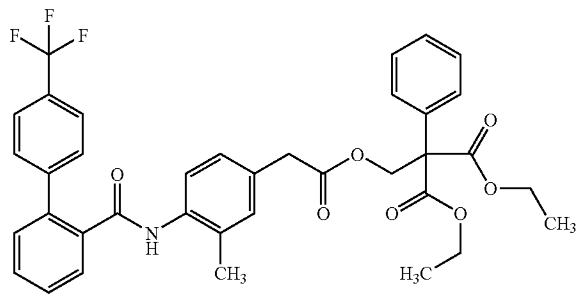 | 1.21(6H, t, J=7.1Hz), 1.67(3H, s), 3.47(2H, s), 4.20(4H, q, J=7.1Hz), 4.82(2H, s), 6.89((1H, brs), 6.92(1H, brs), 7.00(1H, d, J=10.6Hz), 7.30(5H, brs), 7.42-7.84(9H, m). |
| 1-4 | 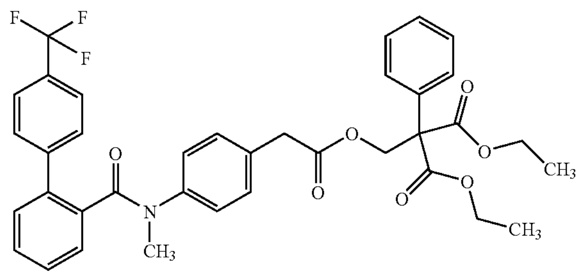 | 1.22(6H, t, J=7.2Hz) 3.23 (3H, s), 3.40(2H, s), 4.21(4H, q, J=7.2Hz), 4.83(2H, s), 6.10(2H, d, J=8.3Hz), 6.70(2H, d, J=8.3Hz), 7.07-7.61(13H, m) |
| 1-5 | m.p. 105-109 | 0.93(3H, t, J=7.5Hz), 1.05(6H, t, J=7.3Hz), 1.94(2H, q, J=7.5Hz), 3.13-3.28(4H, m), 3.53(2H, s), 4.83(2H, s), 6.80-7.84(19H, m) |

TABLE 2

| Example | Structure | NMR (δ, 300 MHz, CDCl₃) |
|---|---|---|
| 1-6 | 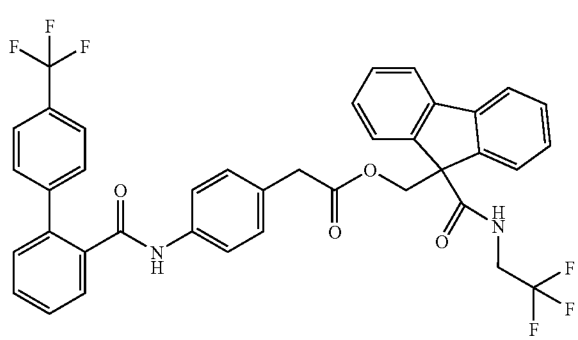 | 3.56(2H, s), 3.65-3.78(2H, s), 4.55(2H, s), 5.49(1H, br), 7.01(1H, brs), 7.05-7.83(20H, m). |

TABLE 2-continued
| Example | Structure | NMR (δ, 300 MHz, CDCl₃) |
|---|---|---|
| 1-7 | 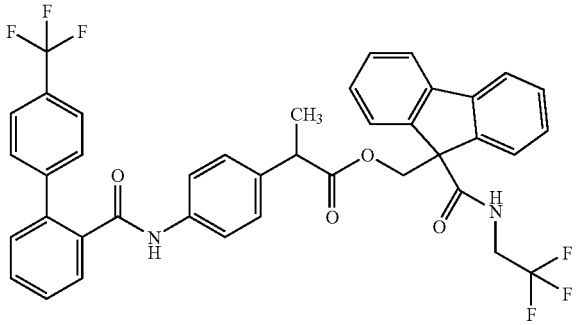 | 1.39(3H, d, J=7.2 Hz), 3.48-3.68(2H, m), 3.70-3.89(2H, m), 4.44 (1H, d, J=10.6Hz), 4.66 (1H, d, J=10.6Hz), 5.46 (1H, br), 6.96((1H, brs), 7.02-7.84(20H, m). |
| 1-8 | 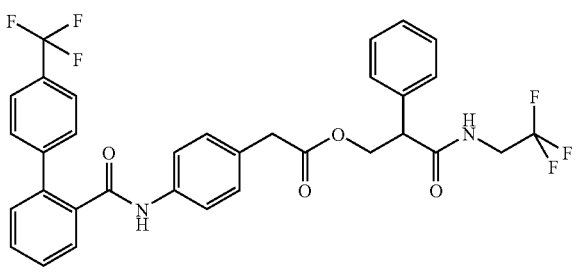 | 3.50(2H, s), 3.68-4.00 (3H, m), 4.42(1H, dd, J=6.0, 11.0 Hz), 4.62(1H, dd, J=7.9, 11.0Hz), 5.68 (1H, t, J=6.8 Hz), 6.95(1H, s), 7.03-7.17(4H, m), 7.17-7.36(5H, m), 7.44(1H, dd, J=1.5, 7.6Hz), 7.48-7.64(4H, m), 7.65-7.71(2H, m), 7.80 (1H, dd, J=1.5, 7.6 Hz) |
| 1-9 | 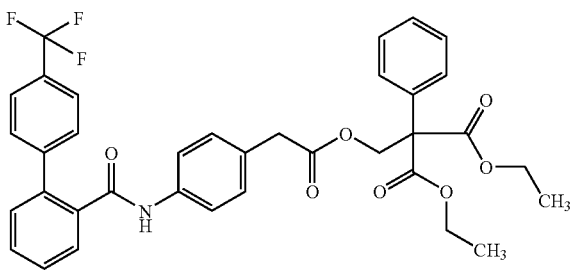 | 1.20(6H, t, J=7.2 Hz), 3.51(2H, s), 4.20(4H, q, J=7.2 Hz), 4.81(2H, s), 6.92(1H, br-s), 7.04-7.18(4H, m), 7.24-7.35(5H, m), 7.44(1H, dd, J=1.5, 7.1 Hz), 7.48-7.64(4H, m), 7.65-7.73(2H, m), 7.81(1H, dd, J=1.5, 7.1Hz) |
| 1-10 | 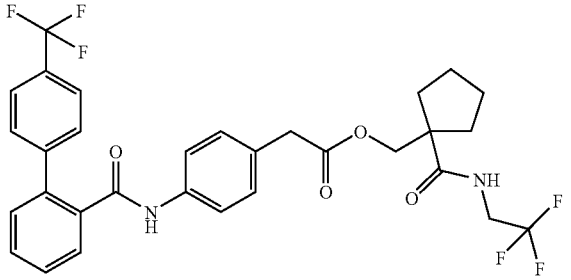 | 1.47-1.76(6H, m), 1.90-2.03(2H, m), 3.60(2H, s), 3.71-3.85(2H, m), 4.10(2H, s), 6.94(1H, br-s), 7.12-7.20(4H, m), 7.44(1H, dd, J=1.2, 7.4 Hz), 7.49-7.64(4H, m), 7.65-7.72(2H, m), 7.80(1H, dd, J=1.2, 7.4 Hz) |
TABLE 3
| Example | Structure | NMR (δ, 300 MHz, CDCl₃) |
|---|---|---|
| 1-11 | 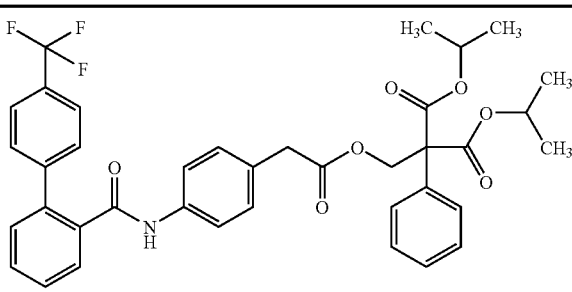 | 1.18(6H, d, J=6.4 Hz), 1.20(6H, d, J=6.0 Hz), 3.50(2H, s), 4.80(2H, s), 5.08(1H, sept, J=6.4 Hz), 5.08(1H, sept, J=6.0 Hz), 6.92(1H, s), 7.05-7.16(4H, m), 7.27-7.32(5H, m), 7.41-7.47(1H, m), 7.49-7.63(4H, m), 7.65-7.72(2H, m), 7.80 (1H, dd, J=1.5, 7.1 Hz) |

TABLE 3-continued
| Example | Structure | NMR (δ, 300 MHz, CDCl₃) |
|---|---|---|
| 1-12 | 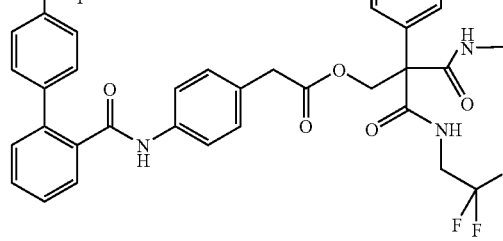 | 3.53(2H, s), 3.74-3.97(4H, m), 4.87(2H, s), 6.94(1H, s), 7.00-7.07(2H, m), 7.09-7.20(4H, m), 7.31-7.47(6H, m), 7.49-7.64(4H, m), 7.65-7.72(2H, m), 7.80 (1H, dd, J=1.5, 7.5 Hz) |
| 1-13 | 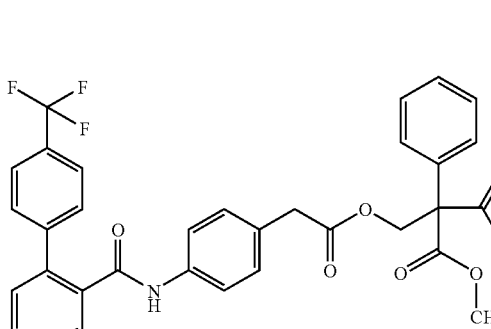 | 3.51(2H, s), 3.71(6H, s), 4.81(2H, s), 6.92(1H, br-s), 7.05-7.16(4H, m), 7.22-7.35(5H, m), 7.41-7.46(1H, m), 7.49-7.63(4H, m), 7.65-7.71(2H, m), 7.81 (1H, dd, J=1.5, 7.2 Hz) |
| 1-14 | 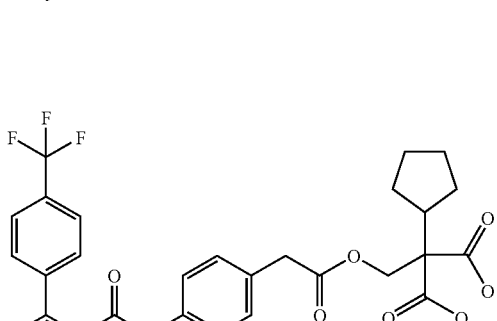 | 1.20(6H, t, J=7.1 Hz), 1.29-1.81(10H, br), 2.40(2.53(1H, m), 3.52(2H, s), 4.13(4H, q, J=7.1 Hz), 4.48(2H, s), 6,93(1H, brs), 7.14(4H, brs), 7.39-7.83(8H, m). |
| 1-15 | 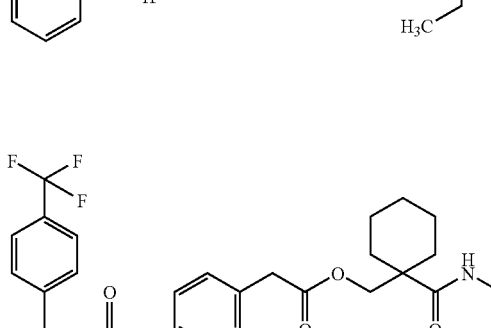<br>m.p. 108.8-112.4 | 1.27-1.44(5H, m), 1.46-1.61(3H, m), 1.79-1.90(2H, m), 3.57 (2H, s), 3.72-3.87(2H, m), 4.07(2H, s), 5.71-5.81(1H, m), 6.94(1H, br-s), 7.10-7.21(4H, m), 7.40-7.47(1H, m), 7.49-7.63(4H, m), 7.65-7.72(2H, m), 7.77-7.83(1H, m) |

TABLE 4

| Example | Structure | NMR (δ, 300 MHz, CDCl₃) |
|---|---|---|
| 1-16 | (structure) m.p. 93-95 | 1.22(6H, t, J=7.2 Hz), 3.57(2H, s), 4.21(4H, q, J=7.2 Hz), 4.83(2H, s), 7.20(1H, d, J=8.5 Hz), 7.28-7.67(12H, m), 7.76(1H, d, J=7.4) |
| 1-17 | (structure) m.p. 99-103 | 1.20(6H, t, J=7.1 Hz), 3.53(2H, s), 4.19(4H, q, J=7.1Hz), 4.82(2H, s), 6.91(1H, d, J=8.3 Hz), 7.11-7.56(16H, m), 8.33(1H, dd, J=7.8, 1.8 Hz), 9.62(1H, br.s) |
| 1-18 | (structure) | 1.05(3H, m), 1.22(6H, t, J=7.2 Hz), 1.58(2H, m), 1.99(2H, m), 3.57(2H, s), 4.21(6H, m), 4.85(2H, s), 7.04-7.60(12H, m), 8.30(1H, m), 10.07(1H, br.s) |
| 1-19 | (structure) | 1.22(6H, t, J=6.9 Hz), 3.60(2H, s), 4.20(4H, q, J=6.9 Hz), 4.85(2H, s), 7.12-7.37(9H, m), 7.63-7.73(2H, m), 7.79-7.86(1H, m), 7.90-8.00(1H, m). |
| 1-20 | (structure) | 1.18(6H, t, J=6.8 Hz), 3.51(2H, s), 4.17(4H, q, J=6.8 Hz), 4.80(2H, s), 6.70(2H, d, J=12 Hz), 7.09(2H, d, J=12 Hz), 7.27(5H, brs), 7.41-7.83(8H, m), 8.21(1H, d, J=10 Hz). |

TABLE 5

| Example | Structure | NMR (δ, 300 MHz, CDCl₃) |
|---|---|---|
| 1-21 | 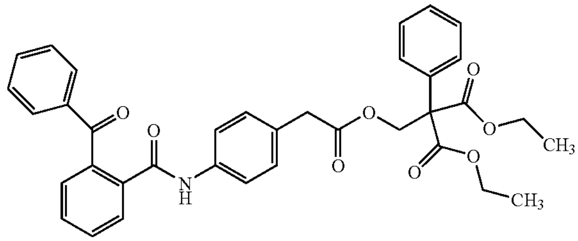 | 1.18(6H, t, J=7.2 Hz), 3.49(2H, s), 4.15(4H, q, J=7.2 Hz), 4.80(2H, s), 7.07(1H, d, J=8.6 Hz), 7.27-7.54(17H, m), 7.88(1H, d, J=6.2 Hz) |
| 1-22 | 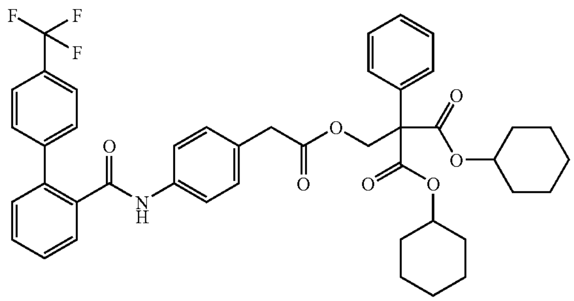 | 1.16-1.83(20H, m), 3.50(2H, s), 4.80-4.91(2H, m), 4.82(2H, s), 6.93(1H, br-s), 7.05-7.17(4H, m), 7.27-7.34(5H, m), 7.41-7.47(1H, m), 7.49-7.63(4H, m), 7.65-7.72(2H, m), 7.80 (1H, dd, J=1.5, 7.2 Hz) |
| 1-23 | 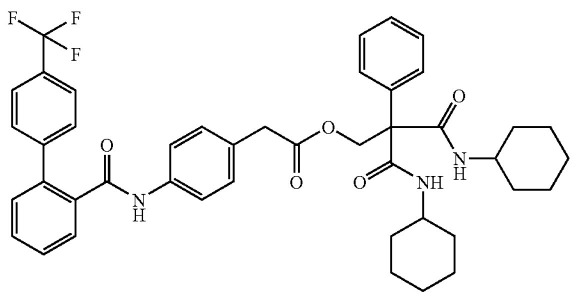 | 0.95-1.22(6H, m), 1.23-1.43(4H, m), 1.50-1.71(6H, m), 1.71-1.90(4H, m), 3.52 (2H, s), 3.69-3.83(2H, m), 4.84(2H, s), 6.95(1H, br-s), 7.04-7.35(11H, m), 7.41-7.48(1H, m), 7.49-7.65(4H, m), 7.66-7.73(2H, m), 7.77-7.84(1H, m) |
| 1-24 | 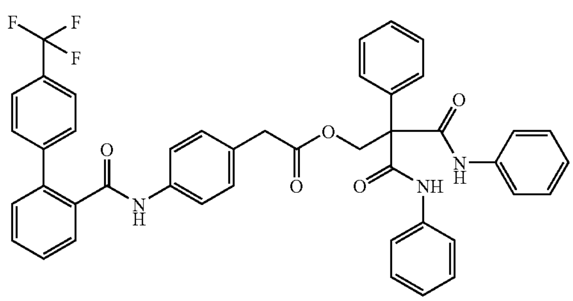 | 3.58(2H, s), 5.06(2H, s), 6.81(1H, br-s), 6.99-7.05(4H, m), 7.08-7.16(2H, m), 7.24-7.47(14H, m), 7.50-7.67(6H, m), 7.80 (1H, dd, J=1.5, 7.5 Hz), 9.08(2H, br-s) |
| 1-25 | 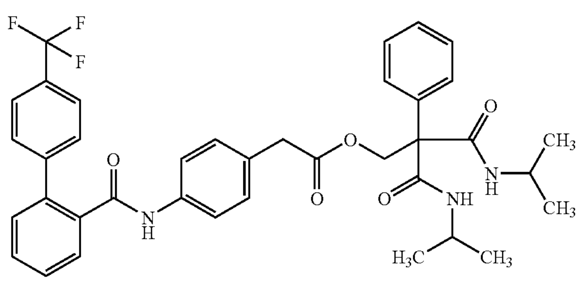 | 1.04(6H, d, J=6.4 Hz), 1.09(6H, d, J=6.8 Hz), 3.52(2H, s), 3.95-4.09(2H, m), 4.83(2H, s), 6.92-7.03(3H, m), 7.03-7.10(2H, m), 7.11-7.23(4H, m), 7.27-7.36(3H, m), 7.41-7.47(1H, m), 7.49-7.64(4H, m), 7.65-7.72(2H, m), 7.80 (1H, dd, J=1.5, 7.5 Hz) |

TABLE 6

| Example | Structure | NMR (δ, 300 MHz, CDCl₃) |
|---|---|---|
| 1-26 | 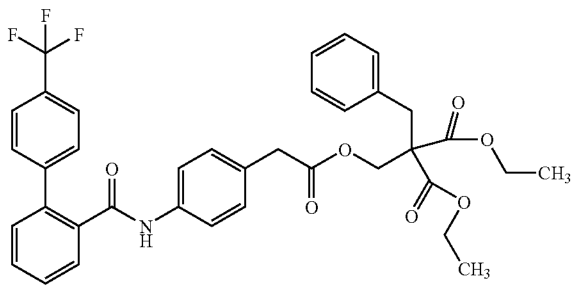 | 1.19(6H, t, J=7.1 Hz), 3.24(2H, s), 3.59(2H, s), 4.15(4H, q, J=7.1 Hz), 4.32(2H, s), 6.80-6.88(2H, m), 6.93(1H, brs), 7.11-7.28(7H, m), 7.39-7.83(8H, m) |
| 1-27 | 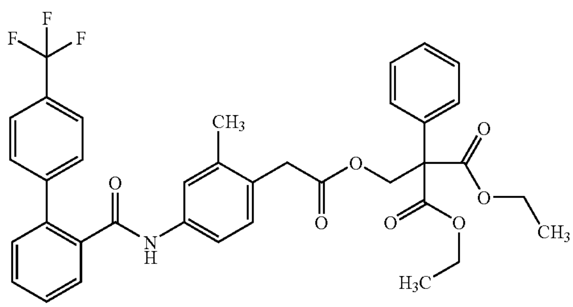 | 1.21(6H, t, J=7.1 Hz), 2.14(3H, s), 3.51(2H, s), 4.19(4H, q, J=7.1 Hz), 4.80(2H, s), 6.87(1H, brs), 6.91-7.02(3H, m), 7.19-7.34(5H, m), 7.40-7.85(8H, m). |
| 1-28 | 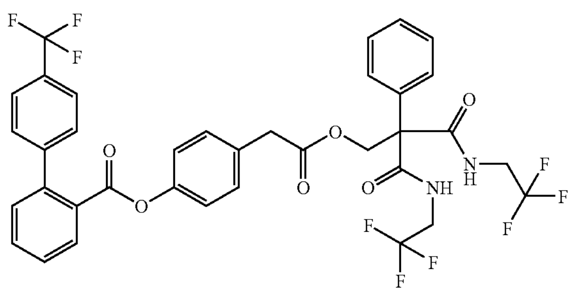 | 3.56(2H, s), 3.71-3.95 (4H, m), 4.87(2H, s), 6.75-6.83(2H, m), 7.05-7.19(4H, m), 7.29-7.44(6H, m), 7.47-7.60(3H, m), 7.62-7.73(3H, m), 8.05-8.12(1H, m) |
| 1-29 | 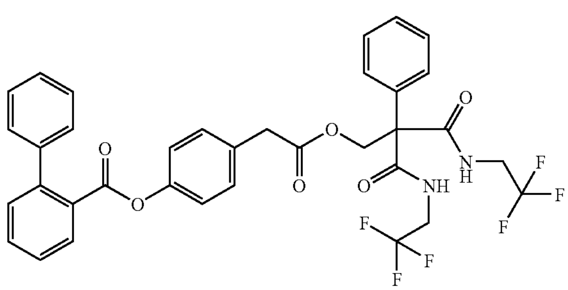 | 3.55(2H, s), 3.70-3.94 (4H, m), 4.86(2H, s), 6.71-6.79(2H, m), 7.01-7.09(2H, m), 7.11-7.18(2H, m), 7.27-7.54(12H, m), 7.57-7.66(1H, m), 7.94-8.01(1H, m) |
| 1-30 | 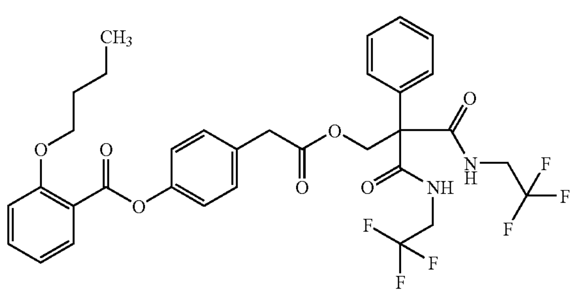 | 0.95(3H, t, J=7.4 Hz), 1.45-1.60(2H, m), 1.76-1.88(2H, m), 3.62 (2H, s), 3.79-3.97(4H, m), 4.08(2H, t, J=6.4 Hz), 4.90(2H, s), 6.99-7.06(2H, m), 7.10-7.21(6H, m), 7.31-7.41(5H, m), 7.48-7.56(1H, m), 7.96 (1H, dd, J=1.8, 8.0 Hz) |

TABLE 7

| Example | Structure | NMR (δ, 300 MHz, CDCl₃) |
|---|---|---|
| 1-31 | 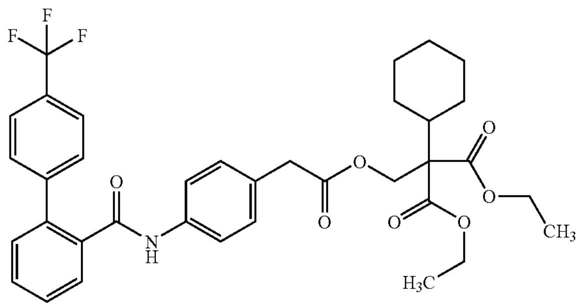 | 0.97-1.10(6H, m), 1.12 (6H, t, J=6.8 Hz), 1.54-1.78(4H, m), 2.05-2.17 (1H, m), 3.54(2H, s), 4.13 (4H, q, J=6.8 Hz), 4.50 (2H, s), 6.93(1H, brs), 7.14(4H, brs), 7.40-7.82(8H, m). |
| 1-32 | 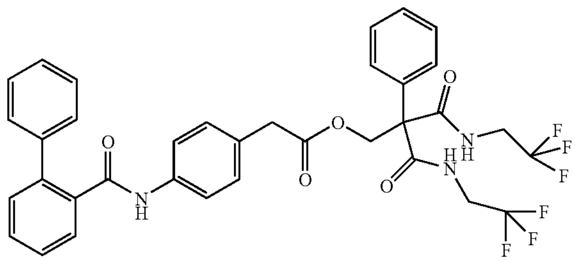 | 3.51(2H, s), 3.85(4H, m), 4.86(2H, s), 6.88(1H, s), 7.00-7.54(19H, m), 7.89(1H, m) |
| 1-33 | 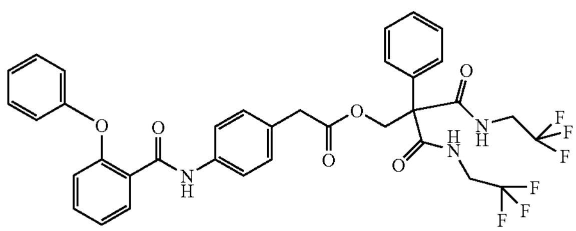 | 3.56(2H, s), 3.84(4H, m), 4.86(2H, s), 6.91(1H, d, J=8.3 Hz), 7.07-7.55(18H, m), 8.32(1H, dd, J=7.9, 1.9Hz), 9.64(1H, s) |
| 1-34 | 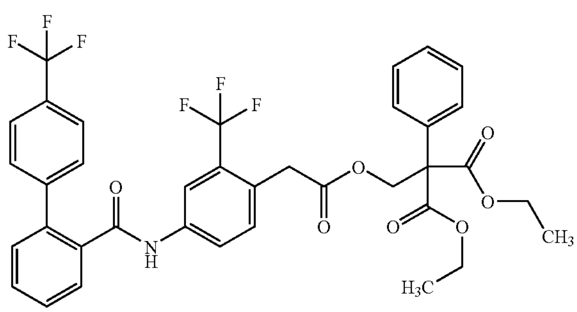 | 1.23(6H, t, J=7.1 Hz), 3.70(2H, s), 4.22(4H, t, J=7.1 Hz), 4.81(2H, s), 7.02(1H, brs), 7.13-7.97(16H, m). |
| 1-35 | m.p. 100.5-104.0 | 0.85(6H, t, J=7.5 Hz), 1.37-1.51(4H, m), 3.13-3.22(4H, m), 3.53(2H, s), 4.84(2H, s), 6.96(1H, br-s), 7.02-7.09(2H, m), 7.10-7.24(6H, m), 7.27-7.35(3H, m), 7.41-7.47(1H, m), 7.49-7.63(4H, m), 7.65-7.72(2H, m), 7.80(1H, dd, J=1.6, 8.0 Hz) |

TABLE 8

| Example | Structure | NMR (δ, 300 MHz, CDCl$_3$) |
|---|---|---|
| 1-36 | 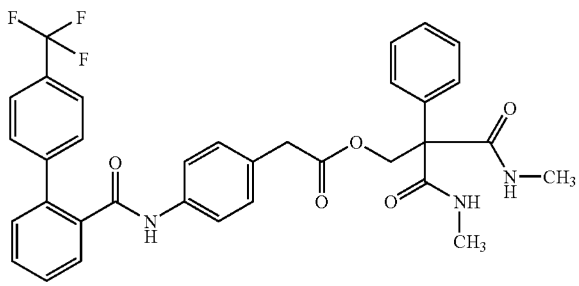 | 2.73(6H, d, J=4.9 Hz), 3.53 (2H, s), 4.81(2H, s), 6.94 (1H, br-s), 7.01-7.09(4H, m), 7.11-7.21(4H, m), 7.27-7.35(3H, m), 7.41-7.47(1H, m), 7.49-7.63(4H, m), 7.66-7.72(2H, m), 7.81 (1H, dd, J=1.5, 7.5 Hz) |
| 1-37 | 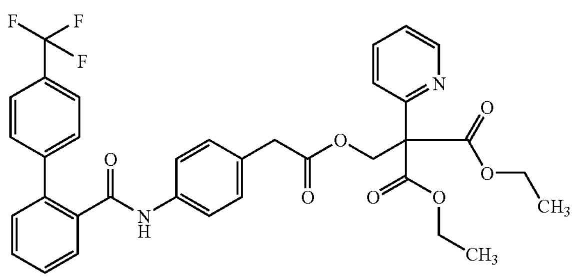 | 1.20(6H, t, J=7.0 Hz), 3.50 (2H, s), 4.21(4H, q, J=7.0 Hz), 4.90(2H, s), 6.93(1H, br-s), 7.04-7.15(4H, m), 7.15-7.21(1H, m), 7.38-7.47(2H, m), 7.49-7.64(5H, m), 7.66-7.72(2H, m), 7.81 (1H, dd, J=1.5, 7.5 Hz), 8.46-8.51(1H, m) |
| 1-38 | 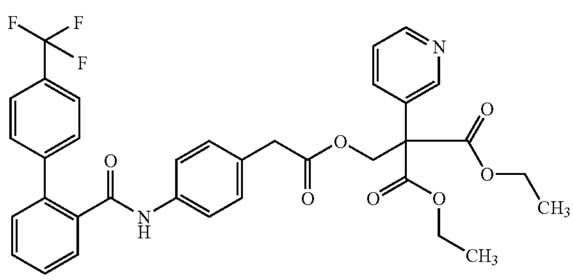 | 1.22(6H, t, J=7.2 Hz), 3.51 (2H, s), 4.21(4H, q, J=7.2 Hz), 4.82(2H, s), 6.98(1H, br-s), 7.03-7.17(4H, m), 7.22(1H, dd, J=5.0, 8.5 Hz), 7.41-7.47(1H, m), 7.48-7.63(5H, m), 7.64-7.72(2H, m), 7.77-7.83(1H, m), 8.50-8.57(2H, m) |
| 1-39 | 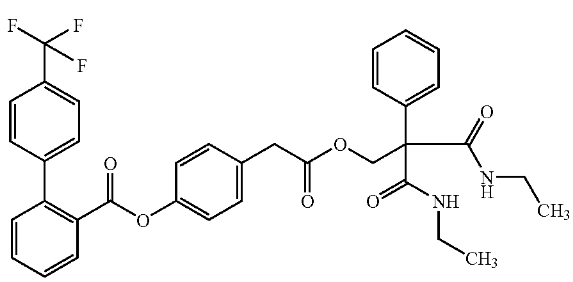 | 1.04(6H, t, J=7.4 Hz), 3.16-3.29(4H, m), 3.55 (2H, s), 4.84(2H, s), 6.75-6.83(2H, m), 7.04-7.14 (4H, m), 7.17-7.22(2H, m), 7.27-7.35(3H, m), 7.41(1H, dd, J=1.1, 7.6 Hz), 7.47-7.54(2H, m), 7.56(1H, dd, J=1.5, 7.6 Hz), 7.61-7.72(3H, m), 8.08(1H, dd, J=1.1, 7.6 Hz) |
| 1-40 | 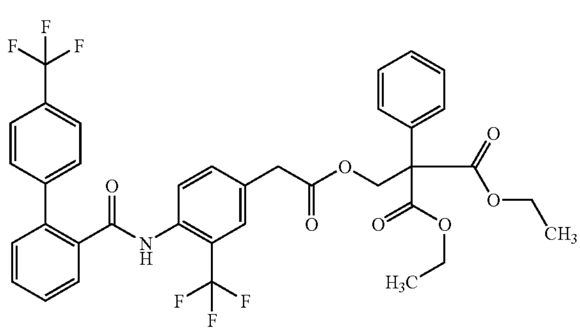 | 1.20(6H, t, J=7.1 Hz), 3.55 (2H, s), 4.21(4H, q, J=7.1 Hz), 4.84(2H, s), 7.20-7.77(16H, m), 8.16(1H, br) |

TABLE 9

| Example | Structure | NMR (δ, 300 MHz, CDCl₃) |
|---|---|---|
| 1-41 | 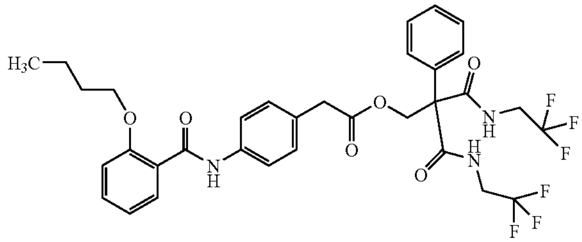 | 1.01(3H, t, J=7.2 Hz), 1.60 (2H, m), 1.96(2H, m), 3.59 (2H, s), 3.84(4H, m), 4.21 (2H, t, J=6.5 Hz), 4.89 (2H, s), 7.00(1H, d, J=8.3 Hz), 7.09-7.16(5H, m), 7.32-7.58(8H, m), 8.26 (1H, dd, J=8.0, 1.9 Hz), 10.07(1H, br.s) |
| 1-42 | 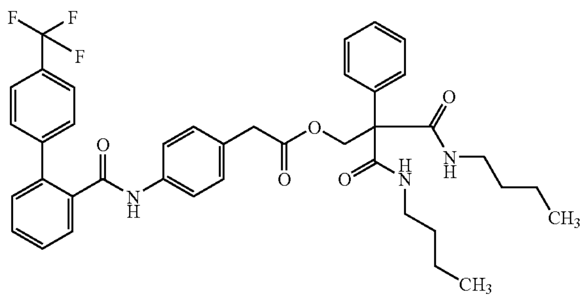 | 0.88(6H, t, J=7.1 Hz), 1.19-1.34(4H, m), 1.35-1.48(4H, m), 3.16-3.26 (4H, m), 3.52(2H, s), 3.16-3.26(4H, m), 3.52(2H, s), 4.84(2H, s), 6.95(1H, br-s), 7.02-7.23(8H, m), 7.27-7.36(3H, m), 7.40-7.47 (1H, m), 7.49-7.63(4H, m), 7.64-7.73(2H, m), 7.81(1H, dd, J=1.5, 7.5 Hz) |
| 1-43 | 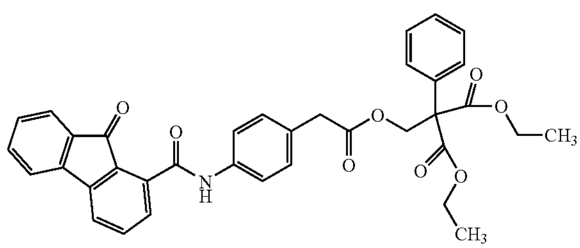 | 1.22(6H, t, J=7.1 Hz), 3.58 (2H, s), 4.22(4H, q, J=7.1 Hz), 4.95(2H, s), 6.23(2H, d, J=8.5 Hz), 7.30-7.73 (10H, m), 7.87(2H, d, J=8.5 Hz), 8.36(1H, dd, J=6.8, 2.3 Hz), 12.3(1H, brs) |
| 1-44 | 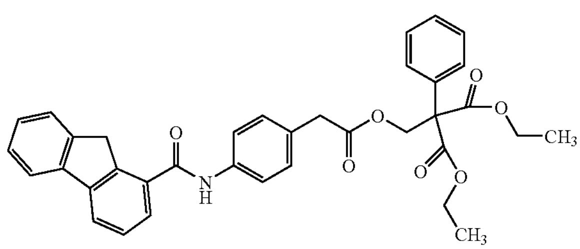 | 1.24(6H, t, J=7.1 Hz), 3.58 (2H, s), 4.23(4H, q, J=7.1 Hz), 4.27(2H, s), 4.85(2H, s), 7.22(2H, d, J=8.5 Hz), 7.27-7.98(13H, m), 7.61 (2H, d, J=8.5 Hz) |
| 1-45 | m.p. 175-177 | 1.05(6H, t, J=7.3 Hz), 1.69 (3H, s), 3.14-3.30(4H, m), 3.49(2H, s), 4.83(2H, s), 6.77(1H, brs), 6.89(1H, brs), 6.92-7.85(17H, m). |

TABLE 10

| Example | Structure | NMR (δ, 300 MHz, CDCl₃) |
|---|---|---|
| 1-46 | 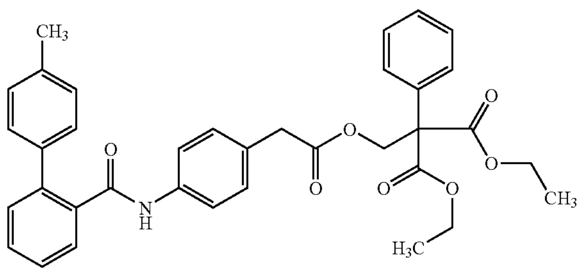 | 1.20(6H, t, J=7.1 Hz), 2.38 (3H, s), 3.49(2H, s), 4.19 (4H, q, J=7.1 Hz), 4.81 (2H, s), 6.90(1H, brs), 7.05 (4H, brs), 7.19-7.56(12H, m), 7.88(1H, d, J=7.1 Hz). |
| 1-47 | 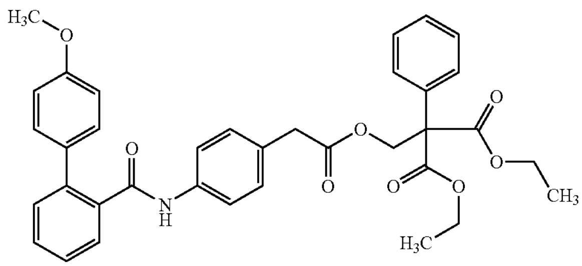 | 1.20(6H, t, J=7.1 Hz), 3.49 (2H, s), 3.81(3H, s), 4.19 (4H, q, J=7.1 Hz), 4.81 (2H, s), 6.87-7.56(17H, m), 7.86(1H, d, J=7.6 Hz) |
| 1-48 | 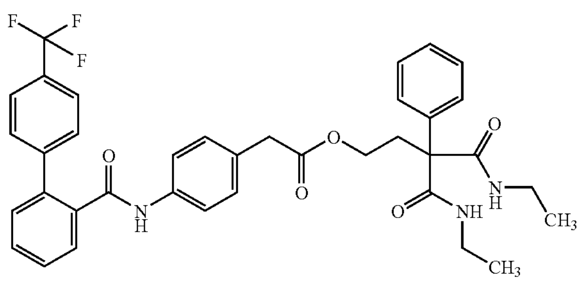 | 1.12(6H, t, J=7.2 Hz), 2.49-2.58(2H, m), 3.30 (4H, dq, J=5.6, 7.2 Hz), 3.54(2H, s), 4.07-4.15(2H, m), 6.94(1H, br-s), 7.11-7.18(4H, m), 7.22-7.37 (5H, m), 7.41-7.46(1H, m), 7.48-7.63(6H, m), 7.65-7.71(2H, m), 7.80 (1H, dd, J=1.5, 7.5 Hz) |
| 1-49 | 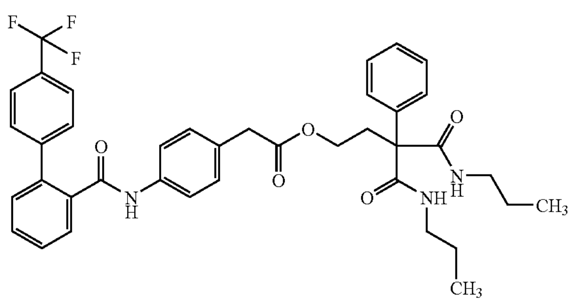 | 0.87(6H, t, J=7.2 Hz), 1.51 (4H, tq, J=7.2, 7.2 Hz), 2.50-2.59(2H, m), 3.18-3.27(4H, m), 3.54 (2H, s), 4.07-4.15(2H, m), 6.95(1H, br-s), 7.12-7.18 (4H, m), 7.23-7.36(5H, m), 7.41-7.46(1H, m), 7.48-7.63(6H, m), 7.65-7.71(2H, m), 7.80 (1H, dd, J=1.5, 7.5 Hz) |
| 1-50 | 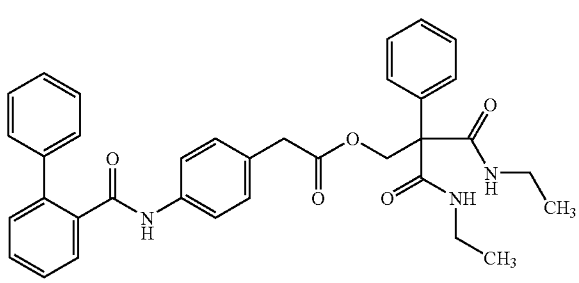 | 1.05(6H, t, J=7.1 Hz), 3.17-3.28(4H, m), 3.51 (2H, s), 4.82(2H, s), 6.87 (1H, br-s), 6.97-7.22(8H, m), 7.27-7.35(3H, m), 7.39-7.59(8H, m), 7.90 (1H, dd, J=1.5, 7.5 Hz) |

TABLE 11

| Exampole | Structure | NMR (δ, 300 MHz, CDCl₃) |
|---|---|---|
| 1-51 | 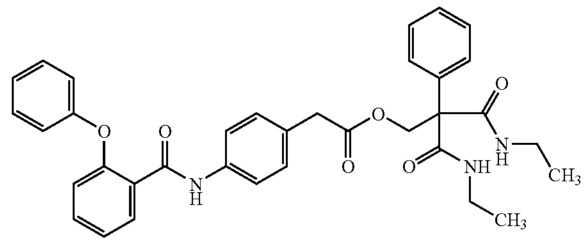 | 1.03(6H, t, J=7.1 Hz), 3.16-3.28(4H, m), 3.56 (2H, s), 4.82(2H, s), 6.88-6.94(1H, m), 7.02-7.34(13H, m), 7.39-7.49(3H, m), 7.51-7.59(2H, m), 8.34 (1H, dd, J=1.9, 7.9 Hz), 9.63(1H, br-s) |
| 1-52 | 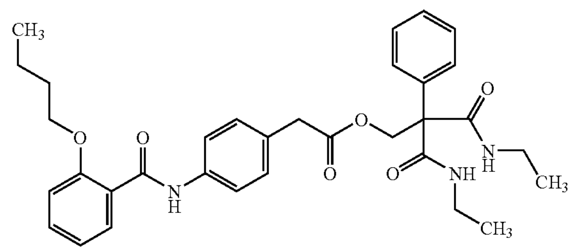 | 1.05(3H, t, J=7.2 Hz), 1.07(6H, t, J=7.2 Hz), 1.54-1.68(2H, m), 1.92-2.05(2H, m), 3.19-3.31(4H, m), 3.58 (2H, s), 4.23(2H, q, J=6.4 Hz), 4.85(2H, s), 7.02(1H, d, J=8.3 Hz), 7.06-7.38 (10H, m), 7.44-7.53(1H, m), 7.57-7.65(2H, m), 8.30(1H, dd, J=1.9, 7.9 Hz), 10.08(1H, br-s) |
| 1-53 | 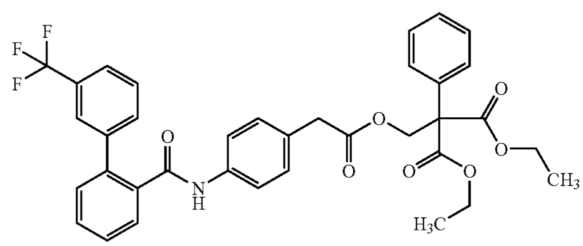 | 1.23(6H, t, J=7.1 Hz), 3.53(2H, s), 4.23(4H, q, J=7.1 Hz), 4.84(2H, s), 6.95(1H, brs), 7.10(2H, d, J=8.3 Hz), 7.17(2H, d, J=8.3 Hz), 7.32(5H, brs), 7.41-7.87(8H, m). |
| 1-54 | 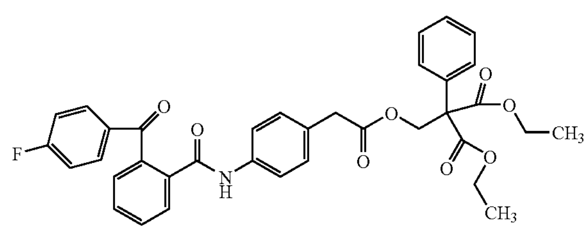 | 1.19(6H, t, J=7.1 Hz), 3.50(2H, s), 4.16(2H, q, J=7.1 Hz), 4.17(2H, q, J=7.1 Hz), 4.80(2H, s), 6.89-7.90(17H, m) |
| 1-55 | 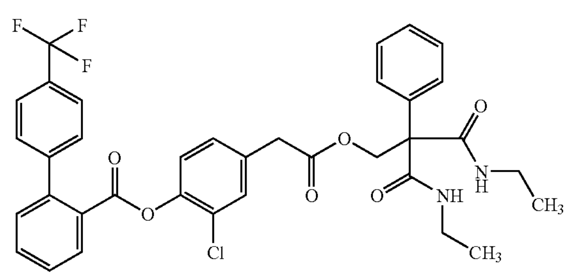 | 1.05(6H, t, J=7.2 Hz), 3.19-3.31(4H, m), 3.54 (2H, s), 4.86(2H, s), 6.90 (1H, d, J=8.3 Hz), 7.02-7.11 (3H, m), 7.16-7.23(2H, m), 7.25-7.36(4H, m), 7.41 (1H, dd, J=1.2, 7.5 Hz), 7.48-7.61(3H, m), 7.62-7.71(3H, m), 8.21 (1H, dd, J=1.5, 7.5 Hz) |

TABLE 12

| Example | Structure | NMR (δ, 300 MHz, CDCl₃) |
|---------|-----------|--------------------------|
| 1-56 | 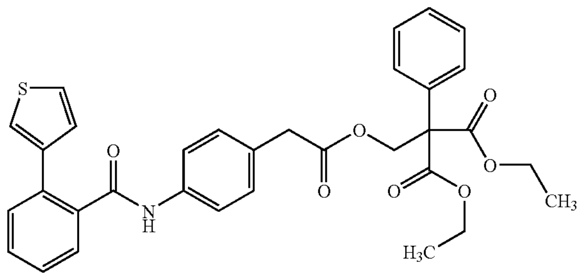 | 1.21(6H, t, J=7.1 Hz), 3.51 (2H, s), 4.20(4H, q, J=7.1 Hz), 4.82(2H, s), 6.99-7.57 (16H, m), 7.84(1H, d, J=7.2 Hz). |
| 1-57 | 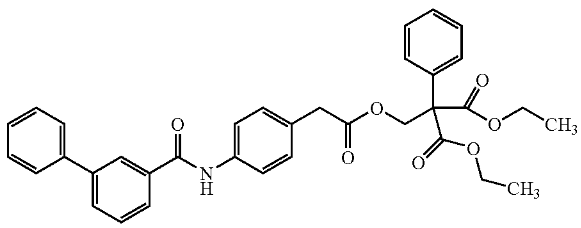 | 1.23(6H, t, J=7.2 Hz), 3.57 (2H, s), 4.22(4H, q, J=7.2 Hz), 4.85(2H, s), 7.19-8.08 (19H, m) |
| 1-58 | 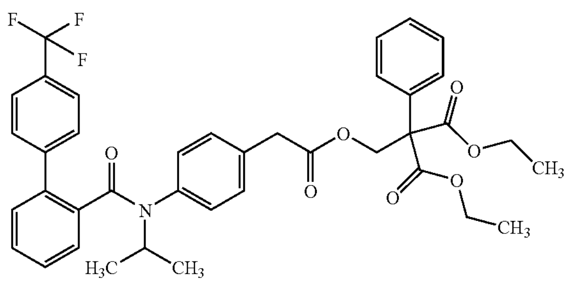 | 0.94(6H, d, J=6.8 Hz), 1.22 (6H, t, J=7.1 Hz), 3.40(2H, s), 4.20(4H, q, J=7.1 Hz), 4.82(2H, s), 4.99(1H, m), 6.16(1H, br.s), 6.78(2H, d, J=8.6 Hz), 7.08(1H, dd, J=8.6, 1.5 Hz), 7.20-7.74(13H, m) |
| 1-59 | 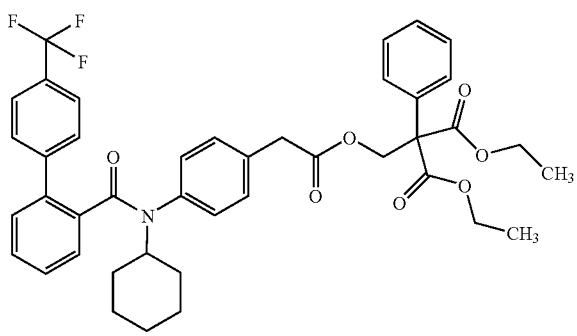 | 0.89(4H, m), 1.22(6H, t, J=7.1 Hz), 1.28-1.78(6H, m), 3.40(2H, s), 4.20(4H, q, J=7.1 Hz), 4.62(1H, m), 4.82(2H, s), 6.15(1H, br.s), 6.75(2H, m), 7.06-7.74 (14H, m) |
| 1-60 | 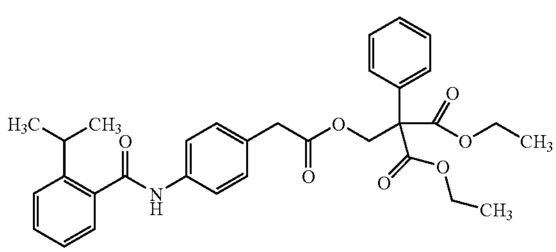 | 1.23(6H, t, J=6.9 Hz), 1.28(6H, d, J=6.9 Hz), 3.40(1H, sep, J=6.9 Hz), 3.56(2H, s), 4.22(4H, q, J=6.9 Hz), 4.84(2H, s), 7.12-7.61(14H, m) |

TABLE 13

| Example | Structure | NMR (δ, 300 MHz, CDCl₃) |
|---|---|---|
| 1-61 | 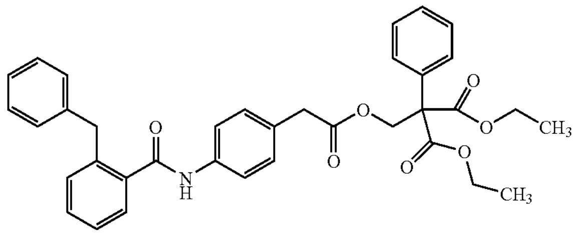 | 1.22(6H, t, J=7.1 Hz), 3.53 (2H, s), 4.22(4H, q, J=7.1 Hz), 4.23(2H, s), 4.83(2H, s), 6.98-7.61(19H, m) |
| 1-62 | 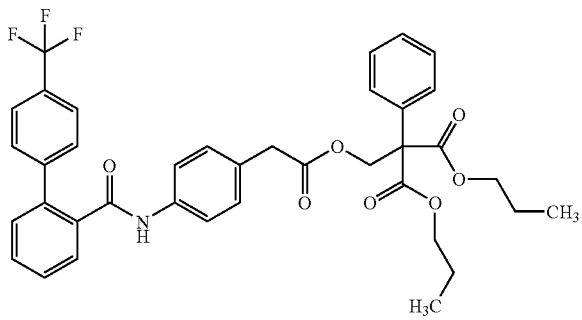 | 0.86(6H, t, J=7.3 Hz), 1.50-1.69(4H, m), 3.50 (2H, s), 4.10(4H, t, J=6.6 Hz), 4.83(2H, s), 6.93(1H, brs), 7.08(2H, d, J=8.6 Hz), 7.13(2H, d, J=8.6 Hz), 7.29 (5H, brs), 7.40-7.83(8H, m) |
| 1-63 | 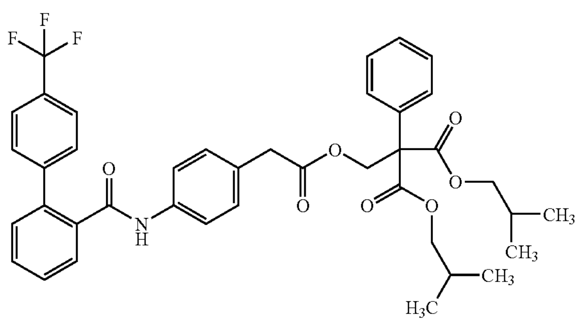 | 0.84(12H, d, J=6.6 Hz), 1.80-1.97(2H, m), 3.50 (2H, s), 3.92(4H, d, J=6.6 Hz), 4.84(2H, s), 6.93(1H, brs), 7.08(2H, d, J=5.5 Hz), 7.13(2H, d, J=5.5 Hz), 7.29 (5H, brs), 7.40-7.84(8H, m). |
| 1-64 | 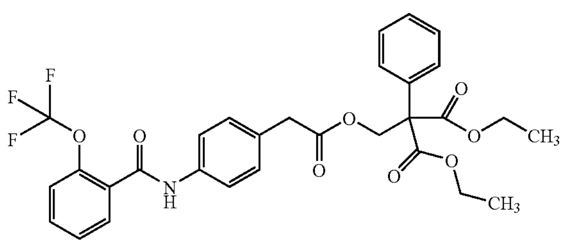 | 1.22(6H, t, J=7.1 Hz), 3.57(2H, s), 4.21(4H, q, J=7.1 Hz), 4.84(2H, s), 7.21(2H, d, J=8.5 Hz), 7.23-7.60(8H, m), 7.57(2H, d, J=8.5 Hz), 8.09(1H, dd, J=7.8, 1.8 Hz), 8.26 (1H, brs) |
| 1-65 | 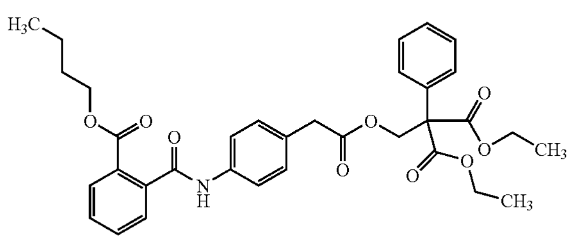 | 0.84(3H, t, J=7.3 Hz), 1.23 (6H, t, J=7.1 Hz), 1.23-1.46(2H, m), 1.50-1.69 (2H, m), 3.55(2H, s), 4.23(4H, q, J=7.1 Hz), 4.25 (2H, q, J=6.7 Hz), 4.84(2H, s), 7.19(2H, d, J=8.4 Hz), 7.21-7.37(5H, m), 7.44-7.64(3H, m), 7.56 (2H, d, J=8.4 Hz), 7.64 (1H, brs), 7.95(1H, d, J=7.6 Hz) |

TABLE 14

| Example | Structure | NMR (δ, 300 MHz, CDCl$_3$) |
|---|---|---|
| 1-66 | 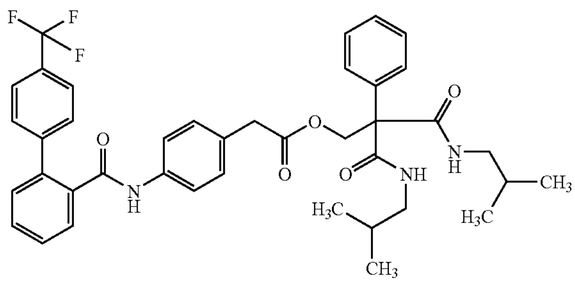 | 0.84(12H, d, J=6.8 Hz), 1.63-1.79(2H, m), 2.97-3.15(4H, m), 3.52 (2H, s), 4.86(2H, s), 6.94 (1H, br-s), 7.01-7.08 (2H, m), 7.10-7.25(6H, m), 7.27-7.36(3H, m), 7.40-7.47(1H, m), 7.48-7.63(4H, m), 7.64-7.72(2H, m), 7.80 (1H, dd, J=1.5, 8.0 Hz) |
| 1-67 | 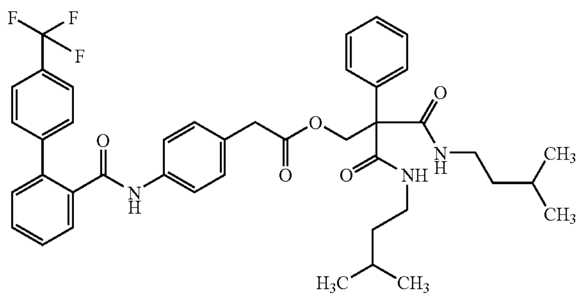 | 0.87(12H, d, J=6.8 Hz), 1.27-1.38(4H, m), 1.46-1.61(2H, m), 3.18-3.28(4H, m), 3.52 (2H, s), 4.84(2H, s), 6.94 (1H, br-s), 7.01-7.22(8H, m), 7.27-7.35(3H, m), 7.41-7.47(1H, m), 7.49-7.63(4H, m), 7.65-7.72(2H, m), 7.80 (1H, dd, J=1.5, 7.5 Hz) |
| 1-68 | 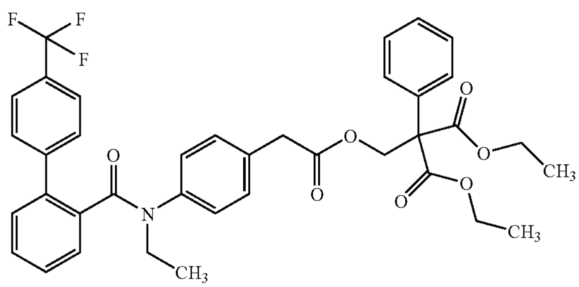 | 1.07(3H, t, J=7.2 Hz), 1.22(6H, t, J=7.1 Hz), 3.40(2H, s), 3.72(2H, q, J=7.2 Hz), 4.20 (4H, q, J=7.1 Hz), 4.83 (2H, s), 6.14(2H, d, J=8.3 Hz), 6.74(2H, d, J=8.3 Hz), 7.07(1H, dd, J=9.1, 1.5 Hz), 7.23-7.61(12H, m) |
| 1-69 | 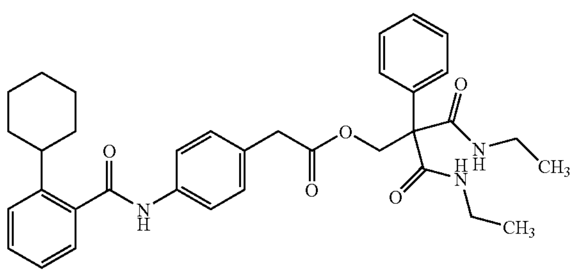 | 1.09(6H, t, J=7.1 Hz), 1.26-1.50(6H, m), 1.81 (4H, m), 2.99(1H, m), 3.26(4H, dq, J=7.1, 7.1 Hz), 3.59(2H, s), 4.85(2H, s), 7.10-7.42(14H, m), 7.56 (2H, d, J=8.3 Hz) |
| 1-70 | 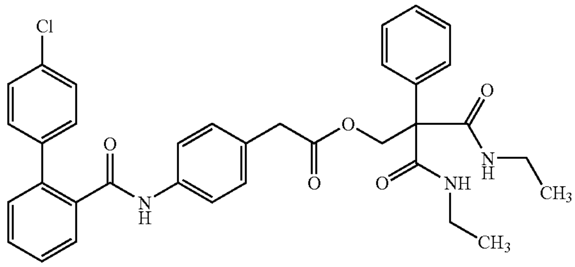 | 1.05(6H, t, J=7.2 Hz), 3.18-3.30(4H, m), 3.53 (2H, s), 4.83(2H, s), 6.93 (1H, br-s), 7.02-7.23(8H, m), 7.27-7.36(3H, m), 7.37-7.45(5H, m), 7.45-7.59(2H, m), 7.80 (1H, dd, J=1.1, 7.5 Hz) |

TABLE 15

| Example | Structure | NMR (δ, 300 MHz, CDCl₃) |
|---|---|---|
| 1-71 | 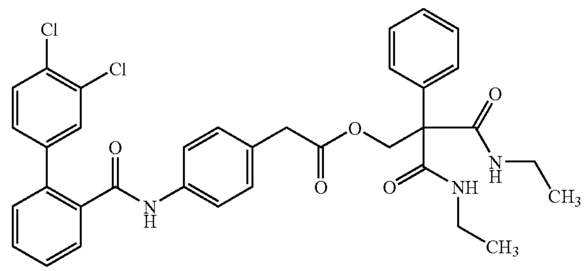 | 1.05(6H, t, J=7.2 Hz), 3.18-3.30(4H, m), 3.54 (2H, s), 4.84(2H, s), 7.02-7.14(5H, m), 7.17-7.35 (8H, m), 7.37-7.62(5H, m), 7.74(1H, dd, J=1.5, 7.5 Hz) |
| 1-72 | m.p. 126.4-127.8 | 0.85(6H, t, J=7.5 Hz), 1.44(4H, tq, J=7.5, 7.5 Hz), 1.68(3H, s), 3.12-3.22(4H, m), 3.49(2H, s), 4.85(2H, s), 6.77(1H, br-s), 6.87-6.92(1H, m), 6.94-7.01(1H, m), 7.11-7.25(4H, m), 7.27-7.36(3H, m), 7.40-7.47(1H, m), 7.50-7.73(6H, m), 7.75-7.85(2H, m) |
| 1-73 | 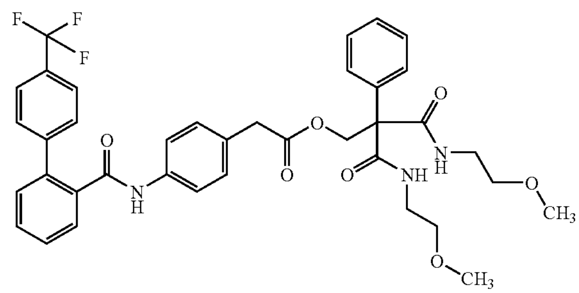 | 3.29(6H, s), 3.36-3.48 (8H, m), 3.53(2H, s), 4.85 (2H, s), 6.97(1H, br-s), 7.04-7.18(4H, m), 7.19-7.40(8H, m), 7.41-7.47 (1H, m), 7.49-7.64(4H, m), 7.66-7.73(2H, m), 7.77-7.84(1H, m) |
| 1-74 | 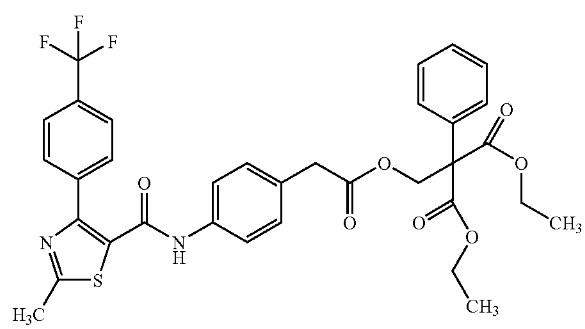 | 1.22(6H, t, J=7.1 Hz), 2.78(3H, s), 3.52(2H, s), 4.21(4H, q, J=7.1 Hz), 4.82(2H, s), 7.11(2H, d, J= 8.5 Hz), 7.19(2H, d, J=8.5 Hz), 7.20-7.35(6H, m), 7.77(2H, d, J=8.3 Hz), 7.86(2H, d, J=8.3 Hz) |
| 1-75 | 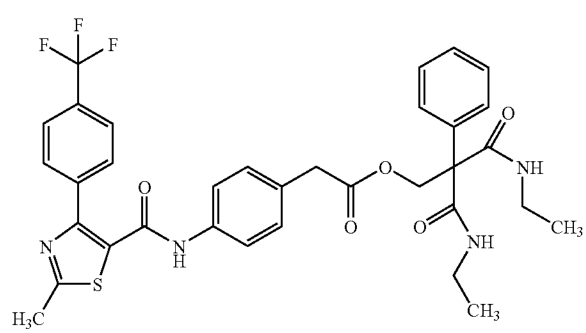 | 1.06(6H, t, J=7.3 Hz), 2.78(3H, s), 3.20-3.29(4H, m), 3.55(2H, s), 4.84(2H, s), 6.98-7.34(12H, m), 7.77(2H, d, J=8.3 Hz), 7.86(2H, d, J=8.3 Hz) |

TABLE 16
| Example | Structure | NMR (δ, 300 MHz, CDCl$_3$) |
|---|---|---|
| 1-76 | 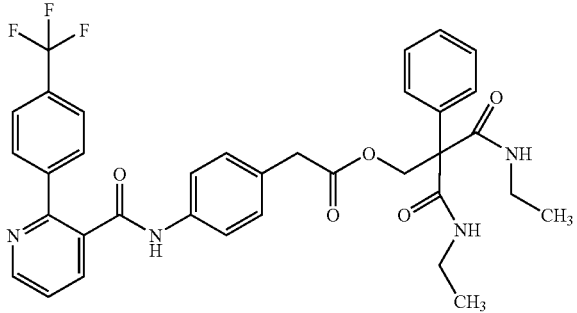 | 1.06(6H, t, J=7.3 Hz), 3.19-3.28(4H, m), 3.54 (2H, s), 4.83(2H, s), 6.99-7.48(13H, m), 7.71(2H, d, J=8.2 Hz), 7.86(2H, d, J=8.2 Hz), 8.05-8.13(1H, m), 8.75-8.84(1H, m) |
| 1-77 | 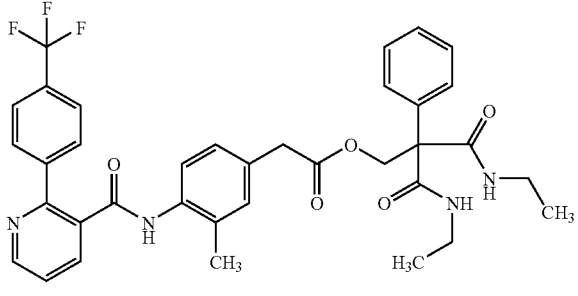 | 1.06(6H, t, J=7.2 Hz), 1.64(3H, s), 3.12-3.33 (4H, m), 3.51(2H, s), 4.84 (2H, s), 6.84(1H, brs), 6.91 (1H, brs), 6.98-7.98(12H, m), 8.16(1H, d, J=8.1 Hz), 8.84(1H, d, J=4.4 Hz). |
| 1-78 | 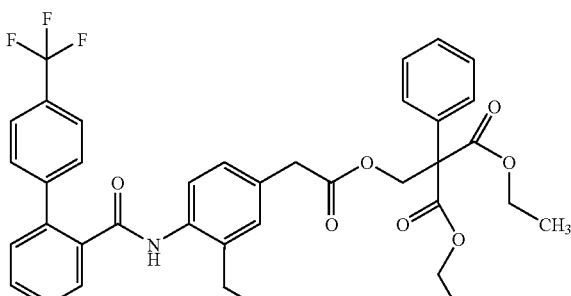 | 0.92(3H, t, J=7.5 Hz), 1.20(6H, t, J=7.1 Hz), 1.94 (2H, q, J=7.5 Hz), 3.50(2H, s), 4.20(4H, q, J=7.1 Hz), 4.82(2H, s), 6.79-7.83 (17H, m) |
| 1-79 | 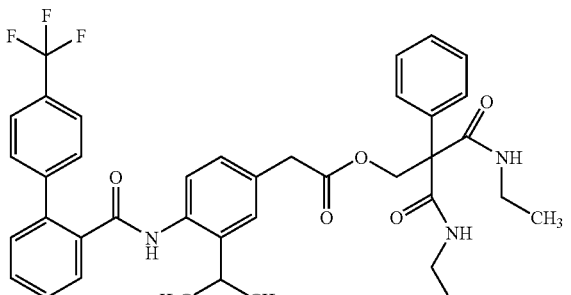 | 0.96(6H, d, J=6.6 Hz), 1.05(6H, t, J=7.1 Hz), 2.15 (1H, sep, J=6.6 Hz), 3.19-3.29(4H, m), 3.54(2H, s), 4.83(2H, s), 6.81-7.84 (19H, m) |

TABLE 16-continued

| Example | Structure | NMR (δ, 300 MHz, CDCl₃) |
|---|---|---|
| 1-80 | m.p. 91.5-94.8 | 0.96(6H, d, J=6.8 Hz), 1.20(6H, t, J=7.1 Hz), 2.16 (1H, sep, J=6.8 Hz), 4.20 (4H, q, J=7.1 Hz), 4.82 (2H, s), 6.79-7.82(17H, m) |

TABLE 17

| Example | Structure | NMR (δ, 300 MHz, CDCl₃) |
|---|---|---|
| 1-81 | m.p. 147-158 | 0.95(3H, t, J=7.7 Hz), 1.13 (6H, t, J=7.2 Hz), 1.99(2H, q, J=7.7 Hz), 2.54(2H, t, J=7.9 Hz), 3.20-3.38 (4H, m), 3.53(2H, s), 4.11 (2H, t, J=7.9 Hz), 6.79-7.84(19H, m) |
| 1-82 | 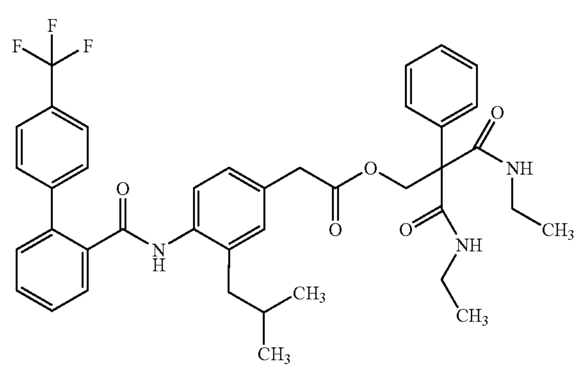 | 0.72(6H, d, J=6.6 Hz), 1.06 (6H, t, J=7.2 Hz), 1.26-1.44(1H, m), 1.89(2H, d, J=7.3 Hz), 3.20-3.27(4H, m), 3.52(2H, s), 4.83(2H, s), 6.82-7.88(19H, m) |

TABLE 17-continued

| Example | Structure | NMR (δ, 300 MHz, CDCl₃) |
|---|---|---|
| 1-83 | 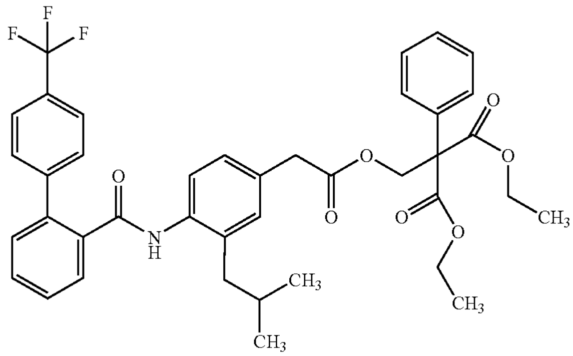 | 0.71(6H, d, J=6.5 Hz), 1.21 (6H, t, J=7.1 Hz), 1.26-1.43(1H, m), 1.88(2H, d, J=7.3 Hz), 3.49(2H, s), 4.21(4H, q, J=7.1 Hz), 4.83(2H, s), 6.79-7.87 (17H, m) m.p. 80-86 |
| 1-84 | 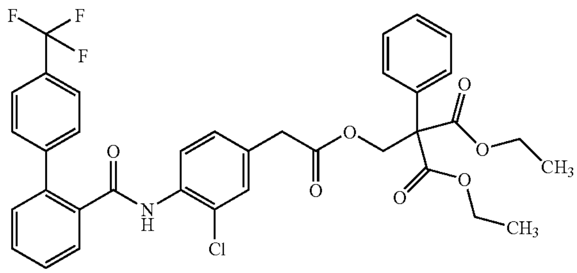 | 1.21(6H, t, J=7.2 Hz), 3.48 (2H, s), 4.22(4H, q, J=7.2 Hz), 4.83(2H, s), 7.08(1H, d, J=8.7 Hz), 7.12(1H, s), 7.25-7.67(13H, m), 7.84 (1H, dd, J=1.5, 7.5 Hz), 8.37(1H, d, J=8.7 Hz) |
| 1-85 | 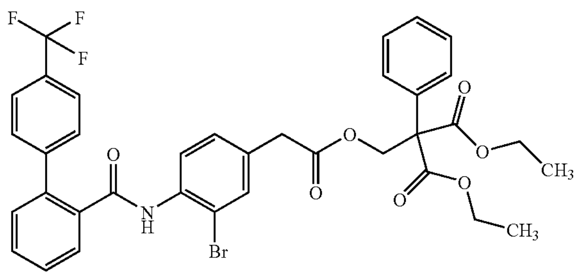 | 1.21(6H, t, J=7.1 Hz), 3.48 (2H, s), 4.22(4H, q, J=7.1 Hz), 4.83(2H, s), 7.13(1H, d, J=7.9 Hz), 7.28-7.67 (14H, m), 7.82(1H, dd, J= 1.5, 7.5 Hz), 8.35(1H, d, J=8.7 Hz) |

Example 2

{3-Dimethylcarbamoyl-4-[(4'-trifluoromethylbiphenyl-2-carbonyl)amino]phenyl}acetic acid 2,2-bisethylcarbamoyl-2-phenylethyl ester a) 5-Chloro-N,N-dimethyl-2-nitrobenzamide

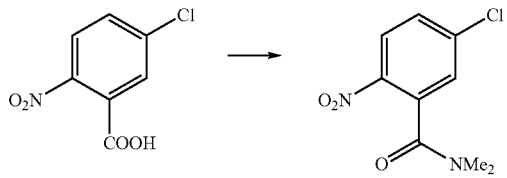

The acid chloride obtained from 5-chloro-2-nitrobenzoic acid (5.0 g) in a similar manner to Example 1d) was subjected to reactions similar to those in Example 1e) to give the title compound (5.5 g).

b) 2-(3-Dimethylcarbamoyl-4-nitrophenyl)malonic acid tert-butyl ester methyl ester

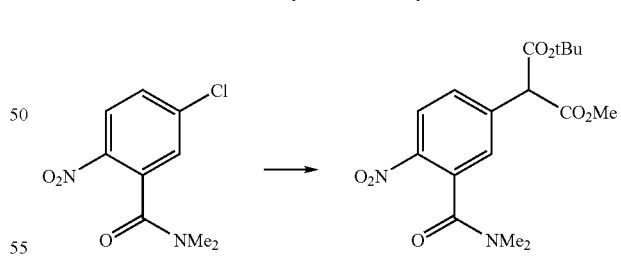

Sodium hydride (350 mg) was dissolved in dimethylformamide (10 mL)), and the solution was cooled to 0° C. After addition of tert-butyl methyl malonate (1.52 g), the mixture was stirred for one hour, and the 5-chloro-N,N-dimethyl-2-nitrobenzamide (1.0 g) obtained in Example 2a) was added thereto. The mixture was stirred at 70° C. for 4.5 hours and water was added thereto. The resulting solution was concentrated, diluted with ethyl acetate and washed with water. The organic layer was dried over sodium sulfate and purified by column chromatography on silica gel with ethyl acetate:hexane=1:1 to give the title compound (1.29 g).

c) (3-Dimethylcarbamoyl-4-nitrophenyl)acetic acid methyl ester

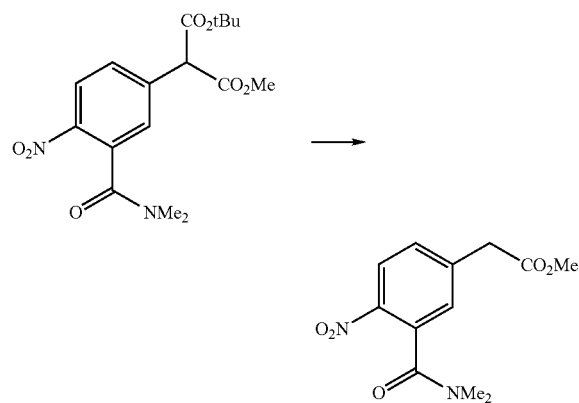

The 2-(3-dimethylcarbamoyl-4-nitrophenyl)malonic acid tert-butyl ester methyl ester (1.22 g) obtained in Example 2b) was dissolved in dichloromethane (10 mL), and the solution was cooled to 0° C. After addition of trifluoroacetic acid (10 mL), the mixture was stirred at room temperature for 6 hours, and concentrated, followed by azeotropic distillation with toluene. The residue was purified by column chromatography on silica gel with ethyl acetate:hexane=3:1 to give the title compound (712 mg).

d) (4-Amino-3-dimethylcarbamoylphenyl)acetic acid methyl ester

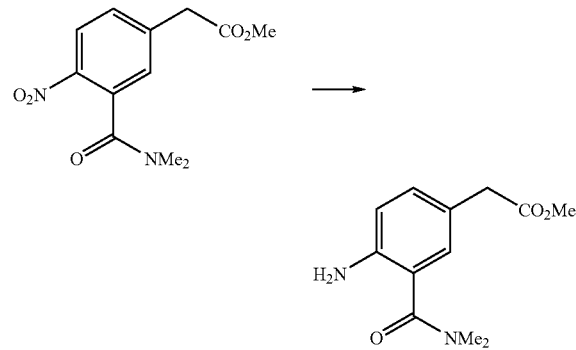

The (3-dimethylcarbamoyl-4-nitrophenyl)acetic acid methyl ester (683 mg) obtained in Example 2c) was subjected to reactions similar to those in Example 1-3d) to give the title compound (627 mg).

e) {3-Dimethylcarbamoyl-4-[(4'-trifluoromethylbiphenyl-2-carbonyl)amino]phenyl}acetic acid

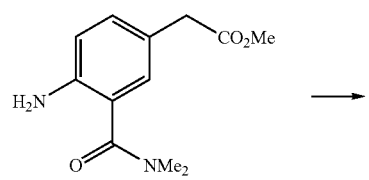

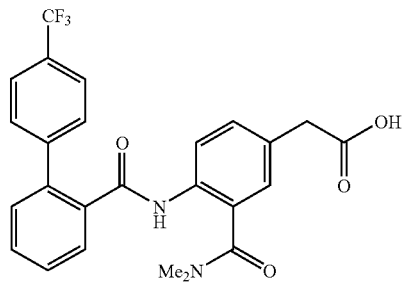

The (4-amino-3-dimethylcarbamoylphenyl)acetic acid methyl ester (627 mg) obtained in Example 2d) was subjected to reactions similar to those in Example 1e) and Example 1f) to give the title compound (1.07 g)(see Table 65).

f) {3-Dimethylcarbamoyl-4-[(4'-trifluoromethylbiphenyl-2-carbonyl)amino]phenyl}acetic acid 2,2-bisethylcarbamoyl-2-phenylethyl ester

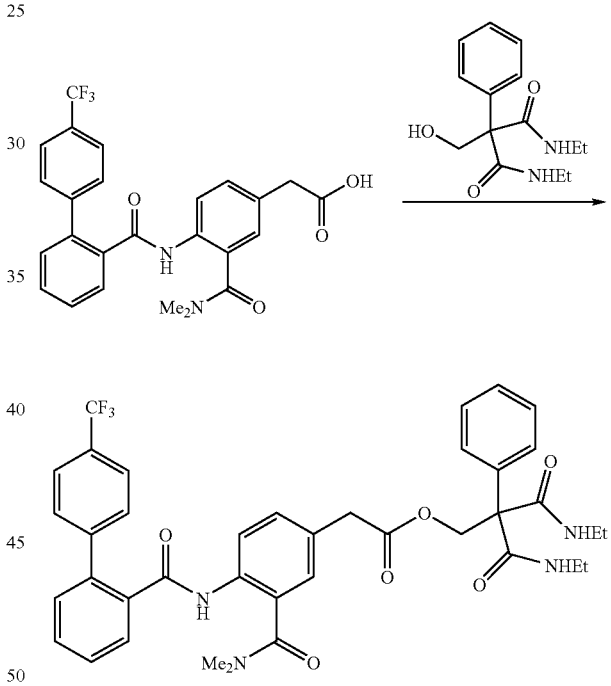

The {3-Dimethylcarbamoyl-4-[(4'-trifluoromethyl-biphenyl-2-carbonyl)amino]phenyl}acetic acid (517 mg) obtained in Example 2e) was subjected to reactions similar to those in Example 1g) to give the title compound (387 mg) (see Table 18).

Examples 2-2 to 2-119

Compounds of Examples 2-2 to 2-119 were obtained in a similar manner to Example 2. The compounds thus obtained were shown in Tables 18 to 41. In addition, compound of Example 2-17e) was obtained in a similar manner to Example 2e) and the compounds thus obtained were shown in Table 65.

TABLE 18

| Example | Structure | NMR (δ, 300 MHz, CDCl₃) |
|---|---|---|
| 2 | 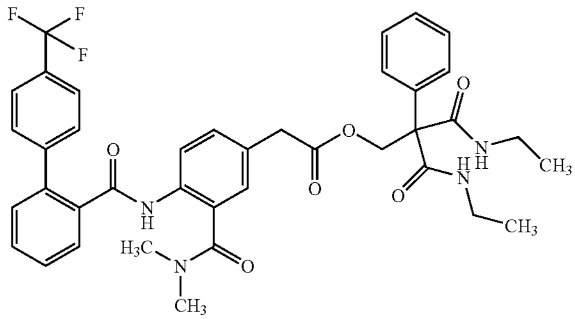 | 1.07(6H, t, J=7.2 Hz), 2.85(3H, br.s), 2.95(3H, br.s), 3.26(4H, dq, J=7.2, 7.2 Hz), 3.54(2H, s), 4.84(2H, s), 7.04-7.68(17H, m), 8.37(1H, d, J=8.3 Hz), 9.16(1H, br.s) |
| 2-2 | 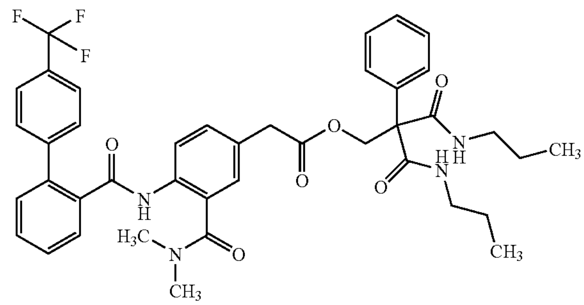 | 0.86(6H, t, J=7.2 Hz), 1.46(4H, tq, J=7.2, 7.2 Hz), 2.85(3H, br.s), 2.95(3H, br.s), 3.19(4H, dt, J=7.2, 7.2 Hz), 3.54(2H, s), 4.85(2H, s), 7.03-7.68(17H, m), 8.37(1H, d, J=8.7 Hz), 9.17(1H, br.s) |
| 2-3 | 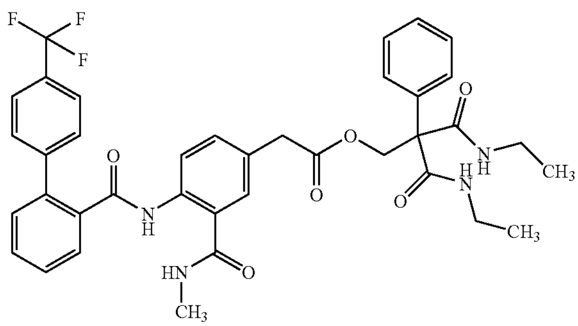 | 1.07(6H, t, J=7.1 Hz), 2.83(3H, d, J=4.5 Hz), 3.24(4H, dq, J=7.1, 7.1 Hz), 3.59(2H, s), 4.80(2H, s), 7.10-7.76(18H, m), 8.53(1H, d, J=8.3 Hz), 11.55(1H, br.s) |
| 2-4 | m.p. 128-129 | 1.12(6H, t, J=J=7.3 Hz), 2.53(2H, t, J=7.7 Hz), 2.86(3H, brs), 2.95(3H, brs), 3.20-3.40(4H, m), 3.54(2H, s), 4.12(2H, t, J=7.7 Hz), 7.09(1H, brs), 7.17-7.45(14H, m), 8.36(1H, d, J=8.4 Hz), 9.24(1H, brs). |

TABLE 18-continued
| Example | Structure | NMR (δ, 300 MHz, CDCl$_3$) |
|---|---|---|
| 2-5 | 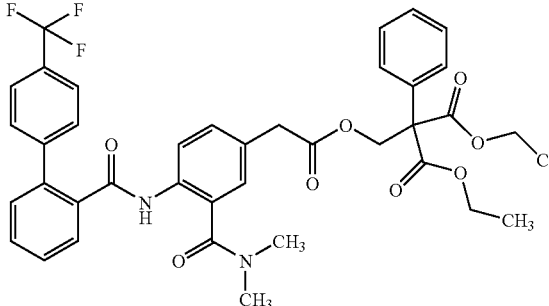 m.p. 114-116 | 1.21(6H, t, J=7.1 Hz), 2.81(3H, brs), 2.92(3H, brs), 3.50(2H, s), 4.20(4H, q, J=7.1 Hz), 4.82(2H, s), 6.99(1H, brs), 7.17-7.71(14H, m), 8.33(1H, d, J=8.5 Hz), 9.14(1H, brs). |
TABLE 19
| Example | Structure | NMR (δ, 300 MHz, CDCl$_3$) |
|---|---|---|
| 2-6 | 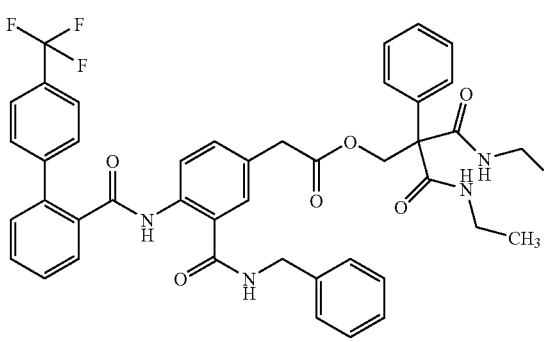 | 0.98(6H, t, J=7.3 Hz), 3.12(4H, dq, J=7.3, 7.3 Hz), 3.58(2H, s), 4.50(2H, d, J=5.9 Hz), 4.79(2H, s), 7.01-7.59(16H, m), 7.72(1H, dd, J=7.0, 1.8 Hz), 8.23(1H, m), 8.51(1H, d, J=8.5 Hz), 11.49(1H, br.s) |
| 2-7 | 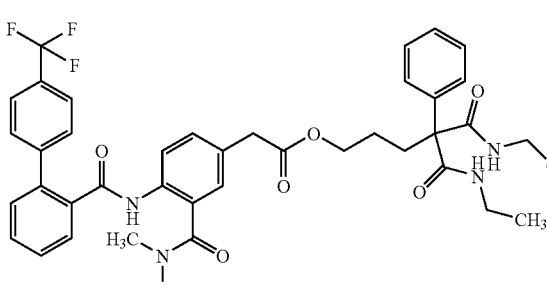 | 1.07(6H, t, J=7.3 Hz), 1.66(2H, m), 2.28(2H, m), 2.87(3H, br.s), 2.93(3H, br.s), 3.24(4H, dq, J=7.3, 7.3 Hz), 3.57(2H, s), 4.11(2H, t, J=6.9 Hz), 7.13-7.66(17H, m), 8.36(1H, d, J=8.4 Hz), 9.08(1H, br.s) |
| 2-8 | 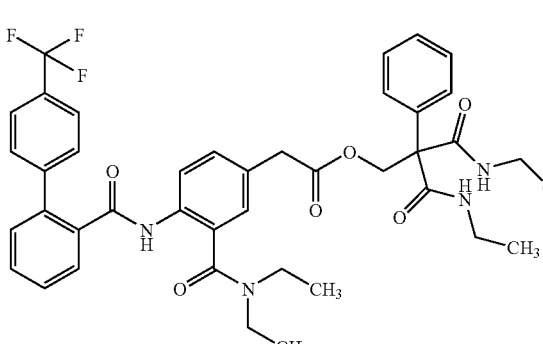 | 1.08(6H, t, J=7.2 Hz), 0.98-1.21(6H, brd), 3.26(4H, dq, J=7.2, 7.2 Hz), 3.12-3.51(4H, brd), 3.56(2H, s), 4.84(2H, s), 7.06-7.63(17H, m), 8.21(1H, d, J=8.7 Hz), 8.88(1H, s) |

TABLE 19-continued

| Example | Structure | NMR (δ, 300 MHz, CDCl₃) |
|---|---|---|
| 2-9 | m.p. 108-117 | 1.07(6H, t, J=7.1 Hz), 0.93-1.59(6H, brd), 3.26(4H, dq, J=7.2, 7.2 Hz), 3.56(2H, s), 3.41-3.95(2H, brd), 4.84(2H, s), 7.01-7.62(17H, m), 8.08(1H, d, J=8.3 Hz), 8.70(1H, br.s) |
| 2-10 | 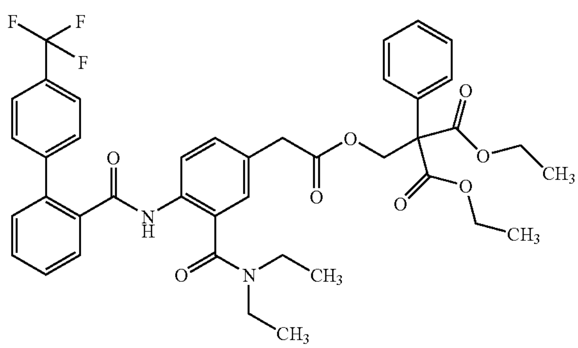 | 1.21(6H, t, J=7.1 Hz), 0.95-1.27(6H, brd), 3.08-3.49(4H, brd), 3.52(2H, s), 4.21(4H, q, J=7.1 Hz), 4.83(2H, s), 7.06(1H, d, J=1.9 Hz), 7.19(1H, dd, J=8.7, 1.9 Hz), 7.31-7.63(13H, m), 8.19(1H, d, J=8.7 Hz), 8.90(1H, br.s) |

TABLE 20

| Example | Structure | NMR (δ, 300 MHz, CDCl₃) |
|---|---|---|
| 2-11 | 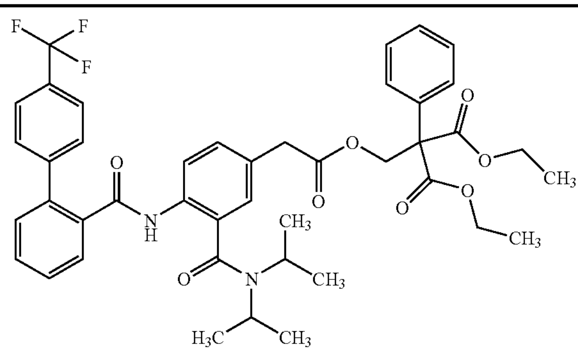 | 1.21(6H, t, J=7.1 Hz), 1.00-1.52(12H, brd), 3.52(2H, s), 3.49-3.92(2H, brd), 4.20(4H, q, J=7.1 Hz), 4.82(2H, s), 7.02(1H, d, J=1.9 Hz), 7.17(1H, dd, J=8.4, 1.9 Hz), 7.31-7.64(13H, m), 8.06(1H, d, J=8.4 Hz), 8.72(1H, br.s) |
| 2-12 | 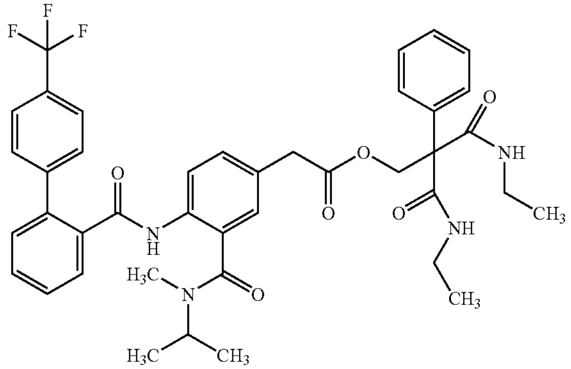 | 1.01-1.21(6H, m), 1.07(6H, t, J=7.3 Hz), 2.78(3H, brs), 3.20-3.31(4H, m), 3.56(2H, s), 3.82-4.27(1H, m), 4.84(2H, s), 6.99-7.63(17H, m), 8.19(1H, d, J=8.4 Hz), 8.98(1H, br.s) |

TABLE 20-continued
| Example | Structure | NMR (δ, 300 MHz, CDCl₃) |
|---|---|---|
| 2-13 | 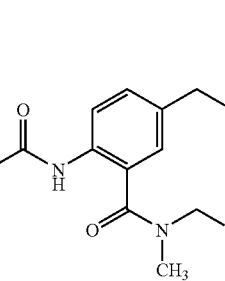 m.p.116.5-119.0 | 0.98-1.27(3H, br), 1.21 (6H, t, J=7.1 Hz), 2.73-2.96(3H, br), 3.05-3.49 (2H, br), 3.51(2H, s), 4.21(4H, q, J=7.1 Hz), 4.82(2H, s), 7.00-7.08(1H, m), 7.19(1H, dd, J=1.9, 8.3 Hz), 7.24-7.36(5H, m), 7.39(1H, dd, J=1.5, 7.9 Hz), 7.43-7.70(7H, m), 8.28(1H, d, J=8.6 Hz), 8.92-9.18(1H, br) |
| 2-14 | 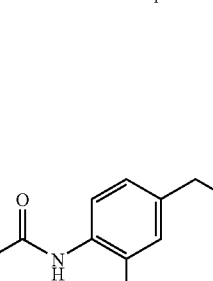 | 1.00-1.23(3H, br), 1.08 (6H, t, J=7.2 Hz), 2.79-2.96(3H, br), 3.10-3.49 (2H, br), 3.26(4H, dq, J=5.2, 7.2 Hz), 3.55(2H, s), 4.84(2H, s), 7.04(1H, d, J=1.8 Hz), 7.07-7.14 (2H, m), 7.15-7.24(3H, m), 7.28-7.37(3H, m), 7.37-7.43(1H, m), 7.44-7.69 (7H, m), 8.30(1H, d, J=8.3 Hz), 8.88-9.17(1H, br) |
| 2-15 | 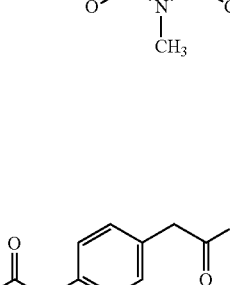 | 1.02-1.24(3H, br), 1.12 (6H, t, J=7.2 Hz), 2.47-2.59(2H, m), 2.80-2.96 (3H, br), 3.10-3.51(2H, br), 3.30(4H, dq, J=5.7, 7.2 Hz), 3.55(2H, s), 4.07-4.18(2H, m), 7.09(1H, d, J=1.5 Hz), 7.22-7.43(7H, m), 7.43-7.70(9H, m), 8.28 (1H, d, J=8.3 Hz), 8.85-9.14(1H, br) |
TABLE 21
| Example | Structure | NMR (δ, 300 MHz, CDCl₃) |
|---|---|---|
| 2-16 | 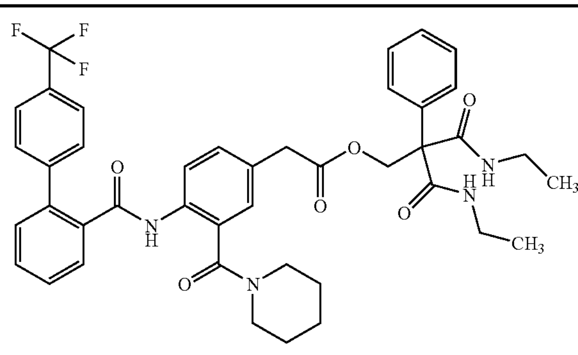 | 1.07(6H, t, J=7.2 Hz), 1.32-1.71(5H, br), 3.10-3.79(8H, m), 3.54 (2H, s), 4.84(2H, s), 7.03-7.79(15H, m), 8.28(1H, d, J=8.5 Hz), 9.04(1H, brs). |

TABLE 21-continued
| Example | Structure | NMR (δ, 300 MHz, CDCl₃) |
|---|---|---|
| 2-17 | 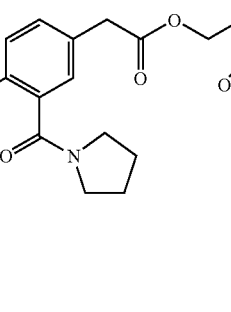 | 1.07(6H, t, J=7.2 Hz), 2.02-2.78(4H, br), 3.21-3.53(8H, m), 3.54 (2H, m), 4.84(2H, s), 7.03-7.72(15H, m), 8.34(1H, d, J=7.2 Hz), 9.83(1H, brs). |
| 2-18 | 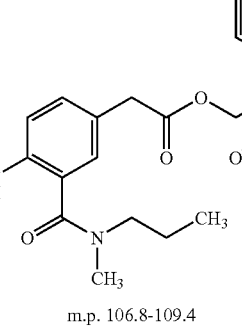<br>m.p. 106.8-109.4 | 0.65-1.01(3H, br), 1.21 (6H, t, J=7.2 Hz), 1.43-1.66(2H, br), 2.75-2.98 (3H, br), 3.05-3.41(2H, br), 3.51(2H, s), 4.21(4H, q, J=7.2 Hz), 4.82(2H, s), 7.04(1H, br-s), 7.19(1H, dd, J=1.9, 8.6 Hz), 7.24-7.35(5H, m), 7.39(1H, dd, J=1.5, 7.5 Hz), 7.43-7.69(7H, m), 8.18-8.31 (1H, br), 8.94-9.18(1H, br) |
| 2-19 | 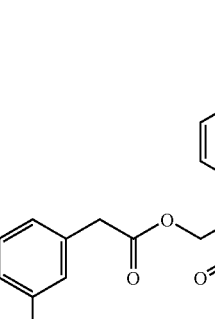 | 0.68-0.99(3H, br), 1.08 (6H, t, J=7.1 Hz), 1.42-1.69(2H, br), 2.79-2.98 (3H, br), 3.06-3.42(2H, br), 3.26(4H, dq, J=5.6, 7.1 Hz), 3.55(2H, s), 4.84(2H, s), 7.04(1H, d, J=1.8 Hz), 7.11(2H, br-t, J=5.6 Hz), 7.15-7.24(3H, m), 7.27-7.36(3H, m), 7.37-7.43 (1H, m), 7.44-7.69(7H, m), 8.21-8.35(1H, br), 8.92-9.18(1H, br) |
| 2-20 | 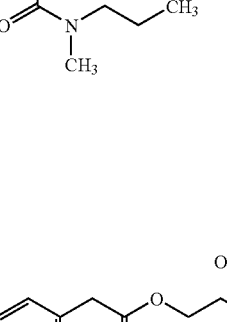 | 0.67-1.00(3H, br), 1.13 (6H, t, J=7.1 Hz), 1.43-1.67(2H, br), 2.48-2.59 (2H, m), 2.82-2.98(3H, br), 3.06-3.42(2H, br), 3.30(4H, dq, J=5.6, 7.1 Hz), 3.54(2H, s), 4.07-4.17 (2H, m), 7.09(1H, d, J=2.2 Hz), 7.22-7.42(7H, m), 7.43-7.69(9H, m), 8.20-8.34(1H, br), 8.89-9.14 (1H, br) |

TABLE 22
| Example | Structure | NMR (δ, 300 MHz, CDCl₃) |
|---|---|---|
| 2-21 | 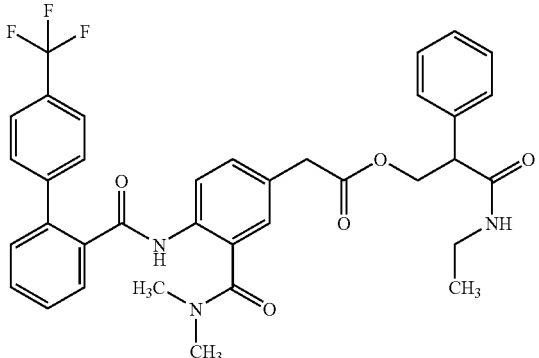 | 1.04(3H, t, J=7.2 Hz), 2.84 (3H, brs), 2.95(3H, brs), 3.16-3.29(2H, m), 3.50 (2H, s), 3.64(1H, dd, J=7.7, 6.5 Hz), 3.91(1H, dd, J= 10.9, 6.5 Hz), 4.64(1H, dd, J=10.9, 7.7 Hz), 5.28-5.38(1H, m), 7.00-7.71 (15H, m), 8.34(1H, d, J= 8.5 Hz), 9.15(1H, brs) |
| 2-22 | 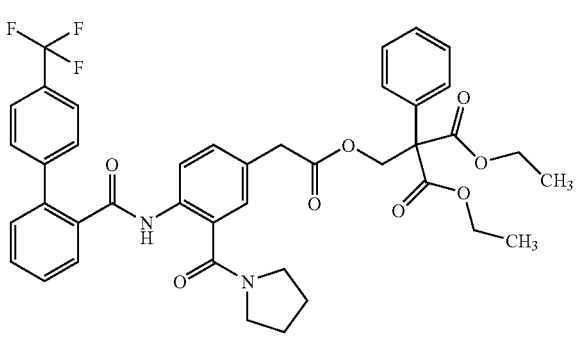<br>m.p. 130-131 | 1.21(6H, t, J=7.1 Hz), 1.73-2.00(4H, m), 3.22-3.53(4H, m), 3.51 (2H, s), 4.20(4H, q, J= 7.1 Hz), 4.83(2H, s), 7.15-7.70(15H, m), 8.33(1H, d, J=8.9 Hz), 9.84(1H, brs). |
| 2-23 | 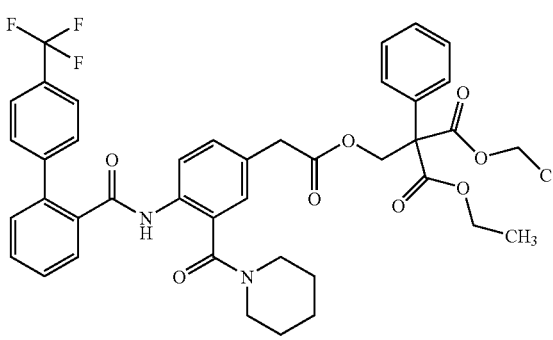<br>m.p. 118–120 | 1.21(6H, t, J=7.1 Hz), 1.35-1.70(6H, br), 3.00-3.76(4H, br), 3.51 (2H, s), 4.20(4H, q, J= 7.1 Hz), 4.82(2H, s), 7.03 (1H, d, J=2.0 Hz), 7.12-7.68(14H, m), 8.26(1H, d, J=8.5 Hz), 9.06(1H, brs). |
| 2-24 | 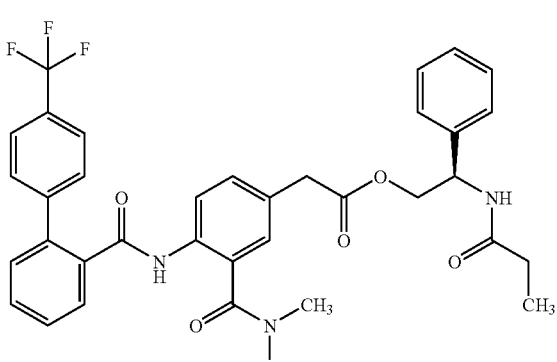 | 1.11(3H, t, J=7.6 Hz), 2.19(2H, q, J=7.6 Hz), 2.84 (3H, brs), 2.95(3H, brs), 3.54(2H, s), 4.28(1H, dd, J=11.3, 4.9 Hz), 4.41(1H, dd, J=11.3, 7.0 Hz), 5.25-5.33(1H, m), 5.87(1H, d, J=8.3 Hz), 7.04-7.71(15H, m), 8.36(1H, d, J=8.5 Hz), 9.14(1H, brs) |

TABLE 22-continued
| Example | Structure | NMR (δ, 300 MHz, CDCl₃) |
|---|---|---|
| 2-25 |  m.p. 95-98 | 1.11(3H, t, J=7.5 Hz), 2.19(2H, q, J=7.5 Hz), 2.84 (3H, brs), 2.95(3H, brs), 3.54(2H, s), 4.29(1H, dd, J=11.3, 4.9 Hz), 4.41(1H, dd, J=11.3, 7.0 Hz), 5.26-5.33(1H, m), 5.86(1H, d, J=7.9 Hz), 7.04-7.71(15H, m), 8.36(1H, d, J=8.7 Hz), 9.14(1H, brs) |
TABLE 23
| Example | Structure | NMR (δ, 300 MHz, CDCl₃) |
|---|---|---|
| 2-26 | m.p. 152-155 | 2.53(4H, s), 2.89(3H, brs), 2.96(3H, brs), 3.55(2H, s), 4.66(1H, dd, J=10.9, 5.3 Hz), 5.10(1H, t, J=10.9 Hz), 5.37(1H, dd, J=10.9, 5.3 Hz), 7.07-7.69(15H, m), 8.35(1H, d, J=8.7 Hz), 9.17(1H, brs) |
| 2-27 | 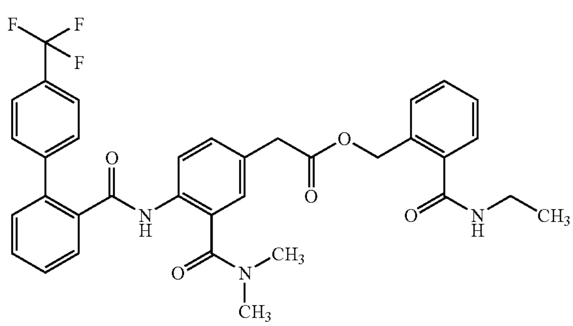 | 1.19(3H, t, J=7.2 Hz), 2.70-3.01(6H, br), 3.41(2H, dq, J=5.6, 7.2 Hz), 3.60(2H, s), 5.32(2H, s), 6.18(1H, br-t, J=5.6 Hz), 7.04(1H, d, J=1.9 Hz), 7.21-7.29(1H, m), 7.30-7.56(7H, m), 7.56-7.66(4H, m), 7.69 (1H, dd, J=1.5, 7.1 Hz), 8.35(1H, d, J=8.7 Hz), 9.09(1H, br-s) |
| 2-28 | 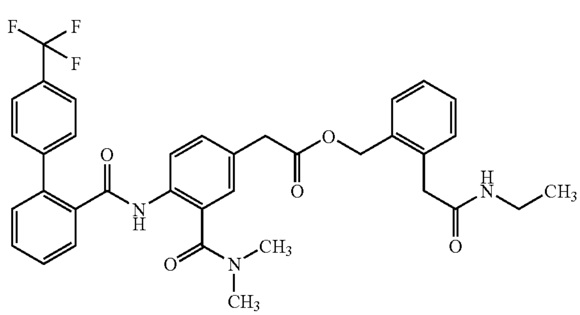 | 1.04(3H, t, J=7.1 Hz), 2.70-3.00(6H, br), 3.22(2H, dq, J=5.7, 7.1 Hz), 3.53(2H, s), 3.57(2H, s), 5.13(2H, s), 5.43-5.54(1H, br), 7.08(1H, d, J=1.9 Hz), 7.21-7.43(6H, m), 7.44-7.66(6H, m), 7.69(1H, dd, J=1.5, 7.2 Hz), 8.34(1H, d, J=8.6 Hz), 9.10(1H, br-s) |

TABLE 23-continued

| Example | Structure | NMR (δ, 300 MHz, CDCl₃) |
|---------|-----------|--------------------------|
| 2-29 | 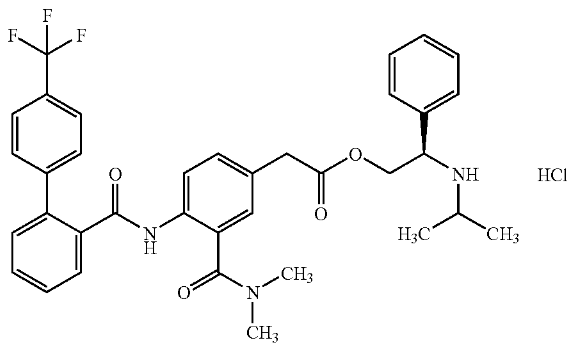 | 1.26-1.68(6H, m), 2.61-3.00(6H, m), 2.93-3.12(1H, m), 3.58-4.01 (1H, m), 4.28-5.03(3H, m), 7.09-8.32(17H, m), 9.14 (1H, brs), 9.40-10.24(2H, m) |
| 2-30 | 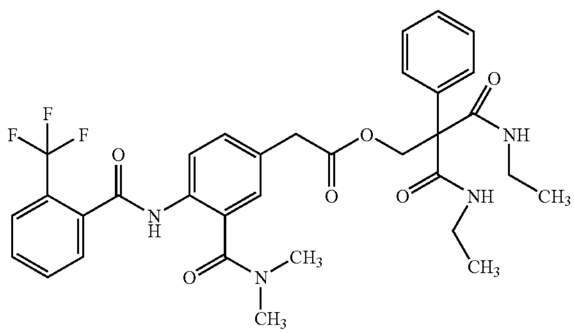 | 1.10(6H, t, J=7.3 Hz), 3.06 (6H, brs), 3.21-3.42(4H, m), 3.61(2H, s), 4.86(2H, s), 7.06-7.77(13H, m), 8.37 (1H, d, J=8.5 Hz), 9.21 (1H, brs) |

TABLE 24

| Example | Structure | NMR (δ, 300 MHz, CDCl₃) |
|---------|-----------|--------------------------|
| 2-31 | m.p 106-110 | 1.23(6H, t, J=7.1 Hz), 2.98 (3H, brs), 3.05(3H, brs), 4.22(4H, q, J=7.1 Hz), 4.85 (2H, s), 7.11-7.75(11H, m), 8.35(1H, d, J=8.5 Hz), 9.21(1H, brs) |
| 2-32 | 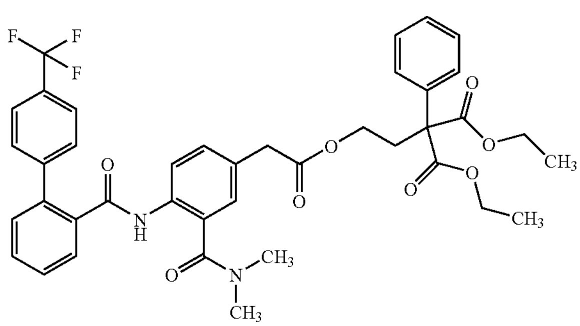 | 1.24(6H, t, J=7.2 Hz), 2.61 (2H, t, J=7.1 Hz), 2.86(3H, br.s), 2.94(3H, br.s), 3.46 (2H, s), 4.07(2H, t, J=7.1 Hz), 4.23(4H, q, J=7.21 Hz), 7.08(1H, d, J=1.9 Hz), 7.23-7.68(14H, m), 8.36 (1H, d, J=8.6 Hz), 9.15(1H, br.s) |

TABLE 24-continued

| Example | Structure | NMR (δ, 300 MHz, CDCl₃) |
|---|---|---|
| 2-33 | m.p. 125-128 | 1.22(6H, t, J=7.2 Hz), 2.83 (3H, br.s), 2.94(3H, br.s), 3.51(2H, s), 4.21(4H, q, J=7.2 Hz), 4.83(2H, s), 7.00-7.51(14H, m), 7.68(1H, dd, J=7.6, 1.5 Hz), 8.37(1H, d, J=8.3 Hz), 8.93(1H, br.s) |
| 2-34 | m.p. 124-128 | 1.22(6H, t, J=7.2 Hz), 2.86 (3H, br.s), 2.95(3H, br.s), 3.51(2H, s), 4.21(4H, q, J=7.2 Hz), 4.83(2H, s), 7.01 (1H, d, J=2.2 Hz), 7.19-7.53(13H, m), 7.68(1H, dd, J=7.6, 1.5 Hz), 8.40(1H, d, J=8.3 Hz), 9.01(1H, br.s) |
| 2-35 | 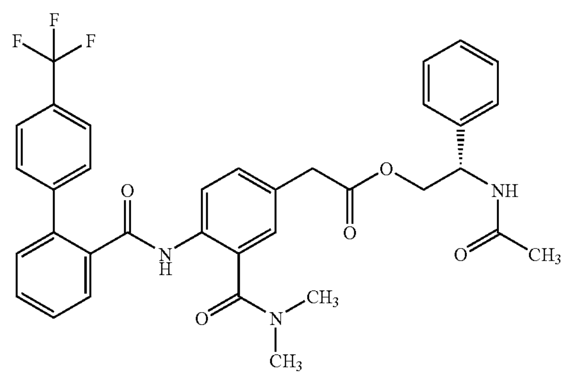 | 1.96(3H, s), 2.84(3H, brs), 2.95(3H, brs), 3.54(2H, s), 4.29(1H, dd, J=11.6, 5.0 Hz), 4.39(1H, dd, J=11.6, 7.1 Hz), 5.23-5.33(1H, m), 5.90(1H, d, J=8.1 Hz), 6.99-7.71(15H, m), 8.36 (1H, d, J=8.5 Hz), 9.14(1H, brs) |

TABLE 25

| Example | Structure | NMR (δ, 300 MHz, CDCl₃) |
|---|---|---|
| 2-36 | 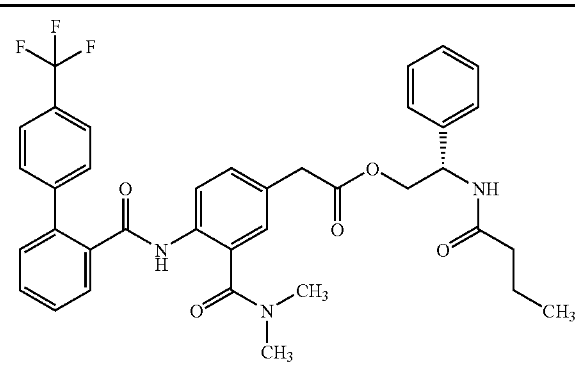 | 0.92(3H, t, J=7.4 Hz), 1.56-1.68(2H, m), 2.14(2H, t, J=7.5 Hz), 2.84(3H, brs), 2.95(3H, brs), 3.54 (2H, s), 4.29(1H, dd, J=11.4, 4.9 Hz), 4.40(1H, dd, J=11.4, 7.1 Hz), 5.23-5.33(1H, m), 5.90 (1H, d, J=8.1 Hz), 7.05 (1H, d, J=2.0 Hz), 7.15-7.72(14H, m), 8.36(1H, d, J=8.5 Hz), 9.15(1H, brs) |

TABLE 25-continued

| Example | Structure | NMR (δ, 300 MHz, CDCl₃) |
|---|---|---|
| 2-37 | 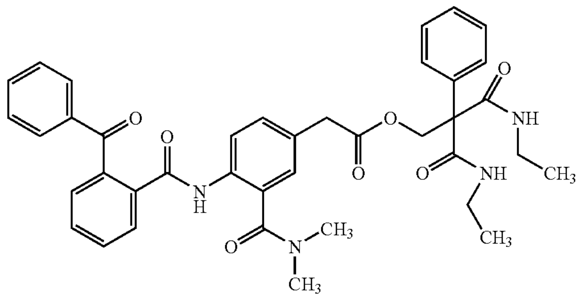 | 1.07(3H, t, J=7.3 Hz), 1.08(3H, t, J=7.3 Hz), 2.97(3H, s), 3.10(3H, s), 3.18-3.31(4H, m), 3.59(2H, s), 4.87(2H, d, J=4.1 Hz), 6.38(1H, d, J=8.2 Hz), 6.92-7.64(18H, m), 7.83(1H, d, J=6.8 Hz) |
| 2-38 | 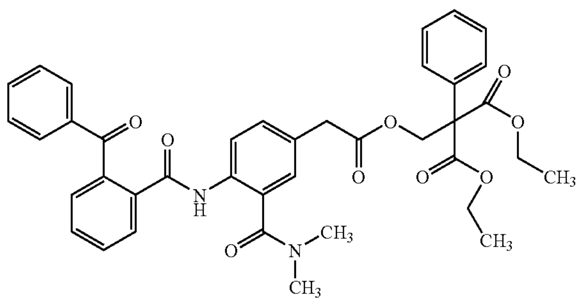 | 1.21(6H, t, J=7.1 Hz), 2.96(3H, s), 3.07(3H, s), 3.55(2H, d, J=2.1 Hz), 4.19 (2H, q, J=7.1 Hz), 4.20 (2H, q, J=7.1 Hz), 4.82 and 4.89(2H, each d, J=11.2 Hz), 6.36(1H, d, J=8.2 Hz), 6.93-7.59(16H, m), 7.83 (1H, d, J=6.8 Hz) |
| 2-39 | m.p. 108.8-112.4 | 2.73-3.00(6H, br), 3.52 (2H, s), 3.72(6H, s), 4.82 (2H, s), 7.03(1H, d, J=1.9 Hz), 7.16-7.36(6H, m), 7.40(1H, dd, J=1.5, 7.5 Hz), 7.45-7.65(6H, m), 7.69(1H, dd, J=1.5, 7.2 Hz), 8.35(1H, d, J=8.7 Hz), 9.17(1H, br-s) |
| 2-40 | m.p. 110-111 | 1.21(6H, t, J=7.1 Hz), 1.31-1.60(6H, m), 1.67-1.82(2H, m), 2.40-2.57(1H, m), 2.88 (3H, brs), 2.94(3H, brs), 3.53(2H, s), 4.14(4H, q, J= 7.1 Hz), 4.48(2H, s), 7.09 (1H, d, J=1.8 Hz), 7.2-7.72(9H, m), 8.37(1H, d, J=8.4 Hz), 9.16(1H, brs). |

TABLE 26

| Example | Structure | NMR (δ, 300 MHz, CDCl₃) |
|---|---|---|
| 2-41 | m.p. 108-110 | 0.95-1.19(6H, m), 1.21 (6H, t, J=9.5 Hz), 1.60-1.80(4H, m), 2.00-2.18 (1H, m), 2.88(3H, brs), 2.95(3H, brs), 3.52(2H, s), 4.14(4H, q, J=9.5 Hz), 4.50(2H, s), 7.09(1H, d, J=2.7 Hz), 7.19-7.73(9H, m), 8.38(1H, d, J=11.3 Hz), 9.18(1H, brs). |
| 2-42 | m.p. 121-124 | 1.22(6H, t, J=7.2 Hz), 2.84(3H, br.s), 2.94(3H, br.s), 3.51(2H, s), 4.21 (4H, q, J=7.2 Hz), 4.83 (2H, s), 7.01(1H, d, J= 1.9 Hz), 7.20(1H, dd, J= 8.7, 1.9 Hz), 7.26-7.51 (12H, m), 7.68(1H, dd, J= 7.5, 1.5 Hz), 8.40(1H, d, J=8.7 Hz), 9.00(1H, br.s) |
| 2-43 | 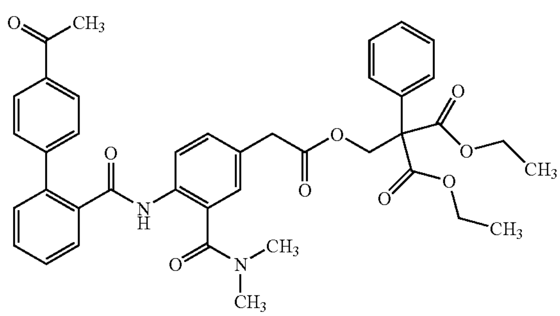 | 1.21(6H, t, J=7.2 Hz), 2.57(3H, s), 2.75(3H, br.s), 2.94(3H, br.s), 3.50(2H, s), 4.20(4H, q, J=7.2 Hz), 4.82 (2H, s), 7.00(1H, d, J= 1.9 Hz), 7.18(1H, dd, J= 8.6, 1.9 Hz), 7.26-7.59 (11H, m), 7.70(1H, dd, J= 7.6, 1.5 Hz), 7.95(1H, d, J=8.3 Hz), 8.35(1H, d, J=8.6 Hz), 9.13(1H, br.s) |
| 2-44 | 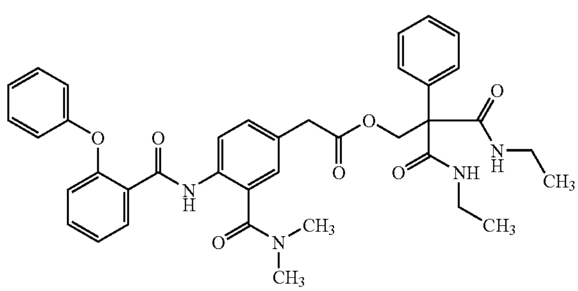 | 1.07(6H, t, J=7.3 Hz), 2.76(3H, s), 2.86(3H, s), 3.21-3.30(4H, m), 3.57 (2H, s), 4.83(2H, s), 6.82 (1H, d, J=8.3 Hz), 6.98-7.45(16H, m), 8.24(1H, dd, J=7.8, 1.8 Hz), 8.44 (1H, d, J=8.5 Hz), 10.4 (1H, brs) |

TABLE 26-continued

| Example | Structure | NMR (δ, 300 MHz, CDCl₃) |
|---|---|---|
| 2-45 | 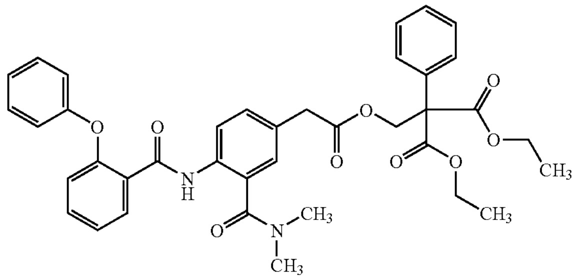 | 1.22(6H, t, J=7.1 Hz), 2.75(3H, s), 2.82(3H, s), 3.54(2H, s), 4.21(4H, q, J=7.1 Hz), 4.83(2H, s), 6.82 (1H, d, J=7.6 Hz), 7.05(1H, d, J=2.0 Hz), 7.09-7.46 (13H, m), 8.24(1H, dd, J= 7.8, 1.8 Hz), 8.42(1H, d, J=8.5 Hz), 10.4(1H, brs) |

TABLE 27

| Example | Structure | NMR (δ, 300 MHz, CDCl₃) |
|---|---|---|
| 2-46 | 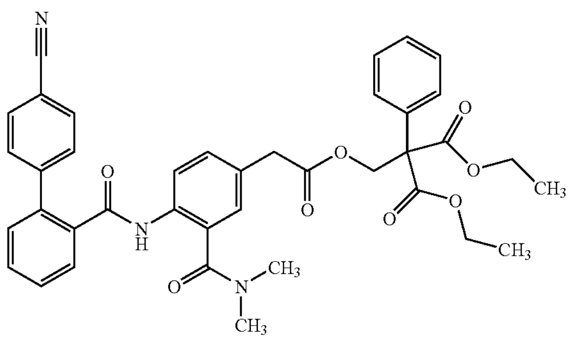 | 1.22(6H, t, J=7.2 Hz), 2.90 (3H, br.s), 2.97(3H, br.s), 3.52(2H, s), 4.21(4H, q, J=7.2 Hz), 4.83(2H, s), 7.05(1H, d, J=1.9 Hz), 7.20 (1H, dd, J=8.7, 1.9 Hz), 7.29-7.73(13H, m), 8.33 (1H, d, J=8.7 Hz), 9.27 (1H, br.s) |
| 2-47 | 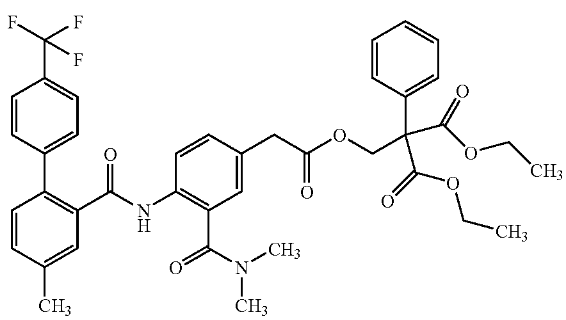 | 1.21(6H, t, J=7.2 Hz), 2.44 (3H, s), 2.77(3H, br.s), 2.91(3H, br.s), 3.50(2H, s), 4.20(4H, q, J=7.2 Hz), 4.82 (2H, s), 7.01(1H, d, J=2.2 Hz), 7.19(1H, dd, J=8.7, 2.2 Hz), 7.30-7.59(12H, m), 8.35(1H, d, J=8.7 Hz), 9.08(1H, br.s) |
| 2-48 | m.p. 105-108 | 1.21(6H, t, J=7.1 Hz), 2.44 (3H, s), 2.80(3H, br.s), 2.94(3H, br.s), 3.50(2H, s), 4.20(4H, q, J=7.1 Hz), 4.82 (2H, s), 7.02(1H, d, J=2.2 Hz), 7.16-7.30(8H, m), 7.56-7.63(5H, m), 8.35 (1H, d, J=8.7 Hz), 9.14 (1H, br.s) |

TABLE 27-continued

| Example | Structure | NMR (δ, 300 MHz, CDCl$_3$) |
|---|---|---|
| 2-49 | 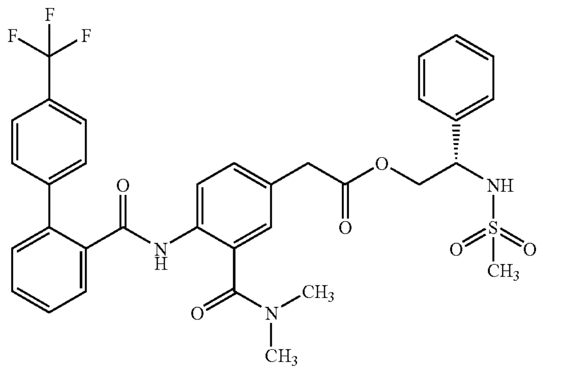 | 2.65(3H, s), 2.86(3H, brs), 2.95(3H, brs), 3.61(2H, s), 4.23-4.30(2H, m), 4.71-4.79(1H, m), 4.98 ((1H, d, J=7.1 Hz), 7.09 (1H, d, J=1.9 Hz), 7.18-7.71(14H, m), 8.37(1H, d, J=8.7 Hz), 9.16(1H, brs) |
| 2-50 | 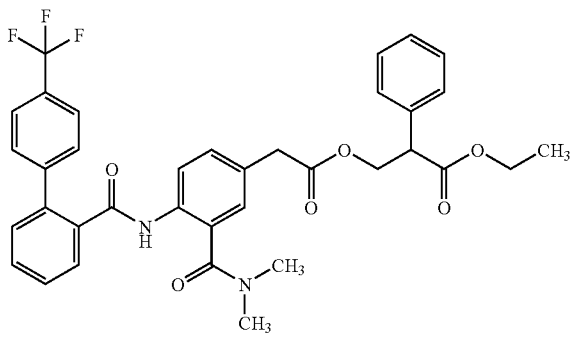 | 1.19(3H, t, J=7.1 Hz), 2.86 (3H, brs), 2.95(3H, brs), 3.52(2H, s), 3.89(1H, dd, J=9.1, 6.0 Hz), 4.02-4.19(2H, m), 4.34(1H, dd, J=10.9, 6.0 Hz), 4.58(1H, dd, J=10.9, 9.1 Hz), 7.06 (1H, d, J=2.3 Hz), 7.18-7.71(14H, m), 8.36(1H, d, J=8.6 Hz), 9.17(1H, brs) |

TABLE 28

| Example | Structure | NMR (δ, 300 MHz, CDCl$_3$) |
|---|---|---|
| 2-51 | 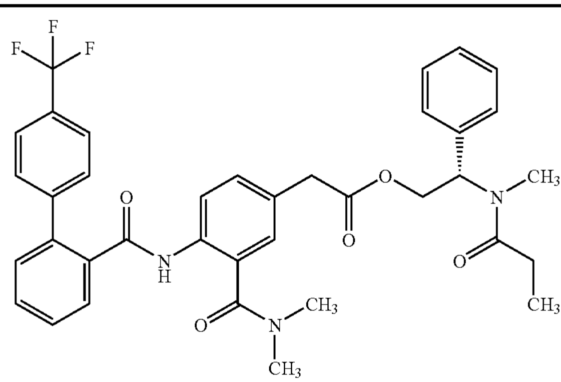 | 1.12-1.18(3H, m), 2.21-2.46(2H, m), 2.64-3.49(9H, m), 3.55-3.58(2H, m), 4.45-5.29(2H, m), 6.11-6.19(1H, m), 7.12-7.70(15H, m), 8.33-8.38(1H, m), 9.17 (1H, brs) Conformer |
| 2-52 | 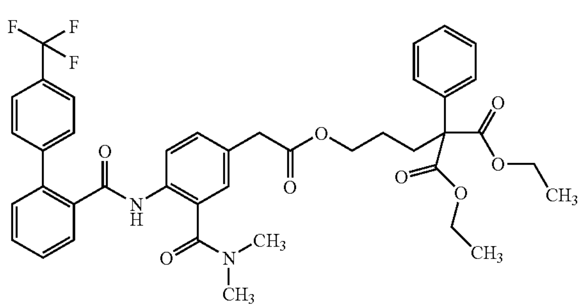 | 1.24(6H, t, J=7.0 Hz), 1.50-1.64(2H, m), 2.25-2.36(2H, m), 2.77-3.02 (6H, br), 3.54(2H, s), 3.99-4.08(2H, m), 4.16-4.29 (4H, m), 7.10(1H, d, J= 1.9 Hz), 7.24-7.43(7H, m), 7.44-7.57(2H, m), 7.59-7.64(4H, m), 7.68 (1H, dd, J=1.5, 7.2 Hz), 8.36(1H, d, J=8.7 Hz), 9.16 (1H, s) |

TABLE 28-continued

| Example | Structure | NMR (δ, 300 MHz, CDCl₃) |
|---|---|---|
| 2-53 | 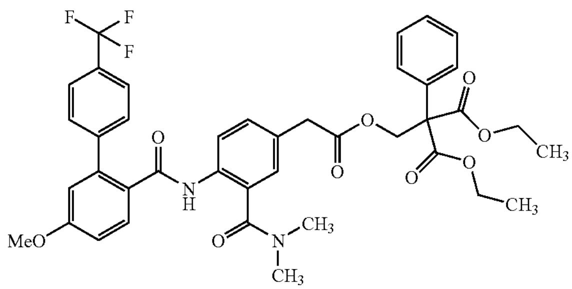 | 1.21(6H, t, J=7.0 Hz), 2.82(3H, br.s), 2.95(3H, br.s), 3.50(2H, s), 3.88(3H, s), 4.21(4H, q, J=7.0 Hz), 4.82(2H, s), 6.87(1H, d, J=2.6 Hz), 6.99(1H, dd, J=8.5, 2.6 Hz), 7.03(1H, d, J=1.8 Hz), 7.18(1H, dd, J=8.5, 1.8 Hz), 7.29-7.69 (10H, m), 8.35(1H, d, J=8.8 Hz), 9.17(1H, br.s) |
| 2-54 | 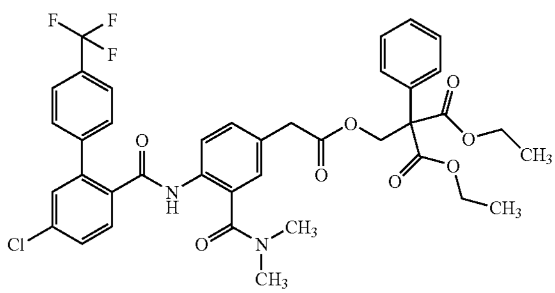 | 1.21(6H, t, J=7.0 Hz), 2.81(3H, br.s), 2.94(3H, br.s), 3.51(2H, s), 4.20(4H, q, J=7.0 Hz), 4.83(2H, s), 7.04(1H, d, J=2.2 Hz), 7.19 (1H, dd, J=8.4, 2.2 Hz), 7.30-7.66(12H, m), 8.33 (1H, d, J=8.5 Hz), 9.29 (1H, br.s) |
| 2-55 | mp 102-105 | 1.20(6H, t, J=7.1 Hz), 2.11(3H, s), 2.88(3H, brs), 3.04(3H, brs), 3.48(2H, s), 4.19(4H, q, J=7.1 Hz), 4.81 (2H, s), 7.04(1H, d, J=2.0 Hz), 7.12(1H, dd, J=2.0 Hz, J=8.5 Hz), 7.24-7.50(10H, m), 7.60(2H, d, J=8.1 Hz), 8.10(1H, d, J=8.5 Hz), 9.06(1H, brs). |

TABLE 29

| Example | Structure | NMR (δ, 300 MHz, CDCl₃) |
|---|---|---|
| 2-56 | 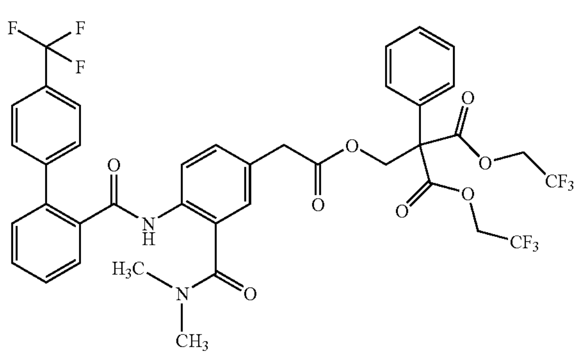 | 2.81(3H, brs), 2.93(3H, brs), 3.52(2H, s), 4.45-4.60(4H, m), 4.88(2H, s), 7.02(1H, d, J=2.0 Hz), 7.19 (1H, dd, J=2.0 Hz), J=8.7 Hz), 7.23-7.64(12H, m), 7.68(1H, dd, J=2.0 Hz, J=8.1 Hz), 8.34(1H, d, J=8.1 Hz), 9.10(1H, brs). |

TABLE 29-continued
| Example | Structure | NMR (δ, 300 MHz, CDCl₃) |
|---|---|---|
| 2-57 | 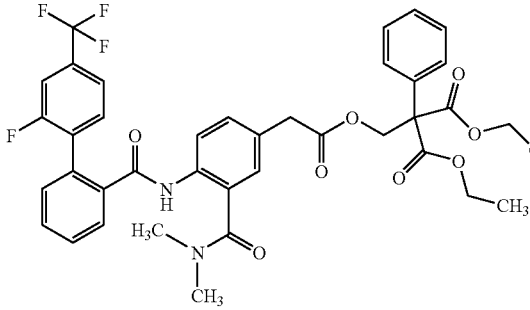 mp 116.5-119.5 | 1.21(6H, t, J=7.1 Hz), 2.95 (3H, brs), 3.01(3H, brs), 3.52(2H, s), 4.21(4H, q, J=7.1 Hz), 4.83(2H, s), 7.10 (1H, s), 7.14-7.63(12H, m), 7.75((1H, d, J=6.6 Hz), 8.22(1H, d, J=8.7 Hz), 9.34(1H, brs). |
| 2-58 | 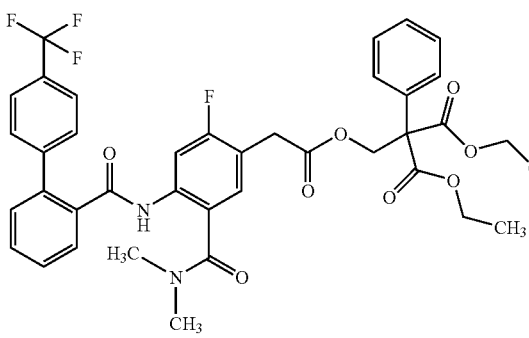 mp 119-121 | 1.23(6H, t, J=7.1 Hz), 2.85 (6H, br-s), 3.55(2H, s), 4.22(4H, q, J=7.1 Hz), 4.83 (2H, s), 7.03((1H, d, J=7.6 Hz), 7.24-7.74(13H, m), 8.36(1H, d, J=12.2 Hz), 9.45(1H, br-s). |
| 2-59 | 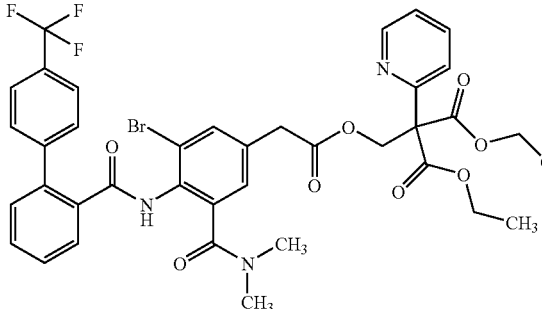 | 1.22(6H, t, J=7.1 Hz), 2.87 (3H, s), 2.96(3H, s), 3.51 (2H, s), 4.22(4H, q, J=7.1 Hz), 4.85(2H, s), 7.06(1H, brs), 7.25-7.68(14H, m), 7.77(1H, d, J=7.1 Hz). |
| 2-60 | 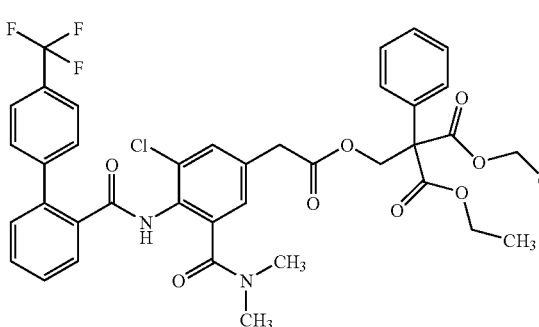 | 1.22(6H, t, J=7.1 Hz), 2.86 (3H, brs), 2.95(3H, s), 3.50(2H, s), 4.22(4H, q, J=7.1 Hz), 4.85(2H, s), 7.00(1H, d, J=1.5 Hz), 7.20-7.66(13H, m), 7.73 (1H, dd, J=1.5 Hz, J=7.1 Hz), 7.97(1H, brs). |

TABLE 30

| Example | Structure | NMR (δ, 300 MHz, CDCl₃) |
|---|---|---|
| 2-61 | mp 131-133 | 1.21(6H, t, J=7.2 Hz), 2.88 (3H, brs), 2.97(3H, brs), 3.52(2H, s), 4.20(4H, q, J=7.2 Hz), 4.83(2H, s), 7.07 (1H, d, J=2.2 Hz), 7.18-7.72(13H, m), 8.33(1H, d, J=8.4 Hz), 9.33(1H, brs). |
| 2-62 | mp 120-125 | 1.21(6H, t, J=7.1 Hz), 2.87 (3H, brs), 2.96(3H, brs), 3.52(2H, s), 4.21(4H, q, J=7.1 Hz), 4.83(2H, s), 7.07 (1H, d, J=1.8 Hz), 7.17-7.72(13H, m), 8.32(1H, d, J=8.4 Hz), 9.32(1H, br-s). |
| 2-63 | 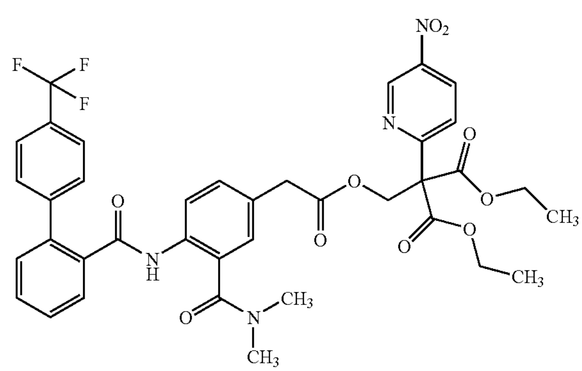 | 1.22(6H, t, J=7.2 Hz), 2.83 (3H, brs), 2.94(3H, brs), 3.48(2H, s), 4.23(4H, q, J=7.21 Hz), 4.94(2H, s), 6.98 (1H, d, J=1.9 Hz), 7.12-7.76(10H, m), 8.30(1H, d, J=8.3 Hz), 8.38(1H, dd, J=2.6 Hz, J=8.9 Hz), 9.08 (1H, brs), 9.22(1H, d, J=2.6 Hz). |
| 2-64 | 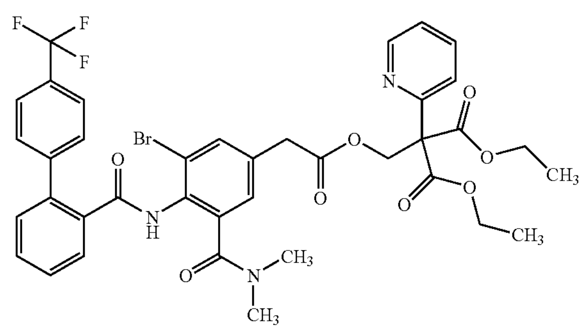 | 1.21(6H, t, J=7.2 Hz), 2.83 (3H, brs), 2.94(3H, brs), 3.48(2H, s), 3.49(1H, brs), 3.71(1H, brs), 4.20(4H, q, J=7.2 Hz), 4.88(2H, s), 6.83(1H, dd, J=3.0 Hz), J=8.3 Hz), 7.03(1H, d, J=1.9 Hz), 7.11-7.72(10H, m), 7.83(1H, d, J=3.1 Hz), 8.25(1H, d, J=8.6 Hz), 9.14 (1H, brs). |

TABLE 30-continued

| Example | Structure | NMR (δ, 300 MHz, CDCl₃) |
|---|---|---|
| 2-65 | mp 149-155 | 1.21(6H, t, J=7.2 Hz), 2.83 (3H, brs), 2.93(3H, brs), 3.49(2H, s), 4.21(4H, q, J=7.2 Hz), 4.93(2H, s), 7.03 (1H, d, J=1.9 Hz), 7.13-7.73(12H, m), 8.33(1H, d, J=8.6 Hz), 8.47(1H, d, J=3.8 Hz), 9.17(1H, brs). |

TABLE 31

| Example | Structure | NMR (δ, 300 MHz, CDCl₃) |
|---|---|---|
| 2-66 | 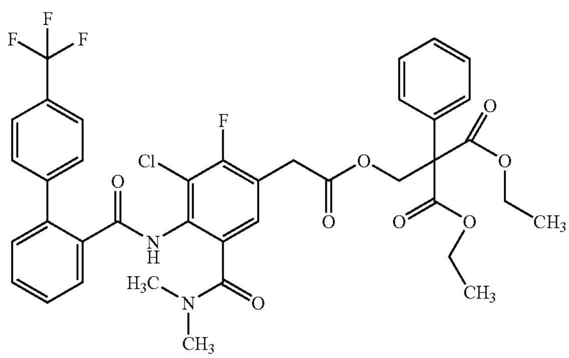 | 1.23(6H, t, J=7.2 Hz), 2.88 (3H, s), 2.97(3H, s), 3.61 (2H, s), 4.23(4H, q, J=7.2 Hz), 4.85(2H, s), 7.03(1H, d, J=7.1 Hz), 7.23-7.68 (12H, m), 7.74(1H, dd, J=1.1 Hz, J=7.5 Hz), 7.84(1H, brs). |
| 2-67 | 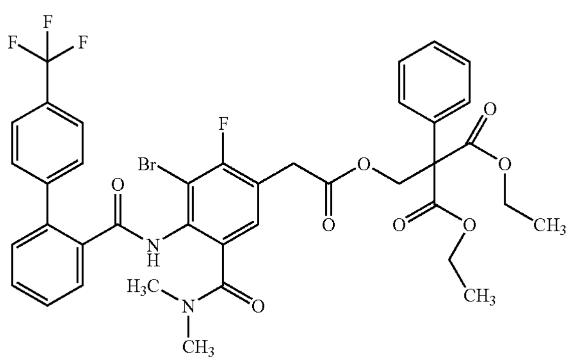 | 1.23(6H, t, J=7.2 Hz), 2.88 (3H, s), 2.96(3H, s), 3.62 (2H, s), 4.23(4H, q, J=7.2 Hz), 4.85(2H, s), 7.09(1H, d, J=7.5 Hz), 7.24-7.68 (12H, m), 7.74-7.80(2H, m). |
| 2-68 | 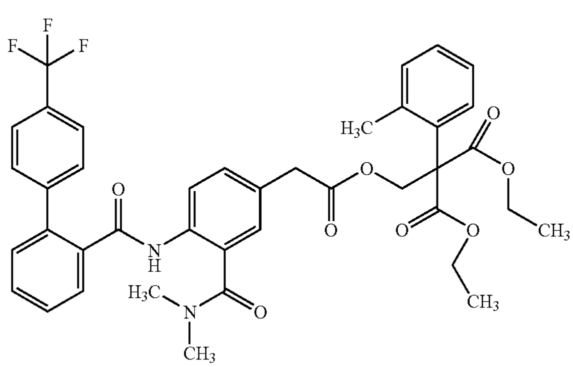 | 1.22(6H, t, J=7.2 Hz), 2.26 (3H, s), 2.84(3H, brs), 2.95 (3H, brs), 3.48(2H, s), 4.10-4.61(4H, m), 4.88 (2H, s), 6.99-7.73(14H, m), 8.43(1H, d, J=8.3 Hz), 9.18(1H, brs). |

TABLE 31-continued

| Example | Structure | NMR (δ, 300 MHz, CDCl₃) |
|---|---|---|
| 2-69 | 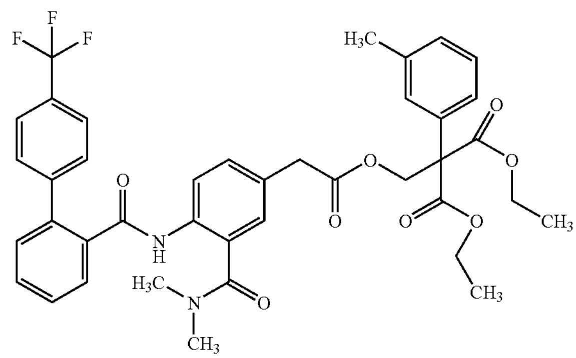 | 1.21(6H, t, J=7.2 Hz), 2.32 (3H, s), 2.81(3H, brs), 2.93 (3H, brs), 3.51(2H, s), 4.20(4H, q, J=7.2 Hz), 4.81 (2H, s), 7.01-7.74(14H, m), 8.36(1H, d, J=8.3 Hz), 9.19(1H, br-s). |
| 2-70 | 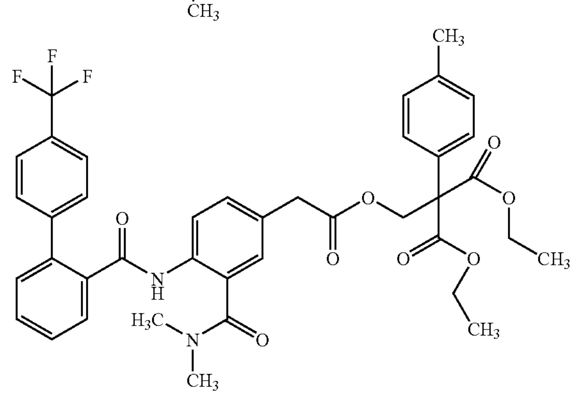 | 1.21(6H, t, J=7.2 Hz), 2.33 (3H, s), 2.82(3H, brs), 2.94 (3H, brs), 3.51(2H, s), 4.20(4H, q, J=7.2 Hz), 4.81 (2H, s), 7.01-7.74(14H, m), 8.35(1H, d, J=8.3 Hz), 9.19(1H, brs). |

TABLE 32

| Example | Structure | NMR (δ, 300 MHz, CDCl₃) |
|---|---|---|
| 2-71 | 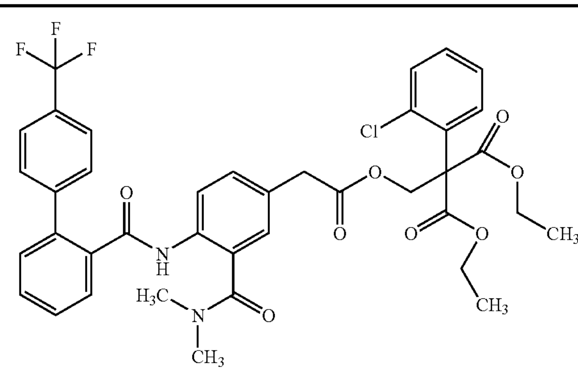 | 1.24(6H, t, J=7.2 Hz), 2.84 (3H, br-s), 2.95(3H, brs), 3.44(2H, s), 4.12-4.35(4H, m), 4.94(2H, s), 7.00(1H, d, J=2.2 Hz), 7.05-7.73 (13H, m), 8.31(1H, d, J= 8.3 Hz), 9.19(1H, brs). |
| 2-72 | | 1.22(6H, t, J=7.1 Hz), 2.81 (3H, brs), 2.94(3H, brs), 3.51(2H, s), 4.21(4H, q, J=7.1 Hz), 4.80(2H, s), 7.03(1H, d, J=2.2 Hz), 7.14-7.64(12H, m), 7.70 (1H, dd, J=1.6 Hz, J=7.2 Hz), 8.36(1H, d, J=8.6 Hz), 9.19(1H, brs). | mp 122.2–125.0

TABLE 32-continued
| Example | Structure | NMR (δ, 300 MHz, CDCl₃) |
|---|---|---|
| 2-73 | 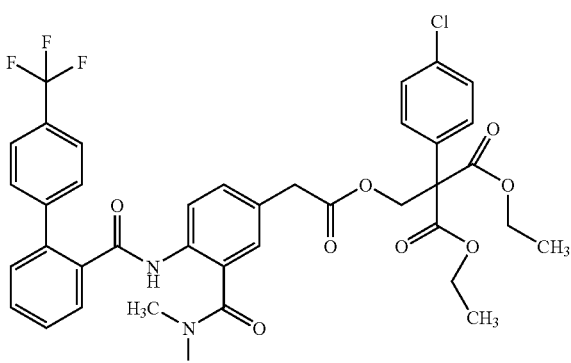 mp 132.0–134.4 | 1.21(6H, t, J=7.2 Hz), 2.80 (3H, brs), 2.94(3H, brs), 3.50(2H, s), 4.20(4H, q, J=7.2 Hz), 4.80(2H, s), 7.02(1H, d, J=2.3 Hz), 7.18-7.71(13H, m), 8.36 (1H, d, J=8.3 Hz), 9.18(1H, brs). |
| 2-74 | 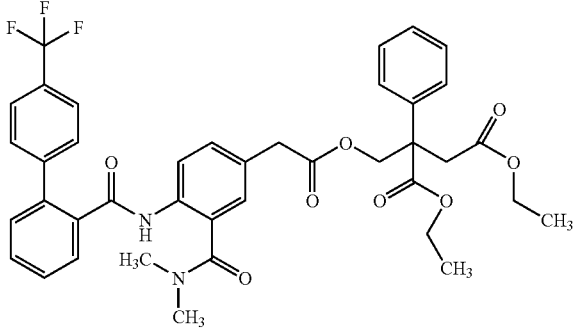 | 1.16(3H, t, J=7.0 Hz), 1.18 (3H, t, J=7.2 Hz), 2.82 (3H, brs), 2.93(3H, brs), 3.04(1H, d, J=16.5 Hz), 3.20(H, d, J=16.5 Hz), 3.46 (2H, s), 4.04-4.20(4H, m), 4.75(1H, d, J=11.4 Hz), 4.82(1H, d, J=11.4 Hz), 6.98(1H, d, J=2.2 Hz), 7.11-7.72(4H, m), 8.34 (1H, d, J=8.8 Hz), 9.17 (1H, brs). |
| 2-75 | 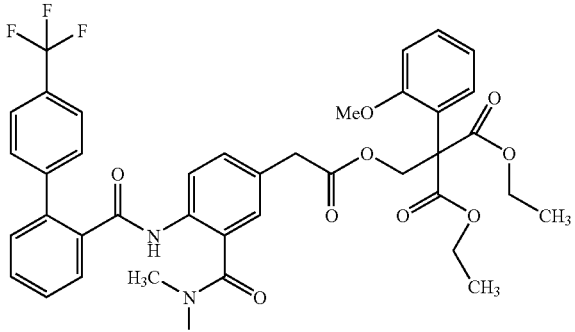 mp 121.0–124.0 | 1.22(6H, t, J=7.1 Hz), 2.84 (3H, brs), 2.94(3H, brs), 3.44(2H, s), 3.74(3H, s), 4.22(4H, q, J=7.1 Hz), 4.81 (2H, s), 6.84-7.71(14H, m), 8.32(1H, d, J=8.7 Hz), 9.18(1H, brs). |

TABLE 33

| Example | Structure | NMR (δ, 300 MHz, CDCl₃) |
|---|---|---|
| 2-76 | 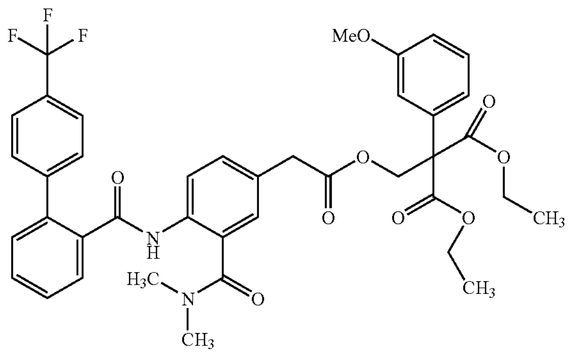 | 1.21(6H, t, J=7.1 Hz), 2.82 (3H, brs), 2.94(3H, brs), 3.51(2H, s), 3.77(3H, s), 4.20(4H, q, J=7.1 Hz), 4.81 (2H, s), 6.83-6.91(3H, m), 7.04(1H, d, J=1.9 Hz), 7.18-7.71(10H, m), 8.35 (1H, d, J=8.3 Hz), 9.19 (1H, brs). |
| 2-77 | 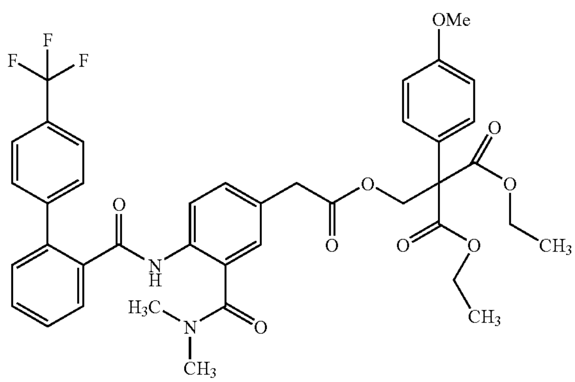 | 1.21(6H, t, J=7.1 Hz), 2.80 (3H, brs), 2.93(3H, brs), 3.51(2H, s), 3.79(3H, s), 4.20(4H, q, J=7.1 Hz), 4.80 (2H, s), 6.84(2H, dt, J=8.6 Hz, J=3.4 Hz), 7.03(1H, d, J=1.9 Hz), 7.19-7.71 (11H, m), 8.36(1H, d, J=8.7 Hz), 9.18(1H, brs). |
| 2-78 | m.p. 118–119 | 1.21(6H, t, J=7.2 Hz), 2.82 (3H, brs), 2.94(3H, brs), 3.52(2H, s), 4.21(4H, q, J=7.2 Hz), 4.83(2H, s), 7.05(1H, s), 7.19-7.30(6H, m), 7.61-7.84(7H, m), 8.34 (1H, d, J=8.3 Hz), 9.40 (1H, brs) |
| 2-79 | m.p. 135–138 | 1.20(6H, t, J=7.2 Hz), 2.86 (3H, brs), 3.06(3H, brs), 3.50(2H, s), 4.20(4H, q, J=7.2 Hz), 4.82(2H, s), 7.06(1H, s), 7.15(1H, dd, J=2.1, 8.3 Hz), 7.28-7.63 (12H, m), 8.14(1H, d, J=8.3 Hz), 9.25(1H, brs) |

TABLE 33-continued

| Example | Structure | NMR (δ, 300 MHz, CDCl₃) |
|---|---|---|
| 2-80 | 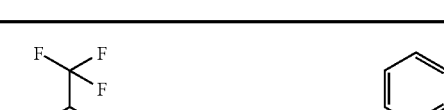<br>m.p. 128–130 | 1.21(6H, t, J=7.0 Hz), 2.83 (3H, brs), 3.00(3H, brs), 3.51(2H, s), 4.21(4H, q, J=7.0 Hz), 4.82(2H, s), 7.05(1H, d, J=2.2 Hz), 7.19 (1H, dd, J=2.2, 8.4 Hz), 7.25-7.65(12H, m), 8.27 (1H, d, J=8.4 Hz), 9.28 (1H, brs) |

TABLE 34

| Example | Structure | NMR (δ, 300 MHz, CDCl₃) |
|---|---|---|
| 2-81 | 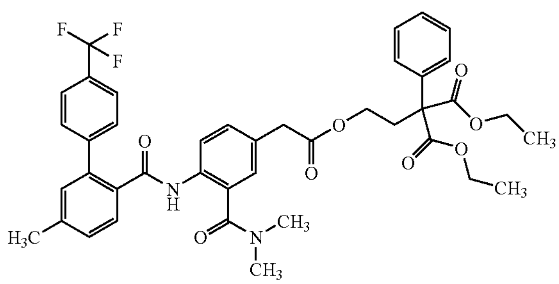 | 1.24(6H, t, J=7.2 Hz), 2.44 (3H, s), 2.61(3H, t, J=7.1 Hz), 2.86(3H, brs), 2.95 (3H, brs), 3.46(2H, s), 4.07 (2H, t, J=7.1 Hz), 4.23(4H, q, J=7.2 Hz), 4.82(2H, s), 7.07-7.63(14H, m), 8.37 (1H, d, J=8.7 Hz), 9.12 (1H, brs) |
| 2-82 | 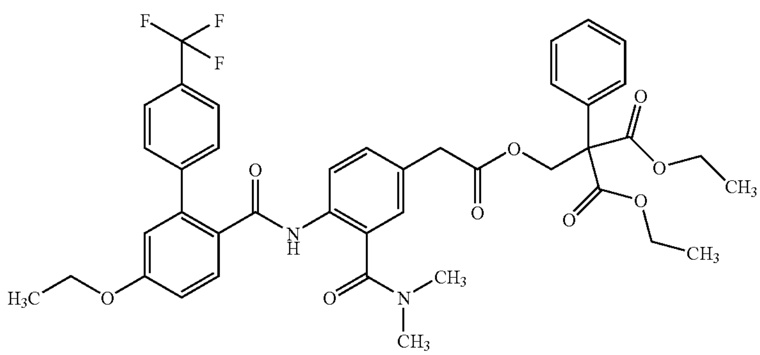 | 1.21(6H, t, J=7.1 Hz), 1.45 (3H, t, J=7.2 Hz), 2.81(3H, brs), 2.95(3H, brs), 3.50 (2H, s), 4.11(2H, q, J=7.2 Hz), 4.21(4H, q, J=7.1 Hz), 4.82(2H, s), 6.86(1H, d, J=2.6 Hz), 6.97(1H, dd, J=2.6, 8.7 Hz), 7.03(1H, d, J=1.9 Hz), 7.18(1H, dd, J=1.9, 8.7 Hz), 7.28-7.30(5H, m), 7.56-7.67(5H, m), 8.36 (1H, d, J=8.7 Hz), 9.17(1H, brs) |
| 2-83 | 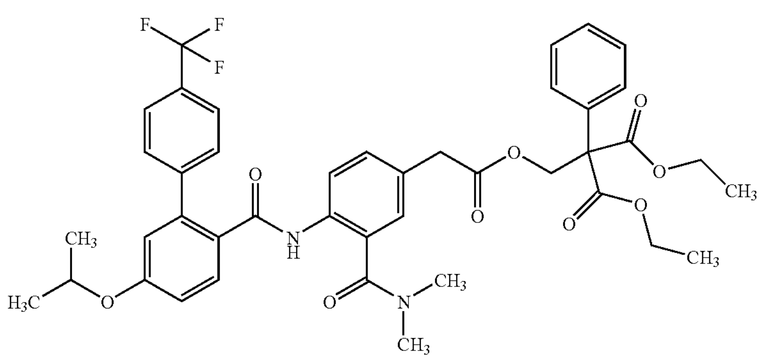 | 1.21(6H, t, J=7.2 Hz), 1.28 (6H, d, J=6.0 Hz), 2.81(3H, brs), 2.95(3H, brs), 4.21 (4H, q, J=7.2 Hz), 4.64(1H, sept, J=6.0 Hz), 4.82(2H, s), 6.85(1H, d, J=2.2 Hz), 6.96(1H, dd, J=2.6, 8.7 Hz), 7.03(1H, d, J=2.2 Hz), 7.18(1H, dd, J=8.7, 1.9 Hz), 7.28-7.30(5H, m), 7.56-7.66(5H, m), 8.36 (1H, d, J=8.3 Hz), 9.16 (1H, brs) |

TABLE 34-continued

| Example | Structure | NMR (δ, 300 MHz, CDCl₃) |
|---|---|---|
| 2-84 | 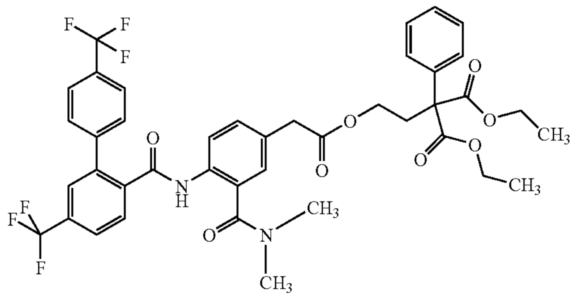 | 1.24(6H, t, J=7.2 Hz), 2.61 (2H, t, J=7.1 Hz), 2.89(3H, brs), 2.94(3H, brs), 3.47 (2H, s), 4.08(2H, t, J=7.1 Hz), 4.24(4H, q, J=7.2 Hz), 7.11-7.39(7H, m), 7.61-7.83(7H, m), 8.34(1H, d, J=8.7 Hz), 9.36(1H, brs) |
| 2-85 | m.p. 107–109 | 1.20(6H, t, J=7.2 Hz), 2.81 (3H, brs), 3.02(3H, brs), 3.49(2H, s), 3.78(3H, s), 4.20(4H, q, J=7.2 Hz), 4.81 (2H, s), 7.02(1H, d, J=1.9 Hz), 7.07(1H, d, J=8.3 Hz), 7.15(1H, dd, J=2.3, 8.7 Hz), 7.24-7.30(6H, m), 7.41-7.60(5H, m), 8.22 (1H, d, J=8.7 Hz), 9.05 (1H, brs) |

TABLE 35

| Example | Structure | NMR (δ, 300 MHz, CDCl₃) |
|---|---|---|
| 2-86 | m.p. 125–129 | 1.21(6H, t, J=7.2 Hz), 2.48 (3H, s), 2.69(3H, brs), 2.91 (3H, brs), 3.50(2H, s), 4.21 (4H, q, J=7.2 Hz), 4.82 (2H, s), 6.99(1H, d, J=2.2 Hz), 7.20(1H, dd, J=1.5, 8.3 Hz), 7.28-7.41(8H, m), 7.57-7.64(4H, m), 8.18 (1H, d, J=8.6 Hz), 8.81 (1H, brs) |
| 2-87 | 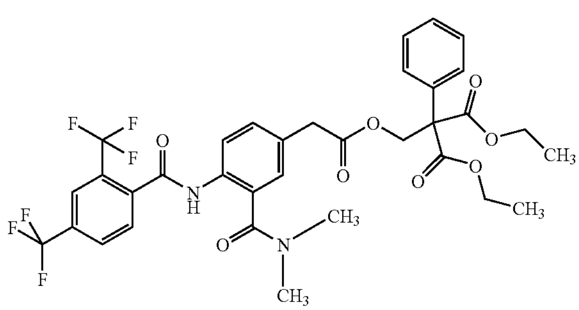 | 1.23(6H, t, J=7.2 Hz), 3.00 (3H, brs), 3.03(3H, brs), 3.58(2H, s), 4.22(4H, q, J= 7.2 Hz), 4.85(2H, s), 7.18 (1H, d, J=1.9 Hz), 7.28-7.33(6H, m), 7.79(1H, d, J=7.9 Hz), 7.92(1H, d, J= 7.9 Hz), 7.99(1H, s), 8.35 (1H, d, J=8.3 Hz), 9.46 (1H, s) |

TABLE 35-continued

| Example | Structure | NMR (δ, 300 MHz, CDCl₃) |
|---|---|---|
| 2-88 | m.p. 129–131 | 1.21(6H, t, J=7.2 Hz), 2.33 (3H, s), 2.76(3H, brs), 2.93 (3H, brs), 3.50(2H, s), 4.21 (4H, q, J=7.2 Hz), 4.82 (2H, s), 6.99(1H, d, J=1.2 Hz), 7.14-7.51(13H, m), 7.65(1H, d, J=7.6 Hz), 8.34 (1H, d, J=8.6 Hz), 8.78 (1H, brs) |
| 2-89 | m.p. 81–82 | 1.24(6H, t, J=7.2 Hz), 1.29 (3H, t, J=7.6 Hz), 2.92(2H, q, J=7.6 Hz), 3.03(6H, brs), 3.57(2H, s), 4.23(4H, q, J=7.2 Hz), 4.85(2H, s), 7.18(1H, d, J=2.3 Hz), 7.27-7.33(6H, m), 7.51-7.60(3H, m), 8.40 (1H, d, J=8.2 Hz), 9.51 (1H, brs) |
| 2-90 | m.p. 110–112 | 1.21(6H, t, J=7.1 Hz), 1.22 (3H, t, J=6.9 Hz), 2.64(H, q, J=6.9 Hz), 2.75(3H, brs), 2.93(3H, brs), 3.50(2H, s), 4.21(4H, q, J=7.1 Hz), 4.82 (2H, s), 6.99(1H, d, J=1.8 Hz), 7.17-7.66(14H, m), 8.30(1H, d, J=8.3 Hz), 8.76 (1H, brs) |

TABLE 36

| Example | Structure | NMR (δ, 300 MHz, CDCl₃) |
|---|---|---|
| 2-91 | 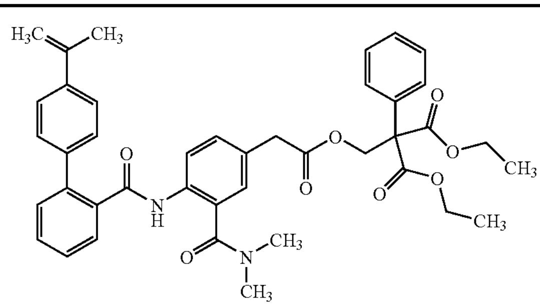 | 1.21(6H, t, J=7.1 Hz), 2.13 (3H, s), 2.71(3H, brs), 2.89 (3H, brs), 3.49(2H, s), 4.20 (4H, q, J=7.1 Hz), 4.82 (2H, s), 5.10(1H, s), 5.43 (1H, s), 6.98(1H, d, J=2.2 Hz), 7.19(1H, dd, J=1.9, 8.3 Hz), 7.28-7.53(12H, m), 7.67(1H, d, J=7.6 Hz), 8.39(1H, d, J=8.6 Hz), 8.87 (1H, brs) |

TABLE 36-continued
| Example | Structure | NMR (δ, 300 MHz, CDCl$_3$) |
|---|---|---|
| 2-92 | 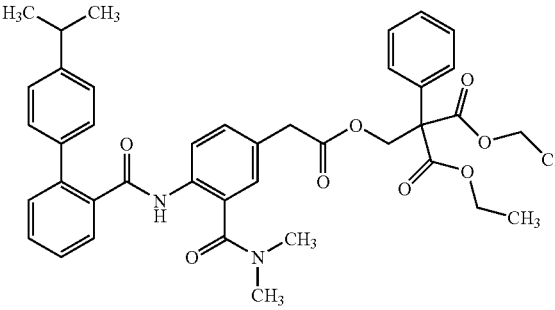 m.p. 107–110 | 1.21(6H, t, J=7.1 Hz), 1.21 (6H, t, J=7.1 Hz), 2.76(3H, brs), 2.89(1H, sept, J=7.1 Hz), 2.94(3H, brs), 3.50 (2H, s), 4.21(4H, q, J=7.1 Hz), 4.82(2H, s), 7.01(1H, d, J=1.9 Hz), 7.14-7.51 (13H, m), 7.62(1H, d, J=6.4 Hz), 8.21(1H, d, J=8.3 Hz), 8.70(1H, brs) |
| 2-93 | 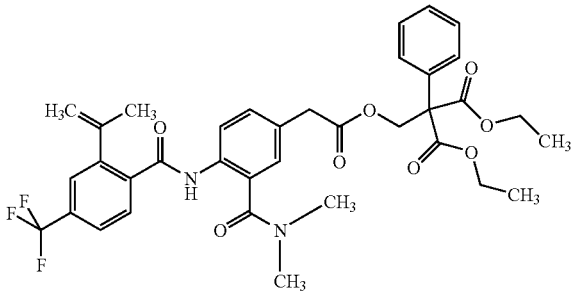 | 1.23(6H, t, J=7.2 Hz), 2.12 (3H, s), 2.99(3H, brs), 3.04 (3H, brs), 3.56(2H, s), 4.23 (4H, q, J=7.2 Hz), 4.85 (2H, s), 5.15(1H, s), 5.23 (1H, s), 7.15(1H, d, J=1.8 Hz), 7.25-7.31(6H, m), 7.55(1H, s), 7.61(1H, d, J=7.9 Hz), 7.73(1H, d, J=7.9 Hz), 8.36(1H, d, J=8.3 Hz), 9.35(1H, m) |
| 2-94 | 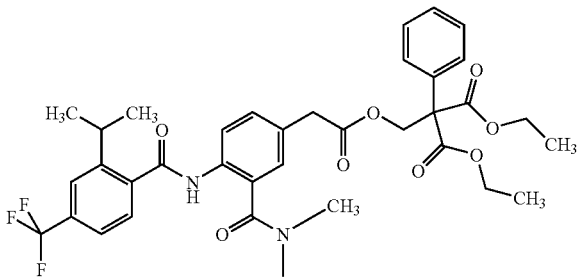 | 1.24(6H, t, J=7.2 Hz), 1.29 (6H, t, J=6.8 Hz), 3.03(6H, brs), 3.44(1H, sept, J=6.8 Hz), 3.57(2H, s), 4.23 (4H, q, J=7.2 Hz), 4.85 (2H, s), 7.18(1H, d, J=1.9 Hz), 7.26-7.33(6H, m), 7.52(2H, s), 7.63(1H, s), 8.41(1H, d, J=8.3 Hz), 9.44 (1H, brs) |
| 2-95 | 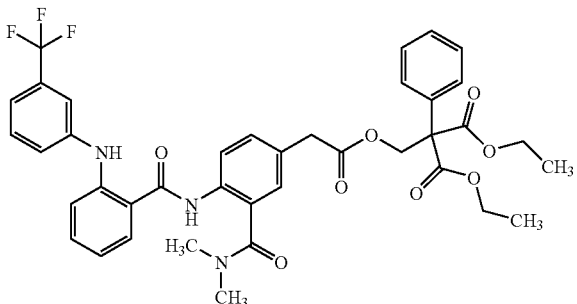 | 1.23(6H, t, J=7.1 Hz), 3.01 (3H, brs), 3.10(3H, brs), 3.57 (2H, s), 4.23(4H, q, J=7.1 Hz), 4.85(2H, s), 6.91-6.96(1H, m), 7.20-7.41 (12H, m), 7.46(1H, s), 7.66 (1H, d, J=7.7 Hz), 8.29 (1H, d, J=8.3 Hz), 9.78 (1H, s), 10.17(1H, brs) |

TABLE 37
| Example | Structure | NMR (δ, 300 MHz, CDCl₃) |
|---|---|---|
| 2-96 | 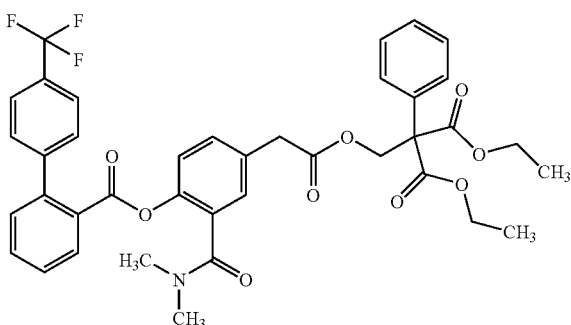 | 1.21(6H, t, J=7.1 Hz), 2.75 (3H, brs), 3.02(3H, brs), 3.55(2H, s), 4.20(4H, q, J= 7.1 Hz), 4.84(2H, s), 6.92 (1H, d, J=8.3 Hz), 7.15-7.68(14H, m), 8.07(1H, dd, J=1.3, 7.7 Hz) |
| 2-97 | 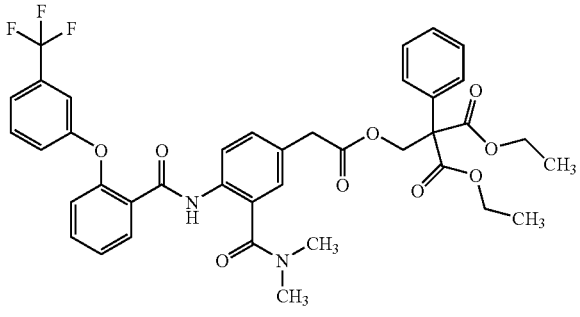 | 1.22(6H, t, J=7.1 Hz), 2.83 (3H, brs), 2.86(3H, brs), 3.53(2H, s), 4.21(4H, q, J= 7.1 Hz), 4.83(2H, s), 6.85 (1H, d, J=7.7 Hz), 7.07 (1H, d, J=2.0 Hz), 7.20-7.52(12H, m), 8.25(1H, dd, J=1.8, 7.9 Hz), 8.41(1H, d, J=8.5 Hz), 10.48(1H, brs) |
| 2-98 | 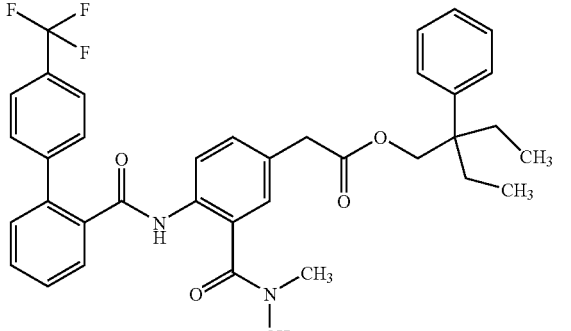 | 0.65(6H, t, J=7.4 Hz), 1.69 (4H, q, J=7.4 Hz), 2.81 (3H, brs), 2.94(3H, brs), 3.50(2H, s), 4.30(2H, s), 7.02(1H, d, J=1.8 Hz), 7.18-7.62(13H, m), 7.70 (1H, d, J=7.3 Hz), 8.35(1H, d, J=8.5 Hz), 9.15(1H, brs) |
| 2-99 | 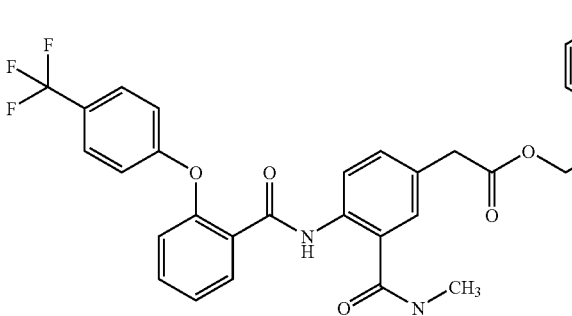 | 1.21(6H, t, J=7.1 Hz), 2.87 (6H, brs), 3.53(2H, s), 4.21 (4H, q, J=7.1 Hz), 4.83 (2H, s), 6.92(1H, d, J=7.6 Hz), 7.08(1H, d, J=2.1 Hz), 7.20-7.48(10H, m), 7.63 (2H, d, J=8.7 Hz), 8.23 (1H, dd, J=1.7, 7.9 Hz), 8.35(1H, d, J=8.5 Hz), 10.38(1H, brs) |

TABLE 37-continued

| Example | Structure | NMR (δ, 300 MHz, CDCl₃) |
|---|---|---|
| 2-100 | 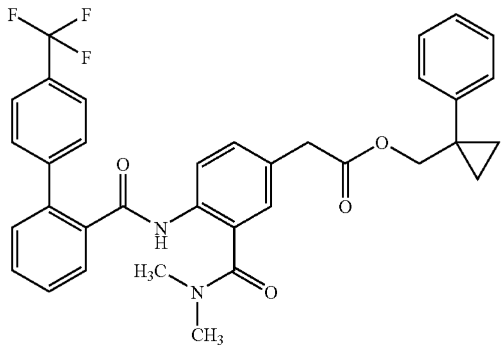 | 0.85-0.93(4H, m), 2.78 (3H, brs), 2.93(3H, brs), 3.52(2H, s), 4.16(2H, s), 7.04(1H, d, J=2.1 Hz), 7.17-7.61(13H, m), 7.70 (1H, dd, J=1.5, 7.2 Hz), 8.35(1H, d, J=9.0 Hz), 9.15 (1H, brs) |

TABLE 38

| Example | Structure | NMR (δ, 300 MHz, CDCl₃) |
|---|---|---|
| 2-101 | 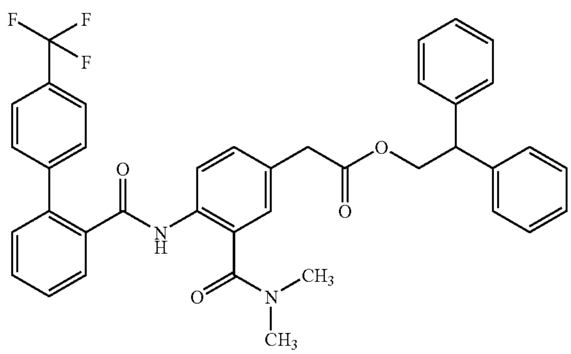 | 2.79(3H, brs), 2.94(3H, brs), 3.45(2H, s), 4.31(1H, t, J=7.6 Hz), 4.62(2H, d, J=7.6 Hz), 6.96(1H, d, J=2.0 Hz), 7.15-7.69 (19H, m), 8.30(1H, d, J= 8.5 Hz), 9.15(1H, brs) |
| 2-102 | mp. 103.0–109.0 | 1.62-1.76(4H, m), 1.82-1.99(4H, m), 2.78 (3H, brs), 2.93(3H, brs), 3.44(2H, s), 4.08(2H, s), 6.97(1H, d, J=2.0 Hz), 7.09-7.26(6H, m), 7.35-7.72(8H, m), 8.34(1H, d, J=8.5 Hz), 9.15(1H, brs) |
| 2-103 | 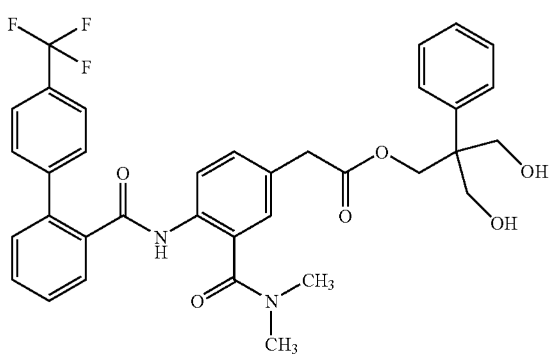 | 2.40(1H, t, J=5.7 Hz), 2.42(1H, t, J=6.3 Hz), 3.53 (2H, s), 2.80(3H, brs), 2.93(3H, brs), 3.82(2H, dd, J=6.3, 11.4 Hz), 3.96 (2H, dd, J=5.7, 11.4 Hz), 4.58(2H, s), 7.01(1H, d, J=1.8 Hz), 7.14-7.71(14H, m), 8.29(1H, d, J=8.4 Hz), 9.05(1H, brs) |

TABLE 38-continued
| Example | Structure | NMR (δ, 300 MHz, CDCl₃) |
|---|---|---|
| 2-104 | 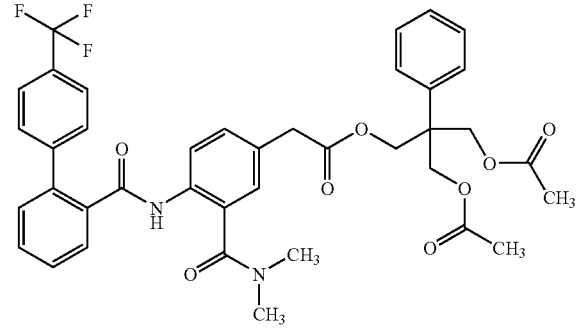 | 1.98(6H, s), 2.83(3H, brs), 2.93(3H, brs), 3.49(2H, s), 4.40(4H, s), 4.44(2H, s), 7.00(1H, d, J=2.2 Hz), 7.15 (1H, dd, J=2.2, 8.4 Hz), 7.22-7.65(12H, m), 7.70 (1H, dd, J=1.9, 7.0 Hz), 8.32(1H, d, J=8.4 Hz), 9.13 (1H, brs) |
| 2-105 | 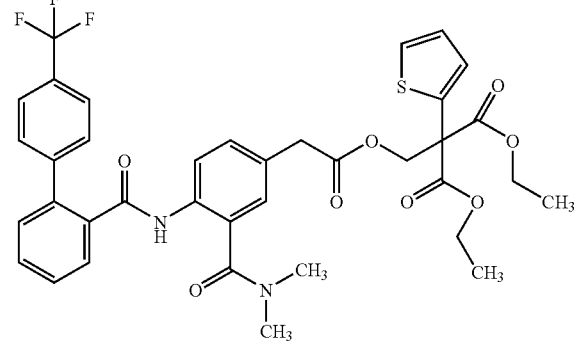<br>mp 98.8–103.3 | 1.23(6H, t, J=7.1 Hz), 2.83(3H, brs), 2.94(3H, brs), 3.51(2H, s), 4.22(4H, q, J=7.1 Hz), 4.82(2H, s), 6.94-7.04(3H, m), 7.16-7.71(10H, m), 8.34 (1H, d, J=8.5 Hz), 9.17 (1H, brs) |
TABLE 39
| Example | Structure | NMR (δ, 300 MHz, CDCl₃) |
|---|---|---|
| 2-106 | 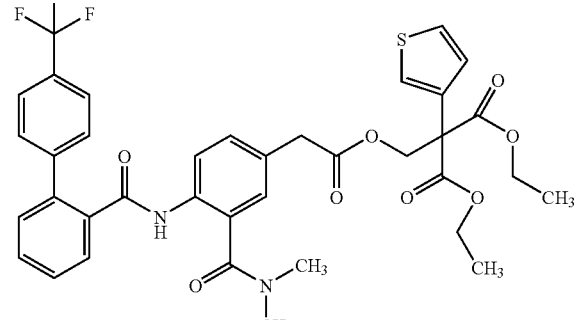<br>mp. 116.1–121.6 | 1.22(6H, t, J=7.1 Hz), 2.81 (3H, brs), 2.93(3H, brs), 3.50(2H, s), 4.20(4H, q, J= 7.1 Hz), 4.79(2H, s), 7.01-7.04(2H, m), 7.25-7.71 (11H, m), 8.35(1H, d, J= 8.5 Hz), 9.17(1H, brs) |

TABLE 39-continued

| Example | Structure | NMR (δ, 300 MHz, CDCl₃) |
|---|---|---|
| 2-107 | 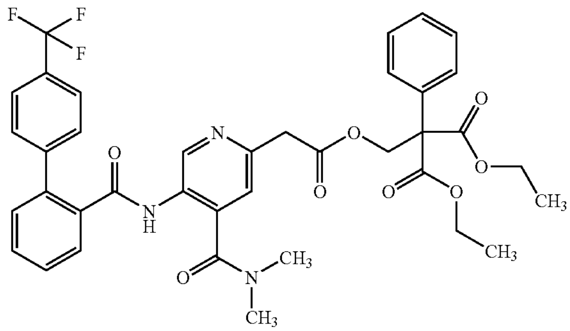 | 1.25(6H, t, J=7.1 Hz), 2.75 (3H, brs), 2.92(3H, brs), 3.78(2H, s), 4.22(4H, q, J=7.1 Hz), 4.85(2H, s), 6.98 (1H, s), 7.28-7.72(13H, m), 8.71(1H, s), 9.52(1H, brs) |
| 2-108 | 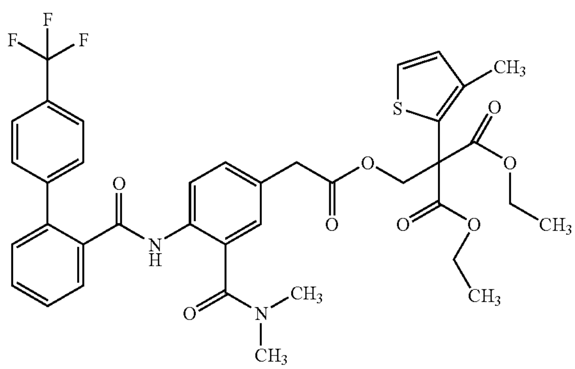 | 1.22(6H, t, J=7.2 Hz), 2.13 (3H, s), 2.85(3H, brs), 2.93 (3H, brs), 3.50(2H, s), 4.16-4.26(4H, m), 4.80 (2H, s), 6.78(1H, d, J=5.1 Hz), 7.05(1H, d, J=2.2 Hz), 7.15(1H, d, J=5.2 Hz), 7.16-7.64(8H, m), 7.69 (1H, d, J=1.5, 7.3 Hz), 8.33 (1H, d, J=8.5 Hz), 9.16 (1H, brs) |
| 2-109 | mp. 104.6–108.3 | 1.22(6H, t, J=7.2 Hz), 2.44 (3H, s), 2.84(3H, brs), 2.94 (3H, brs), 3.52(2H, s), 4.20(4H, q, J=7.2 Hz), 4.78 (2H, s), 6.58(1H, dd, J=1.2, 3.5 Hz), 6.76(1H, d, J=3.5 Hz), 7.04(1H, d, J=2.0 Hz), 7.20(1H, dd, J=2.1, 8.6 Hz), 7.37-7.62(7H, m), 7.68(1H, dd, J=1.4, 7.6 Hz), 8.33(1H, d, J=8.4 Hz), 9.17(1H, brs) |
| 2-110 | mp. 121.5–124.7 | 1.22(6H, t, J=7.1 Hz), 2.85 (3H, brs), 2.94(3H, brs), 3.46(2H, s), 4.23(4H, q, J=7.1 Hz), 4.97(2H, s), 7.00 (1H, d, J=2.2 Hz), 7.13-7.16(1H, m), 7.36(1H, d, J=3.3 Hz), 7.38-7.71(8H, m), 7.75(1H, d, J=3.3 Hz), 8.31(1H, d, J=8.5 Hz), 9.16 (1H, brs) |

TABLE 40

| Example | Structure | NMR (δ, 300 MHz, CDCl₃) |
|---|---|---|
| 2-111 | mp 96–98 | 0.97(6H, d, J=7.2 Hz), 1.21 (6H, t, J=7.2 Hz), 2.45(1H, sep. J=7.2 Hz), 2.88(3H, brs), 2.94(2H, brs), 3.52 (2H, s), 4.15(4H, q, J= 7.2 Hz), 4.50(2H, s), 7.09 (1H, d, J=2.3 Hz), 7.20-7.72(9H, m), 8.34(1H, d, J=8.3 Hz), 9.15(1H, brs). |
| 2-112 | mp 100–104.5 | 0.90(3H, t, J=7.2 Hz), 0.92 (3H, t, J=6.5 Hz), 0.95-1.10(1H, m), 1.21(3H, t, J= 7.2 Hz), 1.48-1.62(1H, m), 2.05-2.16(1H, m), 2.88 (3H, brs), 2.94(3H, brs), 3.52(2H, s), 4.14(4H, q, J= 7.2 Hz), 4.51(2H, s), 7.09 (1H, d, J=1.9 Hz), 7.21-7.72(9H, m), 8.36(1H, d, J=8.3 Hz), 9.16(1H, brs). |
| 2-113 | mp 106–109.5 | 0.83(6H, d, J=6.4 Hz), 1.21 (6H, t, J=7.2 Hz), 1.51-1.65(1H, m), 1.88(2H, d, J= 6.4 Hz), 2.88(3H, brs), 2.94 (3H, brs), 3.53(2H, s), 4.15 (4H, q, J=7.2 Hz), 4.52(2H, s), 7.08(1H, d, J=2.3 Hz), 7.22-7.71(9H, m), 8.37(1H, d, J=8.3 Hz), 9.16 (1H, brs). |
| 2-114 | mp 98–99.5 | 0.88(3H, t, J=7.2 Hz), 1.09-1.31(2H, m), 1.21 (6H, t, J=7.2 Hz), 1.79-1.93(2H, m), 2.89(3H, brs), 2.94(3H, brs), 3.53(2H, s), 4.15(4H, q, J=7.2 Hz), 4.49(2H, s), 7.09(1H, brs), 7.21-7.74(9H, m), 8.37 (1H, d, J=8.3 Hz), 9.15 (1H, brs). |

TABLE 40-continued

| Example | Structure | NMR (δ, 300 MHz, CDCl₃) |
|---|---|---|
| 2-115 | mp 86.5–90.0 | 0.83(3H, t, J=7.5 Hz), 1.21 (6H, t, J=7.2 Hz), 1.96(2H, q, J=7.5 Hz), 2.88(3H, brs), 2.94(3H, brs), 3.53 (2H, s), 4.16(4H, q, J= 7.2 Hz), 4.50(2H, s), 7.08 (1H, d, J=1.9 Hz), 7.21-7.74(9H, m), 8.36(1H, d, J=8.7 Hz), 9.15(1H, brs). |

TABLE 41

| Example | Structure | NMR (δ, 300 MHz, CDCl₃) |
|---|---|---|
| 2-116 | mp 97.5-98.0 | 0.86(3H, t, J=7.2 Hz), 1.06-1.36(4H, m), 1.21 (6H, t, J=7.2 Hz), 1.84-1.94(2H, m), 2.88(3H, brs), 2.94(3H, brs), 3.53(2H, s), 4.15(4H, q, J=7.2 Hz), 4.49 (2H, s), 7.08(1H, d, J=2.3 Hz), 7.21-7.71(9H, m), 8.37(1H, d, J=8.6 Hz), 9.16(1H, brs). |
| 2-117 | mp 76.9-82.0 | 1.21(6H, t, J=7.1 Hz), 2.67(2H, d, J=7.4 Hz), 2.87 (3H, brs), 2.95(3H, brs), 3.54(2H, s), 4.10-4.20(4H, m), 4.47(2H, s), 5.00-5.10(2H, m), 5.56-5.67 (1H, m), 7.09(1H, d, J= 2.1 Hz), 7.24(1H, d, J=2.0 Hz), 7.38-7.68(7H, m), 7.70(1H, d, J=1.4 Hz), 8.37(1H, d, J=8.4 Hz), 9.14(1H, brs) |

TABLE 41-continued

| Example | Structure | NMR (δ, 300 MHz, CDCl₃) |
|---|---|---|
| 2-118 | 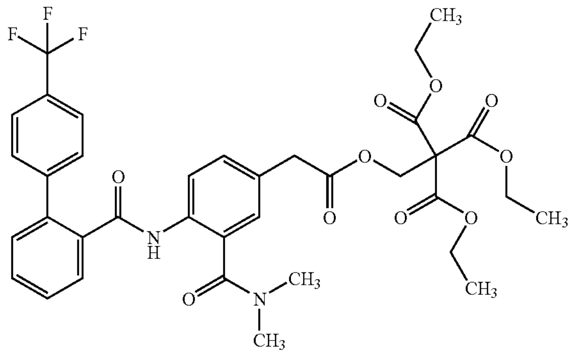 | 1.25(9H, t, J=7.2 Hz), 2.89(3H, brs), 2.95(3H, brs), 3.56(2H, s), 4.23(6H, q, J=7.2 Hz), 4.70(2H, s), 7.11(1H, d, J=1.8 Hz), 7.24(1H, d, J=2.2 Hz), 7.28-7.70(8H, m), 8.36 (1H, d, J=8.8 Hz), 9.16 (1H, brs) |
| 2-119 | mp. 72.3-78.6 | 0.87(3H, t, J=7.2 Hz), 0.92(3H, t, J=6.8 Hz), 1.00-1.16(2H, m), 1.20 (6H, t, J=7.1 Hz), 1.38-1.53(2H, m), 2.18-2.23 (1H, m), 2.88(3H, brs), 2.95(3H, brs), 3.52(2H, s), 4.08-4.18(4H, m), 4.50(2H, d, J=2.1 Hz), 7.08(1H, d, J=1.9 Hz), 7.22-7.69(9H, m), 8.35 (1H, d, J=8.6 Hz), 9.15 (1H, brs) |

Example 3

2-(2-{3-Ethoxy-4-[(4'-trifluoromethylbiphenyl-2-carbonyl)amino]phenyl}acetoxymethyl)-2-phenyl-malonic acid diethyl ester a) 3-Ethoxy-4-nitrobenzoic acid methyl ester To a suspension of sodium hydride (60% mineral oil: 1.20 g) in dimethylformamide (50 mL) was added 3-hydroxy-4-nitrobenzoic acid methyl ester (4.93 g) under ice-cooling, and the mixture was stirred at room temperature for 30 minutes. After addition of ethyl iodide (4.4 g), the solution was stirred at 60° C. overnight, cooled down to room temperature, poured into saturated aqueous ammonium chloride, and extracted with ethyl acetate-tetrahydrofuran. The organic layer was washed with saturated aqueous ammonium chloride and saturated brine, dried over sodium sulfate and concentrated to give a solid, which was washed with ethyl acetate-hexane to afford 3-ethoxy-4-nitrobenzoic acid methyl ester (3.30 g) as a pale yellow solid.

b) 3-Ethoxy-4-nitrobenzoic acid chloride

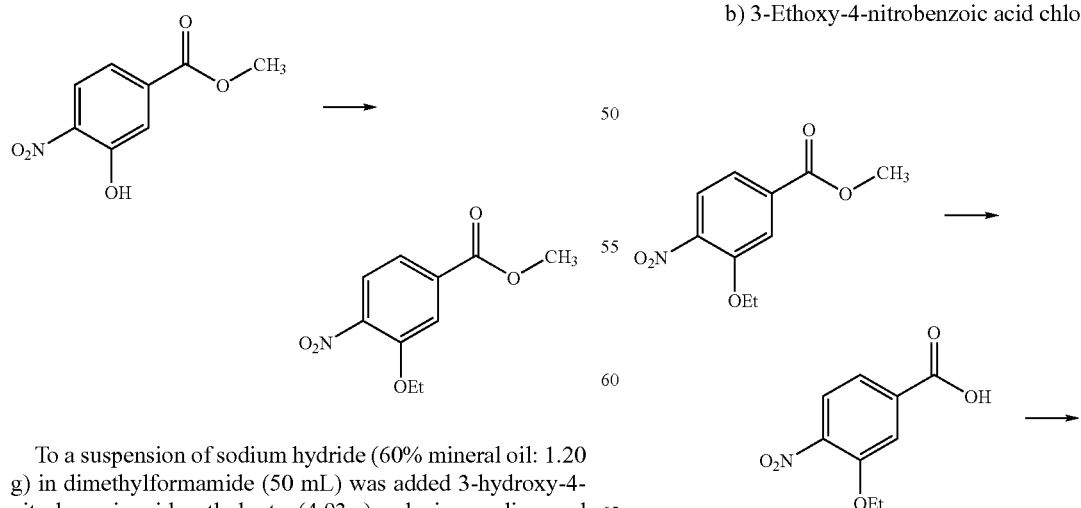

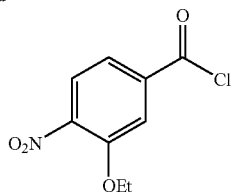

3-Ethoxy-4-nitrobenzoic acid chloride was obtained in a similar manner to Example 1f) and Example 1d) from the 3-ethoxy-4-nitrobenzoic acid methyl ester obtained in Example 3a).

c) 2'-Diazo-3-ethoxy-4-nitroacetophenone

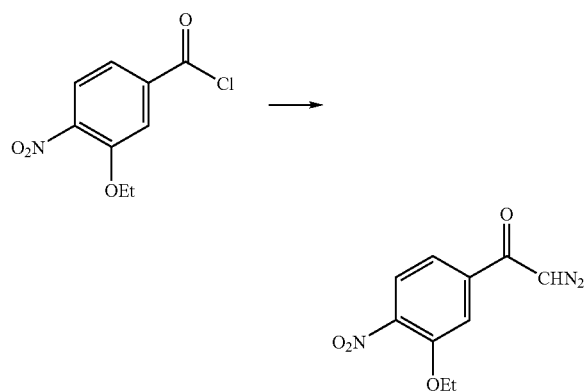

A solution of the 3-ethoxy-4-nitrobenzoic acid chloride (2.06 g) obtained in Example 3b) in diethyl ether (30 mL) was added dropwise to a mixture of diazomethane in diethyl ether (0.35M, 64 mL) and triethylamine (3.12 mL) under ice-cooling. The mixture was stirred for 2 hours under ice-cooling and the temperature was raised to room temperature, followed by stirring overnight. After addition of acetic acid (1 mL), the mixture was stirred at room temperature for one hour and evaporated to remove the solvent. The residue was purified by column chromatography on silica gel with hexane:ethyl acetate=5:2 to give the title compound (1.80 g) as a yellow solid.

d) 3-Ethoxy-4-nitrophenylacetic acid ethyl ester

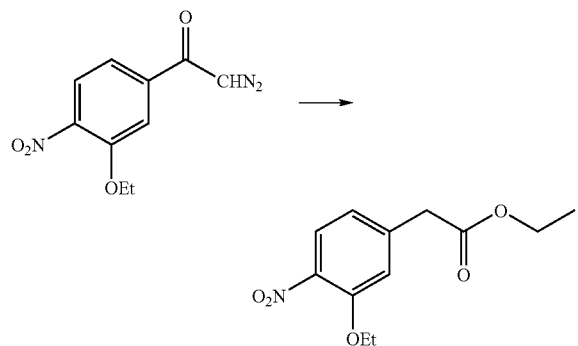

A solution of silver benzoate (270 mg) in triethylamine (2.7 ml) was added dropwise in 10 divided doses to a solution of the 2'-diazo-3-ethoxy-4-nitroacetophenone (1.80 g) obtained in Example 3c) in ethanol (25 mL) under reflux. The mixture was refluxed for 9 hours and the reaction solution was filtered through a Celite pad. The filtrate was concentrated, and the concentrate was diluted with diethyl ether and washed with 10% aqueous sodium carbonate, water and saturated brine. The organic layer was dried over sodium sulfate and purified by column chromatography on silica gel with hexane:ethyl acetate=4:1 to give the title compound (1.27 g) as a yellow solid.

e) 4-Amino-3-ethoxyphenylacetic acid ethyl ester

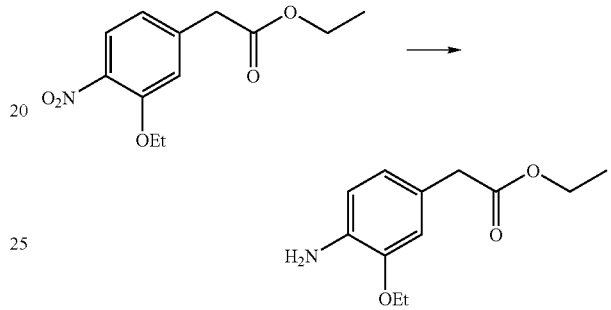

The 3-ethoxy-4-nitrophenyl-acetic acid ethyl ester (1.27 g) obtained in Example 3d) was subjected to reactions similar to those in Example 1-3d) to give the title compound (1.12 g) as a brown oil.

f) 2-(2-{3-Ethoxy-4-[(4'-trifluoromethylbiphenyl-2-carbonyl)amino]phenyl}acetoxymethyl)-2-phenyl-malonic acid diethyl ester

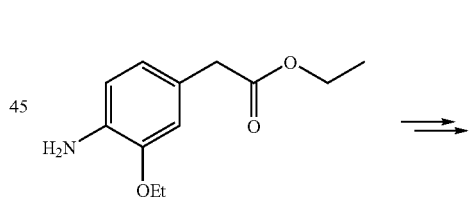

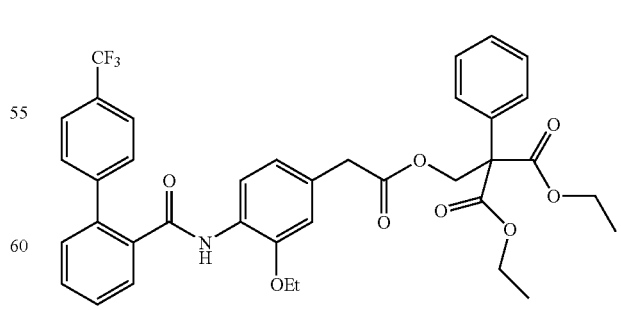

The 4-amino-3-ethoxyphenylacetic acid ethyl ester obtained in Example 3e) and the 2-hydroxymethyl-2-phenyl malonic acid diethyl ester obtained in Example 1-2a) were subjected to reactions similar to those in Examples 1e), 1f) and 1 g) to give the title compound (0.159 g) (see Table 42).

Example 3-2

{3-Hydroxy-4-[(4'-trifluoromethylbiphenyl-2-carbonyl)amino]phenyl}acetic acid 2,2-bisethylcarbamoyl-2-phenylethyl ester

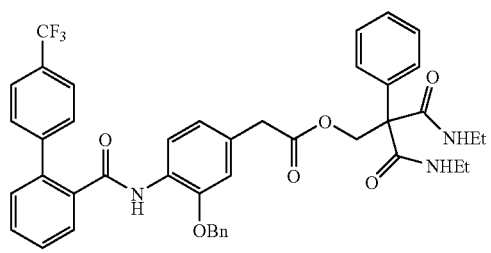

-continued

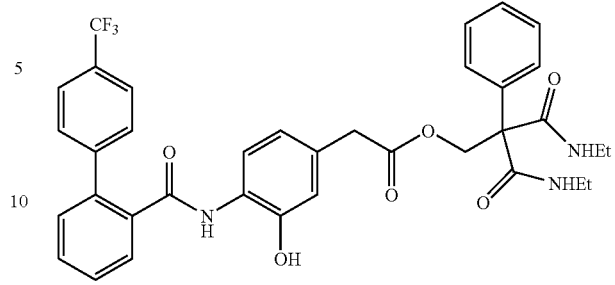

{3-Benzyloxy-4-[(4'-trifluoromethylbiphenyl-2-carbonyl)amino]phenyl}acetic acid 2,2-bisethylcarbamoyl-2-phenylethyl ester (300 mg) obtained in a similar manner to Example 3, except that reduction of the nitro group was carried out with iron dust, was subjected to reactions in a similar manner to Example 1-2c) to give the title compound (244 mg) (See Table 42).

Examples 3-3 to 3-16

Compounds of Examples 3-3 to 3-16 were obtained in a similar manner to Examples 3 to 3-2. The compounds thus obtained were shown in Tables 42 to 45.

TABLE 42

| Example | Structure | NMR (δ, 300 MHz, CDCl$_3$) |
|---|---|---|
| 3 | 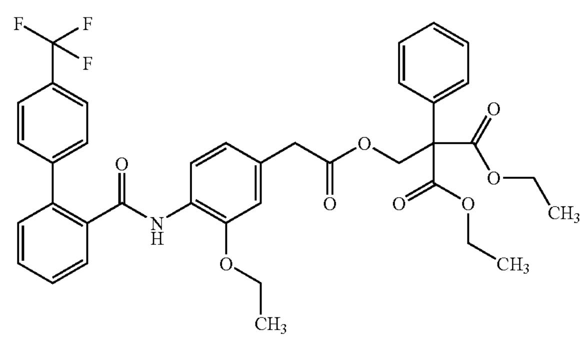 | 1.19(6H, t, J=7.1 Hz), 1.20(3H, t, J=7.1 Hz), 3.49(2H, s), 3.77(2H, q, J=7.1 Hz), 4.18(4H, q, J=7.1 Hz), 4.83(2H, s), 6.59(1H, d, J=1.5 Hz), 6.75(1H, dd, J=1.5, 8.2 Hz), 7.25-7.33(5H, m), 7.44(1H, dd, J=1.5, 7.2 Hz), 7.49-7.66(6H, m), 7.70-7.76(1H, m), 7.80 (1H, dd, J=1.5, 7.2 Hz), 8.35(1H, d, J=8.0 Hz) |
| 3-2 | 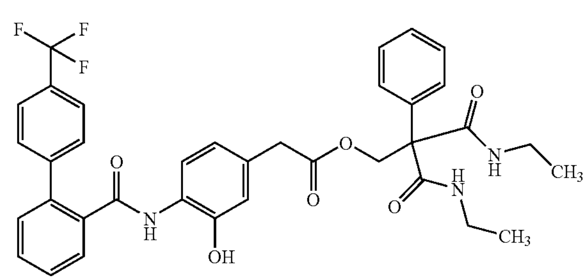 | 1.05(6H, t, J=7.2 Hz), 3.23 (4H, dq, J=7.2, 7.2 Hz), 3.48(2H, s), 4.83(2H, s), 6.48(1H, d, J=7.9 Hz), 6.55(1H, dd, J=7.9, 1.9 Hz), 6.77(1H, d, J=1.5 Hz), 7.17-7.86(15H, m), 8.58(1H, s) |

TABLE 42-continued

| Example | Structure | NMR (δ, 300 MHz, CDCl₃) |
|---|---|---|
| 3-3 | m.p. 112-114 | 1.05(6H, t, J=7.2 Hz), 3.23 (4H, dq, J=7.2, 7.2 Hz), 3.53(2H, s), 3.55(3H, s), 4.83(2H, s), 6.60(1H, s), 6.73(1H, d, J=7.9 Hz), 7.10-7.66(15H, m), 7.85(1H, dd, J=7.5, 1.5 Hz), 8.33(1H, d, J=7.9 Hz) |
| 3-4 | 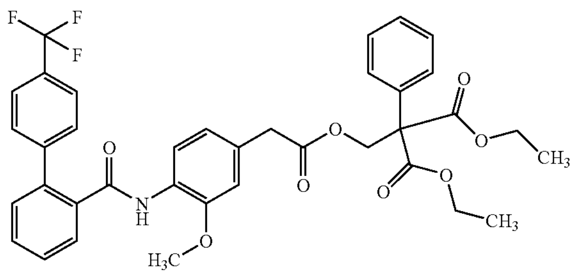 | 1.19(6H, t, J=6.9 Hz), 3.50 (5H, s), 4.17(4H, q, J=6.9 Hz), 4.83(2H, s), 6.58(1H, s), 6.75(1H, d, J=6.9 Hz), 7.26-7.65(13H, m), 7.85(1H, d, J=7.3 Hz), 8.31(1H, d, J=8.1 Hz) |
| 3-5 | 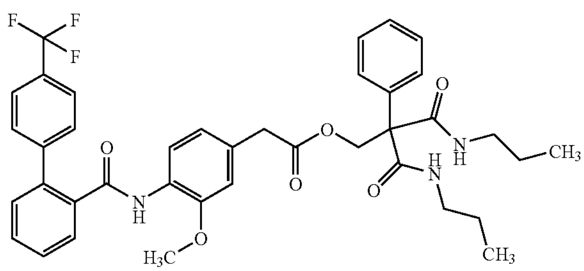 | 0.84(6H, t, J=7.2 Hz), 1.43(4H, tq, J=7.2, 7.2 Hz), 3.16(4H, m), 3.52(2H, s), 3.55(3H, s), 4.83(2H, s), 6.60(1H, br.s), 6.72(1H, dd, J=8.3, 1.5 Hz), 7.12-7.66(15H, m), 7.84(1H, dd, J=7.9, 1.9 Hz), 8.33(1H, d, J=7.9 Hz) |

TABLE 43

| Example | Structure | NMR (δ, 300 MHz, CDCl₃) |
|---|---|---|
| 3-6 | 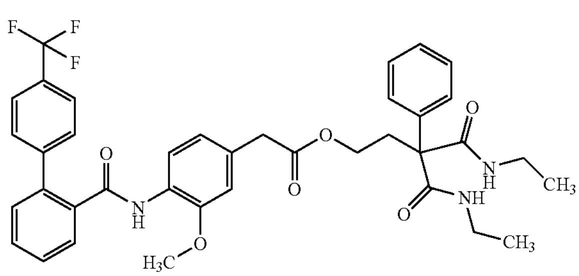 | 1.13(6H, t, J=7.2 Hz), 2.55 (2H, t, J=8.0 Hz), 3.30(4H, dq, J=7.2, 7.2 Hz), 3.53 (2H, s), 3.57(3H, s), 4.12 (2H, t, J=8.0 Hz), 6.67(1H, br.s), 6.82(1H, dd, J=8.3, 1.9 Hz), 7.26-7.66(15H, m), 7.84(1H, dd, J=7.9, 1.9 Hz), 8.33(1H, d, J=7.9 Hz) |

TABLE 43-continued

| Example | Structure | NMR (δ, 300 MHz, CDCl$_3$) |
|---|---|---|
| 3-7 | 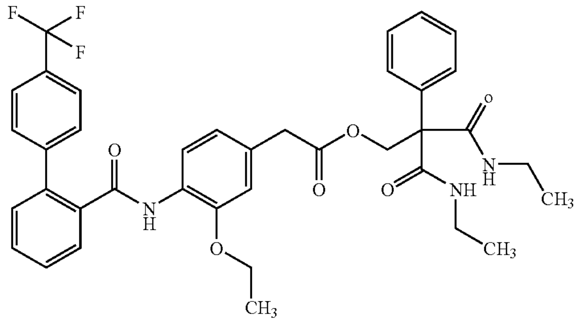 | 1.05(6H, t, J=7.2 Hz), 1.24 (3H, t, J=7.1 Hz), 3.17-3.29(4H, m), 3.52(2H, s), 3.83(2H, q, J=7.1 Hz), 4.82 (2H, s), 6.60(1H, d, J=1.5 Hz), 6.69-6.76(1H, m), 7.04-7.14(2H, m), 7.15-7.22(2H, m), 7.25-7.34 (3H, m), 7.41-7.47(1H, m), 7.49-7.66(6H, m), 7.73 (1H, br-s), 7.77-7.83(1H, m), 8.37(1H, d, J=8.3 Hz) |
| 3-8 | 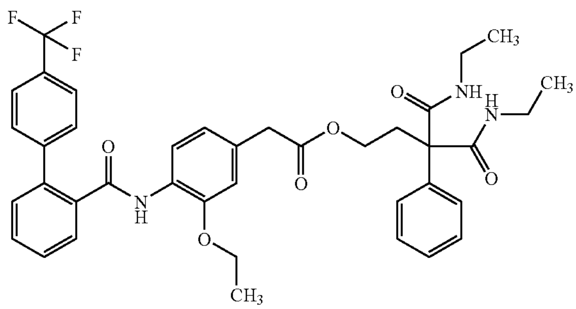 | 1.13(6H, t, J=7.2 Hz), 1.24 (3H, t, J=7.1 hz), 2.49-2.59(2H, m), 3.31(4H, dq, J=5.3, 7.2 Hz), 3.52(2H, s), 3.87(2H, q, J=7.1 Hz), 4.07-4.17(2H, m), 6.68 (1H, d, J=1.5 Hz), 6.78-6.84(1H, m), 7.23-7.37 (5H, m), 7.41-7.47(1H, m), 7.48-7.66(8H, m), 7.73 (1H, s), 7.76-7.82(1H, m), 8.37(1H, d, J=8.3 Hz) |
| 3-9 | 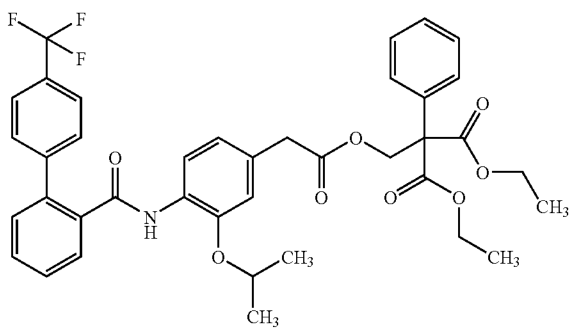 | 1.10(6H, d, J=6.0 Hz), 1.19 (6H, t, J=7.2 Hz), 3.48(2H, s), 4.19(4H, q, J=7.2 Hz), 4.36(1H, sept, J=6.0 Hz), 4.82(2H, s), 6.62(1H, d, J= 1.5 Hz), 6.70-6.77(1H, m), 7.27-7.32(5H, m), 7.41-7.46(1H, m), 7.49-7.67 (6H, m), 7.72-7.82(2H, m), 8.39(1H, d, J=8.2 Hz) |
| 3-10 | 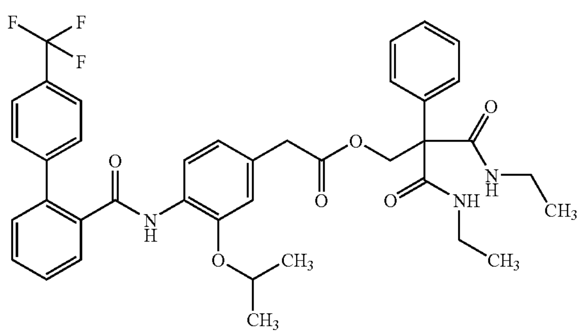 | 1.05(6H, t, J=7.2 Hz), 1.13 (6H, d, J=6.1 Hz), 3.23(4H, dq, J=5.6, 7.2 Hz), 3.52 (2H, s), 4.40(1H, sept, J= 6.1 Hz), 4.82(2H, s), 6.62 (1H, d, J=1.5 Hz), 6.67-6.75(1H, m), 7.10(2H, br-t, J=5.6 Hz), 7.16-7.23(2H, m), 7.24-7.35(3H, m), 7.44 (1H, dd, J=1.5, 7.6 Hz), 7.50-7.70(6H, m), 7.71-7.82(2H, m), 8.40(1H, d, J=8.3 Hz) |

TABLE 44

| Example | Structure | NMR (δ, 300 MHz, CDCl₃) |
|---|---|---|
| 3-11 | 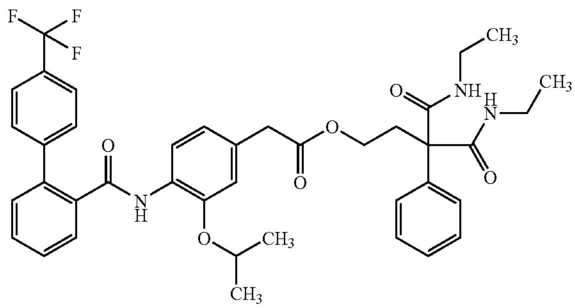 | 1.13(6H, t, J=7.2 Hz), 1.13 (6H, d, J=6.1 Hz), 2.48-2.60(2H, m), 3.31(4H, dq, J=5.7, 7.2 Hz), 3.52(2H, s), 4.07-4.17(2H, m), 4.43 (1H, sept, J=6.1 Hz), 6.69 (1H, d, J=1.5 Hz), 6.79 (1H, dd, J=1.5, 8.3 Hz), 7.23-7.37(5H, m), 7.41-7.46(1H, m), 7.48-7.68 (8H, m), 7.72-7.82(2H, m), 8.40(1H, d, J=8.3 Hz) |
| 3-12 | 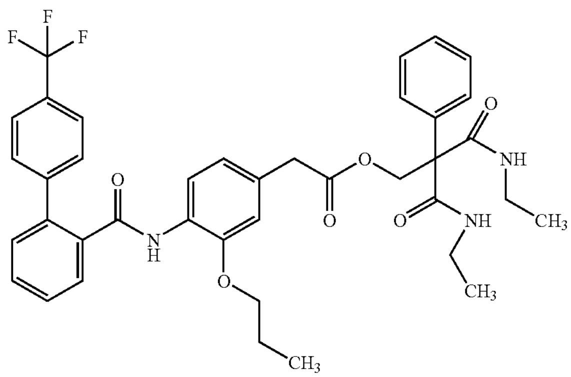 | 0.90(3H, t, J=7.4 Hz), 1.05 (6H, t, J=7.3 Hz), 1.53-1.69(2H, m), 3.16-3.30 (4H, m), 3.53(2H, s), 3.75 (2H, t, J=6.7 Hz), 4.82(2H, s), 6.58-6.74(2H, m), 7.02-7.78(16H, m), 8.36 (1H, d, J=8.2 Hz) |
| 3-13 | 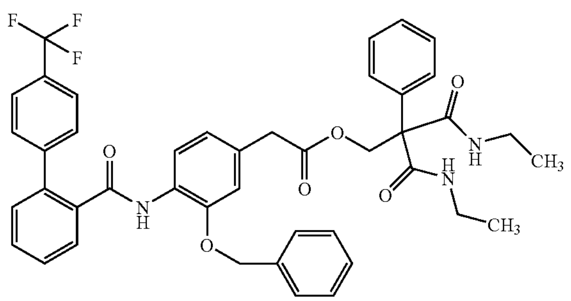 | 1.04(6H, t, J=7.2 Hz), 3.23 (4H, dq, J=7.2, 7.2 Hz), 3.52(2H, s), 4.82-4.86(4H, m), 6.70-7.79(16H, m), 7.71(1H, br.s), 7.78(1H, dd, J=7.1, 1.9 Hz), 8.40 (1H, d, J=8.3 Hz) |
| 3-14 | 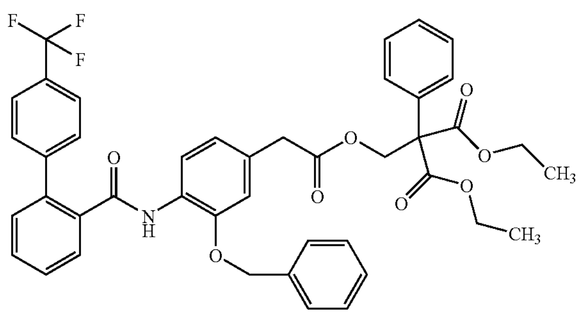 | 1.19(6H, t, J=7.1 Hz), 3.49 (2H, s), 4.17(4H, q, J=7.1 Hz), 4.78(2H, s), 4.83(2H, s), 6.70(1H, d, J=1.9 Hz), 6.78(1H, dd, J=8.3, 1.5 Hz), 7.21-7.57(12H, m), 7.70(1H, br.s), 7.77(1H, dd, J=7.2, 1.9 Hz), 8.38 (1H, d, J=8.3 Hz) |
| 3-15 | 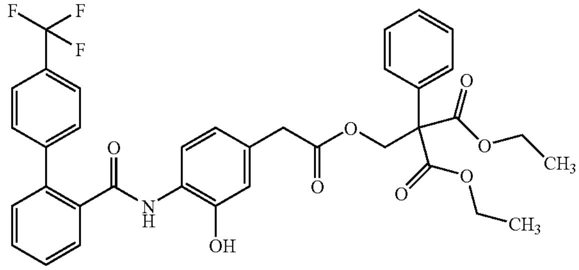 | 1.20(6H, t, J=7.2 Hz), 3.47 (2H, s), 4.19(4H, q, J=7.2 Hz), 4.82(2H, s), 6.29(1H, d, J=7.9 Hz), 6.57(1H, dd, J=7.9, 1.9 Hz), 6.79(1H, d, J=1.9 Hz), 7.18(1H, br.s) 7.28-7.74(11H, m), 7.86 (1H, dd, J=7.9, 1.5 Hz), 8.39(1H, s) |

TABLE 45

| Example | Structure | NMR (δ, 300 MHz, CDCl₃) |
|---|---|---|
| 3-16 | 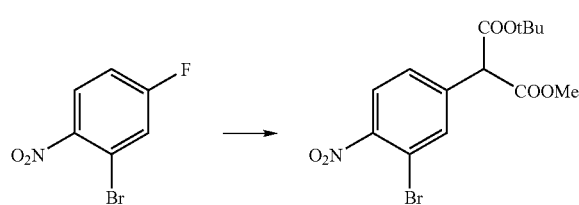 | 1.17(6H, t, J=7.1 Hz), 3.54(2H, s), 3.72(3H, s), 4.16(4H, q, J=7.1 Hz), 4.83(2H, s), 6.72-6.80(3H, m), 7.29-7.66(12H, m), 8.14(1H, dd, J=1.3, 7.7 Hz) |

Example 4

2-{3-Dimethylamino-4-[(4'-trifluoromethylbiphenyl-2-carbonyl)amino]phenyl}acetic acid 2,2-bisethyl-carbamoyl-2-phenylethyl ester a) 2-(3-Bromo-4-nitrophenyl)malonic acid tert-butyl ester methyl ester Sodium hydride (60%, mineral oil; 0.985 g) was suspended in dimethylformamide (20 mL), and a solution of tert-butyl methyl malonate (4.29 g) in dimethylformamide (5 mL) was added dropwise thereto under ice-cooling. After foam generation is stopped, a solution of 2-bromo-4-fluoro-1-nitrobenzene (2.71 g) in dimethylformamide (5 mL) was added dropwise thereto at the same temperature, and the mixture was further stirred at 60° C. for 3 hours, and then concentrated. The residue was neutralized with 1N hydrochloric acid and extracted with ethyl acetate. The extract was washed with saturated brine, dried over sodium sulfate and concentrated. The residue was purified by column chromatography on silica gel with ethyl acetate:hexane=1:4 to 1:5 to give the title compound (7.54 g) as an oil.

b) (3-Bromo-4-nitrophenyl)acetic acid methyl ester

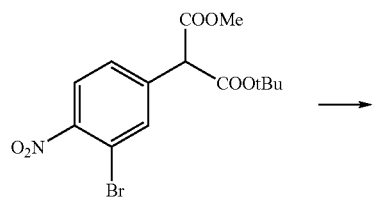

The 2-(3-bromo-4-nitrophenyl)malonic acid tert-butyl ester methyl ester (1.18 g) obtained in Example 4 a) was dissolved in chloroform (10 mL), trifluoroacetic acid (10 g) was added thereto under ice-cooling, and the mixture was stirred at room temperature for 5 hours. The reaction mixture was poured gradually into ice and saturated aqueous sodium bicarbonate, and extracted with ethyl acetate. The extract was washed with water and saturated brine, dried over sodium sulfate and concentrated to give the title compound (0.820 g) as a pale yellow oil.

c) (3-Dimethylamino-4-nitrophenyl)acetic acid methyl ester

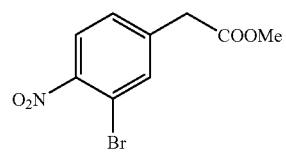

The (3-bromo-4-nitrophenyl)acetic acid methyl ester (0.320 g) obtained in Example 4 b) was dissolved in tetrahydrofuran (10 mL). To this solution were added triethylamine (0.237 g) and dimethylamine (2M tetrahydrofuran; 0.58 mL), and stirred overnight while heating. The reaction mixture was concentrated and purified by column chromatography on silica gel with ethyl acetate:hexane=1:4 to give the title compound (0.145 g) as an orange oil.

d) (4-Amino-3-dimethylaminophenyl)acetic acid methyl ester

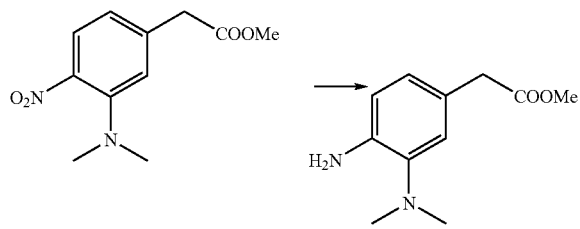

The (3-dimethylamino-4-nitrophenyl)acetic acid methyl ester (0.245 g) obtained in Example 4 c) was subjected to reactions similar to those in Example 1-3 d) to give the title compound (0.188 g) as a red oil.

e) 2-{3-Dimethylamino-4-[(4'-trifluoromethylbiphenyl-2-carbonyl)amino]phenyl}acetic acid 2,2-bisethylcarbamoyl-2-phenylethyl ester

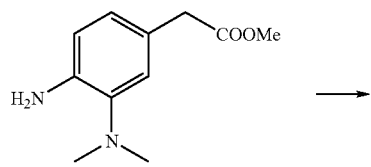

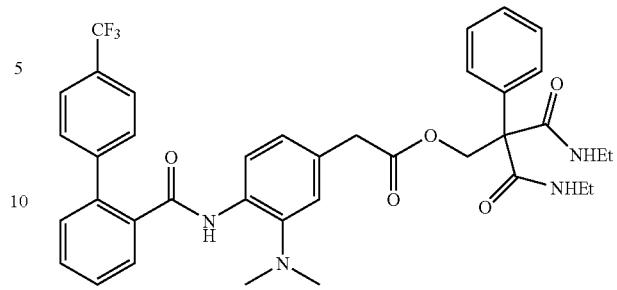

The (4-amino-3-dimethylaminophenyl)acetic acid methyl ester (0.188 g) obtained in Example 4 d) was subjected to reactions similar to those in Example 1e), 1f) and 1g) to give the title compound (0.058 g) (See Table 46).

Examples 4-2 to 4-8

Compounds of Examples 4-2 to 4-8 were obtained in a similar manner to Example 4. The compounds thus obtained were shown in Tables 46 to 47.

TABLE 46

| Example | Structure | NMR (δ, 300 MHz, CDCl$_3$) |
|---|---|---|
| 4 | 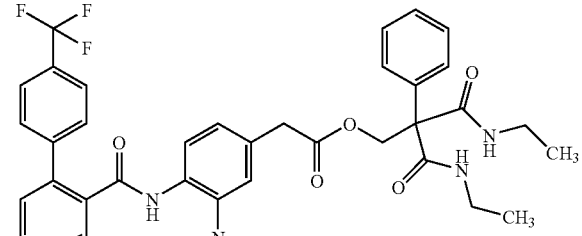 | 1.04(6H, t, J=7.2 Hz), 2.26(6H, s), 3.23(4H, m), 3.51(2H, s), 4.83(2H, s), 6.86-7.80(15H, m), 8.40(1H, d, J=8.7 Hz), 8.45(1H, brs). |
| 4-2 | 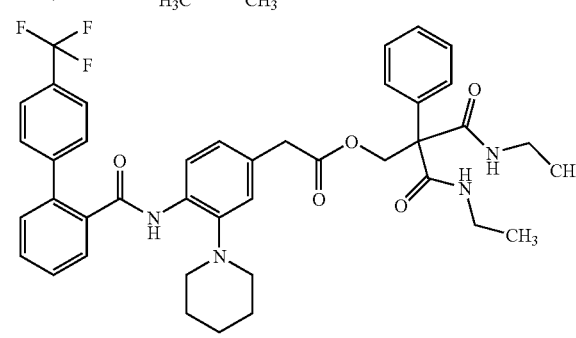 | 1.05(6H, t, J=7.3 Hz), 1.49(6H, br.s), 2.48(4H, br.s), 3.24(4H, dq, J=7.3, 7.3 Hz), 3.53(2H, s), 4.84(2H, s), 6.93(2H, m), 7.20-7.70(15H, m), 8.40(1H, d, J=9.2 Hz), 8.54(1H, br.s) |
| 4-3 | 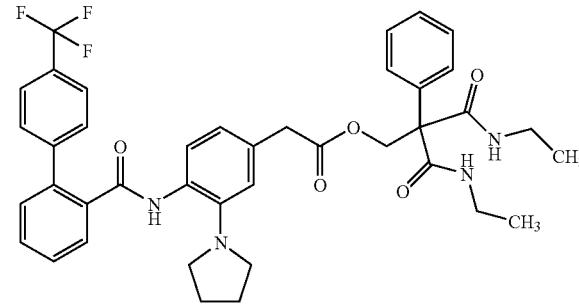 | 1.04(6H, t, J=7.3 Hz), 1.76(4H, m), 2.59(4H, t, J=6.2 Hz), 3.23(4H, dq, J=7.3, 7.3 Hz), 3.51(2H, s), 4.83(2H, s), 4.82(2H, m), 7.12-7.63(14H, m), 7.74(1H, dd, J=7.3, 1.4 Hz), 8.18(1H, br.s), 8.30(1H, d, J=8.1 Hz) |

TABLE 46-continued

| Example | Structure | NMR (δ, 300 MHz, CDCl₃) |
|---|---|---|
| 4-4 | 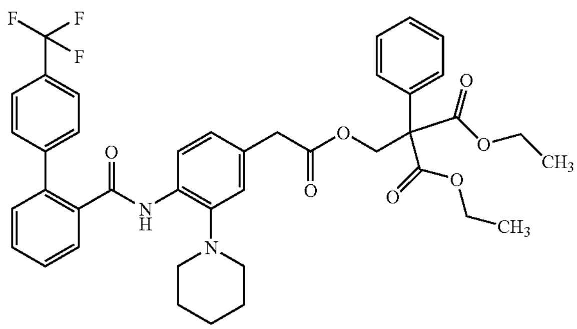 | 1.20(6H, t, J=7.1 Hz), 1.48(6H, br.s), 2.47(4H, br.s), 3.49(2H, s), 4.19(4H, q, J=7.1 Hz), 4.83(2H, s), 6.92-7.72(15H, m), 8.39(1H, d, J=8.3 Hz), 8.56(1H, br.s) |
| 4-5 | 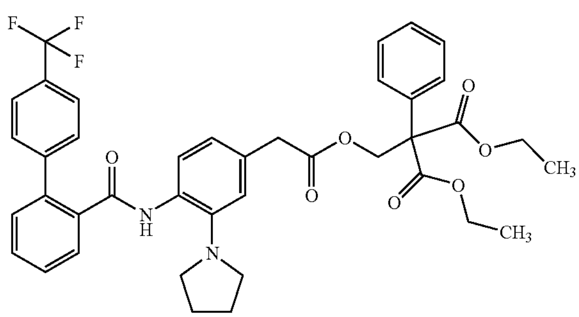 | 1.20(6H, t, J=7.2 Hz), 1.74(4H, m), 2.57(4H, m), 3.48(2H, s), 4.19(4H, q, J=7.2 Hz), 4.82(2H, s), 6.90(2H, m), 7.30-7.63(12H, m), 7.74(1H, dd, J=7.2, 1.5 Hz), 8.20(1H, br.s), 8.29(1H, d, J=8.7 Hz) |

TABLE 47

| Example | Structure | NMR (δ, 300 MHz, CDCl₃) |
|---|---|---|
| 4-6 | 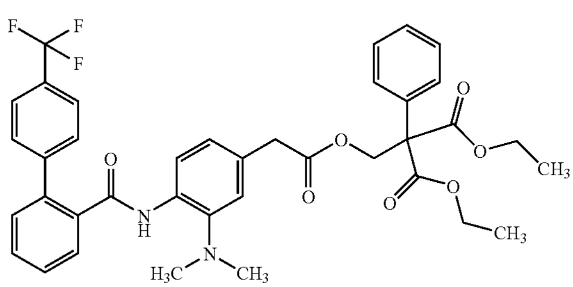 | 1.20(6H, t, J=7.1 Hz), 2.24(6H, s), 3.48(2H, s), 4.19(4H, q, J=7.1 Hz), 4.82(2H, s), 6.88-6.98(2H, m), 7.29(5H, brs), 7.43(1H, d, J=7.2 Hz), 7.48-7.60(2H, m), 7.62(4H, s), 7.77(1H, d, J=7.5 Hz), 8.39(1H, d, J=8.3 Hz), 8.47(1H, brs). |
| 4-7 | 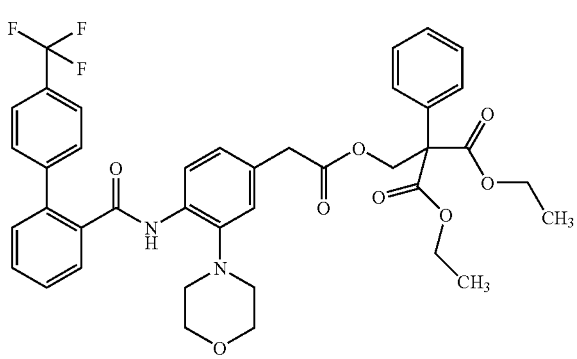 | 1.21(6H, t, J=7.0 Hz), 2.38-2.47(4H, m), 3.51(2H, s), 3.53-3.60(4H, m), 4.20(4H, q, J=7.0 Hz), 4.84(2H, s), 6.93(1H, s), 7.00(1H, dd, J=1.5, 7.4 Hz), 7.29-7.35(5H, m), 7.47-7.68(7H, m), 7.73(1H, dd, J=1.8, 7.4 Hz), 8.42-8.51(2H, m) |

TABLE 47-continued

| Example | Structure | NMR (δ, 300 MHz, CDCl₃) |
|---|---|---|
| 4-8 | 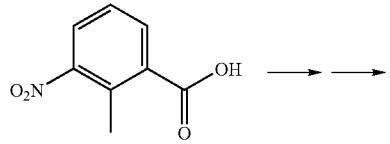 | 0.67(6H, t, J=7.0 Hz), 1.21(6H, t, J=7.2 Hz), 2.64(4H, q, J=7.0 Hz), 3.49(2H, s), 4.21(4H, q, J=7.2 Hz), 4.83(2H, s), 6.90-7.01(2H, m), 7.28-7.35(5H, m), 7.42-7.65(7H, m), 7.69(1H, dd, J=1.5, 7.2 Hz), 8.41(1H, d, J=8.3 Hz), 8.85(1H, br-s) |

Example 5

2-[2-(2-{2-methyl-3-[(4'-trifluoromethylbiphenyl-2-carbonyl)amino]phenyl}acetoxy)ethyl]-2-phenylmalonic acid diethyl ester a) 2'-Diazo-3-nitro-2-methylacetophenone 2-Methyl-3-nitrobenzoic acid (500 mg) was subjected to reactions similar to those in Example 3b) and 3c) to give the title compound (377 mg).

b) 2-Methyl-3-nitrophenylacetic acid ethyl ester

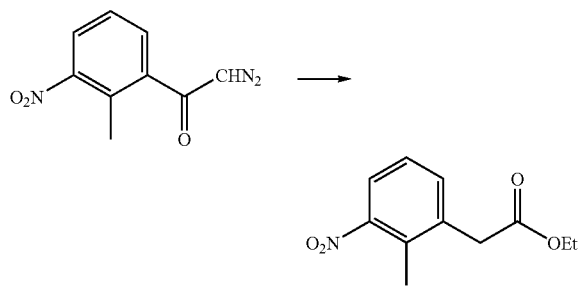

The 2'-diazo-3-nitro-2-methylacetophenone (377 mg) obtained in Example 5a) was subjected to reactions similar to those in Example 3d) to give the title compound (363 mg).

c) 2-Methyl-3-nitrophenylacetic acid

The 2-methyl-3-nitrophenylacetic acid ethyl ester (352 mg) obtained in Example 5b) was subjected to reactions similar to those in Example 1f) to give the title compound (307 mg).

d) 2-(2-Benzyloxyethyl)-2-phenylmalonic acid diethyl ester

Sodium hydride (406 mg) was dissolved in dimethylformamide (20 mL) and the solution was cooled to 0° C. To this solution was added phenylmalonic acid diethyl ester (2.0 g), and the mixture was stirred at room temperature for 30 minutes. Bromoethyl benzyl ether (2.0 g) was further added thereto, stirred at 60° C. for 4 hours, and water was added thereto. The reaction mixture was concentrated, diluted with ethyl acetate, washed with water, dried over sodium sulfate and purified by column chromatography on silica gel with ethyl acetate:hexane=1:9 to give the title compound (1.2 g).

e) 2-(2-Hydroxyethyl)-2-phenylmalonic acid diethyl ester

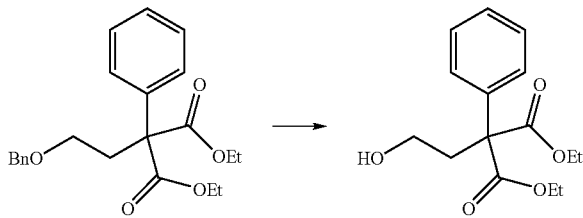

The 2-(2-benzyloxyethyl)-2-phenylmalonic acid diethyl ester (1.2 g, not purified) obtained in Example 5d) was subjected to reactions similar to those in Example 1-2c) to give the title compound (726 mg).

f) 2-{2-[2-(2-Methyl-3-nitrophenyl)acetoxy]ethyl}-2-phenylmalonic acid diethyl ester

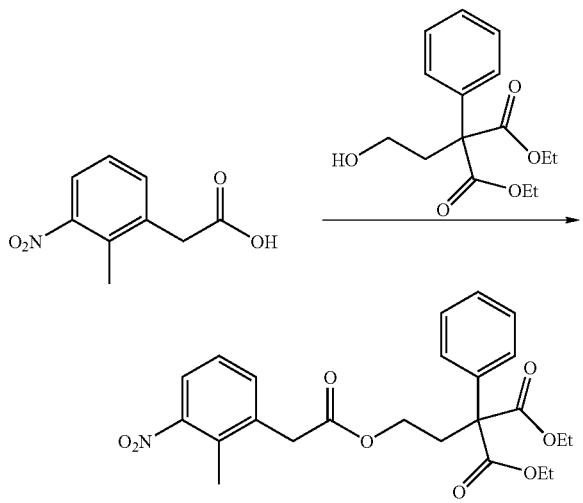

The 2-methyl-3-nitrophenylacetic acid (307 mg) obtained in Example 5c), 4-dimethylaminopyridine (217 mg) and the 2-(2-hydroxyethyl)-2-phenylmalonic acid diethyl ester (250 mg) obtained in Example 5e) were subjected to reactions similar to those in Example 1-3c) to give the title compound (366 mg).

g) 2-[2-(2-{2-methyl-3-[(4'-trifluoromethylbiphenyl-2-carbonyl)amino]phenyl}acetoxy)ethyl]-2-phenylmalonic acid diethyl ester

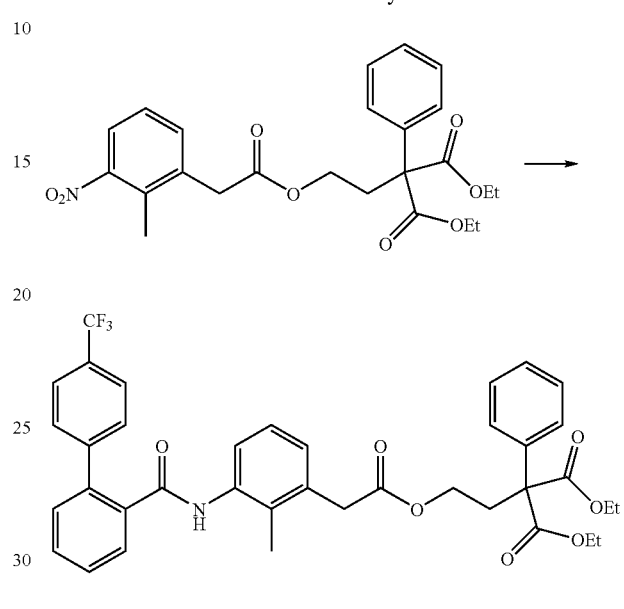

The 2-{2-[2-(2-methyl-3-nitrophenyl)acetoxy]ethyl}-2-phenylmalonic acid diethyl ester (345 mg) obtained in Example 5f) was subjected to reactions similar to those in Example 1-3d) and 1-3e) to give the title compound (318 mg) (See Table 48).

Examples 5-2 to 5-18

Compounds of Examples 5-2 to 5-18 were obtained in a similar manner to Example 5. The compounds thus obtained were shown in Tables 48 to 51.

TABLE 48

| Example | Structure | NMR (δ, 300 MHz, CDCl₃) |
| --- | --- | --- |
| 5 | ![structure] | 1.23(6H, t, J=7.0 Hz), 1.70(3H, s), 2.61(2H, t, J=7.0 Hz), 3.50(2H, s), 4.07(2H, t, J=7.0 Hz), 4.21(4H, q, J=7.0 Hz), 6.84(1H, br.s), 6.98(1H, d, J=7.7 Hz), 7.13-7.71(15H, m), 7.80(1H, d, J=7.0 Hz) |

TABLE 48-continued

| Example | Structure | NMR (δ, 300 MHz, CDCl₃) |
|---|---|---|
| 5-2 | 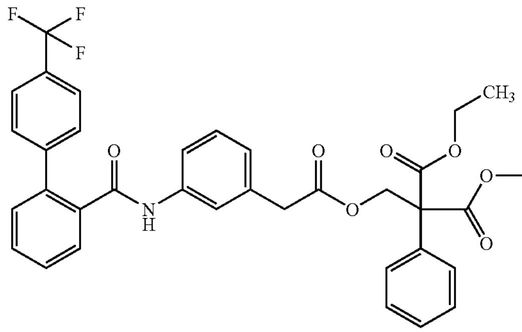 | 1.17(6H, t, J=7.1 Hz), 3.50(2H, s), 4.14(4H, q, J=7.1 Hz), 4.83(2H, s), 6.83(1H, s), 6.91(1H, d, J=7.5 Hz), 6.99(1H, br.s), 7.16-7.81(15H, m) |
| 5-3 | m.p. 88-91 | 1.23(6H, t, J=7.2 Hz), 2.62(2H, t, J=7.2 Hz), 3.41(2H, s), 4.13(2H, t, J=7.2 Hz), 4.20(4H, q, J=7.2 Hz), 7.05-7.79(18H, m) |
| 5-4 | 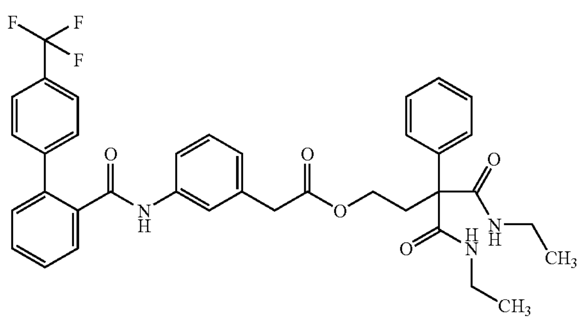 | 1.10(6H, t, J=7.2 Hz), 2.53-2.61(2H, m), 3.28 (4H, dq, J=5.3, 7.2 Hz), 3.54(2H, s), 4.07-4.17(2H, m), 6.95-7.10(3H, m), 7.14-7.36(7H, m), 7.40-7.46(1H, m), 7.46-7.62 (6H, m), 7.64-7.71(2H, m), 7.77(1H, dd, J=1.5, 7.5 Hz) |
| 5-5 | 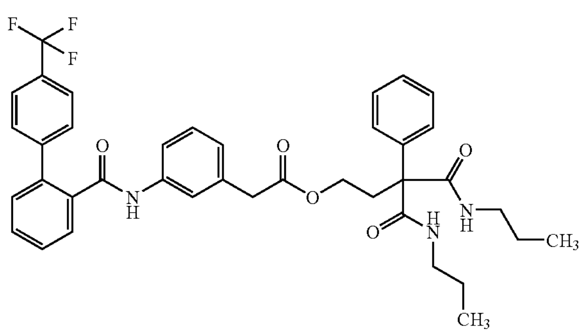 | 0.85(6H, t, J=7.2 Hz), 1.49(4H, tq, J=7.2, 7.2 Hz), 2.54-2.63(2H, m), 3.16-3.25(4H, m), 3.53 (2H, s), 4.08-4.17(2H, m), 6.96-7.01(1H, m), 7.03-7.10(2H, m), 7.15-7.36(7H, m), 7.40-7.46(1H, m), 7.47-7.62(6H, m), 7.65-7.71(2H, m), 7.77 (1H, dd, J=1.5, 7.5 Hz) |

TABLE 49

| Example | Structure | NMR (δ, 300 MHz, CDCl$_3$) |
|---|---|---|
| 5-6 | 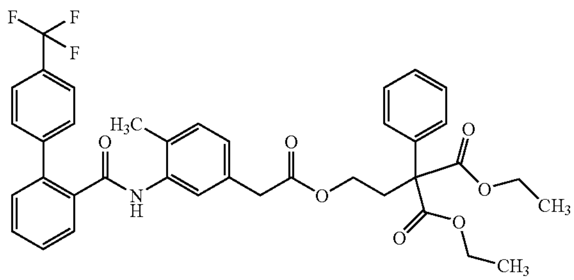 | 1.24(6H, t, J=7.4 Hz), 1.68(3H, s), 2.65(2H, t, J=7.3 Hz), 3.50(2H, s), 4.09(2H, t, J=7.3 Hz), 4.22(4H, q, J=7.4 Hz), 6.81(1H, br.s), 6.92-7.83(16H, m) |
| 5-7 | 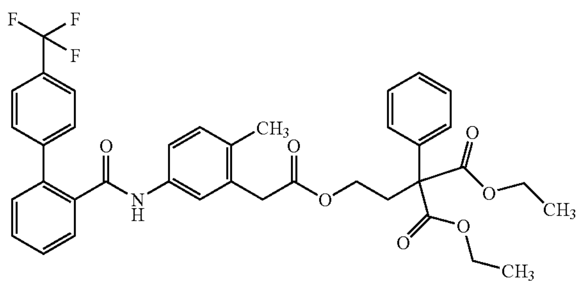 | 1.23(6H, t, J=7.4 Hz), 2.20(3H, s), 2.63(2H, t, J=7.0 Hz), 3.47(2H, s), 4.08(2H, t, J=7.0 Hz), 4.21(4H, q, J=7.4 Hz), 6.94(1H, s), 7.07-7.81(16H, m) |
| 5-8 | 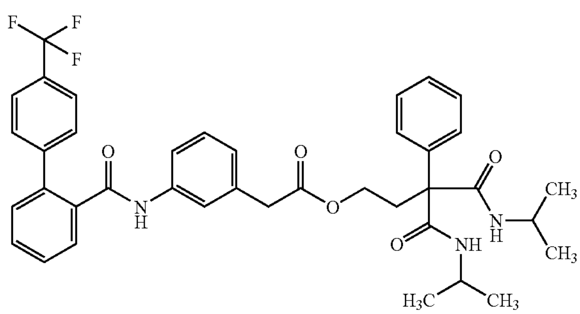 | 1.11(6H, d, J=6.4 Hz), 1.13(6H, d, J=6.8 Hz), 2.49-2.58(2H, m), 3.53(2H, s), 3.98-4.15(4H, m), 6.96-7.01(1H, m), 7.03-7.16(3H, m), 7.17-7.37(8H, m), 7.40-7.61(5H, m), 7.64-7.71(2H, m), 7.77(1H, dd, J=1.5, 7.6 Hz) |
| 5-9 | 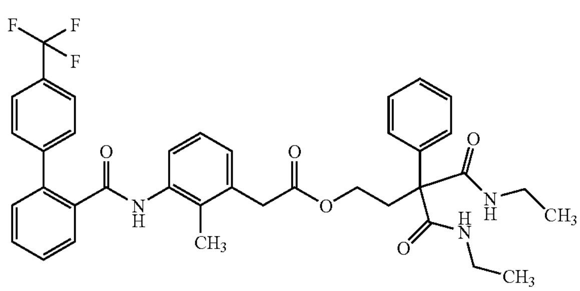 | 1.11(6H, t, J=7.0 Hz), 1.72(3H, s), 2.52(2H, t, J=7.9 Hz), 3.29(4H, dq, J=7.0, 7.0 Hz), 3.57(2H, s), 4.08(2H, t, J=7.9 Hz), 6.85(1H, br.s), 6.99-7.81(18H, m) |
| 5-10 | 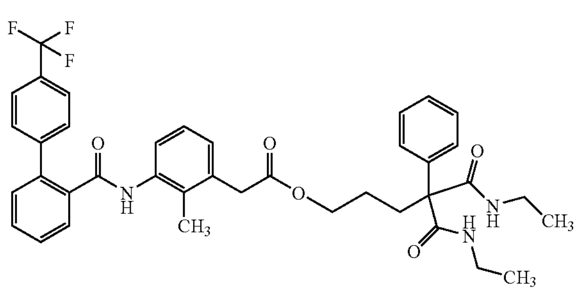 | 0.98(6H, t, J=7.1 Hz), 1.53(2H, m), 1.79(3H, s), 1.95(2H, m), 3.09(4H, dq, J=7.1, 7.1 Hz), 3.64(2H, s), 4.06(2H, t, J=5.7 Hz), 7.03-7.62(18H, m), 8.02(1H, br.s) |

TABLE 50

| Example | Structure | NMR (δ, 300 MHz, CDCl₃) |
|---|---|---|
| 5-11 | 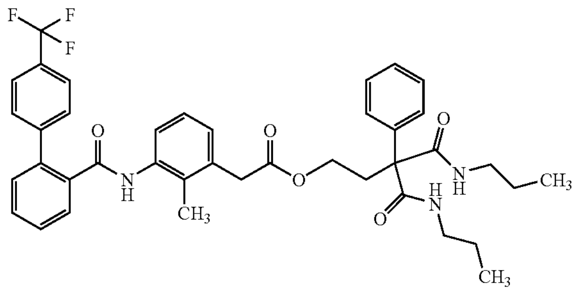 | 0.86(6H, t, J=7.1 Hz), 1.50(4H, tq, J=7.1, 7.1 Hz), 2.53(2H, t, J=7.9 Hz), 3.21(4H, m), 3.57(2H, s), 4.08(2H, t, J=7.9 Hz), 6.85(1H, br.s), 7.00(1H, d, J=7.5 Hz), 7.14-7.80(17H, m) |
| 5-12 | 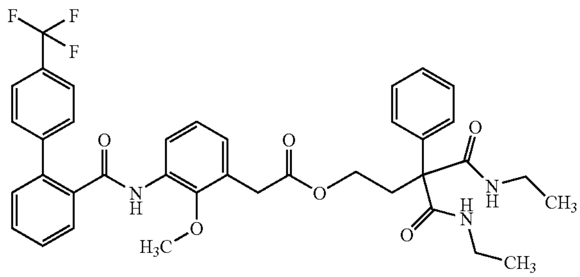 | 1.11(6H, t, J=7.2 Hz), 2.53(2H, t, J=7.9 Hz), 3.22(3H, d), 3.29(4H, dq, J=7.2, 7.2 Hz), 3.55(2H, s), 4.09(2H, t, J=7.9 Hz), 6.95(1H, dd, J=7.5, 1.5 Hz), 7.04-7.64(16H, m), 7.74(1H, dd, J=7.5, 1.5 Hz), 8.34(1H, dd, J=8.3, 1.1 Hz) |
| 5-13 | m.p. 78-81 | 1.23(6H, t, J=7.1 Hz), 2.61(2H, t, J=7.2 Hz), 3.22(3H, s), 3.49(2H, s), 4.08(2H, t, J=7.2 Hz), 4.21(4H, q, J=7.1 Hz), 6.93(1H, dd, J=7.6, 1.5 Hz), 7.28-7.75(14H, m), 7.73(1H, dd, J=7.6, 1.5 Hz), 8.33(1H, dd, J=8.3, 1.5 Hz) |
| 5-14 | 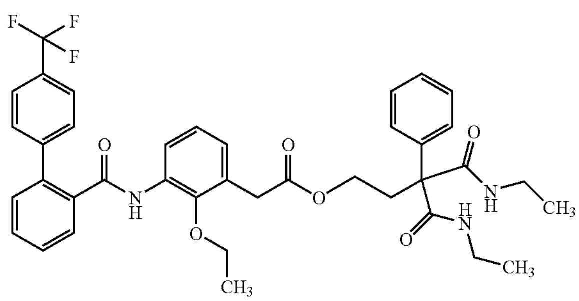 | 1.11(6H, t, J=7.4 Hz), 1.15(3H, t, J=7.2 Hz), 2.52(2H, t, J=7.5 Hz), 3.29(6H, m), 3.54(2H, s), 4.09(2H, t, J=7.5 Hz), 6.95(1H, dd, J=7.9, 1.1 Hz), 7.10(1H, dd, J=7.9, 7.9 Hz), 7.24-7.73(16H, m), 8.36(1H, d, J=8.3 Hz) |
| 5-15 | 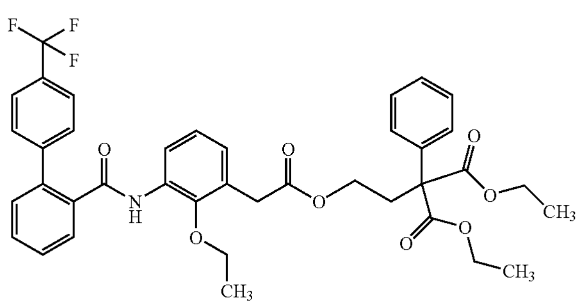 | 1.15(3H, t, J=7.2 Hz), 1.23(6H, t, J=7.2 Hz), 2.61(2H, t, J=7.2 Hz), 3.29(2H, q, J=7.2 Hz), 3.49(2H s), 4.07(2H, t, J=7.2 Hz), 4.21(4H, q, J=7.2 Hz), 6.94(1H, dd, J=7.5, 1.5 Hz), 7.08(1H, dd, J=7.9, 7.9 Hz), 7.30-7.73(14H, m), 8.34(1H, dd, J=7.9, 1.5 Hz) |

TABLE 51

| Example | Structure | NMR (δ, 300 MHz, CDCl₃) |
|---|---|---|
| 5-16 | 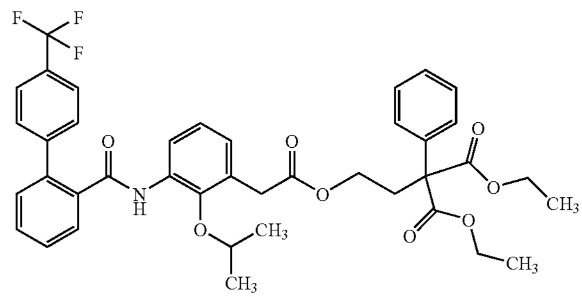 | 1.05(6H, d, J=6.4 Hz), 1.23(6H, t, J=7.2 Hz), 2.62(2H, t, J=7.2 Hz), 3.51(2H, s), 3.85(1H, sep, J=6.4 Hz), 4.10(2H, t, J=7.2 Hz), 4.20(4H, q, J=7.2 Hz), 6.95(1H, dd, J=7.9, 1.5 Hz), 7.07(1H, dd, J=7.9, 7.9 Hz), 7.30-7.61(12H, m), 7.68(1H, dd, J=7.9, 1.5 Hz), 7.75(1H, br.s), 8.28(1H, dd, J=7.9, 1.5 Hz) |
| 5-17 | 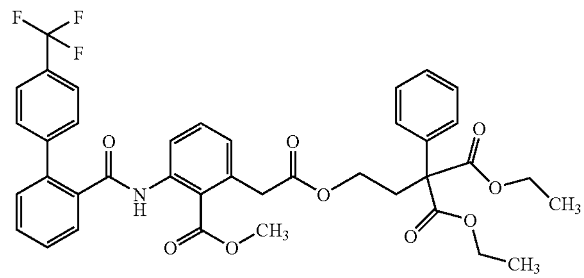 | 1.23(6H, t, J=7.1 Hz), 2.61(2H, t, J=7.1 Hz), 3.71(3H, s), 3.75(2H, s), 4.07(2H, t, J=7.1 Hz), 4.22(4H, q, J=7.1 Hz), 6.94(1H, d, J=7.6 Hz), 7.29-7.62(13H, m), 7.72(1H, dd, J=1.4, 7.6 Hz), 8.47(1H, d, J=8.3 Hz), 10.25(1H, brs) |
| 5-18 | 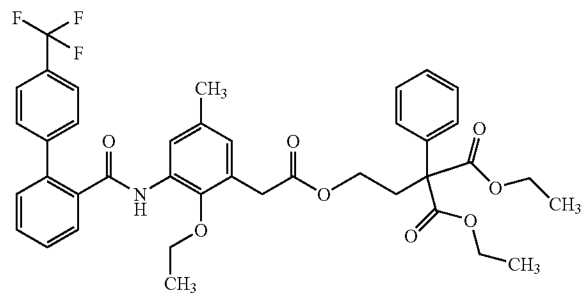 | 1.13(3H, t, J=7.2 Hz), 1.23(6H, t, J=7.1 Hz), 2.30(3H, s), 2.61(2H, t, J=7.1 Hz), 3.25(2H, q, J=7.2 Hz), 3.44(2H, s), 4.07(2H, t, J=7.1 Hz), 4.21(4H, q, J=7.1 Hz), 6.75(1H, s), 7.30-7.69(14H, m), 8.19(1H, brs) |

Example 6

4-[(4'-Trifluoromethylbiphenyl-2-carbonyl)amino]benzoic acid 2-[9-(2,2,2-trifluoroethylcarbamoyl)-9H-fluoren-9-yl]ethyl ester a) 4-[(4'-Trifluoromethylbiphenyl-2-carbonyl)amino]benzoic acid ethyl ester

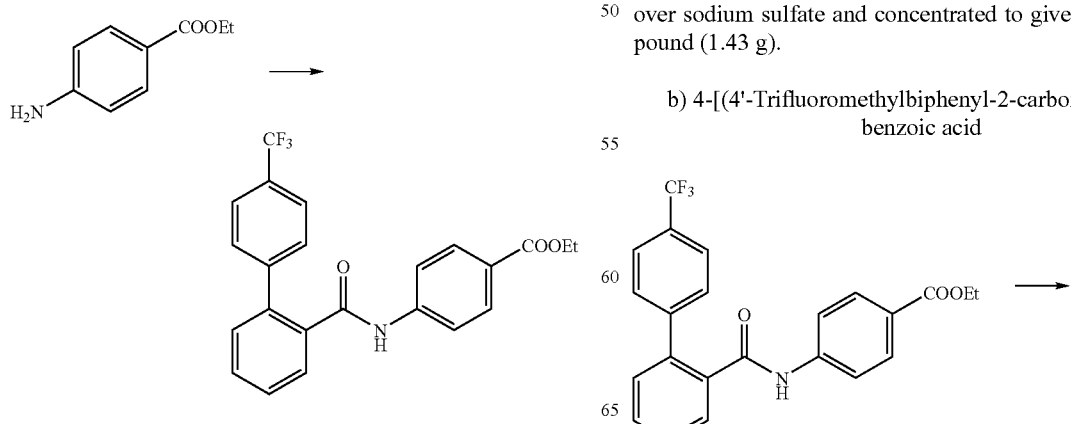

4-Aminobenzoic acid ethyl ester (0.568 g) and triethylamine (0.570 g) were dissolved in methylene chloride (20 mL), and to this solution was dropwise added a solution of 4'-trifluoromethylbiphenyl-2-carboxylic acid chloride, which is prepared from 4'-trifluoromethylbiphenyl-2-carboxylic acid (1.00 g) in a similar manner to Example 1d), in methylene chloride under ice-cooling. The solution was stirred at room temperature for 2 hours, followed by addition of methylene chloride (100 mL). The reaction mixture was washed with 2N hydrochloric acid and saturated brine, dried over sodium sulfate and concentrated to give the title compound (1.43 g).

b) 4-[(4'-Trifluoromethylbiphenyl-2-carbonyl)amino]benzoic acid

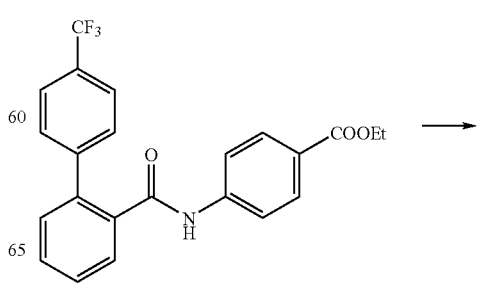

-continued

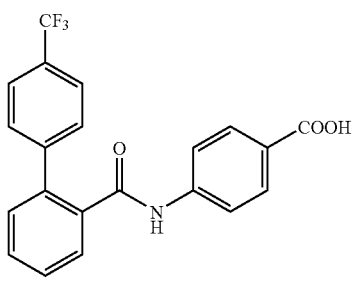

The 4-[(4'-trifluoromethylbiphenyl-2-carbonyl)amino]benzoic acid ethyl ester (0.700 g) obtained in Example 6a) was subjected to reactions similar to Example 1f) to give the title compound (0.680 g) as a white solid.

c) 9-[2-(Tert-butyldimethylsilanyloxy)ethyl]-9H-fluoren-9-carboxylic acid (2,2,2-trifluoroethyl)amide

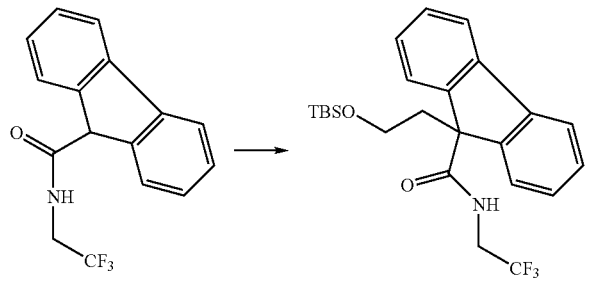

9H-Fluorene-9-carboxylic acid (2,2,2-trifluoroethyl)amide (3.00 g) was dissolved in tetrahydrofuran (100 mL), and to this solution was added dropwise a 1.5M solution (13.7 mL) of lithium diisopropylamide under ice-cooling. The mixture was stirred for one hour under ice-cooling, and to this was added a solution of tert-butyldimethylsilanyloxyethyl bromide (2.46 g) in tetrahydrofuran (5 mL). The temperature was gradually raised from under ice-cooling to room temperature, and the mixture was stirred overnight. Saturated aqueous ammonium chloride was added to the reaction mixture under ice-cooling and then extracted with ethyl acetate (50 mL×2). The extract was washed with saturated brine, dried over sodium sulfate and purified by column chromatography on silica gel with ethyl acetate:hexane=1:2.5 to give the title compound (6.00 g).

d) 9-(2-Hydroxyethyl)-9H-fluoren-9-carboxylic acid (2,2,2-trifluoroethyl)amide

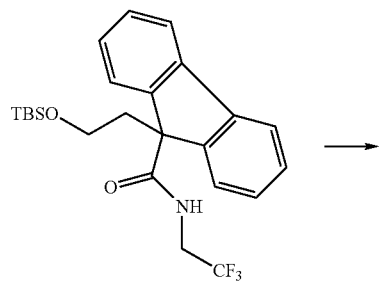

-continued

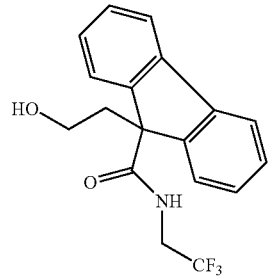

The 9-[2-(Tert-butyldimethylsilanyloxy)ethyl]-9H-fluoren-9-carboxylic acid (2,2,2-trifluoroethyl)amide (6.00 g) obtained in Example 6c) was dissolved in tetrahydrofuran (13 mL)—acetic acid (39 mL)—water (13 mL). The solution was stirred at room temperature for 20 hours and concentrated in vacuo. The residue was purified by column chromatography on silica gel with ethyl acetate:hexane=1:1 to give the title compound (3.80 g).

e) 4-[(4'-Trifluoromethylbiphenyl-2-carbonyl)amino]benzoic acid 2-[9-(2,2,2-trifluoromethylcarbamoyl)-9H-fluoren-9-yl]ethyl ester

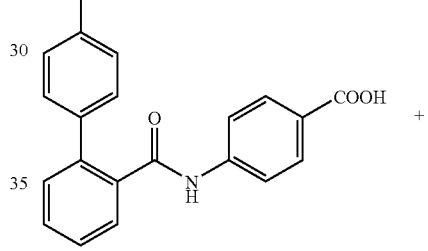

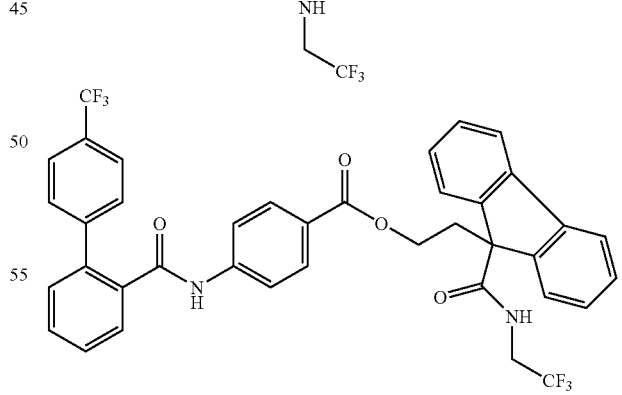

The 4-[(4'-trifluoromethylbiphenyl-2-carbonyl)amino]benzoic acid (0.345 g) obtained in Example 6b) and the 9-(2-hydroxyethyl)-9H-fluoren-9-carboxylic acid (2,2,2-trifluoroethyl)amide (0.300 g) obtained in Example 6d) were subjected to reactions similar to those in Example 1g) to give the title compound (0.390 g) as a colorless solid (see Table 52).

Examples 6-2 to 6-22

Compounds of Examples 6-2 to 6-22 were obtained in a similar manner to Examples 6, 1-2b), 1-2c) and 1-2d). The compounds thus obtained were shown in Tables 52 to 56.

TABLE 52

| Example | Structure | NMR (δ, 300 MHz, CDCl$_3$) |
| --- | --- | --- |
| 6 | 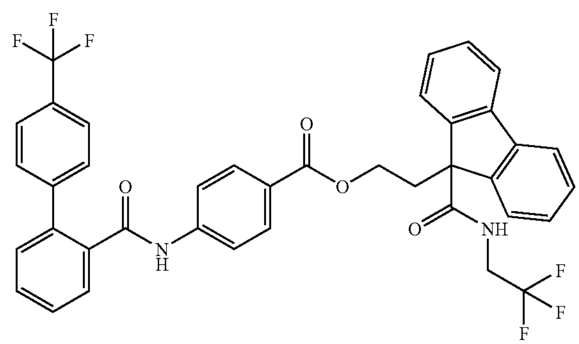 | 2.98(2H, t, J=6.8 Hz), 3.63-3.71(2H, m), 3.81(2H, t, J=6.8 Hz), 5.27(1H, br), 7.00(1H, brs), 7.12(2H, m), 7.30-7.84(18H, m). |
| 6-2 | 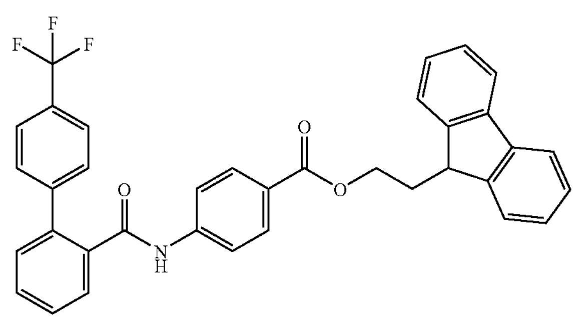 | 2.45-2.58(2H, m), 4.10-4.18(1H, m), 4.21(2H, t, J=7.5 Hz), 7.02(1H, brs), 7.14-7.88(20H, m). |
| 6-3 | 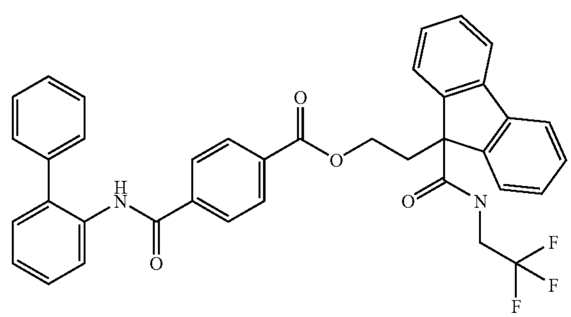 | 3.01(2H, t, J=6.6 Hz), 3.60-3.74(2H, m), 3.86(2H, t, J=6.6 Hz), 5.27(18H, m), 7.20-7.61(18H, m), 7.75(2H, d, J=6.6 Hz), 7.97(1H, brs), 8.52(1H, d, J=8.4 Hz). |
| 6-4 | 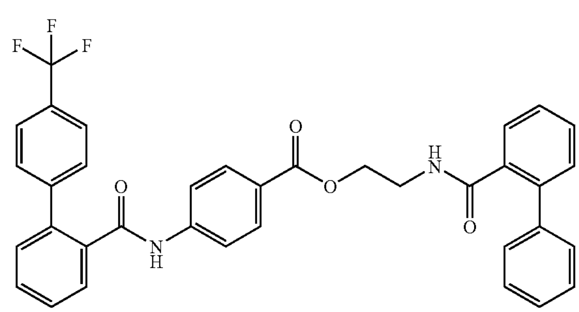 | 3.56(2H, t, J=5.2 Hz), 4.06(2H, t, J=5.2 Hz), 5.52(1H, br), 7.08(1H, brs), 7.15-7.98(21H, m). |

TABLE 52-continued
| Example | Structure | NMR (δ, 300 MHz, CDCl₃) |
|---------|-----------|--------------------------|
| 6-5 | 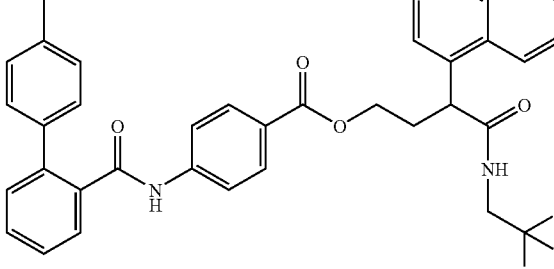 | 3.42-3.54(2H, m), 3.55(2H, s), 4.26(2H, t, J=6.6 Hz), 5.52(1H, br), 7.06(1H, brs), 7.18-7.88(21H, m). |
TABLE 53
| Example | Structure | NMR (δ, 300 MHz, CDCl₃) |
|---------|-----------|--------------------------|
| 6-6 | 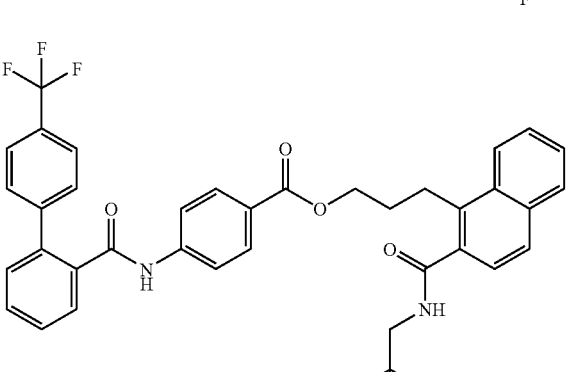 | 2.31-2.42(1H, m), 2.80-2.93(1H, m), 3.73-3.89(2H, m), 4.16-4.26(1H, m), 4.32-4.43(2H, m), 5.62(1H, br), 7.09((1H, brs), 7.26-8.01(19H, m). |
| 6-7 | 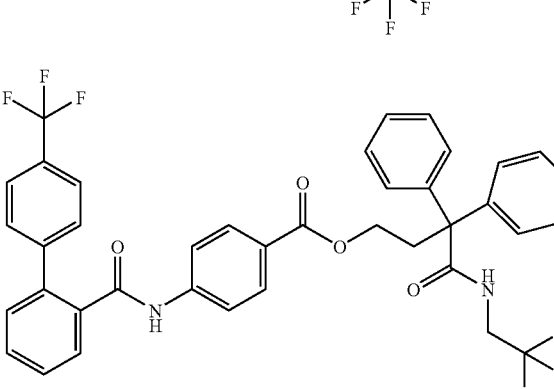 | 2.15-2.29(2H, m), 3.34(2H, t, J=7.9 Hz), 4.01-4.18(2H, m), 4.40(2H, t, J=6.2 Hz), 6.15(1H, br), 7.08(1H, brs), 7.18-7.98(17H, m), 7.92(1H, d, J=8.4 Hz). |
| 6-8 | 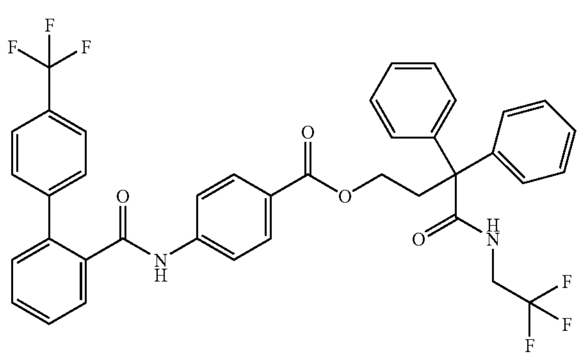 | 2.88(2H, t, J=8.3 Hz), 3.83-3.93(2H, m), 4.23(2H, t, J=8.3 Hz), 5.90(1H, t, J=6.4 Hz), 7.01(1H, brs), 7.16-7.86(22H, m). |

TABLE 53-continued
| Example | Structure | NMR (δ, 300 MHz, CDCl₃) |
|---|---|---|
| 6-9 | 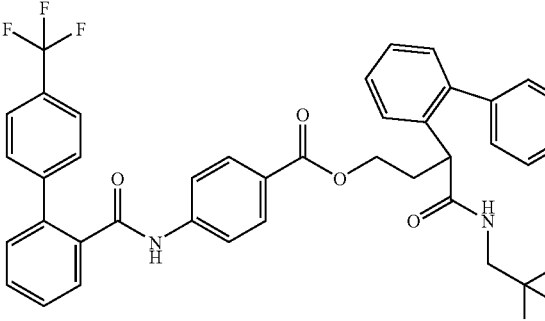 | 2.12-2.29(1H, m), 2.56-2.68(1H, m), 3.70-3.80(3H, m), 4.09-4.29(2H, m), 5.41(1H, br), 7.05(1H, brs), 7.12-7.78(20H, m), 7.86(1H, d, J=7.5 Hz). |
| 6-10 | 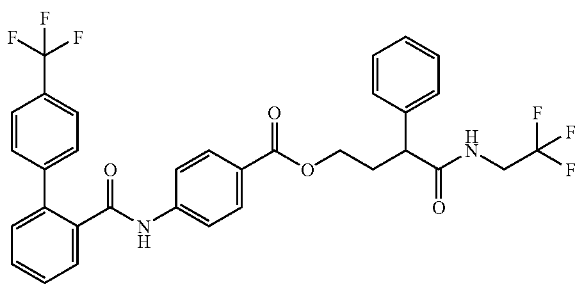 | 2.16-2.30(2H, m), 2.62-2.72(2H, m), 3.61(1H, t, J=7.5 Hz), 3.71-3.99(4H, m), 4.12-4.37(4H, m), 5.67(1H, br), 7.05(1H, brs), 7.15-7.91(17H, m). |
TABLE 54
| Example | Structure | NMR (δ, 300 MHz, CDCl₃) |
|---|---|---|
| 6-11 | 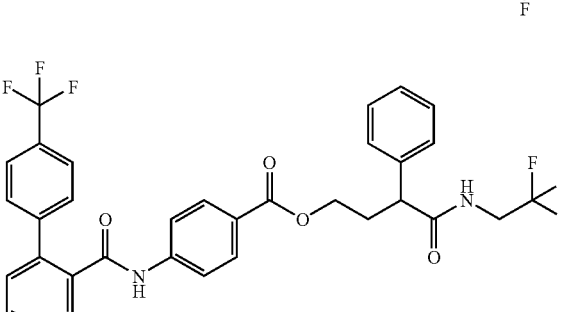 | 3.49(2H, t, J=6.9 Hz), 4.09-4.29(2H, m), 4.56(2H, t, J=6.9 Hz), 6.34(1H, br). 7.08(1H, brs), 7.12-8.00(18H, m). |
| 6-12 | 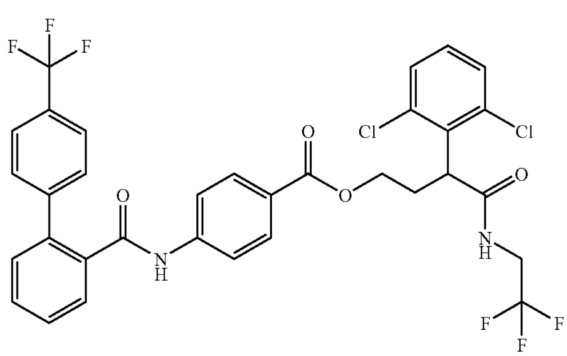 | 2.39-2.50(1H, m), 2.93-3.05(1H, m), 3.78-4.06(2H, m), 4.20-4.41(2H, m), 4.77(1H, d, J=6.4 Hz, J=9.6 Hz), 5.42(1H, 1H, t, J=6.4 Hz), 7.07(1H, brs), 7.19-7.88(15H, m). |

TABLE 54-continued
| Example | Structure | NMR (δ, 300 MHz, CDCl₃) |
|---|---|---|
| 6-13 | 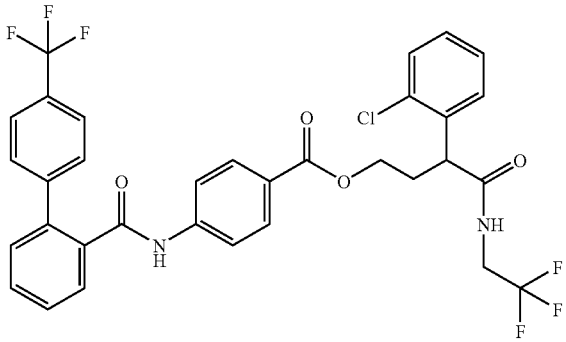 | 2.19-2.30(1H, m), 2.62-2.73(1H, m), 3.79-3.82(2H, m), 4.20-4.40(3H, m), 5.80(1H, t, J=6.4 Hz), 7.06(1H, brs), 7.16-7.92(16H, m). |
| 6-14 | 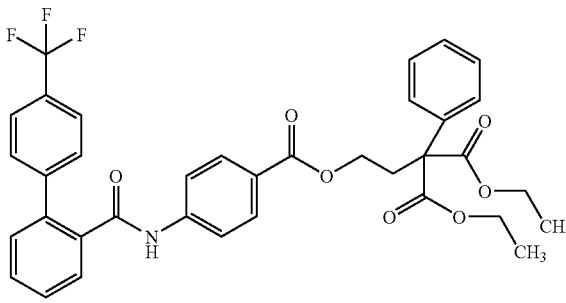 | 1.22(6H, t, J=7.1 Hz), 2.77(2H, t, J=6.9 Hz), 4.21(4H, q, J=7.12 Hz), 4.30(2H, t, J=6.9 Hz), 7.06(1H, brs), 7.19-7.88(17H, m) |
| 6-15 | 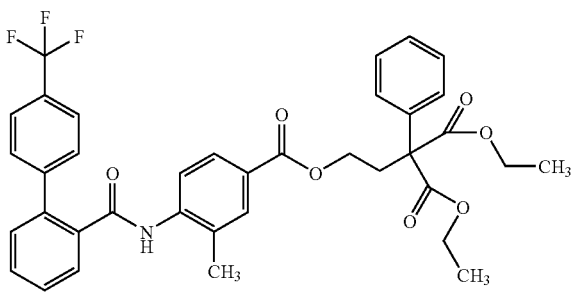 | 1.23(6H, t, J=7.1 Hz), 1.64(3H, s), 2.77(2H, t, J=6.9 Hz), 4.21(4H, q, J=7.1 Hz), 4.29(2H, t, J=6.9 Hz), 6.93(1H, brs), 7.20-8.24(16H, m) |
TABLE 55
| Example | Structure | NMR (δ, 300 MHz, CDCl₃) |
|---|---|---|
| 6-16 | 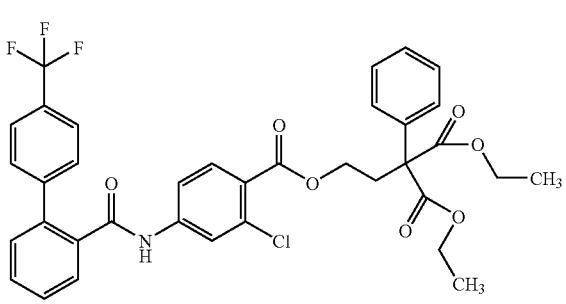 | 1.22(3H, t, J=7.1 Hz), 1.23(3H, t, J=7.1 Hz), 2.76(2H, t, J=6.9 Hz), 4.20(2H, q, J=7.1 Hz), 4.21(2H, q, J=7.1 Hz), 4.29(2H, t, J=6.9 Hz), 6.95-7.91(17H, m) |

TABLE 55-continued

| Example | Structure | NMR (δ, 300 MHz, CDCl₃) |
|---|---|---|
| 6-17 | 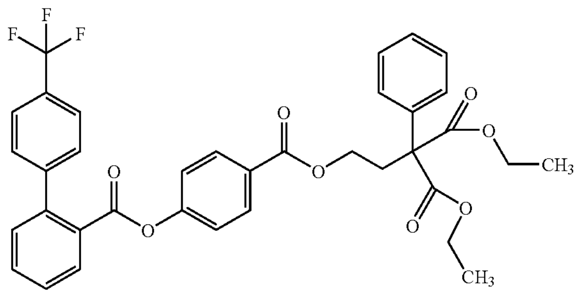 | 1.22(6H, t, J=7.1 Hz), 2.77(2H, t, J=6.9 Hz), 4.20(4H, q, J=7.1 Hz), 4.31(2H, t, J=6.9 Hz), 6.93(2H, d, J=8.8 Hz), 7.26-8.13(13H, m), 7.92(2H, d, J=8.8 Hz) |
| 6-18 | 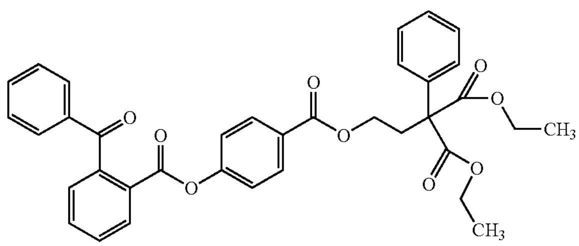 | 1.22(6H, t, J=7.1 Hz), 2.76(2H, t, J=6.9 Hz), 4.20(4H, q, J=7.1 Hz), 4.30(2H, t, J=6.9 Hz), 6.85(2H, d, J=8.8 Hz), 7.21-7.81(13H, m), 7.88(2H, d, J=8.8 Hz), 8.21(1H, dd, J=7.6, 1.3) |
| 6-19 | 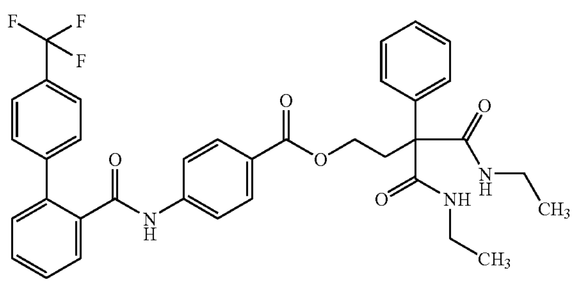 | 1.14(6H, t, J=7.2 Hz), 2.63-2.71(2H, m), 3.31(4H, dq, J=5.6, 7.2 Hz), 4.29-4.38(2H, m), 7.15-7.20(1H, m), 7.23-7.38(7H, m), 7.41-7.47(1H, m), 7.49-7.63(4H, m), 7.64-7.75(4H, m), 7.81(1H, dd, J=1.5, 7.5 Hz), 7.86-7.93(2H, m) |
| 6-20 | 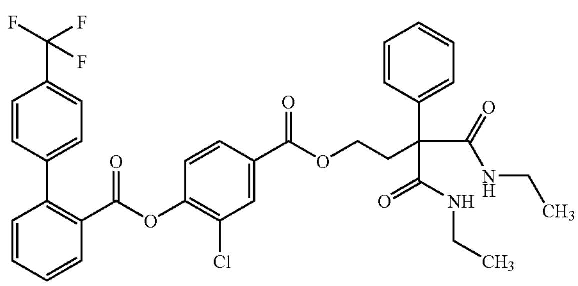 | 1.14(6H, t, J=7.1 Hz), 2.65-2.74(2H, m), 3.31(4H, dq, J=5.7, 7.1 Hz), 4.33-4.43(2H, m), 7.08(1H, d, J=8.3 Hz), 7.27-7.44(6H, m), 7.47-7.61(5H, m), 7.63-7.72(3H, m), 7.90(1H, dd, J=1.9, 8.6 Hz), 8.07(1H, d, J=1.9 Hz), 8.23(1H, dd, J=1.5, 7.9 Hz) |

TABLE 56

| Example | Structure | NMR (δ, 300 MHz, CDCl₃) |
|---|---|---|
| 6-21 | 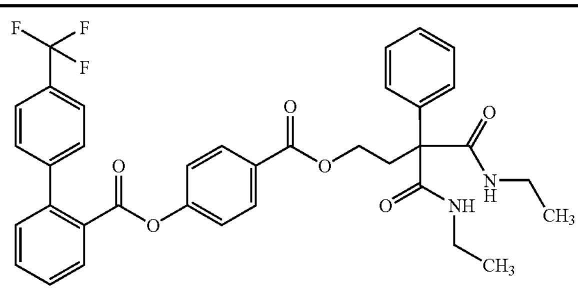 | 1.14(6H, t, J=7.2 Hz), 2.64-2.73(2H, m), 3.32(4H, dq, J=5.6, 7.2 Hz), 4.31-4.41(2H, m), 6.91-6.98(2H, m), 7.26-7.36(5H, m), 7.41(1H, dd, J=1.1, 7.5 Hz), 7.47-7.59(3H, m), 7.60-7.71(5H, m), 7.94-8.01(2H, m), 8.11(1H, dd, J=1.1, 7.5 Hz) |

TABLE 56-continued

| Example | Structure | NMR (δ, 300 MHz, CDCl₃) |
|---|---|---|
| 6-22 | 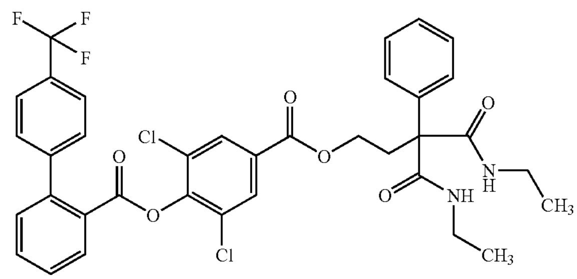 | 1.13(6H, t, J=7.2 Hz), 2.66-2.75(2H, m), 3.32(4H, dq, J=5.3, 7.2 Hz), 4.36-4.45(2H, m), 7.27-7.46(8H, m), 7.48-7.54(2H, m), 7.55-7.73(4H, m), 7.99(2H, s), 8.32(1H, dd, J=1.1, 7.9 Hz) |

Example 7

Trans-4-[(4'-trifluoromethylbiphenyl-2-carbonyl) amino]cyclohexanecarboxylic acid 2-[9-(2,2,2-trifluoroethylcarbamoyl)-9H-fluoren-9-yl]ethyl ester a) 4-[(4'-Trifluoromethylbiphenyl-2-carbonyl)amino) cyclohexanecarboxylic acid

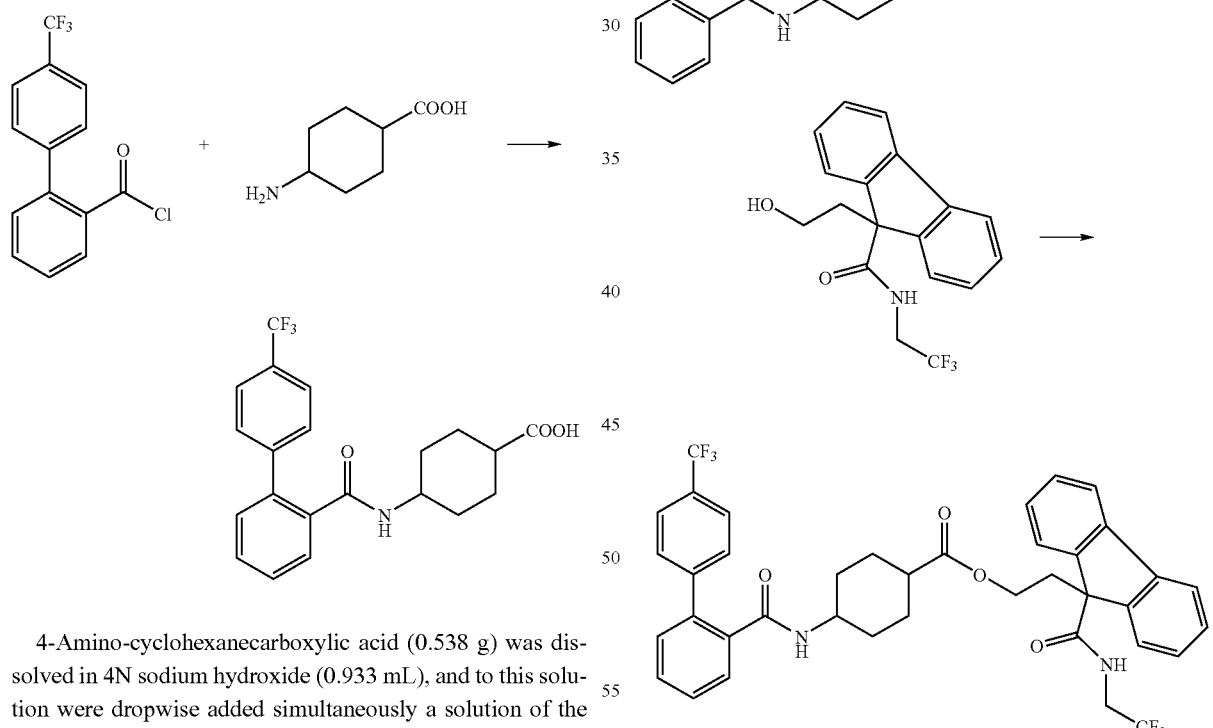

4-Amino-cyclohexanecarboxylic acid (0.538 g) was dissolved in 4N sodium hydroxide (0.933 mL), and to this solution were dropwise added simultaneously a solution of the acid chloride which is obtained from 4'-trifluoromethylbiphenyl-2-carboxylic acid (1.0 g) in a similar manner to Example 1d) in tetrahydrofuran (5 mL) and 4N aqueous sodium hydroxide (0.933 mL) under ice-cooling. The mixture was stirred at room temperature for one hour, acidified with 2N hydrochloric acid and extracted with ethylacetate. The extract was washed with saturated brine and dried over sodium sulfate to give the title compound (1.20 g) as a colorless powdery solid.

b) Trans-4-[(4'-trifluoromethylbiphenyl-2-carbonyl) amino]cyclohexanecarboxylic acid 2-[9-(2,2,2-trifluoroethylcarbamoyl)-9H-fluoren-9-yl]ethyl ester The 4-[(4'-trifluoromethylbiphenyl-2-carbonyl)amino]cyclohexanecarboxylic acid (0.570 g) obtained in Example 7a) and 9-(2-hydroxyethyl)-9H-fluoren-9-carboxylic acid (2,2,2-trifluoroethyl)amide (0.500 g) obtained in Example 6d) were treated in a similar manner to Example 1g) to give the title compound (0.534 g) as a colorless solid (see Table 57).

Examples 7-2 to 7-5

Compounds of Examples of 7-2 to 7-5 were obtained in a similar manner to Example 7. The compounds thus obtained were shown in Table 57.

TABLE 57

| Example | Structure | NMR (δ, 300 MHz, CDCl₃) |
|---|---|---|
| 7 | [structure] m.p. 156.3-158.0 | 1.08-1.20(4H, m), 1.28-1.42(4H, m), 1.87-1.94(1H, m), 2.80(2H, t, J=7.1 Hz), 3.52(2H, t, J=7.1 Hz), 3.65(1H, m), 3.89(1H, br), 5.18(1H, d, J=8.3 Hz), 5.25(1H, t, J=6.4 Hz), 7.29-7.79(16H, m). |
| 7-2 | [structure] | 0.60-0.71(2H, m), 1.05-1.27(2H, m), 1.53-1.86(4H, m), 2.82(2H, t, 6.9Hz), 3.54(2H, t, J=6.9 Hz), 3.56-3.73(2H, m), 4.96(1H, d, J=8.3 Hz), 5.27(1H, t, J=7.7 Hz), 7.30-7.80(16H, m). |
| 7-3 | [structure] | 1.33-1.73(8H, m), 2.00-2.13(1H, m), 2.22-2.37(1H, m), 2.45-2.60(1H, m), 3.52(1H, t, J=7.0 Hz), 3.66-4.11(4H, m), 5.30(1H, d, J=11.3 Hz), 5.72(1H, t, J=8.2 Hz), 7.20-7.33(13H, m). |
| 7-4 | [structure] | 1.09-1.20(2H, m), 1.24(6H, t, J=7.2 Hz), 1.36-1.53(6H, m), 2.27-2.38(1H, m), 3.82-3.95(1H, m), 4.22(4H, q, J=7.2 Hz), 4.80(2H, s), 5.21(1H, br-d, J=7.9 Hz), 7.22-7.39(6H, m), 7.42-7.57(4H, m), 7.60-7.70(3H, m) |

TABLE 57-continued

| Example | Structure | NMR (δ, 300 MHz, CDCl₃) |
|---|---|---|
| 7-5 | (structure) | 1.12-2.27(9H, m), 1.24(6H, t, J=7.2 Hz), 2.60(2H, t, J=7.2 Hz), 3.59-3.78 and 3.90-4.15(1H, m), 4.02(2H, t, J=7.2 Hz), 4.22(4H, q, J=7.2 Hz), 4.98 and 5.30(1H, each d, J=8.4 Hz), 7.18-7.22(13H, m) cis, trans mixture |

Example 8

2-Phenyl-2-(2-{4-[(4'-trifluoromethylbiphenyl-2-carbonyl)amino]piperidin-1-yl}acetoxymethyl)malonic acid diethyl ester a) 1-Benzyl-4-(4'-trifluoromethylbiphenyl-2-carbonylamino)piperidine

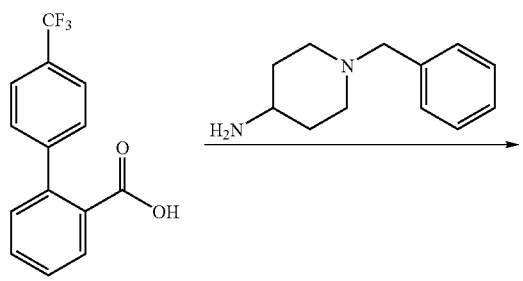

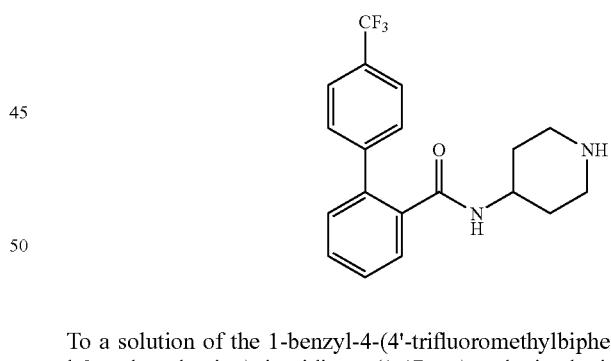

4'-Trifluoromethyl-biphenyl-carboxylic acid (5.0 g) was dissolved in dimethylformamide (50 mL), and to this solution were added at room temperature 4-amino-1-benzylpiperidine (3.55 g), 1-hydroxybenzotriazole hydrate (3.0 g) and 1-ethyl-3-(3'-dimethylaminopropyl)carbodiimide hydrochloride (3.58 g). The mixture was stirred at room temperature overnight, and the reaction solution was concentrated in vacuo to precipitate crystals. The crystals were washed successively with saturated aqueous sodium bicarbonate and water, and dried in vacuo to give the title compound (7.42 g).

b) 4-(4'-Trifluoromethylbiphenyl-2-carbonylamino)piperidine

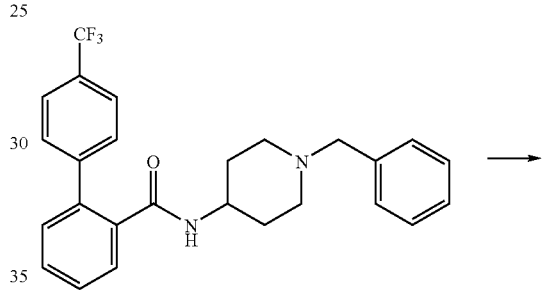

To a solution of the 1-benzyl-4-(4'-trifluoromethylbiphenyl-2-carbonylamino)piperidine (1.47 g) obtained in Example 8a) in tetrahydrofuran-methanol (1:1; 50 mL) was added palladium hydroxide (300 mg) in a stream of argon under ice-cooling. The mixture was stirred for one day at normal pressure under hydrogen atmosphere, and further stirred for one day at normal pressure under hydrogen atmosphere after further addition of palladium hydroxide (300 mg). The reaction mixture was filtered through a Celite pad and washed with methanol. The filtrate and the washings were combined, concentrated in vacuo and purified by column chromatography on silica gel with chloroform:methanol: aqueous ammonia=100:10:1 to give the title compound (1.03 g).

c) [4-(4'-Trifluoromethylbiphenyl-2-carbonyl-amino)piperidin-1-yl]acetic acid ethyl ester

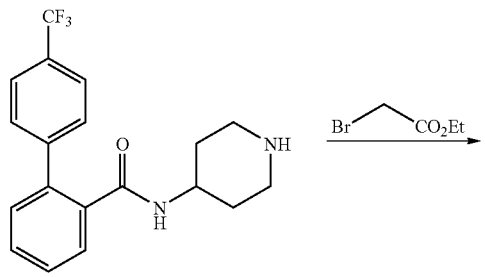

To a solution of 4-(4'-trifluoromethylbiphenyl-2-carbonylamino)piperidine (1.03 g) obtained in Example 8b) in dimethylformamide (5 mL) were added potassium carbonate (276 mg) and bromoacetic acid ethyl ester (223 μL). The mixture was stirred overnight at ambient temperature of 90° C., and then concentrated in vacuo. The residue was distributed with water and chloroform, and the aqueous layer was further extracted with chloroform. The organic layers were combined, washed with saturated brine, dried over sodium sulfate, concentrated in vacuo and purified by column chromatography on silica gel with chloroform:methanol=30:1 to give the title compound (598 mg).

d) [4-(4'-Trifluoromethylbiphenyl-2-carbonyl-amino)piperidin-1-yl]acetic acid

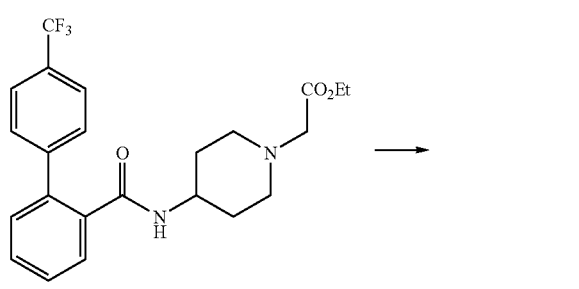

To a solution of [4-(4'-trifluoromethylbiphenyl-2-carbonylamino)piperidin-1-yl]acetic acid ethyl ester (595 mg) obtained in Example 8c) in tetrahydrofuran-methanol (1:2; 10.2 mL) was added 1M aqueous lithium hydroxide (6.8 mL), and the mixture was stirred at room temperature for 6 hours. The reaction solution was concentrated in vacuo and 2N hydrochloric acid was added to the residue to adjust the pH to about 3, thereby crystals were precipitated. The crystals were collected by filtration, washed with cold water and dried in vacuo to give the title compound (411 mg).

e) 2-Phenyl-2-(2-{4-[(4'-trifluoromethylbiphenyl-2-carbonyl)amino]piperidin-1-yl}acetoxymethyl)malonic acid diethyl ester

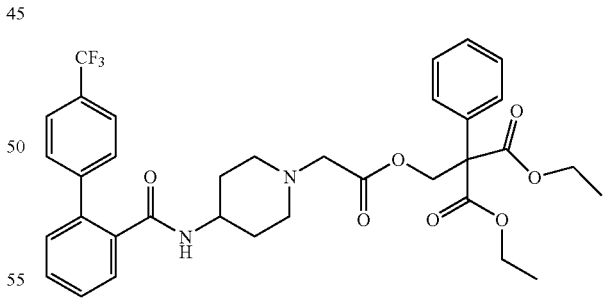

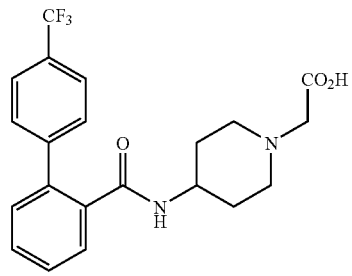

The [4-(4'-trifluoromethylbiphenyl-2-carbonyl-amino)piperidin-1-yl]acetic acid obtained in Example 8d) and the 2-hydroxymethyl-2-phenylmalonic acid diethyl ester obtained in Example 1-2a) were subjected to reactions similar to those in Example 1g) to give the title compound (90 mg) (see Table 58).

TABLE 58

| Example | Structure | NMR (δ, 300 MHz, CDCl₃) |
|---|---|---|
| 8 | 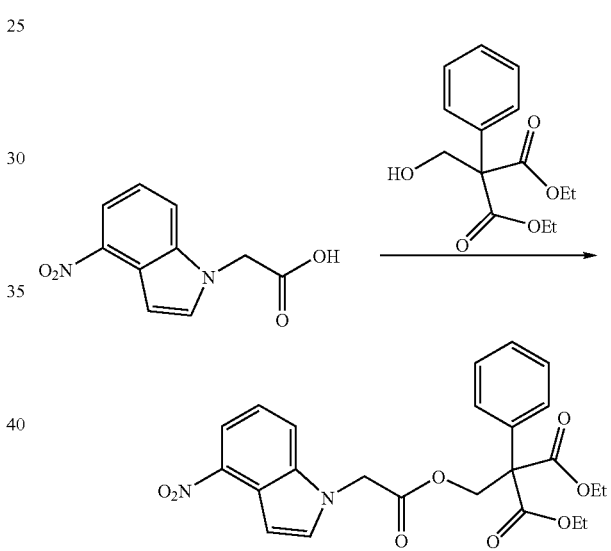 | 1.07-1.19(2H, m), 1.25(6H, t, J=7.0 Hz), 1.54-1.68(2H, m), 2.10-2.22(2H, m), 2.52-2.62(2H, m), 3.08(2H, s), 3.70-3.85(1H, m), 4.24(4H, q, J=7.0 Hz), 4.85(2H, s), 5.07-5.16(1H, m), 7.28-7.39(6H, m), 7.42-7.57(4H, m), 7.61-7.71(3H, m) |

Example 9

2-Phenyl-2-(2-{4-[(4'-trifluoromethylbiphenyl-2-carbonyl)amino]indol-1-yl}acetoxymethyl)malonic acid diethyl ester a) (4-Nitroindol-1-yl)acetic acid ethyl ester

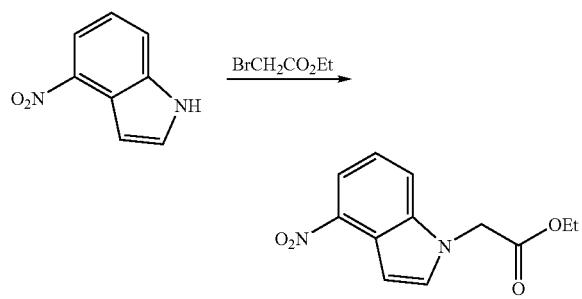

Sodium hydride (60%/mineral oil: 81 mg) was dissolved in dimethylformamide (5 mL), and the solution was cooled to 0° C. After addition of 4-nitroindole (300 mg), the mixture was stirred for one hour, and bromoacetic acid ethyl ester (340 mg) was added thereto, followed by stirring at 0° C. for 4 hours. Water was added thereto and the mixture was concentrated, diluted with ethyl acetate, washed with water, dried over sodium sulfate, then concentrated to give the title compound (367 mg)

b) (4-Nitroindol-1-yl)acetic acid

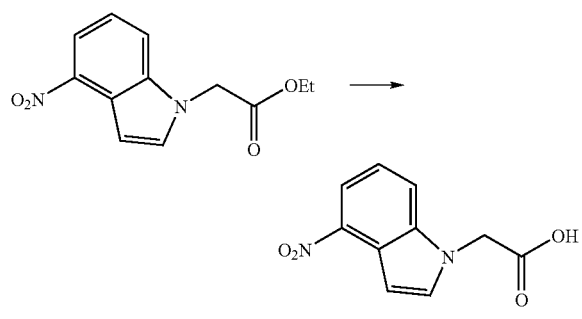

The (4-nitroindol-1-yl)acetic acid ethyl ester obtained in Example 9a) was subjected to reactions similar to those in Example 1f) to give the title compound (243 mg).

c) 2-[2-(3-Nitroindol-1-yl)acetoxymethyl]-2-phenyl-malonic acid diethyl ester

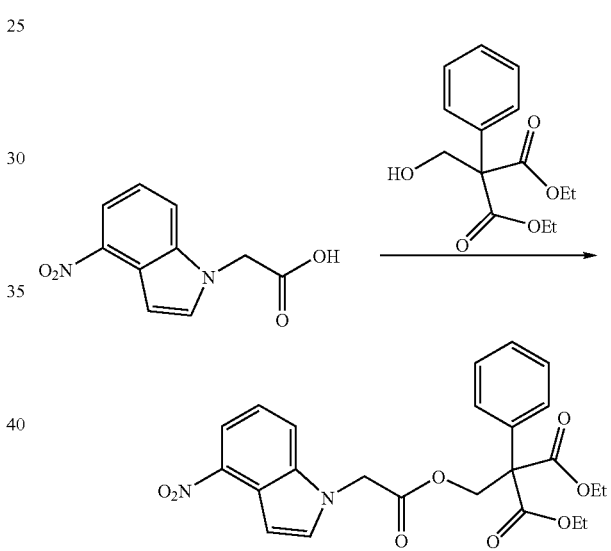

The (4-nitroindol-1-yl)acetic acid (229 mg) obtained in Example 9b), 4-dimethylaminopyridine (143 mg) and the 2-hydroxymethyl-2-phenylmalonic acid diethyl ester (240 mg) obtained in Example 1-2a) were subjected to reactions similar to those in Example 1-3c) to give the title compound (301 mg).

d) 2-[2-(4-Aminoindol-1-yl)acetoxymethyl]-2-phenylmalonic acid diethyl ester

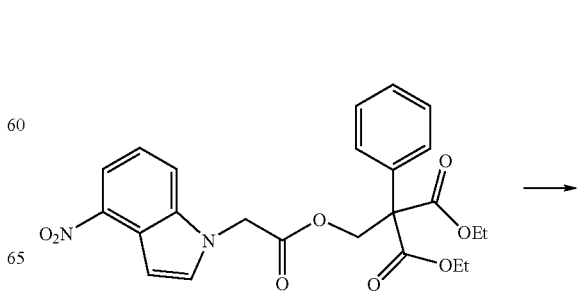

-continued

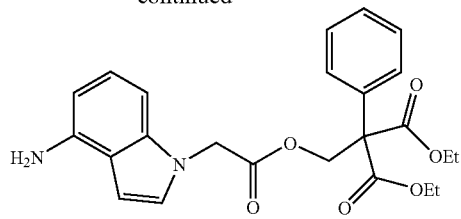

The 2-[2-(3-Nitroindol-1-yl)acetoxymethyl]-2-phenylmalonic acid diethyl ester (100 mg) obtained in Example 9c) was dissolved in tetrahydrofuran (2 mL), ethanol (4 mL) and water (1 mL), and to the solution were added ammonium chloride (57 mg) and reduced iron (60 mg). The mixture was stirred at 100° C. for 2 hours, cooled, and filtered through a Celite pad. The filtrate was concentrated and diluted with ethyl acetate. The extract was washed successively with saturated aqueous sodium bicarbonate, water and saturated brine, dried over sodium sulfate, and concentrated to give the title compound (93 mg).

e) 2-Phenyl-2-(2-{4-[(4'-trifluoromethylbiphenyl-2-carbonyl)amino]indol-1-yl}acetoxymethyl)malonic acid diethyl ester

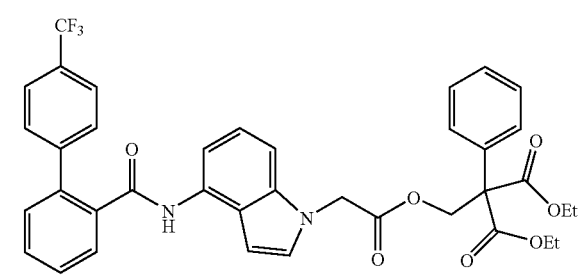

The 2-[2-(4-aminoindol-1-yl)acetoxymethyl]-2-phenyl-malonic acid diethyl ester obtained in Example 9d) was treated in a similar manner to Example 1e) to give the title compound (119 mg) (see Table 59).

Example 9-2

2-(2-{2-methyl-4-[(4'-trifluoromethylbiphenyl-2-carbonyl}amino]benzimidazol-1-yl}acetoxymethyl)-2-phenyl-malonic acid diethyl ester a) 2-Methyl-4-nitro-1H-benzimidazole

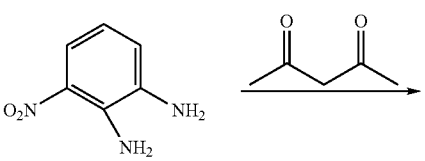

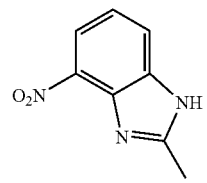

3-Nitrobenzene-1,2-diamine (1.0 g) was dissolved in ethanol (90 mL) and 5N hydrochloric acid (24 mL), and to this solution was added 2,4-pentanedione (1.3 g). The mixture was heated for 3 hours under reflux, cooled down to room temperature and concentrated. To this concentrate was added ethyl acetate, and the mixture was washed successively with saturated aqueous sodium bicarbonate and water, and dried over sodium sulfate to give the title compound (1.1 g).

b) (2-Methyl-4-nitrobenzimidazol-1-yl)acetic acid ethyl ester

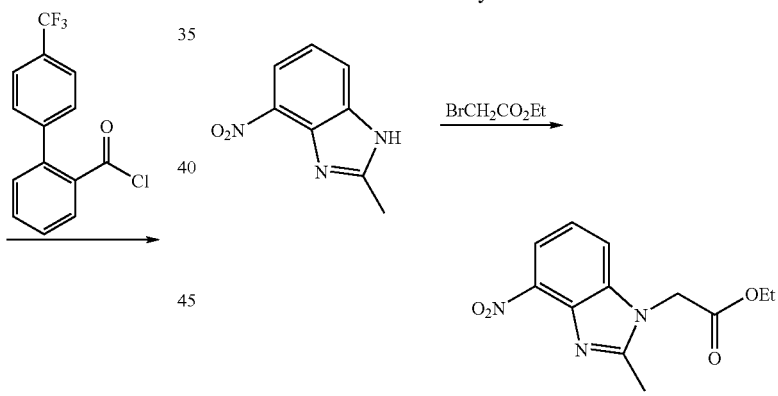

The 2-methyl-4-nitro-1H-benzimidazole (1.1 g) obtained in Example 9-2a) was subjected to reactions similar to those in Example 9a) to give the title compound (1.44 g).

c) 2-(2-{2-Methyl-4-[(4'-trifluoromethylbiphenyl-2-carbonyl)amino]benzimidazol-1-yl}acetoxymethyl)-2-phenyl-malonic acid diethyl ester

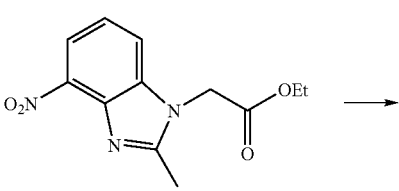

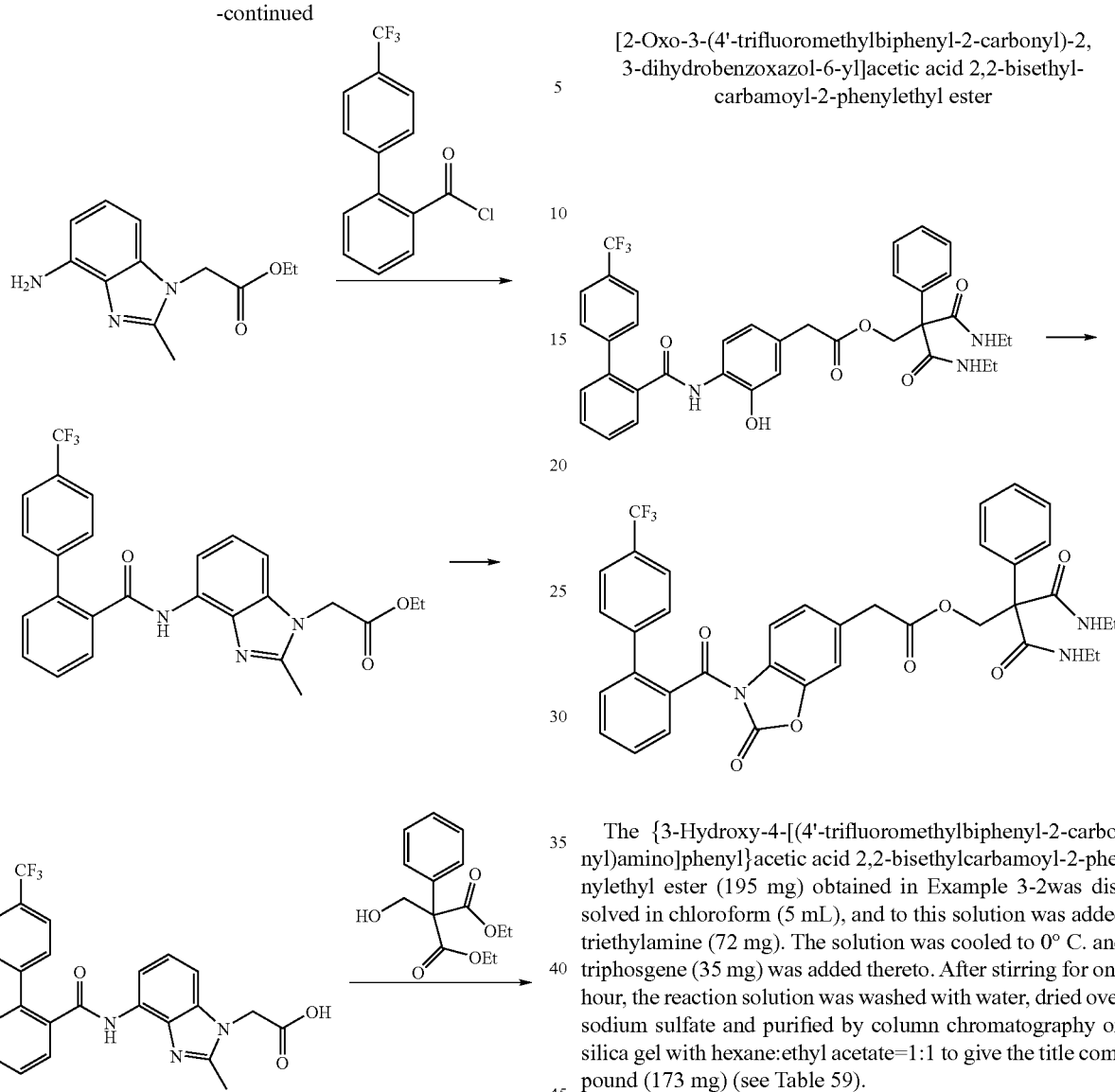

Example 9-3

[2-Oxo-3-(4'-trifluoromethylbiphenyl-2-carbonyl)-2,3-dihydrobenzoxazol-6-yl]acetic acid 2,2-bisethyl-carbamoyl-2-phenylethyl ester

The {3-Hydroxy-4-[(4'-trifluoromethylbiphenyl-2-carbonyl)amino]phenyl}acetic acid 2,2-bisethylcarbamoyl-2-phenylethyl ester (195 mg) obtained in Example 3-2 was dissolved in chloroform (5 mL), and to this solution was added triethylamine (72 mg). The solution was cooled to 0° C. and triphosgene (35 mg) was added thereto. After stirring for one hour, the reaction solution was washed with water, dried over sodium sulfate and purified by column chromatography on silica gel with hexane:ethyl acetate=1:1 to give the title compound (173 mg) (see Table 59).

Example 9-4

2-(2-{3-Ethoxycarbonyl-4-[(4'-trifluoromethylbiphenyl-2-carbonyl)amino]phenyl}acetoxymethyl)-2-phenylmalonic acid diethyl ester a) 5-Chloro-2-nitrobenzoic acid chloride

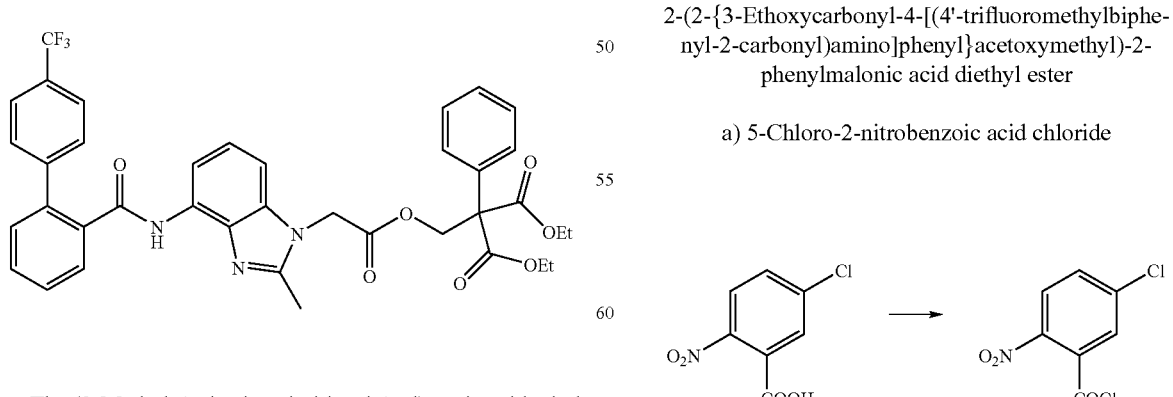

5-Chloro-2-nitrobenzoic acid was subjected to reactions similar to those in Example 1d) to give the title compound.

The (2-Methyl-4-nitrobenzimidazol-1-yl)acetic acid ethyl ester (500 mg) obtained in Example 9-2b) was subjected to reactions similar to those in Examples 9d), 1d), 1e), 1f) and 1g) to give the title compound (152 mg) (see Table 59).

b) 5-Chloro-2-nitrobenzoic acid ethyl ester

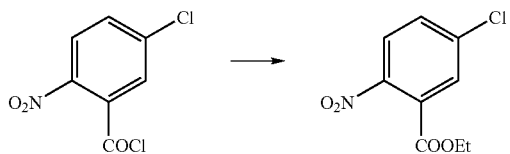

To a mixture of ethanol (1.23 mL), triethylamine (3.05 mL) and tetrahydrofuran (35 mL) was dropwise added a solution of 5-chloro-2-nitrobenzoic acid chloride (4.44 g) obtained in Example 9-4a) in tetrahydrofuran (10 mL) under ice-cooling. The mixture was stirred at room temperature overnight, and water was then added. The solution was diluted with ethyl acetate, and the organic layer was washed successively with saturated aqueous sodium bicarbonate and saturated brine, dried over sodium sulfate and concentrated to give the title compound (4.43 g) as a pale brown solid.

c) 3-Ethoxycarbonyl-4-nitrophenylmalonic acid dibenzyl ester

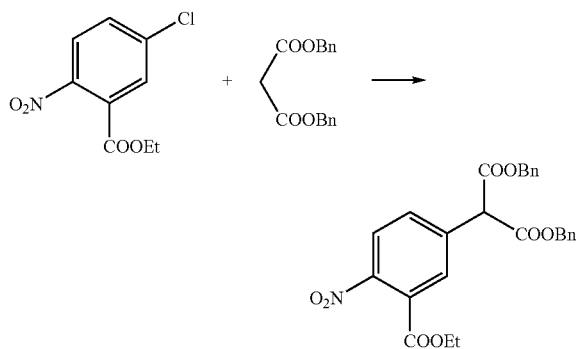

The 5-chloro-2-nitrobenzoic acid ethyl ester (4.40 g) obtained in Example 9-4b) and malonic acid dibenzyl ester were subjected to reactions similar to those in Example 1-3a) to give the title compound (4.61 g).

d) 4-Amino-3-ethoxycarbonylphenylacetic acid

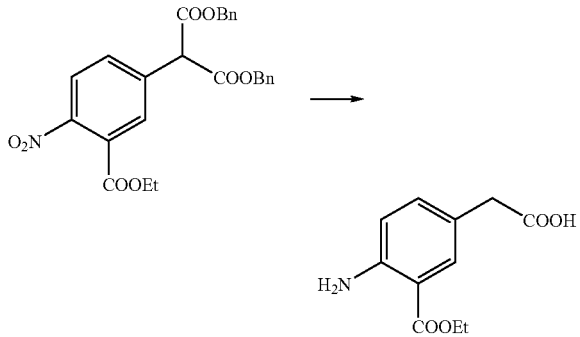

The 3-ethoxycarbonyl-4-nitrophenylmalonic acid dibenzyl ester (1.51 g) obtained in Example 9-4c) was subjected to reactions similar to those in Example 1-3d) to give the title compound (4.59 g).

e) 3-Ethoxycarbonyl-4-[(4'-trifluoromethylbiphenyl-2-carbonyl)amino]phenylacetic acid

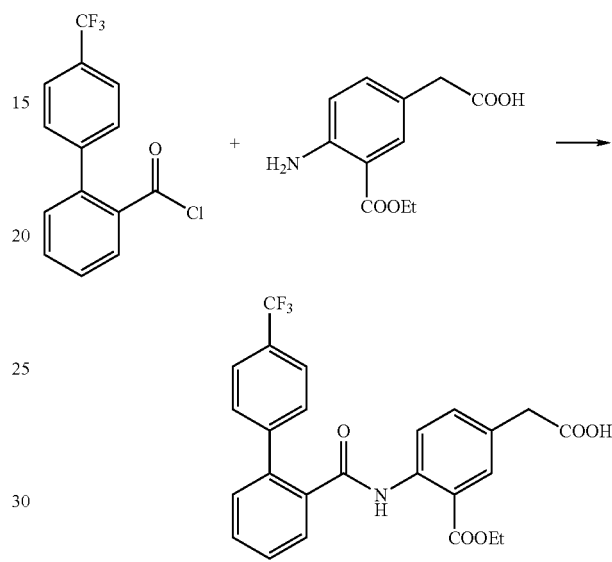

The 4-amino-3-ethoxycarbonylphenylacetic acid (1.51 g) obtained in Example 9-4d) and 4'-trifluoromethylbiphenyl-2-carboxylic acid chloride (1.99 g) were subjected to reactions similar to those in Example 7a) with the proviso that sodium bicarbonate was used as a base, thereby the title compound (1.87 g) was given as a pale yellow amorphous powder.

f) 2-(2-{3-Ethoxycarbonyl-4-[(4'-trifluoromethylbiphenyl-2-carbonyl)amino]phenyl}acetoxymethyl)-2-phenylmalonic acid diethyl ester

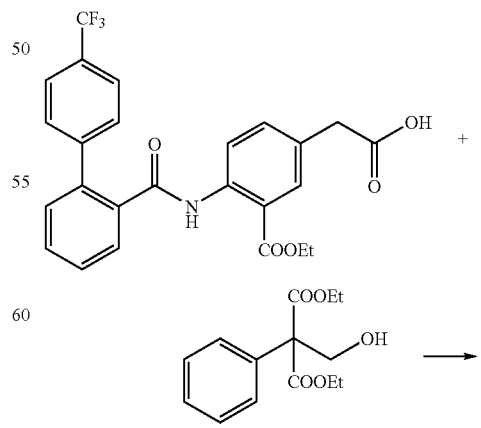

-continued

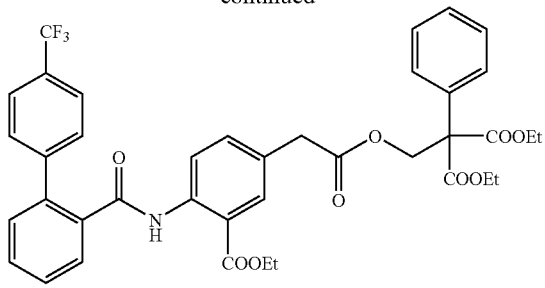

The 3-ethoxycarbonyl-4-[(4'-trifluoromethylbiphenyl-2-carbonyl)amino]phenylacetic acid (0.532 g) obtained in Example 9-4e) and the 2-hydroxymethyl-2-phenylmalonic acid diethyl ester (1.04 g) obtained in Example 1-2a) were treated in a similar manner to Example 1g) to give the title compound (0.524 g) (see Table 59).

Example 9-5

2-(3-{3-Dimethylcarbamoyl-4-[(4'-trifluoromethyl-biphenyl-2-carbonyl)-amino]-phenyl}-propionyloxymethyl)-2-phenyl-malonic acid diethyl ester a) 5-Methyl-2-nitrobenzoic acid chloride

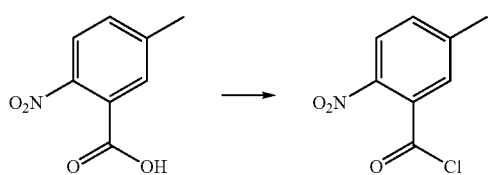

5-Methyl-2-nitrobenzoic acid was treated in a similar manner to Example 1d) to give the title compound.

b) 5, N,N-Trimethyl-2-nitrobenzamide

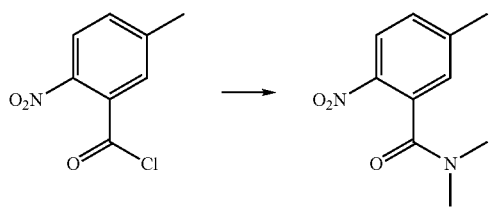

The 5-methyl-2-nitrobenzoic acid chloride obtained in Example 9-5a) was treated in a similar manner to Example 1e) to give the title compound.

c) 5-Bromomethyl-N,N-dimethyl-2-nitrobenzamide

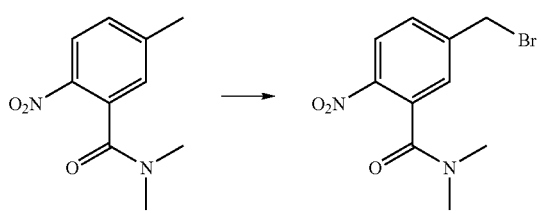

The 5, N,N-Trimethyl-2-nitrobenzamide (4.16 g) obtained in Example 9-5b), N-bromosuccinimide (3.56 g) and 2,2'-azobisisobutyronitrile (328 mg) were suspended in carbon tetrachloride (80 mL). The suspension was stirred at 90° C. for 2 hours, filtered through a Celite pad and purified by column chromatography on silica gel with hexane:ethyl acetate=5:4 to give the title compound (602 mg).

d) 3-(3-Dimethylcarbamoyl-4-nitrophenyl)-2-methoxy-carbonylpropionic acid benzyl ester

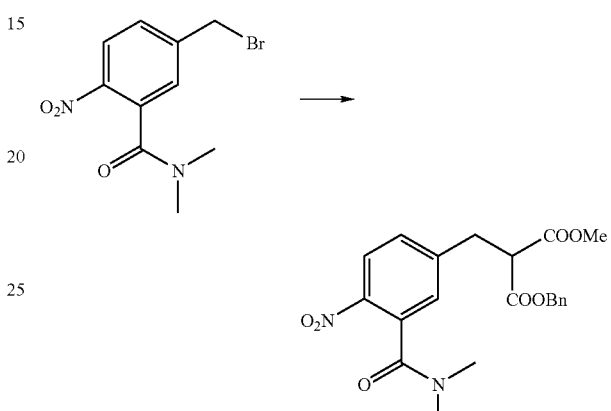

The 5-bromomethyl-N,N-dimethyl-2-nitrobenzamide (0.597 g) obtained in Example 9-5c) and malonic acid benzyl ester methyl ester were subjected to reactions similar to those in Example 9-4c) to give the title compound (0.491 g).

e) 3-(4-Amino-3-dimethylcarbamoylphenyl)-2-methoxycarbonyl-propionic acid

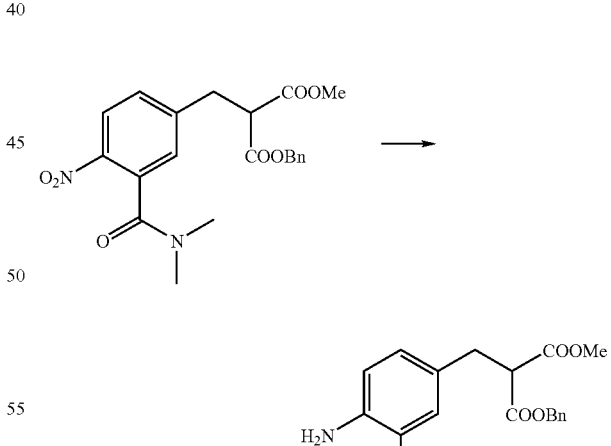

The 3-(3-dimethylcarbamoyl-4-nitrophenyl)-2-methoxy-carbonyl-propionic acid benzyl ester (0.490 g) obtained in Example 9-5d) was subjected to reactions similar to those in Example 1-2c) to give the title compound (0.353 g).

f)
3-(4-Amino-3-dimethylcarbamoylphenyl)propionic acid methyl ester

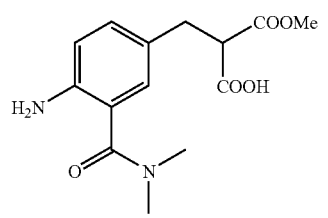

The 3-(4-amino-3-dimethylcarbamoylphenyl)-2-methoxycarbonylpropionic acid (347 mg) obtained in Example 9-5e) was stirred at 150° C. for 40 minutes, cooled down to room temperature, and purified by column chromatography on silica gel with hexane:ethyl acetate (1:1 to 0:1) to give the title compound (180 mg).

g) 2-(3-{3-Dimethylcarbamoyl-4-[(4'-trifluoromethyl-biphenyl-2-carbonyl)amino]phenyl}propionyloxymethyl)-2-phenylmalonic acid diethyl ester

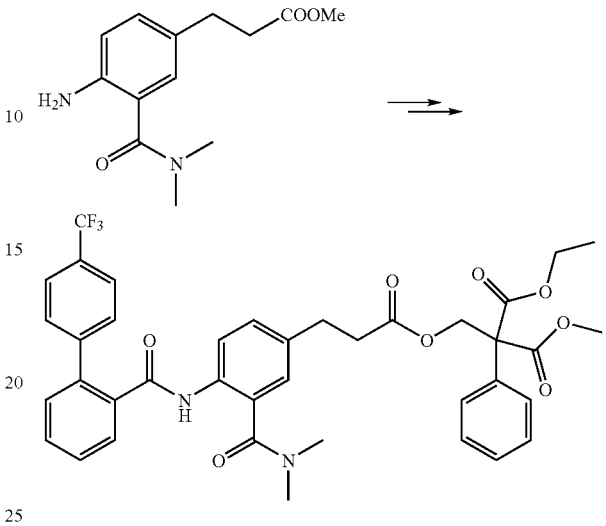

The 3-(4-amino-3-dimethylcarbamoylphenyl)propionic acid methyl ester (0.138 g) obtained in Example 9-5f) was subjected to reactions similar to those in Examples 1e), 1f) and 1g) to give the title compound (0.158 g) (see Table 59).

Examples 9-6 to 9-29

Compounds of Examples 9-6 to 9-29 were obtained in a similar manner to Examples 9 to 9-5. The compounds thus obtained were shown in Tables 59 to 64.

TABLE 59

| Example | Structure | NMR (δ, 300 MHz, CDCl$_3$) |
|---|---|---|
| 9 | 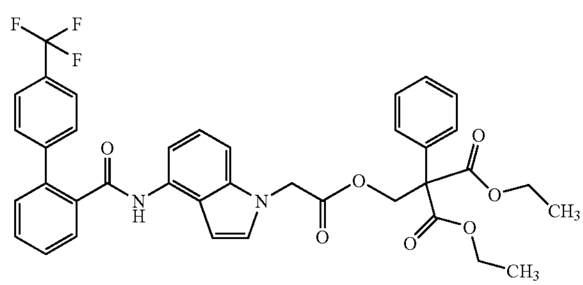 | 1.18(6H, t, J=7.2 Hz), 4.15 (4H, q, J=7.2 Hz), 4.73(2H, s), 4.85(2H, s), 5.56(1H, d, J=3.0 Hz), 6.85(1H, d, J=3.4 Hz), 6.91(1H, d, J=8.3 Hz), 7.16-7.78(16H, m), 7.92(1H, d, J=6.8 Hz) |
| 9-2 | 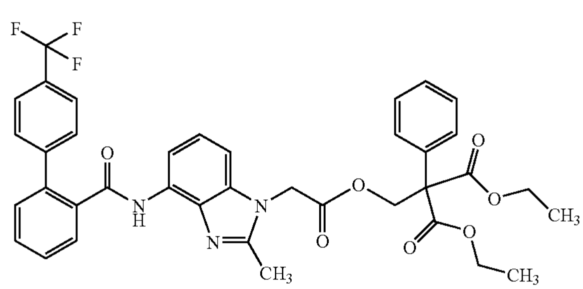 | 1.17(6H, t, J=7.1 Hz), 2.38 (3H, s), 4.13(4H, q, J=7.1 Hz), 4.70(2H, s), 4.87(2H, s), 6.84(1H, d, J=7.9 Hz), 7.12-7.63(13H, m), 7.80 (1H, dd, J=7.5, 1.5 Hz), 8.18(1H, d, J=7.9 Hz), 8.41 (1H, s) |

TABLE 59-continued

| Example | Structure | NMR (δ, 300 MHz, CDCl₃) |
|---------|-----------|--------------------------|
| 9-3 | 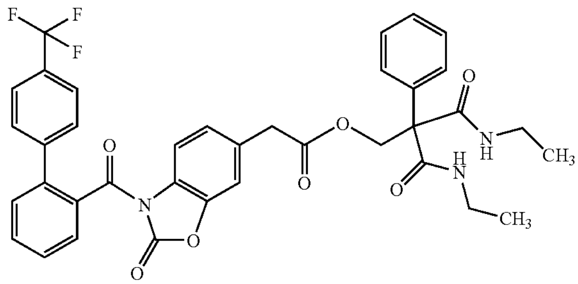 | 1.08(6H, t, J=7.2 Hz), 3.27 (4H, dq, J=7.2, 7.2 Hz), 3.61(2H, s), 4.88(2H, s), 6.93(1H, d, J=1.1 Hz), 7.04 (1H, dd, J=8.3, 1.5 Hz), 7.11-7.70(15H, m), 7.79 (1H, d, J=8.3 Hz) |
| 9-4 | 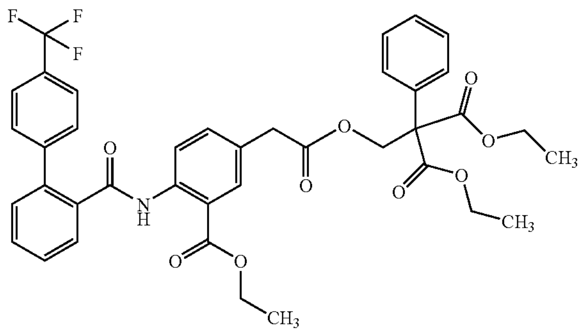 | 1.21(6H, t, J=7.1 Hz), 1.35 (3H, t, J=7.1 Hz), 3.55(2H, s), 4.15-4.30(6H, m), 4.83 (2H, s), 7.24-7.38(6H, m), 7.41-7.47(1H, m), 7.48-7.62(6H, m), 7.76 (1H, dd, J=1.5, 7.5 Hz), 7.81(1H, d, J=1.9 Hz), 8.68 (1H, d, J=8.7 Hz), 11.23 (1H, br-s) |
| 9-5 | 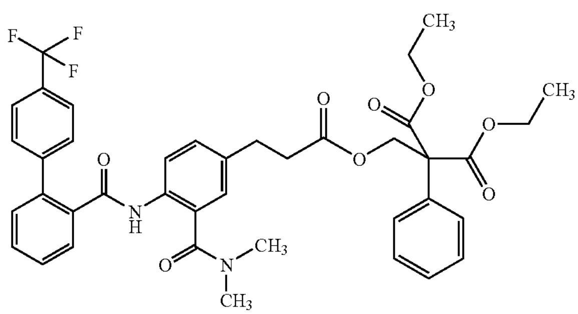 | 1.24(6H, t, J=7.0 Hz), 2.53 (2H, t, J=7.3 Hz), 2.76-3.00(6H, br), 2.81(2H, t, J=7.3 Hz), 4.24(4H, q, J=7.0 Hz), 4.81(2H, s), 6.96(1H, d, J=2.3 Hz), 7.17(1H, dd, J=1.2, 8.4 Hz), 7.29-7.37 (5H, m), 7.37-7.42(1H, m), 7.44-7.57(2H, m), 7.60-7.64(4H, m), 7.68 (1H, dd, J=1.5, 7.4 Hz), 8.28(1H, d, J=8.4 Hz), 9.05 (1H, br-s) |

TABLE 60

| Example | Structure | NMR (δ, 300 MHz, CDCl₃) |
|---------|-----------|--------------------------|
| 9-6 | 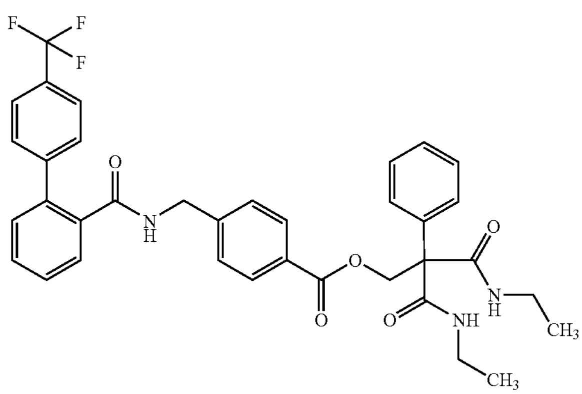 | 1.12(6H, t, J=7.2 Hz), 3.30 (4H, dq, J=5.7, 7.2 Hz), 4.39(2H, d, J=6.0 Hz), 5.08(2H, s), 5.59(1H, br-t, J=6.0 Hz), 6.97-7.03(2H, m), 7.28-7.42(8H, m), 7.43-7.55(4H, m), 7.56-7.61(2H, m), 7.66-7.71(1H, m), 7.76-7.83(2H, m) |

TABLE 60-continued

| Example | Structure | NMR (δ, 300 MHz, CDCl$_3$) |
|---|---|---|
| 9-7 | 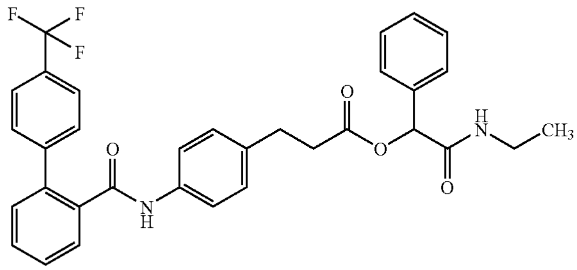 | 1.08(3H, t, J=7.2 Hz), 2.64-2.82(2H, m), 2.86-2.97(2H, m), 3.13-3.36(2H, m), 5.87-5.98(1H, br), 6.03(1H, s), 7.00(1H, s), 7.04-7.15 (4H, m), 7.30-7.40 (5H, m), 7.43(1H, dd, J=1.1, 7.5 Hz), 7.48-7.63(4H, m), 7.63-7.71(2H, m), 7.78 (1H, dd, J= 1.5, 7.5 Hz) |
| 9-8 | 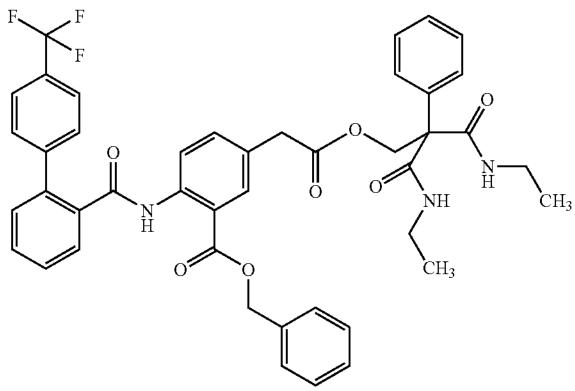 | 1.04(6H, t, J=7.2 Hz), 3.23 (4H, dq, J=5.7, 7.2 Hz), 3.55(2H, s), 4.85(2H, s), 5.23(2H, s), 7.08(2H, br-t, J= 5.7 Hz), 7.14-7.22(2H, m), 7.23-7.47(10H, m), 7.48-7.64(6H, m), 7.76(1H, dd, J=1.5, 7.1 Hz), 7.81(1H, d, J=2.2 Hz), 8.69(1H, d, J=8.7 Hz), 11.17(1H, br-s) |
| 9-9 | 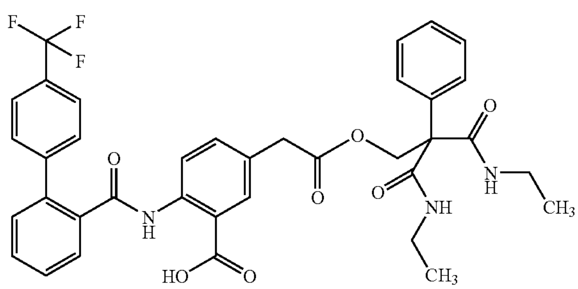 | 1.05(6H, t, J=7.2 Hz), 3.25 (4H, dq, J=5.6, 7.2 Hz), 3.58(2H, s), 4.86(2H, s), 7.11-7.63(15H, m), 7.72(1H, dd, J=1.5, 7.5 Hz), 7.83(1H, dd, J=1.9 Hz), 8.66(1H, d, J=8.6 Hz), 11.10(1H, br-s) |
| 9-10 | 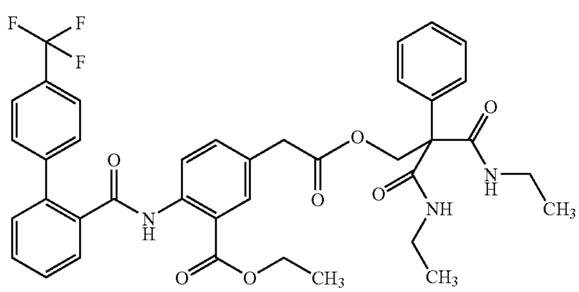 | 1.07(6H, t, J=7.2 Hz), 1.36 (3H, t, J=7.2 Hz), 3.26(4H, dq, J= 5.4, 7.2 Hz), 3.58(2H, s), 4.26(2H, q, J=7.2 Hz), 4.86(2H, s), 7.10(2H, br-t, J=5.4 Hz), 7.16-7.37(6H, m), 7.40-7.64(7H, m), 7.77(1H, dd, J=1.9, 7.1 Hz), 7.80(1H, d, J=1.9 Hz), 8.69(1H, d, J=8.7 Hz), 11.22(1H, br-s) |

TABLE 61

| Example | Structure | NMR (δ, 300MHz, CDCl₃) |
|---|---|---|
| 9-11 | 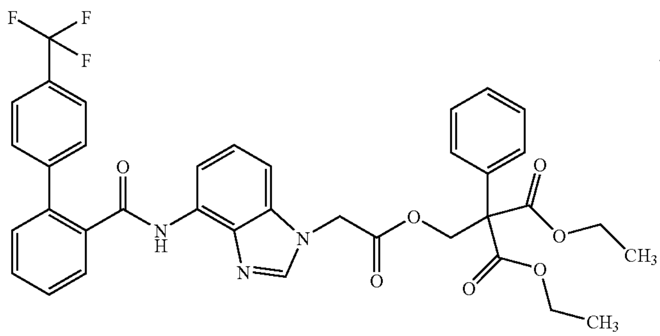 | 1.19(6H, t, J=7.2Hz), 4.17(4H, q, J=7.2Hz), 4.79(2H, s), 4.90(2H, s), 6.94(1H, d, J=8.0Hz), 7.15–7.63(13H, m), 7.82(1H, d, J=7.5Hz), 8.25(1H, d, J=8.0Hz), 8.47(1H, br.s) |
| 9-12 | m.p 139.4-141.0 | 1.15(6H, t, J=7.2Hz), 2.64–2.73(2H, m), 3.32(4H, dq, J=5.3, 7.2Hz), 4.31–4.44(2H, m), 4.41(2H, d, J=6.0Hz), 5.62(1H, br-t, J=6.0Hz), 7.10–7.16(1H, m), 7.24–7.39(7H, m), 7.42–7.58(6H, m), 7.62–7.72(3H, m), 7.74–7.78(1H, m), 7.85–7.92(1H, m) |
| 9-13 | 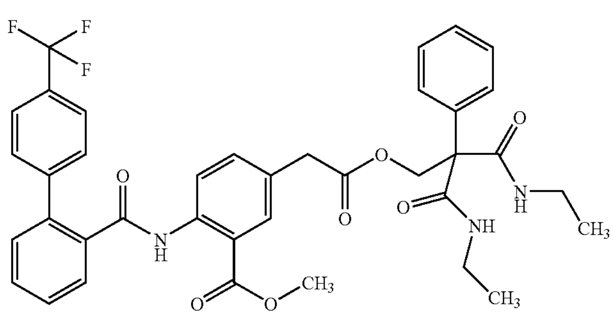 | 1.07(6H, t, J=7.1Hz), 3.26(4H, dq, J=5.7, 7.1Hz), 3.57(2H, s), 3.81(3H, s), 4.86(2H, s), 7.10(6H, br-t, J=5.7Hz), 7.16–7.23(2H, m), 7.25–7.37(4H, m), 7.41–7.63(7H, m), 7.77(1H, dd, J=1.5, 7.5Hz), 7.80(1H, d, J=2.2Hz), 8.68(1H, d, J=8.3Hz), 11.15(1H, br-s) |
| 9-14 | 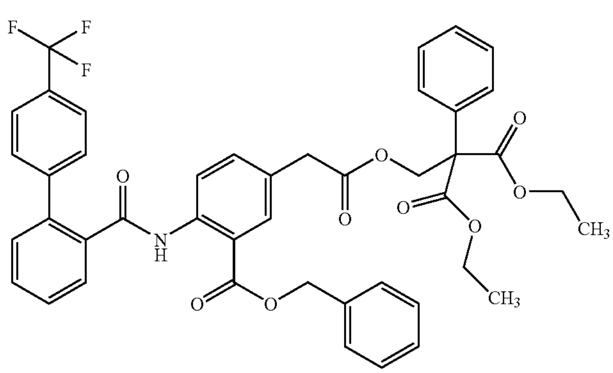 | 1.19(6H, t, J=7.0Hz), 3.52(2H, s), 4.19(4H, q, J=7.0Hz), 4.82(2H, s), 5.23(2H, s), 7.24–7.29(5H, m), 7.32–7.46(7H, m), 7.49–7.62(6H, m), 7.74–7.79(1H, m), 7.82(1H, d, J=2.2Hz), 8.67(1H, d, J=8.8Hz), 11.17(1H, br-s) |

TABLE 61-continued
| Example | Structure | NMR (δ, 300MHz, CDCl₃) |
|---|---|---|
| 9-15 | 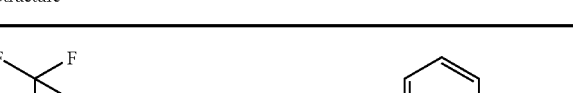 | 1.21(6H, t, J=7.1Hz), 3.56(2H, s), 4.21(4H, q, J=7.1Hz), 4.85(2H, s), 7.23–7.32(5H, m), 7.36–7.63(8H, m), 7.77(1H, dd, J=1.5, 7.5Hz), 7.86(1H, d, J=1.9Hz), 8.70(1H, br-d, J=8.3Hz), 10.89(1H, br-s) |
TABLE 62
| Example | Structure | NMR (δ, 300MHz, CDCl₃) |
|---|---|---|
| 9-16 | 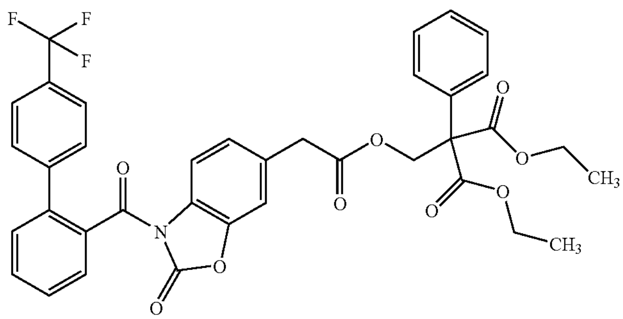 | 1.22(6H, t, J=7.1Hz), 3.57(2H, s), 4.23(4H, q, J=7.1Hz), 4.85(2H, s), 6.92(1H, s), 7.03(1H, d, J=8.3Hz), 7.30–7.69(13H, m), 7.77(1H, d, J=8.3Hz) |
| 9-17 | 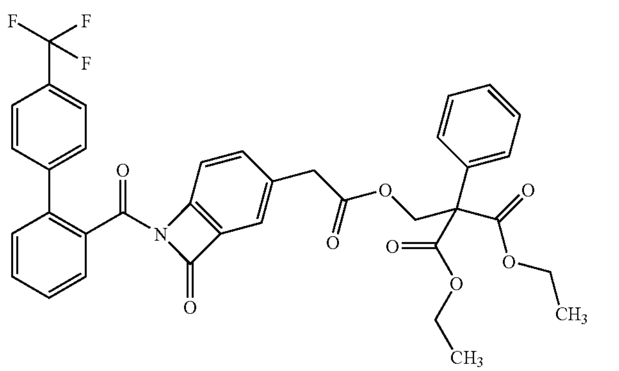 | 1.23(6H, t, J=7.1Hz), 3.67(2H, s), 4.23(4H, q, J=7.1Hz), 4.85(2H, s), 7.23–7.34(6H, m), 7.42–7.49(3H, m), 7.52–7.67(5H, m), 7.95(1H, d, J=1.9Hz), 8.05(1H, dd, J=1.5, 7.5Hz) |
| 9-18 | 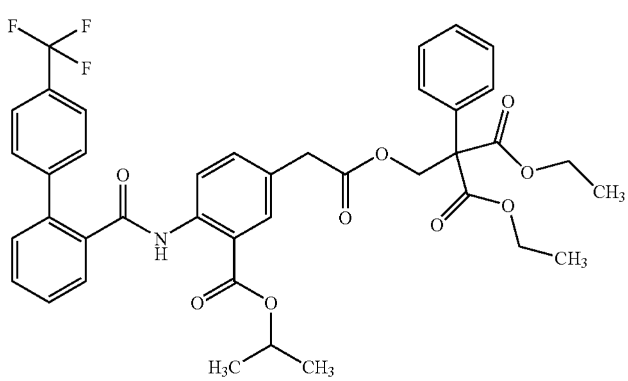 | 1.21(6H, t, J=7.2Hz), 1.31(6H, d, J=6.4Hz), 3.55(2H, s), 4.21(4H, q, J=7.2Hz), 4.83(2H, s), 5.09(1H, sept, J=6.4Hz), 7.24–7.38(6H, m), 7.41–7.47(1H, m), 7.48–7.62(6H, m), 7.73–7.81(2H, m), 8.68(1H, d, J=8.6Hz), 11.33(1H, br-s) |

TABLE 62-continued

| Example | Structure | NMR (δ, 300MHz, CDCl₃) |
|---|---|---|
| 9-19 | 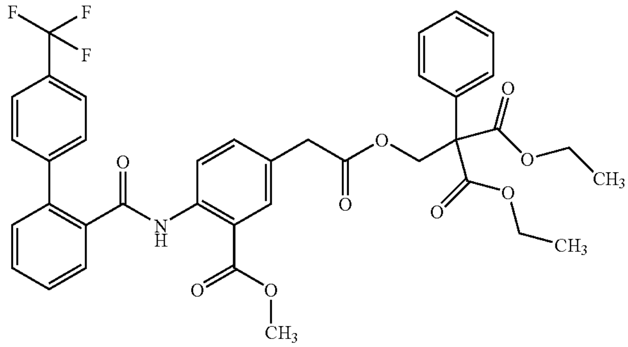 | 1.21(6H, t, J=7.1Hz), 3.54(2H, s), 3.80(3H, s), 4.21(4H, q, J=7.1Hz), 4.83(2H, s), 7.24–7.38(6H, m), 7.44(1H, dd, J=1.6, 7.1Hz), 7.50–7.62(6H, m), 7.77(1H, dd, J=1.5, 7.1Hz), 7.81(1H, d, J=2.3Hz), 8.67(1H, d, J=8.7Hz), 11.15(1H, br-s) |
| 9-20 | 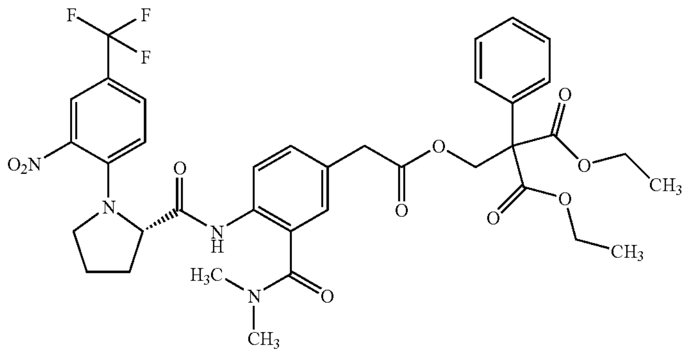 | 1.21(6H, t, J=7.1Hz), 1.85–2.03(2H, m), 2.05–2.27(2H, m), 2.50–2.67(1H, m), 2.81(3H, brs), 2.88(3H, brs), 3.02–3.16(1H, m), 3.51(2H, s), 3.71–3.86(1H, m), 4.20(4H, q, J=7.1Hz), 4.82(2H, s), 6.99(1H, d, J=9.0Hz), 7.05(1H, d, J=1.8 Hz), 7.18(1H, dd, J=1.9Hz, J=8.3Hz), 7.22–7.37(5H, m), 7.56(1H, dd, J=1.8H, J=9.0Hz), 8.01(1H, brs), 8.08(1H, d, J=8.3Hz), 9.29(1H, brs). |

TABLE 63

| Example | Structure | NMR (δ, 300MHz, CDCl₃) |
|---|---|---|
| 9-21 | 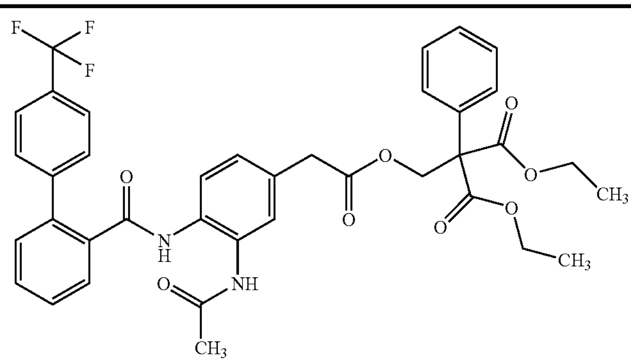 | 1.18(6H, t, J=7.1Hz), 2.03(3H, s), 3.53(2H, s), 4.14(4H, q, J=7.1Hz), 4.86(2H, s), 6.97–7.05(2H, m), 7.24–7.81(15H, m), 8.35(1H, brs). |
| 9-22 | mp 146.4-148.6 | 1.20(6H, t, J=7.2Hz), 3.52(2H, s), 3.72(3H, s), 4.18(4H, q, J=7.2Hz), 4.83(2H, s), 6.83(1H, brs), 4.95(1H, dd, J=1.8Hz, J=8.3Hz), 7.14(1H, d, J=8.3Hz), 7.18=7.80(15H, m). |

TABLE 63-continued

| Example | Structure | NMR (δ, 300MHz, CDCl₃) |
|---|---|---|
| 9-23 | 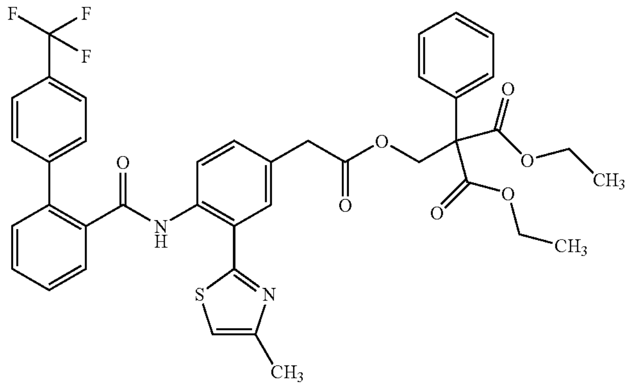 | 1.20(6H, t, J=7.1Hz), 2.36(3H, s), 3.57(2H, s), 4.20(4H, q, J=7.1Hz), 4.85(2H, s), 6.85(1H, s), 7.18–7.59(14H, m), 8.67(1H, d, J=8.6Hz), 12.71(1H, brs) |
| 9-24 | 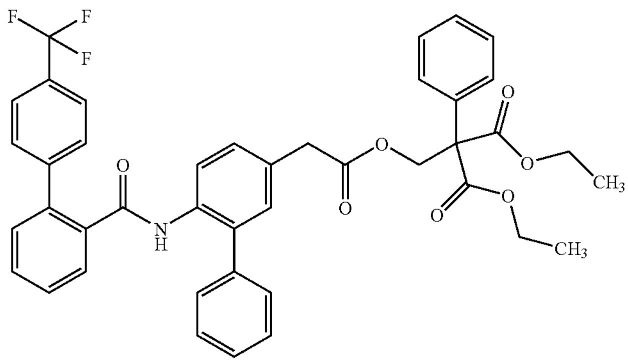 | 1.19(6H, t, J=7.2Hz), 3.53(2H, s), 4.17(4H, q, J=7.2Hz), 4.82(2H, s), 6.89–6.96(3H, m), 7.17–7.55(17H, m), 7.67(1H, dd, J=1.5, 7.5Hz), 8.45(1H, d, J=8.7Hz) |
| 9-25 | 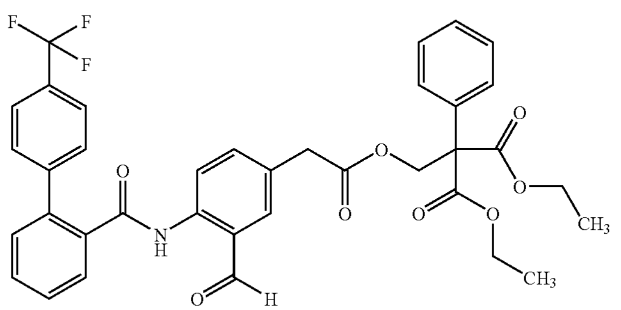 | 1.21(6H, t, J=7.1Hz), 3.59(2H, s), 4.21(4H, q, J=7.1Hz), 4.87(2H, s), 7.27–7.78(15H, m), 8.67(1H, d, J=8.3Hz), 9.61(1H, brs), 11.1(1H, brs) |

TABLE 64

| Example | Structure | NMR (δ, 300MHz, CDCl₃) |
|---|---|---|
| 9-26 | 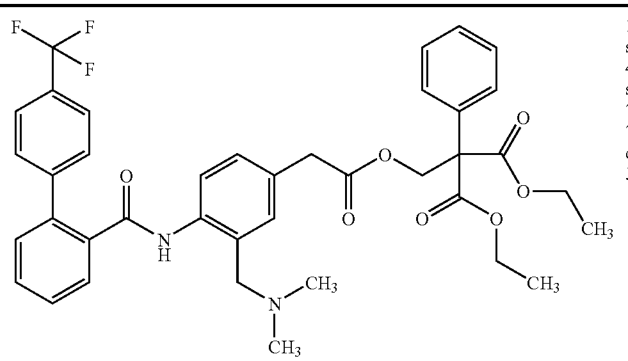 | 1.20(6H, t, J=7.0Hz), 1.94(6H, s), 3.14(2H, s), 3.48(2H, s), 4.19(4H, q, J=7.0Hz), 4.81(2H, s), 6.83(1H, d, J=2.0Hz), 7.08(1H, dd, J=2.0, 8.0Hz), 7.27–7.59(12H, m), 7.68(1H, dd, J=1.2, 7.6Hz), 8.22(1H, d, J=8.5Hz), 10.7(1H, brs) |

TABLE 64-continued

| Example | Structure | NMR (δ, 300MHz, CDCl₃) |
|---|---|---|
| 9-27 | 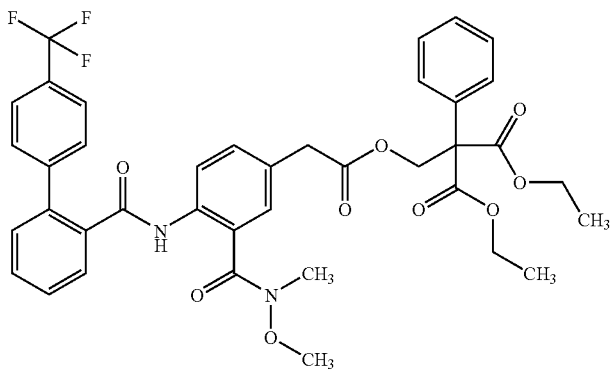 | 1.21(6H, t, J=7.1Hz), 3.20(3H, s), 3.36(3H, s), 3.52(2H, s), 4.21(4H, q, J=7.1Hz), 4.82(2H, s), 7.23–7.61(14H, m), 7.71(1H, d, J=7.3Hz), 8.31(1H, d, J=8.4Hz), 9.49(1H1, brs) |
| 9-28 | 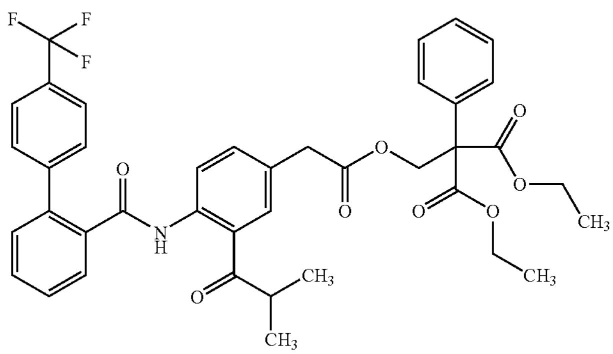 | 1.06(6H, d, J=6.9Hz), 1.20(6H, t, J=7.2Hz), 3.42–3.51(1H, m), 3.56(2H, s), 4.20(4H, q, J=7.2Hz, 4.85(2H, s), 7.28–7.77(15H, m), 8.72(1H, d, J=8.7Hz), 11.81(1H, brs) |
| 9-29 | 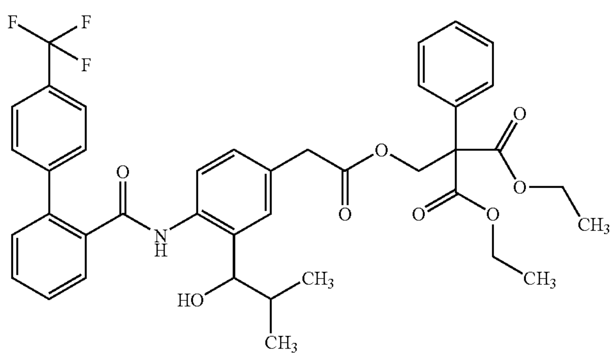 | 0.49(3H, d, J=6.6Hz), 0.90(3H, d, J=6.6Hz), 1.14–1.25(6H, m), 1.40–1.58(1H, m), 2.41(1H, d, J=3.6Hz), 3.51(2H, d, J=3.6Hz), 3.81–3.88(1H, m), 4.02–4.18(4H, m), 4.83(2H, s), 6.79(1H, s), 7.05–7.69(14H, m), 8.19(1H, d, J=8.1Hz), 9.01(1H, brs) |

TABLE 65

| Compound | structure | NMR(δ, 300MHz, CDCl₃) |
|---|---|---|
| 2e) | 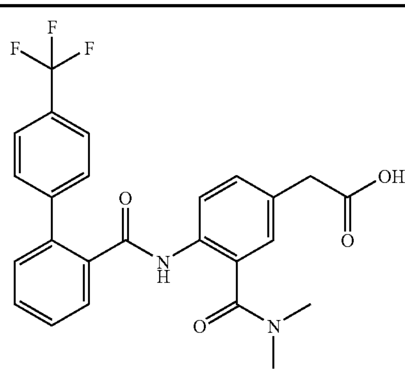 | 2.86(3H, brs), 2.93(3H, brs), 3.56(2H, s), 7.09(1H, d, J=2.0Hz), 7.23–7.71(9H, m), 8.29(1H, d, J=8.7Hz), 9.06(1H, brs). |

TABLE 65-continued

| Compound | structure | NMR(δ, 300MHz, CDCl₃) |
|---|---|---|
| 2-17 e) | (structure) | 1.75–1.99(4H, m), 3.32–3.52(4H, m), 3.53(2H, s), 7.20–7.69(10H, m), 8.22(1H, d, J=4.4Hz), 9.74(1H, brs). |

Formulation

Hereinafter, the present invention will be illustrated specifically by references of formulations.

Formulation 1

A film with a controlled thickness was prepared by use of a gelatin shell composition (a) in accordance with the conventional method. Two sheets of the film were inserted into a rotating left-right symmetric metallic die rolls and molded into outer shells of soft capsules, while a filling solution (b) was injected into the outer shells of the soft capsules, and simultaneously the outer shells of the softcapsules were melted and sealed by the rotation of the die rolls, then the capsules were cut from the film. The capsules were dried in a rotary dryer, and allowed to dry for 4 days to give soft capsules. Hereinafter, specific examples of formulations were given.

| Formulation 1-1 | |
|---|---|
| (a) film composition | |
| gelatin | 100 parts |
| sugar alcohol solution derived from corn starch | 30 parts |
| purified water | 100 parts |
| (b) filling solution (per capsule) | |
| propylene glycol fatty acid ester | 295 mg |
| ethanol | 105 mg |

| Formulation 1-2 | |
|---|---|
| (a) film composition | |
| gelatin | 100 parts |
| sugar alcohol solution derived from corn starch | 30 parts |
| purified water | 100 parts |
| (b) filling solution (per capsule) | |
| compound of Example 2-5 | 5 mg |
| propylene glycol fatty acid ester | 291 mg |
| ethanol | 104 mg |

| Formulation 1-3 | |
|---|---|
| (a) film composition | |
| gelatin | 100 parts |
| sugar alcohol solution derived from corn starch | 30 parts |
| purified water | 100 parts |
| (b) filling solution (per capsule) | |
| compound of Example 2-5 | 5 mg |
| propylene glycol fatty acid ester | 277 mg |
| ethanol | 148 mg |

Formulation 2

The compound of Example 2-22, an excipient and a binder were mixed in a usual method to prepare granulated powder. The powder obtained was blended with a disintegrator and a lubricant to prepare a powder for tablets in a usual method. The powder was compressed to give tablets in a usual method. Specific examples of formulations were hereinafter given.

| Formulation 2-1 | |
|---|---|
| compound of Example 2-22 | 5 mg |
| lactose | 133.06 mg |
| crystalline cellulose | 18 mg |
| hydroxypropyl methylcellulose 2910 | 5.4 mg |
| crospovidone | 18 mg |
| magnesium stearate | 0.54 mg |

| Formulation 2-2 | |
|---|---|
| compound of Example 2-22 | 5 mg |
| lactose | 92.44 mg |
| corn starch | 15 mg |
| hydroxypropyl methylcellulose 2910 | 3.6 mg |
| carboxymethyl starch | 3.6 mg |
| magnesium stearate | 0.36 mg |

| Formulation 2-3 | |
|---|---|
| compound of Example 2-22 | 5 mg |
| D-mannitol | 158.4 mg |
| hydroxypropyl methylcellulose 2910 | 6 mg |
| calcium silicate | 20 mg |
| crospovidone | 10 mg |
| magnesium stearate | 0.6 mg |

Pharmacological Test

Test Example 1

Inhibition of Interliposomal Triglyceride (TG) Transfer Activity by MTP

Microsomal triglyceride transfer protein (MTP) from bovine liver was partially purified in such a way described below. A buffer (50 mM Tris, 250 mM sucrose, 1 mM EDTA, 0.02% $NaN_3$ (pH 7.4)) for making a homogenate preparation was added to bovine liver, and the mixture was homogenated under ice-cooling, then centrifuged at 10,000×g (4° C., 30 minutes). The supernatant was adjusted to pH 5.1 with hydrochloric acid, and stirred for 30 minutes. The solution was further centrifuged at 10,000×g (4° C., 30 minutes), and 1 mM Tris buffer was added to the precipitated residue, and the mixture was adjusted to pH 8.6 with sodium hydroxide. After addition of 2.7M ammonium sulfate solution, the mixture was stirred for 30 minutes, then centrifuged at 10,000×g (4° C., 40 minutes). The resulting supernatant was served as a crude extraction fraction of MTP and stored at −80° C. under freezing. In its practical use, the crude extraction fraction of MTP was purified by column chromatography on diethylaminoethyl (DEAE) Sepharose using FPLC (Fast Performance Liquid Chromatography) system, and the purified MTP was used for the test.

Small unilamellar-vesicle (SUV) liposome (donor, 0.25 mol % triolein, 5 mol % cardiolipin) labeled with $^{14}C$-triolein and non-labeled SUV liposome (acceptor, 0.25 mol % triolein) were prepared. A fixed amount of donor and acceptor, and MTP were mixed with a sample dissolved in DMSO or with DMSO. The mixture was incubated in a 15 mM Tris hydrochloride buffer (pH 7.4) containing 40 mM sodium chloride, 1 mM EDTA (ethylenediaminetetraacetic acid), 0.02% $NaN_3$ and 0.5% bovine serum albumin at 37° C. for one hour. After completion of the incubation, a suspension of DEAE cellulose (50% v/v) in 15 mM Tris hydrochloride buffer (pH 7.4) was added to the above solution, and the mixture was centrifuged to separate the donor and the acceptor. The radioactivity in the acceptor was measured by liquid scintillation counter. The value obtained by subtracting the radioactivity in the blank from the amount of radioactivity in the acceptor of a DMSO group was determined as MTP-mediated TG transfer activity, and it was compared with the value obtained by subtracting the radioactivity in the blank from the radioactivity in a sample group. The blank was prepared by adding 15 mM Tris-HCl buffer (pH 7.4) in place of MTP. Inhibition rate (%) was calculated from the values obtained according to the following equation.

Inhibition rate (%)=100×(1 minus ((radioactivity of sample group minus radioactivity of blank group)/(radioactivity of DMSO group minus radioactivity of blank group))).

50% Inhibition rate ($IC_{50}$) was determined on the basis of the above equation. The results were shown in Table 66 to 70.

Test Example 2

Inhibition of Apolipoprotein B Secretion from HepG2 Cells

HepG2 cells were suspended in Dulbecco's Modified Eagle's Medium (DMEM) (containing 10% fetal bovine serum, 100 units/mL penicillin and 100 μg/mL streptomycin), and placed on a 96-well plate (4×10$^4$ cells/well), then incubated for 24 hours. After removal of the medium, DMEM was replaced by a medium containing a sample dissolved in DMSO or a medium containing DMSO (concentration of DMSO: 0.5%) and incubation was further performed for 24 hours, after which the supernatant was recovered, and concentration of apo B in the supernatant was assayed by Enzyme-Linked Immunosorbent Assay (ELISA)

ELISA was carried out as follows. Anti-human apo B monoclonal antibody (0.5 μg/well) diluted with a solution of sodium carbonate in sodium bicarbonate buffer (50 mL, pH 9.6) was placed in a 96-well plate for ELISA, and allowed to stand at room temperature for 15 hours. After washing the plate, a blocking solution (250 μL/well) was placed in the well, and allowed to stand at room temperature for 1.5 hours. After washing the plate, a standard and a sample (100 μL/well) were placed in the well and allowed to stand at room temperature for one hour. The standard was prepared by adjusting the concentration of the purified human apo B with the DMEM to 0 to 1000 ng/mL. After washing the plate, an anti-human apo B polyclonal antibody labeled with a horse radish peroxidase which was diluted in 1:1000 with DEME (100 μL/well), and allowed to stand at room temperature for one hour. After washing the plate, 2,2-azinobis(3-ethylbenzothiazoline-6-sulfonic acid) solution (100 μL/well) was placed in the well, and allowed to stand at room temperature for one hour. The reaction was stopped by addition of 2% oxalic acid (100 μL/well), and absorbency at 405 nm was measured. Concentration of apo B in the sample was calculated on the basis of a standard curve of the standard. Inhibition rate (%) was calculated from the assayed values in accordance with the following equation.

Inhibition rate (%)=100×(1 minus (concentration of apo B in sample group/concentration of apo B in DMSO group).

Based on the above equation, 50% inhibition concentration ($IC_{50}$) was determined.

The results were shown in Tables 66 to 70.

TABLE 66

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 1 | 0.6 | 5.8 | 1-2 | 42 | 850 |
| 1-3 | 4.7 | 5.75 | 1-4 | 3.4 | 190 |
| 1-5 | 0.66 | 0.65 | 1-6 | 1.2 | 5.5 |
| 1-7 | 7.55 | 330 | 1-8 | 37.5 | 720 |
| 1-9 | 5.95 | 3.2 | 1-11 | 32 | 22 |
| 1-12 | 7.6 | 63 | 1-13 | 5.8 | 170 |
| 1-14 | 82 | 55 | 1-22 | 66.5 | 179.5 |
| 1-23 | 54 | 63 | 1-25 | 5 | 8.4 |
| 1-26 | 630 | 620 | 1-27 | 7 | 26 |
| 1-28 | 35 | 640 | 1-31 | 84.5 | 61 |
| 1-32 | 8.6 | 720 | 1-34 | 23 | 100 |
| 1-35 | 1.0 | 6.9 | 1-36 | 2.0 | 150 |
| 1-37 | 3.5 | 47 | 1-38 | 6.0 | 320 |
| 1-39 | 0.66 | 160 | 1-40 | 6.9 | 2.1 |
| 1-42 | 4.4 | 35 | 1-45 | 0.39 | 0.46 |
| 1-47 | 4.5 | 750 | 1-48 | 3.2 | 9.7 |
| 1-49 | 20 | 5.3 | 1-51 | 0.96 | 530 |
| 1-52 | 10 | 690 | 1-53 | 0.43 | 860 |
| 1-62 | 5.0 | 46 | 1-63 | 16 | 90 |
| 1-66 | 16 | 9.3 | 1-67 | 27 | 28 |
| 1-69 | 9.1 | 90 | 1-70 | 1.6 | 270 |
| 1-71 | 1.8 | 120 | 1-72 | 0.44 | 2.7 |
| 1-73 | — | 39 | 1-74 | — | 680 |

TABLE 67

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 1-75 | — | 97 | 1-76 | — | 120 |
| 1-77 | — | 360 | 1-78 | — | 11 |
| 1-79 | — | 0.59 | 1-80 | — | 8.2 |
| 1-81 | — | 0.49 | 1-82 | — | 0.53 |
| 1-83 | — | 0.23 | 1-84 | — | 4.4 |
| 1-85 | — | 3.2 | — | — | — |
| 2 | 0.62 | 1.5 | 2-2 | 1.4 | 1.3 |
| 2-3 | 2.1 | 2.0 | 2-4 | 0.94 | 0.29 |
| 2-5 | 1.4 | 0.55 | 2-7 | 1.1 | 0.56 |
| 2-8 | — | 0.99 | 2-10 | — | 1.4 |
| 2-12 | — | 7.0 | 2-13 | — | 0.74 |
| 2-14 | — | 1.2 | 2-15 | — | 0.53 |
| 2-16 | — | 2.7 | 2-18 | — | 0.69 |
| 2-19 | — | 26 | 2-20 | — | 0.64 |
| 2-21 | 1.8 | 8.9 | 2-22 | 1.4 | 0.44 |
| 2-23 | 2.7 | 0.61 | 2-24 | — | 28 |
| 2-25 | — | 6.3 | 2-26 | — | 8.2 |
| 2-29 | — | 91 | 2-30 | — | 27 |
| 2-31 | — | 43 | 2-32 | — | 1.7 |
| 2-33 | — | 13 | 2-34 | — | 2.0 |
| 2-35 | — | 38 | 2-36 | — | 7.4 |
| 2-39 | 0.74 | 0.76 | 2-40 | — | 0.99 |
| 2-41 | — | 1.2 | 2-42 | — | 1.8 |

TABLE 68

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 2-43 | — | 9.0 | 2-44 | — | 33 |
| 2-45 | — | 39 | 2-46 | — | 2.9 |
| 2-47 | — | 1.2 | 2-48 | — | 0.36 |

TABLE 68-continued

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 2-49 | — | 49 | 2-50 | — | 21 |
| 2-51 | — | 47 | 2-53 | — | 4.6 |
| 2-54 | — | 8.5 | 2-55 | — | 4.2 |
| 2-56 | — | 0.93 | 2-57 | — | 0.56 |
| 2-58 | — | 1.9 | 2-59 | — | 0.99 |
| 2-60 | — | 1.3 | 2-61 | — | 0.38 |
| 2-62 | — | 0.37 | 2-66 | — | 57 |
| 2-67 | — | 43 | 2-68 | — | 2.25 |
| 2-69 | — | 0.91 | 2-70 | — | 2.34 |
| 2-71 | — | 0.54 | 2-72 | — | 0.95 |
| 2-73 | — | 2.93 | 2-74 | — | 0.84 |
| 2-75 | — | 12.54 | 2-76 | — | 0.85 |
| 2-77 | — | 2.74 | 2-78 | — | 0.14 |
| 2-79 | — | 1.3 | 2-80 | — | 0.79 |
| 2-81 | — | 0.96 | 2-82 | — | 4.41 |
| 2-83 | — | 8.87 | 2-84 | — | 2.01 |
| 2-85 | — | 0.49 | 2-86 | — | 0.42 |
| 2-88 | — | 1.92 | 2-90 | — | 1.74 |
| 2-91 | — | 0.54 | 2-92 | — | 1.47 |
| 2-93 | — | 45.8 | 2-95 | — | 18 |

TABLE 69

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 2-96 | — | 81 | 2-97 | — | 22 |
| 2-98 | — | 0.97 | 2-99 | — | 19 |
| 2-102 | — | 14.63 | 2-103 | — | 42.6 |
| 2-104 | — | 3.58 | 2-105 | — | 0.2 |
| 2-106 | — | 0.44 | 2-107 | — | 50 |
| 2-108 | — | 0.82 | 2-109 | — | 0.93 |
| 2-110 | — | 0.65 | 2-114 | — | 3.1 |
| 2-115 | — | 44 | 2-117 | — | 38 |
| 2-118 | — | 49 | — | — | — |
| 3 | — | 1.9 | 3-2 | — | 4.2 |
| 3-3 | 0.40 | 1.0 | 3-4 | 2.1 | 13 |
| 3-5 | — | 2.2 | 3-6 | 5.0 | 0.63 |
| 3-7 | — | 0.35 | 3-8 | 3.7 | 0.38 |
| 3-9 | — | 1.6 | 3-10 | 2.7 | 0.31 |
| 3-11 | — | 0.36 | 3-12 | — | 0.72 |
| 3-13 | — | 1.9 | 3-14 | 13 | 64 |
| 3-15 | — | 49.9 | — | — | — |
| 4 | — | 0.33 | 4-2 | — | 16 |
| 4-3 | — | 7.9 | 4-5 | — | 5.2 |
| 4-6 | — | 7.5 | 4-7 | — | 15 |
| 4-8 | — | 10 | — | — | — |
| 5 | 3.1 | 19 | 5-2 | 66.5 | 875 |
| 5-3 | 6.2 | 86.5 | 5-4 | 2.4 | 57 |

TABLE 70

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 5-5 | 4.5 | 5.0 | 5-6 | 3.9 | 260 |
| 5-8 | 14 | 340 | 5-9 | 4.0 | 28 |
| 5-10 | 6.2 | 300 | 5-11 | 1.3 | 5.1 |
| 5-12 | — | 1.3 | 5-13 | — | 2.4 |
| 5-14 | — | 0.34 | 5-15 | — | 6.4 |
| 5-16 | — | 3.0 | 5-17 | — | 5.2 |
| 6 | 3.47 | 58.3 | 6-3 | 5.2 | 510 |
| 6-8 | 50 | 630 | 6-10 | 22 | 870 |

TABLE 70-continued

| Example | Test Example 1 MTP inhibition IC$_{50}$ (nM) | Test Example 2 Inhibition of apo B secretion IC$_{50}$ (nM) | Example | Test Example 1 MTP inhibition IC$_{50}$ (nM) | Test Example 2 Inhibition of apo B secretion IC$_{50}$ (nM) |
|---|---|---|---|---|---|
| 6-14 | 6.3 | 87 | 6-15 | 2.0 | 57 |
| 6-16 | 2.9 | 170 | 6-17 | 2.3 | 420 |
| 6-19 | 3.2 | 35 | 6-21 | 9.8 | 920 |
| 7 | 4.97 | 60.0 | 7-2 | 2.46 | 26 |
| 7-5 | 16.2 | 237 | — | — | — |
| 8 | 33 | 595 | — | — | — |
| 9 | 11 | 260 | 9-2 | 4.2 | 450 |
| 9-3 | — | 59 | 9-4 | — | 9.9 |
| 9-5 | — | 3.1 | 9-6 | — | 59 |
| 9-8 | — | 6.9 | 9-10 | — | 2.3 |
| 9-11 | 20 | 210 | 9-13 | — | 0.53 |
| 9-14 | — | 41 | 9-17 | — | 23 |
| 9-21 | — | 20 | 9-22 | — | 0.96 |
| 9-23 | — | 8.77 | 9-24 | — | 7.86 |
| 9-27 | — | 0.82 | — | — | — |

Test Example 3

Olive Oil-Loading Test

Syrian hamsters (9-11 weeks of age) under non-fasted conditions were used in the test. Blood was collected previously from orbital venous plexus, and a sample was suspended in 0.5% methyl cellulose (vehicle) and the suspension was forced to be administered orally to the hamsters at a dose of 0.3, 1, 3 or 10 mg/2 mL/kg. Only vehicle in the same volume was administered to the control group. Olive oil (2 mL/kg) was forced to be administered orally 30 minutes after the administration of the sample, and blood was collected from orbital venous plexus 4 hours later. Plasma was recovered from the blood, and the amount of triglyceride (TG) in the plasma was determined by automatic analyzer (Hitachi Co.). The data was expressed in terms of $\Delta TG(mg/dL)$=the value at $4^{th}$ hr minus the value before administration. Inhibition rate (%) was calculated from the data obtained on the basis of the following equation.

Inhibition rate (%)=100×(1 minus $\Delta TG$ of sample group/ $\Delta TG$ of control group). The results were shown in Table 71.

TABLE 71

| Example | Test Example 3 Inhibition of fat absorption after olive oil-loading in Hamster (( )mg/kg.p.o) Inhibition rate (%) | Example | Test Example 3 Inhibition of fat absorption after olive oil-loading in Hamster (( )mg/kg.p.o) Inhibition rate (%) |
|---|---|---|---|
| 1 | 57(100) | 1-3 | 65(100) |
| 1-5 | 59(3) | 1-6 | 54(10) |
| 1-35 | 59(100) | 1-45 | 71(100) |
| 1-66 | 52(100) | 1-72 | 54(100) |
| 2 | 95(10) | 2-2 | 96(10) |
| 2-3 | 68(3) | 2-4 | 78(3) |
| 2-5 | 70(3) | 2-7 | 58(3) |
| 2-8 | 89(3) | 2-13 | 70(3) |
| 2-14 | 80(3) | 2-15 | 81(3) |
| 2-18 | 58(3) | 2-22 | 61(3) |
| 2-25 | 55(3) | 2-39 | 68(3) |
| 2-48 | 87(3) | — | — |
| 3-3 | 78(10) | 3-5 | 80(10) |
| 3-6 | 52(3) | 3-7 | 74(3) |
| 3-8 | 60(3) | 3-10 | 85(3) |
| 3-11 | 75(3) | — | — |

TABLE 71-continued

| Example | Test Example 3 Inhibition of fat absorption after olive oil-loading in Hamster (( )mg/kg.p.o) Inhibition rate (%) | Example | Test Example 3 Inhibition of fat absorption after olive oil-loading in Hamster (( )mg/kg.p.o) Inhibition rate (%) |
|---|---|---|---|
| 5-9 | 78(100) | 5-11 | 64(100) |
| 9-10 | 54(3) | 9-13 | 70(3) |

Test Example 4

Liver TG Release Inhibition Test

Syrian hamsters (9 to 11 weeks of age) which were fasted for one day were used in the test. Blood was collected previously from orbital venous plexus, and a sample was forced to be administered orally to the hamsters at a dose of 30, 100 or 300 mg/2 mL/kg, and the same amount of vehicle was administered to the control group. Triton WR 1339 (2 mL/kg) was intravenously administered to the hamsters 30 minutes after the above administration. Two hours later, blood was collected from orbital venous plexus, and plasma was separated from the blood. The amount of TG in the plasma was determined by automatic analyzer (Hitachi Co.). The data was expressed in terms of TG release velocity (mg/dL/min)= (value at $2^{nd}$ hour minus value before administration)/120. Inhibition rate (%) was calculated from the data obtained on the basis of the following equation.

Inhibition rate (%)=100×(1 minus TG release velocity of sample/TG release velocity of control group). The results were shown in Table 72.

TABLE 72

| Example No. | Test Example 4 Inhibition of liver TG release in Hamster (( )mg/kg.p.o) Inhibition rate(%) | Example No. | Test Example 4 Inhibition of liver TG release in Hamster (( )mg/kg.p.o) Inhibition rate(%) |
|---|---|---|---|
| 1 | 19(300) | 1-6 | 0(100) |
| 1-35 | 9(300) | 2-5 | 0(100) |

TABLE 72-continued

| Example No. | Test Example 4 Inhibition of liver TG release in Hamster (( )mg/kg.p.o) Inhibition rate(%) | Example No. | Test Example 4 Inhibition of liver TG release in Hamster (( )mg/kg.p.o) Inhibition rate(%) |
|---|---|---|---|
| 2-22 | 0(30) | 2-39 | 6(100) |
| 3-3 | 18(100) | — | — |

Test Example 5

Combination Use Test

Japanese white rabbits (male, 19 weeks of age, JW, purchased from Kitayama Labes Co., Ltd.) were fed previously in such a way that they were fed a high cholesterol diet (0.3% cholesterol+3% peanut oil-added RC-4, Product of Oriental Yeast Co., Ltd.) of 70 g/day under limited feeding for one day. The rabbits thus fed were used as a cholesterol-loaded rabbit model, and the grouping of such model was carried out in such a way that there might be no variation in the amount of plasma cholesterol among each group (five rabbits/group).

After collection of blood from auricular artery, compounds of Examples 2 to 5, simvastatin, and compounds of Examples 2 to 5 plus simvastatin were added to a high cholesterol diet in the dose as shown in Table below, and the rabbits were fed such diet. The rabbits were fed 70 g of each diet every morning. Blood was collected from auricular artery 6 hours after the feeding on the 4$^{th}$ day of the administration, and cholesterol level in plasma was assayed. In the table, increased amount of plasma cholesterol during from the time of grouping to the 4$^{th}$ day was shown.

TABLE 73

|  | Increased amount of total cholesterol (mg/dl) |
|---|---|
| Control | 80.0 |
| Simvastatin (1 mg/kg) | 48.6 |
| Example 2-5 (10 mg/kg) | 8.6 |
| Example 2-5 (10 mg/kg) + Simvastatin (1 mg/kg) | 2.1 |

Test Example 6

Determination of the Concentration in Plasma

Syrian hamsters (9-15 weeks of age) under non-fasted conditions were used in the test. A sample was suspended in 0.5% methyl cellulose (vehicle), and the suspension was forced to be administered orally to the hamsters at a dose of 30 or 100 mg/2 mL/kg. After a fixed period of time, blood was partly collected from orbital venous plexus, and the hamsters were subjected to laparotomy under ether anesthesia, and then blood was collected from portal vein. The blood was immediately cooled with ice to separate plasma. A portion of the plasma was extracted with an organic solvent and the supernatant was recovered. Concentration of the sample (unchanged form) and that of the metabolite in the supernatant were determined quantitatively by high performance liquid chromatography/mass spectrometry (LC/MS) comparing with chromatogram of synthetic standard.

TABLE 74

| Compound | Dose (mg/kg) | Component | Blood of portal vein (μM) | | | Peripheral blood (μM) | | |
|---|---|---|---|---|---|---|---|---|
| | | | 1 h | 2 h | 4 h | 1 h | 2 h | 4 h |
| 1-2 | 30 | Unaltered form | <0.2 | <0.2 | <0.2 | <0.2 | <0.2 | <0.2 |
| | | Metabolite | 1.6 | 2.2 | 6.7 | 0.9 | 1.3 | 2.9 |
| 1-12 | 30 | Unaltered form | <0.2 | <0.2 | <0.2 | <0.2 | <0.2 | <0.2 |
| | | Metabolite | 11.8 | 18.2 | 24.4 | 7.3 | 12.1 | 15.4 |
| 1-13 | 30 | Unaltered form | <0.2 | <0.2 | <0.2 | <0.2 | <0.2 | <0.2 |
| | | Metabolite | 11.8 | 20.6 | 27.3 | 10.9 | 16.9 | 18.3 |
| 2-5 | 30 | Unaltered form | 0.01 | 0.03 | 0.01 | <0.02 | <0.02 | <0.02 |
| | | Metabolite | 0.33 | 0.73 | 0.38 | 0.01 | 0.01 | 0.02 |

Test Example 7

Metabolic Stability Test in Liver S9 and Small Intestine S9

Human and hamster liver S9 (final concentration: 2 mg protein/mL), and human and hamster small intestine S9 (final concentration: 2 mg protein/mL) were each suspended in 100 mM potassium phosphate buffer (pH 7.4, containing β-nicotinamide adenine dinucleotide phosphate: 1.3 mM, D-glucose-6-phosphate: 3.3 mM, magnesium chloride: 3.3 mM, glucose-6-phosphate dehydrogenase: 0.4 U/mL). The suspensions were mixed with a solution of a sample (Example 2-5) in DMSO. The solutions were incubated at 37° C. for 0, 10 and 60 minutes, and an organic solvent was added thereto. The solutions were centrifuged, and the concentration of the sample (unchanged form) in the supernatant was determined by high performance liquid chromatography/mass spectrometry (LC/MS). Based on the data obtained, remaining rate (%) was calculated according to the following equation.

Remaining rate(%)=amount of sample 10 or 60 minutes after incubation/amount of sample at zero time after incubation×100

TABLE 75

|  | human | | hamster | |
|---|---|---|---|---|
|  | Remaining rate (%) after 10 min. | Remaining rate (%) after 60 min. | Remaining rate (%) after 10 min. | Remaining rate (%) after 60 min. |
| Small intestine S9 | 97.6 | 91.5 | 29.0 | 14.1 |
| Liver S9 | 7.9 | 4.3 | 2.4 | 0 |

Test Example 8

Inhibitory Activity on MTP and apo B Secretion Inhibition by Metabolites

In a similar manner to Test Examples 1 and 2, the activity of metabolites was assayed. The results were shown in Table below.

TABLE 76

| Compound | Main metabolite | MTP inhibition IC$_{50}$ (nM) | Inhibition of apo B secretion IC$_{50}$ (nM) |
|---|---|---|---|
| 1 | (structure) | >1000 | >10000 |
|  | (structure) | >1000 | >10000 |
| 1-35 | (structure) | >1000 | >10000 |
|  | (structure) | >1000 | >10000 |

TABLE 77

| Compound | Main metabolite | MTP inhibition IC$_{50}$ (nM) | Inhibition of apo B secretion IC$_{50}$ (nM) |
|---|---|---|---|
| 2-5 | (structure) | >10000 | >10000 |
|  | (structure) | >1000 | >10000 |
| 2-17 | (structure) | — | >10000 |
|  | (structure) | >1000 | >10000 |

TABLE 78

| Compound | Main metabolite | MTP inhibition IC$_{50}$ (nM) | Inhibition of apo B secretion IC$_{50}$ (nM) |
|---|---|---|---|
| 3-4 | (structure shown) | >1000 | >10000 |
|  | (structure shown) | >1000 | >10000 |

INDUSTRIAL APPLICABILITY

It is apparent from the above Test Examples 1 to 3 that novel compounds and their pharmaceutically acceptable salts of the present invention possess excellent MTP inhibition activity and also strongly inhibit absorption of triglyceride. In addition, as is apparent from Test Example 4, even when compounds of the present invention are administered at high dose, inhibition rate of liver TG release is 18-19% or lower, more effectively 9% or lower, especially effectively 0% or lower, and thus the compounds of the present invention inhibit little of liver TG release. Further, Test Example 6 reveals that active compounds after absorption in the small intestine are present in portal vein in a very small amount, and since most (8-fold to 80-fold amount) of such active compounds are metabolites, they do not reach the liver. Furthermore, it is deduced from Test Example 7 that a small amount of active compound which has reached the liver is metabolized rapidly to a metabolite. In addition, Test Example 8 proves that ester moiety of these metabolites is cleaved by hydrolysis and thus they have little or no MTP inhibitory activity. Further, Test Example 5 reveals that combination use of the compounds of the present invention with other agents for treating hyperlipidemia (statin type agents) can remarkably inhibit the increase of cholesterol and exhibit extremely excellent synergistic effect. These facts elucidate that the compounds of the present invention can be used in combination with other agents, particularly other agents for treating hyperlipidemia, arteriosclerosis, coronary artery diseases, obesity, diabetes or hypertension.

From the fact as mentioned above, it is understood that novel compounds of the present invention and their pharmaceutically acceptable salts can inhibit lipid absorption in the small intestine and further do not inhibit TG release in the liver. This means that the compounds of this invention do not inhibit MTP in the liver, but selectively inhibit MTP in the small intestine.

Therefore, selective inhibition of MTP activity in the small intestine by the compounds of the present invention should lower lipid absorption, which makes it possible to control lipoproteins such as triglyceride, cholesterol and LDL, etc. in blood or to control lipid in cells. Further, since the compounds of the present invention do not affect liver MTP, accumulation of triglyceride does not occur in the liver. Consequently, inhibition of fatty liver generation as an adverse effect might be expected. Therefore, the compounds of the present invention can be said novel MTP inhibitors having no side effects such as a fatty liver, etc. or, in other words, they are novel agents for the treatment or prophylaxis of hyperlipidemia, arteriosclerosis, coronary artery diseases, obesity, diabetes or hypertension, and further for the treatment or prophylaxis of pancreatitis, hypercholesterolemia, hypertriglyceridemia, etc., which rarely act on MTP in the liver and do substantially inhibit only MTP in the small intestine.

The invention claimed is:

1. An ester compound represented by the formula (1')

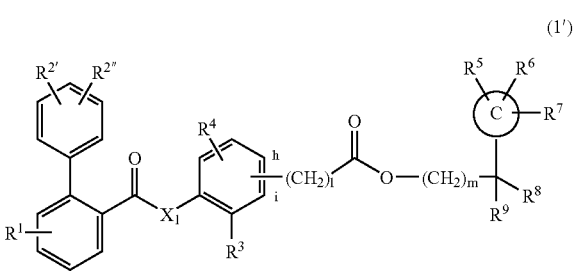

wherein
R$^{2'}$ and R$^{2''}$ are each independently hydrogen, C$_1$-C$_6$ alkyl, C$_3$-C$_7$ cycloalkyl, C$_1$-C$_6$ alkoxy, halogen, halo C$_1$-C$_6$ alkyl, C$_1$-C$_6$ acyl, C$_2$-C$_6$ alkenyl, or cyano;
X$_1$ is —O— or —NR$^{10}$— wherein R$^{10}$ is hydrogen, C$_1$-C$_6$ alkyl, or C$_3$-C$_7$ cycloalkyl;

$R^1$ is hydrogen, $C_1$-$C_6$ alkyl, $C_3$-$C_7$ cycloalkyl, $C_1$-$C_6$ alkoxy, halo $C_1$-$C_6$ alkyl, halo $C_1$-$C_6$ alkyloxy, optionally substituted $C_6$-$C_{14}$ aryl, optionally substituted $C_7$-$C_{16}$ aralkyl, optionally substituted $C_6$-$C_{14}$ aryloxy, optionally substituted $C_7$-$C_{16}$ aralkyloxy, optionally substituted $C_7$-$C_{15}$ arylcarbonyl, $C_2$-$C_7$ alkoxycarbonyl, halogen, $C_2$-$C_6$ alkenyl, —N($R^{40}$)($R^{41}$) wherein $R^{40}$ and $R^{41}$ are each independently hydrogen or optionally substituted $C_6$-$C_{14}$ aryl, $R^3$ and $R^4$ are each independently hydrogen, hydroxy, halogen, optionally substituted $C_1$-$C_6$ alkyl, $C_1$-$C_6$ alkoxy, halo $C_1$-$C_6$ alkyl, $C_7$-$C_{16}$ aralkyloxy, $C_1$-$C_6$ acyl, CON($R^{11}$)($R^{12}$) (wherein $R^{11}$ and $R^{12}$ are each independently hydrogen, $C_1$-$C_6$ alkyl, optionally substituted $C_6$-$C_{14}$ aryl, optionally substituted $C_7$-$C_{16}$ aralkyl, or $C_1$-$C_6$ alkoxy), —(CH$_2$)$_g$—N($R^{13}$)($R^{14}$) (wherein $R^{13}$ and $R^{14}$ are each independently hydrogen, $C_1$-$C_6$ alkyl, $C_2$-$C_7$ alkoxycarbonyl, or $C_1$-$C_6$ acyl, and q is an integer of 0 to 3), or —CO($R^{15}$) (wherein $R^{15}$ is hydroxy, $C_1$-$C_6$ alkoxy, optionally substituted $C_6$-$C_{14}$ aryloxy, optionally substituted $C_7$-$C_{16}$ aralkyloxy or $C_1$-$C_6$ alkyl);

l is an integer of 0 to 3;

m is an integer of 0 to 3;

$R^5$, $R^6$, and $R^7$ are each independently hydrogen $C_1$-$C_6$ alkyl, $C_1$-$C_6$ alkoxy, $C_2$-$C_7$ alkoxycarbonyl, carboxyl, halogen, cyano, nitro, halo $C_1$-$C_6$ alkyl, $C_1$-$C_6$ acyl, hydroxy, amino, optionally substituted $C_6$-$C_{14}$ aryl, or —(CH$_2$)$_r$—CON($R^{16}$)($R^{17}$) (wherein $R^{16}$ and $R^{17}$ are each independently hydrogen, $C_1$-$C_6$ alkyl, or halo $C_1$-$C_6$ alkyl and r is an integer of 0 to 3);

ring C is $C_6$-$C_{14}$ aryl, $C_7$-$C_{15}$ arylcarbonylamino, $C_8$-$C_{17}$ aralkylcarbonylamino, $C_3$-$C_7$ cycloalkyl, or $C_7$-$C_{16}$ aralkyl, or ring C may be taken together with $R^7$ and $R^8$ to form

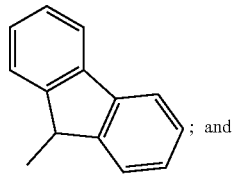; and $R^8$ and $R^9$ are each independently hydrogen, $C_1$-$C_6$ alkyl, optionally substituted $C_6$-$C_{14}$ aryl, hydroxy $C_1$-$C_6$ alkyl, —CON($R^{18}$)($R^{19}$) (wherein $R^{18}$ and $R^{19}$ are each independently hydrogen, $C_1$-$C_6$ alkyl, $C_3$-$C_7$ cycloalkyl, halo $C_1$-$C_6$ alkyl, $C_2$-$C_{12}$ alkoxyalkyl, or optionally substituted $C_6$-$C_{14}$ aryl), —COO($R^{20}$), or —(CH$_2$)$_s$—OCO($R^{20}$) (wherein $R^{20}$ is hydrogen, $C_1$-$C_6$ alkyl, or $C_3$-$C_7$ cycloalkyl, s is an integer of 0 to 3), —N($R^{21}$)($R^{22}$) (wherein $R^{21}$ and $R^{22}$ are each independently hydrogen, $C_1$-$C_6$ alkyl, $C_1$-$C_6$ acyl, or $C_1$-$C_6$ alkylsulfonyl), or $R^8$ and $R^9$ may be taken together to form $C_3$-$C_7$ cycloalkyl, or a pharmaceutically acceptable salt thereof.

2. The ester compound or a pharmaceutically acceptable salt thereof according to claim 1, wherein the ring C is

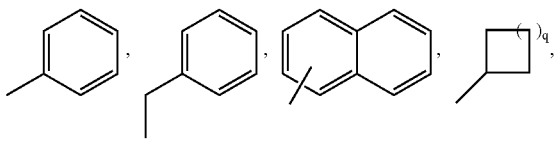

in which q is an integer of 0 to 3.

3. The ester compound or a pharmaceutically acceptable salt thereof according to claim 2, wherein $X_1$ is —$NR^{10}$—.

4. The ester compound or a pharmaceutically acceptable salt thereof according to claim 2, wherein $X_1$ is —O—.

5. The ester compound or a pharmaceutically acceptable salt thereof according to claim 1, wherein the group —(CH$_2$)$_l$— is located at the h-position of the benzene ring in the formula (1').

6. The ester compound or a pharmaceutically acceptable salt thereof according to claim 1, wherein the group —(CH$_2$)$_l$— is located at the i-position of the benzene ring in the formula (1').

7. The ester compound or a pharmaceutically acceptable salt thereof according to claim 1, wherein $R^8$ and $R^9$ are each —CON($R^{18}$)($R^{19}$)— or $R^8$ and $R^9$ are each —COO($R^{20}$)—.

8. The ester compound or a pharmaceutically acceptable salt thereof according to claim 3, wherein the ring C is

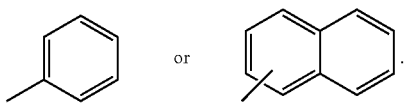

9. The ester compound or a pharmaceutically acceptable salt thereof according to claim 8, wherein ring C is phenyl.

10. The ester compound or a pharmaceutically acceptable salt thereof according to claim 3, wherein the ring C is

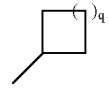

and q is an integer of 0 to 3.

11. An ester compound or a pharmaceutically acceptable salt thereof, which is selected from the group consisting of 2-(2-{3-methyl-4-[(4'-trifluoromethyl-biphenyl-2-carbonyl)-amino]-phenyl}-acetoxymethyl)-2-phenyl-malonic acid diethyl ester, 2-(2-{4-[methyl-(4'-trifluoromethyl-biphenyl-2-carbonyl)-amino]-phenyl}-acetoxymethyl)-2-phenyl-malonic acid diethyl ester, 2-phenyl-2-(2-{4-[(4'-trifluoromethyl-biphenyl-2-carbonyl)-amino]-phenyl}-acetoxymethyl)-malonic acid diethyl ester, 2-phenyl-2-(2-{4-[(4'-trifluoromethyl-biphenyl-2-carbonyl)-amino]-phenyl}-acetoxymethyl)-malonic acid diisopropyl ester, 2-phenyl-2-(2-{4-[(4'-trifluoromethyl-biphenyl-2-carbonyl)-amino]-phenyl}-acetoxymethyl)-malonic acid dimethyl ester, 2-cyclophentyl-2-(2-{4-[(4'-trifluoromethyl-biphenyl-2-carbonyl)-amino]-phenyl}-acetoxymethyl)-malonic acid diethyl ester, 2-phenyl-2-(2-{4-[(4'-trifluoromethyl-biphenyl-2-carbonyl)-amino]-phenyl}-acetoxymethyl)-malonic acid dicyclohexyl ester, 2-benzyl-2-(2-{4-[(4'-trifluoromethyl-biphenyl-2-carbonyl)-amino]-phenyl}-acetoxymethyl)-malonic acid diethyl ester, 2-(2-{2-methyl-4-[(4'-trifluoromethyl-biphenyl-2-carbonyl)-amino]-phenyl}-acetoxymethyl)-2-phenyl-malonic acid diethyl ester, 2-cyclohexyl-2-(2-{4-[(4'-trifluoromethyl-biphenyl-2-carbonyl)-amino]-phenyl}-acetoxymethyl)-malonic acid diethyl ester, 2-phenyl-2-(2-{2-trifluoromethyl-4-[(4'-trifluoromethyl-biphenyl-2-carbonyl)-amino]-phenyl}-acetoxymethyl)-malonic acid diethyl ester,
2-phenyl-2-(2-{3-trifluoromethyl-4-[(4'-trifluoromethyl-biphenyl-2-carbonyl)-amino]-phenyl}-acetoxymethyl)-malonic acid diethyl ester,
2-(2-{4-[(4'-methyl-biphenyl-2-carbonyl)-amino]-phenyl}-acetoxymethyl)-2-phenyl-malonic acid diethyl ester,
2-(2-{4-[(4'-methoxy-biphenyl-2-carbonyl)-amino]-phenyl}-acetoxymethyl)-2-phenyl-malonic acid diethyl ester,
2-phenyl-2-(2-{4-[(3'-trifluoromethyl-biphenyl-2-carbonyl)-amino]-phenyl}-acetoxymethyl)-malonic acid diethyl ester,
2-(2-{4-[isopropyl-(4'-trifluoromethyl-biphenyl-2-carbonyl)-amino]-phenyl}-acetoxymethyl)-2-phenyl-malonic acid diethyl ester,
2-(2-{4-[cyclohexyl-(4'-trifluoromethyl-biphenyl-2-carbonyl)-amino]-phenyl}-acetoxymethyl)-2-phenyl-malonic acid diethyl ester,
2-phenyl-2-(2-{4-[(4'-trifluoromethyl-biphenyl-2-carbonyl)-amino]-phenyl}-acetoxymethyl)-malonic acid dipropyl ester,
2-phenyl-2-(2-{4-[(4'-trifluoromethyl-biphenyl-2-carbonyl)-amino]-phenyl}-acetoxymethyl)-malonic acid diisobutyl ester,
2-(2-{4-[ethyl-(4'-trifluoromethyl-biphenyl-2-carbonyl)-amino]-phenyl}-acetoxymethyl)-2-phenyl-malonic acid diethyl ester,
2-(2-{3-ethyl-4-[(4'-trifluoromethyl-biphenyl-2-carbonyl)-amino]-phenyl}-acetoxymethyl)-2-phenyl-malonic acid diethyl ester,
2-(2-{3-isopropyl-4-[(4'-trifluoromethyl-biphenyl-2-carbonyl)-amino]-phenyl}-acetoxymethyl)-2-phenyl-malonic acid diethyl ester,
2-(2-{3-isobutyl-4-[(4'-trifluoromethyl-biphenyl-2-carbonyl)-amino]-phenyl}-acetoxymethyl)-2-phenyl-malonic acid diethyl ester,
2-(2-{3-chloro-4-[(4'-trifluoromethyl-biphenyl-2-carbonyl)-amino]-phenyl}-acetoxymethyl)-2-phenyl-malonic acid diethyl ester,
2-(2-{3-bromo-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{3-diethylcarbamoyl-4-[(4'-trifluoromethyl-biphenyl-2-carbonyl)-amino]-phenyl}-acetoxymethyl)-2-phenyl-malonic acid diethyl ester,
2-(2-{3-diisopropylcarbamoyl-4-[(4'-trifluoromethyl-biphenyl-2-carbonyl)-amino]-phenyl}-acetoxymethyl)-2-phenyl-malonic acid diethyl ester,
2-(2-{3-(ethyl-methylcarbamoyl)-4-[(4'-trifluoromethyl-biphenyl-2-carbonyl)-amino]-phenyl}-acetoxymethyl)-2-phenyl-malonic acid diethyl ester,
2-[2-(2-{3-dimethylcarbamoyl-4-[(4'-trifluoromethyl-biphenyl-2-carbonyl)-amino]-phenyl}-acetoxy)-ethyl]-2-phenyl-malonic acid diethyl ester,
2-(2-{3-dimethylcarbamoyl-4-[(4'-fluoro-biphenyl-2-carbonyl)-amino]-phenyl}-acetoxymethyl)-2-phenyl-malonic acid diethyl ester,
2-(2-{4-[(4'-bromo-biphenyl-2-carbonyl)-amino]}-3-dimethylcarbamoyl-phenyl}-acetoxymethyl)-2-phenyl-malonic acid diethyl ester,
2-(2-{3-[dimethylcarbamoyl-4-[(4'-trifluoromethyl-biphenyl-2-carbonyl)-amino]-phenyl}-acetoxymethyl)-2-phenyl-malonic acid dimethyl ester,
2-cyclopentyl-2-(2-{3-dimethylcarbamoyl-4-[(4'-trifluoromethyl-biphenyl-2-carbonyl)-amino]-phenyl}-acetoxymethyl)-malonic acid diethyl ester,
2-cyclohexyl-2-(2-{3-dimethylcarbamoyl-4-[(4'-trifluoromethyl-biphenyl-2-carbonyl)-amino]-phenyl}-acetoxymethyl)-malonic acid diethyl ester,
2-(2-{4-[(4'-chloro-biphenyl-2-carbonyl)-amino]-3-dimethylcarbamoyl-phenyl}-acetoxymethyl)-2-phenyl-malonic acid diethyl ester,
2-(2-{4-[(4'-acetyl-biphenyl-2-carbonyl)-amino]-3-dimethylcarbamoyl-phenyl}-acetoxymethyl)-2-phenyl-malonic acid diethyl ester,
2-(2-{4-[(4'-cyano-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(4-methyl-4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(5-methyl-4'-trifluoromethyl-biphenyl-2-carbonyl)-amino]-phenyl}-acetoxymethyl)-2-phenyl-malonic acid diethyl ester,
2-[3-(2-{3-dimethylcarbamoyl-4-[(4'-trifluoromethyl-biphenyl-2-carbonyl)-amino]-phenyl}-acetoxy)-propyl]-2-phenyl-malonic acid diethyl ester,
2-(2-{3-dimethylcarbamoyl-4-[(5-methoxy-4'-trifluoromethyl-biphenyl-2-carbonyl)-amino]-phenyl}-acetoxymethyl)-2-phenyl-malonic acid diethyl ester,
2-(2-{4-[(5-chloro-4'-trifluoromethyl-biphenyl-2-carbonyl)-amino]-3-dimethylcarbamoyl-phenyl}-acetoxymethyl)-2-phenyl-malonic acid diethyl ester,
2-(2-{3-dimethylcarbamoyl-4-[(6-methyl-4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(2'-fluoro-4'-trifluoromethyl-biphenyl-2-carbonyl)-amino]-phenyl}-acetoxymethyl)-2-phenyl-malonic acid diethyl ester,
2-(2-{5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester,
2-(2-{3-bromo-5-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{3-chloro-5-dimethylcarbamoyl-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(3'-fluoro-4'-trifluoromethyl-biphenyl-2-carbonyl)-amino]-phenyl}-acetoxymethyl)-2-phenyl-malonic acid diethyl ester,
2-(2-{4-[(3'-chloro-4'-trifluoromethyl-biphenyl-2-carbonyl)-amino]-3-dimethylcarbamoyl-phenyl}-acetoxymethyl)-2-phenyl-malonic acid diethyl ester,
2-(2-{3-chloro-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester,
2-(2-{3-bromo-5-dimethylcarbamoyl-2-fluoro-4-[(4'-trifluoromethyl-biphenyl-2-carbonyl)-amino]-phenyl}-acetoxymethyl)-2-phenyl-malonic acid diethyl ester,
2-(2-{3-dimethylcarbamoyl-4-[(4'-trifluoromethyl-biphenyl-2-carbonyl)-amino]-phenyl}-acetoxymethyl)-2-o-tolyl-malonic acid diethyl ester,
2-(2-{3-dimethylcarbamoyl-4-[(4'-trifluoromethyl-biphenyl-2-carbonyl)-amino]-phenyl}-acetoxymethyl)-2-m-tolyl-malonic acid diethyl ester, 2-(2-{3-dimethylcarbamoyl-4-[(4'-trifluoromethyl-biphenyl-2-carbonyl)-amino]-phenyl}-acetoxymethyl)-2-p-tolyl-malonic acid diethyl ester, 2-(2-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(3-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(4-chloro-phenyl)-2-(2-{3-dimethylcarbamoyl-4-[(4'-trifluoromethyl-biphenyl-2-carbonyl)-amino]-phenyl}-acetoxymethyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-phenyl-succinic acid diethyl ester, 2-(2-{3-dimethylcarbamoyl-4-[(4'-trifluoromethyl-biphenyl-2-carbonyl)-amino]-phenyl}-acetoxymethyl)-2-(2-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(3-methoxy-phenyl)-malonic acid diethyl ester, 2-(2-{3-dimethylcarbamoyl-4-[(4'-trifluoromethyl-biphenyl-2-carbonyl)-amino]-phenyl}-acetoxymethyl)-2-(4-methoxy-phenyl)-malonic acid diethyl ester, 2-(2-{4-[(5,4'-bis-trifluoromethyl-biphenyl-2-carbonyl)-amino]-3-dimethylcarbamoyl-phenyl}-acetoxymethyl)-2-phenyl-malonic acid diethyl ester, 2-(2-{4-[(6-chloro-4'-trifluoromethyl-biphenyl-2-carbonyl)-amino]-3-dimethylcarbamoyl-phenyl}-acetoxymethyl)-2-phenyl-malonic acid diethyl ester, 2-(2-{3-dimethylcarbamoyl-4-[(6-fluoro-4'-trifluoromethyl-biphenyl-2-carbonyl)-amino]-phenyl}-acetoxymethyl)-2-phenyl-malonic acid diethyl ester, 2-[2-(2-{3-dimethylcarbamoyl-4-[(5-methyl-4'-trifluoromethyl-biphenyl-2-carbonyl)-amino]-phenyl}-acetoxy)-ethyl]-2-phenyl-malonic acid diethyl ester, 2-(2-{3-dimethylcarbamoyl-4-[(5-ethoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-[(5-isopropoxy-4'-trifluoromethyl-biphenyl-2-carbonyl)-amino]-phenyl}-acetoxymethyl)-2-phenyl-malonic acid diethyl ester, 2-[2-(2-{4-[(5,4'-bis-trifluoromethyl-biphenyl-2-carbonyl)-amino]-3-dimethylcarbamoyl-phenyl}-acetoxy)-ethyl)]-2-phenyl-malonic acid diethyl ester, 2-(2-{3-dimethylcarbamoyl-4-(6-methoxy-4'-trifluoromethyl-biphenyl-2-carbonyl)-amino]-phenyl}-acetoxymethyl)-2-phenyl-malonic acid diethyl ester, 2-(2-{3-dimethylcarbamoyl-4-(3-methyl-4'-trifluoro-methyl-biphenyl-2-carbonyl)-amino]-phenyl}-acetoxymethyl)-2-phenyl-malonic acid diethyl ester, 2-(2-{3-dimethylcarbamoyl-4-[(4'-methyl-biphenyl-2-carbonyl)-amino]-phenyl}-acetoxymethyl)-2-phenyl-malonic acid diethyl ester, 2-(2-{3-dimethylcarbamoyl-4-[(4'-ethyl-biphenyl-2-carbonyl)-amino]-phenyl}-acetoxymethyl)-2-phenyl-malonic acid diethyl ester, 2-(2-{3-dimethylcarbamoyl-4-[(4'-isopropenyl-biphenyl-2-carbonyl)-amino]-phenyl}-acetoxymethyl)-2-phenyl-malonic acid diethyl ester, 2-(2-{3-dimethylcarbamoyl-4-[(4'-isopropyl-biphenyl-2-carbonyl)-amino]-phenyl}-acetoxymethyl)-2-phenyl-malonic acid diethyl ester, 2-(2-{3-ethoxy-4-[(4'-trifluoromethyl-biphenyl-2-carbonyl)-amino]-phenyl}-acetoxymethyl)-2-phenyl-malonic acid diethyl ester, 2-(2-{3-methoxy-4-[(4'-trifluoromethyl-biphenyl-2-carbonyl)-amino]-phenyl}-acetoxymethyl)-2-phenyl-malonic acid diethyl ester, 2-(2-{3-isopropoxy-4-[(4'-trifluoromethyl-biphenyl-2-carbonyl)-amino]-phenyl}-acetoxymethyl)-2-phenyl-malonic acid diethyl ester, 2-(2-{3-benzyloxy-4-[(4'-trifluoromethyl-biphenyl-2-carbonyl)-amino]-phenyl}-acetoxymethyl)-2-phenyl-malonic acid diethyl ester, 2-(2-{3-hydroxy-4-[(4'-trifluoromethyl-biphenyl-2-carbonyl)-amino]-phenyl}-acetoxymethyl)-2-phenyl-malonic acid diethyl ester, 2-(2-{3-dimethylamino-4-[(4'-trifluoromethyl-biphenyl-2-carbonyl)-amino]-phenyl}-acetoxymethyl)-2-phenyl-malonic acid diethyl ester, 2-(2-{2-chloro-4-[(4'-trifluoromethyl-biphenyl-2-carbonyl)-amino]-benzoyloxy}-ethyl)-2-phenyl-malonic acid diethyl ester, 2-(2-{3-ethoxycarbonyl-4-[(4'-trifluoromethyl-biphenyl-2-carbonyl)-amino]-phenyl}-acetoxymethyl)-2-phenyl-malonic acid diethyl ester, 2-(3-{3-dimethylcarbamoyl-4-[(4'-trifluoromethyl-biphenyl-2-carbonyl)-amino]-phenyl}-propionyloxymethyl)-2-phenyl-malonic acid diethyl ester, 2-(2-{3-benzyloxycarbonyl-4-[(4'-trifluoromethyl-biphenyl-2-carbonyl)-amino]-phenyl}-acetoxymethyl)-2-phenyl-malonic acid diethyl ester, 2-(2-{3-carboxy-4-[(4'-trifluoromethyl-biphenyl-2-carbonyl)-amino]-phenyl}-acetoxymethyl)-2-phenyl-malonic acid diethyl ester, 2-(2-{3-isopropoxycarbonyl-4-[(4'-trifluoromethyl-biphenyl-2-carbonyl)-amino]-phenyl}-acetoxymethyl)-2-phenyl-malonic acid diethyl ester, 2-(2-{3-methoxycarbonyl-4-[(4'-trifluoromethyl-biphenyl-2-carbonyl)-amino]-phenyl}-acetoxymethyl)-2-phenyl-malonic acid diethyl ester, 2-(2-{3-acetylamino-4-[(4'-trifluoromethyl-biphenyl-2-carbonyl)-amino]-phenyl}-acetoxymethyl)-2-phenyl-malonic acid diethyl ester, 2-(2-{3-methoxycarbonylamino-4-[(4'-trifluoromethyl-biphenyl-2-carbonyl)-amino]-phenyl}-acetoxymethyl)-2-phenyl-malonic acid diethyl ester, 2-phenyl-2-(2-{6-[(4'-trifluoromethyl-biphenyl-2-carbonyl)-amino]-biphenyl-3-yl}-acetoxymethyl)-malonic acid diethyl ester, 2-(2-{3-formyl-[(4'-trifluoromethyl-biphenyl-2-carbonyl)-amino]-phenyl}-acetoxymethyl)-2-phenyl-malonic acid diethyl ester, 2-(2-{3-dimethylaminomethyl-4-[(4'-trifluoromethyl-biphenyl-2-carbonyl)-amino]-phenyl}-acetoxymethyl)-2-phenyl-malonic acid diethyl ester, 2-(2-{3-(methoxy-methylcarbamoyl)-4-[(4'-trifluoro-methyl-biphenyl-2-carbonyl)-amino]-phenyl}-acetoxymethyl)-2-phenyl-malonic acid diethyl ester, 2-(2-{3-isobutyryl-4-[(4'-trifluoromethyl-biphenyl-2-carbonyl)-amino]-phenyl}-acetoxymethyl)-2-phenyl-malonic acid diethyl ester, and 2-(2-{3-(1-hydroxy-2-methyl-propyl)-4-[(4'-trifluoromethyl-biphenyl-2-carbonyl)-amino]-phenyl}-acetoxymethyl)-2-phenyl-malonic acid diethyl ester.

12. An ester compound according to the following structural formula:

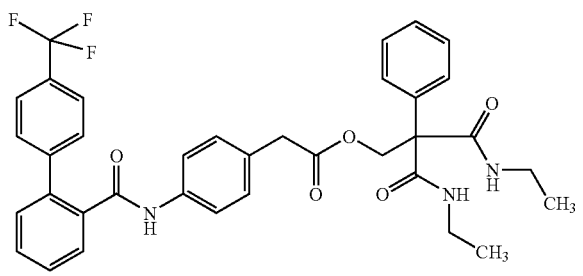

or a pharmaceutically acceptable salt thereof.

13. An ester compound according to the following structural formula:

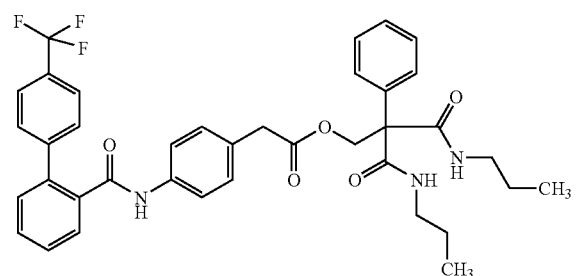

or a pharmaceutically acceptable salt thereof.

14. An ester compound according to the following structural formula:

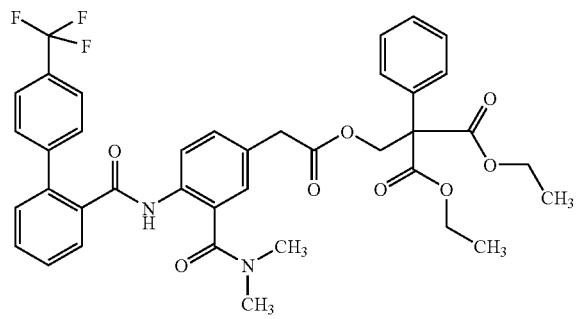

or a pharmaceutically acceptable salt thereof.

15. An ester compound according to the following structural formula:

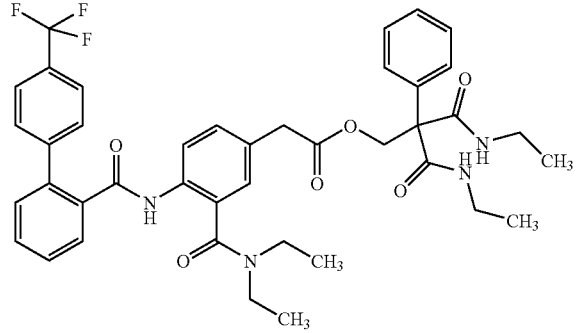

or a pharmaceutically acceptable salt thereof.

16. An ester compound according to the following structural formula:

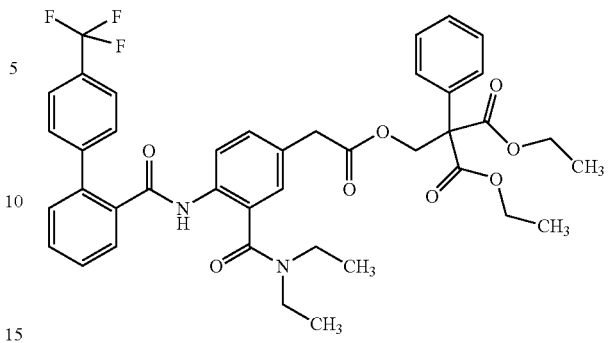

or a pharmaceutically acceptable salt thereof.

17. An ester compound according to the following structural formula:

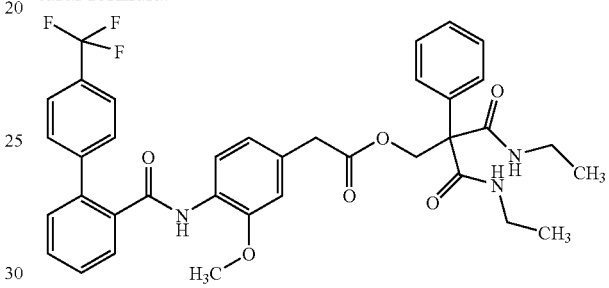

or a pharmaceutically acceptable salt thereof.

18. An ester compound according to the following structural formula:

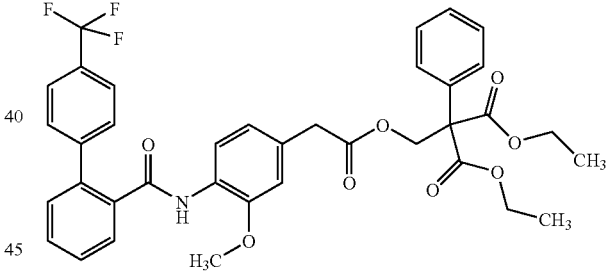

or a pharmaceutically acceptable salt thereof.

19. A method for treating hyperlipidemia, comprising administering to a subject in need thereof, the ester compound according to any one of claims 1-7, 8-10, 11, 12-17, or 18, or a pharmaceutically acceptable salt thereof.

20. A method for treating arteriosclerosis, comprising administering to a subject in need thereof, the ester compound according to any one of claims 1-7, 8-10, 11, 12-17, or 18, or a pharmaceutically acceptable salt thereof.

21. A method for treating a coronary artery disease, comprising administering to a subject in need thereof, the ester compound according to any one of claims 1-7, 8-10, 11, 12-17, or 18, or a pharmaceutically acceptable salt thereof.

22. A method for treating obesity, comprising administering to a subject in need thereof, the ester compound according to any one of claims 1-7, 8-10, 11, 12-17, or 18, or a pharmaceutically acceptable salt thereof.

23. A method for treating diabetes, comprising administering to a subject in need thereof, the ester compound according to any one of claims 1-7, 8-10, 11, 12-17, or 18, or a pharmaceutically acceptable salt thereof.

24. A method for treating hypertension, comprising administering to a subject in need thereof, the ester compound according to any one of claims 1-7, 8-10, 11, 12-17, or 18, or a pharmaceutically acceptable salt thereof.

25. The method according to claim 19, further comprising administering one or more additional antihyperlipidemic drugs.

26. The method according to claim 25 wherein the additional antihyperlipidemic drug is a statin-type drug.

27. The method according to claim 26 wherein the statin-type drug is selected from lovastatin, simvastatin, pravastatin, fluvastatin, atorvastatin, and cerivastatin.

28. The method according to claim 22, further comprising administering one or more additional drugs that are useful for the treatment of obesity.

29. The method according to claim 28 wherein the additional drug is selected from mazindol and orlistat.

30. The method according to claim 22, further comprising administering one or more additional drugs that are useful for the treatment of diabetes.

31. The method according to claim 30, wherein the additional drug is selected from insulin preparations, sulfonylurea drugs, insulin secretagogues, sulfonamide drugs, biguanide drugs, α-glucosidase inhibitors, and insulin resistance improving drugs.

32. The method according to claim 30, wherein the additional drug is selected from insulin, glibenclamide, tolbutamide, glyclopyramide, acetohexamide, glimepiride, tolazamide, gliclazide, nateglinide, glybuzole, metformin hydrochloride, buformin hydrochloride, boglibose, acarbose, and pioglitazone hydrochloride.

33. The method according to claim 24, further comprising administering one or more additional drugs that are useful for the treatment of hypertension.

34. The method according to claim 33, wherein the additional drug is selected from loop diuretics, angiotension converting enzyme inhibitors, angiotension II receptor antagonists, calcium antagonists, beta-blockers, alpha/beta blockers, and alpha blockers.

35. The method according to claim 33, wherein the additional drug is selected from furosemide delayed release, captopril, captopril delayed release, enatapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil, and phentolamine mesylate.

36. An MTP (microsomal triglyceride transfer protein) inhibitor, comprising, as an active ingredient, the ester compound of any one of claims 1-7, 8-10, 11, 12-17, or 18, or a pharmaceutically acceptable salt thereof.

37. A pharmaceutical composition, which comprises the ester compound of any one of claims 1-7, 8-10, 11, 12-17, or 18, or a pharmacuetically acceptable salt thereof, and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 7,625,948 B2 | Page 1 of 1 |
| APPLICATION NO. | : 10/492831 | |
| DATED | : December 1, 2009 | |
| INVENTOR(S) | : Hagiwara et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 348 days Delete the phrase "by 348 days" and insert -- by 356 days --

Signed and Sealed this

Twenty-fourth Day of August, 2010

David J. Kappos
*Director of the United States Patent and Trademark Office*